(12) United States Patent
Shigeta et al.

(10) Patent No.: US 8,440,666 B2
(45) Date of Patent: May 14, 2013

(54) PYRIDAZINONE COMPOUNDS AND P2X7 RECEPTOR INHIBITORS

(75) Inventors: Yukihiro Shigeta, Funabashi (JP); Yutaka Hirokawa, Funabashi (JP); Hiroshi Nagai, Funabashi (JP); Kei Nagae, Funabashi (JP); Tsuneo Watanabe, Funabashi (JP); Megumi Io, Funabashi (JP); Yusuke Shintani, Funabashi (JP); Junji Kamon, Minami-saitama-gun (JP); Masato Horikawa, Minami-saitama-gun (JP); Kazuya Takeuchi, Minami-saitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 432 days.

(21) Appl. No.: 12/680,689

(22) PCT Filed: Oct. 30, 2008

(86) PCT No.: PCT/JP2008/070261
§ 371 (c)(1),
(2), (4) Date: Mar. 29, 2010

(87) PCT Pub. No.: WO2009/057827
PCT Pub. Date: May 7, 2009

(65) Prior Publication Data
US 2010/0286390 A1 Nov. 11, 2010

(30) Foreign Application Priority Data

Oct. 31, 2007 (JP) ................... 2007-284189
Sep. 8, 2008 (JP) ................... 2008-229921

(51) Int. Cl.
| | |
|---|---|
| *C07D 239/70* | (2006.01) |
| *C07D 213/16* | (2006.01) |
| *C07D 237/08* | (2006.01) |
| *C07D 471/04* | (2006.01) |
| *C07D 239/28* | (2006.01) |
| *C07D 413/04* | (2006.01) |
| *A61K 31/517* | (2006.01) |
| *A61K 31/4409* | (2006.01) |
| *A61K 31/50* | (2006.01) |
| *A61K 31/437* | (2006.01) |
| *A61K 31/4965* | (2006.01) |
| *A61P 25/04* | (2006.01) |

(52) U.S. Cl.
USPC ........ 514/247; 514/258.1; 514/357; 514/300; 514/252.1; 544/253; 544/224; 544/242; 544/124; 544/405; 546/329; 546/113

(58) Field of Classification Search ........... 544/224, 544/253, 242, 124, 405; 514/252.1, 247, 514/258.1, 357, 300; 546/329, 113
See application file for complete search history.

(56) References Cited

U.S. PATENT DOCUMENTS

2002/0193414 A1  12/2002  Alcaraz et al.
2008/0153850 A1  6/2008  Ford et al.

FOREIGN PATENT DOCUMENTS

| EP | 1 310 493 | 5/2003 |
| WO | 99 29660 | 6/1999 |
| WO | 01 42194 | 6/2001 |
| WO | 2004 099146 | 11/2004 |
| WO | 2006 003513 | 1/2006 |
| WO | 2006 025783 | 3/2006 |
| WO | 2007 028022 | 3/2007 |
| WO | 2007 109154 | 9/2007 |
| WO | 2007 109192 | 9/2007 |

OTHER PUBLICATIONS

Database Beilstein, 1,6-Dihydro-4-methoxy-6-oxo-1-phenyl-3-pyridazincarbonitril, Beilstein Institute for Organic Chemistry, Retrieved from XFIRE , Database accession/compound with Beilstein Registry No. 4456294, XP 002515056 (abstract only).
Database Beilstein, 5-dimethylamino-2-phenyl-2H-pyridazin-3-one, Beilstein Institute for Organic Chemistry, Retrieved from XFIRE , Database accession/compound with Beilstein Registry No. 160037, XP 002515057 (abstract only).
Database Beilstein, 4-chloro-5-methylamino-2H-pyridazin-3-one, Beilstein Institute for Organic Chemistry, Retrieved from XFIRE , Database accession/compound with Beilstein Registry No. 511799, XP 002515058 (abstract only).
Database Beilstein, 5-dimethylamino-2H-pyridazin-3-one, Beilstein Institute for Organic Chemistry, Retrieved From XFIRE, Database accession/compound with Beilstein Registry No. 638181, XP 002515059 (abstract only).
Database Beilstein, 1,6-Dihydro-4-methoxy-6-oxo-1-phenyl-3-pyridazincarbonitril, Beilstein Institute for Organic Chemistry, Retrieved from XFIRE , Database accession/compound with Beilstein Registry No. 4456294, XP 002515056 (abstract only), Apr. 2008.
Database Beilstein, 5-dimethylamino-2-phenyl-2H-pyridazin-3-one, Beilstein Institute for Organic Chemistry, Retrieved from XFIRE, Database accession/compound with Beilstein Registry No. 160037, XP 002515057 (abstract only), Apr. 2008.
Database Beilstein, 4-chloro-5-methylamino-2H-pyridazin-3-one, Beilstein Institute for Organic Chemistry, Retrieved from XFIRE, Database accession/compound with Beilstein Registry No. 511799, XP 002515058 (abstract only), Apr. 2008.

(Continued)

*Primary Examiner* — Susanna Moore
*Assistant Examiner* — Cecilia M Jaisle
(74) *Attorney, Agent, or Firm* — Oblon, Spivak, McClelland, Maier & Neustadt, L.L.P.

(57) ABSTRACT

Novel pyridazinone compounds of formula (I), which inhibit the purinergic P2X7 receptor and are useful for prevention, therapy and improvement of inflammatory and immunological diseases.

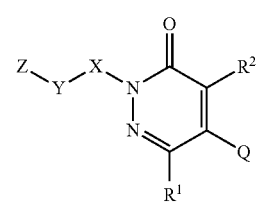

19 Claims, No Drawings

OTHER PUBLICATIONS

Database Beilstein, 5-dimethylamino-2H-pyridazin-3-one, Beilstein Institute for Organic Chemistry, Retrieved from XFIRE, Database accession/compound with Beilstein Registry No. 638181, XP 002515059 (abstract only), Apr. 2008.

North, A. R., "Molecular Physiology of P2X Receptors", Physiol Rev., vol. 82, pp. 1013-1067 (Oct. 2002).

Ferrari, D. et al., "The P2X7 Receptor: A Key Player in IL-1 Processing and Release", The Journal of Immunology, vol. 176, pp. 3877-3883, 8569, (2006).

Chessell, I. P. et al., "Disruption of the $P2X_7$ Purinoceptor Gene Abolishes Chronic Inflammatory and Neuropathic Pain", Pain, vol. 114, pp. 386-396 (2005).

Labasi, J. M. et al., "Absence of the P2X7 Receptor Alters Leukocyte Function and Attenuates an Inflammatory Response", The Journal of Immunology, vol. 168, pp. 6436-6445 (2002).

Honore, P. et al., "A-740003 [N-(1-{[(Cyanoimino)(5-Quinolinylamino)Methyl]Amino}-2,2-Dimethylpropyl)-2-(3,4-Dimethoxyphenyl)Acetamide], A Novel and Selective $P2X_7$ Receptor Antagonist, Dose-Dependently Reduces Neuropathic Pain in the Rat", The Journal of Pharmacology and Experimental Therapeutics, vol. 319, No. 3, pp. 1376-1385 (2006).

PYRIDAZINONE COMPOUNDS AND P2X7 RECEPTOR INHIBITORS

BACKGROUND OF THE INVENTION

1. Technical Field

The present invention relates to novel heterocyclic compounds which inhibit the P2X7 receptor.

2. Background Art

The purinergic P2X7 receptor is a ligand-gated ion channel which becomes permeable to ions such as $Ca^{2+}$ upon the binding of purine nucleotides and is expressed in macrophages, mast cells, T-lymphocytes, B-lymphocytes, antigen presenting cells, osteoclasts, keratinocytes and the like. It is associated with inflammatory and immunological diseases by mediating production of inflammatory cytokines, in particular IL-1β (interleukin-1β) (Non-patent documents 1 and 2). It is also expressed in microglia and associated with pain (Non-patent document 3).

Therefore, P2X7 receptor inhibitors can be useful for treatment of these diseases, and actually, it is known that P2X7 knockout mice are resistant to the development of experimental arthritis and pain and that P2X7 receptor inhibitors attenuate neuropathic pain (Non-patent documents 3 to 5).

Although several P2X7 receptor inhibitors have been known from the following reports (such as Patent documents 1 and 2), further development of such drugs is demanded.

Patent document 1: WO99/29660
Patent document 2: WO2007/109192
Non-patent document 1: Physiol. Rev. 2002: 82, p. 1013-1067
Non-patent document 2: J. Immunol. 2006: 176, p. 3877-3883
Non-patent document 3: Pain 2005: 114, p. 386-396
Non-patent document 4: J. Immunol. 2002: 168, p. 6436-6445
Non-patent document 5: J. Pharmacol. Exp. Ther. 2006: 319, p. 1376-1385

DISCLOSURE OF THE INVENTION

The object of the present invention is to provide novel pyridazinone compounds which inhibit the P2X7 receptor and are useful for inflammatory and immunological diseases.

The present inventors conducted extensive research to find novel low molecular weight compounds having antagonistic action on the P2X7 receptor, and as a result, found that the compounds of the present invention have strong antagonistic action. The present invention was accomplished on the basis of this discovery. Namely, the present invention provides:

(1) A compound represented by the formula (I):

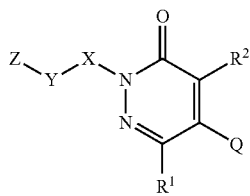

(I)

wherein $R^1$ means a hydrogen atom, a hydroxy group, a nitro group, a cyano group, a carboxy group, a carbamoyl group, an amino group, a halogen atom, a $C_{1-6}$ alkyl group, a $C_{2-6}$ alkenyl group, a $C_{2-6}$ alkynyl group or a $C_{1-6}$ alkoxy group (the $C_{1-6}$ alkyl group, the $C_{2-6}$ alkenyl group, the $C_{2-6}$ alkynyl group and the $C_{1-6}$ alkoxy group are unsubstituted or substituted with one or more halogen atoms), $R^2$ means a hydrogen atom, a hydroxy group, a nitro group, a cyano group, a carboxy group, a carbamoyl group, an amino group, a halogen atom, a $C_{1-6}$ alkyl group, a $C_{2-6}$ alkenyl group, a $C_{1-6}$ alkoxy group, a mono-$C_{1-6}$ alkylamino group, a di-$C_{1-6}$ alkylamino group, a $C_{1-6}$ alkylthio group or a $C_{1-6}$ alkylsulfonyl group (the $C_{1-6}$ alkyl group, the $C_{2-6}$ alkenyl group, the $C_{1-6}$ alkoxy group, the mono-$C_{1-6}$ alkylamino group, the di-$C_{1-6}$ alkylamino group, the $C_{1-6}$ alkylthio group and the $C_{1-6}$ alkylsulfonyl group are unsubstituted or substituted with one or more halogen atoms), Q means any of the structures represented by the formula (II):

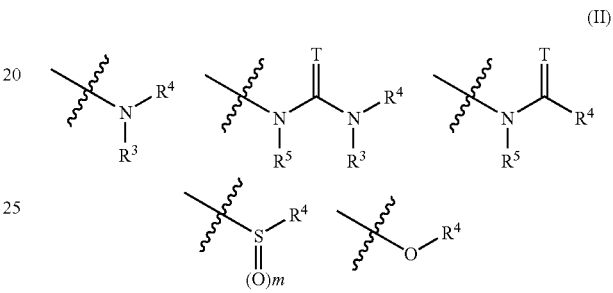

(II)

(wherein each of $R^3$ and $R^5$ independently means a hydrogen atom, a $C_{1-6}$ alkyl group, a $C_{2-6}$ alkenyl group or a $C_{2-6}$ alkynyl group (the $C_{1-6}$ alkyl group, the $C_{2-6}$ alkenyl group and the $C_{2-6}$ alkynyl group are unsubstituted or substituted with one or more halogen atoms), $R^4$ means a $C_{1-20}$ alkyl group, a $C_{2-20}$ alkenyl group or a $C_{2-19}$ heterocyclyl group (the $C_{1-20}$ alkyl group, the $C_{2-20}$ alkenyl group and the $C_{2-19}$ heterocyclyl group are unsubstituted or substituted with one or more identical or different substituents selected from a substituent set $V^1$), or $R^3$ and $R^4$ mean, together with each other, a nitrogen-containing heterocyclyl group (the nitrogen-containing heterocyclyl group is unsubstituted or substituted with one or more identical or different substituents selected from the substituent set $V^1$ or one or more $C_{1-20}$ alkyl groups), m means 0, 1 or 2, and T means an oxygen atom or a sulfur atom), X means a single bond or a $C_{1-6}$ alkylene group (the $C_{1-6}$ alkylene group is unsubstituted or substituted with one or more identical or different substituents selected from the substituent set $V^1$), Y means a single bond, a $C_{2-14}$ arylene group, a $C_{2-9}$ heterocyclylene group (the $C_{2-14}$ arylene group and the $C_{2-9}$ heterocyclylene group are unsubstituted or substituted with one or more identical or different substituents selected from a substituent set $V^2$) or any of the structures represented by the formula (III):

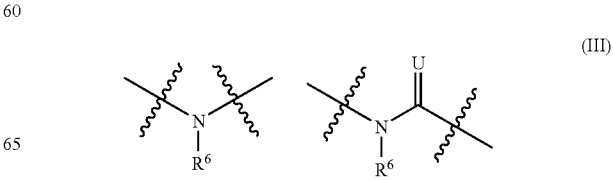

(III)

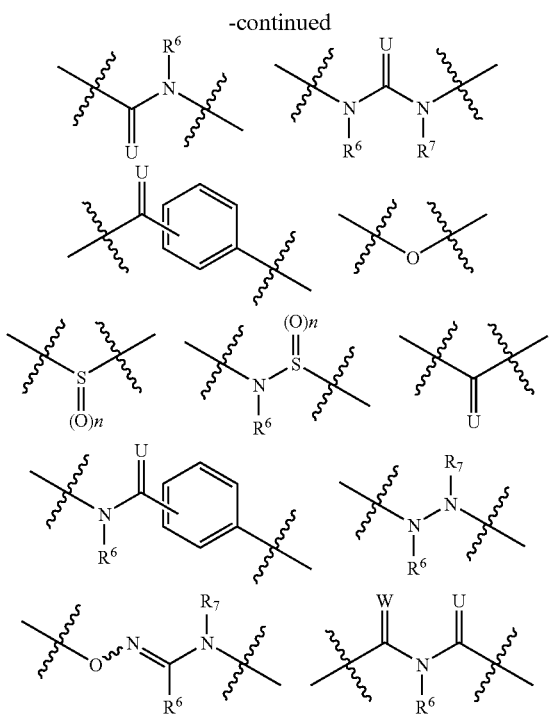

(wherein each of $R^6$ and $R^7$ independently means a hydrogen atom, a $C_{1-6}$ alkyl group, a $C_{2-6}$ alkenyl group (the $C_{1-6}$ alkyl group and the $C_{2-6}$ alkenyl group are unsubstituted or substituted with one or more identical or different substituents selected from the substituent set $V^1$) or a $C_{1-3}$ haloalkyl group, each of U and W independently means an oxygen atom, a sulfur atom or $NOR^{10}$ (wherein $R^{10}$ means a hydrogen atom, a $C_{1-3}$ alkyl group or a $C_{1-3}$ haloalkyl group), and n means 0, 1 or 2), Z means a hydrogen atom, a $C_{1-6}$ alkyl group, a $C_{2-6}$ alkenyl group, a $C_{1-6}$ alkoxy group, a $C_{3-12}$ cycloalkyl group, a $C_{3-12}$ cycloalkenyl group (the $C_{1-6}$ alkyl group, the $C_{2-6}$ alkenyl group, the $C_{1-6}$ alkoxy group, the $C_{3-12}$ cycloalkyl group and the $C_{3-12}$ cycloalkenyl group are unsubstituted or substituted with one or more identical or different substituents selected from the substituent set $V^2$), a $C_{2-14}$ aryl group, a fused $C_{2-14}$ aryl group, a $C_{2-14}$ aryloxy group or a $C_{2-9}$ heterocyclyl group (the $C_{2-14}$ aryl group, the fused $C_{2-14}$ aryl group, the $C_{2-14}$ aryloxy group and the $C_{2-9}$ heterocyclyl group are unsubstituted or substituted with one or more identical or different substituents selected from the substituent set $V^2$), the substituent set $V^1$ consists of carboxy groups, carbamoyl groups, sulfamoyl groups, phosphono groups, sulfo groups, tetrazolyl groups, formyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkyl groups, $C_{2-6}$ alkenyl groups, $C_{1-6}$ alkoxy groups, $C_{2-9}$ heterocyclyl groups, $C_{1-6}$ alkylthio groups and $C_{1-6}$ alkylsulfonyl groups (the mono-$C_{1-6}$ alkylamino groups, the di-$C_{1-6}$ alkylamino groups, the $C_{1-6}$ alkyl groups, the $C_{2-6}$ alkenyl groups, the $C_{1-6}$ alkoxy groups, the $C_{2-9}$ heterocyclyl groups, the $C_{1-6}$ alkylthio groups and the $C_{1-6}$ alkylsulfonyl groups are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more hydroxy groups, one or more amino groups, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more hydroxy groups, one or more amino groups, one or more mono-$C_{1-6}$ alkylamino groups, one or more di-$C_{1-6}$ alkylamino groups, one or more $C_{1-6}$ alkylthio groups or one or more $C_{1-6}$ alkylsulfonyl groups), and the substituent set $V^2$ consists of the substituent set $V^1$, $C_{2-14}$ aryl groups and fused $C_{2-14}$ aryl groups (the $C_{2-14}$ aryl groups and the fused $C_{2-14}$ aryl groups are unsubstituted or substituted with one or more identical or different substituents selected from the substituent set $V^1$), a tautomer, prodrug or pharmaceutically acceptable salt of the compound or a solvate thereof.

(2) A compound represented by the formula (I):

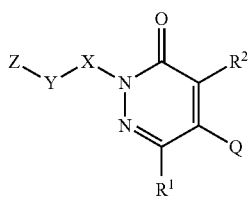

(I)

wherein $R^1$ means a hydrogen atom, a hydroxy group, a cyano group, a carboxy group, a carbamoyl group, an amino group, a halogen atom, a $C_{1-6}$ alkyl group, a $C_{2-6}$ alkenyl group, a $C_{2-6}$ alkynyl group or a $C_{1-6}$ alkoxy group (the $C_{1-6}$ alkyl group, the $C_{2-6}$ alkenyl group, the $C_{2-6}$ alkynyl group and the $C_{1-6}$ alkoxy group are unsubstituted or substituted with one or more halogen atoms), $R^2$ means a hydrogen atom, a hydroxy group, a cyano group, a carboxy group, a carbamoyl group, an amino group, a halogen atom, a $C_{1-6}$ alkyl group, a $C_{2-6}$ alkenyl group, a $C_{1-6}$ alkoxy group, a $C_{1-6}$ alkylthio group or a $C_{1-6}$ alkylsulfonyl group (the $C_{1-6}$ alkyl group, the $C_{2-6}$ alkenyl group, the $C_{1-6}$ alkoxy group, the $C_{1-6}$ alkylthio group and the $C_{1-6}$ alkylsulfonyl group are unsubstituted or substituted with one or more halogen atoms), Q means any of the structures represented by the formula (IV):

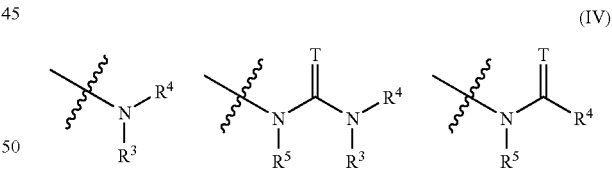

(IV)

(wherein each of $R^3$ and $R^5$ independently means a hydrogen atom, a $C_{1-6}$ alkyl group, a $C_{2-6}$ alkenyl group or a $C_{2-6}$ alkynyl group (the $C_{1-6}$ alkyl group, the $C_{2-6}$ alkenyl group and the $C_{2-6}$ alkynyl group are unsubstituted or substituted with one or more halogen atoms), $R^4$ means a $C_{1-20}$ alkyl group or a $C_{2-20}$ alkenyl group (the $C_{1-20}$ alkyl group and the $C_{2-20}$ alkenyl group are unsubstituted or substituted with one or more identical or different substituents selected from a substituent set $V^1$), or $R^3$ and $R^4$ mean, together with each other, a nitrogen-containing heterocyclyl group (the nitrogen-containing heterocyclyl group is unsubstituted or substituted with one or more identical or different substituents selected from the substituent set $V^1$ or one or more $C_{1-20}$ alkyl groups), and T means an oxygen atom or a sulfur atom), X means a single bond or a $C_{1-6}$ alkylene group (the $C_{1-6}$ alkylene group is unsubstituted or substituted with one or more identical or different substituents selected from the substituent set $V^1$), Y means a single bond, a $C_{2-14}$ arylene group, a $C_{2-9}$ heterocyclylene group (the $C_{2-14}$ arylene group and the $C_{2-9}$ heterocyclylene group are unsubstituted or substituted with one or more identical or different substituents selected from a substituent set $V^2$) or any of the structures represented by the formula (V):

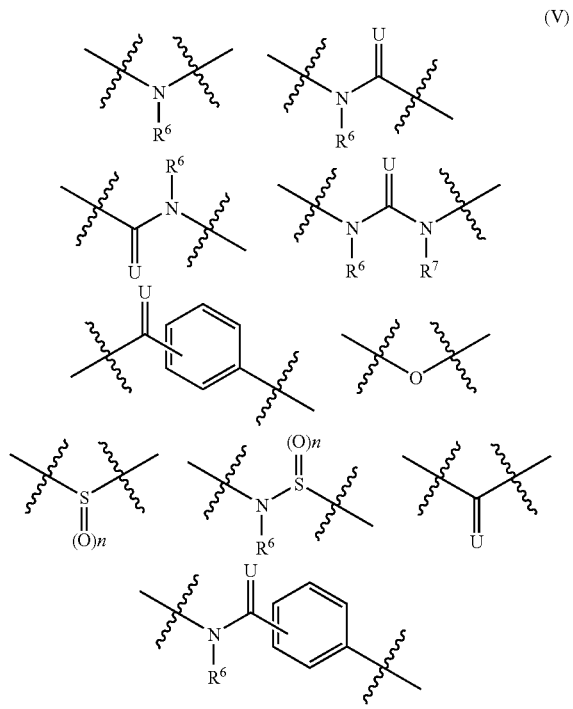

(V)

(wherein each of $R^6$ and $R^7$ independently means a hydrogen atom, a $C_{1-6}$ alkyl group, a $C_{2-6}$ alkenyl group or a $C_{1-3}$ haloalkyl group, U means an oxygen atom, a sulfur atom or $NOR^{10}$ (wherein $R^{10}$ means a hydrogen atom, a $C_{1-3}$ alkyl group or a $C_{1-3}$ haloalkyl group), and n means 0, 1 or 2), Z means a $C_{1-6}$ alkyl group, a $C_{2-6}$ alkenyl group, a $C_{1-6}$ alkoxy group, a $C_{3-12}$ cycloalkyl group, a $C_{3-12}$ cycloalkenyl group (the $C_{1-6}$ alkyl group, the $C_{2-6}$ alkenyl group, the $C_{1-6}$ alkoxy group, the $C_{3-12}$ cycloalkyl group and the $C_{3-12}$ cycloalkenyl group are unsubstituted or substituted with one or more identical or different substituents selected from the substituent set $V^2$), a $C_{2-14}$ aryl group, a fused $C_{2-14}$ aryl group, a $C_{2-14}$ aryloxy group or a $C_{2-9}$ heterocyclyl group (the $C_{2-14}$ aryl group, the fused $C_{2-14}$ aryl group, the $C_{2-14}$ aryloxy group and the $C_{2-9}$ heterocyclyl group are unsubstituted or substituted with one or more identical or different substituents selected from the substituent set $V^2$), the substituent set $V^1$ consists of carboxy groups, carbamoyl groups, sulfamoyl groups, phosphono groups, sulfo groups, tetrazolyl groups, formyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkyl groups, $C_{2-6}$ alkenyl groups, $C_{1-6}$ alkoxy groups, $C_{2-9}$ heterocyclyl groups, $C_{1-6}$ alkylthio groups and $C_{1-6}$ alkylsulfonyl groups (the mono-$C_{1-6}$ alkylamino groups, the di-$C_{1-6}$ alkylamino groups, the $C_{1-6}$ alkyl groups, the $C_{2-6}$ alkenyl groups, the $C_{1-6}$ alkoxy groups, the $C_{2-9}$ heterocyclyl groups, the $C_{1-6}$ alkylthio groups and the $C_{1-6}$ alkylsulfonyl groups are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more hydroxy groups, one or more amino groups, one or more mono-$C_{1-6}$ alkylamino groups, one or more di-$C_{1-6}$ alkylamino groups, one or more $C_{1-6}$ alkylthio groups or one or more $C_{1-6}$ alkylsulfonyl groups), and the substituent set $V^2$ consists of the substituent set $V^1$, $C_{2-14}$ aryl groups and fused $C_{2-14}$ aryl groups (the $C_{2-14}$ aryl groups and the fused $C_{2-14}$ aryl groups are unsubstituted or substituted with one or more identical or different substituents selected from the substituent set $V^1$), a tautomer, prodrug or pharmaceutically acceptable salt of the compound or a solvate thereof.

(3) The compound according to (1) or (2), wherein $R^1$ is a hydrogen atom, a $C_{1-3}$ alkoxy group or a $C_{1-3}$ haloalkoxy group, a tautomer, prodrug or pharmaceutically acceptable salt of the compound or a solvate thereof.

(4) The compound according to (1) or (2), wherein $R^1$ is a hydrogen atom or an ethoxy group, a tautomer, prodrug or pharmaceutically acceptable salt of the compound or a solvate thereof.

(5) The compound according to any one of (1) to (4), wherein $R^2$ is a hydrogen atom, a halogen atom, a $C_{1-3}$ alkoxy group, a $C_{1-3}$ alkyl group, a $C_{1-3}$ alkylthio group or a $C_{1-3}$ alkylsulfonyl group (the $C_{1-3}$ alkoxy group, the $C_{1-3}$ alkyl group, the $C_{1-3}$ alkylthio group and the $C_{1-3}$ alkylsulfonyl group are unsubstituted or substituted with one or more halogen atoms), a tautomer, prodrug or pharmaceutically acceptable salt of the compound or a solvate thereof.

(6) The compound according to (5), wherein $R^2$ is a halogen atom, a tautomer, prodrug or pharmaceutically acceptable salt of the compound or a solvate thereof.

(7) The compound according to any one of (1) to (6), wherein Q is represented by the formula (VI):

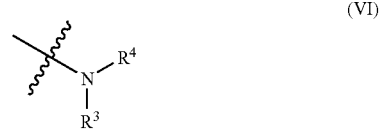

(VI)

(wherein $R^3$ means a hydrogen atom or a $C_{1-6}$ alkyl group (the $C_{1-6}$ alkyl group is unsubstituted or substituted with one or more halogen atoms), and $R^4$ means a $C_{1-20}$ alkyl group or a $C_{2-20}$ alkenyl group (the $C_{1-20}$ alkyl group and the $C_{2-20}$ alkenyl group are unsubstituted or substituted with one or more identical or different substituents selected from the substituent set $V^1$)), a tautomer, prodrug or pharmaceutically acceptable salt of the compound or a solvate thereof.

(8) The compound according to any one of (1) and (3) to (6), wherein Q is represented by the formula (VII):

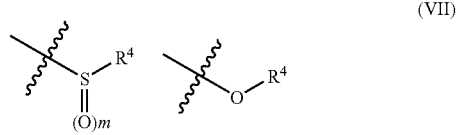

(VII)

(wherein m means 0, 1 or 2, and $R^4$ means a $C_{1-20}$ alkyl group or a $C_{2-20}$ alkenyl group (the $C_{1-20}$ alkyl group and the $C_{2-20}$ alkenyl group are unsubstituted or substituted with one or more identical or different substituents selected from the substituent set $V^1$)), a tautomer, prodrug or pharmaceutically acceptable salt of the compound or a solvate thereof.

(9) The compound according to (7) or (8), wherein $R^3$ means a hydrogen atom, and $R^4$ means a $C_{3-12}$ cycloalkyl group or a $C_{3-12}$ cycloalkenyl group (the $C_{3-12}$ cycloalkyl group and the $C_{3-12}$ cycloalkenyl group are unsubstituted or substituted with one to three identical or different substituents selected from the substituent set $V^1$), a tautomer, prodrug or pharmaceutically acceptable salt of the compound or a solvate thereof.

(10) The compound according to any one of (1) and (3) to (6), wherein $R^3$ means a hydrogen atom, and $R^4$ means a $C_{2-19}$ heterocyclyl group (the $C_{2-19}$ heterocyclyl group is unsubstituted or substituted with one to three identical or different substituents selected from the substituent set $V^1$), a tautomer, prodrug or pharmaceutically acceptable salt of the compound or a solvate thereof.

(11) The compound according to (10), wherein $R^3$ means a hydrogen atom, and $R^4$ means a $C_{2-11}$ heterocyclyl group (the $C_{2-11}$ heterocyclyl group is unsubstituted or substituted with one to three identical or different substituents selected from the substituent set $V^1$), a tautomer, prodrug or pharmaceutically acceptable salt of the compound or a solvate thereof.

(12) The compound according to any one of (1) to (11), wherein X means a $C_{1-6}$ alkylene group (the $C_{1-6}$ alkylene group is unsubstituted or substituted with one or two identical or different substituents selected from the substituent set $V^1$), Y means a single bond or any of the structures represented by the formula (VIII):

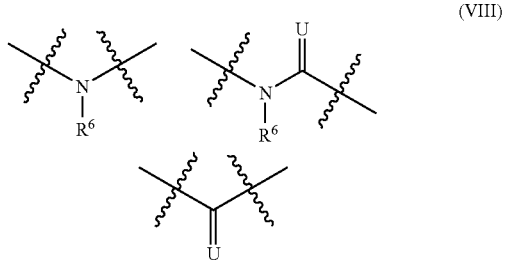

(VIII)

(wherein $R^6$ means a hydrogen atom or a $C_{1-6}$ alkyl group (the $C_{1-6}$ alkyl group is unsubstituted or substituted with one or more halogen atoms), and U means an oxygen atom or a sulfur atom), and Z means a $C_{1-6}$ alkyl group, a $C_{1-6}$ alkoxy group (the $C_{1-6}$ alkyl group and the $C_{1-6}$ alkoxy group are unsubstituted or substituted with one or two identical or different substituents selected from the substituent set $V^2$), a $C_{2-14}$ aryl group, a $C_{2-14}$ aryloxy group or a $C_{2-9}$ heterocyclyl group (the $C_{2-14}$ aryl group, the $C_{2-14}$ aryloxy group and the $C_{2-9}$ heterocyclyl group are unsubstituted or substituted with one substituent selected from the substituent set $V^2$), a tautomer, prodrug or pharmaceutically acceptable salt of the compound or a solvate thereof.

(13) The compound according to any one of (1) to (12), wherein Z means a $C_{1-6}$ alkyl group (the $C_{1-6}$ alkyl group is substituted with a $C_{2-9}$ heteroaryl group (the $C_{2-9}$ heteroaryl group is unsubstituted or substituted with one or two identical or different substituents selected from the substituent set $V^1$)), a tautomer, prodrug or pharmaceutically acceptable salt of the compound or a solvate thereof.

(14) A compound represented by the formula (I):

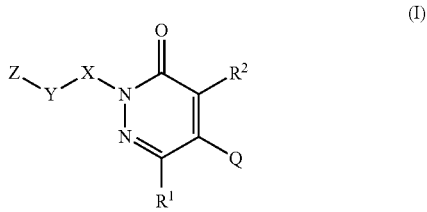

(I)

wherein $R^1$ means a hydrogen atom, a hydroxy group, a cyano group, a carboxy group, a carbamoyl group, an amino group, a halogen atom, a $C_{1-6}$ alkyl group, a $C_{2-6}$ alkenyl group, a $C_{2-6}$ alkynyl group or a $C_{1-6}$ alkoxy group (the $C_{1-6}$ alkyl group, the $C_{2-6}$ alkenyl group, the $C_{2-6}$ alkynyl group and the $C_{1-6}$ alkoxy group are unsubstituted or substituted with one or more halogen atoms), $R^2$ means a $C_{2-14}$ aryl group (the $C_{2-14}$ aryl group is unsubstituted or substituted with one or more identical or different substituents selected from a substituent set $V^2$), Q means any of the structures represented by the formula (II):

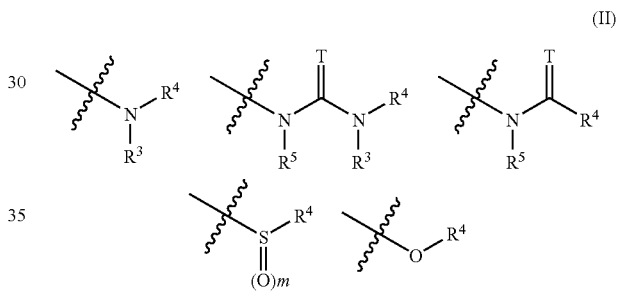

(II)

(wherein each of $R^3$ and $R^5$ independently means a hydrogen atom, a $C_{1-6}$ alkyl group, a $C_{2-6}$ alkenyl group or a $C_{2-6}$ alkynyl group (the $C_{1-6}$ alkyl group, the $C_{2-6}$ alkenyl group and the $C_{2-6}$ alkynyl group are unsubstituted or substituted with one or more halogen atoms), $R^4$ means a $C_{1-20}$ alkyl group or a $C_{2-20}$ alkenyl group (the $C_{1-20}$ alkyl group and the $C_{2-20}$ alkenyl group are unsubstituted or substituted with one or more identical or different substituents selected from a substituent set $V^1$), or $R^3$ and $R^4$ mean, together with each other, a nitrogen-containing heterocyclyl group (the nitrogen-containing heterocyclyl group is unsubstituted or substituted with one or more identical or different substituents selected from the substituent set $V^1$ or one or more $C_{1-20}$ alkyl groups), m means 0, 1 or 2, and T means an oxygen atom or a sulfur atom), X means a $C_{1-6}$ alkylene group (the $C_{1-6}$ alkylene group is unsubstituted or substituted with one or more identical or different substituents selected from the substituent set $V^1$), Y means a structure represented by the formula (IX):

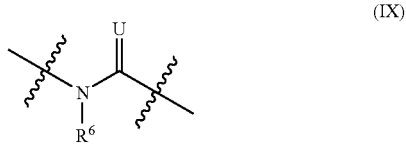

(IX)

(wherein $R^6$ means a hydrogen atom, a $C_{1-6}$ alkyl group, a $C_{2-6}$ alkenyl group or a $C_{1-3}$ haloalkyl group, and U means an oxygen atom, a sulfur atom or $NOR^{10}$ (wherein $R^{10}$ means a hydrogen atom, a $C_{1-3}$ alkyl group or a $C_{1-3}$ haloalkyl group)), Z means a hydrogen atom, a $C_{1-6}$ alkyl group, a $C_{2-6}$ alkenyl group, a $C_{1-6}$ alkoxy group, a $C_{3-12}$ cycloalkyl group, a $C_{3-12}$ cycloalkenyl group (the $C_{1-6}$ alkyl group, the $C_{2-6}$ alkenyl group, the $C_{1-6}$ alkoxy group, the $C_{3-12}$ cycloalkyl group and the $C_{3-12}$ cycloalkenyl group are unsubstituted or substituted with one or more identical or different substituents selected from the substituent set $V^2$), a $C_{2-14}$ aryl group, a fused $C_{2-14}$ aryl group or a $C_{2-9}$ heterocyclyl group (the $C_{2-14}$ aryl group, the fused $C_{2-14}$ aryl group and the $C_{2-9}$ heterocyclyl group are unsubstituted or substituted with one or more identical or different substituents selected from the substituent set $V^2$), the substituent set $V^1$ consists of carboxy groups, carbamoyl groups, sulfamoyl groups, phosphono groups, sulfo groups, tetrazolyl groups, formyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkyl groups, $C_{2-6}$ alkenyl groups, $C_{1-6}$ alkoxy groups, $C_{2-9}$ heterocyclyl groups, $C_{1-6}$ alkylthio groups and $C_{1-6}$ alkylsulfonyl groups (the mono-$C_{1-6}$ alkylamino groups, the di-$C_{1-6}$ alkylamino groups, the $C_{1-6}$ alkyl groups, the $C_{2-6}$ alkenyl groups, the $C_{1-6}$ alkoxy groups, the $C_{2-9}$ heterocyclyl groups, the $C_{1-6}$ alkylthio groups and the $C_{1-6}$ alkylsulfonyl groups are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more hydroxy groups, one or more amino groups, one or more mono-$C_{1-6}$ alkylamino groups, one or more di-$C_{1-6}$ alkylamino groups, one or more $C_{1-6}$ alkylthio groups or one or more $C_{1-6}$ alkylsulfonyl groups), and
the substituent set $V^2$ consists of the substituent set $V^1$, $C_{2-14}$ aryl groups and fused $C_{2-14}$ aryl groups (the $C_{2-14}$ aryl groups and the fused $C_{2-14}$ aryl groups are unsubstituted or substituted with one or more identical or different substituents selected from the substituent set $V^1$), a tautomer, prodrug or pharmaceutically acceptable salt of the compound or a solvate thereof.
(15) The compound according to (14), wherein $R^1$ is a hydrogen atom, a $C_{1-3}$ alkoxy group or a $C_{1-3}$ haloalkoxy group, $R^2$ is a $C_{2-14}$ aryl group,
Q is represented by the formula (VI):

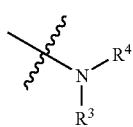

(VI)

(wherein $R^3$ means a hydrogen atom or a $C_{1-6}$ alkyl group (the $C_{1-6}$ alkyl group is unsubstituted or substituted with one or more halogen atoms),
$R^4$ means a $C_{1-20}$ alkyl group (the $C_{1-20}$ alkyl group is unsubstituted or substituted with one or more identical or different substituents selected from the substituent set $V^1$)), and
Z means a $C_{1-6}$ alkyl group (the $C_{1-6}$ alkyl group is substituted with a $C_{2-9}$ heteroaryl group (the $C_{2-9}$ heteroaryl group is unsubstituted or substituted with one or two identical or different substituents selected from the substituent set $V^1$)), a tautomer, prodrug or pharmaceutically acceptable salt of the compound or a solvate thereof.
(16) The compound according to (14), wherein $R^1$ is a hydrogen atom, a $C_{1-3}$ alkoxy group or a $C_{1-3}$ haloalkoxy group, $R^2$ is a $C_{2-14}$ aryl group,
Q means any of the structures represented by the formula (VII):

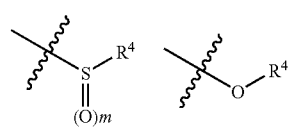

(VII)

(wherein m means 0, 1 or 2, and $R^4$ means a $C_{1-20}$ alkyl group (the $C_{1-20}$ alkyl group is unsubstituted or substituted with one or more identical or different substituents selected from the substituent set $V^1$)), and
Z means a $C_{1-6}$ alkyl group (the $C_{1-6}$ alkyl group is substituted with a $C_{2-9}$ heteroaryl group (the $C_{2-9}$ heteroaryl group is unsubstituted or substituted with one or two identical or different substituents selected from the substituent set $V^1$)), a tautomer, prodrug or pharmaceutically acceptable salt of the compound or a solvate thereof.
(17) A P2X7 receptor inhibitor containing the compound according to any one of (1) to (16), a tautomer, prodrug or pharmaceutically acceptable salt of the compound or a solvate thereof, as an active ingredient.
(18) A preventive, therapeutic or improving agent for diseases against which inhibition of the P2X7 receptor is effective, which contains the P2X7 receptor inhibitor according to (17), as an active ingredient.
(19) A therapeutic agent for rheumatoid arthritis, which contains the P2X7 receptor inhibitor according to (17), as an active ingredient.
(20) Medicament containing the compound according to any one of (1) to (16), a tautomer, prodrug or pharmaceutically acceptable salt of the compound or a solvate thereof, as an active ingredient.

EFFECTS OF THE INVENTION

The present invention provides novel pyridazinone compounds which have excellent inhibitory action on the P2X7 receptor and are useful for inflammatory and immunological diseases.

BEST MODE FOR CARRYING OUT THE INVENTION

Now, the present invention will be described in detail.
In the present invention, "n" denotes normal, "i" denotes iso, "s" denotes secondary, "t" denotes tertiary, "c" denotes cyclo, "o" denotes ortho, "m" denotes meta, "p" denotes para, "rac" denotes racemate, "Ph" denotes phenyl, "Py" denotes pyridyl, "Me" denotes methyl, "Et" denotes ethyl, "Pr" denotes propyl, "Bu" denotes butyl, "Boc" denotes tertiary-butoxycarbonyl, "Ms" denotes methanesulfonyl, "Tf" denotes trifluoromethanesulfonyl, and "MOM" denotes methoxymethyl.
First, the terms in the respective substituents $R^1$ to $R^{10}$ will be explained.
As a halogen atom, fluorine, chlorine, bromine or iodine may be mentioned.

A C$_{1-3}$ alkyl group is an alkyl group containing one to three carbon atoms and may be linear, branched or a C$_3$ cycloalkyl group. As specific examples, methyl, ethyl, n-propyl, i-propyl and c-propyl may be mentioned.

A C$_{1-6}$ alkyl group is an alkyl group containing one to six carbon atoms and may be linear, branched or a C$_{3-6}$ cycloalkyl group. As specific examples, in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A C$_{3-12}$ cycloalkyl group is a cycloalkyl group containing 3 to 12 carbon atoms and may have a fused polycyclic structure, a bridged cyclic structure or a spirocyclic structure. As specific examples, c-propyl, c-butyl, 1-methyl-c-propyl, 2-methyl-c-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl, c-heptyl, c-octyl, c-nonyl, c-decyl, c-undecyl, c-dodecyl, the structures shown below and the like may be mentioned.

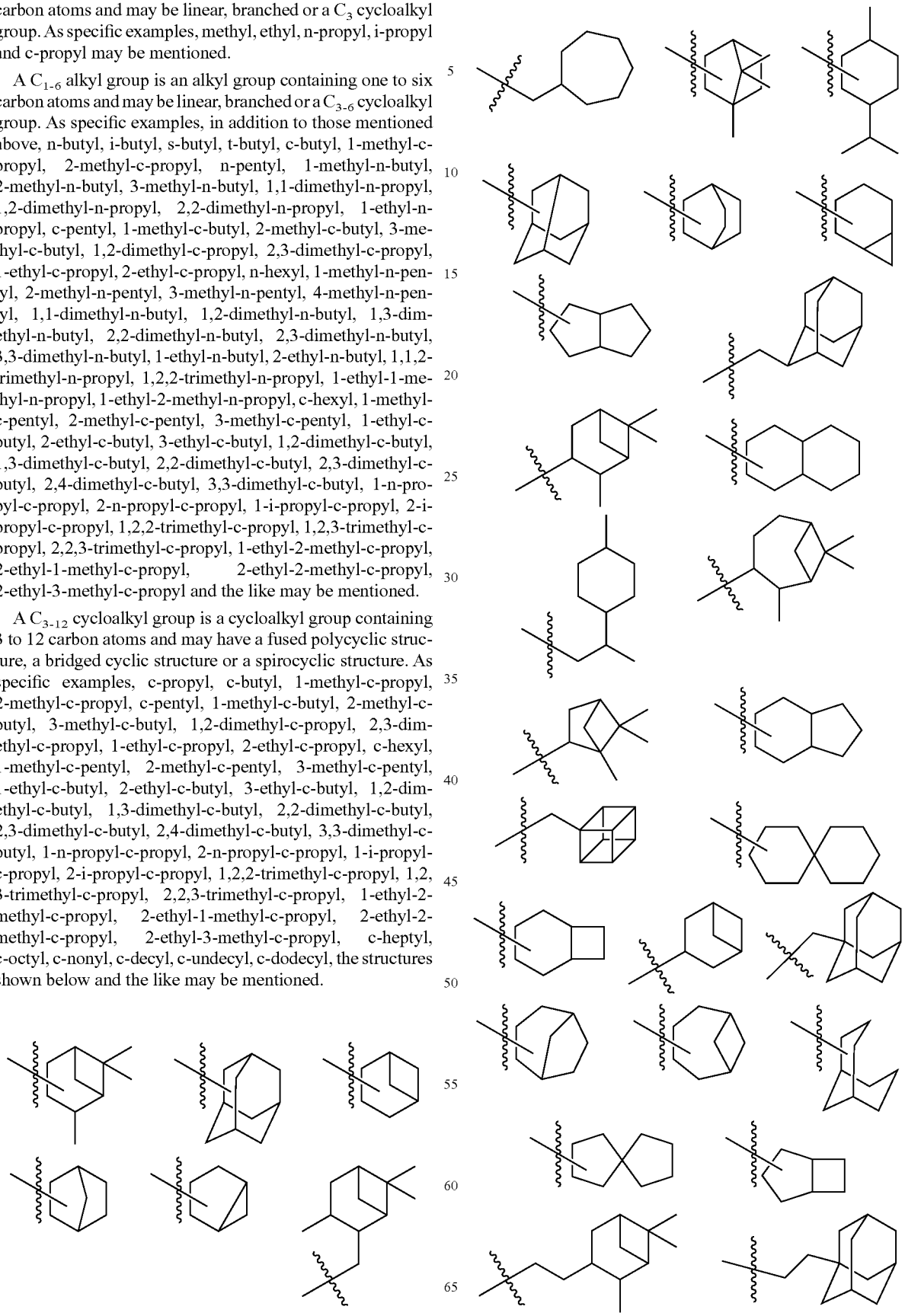

-continued

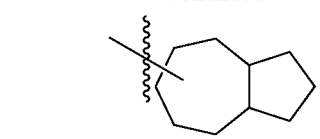

A C$_{7-12}$ cycloalkyl group is a cycloalkyl group containing seven to twelve carbon atoms and may have a fused polycyclic structure, a bridged cyclic structure or a spirocyclic structure. As specific examples, the structures shown below and the like may be mentioned.

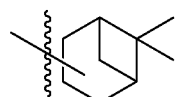 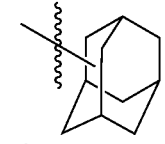 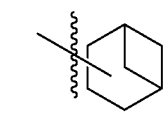

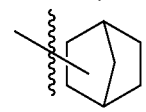 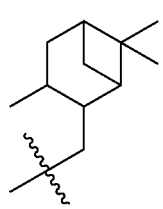

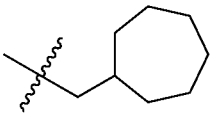 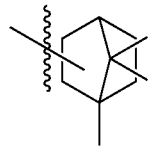 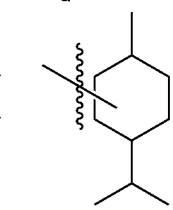

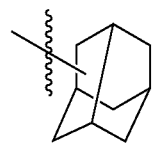 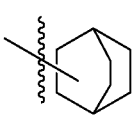 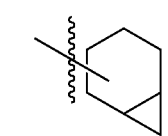

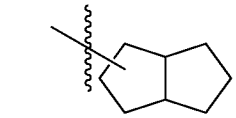 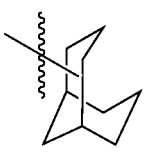

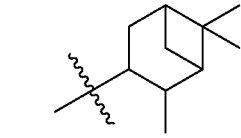 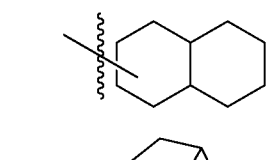

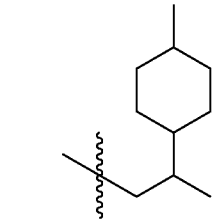 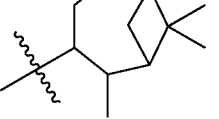

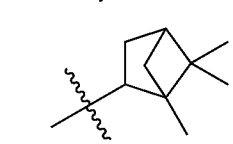 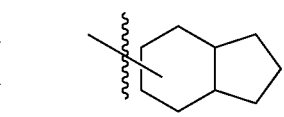

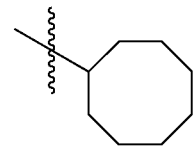 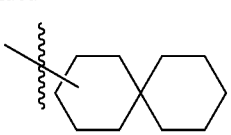

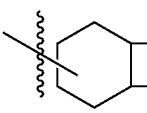 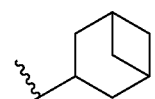 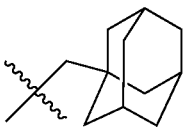

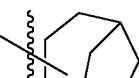 

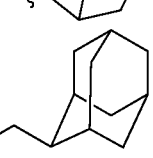 

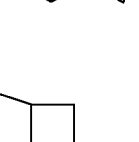 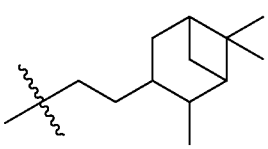

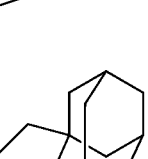 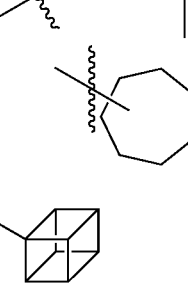

A C$_{8-12}$ cycloalkyl group is a cycloalkyl group containing eight to twelve carbon atoms and may have a fused polycyclic structure, a bridged cyclic structure or a spirocyclic structure. As specific examples, the structures shown below and the like may be mentioned.

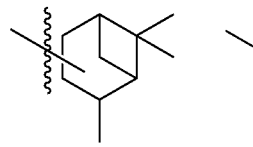  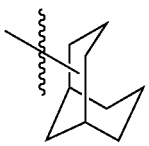

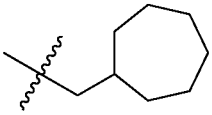 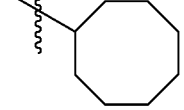

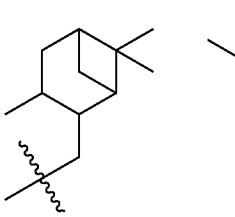 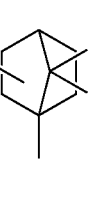 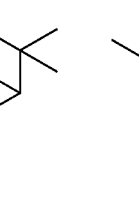 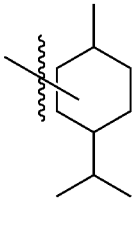

-continued

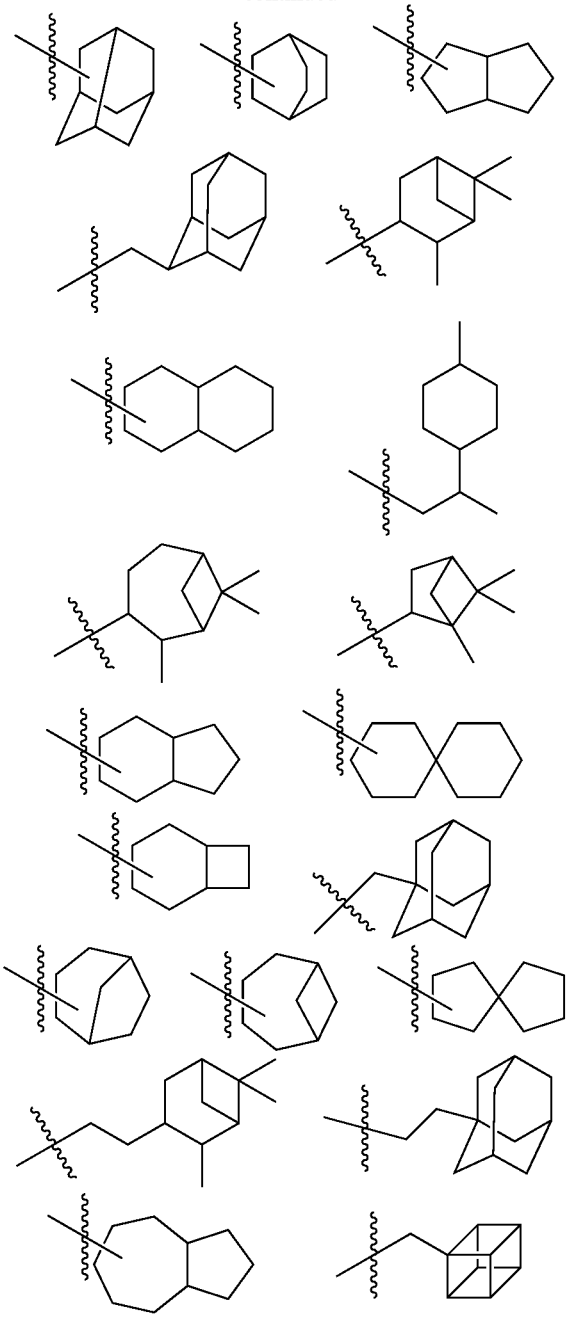

A $C_{1-20}$ alkyl group is an alkyl group containing one to twenty carbon atoms and may be linear, branched or a $C_{3-20}$ cycloalkyl group. Herein, a $C_{3-20}$ cycloalkyl group is a cycloalkyl group containing three to twenty carbon atoms and may have a fused polycyclic structure, a bridged cyclic structure or a spirocyclic structure. As specific examples of $C_{1-20}$ alkyl groups, in addition to those mentioned above, 1-methyl-1-ethyl-n-pentyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4,-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl, n-nonyl, n-undecyl, n-dodecyl, n-tridecyl, n-tetradecyl, n-pentadecyl, n-hexadecyl, n-heptadecyl, n-octadecyl, n-nonadecyl, n-icosanyl, c-heptyl, c-octyl, c-nonyl, c-decyl, c-undecyl, c-dodecyl, c-tridecyl, c-tetradecyl, c-pentadecyl, c-hexadecyl, c-heptadecyl, c-octadecyl, c-nonadecyl, c-icosanyl, the structures shown below and the like may be mentioned.

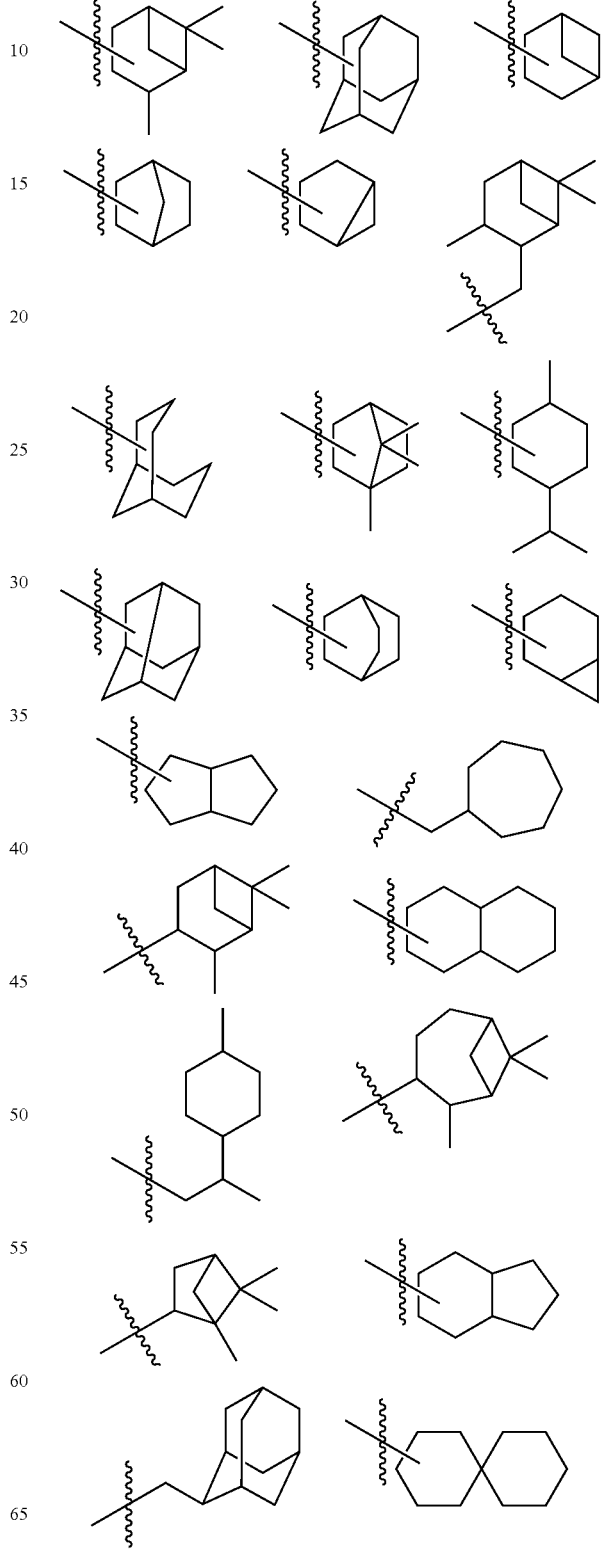

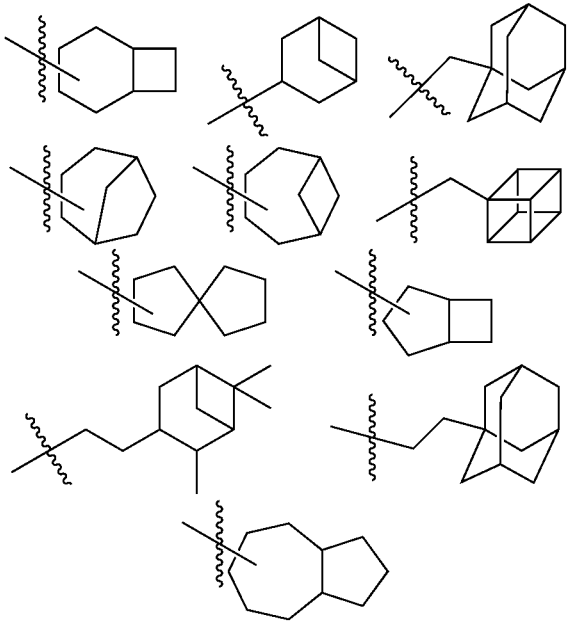

A $C_{2-6}$ alkenyl group means a group obtained by converting arbitrary one, two or three bonds in the above-mentioned $C_{1-6}$ alkyl group (other than a methyl group) to double bonds, and may be linear, branched or a $C_{3-6}$ cycloalkenyl group. As specific examples, ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl, 1-methyl-2-propenyl, 1-pentenyl, 2-pentenyl, 3-pentenyl, 4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, 1-c-pentenyl, 2-c-pentenyl, 3-c-pentenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-n-butylethenyl, 2-methyl-1-pentenyl, 2-methyl-2-pentenyl, 2-methyl-3-pentenyl, 2-methyl-4-pentenyl, 2-n-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-s-butylethenyl, 1,3-dimethyl-1-butenyl, 1,3-dimethyl-2-butenyl, 1,3-dimethyl-3-butenyl, 1-i-butylethenyl, 2,2-dimethyl-3-butenyl, 2,3-dimethyl-1-butenyl, 2,3-dimethyl-2-butenyl, 2,3-dimethyl-3-butenyl, 2-i-propyl-2-propenyl, 3,3-dimethyl-1-butenyl, 1-ethyl-1-butenyl, 1-ethyl-2-butenyl, 1-ethyl-3-butenyl, 1-n-propyl-1-propenyl, 1-n-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-s methyl-2-propenyl, 1-i-propyl-1-propenyl, 1-i-propyl-2-propenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl and the like may be mentioned.

A $C_{2-20}$ alkenyl group means a group obtained by converting arbitrary one, two or three bonds in the above-mentioned $C_{1-20}$ alkyl group (other than a methyl group) to double bonds, and may be linear, branched or a $C_{3-20}$ cycloalkenyl group. Herein, a $C_{3-20}$ cycloalkenyl group means a group obtained by converting arbitrary one, two or three bonds in the above-mentioned $C_{3-20}$ cycloalkyl group to double bonds and may have a fused polycyclic structure, a bridged cyclic structure or a spirocyclic structure. As specific examples of $C_{2-20}$ alkenyl groups, in addition to those mentioned above, 1-methyl-n-hexenyl, 1,2-dimethyl-n-hexenyl, 1-ethyl-n-hexenyl, 1-n-heptenyl, 2-n-heptenyl, 3-n-heptenyl, 4-n-heptenyl, 1-n-octenyl, 2-n-octenyl, 3-n-octenyl, 1-methyl-c-hexenyl, 1,2-dimethyl-c-hexenyl, 1-ethyl-c-hexenyl, 1-c-heptenyl, 2-c-heptenyl, 3-c-heptenyl, 4-c-heptenyl, 1-c-octenyl, 2-c-octenyl, 3-c-octenyl, 4-c-octenyl, 1-decenyl, 2-decenyl, 4-decenyl, 3,7-dimethyl-1-n-octenyl, 3,7-dimethyl-3-n-octenyl, 2-n-nonenyl, 3-n-undecenyl, 1-n-dodecenyl, 3-n-tridecenyl, 2-n-tetradecenyl, 4,6-n-pentadecadienyl, 2-n-nonadecenyl, 4-n-icosenyl, 2-c-nonenyl, 4-c-decenyl, 2-c-undecenyl, 5-c-dodecenyl, 3-c-tridecenyl, 6-c-tetradecenyl, 1-c-pentadecenyl, 5-c-hexadecenyl, 4-c-heptadecenyl, 1-c-octadecenyl, 3-c-nonadecenyl, 2-c-icosenyl, the structures shown below and the like may be mentioned.

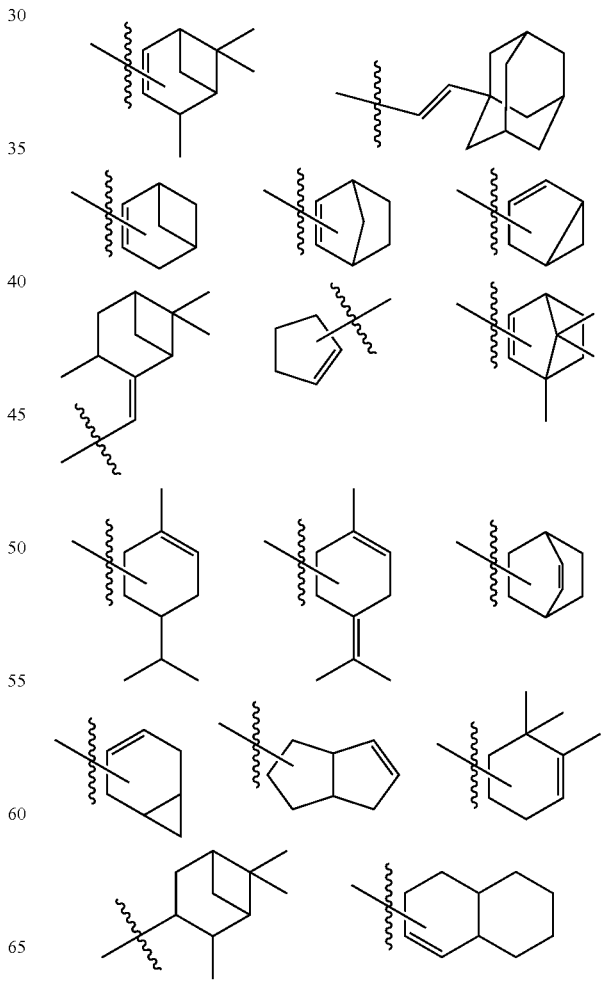

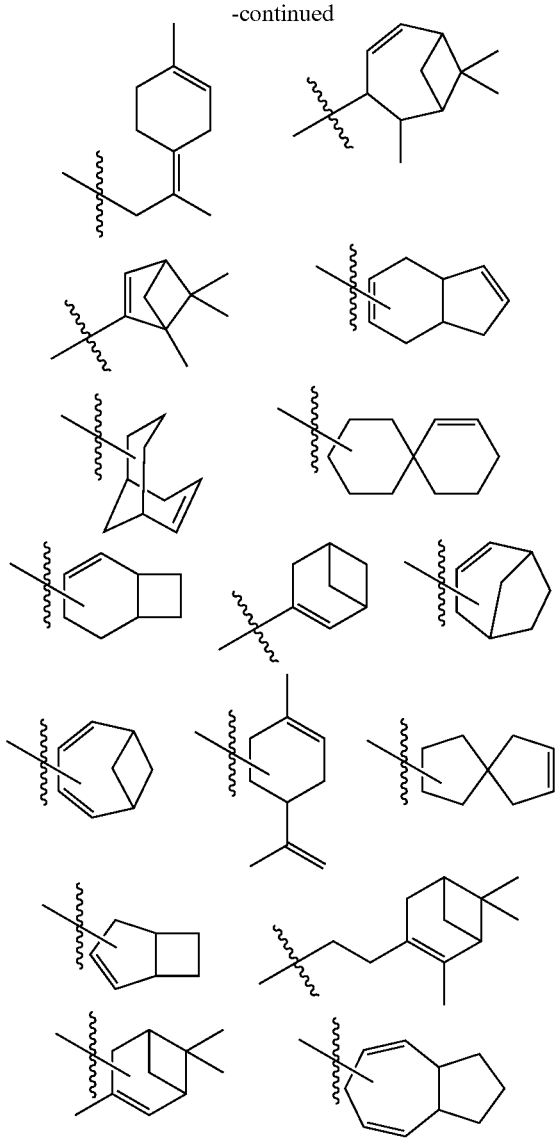

A C$_{3-12}$ cycloalkenyl group means a group obtained by converting arbitrary one, two or three bonds in the above-mentioned C$_{3-12}$ cycloalkyl group to double bonds and may have a fused polycyclic structure, a bridged cyclic structure or a spirocyclic structure. As specific examples, 1-c-pentenyl, 2-c-pentenyl, 3-c-pentenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl, 1-methyl-c-hexenyl, 1,2-dimethyl-c-hexenyl, 1-ethyl-c-hexenyl, 1-c-heptenyl, 2-c-heptenyl, 3-c-heptenyl, 4-c-heptenyl, 1-c-octenyl, 2-c-octenyl, 3-c-octenyl, 4-c-octenyl, 1-c-decenyl, 2-c-decenyl, 4-c-decenyl, 3,7-dimethyl-1-c-octenyl, 3,7-dimethyl-3-c-octenyl, 2-c-nonenyl, 3-c-undecenyl, 1-c-dodecenyl, 3-c-tridecenyl, 2-c-tetradecenyl, 4,6-c-pentadecadienyl, 2-c-hexadecenyl, 5-c-heptadecenyl, 1-c-octadecenyl, 2-c-nonadecenyl, 2-c-undecenyl, 5-c-dodecenyl, the structures shown below and the like may be mentioned.

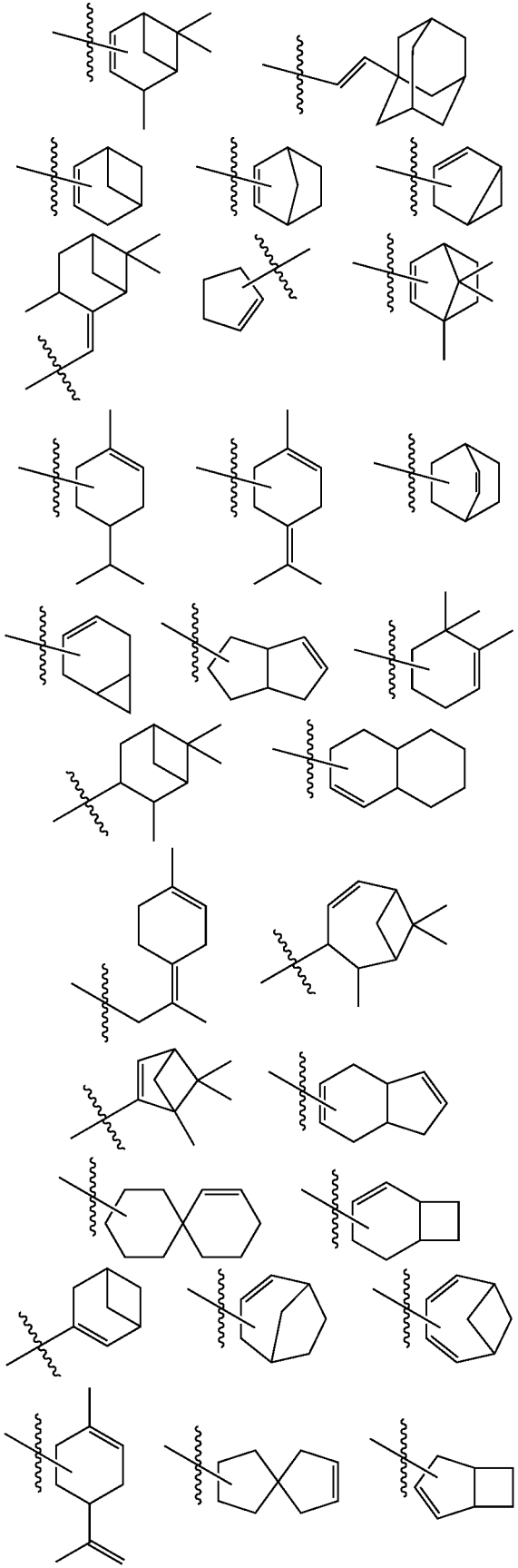

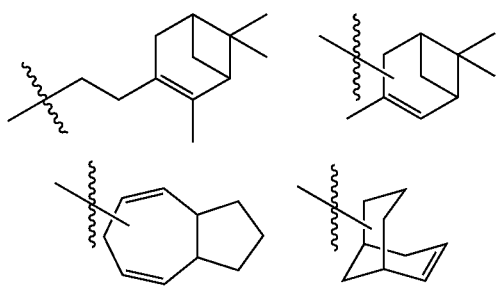

A C$_{7-12}$ cycloalkenyl group means a group obtained by converting arbitrary one, two or three bonds in the above-mentioned C$_{7-12}$ cycloalkyl group to double bonds and may have a fused polycyclic structure, a bridged cyclic structure or a spirocyclic structure. As specific examples, the structures shown below and the like may be mentioned.

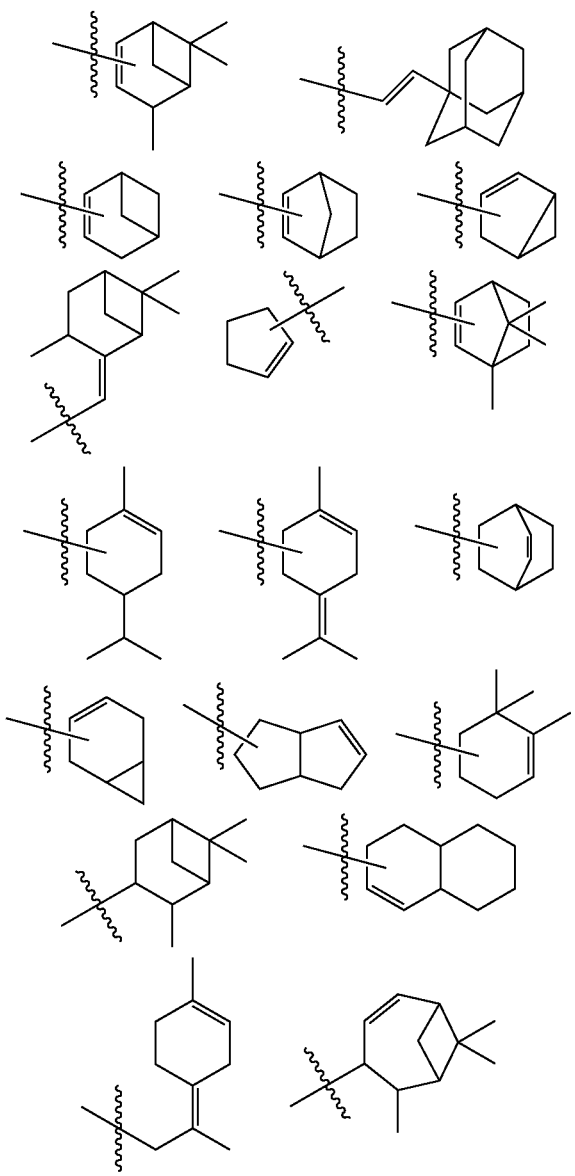

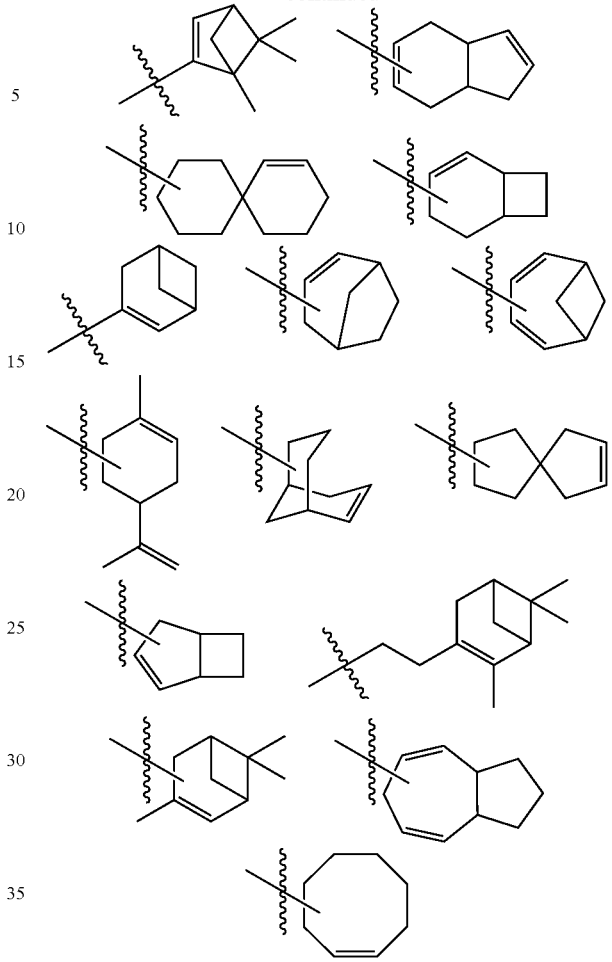

A C$_{2-6}$ alkynyl group means an alkynyl group containing two to six carbon atoms and may be linear, branched or a C$_6$ cycloalkynyl group. As specific examples, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 1-n-propyl-2-propynyl, 2-ethyl-3-butynyl, 1-methyl-1-ethyl-2-propynyl, 1-c-propyl-2-propynyl, 1-i-propyl-2-propynyl and the like may be mentioned.

A C$_{1-3}$ haloalkyl group is a C$_{1-3}$ alkyl group such as those mentioned above which is substituted with one or more halogen atoms such as fluorine atoms, chlorine atoms, bromine atoms and/or iodine atoms. As specific examples, a fluoromethyl group, a difluoromethyl group, a trifluoromethyl group, a chlorofluoromethyl group, a chlorodifluoromethyl group, a chloromethyl group, a dichloromethyl group, a trichloromethyl group, a bromomethyl group, a dibromomethyl group, a tribromomethyl group, a iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoro-n-propyl group, a 2,2-difluoro-n-propyl group, a 2,2,3,3,3-pentafluoro-n-propyl group, a perfluoro-i-propyl group, a 2-fluoro-i-propyl group, a 2,2,2,2,2,2-hexafluoro-i-propyl group, a 2,2-difluoro-c-propyl group, 2,2,3,3-tetrafluoro-c-propyl group and the like may be mentioned.

A $C_{1-6}$ alkoxy group may be linear, branched or a $C_{3-6}$ cycloalkoxy group. As specific examples, methoxy, ethoxy, n-propoxy, i-propoxy, c-propoxy, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-i-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy and the like may be mentioned.

A $C_{1-3}$ alkoxy group is an alkoxy group containing one to three carbon atoms and may be linear, branched or a $C_3$ cycloalkoxy group. As specific examples, methoxy, ethoxy, n-propoxy, i-propoxy, c-propoxy and the like may be mentioned.

A $C_{1-3}$ haloalkoxy group is a $C_{1-3}$ alkoxy group such as those mentioned above in which the alkoxy group is substituted with one or more halogen atoms such as fluorine atoms, chlorine atoms, bromine atoms and/or iodine atoms. As specific examples, a fluoromethoxy group, a difluoromethoxy group, a trifluoromethoxy group, a chlorofluoromethoxy group, a chlorodifluoromethoxy group, a chloromethoxy group, a dichloromethoxy group, a trichloromethoxy group, a bromomethoxy group, a dibromomethoxy group, a tribromomethoxy group, a iodomethoxy group, a diiodomethoxy group, a triiodomethoxy group, a fluoroethoxy group, a difluoroethoxy group, a trifluoroethoxy group, a tetrafluoroethoxy group, a pentafluoroethoxy group, a chloroethoxy group, a dichloroethoxy group, a trichloroethoxy group, a tetrachloroethoxy group, a pentachloroethoxy group, a bromoethoxy group, a dibromoethoxy group, a tribromoethoxy group, a tetrabromoethoxy group, a pentabromoethoxy group, a perfluoro-n-propoxy group, a 2,2-difluoro-n-propoxy group, a 2,2,3,3,3-pentafluoro-n-propoxy group, a perfluoro-i-propoxy group, a 2-fluoro-i-propoxy group, a 2,2,2,2,2,2-hexafluoro-i-propoxy group, a 2,2-difluoro-c-propoxy group, 2,2,3,3-tetrafluoro-c-propoxy group and the like may be mentioned.

A $C_{1-3}$ alkylene group is a linear, branched or cyclic alkylene group having one to three carbon atoms and may be, for example, a methylene group, an ethylene group, a to propylene group, an isopropylene group or a c-propylene group.

A $C_{1-6}$ alkylene group is a linear, branched or cyclic alkylene group having one to six carbon atoms and may be, for example, a methylene group, an ethylene group, a propylene group, an isopropylene group, a c-propylene group, an ethylpropylene group, a butylenes group, an isobutylene group, a c-butylene group, an ethylbutylene group, a pentylene group, a c-pentylene group, a hexylene group or a c-hexylene group.

A $C_{2-14}$ aryl group means a $C_{6-14}$ aryl group containing no hetero atoms as ring constituting atoms or a $C_{2-9}$ aromatic heterocyclic group.

A $C_{6-14}$ aryl group containing no hetero atoms is an aryl group containing six to fourteen carbon atoms, and as specific examples, a phenyl group, a 1-indenyl group, a 2-indenyl group, a 3-indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, a 6-tetrahydronaphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, 9-phenanthryl group and the like may be mentioned.

A $C_{2-9}$ aromatic heterocyclic group means a 5 to 7-membered $C_{2-6}$ heteromonocyclic group or a 8 to 10-membered $C_{5-9}$ fused heterobicyclic group containing from 1 to 3 oxygen atoms, nitrogen atoms or sulfur atoms singly or in combination, and, if contains one or more nitrogen atoms, may be in the form of an N-oxide.

As specific examples of 5 to 7-membered $C_{2-6}$ heteromonocyclic groups, 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group, 3-4H-1,2,4-triazolyl group, 3-1H-1,2,4-triazolyl group, 5-1H-1,2,4-triazolyl group, 4-2H-1,2,3-triazolyl group, 5-2H-1,2,3-triazolyl group, 4-1H-1,2,3-triazolyl group and 5-1H-1,2,3-triazolyl group and the like may be mentioned.

A 8 to 10-membered $C_{5-9}$ fused heterobicyclic group may be a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a benzothienyl group, a 4-benzothienyl group, a 5-benzothienyl group, a 6-benzothienyl group, a 7-benzothienyl group, a 1-isobenzothienyl group, a 4 isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, a 1-indazolyl group, a 2-indazolyl group, a 3-indazolyl group, a 4-indazolyl group, a 5-indazolyl group, a 6-indazolyl group, a 7-indazolyl group, a 2-(7-aza)indazolyl group, a 3-(7-aza)indazolyl group, a 4-(7-aza)indazolyl group, a 5-(7-aza)indazolyl group, a 6-(7-aza)indazolyl group, a 2-(4-aza)indazolyl group, a 3-(4-aza)indazolyl group, a 5-(4-aza)indazolyl group, a 6-(4-aza)indazolyl group, a 7-(4-aza)indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pteridinyl group, a 4-pteridinyl group, a 6-pteridinyl group, a 7-pteridinyl group or the like.

A $C_{2-9}$ heteroaryl group means a 5 to 7-membered $C_{2-6}$ heteromonocyclic group or a 8 to 10-membered $C_{5-9}$ fused heterobicyclic group containing from 1 to 3 oxygen atoms, nitrogen atoms or sulfur atoms singly or in combination, and, if contains one or more nitrogen atoms, may be in the form of an N-oxide.

As specific examples of 5 to 7-membered $C_{2-6}$ heteromonocyclic groups, 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group and the like may be mentioned.

As specific examples of 8 to 10-membered $C_{5-9}$ fused heterobicyclic groups, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, a 3-(7-aza)indazolyl group, a 4-(7-aza)indazolyl group, a 5-(7-aza)indazolyl group, a 6-(7-aza)indazolyl group, a 2-(4-aza)indazolyl group, a 3-(4-aza)indazolyl group, a 5-(4-aza)indazolyl group, a 6-(4-aza)indazolyl group, a 7-(4-aza)indazolyl group, a 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pteridinyl group, a 4-pteridinyl group, a 6-pteridinyl group, a 7-pteridinyl group and the like may be mentioned.

A $C_{2-14}$ arylene group is a bivalent group obtained by removing one hydrogen atom from a ring-constituting atom in the above-mentioned $C_{2-14}$ aryl group and may, for example, be a phenylene group, an indenylene group, a naphthylene group, a tetrahydronaphthylene group, a biphenylene group, a thienylene group, a furylene group, a pyranylene group, a pyrrolylene group, an imdazolylene group, a pyrazolylene group, a thiazolylene group, an isothiazolylene group, an oxazolylene group, a pyridylene group, a pyrazinylene group, a pyrimidinylene group, a pyridazinylene group, an oxadiazolylene group, a thiadiazolylene group, a triazolylene group, a benzofuranylene group, an isobenzofuranylene group, a benzothienylene group, an isobenzothienylene group, a chromenylene group, an indolizinylene group, an isoindolylene group, an indolylene group, an indazolylene group, a purinylene group, a quinolylene group, an isoquinolylene group, a phthalazinylene group, a naphthyridinylene group, a quinoxalinylene group, a quinazolinylene group, a cinnolinylene group, a pteridinylene group or the like.

A $C_{2-19}$ heterocyclyl group means a group derived from the above-mentioned $C_{3-20}$ cycloalkyl group or the above-mentioned $C_{3-20}$ cycloalkenyl groups by replacing one or more arbitrary carbon atoms with atoms arbitrarily selected from nitrogen atoms, oxygen atoms and sulfur atoms, and carbon atoms constituting the ring may be carbonyl or thiocarbonyl. As specific examples,

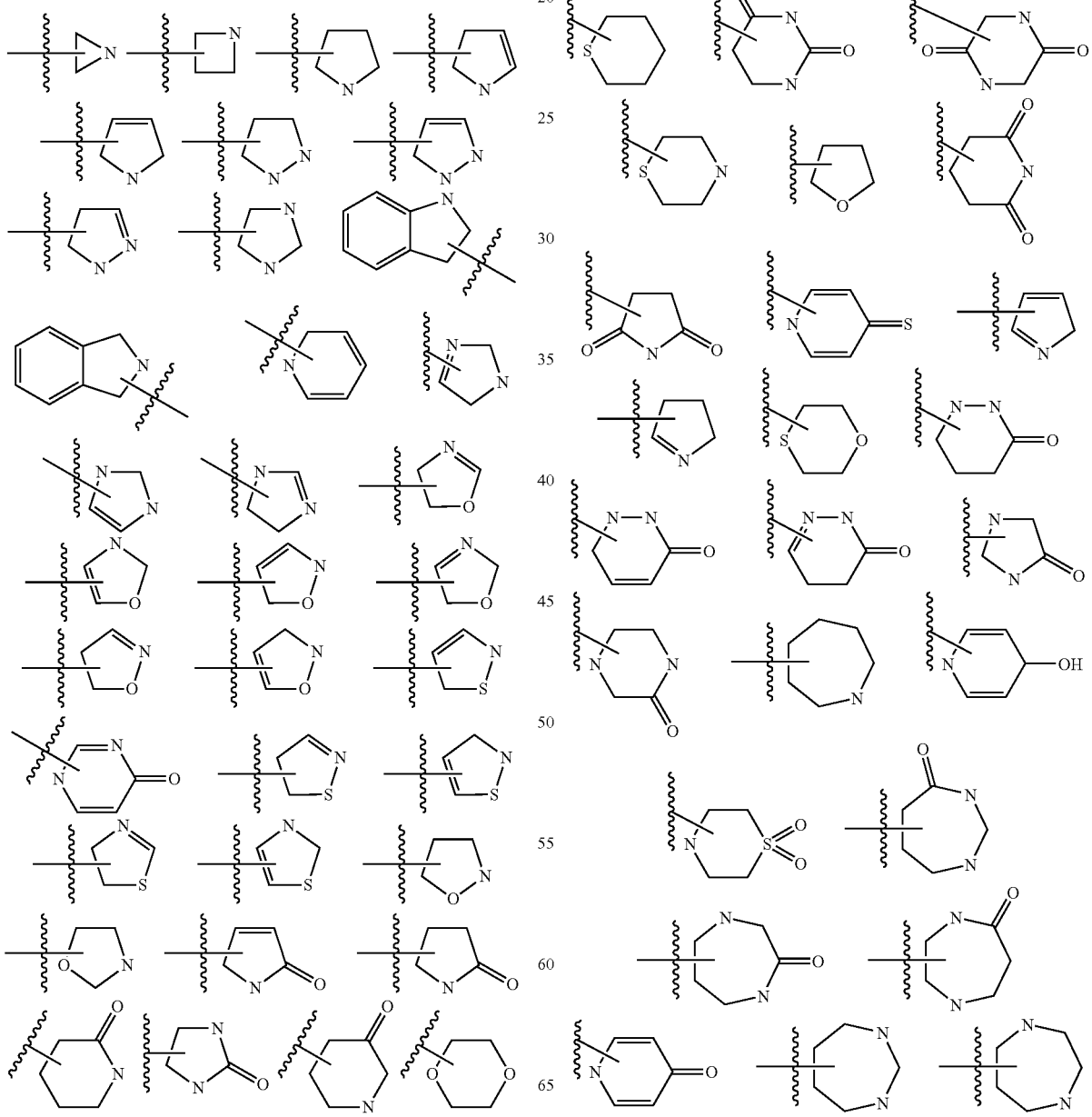

-continued

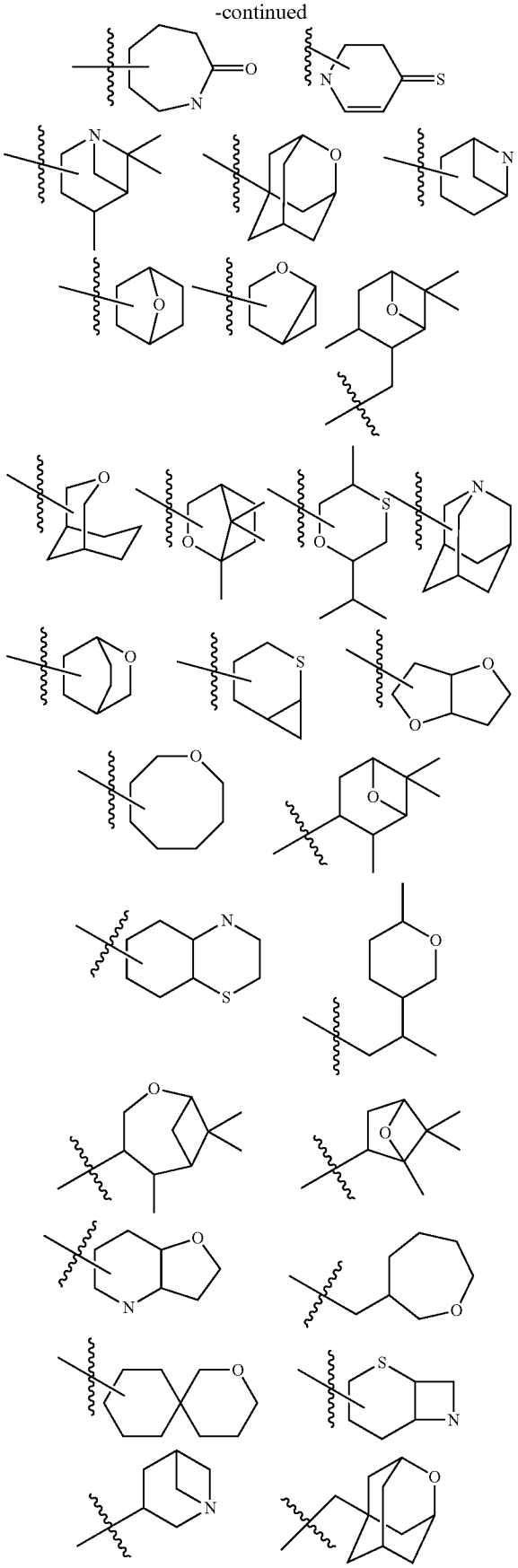
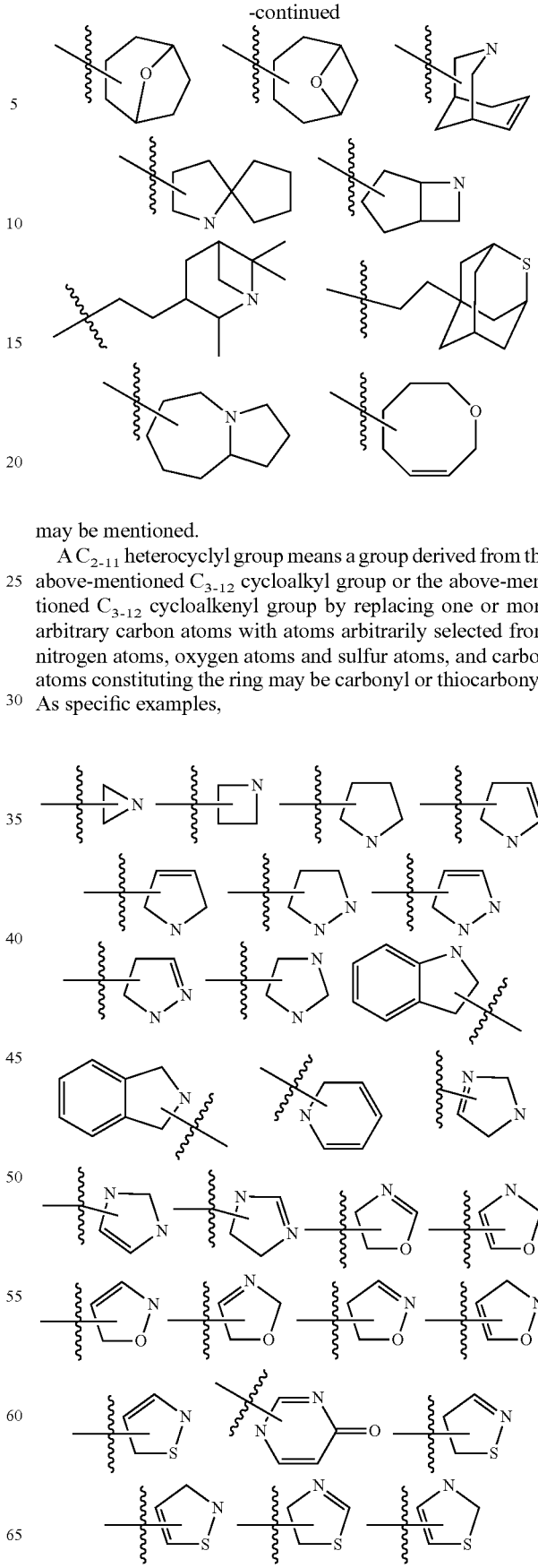

may be mentioned.

A $C_{2-11}$ heterocyclyl group means a group derived from the above-mentioned $C_{3-12}$ cycloalkyl group or the above-mentioned $C_{3-12}$ cycloalkenyl group by replacing one or more arbitrary carbon atoms with atoms arbitrarily selected from nitrogen atoms, oxygen atoms and sulfur atoms, and carbon atoms constituting the ring may be carbonyl or thiocarbonyl. As specific examples,

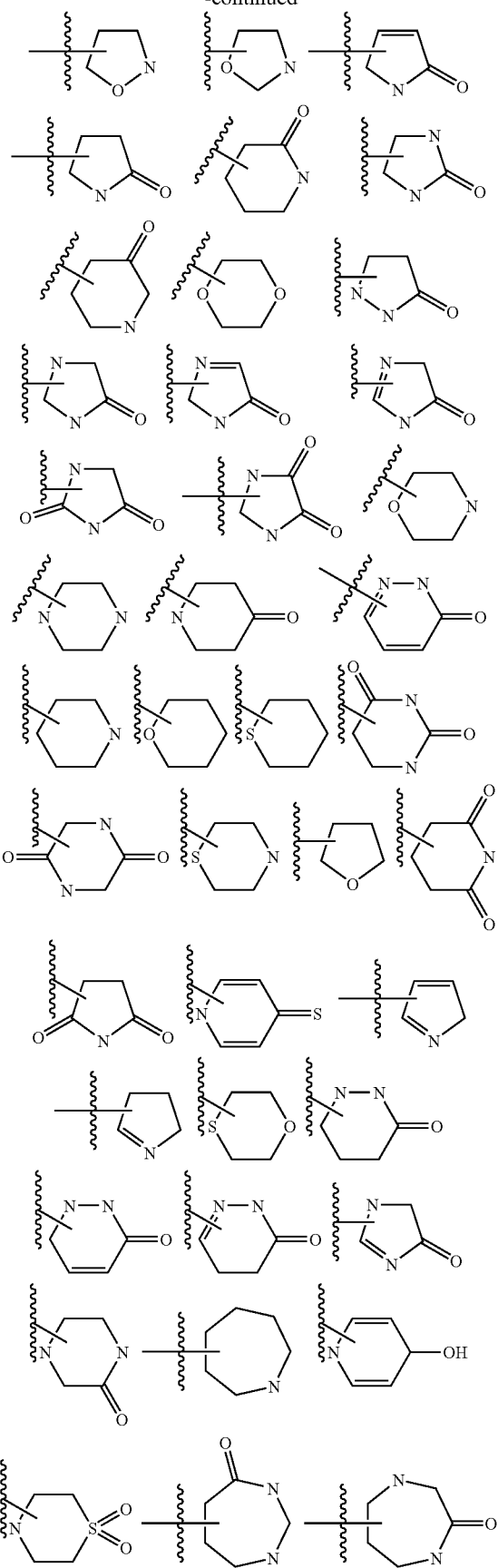
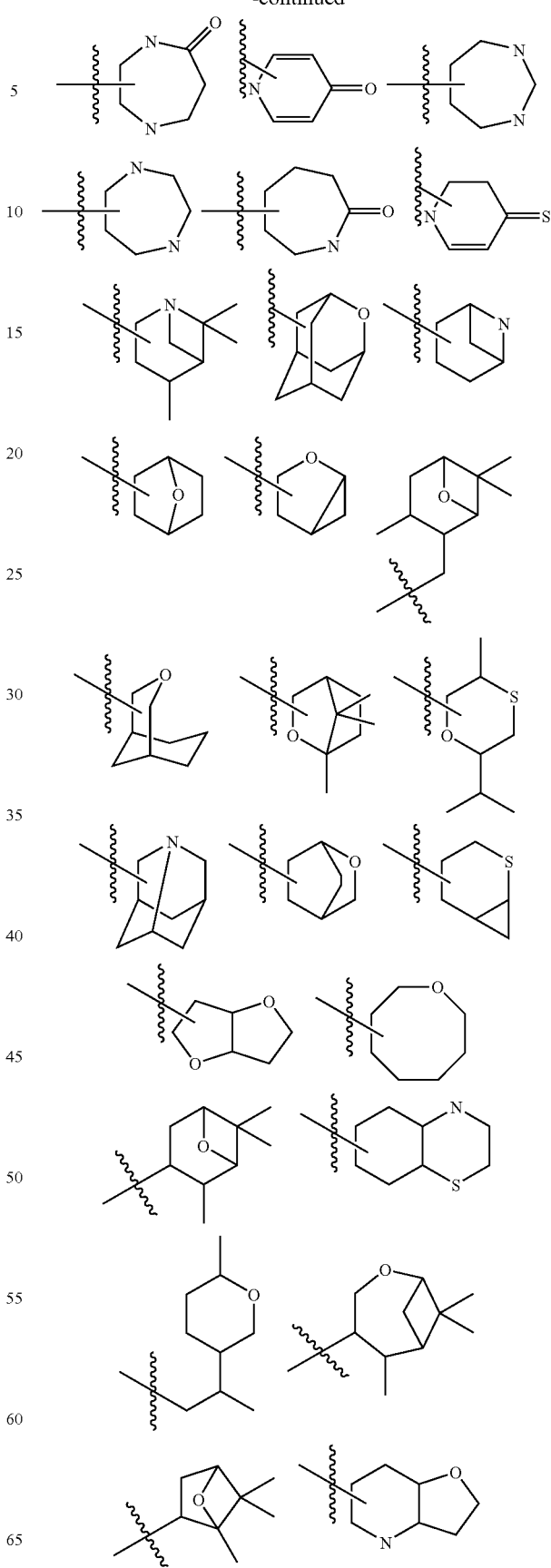

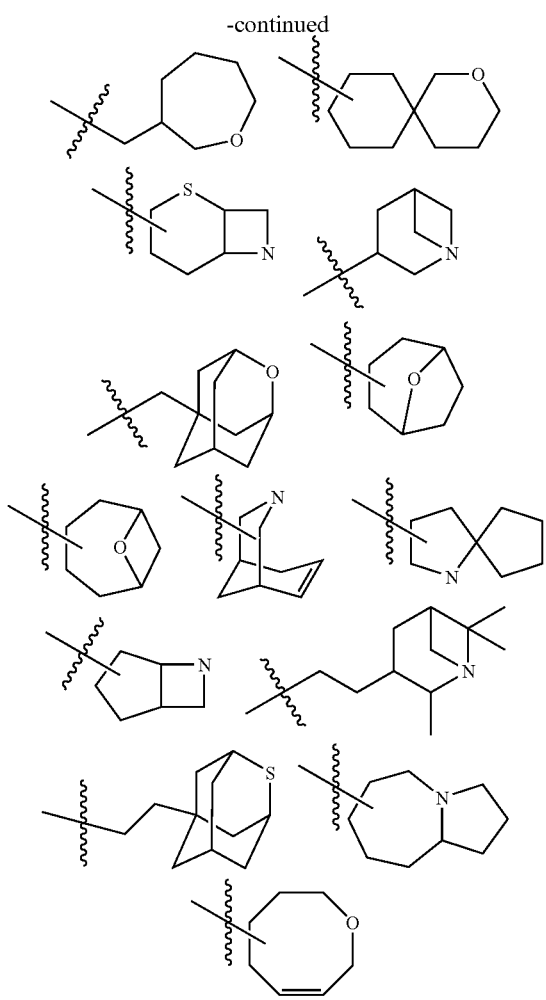
may be mentioned.
A C$_{2-9}$ heterocyclyl group is a heteromonocyclic or heterobicyclic group consisting of at least one atom arbitrarily selected from nitrogen atoms, oxygen atoms and sulfur atoms and two to nine carbon atoms, and carbon atoms constituting the ring may be carbonyl or thiocarbonyl. As specific examples,
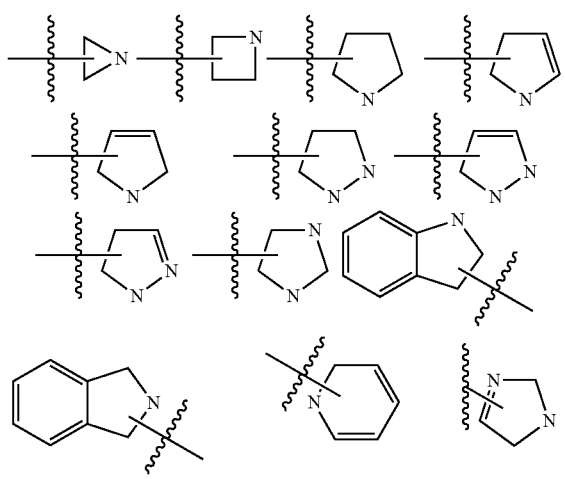
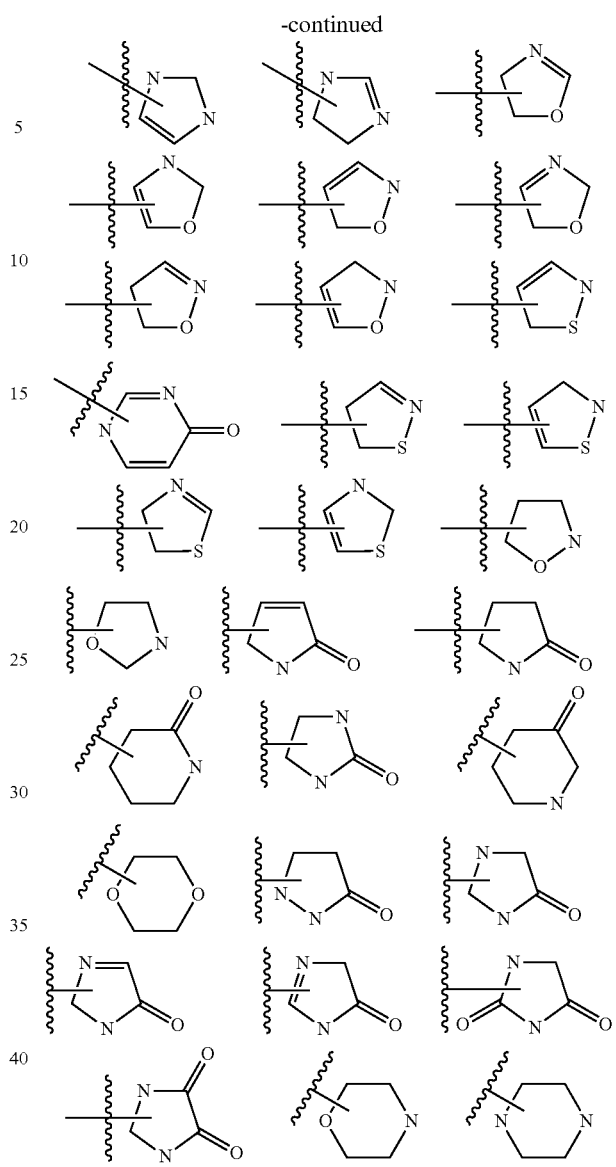
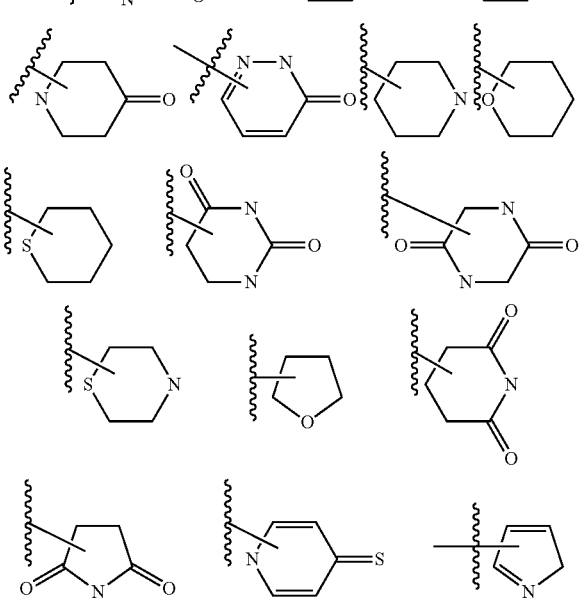

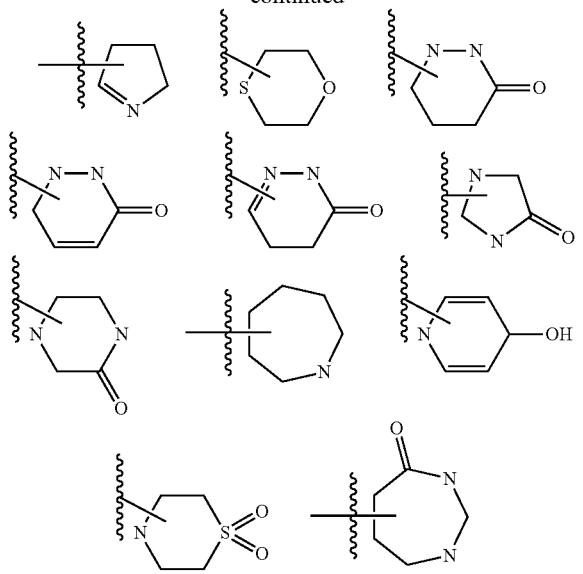
may be mentioned.
A $C_{2-9}$ heterocyclylene group is a bivalent group obtained by removing one hydrogen atom from a ring-constituting atom in the above-mentioned $C_{2-9}$ heterocyclyl group and, for example,
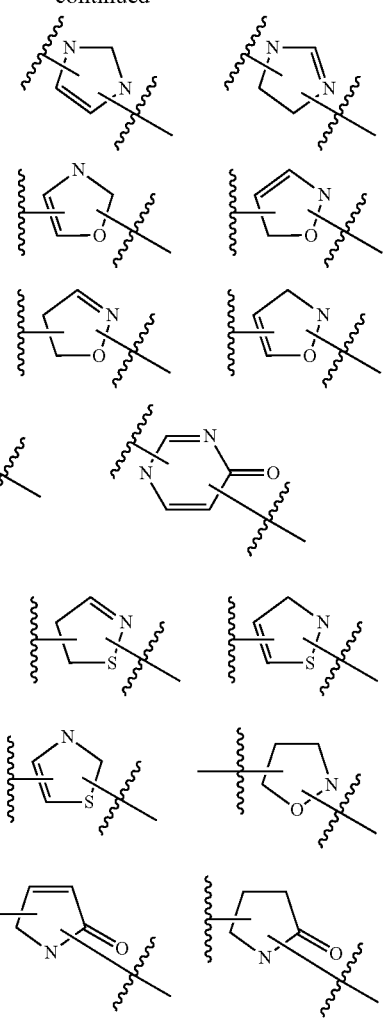
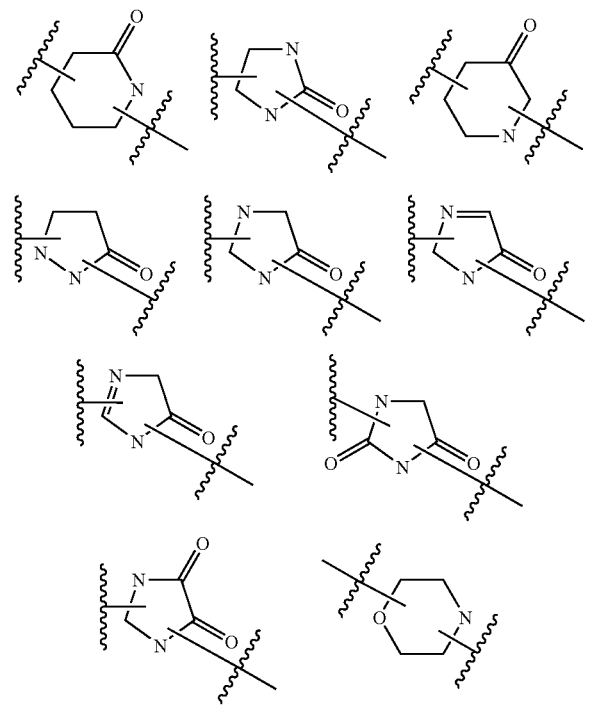

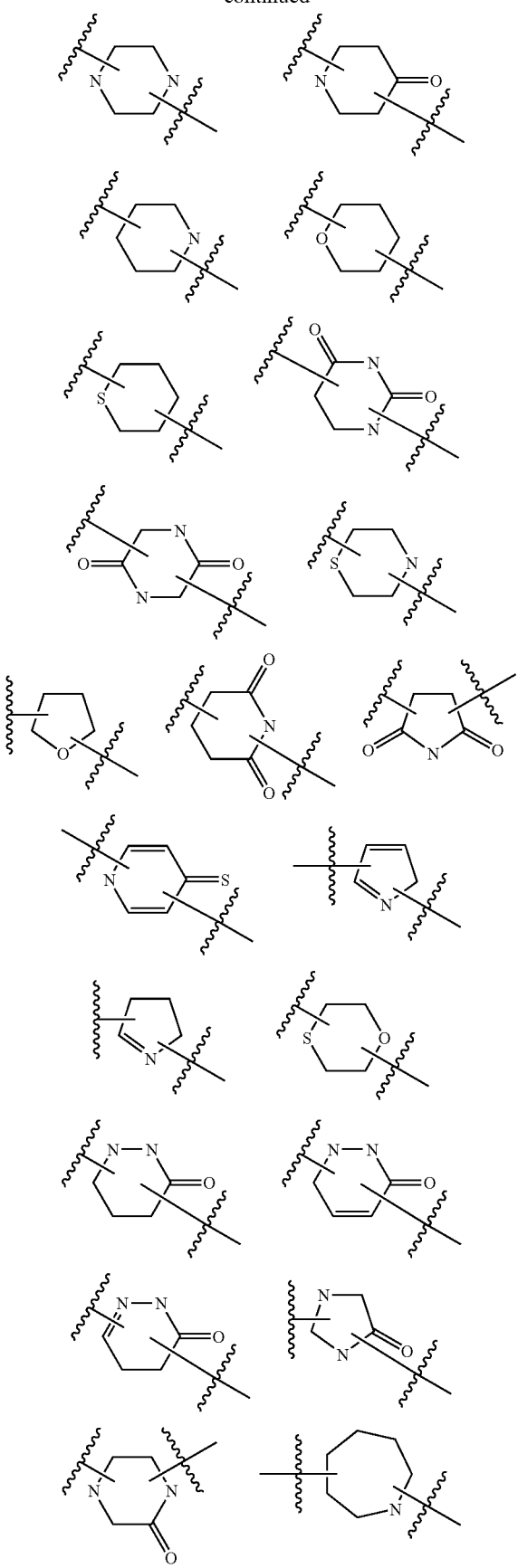
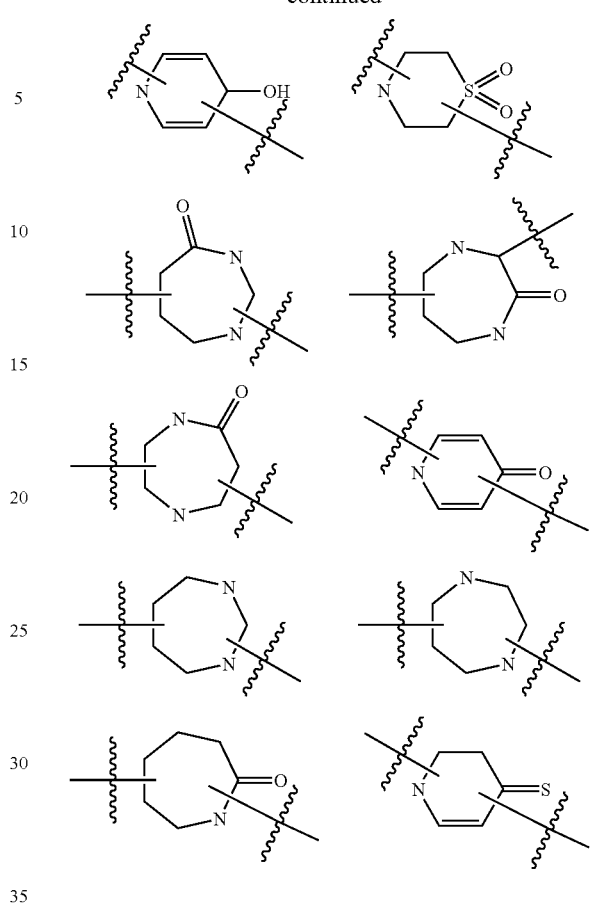

may be mentioned.

A nitrogen-containing heterocyclyl group is a heteromonocyclic or heterobicyclic group containing at least one nitrogen atom and two to nine carbon atoms which may further contain at least one atoms arbitrary selected from oxygen atoms and sulfur atoms, and carbon atoms constituting the ring may be carbonyl or thiocarbonyl. As specific examples,

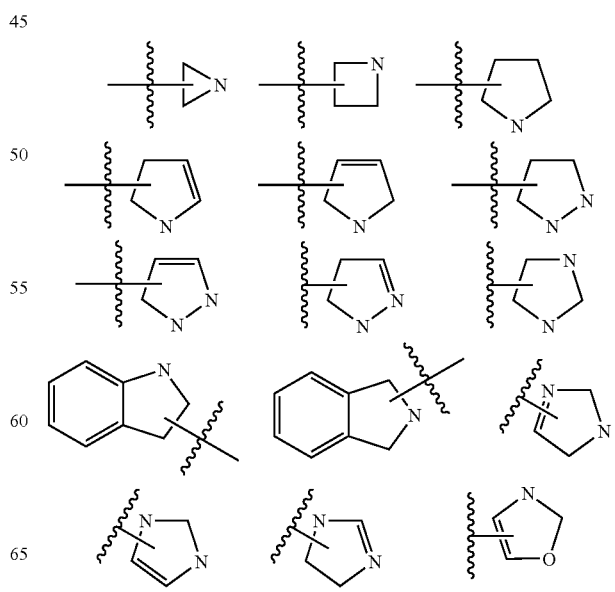

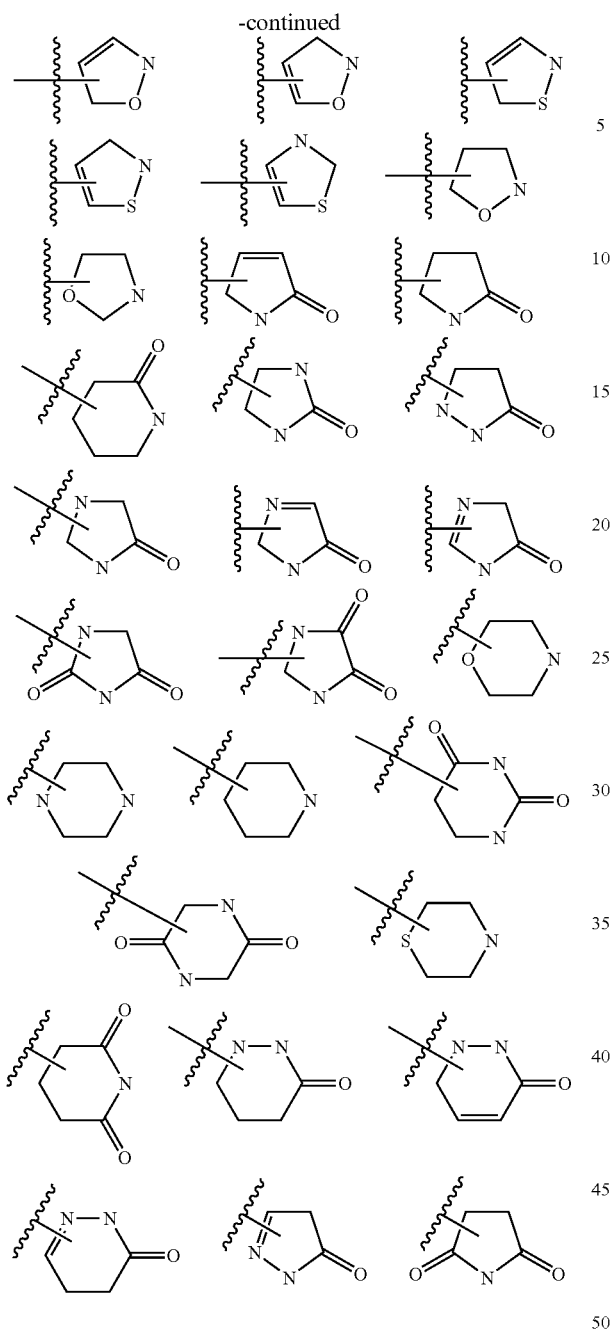

may be mentioned.

A fused $C_{2-14}$ aryl group is a fused bicyclic or tricyclic group consisting of the above-mentioned $C_{2-14}$ aryl group fused with the above-mentioned $C_{2-9}$ heterocyclyl group or the above-mentioned $C_{3-6}$ cycloalkyl group, and as specific examples,

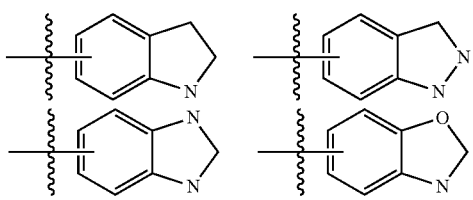

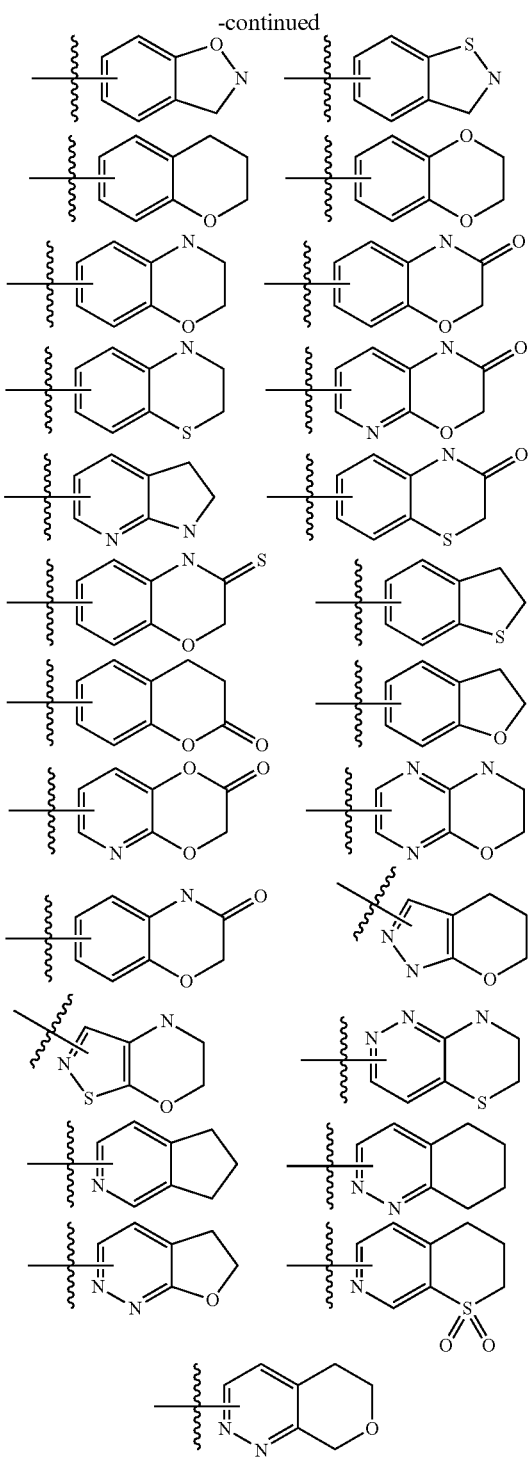

may be mentioned.

A $C_{2-14}$ aryloxy group may be a $C_{6-14}$ aryloxy group containing no hetero atoms as ring constituting atoms or a $C_{2-9}$ aromatic heterocyclyloxy group, and a $C_{2-9}$ aromatic heterocyclyloxy group may be a 5 to 7-membered $C_{2-6}$ heteromonocyclyloxy group or a 8 to 10-membered $C_{5-9}$ fused heterobicyclyloxy group containing from 1 to 3 oxygen atoms, nitrogen atoms or sulfur atoms singly or in combination.

As a $C_{6-14}$ aryloxy group containing no hetero atoms, a phenyloxy group, a 1-indenyloxy group, a 2-indenyloxy group, a 3-indenyloxy group, a 4-indenyloxy group, a 5-indenyloxy group, a 6-indenyloxy group, a 7-indenyloxy group, an α-naphthyloxy group, a β-naphthyloxy group, a 1-tetrahydronaphthyloxy group, a 2-tetrahydronaphthyloxy group, a 5-tetrahydronaphthyloxy group, a 6-tetrahydronaphthyloxy group, an o-biphenylyloxy group, a m-biphenylyloxy group, a p-biphenylyloxy group, a 1-anthryloxy group, a 2-anthryloxy group, a 9-anthryloxy group, a 1-phenanthryloxy group, a 2-phenanthryloxy group, a 3-phenanthryloxy group, a 4-phenanthryloxy group, a 9-phenanthryloxy group or the like may be mentioned.

A 5 to 7-membered $C_{2-6}$ heteromonocyclyloxy group may be a 2-thienyloxy group, a 3-thienyloxy group, a 2-furyloxy group, a 3-furyloxy group, a 2-pyranyloxy group, a 3-pyranyloxy group, a 4-pyranyloxy group, a 1-pyrrolyloxy group, a 2-pyrrolyloxy group, a 3-pyrrolyloxy group, a 1-imidazolyloxy group, a 2-imidazolyloxy group, a 4-imidazolyloxy group, a 1-pyrazolyloxy group, a 3-pyrazolyloxy group, a 4-pyrazolyloxy group, a 2-thiazolyloxy group, a 4-thiazolyloxy group, a 5-s thiazolyloxy group, a 3-isothiazolyloxy group, a 4-isothiazolyloxy group, a 5-isothiazolyloxy group, a 2-oxazolyloxy group, a 4-oxazolyloxy group, a 5-oxazolyloxy group, a 3-isoxazolyloxy group, a 4-isoxazolyloxy group, a 5-isoxazolyloxy group, a 2-pyridyloxy group, a 3-pyridyloxy group, a 4-pyridyloxy group, a 2-pyrazinyloxy group, a 2-pyrimidinyloxy group, a 4-pyrimidinyloxy group, a 5-pyrimidinyloxy group, a 3-pyridazinyloxy group, a 4-pyridazinyloxy group, a 2-1,3,4-oxadiazolyloxy group, a 2-1,3,4-thiadiazolyloxy group, a 3-1,2,4-oxadiazolyloxy group, a 5-1,2,4-oxadiazolyloxy group, a 3-1,2,4-thiadiazolyloxy group, a 5-1,2,4-thiadiazolyloxy group, a 3-1,2,5-oxadiazolyloxy group, a 3-1,2,5-thiadiazolyloxy group or the like.

A 8 to 10-membered $C_{5-9}$ fused heterobicyclyloxy group may be a 2-benzofuranyloxy group, a 3-benzofuranyloxy group, a 4-benzofuranyloxy group, a 5-benzofuranyloxy group, a 6-benzofuranyloxy group, a 7-benzofuranyloxy group, a 1-isobenzofuranyloxy group, a 4-isobenzofuranyloxy group, a 5-isobenzofuranyloxy group, a 2-benzothienyloxy group, a 3-benzothienyloxy group, a 4-benzothienyloxy group, a 5-benzothienyloxy group, a 6-benzothienyloxy group, a 7-benzothienyloxy group, a 1-isobenzothienyloxy group, a 4-isobenzothienyloxy group, 5-isobenzothienyloxy group, a 2-chromenyloxy group, a 3-chromenyloxy group, a 4-chromenyloxy group, a 5-chromenyloxy group, a 6-chromenyloxy group, a 7-chromenyloxy group, a 8-chromenyloxy group, a 1-indolizinyloxy group, a 2-indolizinyloxy group, a 3-indolizinyloxy group, a 5-indolizinyloxy group, a 6-indolizinyloxy group, a 7-indolizinyloxy group, a 8-indolizinyloxy group, a 1-isoindolyloxy group, a 2-isoindolyloxy group, a 4-isoindolyloxy group, a 5-isoindolyloxy group, a 1-indolyloxy group, a 2-indolyloxy group, a 3-indolyloxy group, a 4-indolyloxy group, a 5-indolyloxy group, a 6-indolyloxy group, a 7-indolyloxy group, a 1-indazolyloxy group, a 2-indazolyloxy group, a 3-indazolyloxy group, a 4-indazolyloxy group, a 5-indazolyloxy group, a 6-indazolyloxy group, a 7-indazolyloxy group, a 1-purinyloxy group, a 2-purinyloxy group, a 3-purinyloxy group, a 6-purinyloxy group, a 7-purinyloxy group, a 8-purinyloxy group, a 2-quinolyloxy group, a 3-quinolyloxy group, a 4-quinolyloxy group, a 5-quinolyloxy group, a 6-quinolyloxy group, a 7-quinolyloxy group, a 8-quinolyloxy group, a 1-isoquinolyloxy group, a 3-isoquinolyloxy group, a 4-isoquinolyloxy group, a 5-isoquinolyloxy group, a 6-isoquinolyloxy group, a 7-isoquinolyloxy group, a 8-isoquinolyloxy group, a 1-phthalazinyloxy group, a 5-phthalazinyloxy group, a 6-phthalazinyloxy group, a 1-2,7-naphthyridinyloxy group, a 3-2,7-naphthyridinyloxy group, a 4-2,7-naphthyridinyloxy group, a 1-2,6-naphthyridinyloxy group, a 3-2,6-naphthyridinyloxy group, a 4-2,6-naphthyridinyloxy group, a 2-1,8-naphthyridinyloxy group, a 3-1,8-naphthyridinyloxy group, a 4-1,8-naphthyridinyloxy group, a 2-1,7-naphthyridinyloxy group, a 3-1,7-naphthyridinyloxy group, a 4-1,7-naphthyridinyloxy group, a 5-1,7-naphthyridinyloxy group, a 6-1,7-naphthyridinyloxy group, a 8-1,7-naphthyridinyloxy group, 2-1,6-naphthyridinyloxy group, a 3-1,6-naphthyridinyloxy group, a 4-1,6-naphthyridinyloxy group, a 5-1,6-naphthyridinyloxy group, a 7-1,6-naphthyridinyloxy group, a 8-1,6-naphthyridinyloxy group, a 2-1,5-naphthyridinyloxy group, a 3-1,5-naphthyridinyloxy group, a 4-1,5-naphthyridinyloxy group, a 6-1,5-naphthyridinyloxy group, a 7-1,5-naphthyridinyloxy group, a 8-1,5-naphthyridinyloxy group, a 2-quinoxalinyloxy group, a 5-quinoxalinyloxy group, a 6-quinoxalinyloxy group, a 2-quinazolinyloxy group, a 4-quinazolinyloxy group, a 5-quinazolinyloxy group, a 6-quinazolinyloxy group, a 7-quinazolinyloxy group, a 8-quinazolinyloxy group, a 3-cinnolinyloxy group, a 4-cinnolinyloxy group, a 5-cinnolinyloxy group, a 6-cinnolinyloxy group, a 7-cinnolinyloxy group, a 8-cinnolinyloxy group, a 2-pteridinyloxy group, a 4-pteridinyloxy group, a 6-pteridinyloxy group, a 7-pteridinyloxy group or the like.

A $C_{1-6}$ monoalkylamino group is an amino group containing one $C_{1-6}$ alkyl group and may be linear, branched or $C_{3-6}$ cycloalkylamino group, and as specific examples, methylamino, ethylamino, n-propylamino, propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-c-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino, 2-ethyl-3-methyl-c-propylamino or the like may be mentioned.

A $C_{1-6}$ dialkylamino group is an amino group having two $C_{1-6}$ alkyl groups and may be symmetric or asymmetric. A symmetric $C_{1-6}$ dialkylamino group may be linear, branched or a $C_{3-6}$ cycloalkylamino group, and as specific examples, dimethylamino, diethylamino, di-n-propylamino, di-i-propylamino, di-c-propylamino, di-n-butylamino, di-i-butylamino, di-s-butylamino, di-t-butylamino, di-c-butylamino, di-(1-methyl-c-propyl)amino, di-(2-methyl-c-propyl)amino, di-n-pentylamino, di-(1-methyl-n-butyl)amino, di-(2-methyl-n-butyl)amino, di-(3-methyl-n-butyl)amino, di-(1,1-dimethyl-n-propyl)amino, di-(1,2-dimethyl-n-propyl)amino, di-(2,2- dimethyl-n-propyl)amino, di-(1-ethyl-n-propyl)amino, di-c-pentylamino, di-(1-methyl-c-butyl)amino, di-(2-methyl-c-butyl)amino, di-(3-methyl-c-butyl)amino, di-(1,2-dimethyl-c-propyl)amino, di-(2,3-dimethyl-c-propyl)amino, di-(1-ethyl-c-propyl)amino, di-(2-ethyl-c-propyl)amino, di-n-hexylamino, di-(1-methyl-n-pentyl)amino, di-(2-methyl-n-pentyl)amino, di-(3-methyl-n-pentyl)amino, di-(4-methyl-n-pentyl)amino, di-(1,1-dimethyl-n-butyl)amino, di-(1,2-dimethyl-n-butyl)amino, di-(1,3-dimethyl-n-butyl)amino, di-(2,2-dimethyl-n-butyl)amino, di-(2,3-dimethyl-n-butyl)amino, di-(3,3-dimethyl-n-butyl)amino, di-(1-ethyl-n-butyl)amino, di-(2-ethyl-n-butyl)amino, di-(1,1,2-trimethyl-n-propyl)amino, di-(1,2,2-trimethyl-n-propyl)amino, di-(1-ethyl-1-methyl-n-propyl)amino, di-(1-ethyl-2-methyl-n-propyl)amino, di-c-hexylamino, di-(1-methyl-c-pentyl)amino, di-(2-methyl-c-pentyl)amino, di-(3-methyl-c-pentyl)amino, di-(1-ethyl-c-butyl)amino, di-(2-ethyl-c-butyl)amino, di-(3-ethyl-c-butyl)amino, di-(1,2-dimethyl-c-butyl)amino, di-(1,3-dimethyl-c-butyl)amino, di-(2,2-dimethyl-c-butyl)amino, di-(2,3-dimethyl-c-butyl)amino, di-(2,4-dimethyl-c-butyl)amino, di-(3,3-dimethyl-c-butyl)amino, di-(1-n-propyl-c-propyl)amino, di-(2-n-propyl-c-propyl)amino, di-(1-i-propyl-c-propyl)amino, di-(2-i-propyl-c-propyl)amino, di-(1,2,2-trimethyl-c-propyl)amino, di-(1,2,3-trimethyl-c-propyl)amino, di-(1-ethyl-2-methyl-c-propyl)amino, di-(2,2,3-trimethyl-c-propyl)amino, di-(2-ethyl-1-methyl-c-propyl)amino, di-(2-ethyl-2-methyl-c-propyl)amino, di-(2-ethyl-3-methyl-c-propyl)amino and the like may be mentioned.

An asymmetric $C_{1-6}$ dialkylamino group may be linear, branched or a $C_{3-6}$ cycloalkylamino group, and as specific examples, (methyl, ethyl)amino, (methyl, n-propyl)amino, (methyl, i-propyl)amino, (methyl, c-propyl)amino, (methyl, n-butyl)amino, (methyl, i-butyl)amino, (methyl, s-butyl)amino, (methyl, t-butyl)amino, (methyl, n-pentyl)amino, (methyl, c-pentyl)amino, (methyl, n-hexyl)amino, (methyl, c-hexyl)amino, (ethyl, n-propyl)amino, (ethyl, i-propyl)amino, (ethyl, c-propyl)amino, (ethyl, n-butyl)amino, (ethyl, i-butyl)amino, (ethyl, s-butyl)amino, (ethyl, t-butyl)amino, (ethyl, n-pentyl)amino, (ethyl, c-pentyl)amino, (ethyl, n-hexyl)amino, (ethyl, c-hexyl)amino, (n-propyl, i-propyl)amino, (n-propyl, c-propyl)amino, (n-propyl, n-butyl)amino, (n-propyl, i-butyl)amino, (n-propyl, s-butyl)amino, (n-propyl, t-butyl)amino, (n-propyl, n-pentyl)amino, (n-propyl, c-pentyl)amino, (n-propyl, n-hexyl)amino, (n-propyl, c-hexyl)amino, (i-propyl, c-propyl)amino, (i-propyl, n-butyl)amino, (i-propyl, i-butyl)amino, (i-propyl, s-butyl)amino, (i-propyl, t-butyl)amino, (i-propyl, n-pentyl)amino, (i-propyl, c-pentyl)amino, (i-propyl, n-hexyl)amino, (i-propyl, c-hexyl)amino, (c-propyl, n-butyl)amino, (c-propyl, i-butyl)amino, (c-propyl, s-butyl)amino, (c-propyl, t-butyl)amino, (c-propyl, n-pentyl)amino, (c-propyl, c-pentyl)amino, (c-propyl, n-hexyl)amino, (c-propyl, c-hexyl)amino, (n-butyl, i-butyl)amino, (n-butyl, s-butyl)amino, (n-butyl, t-butyl)amino, (n-butyl, n-pentyl)amino, (n-butyl, c-pentyl)amino, (n-butyl, n-hexyl)amino, (n-butyl, c-hexyl)amino, (i-butyl, s-butyl)amino, (i-butyl, t-butyl)amino, (i-butyl, n-pentyl)amino, (i-butyl, c-pentyl)amino, (i-butyl, n-hexyl)amino, (i-butyl, c-hexyl)amino, (s-butyl, t-butyl)amino, (s-butyl, n-pentyl)amino, (s-butyl, c-pentyl)amino, (s-butyl, n-hexyl)amino, (s-butyl, c-hexyl)amino, (t-butyl, n-pentyl)amino, (t-butyl, c-pentyl)amino, (t-butyl, n-hexyl)amino, (t-butyl, c-hexyl)amino, (n-pentyl, c-pentyl)amino, (n-pentyl, n-hexyl)amino, (n-pentyl, c-hexyl)amino, (c-pentyl, n-hexyl)amino, (c-pentyl, c-hexyl)amino, (n-hexyl, c-hexyl)amino and the like may be mentioned.

A $C_{1-6}$ alkylthio group is a thio group having a $C_{1-6}$ alkyl group and may be linear, branched or a $C_{3-6}$ cycloalkylthio group. As specific examples, methylthio, ethylthio, n-propylthio, i-propylthio, c-propylthio, n-butylthio, i-butylthio, s-butylthio, t-butylthio, c-butylthio, 1-methyl-c-propylthio, 2-methyl-c-propylthio, n-pentylthio, 1-methyl-n-butylthio, 2-methyl-n-butylthio, 3-methyl-n-butylthio, 1,1-dimethyl-n-propylthio, 1,2-dimethyl-n-propylthio, 2,2-dimethyl-n-propylthio, 1-ethyl-n-propylthio, c-pentylthio, 1-methyl-c-butylthio, 2-methyl-c-butylthio, 3-methyl-c-butylthio, 1,2-dimethyl-c-propylthio, 2,3-dimethyl-c-propylthio, 1-ethyl-c-propylthio, 2-ethyl-c-propylthio, n-hexylthio, 1-methyl-n-pentylthio, 2-methyl-n-pentylthio, 3-methyl-n-pentylthio, 4-methyl-n-pentylthio, 1,1-dimethyl-n-butylthio, 1,2-dimethyl-n-butylthio, 1,3-dimethyl-n-butylthio, 2,2-dimethyl-n-butylthio, 2,3-dimethyl-n-butylthio, 3,3-dimethyl-n-butylthio, 1-ethyl-n-butylthio, 2-ethyl-n-butylthio, 1,1,2-trimethyl-n-propylthio, 1,2,2-trimethyl-n-propylthio, 1-ethyl-1-methyl-n-propylthio, 1-ethyl-2-methyl-n-propylthio, c-hexylthio, 1-methyl-c-pentylthio, 2-methyl-c-pentylthio, 3-methyl-c-pentylthio, 1-ethyl-c-butylthio, 2-ethyl-c-butylthio, 3-ethyl-c-butylthio, 1,2-dimethyl-c-butylthio, 1,3-dimethyl-c-butylthio, 2,2-dimethyl-c-butylthio, 2,3-dimethyl-c-butylthio, 2,4-dimethyl-c-butylthio, 3,3-dimethyl-c-butylthio, 1-n-propyl-c-propylthio, 2-n-propyl-c-propylthio, 1-i-propyl-c-propylthio, 2-i-propyl-c-propylthio, 1,2,2-trimethyl-c-propylthio, 1,2,3-trimethyl-c-propylthio, 2,2,3-trimethyl-c-propylthio, 1-ethyl-2-methyl-c-propylthio, 2-ethyl-1-methyl-c-propylthio, 2-ethyl-2-methyl-c-propylthio, 2-ethyl-3-methyl-c-propylthio and the like may be mentioned.

A $C_{1-3}$ alkylthio group is an alkylthio group containing one to three carbon atoms and may be linear, branched or a $C_3$ cycloalkyl group, and as specific examples, methylthio, ethylthio, n-propylthio, propylthio, c-propylthio and the like may be mentioned.

A $C_{1-6}$ alkylsulfonyl is a sulfonyl group having a $C_{1-6}$ alkyl group and may be linear, branched or a $C_{3-6}$ cycloalkylsulfonyl group. As specific examples, methylsulfonyl, ethylsulfonyl, n-propylsulfonyl, propylsulfonyl, c-propylsulfonyl, n-butylsulfonyl, butylsulfonyl, s-butylsulfonyl, t-butylsulfonyl, c-butylsulfonyl, 1-methyl-c-propylsulfonyl, 2-methyl-c-propylsulfonyl, n-pentylsulfonyl, 1-methyl-n-butylsulfonyl, 2-methyl-n-butylsulfonyl, 3-methyl-n-butylsulfonyl, 1,1-dimethyl-n-propylsulfonyl, 1,2-dimethyl-n-propylsulfonyl, 2,2-dimethyl-n-propylsulfonyl, 1-ethyl-n-propylsulfonyl, c-pentylsulfonyl, 1-methyl-c-butylsulfonyl, 2-methyl-c-butylsulfonyl, 3-methyl-c-butylsulfonyl, 1,2-dimethyl-c-propylsulfonyl, 2,3-dimethyl-c-propylsulfonyl, 1-ethyl-c-propylsulfonyl, 2-ethyl-c-propylsulfonyl, n-hexylsulfonyl, 1-methyl-n-pentylsulfonyl, 2-methyl-n-pentylsulfonyl, 3-methyl-n-pentylsulfonyl, 4-methyl-n-pentylsulfonyl, 1,1-dimethyl-n-butylsulfonyl, 1,2-dimethyl-n-butylsulfonyl, 1,3-dimethyl-n-butylsulfonyl, 2,2-dimethyl-n-butylsulfonyl, 2,3-dimethyl-n-butylsulfonyl, 3,3-dimethyl-n-butylsulfonyl, 1-ethyl-n-butylsulfonyl, 2-ethyl-n-butylsulfonyl, 1,1,2-trimethyl-n-propylsulfonyl, 1,2,2-trimethyl-n-propylsulfonyl, 1-ethyl-1-methyl-n-propylsulfonyl, 1-ethyl-2-methyl-n-propylsulfonyl, c-hexylsulfonyl, 1-methyl-c-pentylsulfonyl, 2-methyl-c-pentylsulfonyl, 3-methyl-c-pentylsulfonyl, 1-ethyl-c-butylsulfonyl, 2-ethyl-c-butylsulfonyl, 3-ethyl-c-butylsulfonyl, 1,2-dimethyl-c-butylsulfonyl, 1,3-dimethyl-c-butylsulfonyl, 2,2-dimethyl-c-butylsulfonyl, 2,3-dimethyl-c-butylsulfonyl, 2,4-dimethyl-c-butylsulfonyl, 3,3-dimethyl-c-butylsulfonyl, 1-n-propyl-c-propylsulfonyl, 2-n-propyl-c-propylsulfonyl, 1-i-propyl-c-propylsulfonyl, 2-i-propyl-c-propylsulfonyl, 1,2,2-trimethyl-c-propylsulfonyl, 1,2,3-trimethyl-c-propylsulfonyl, 2,2,3-trimethyl-c-propylsulfonyl, 1-ethyl-2-methyl-c-propylsulfonyl, 2-ethyl- 1-methyl-c-propylsulfonyl, 2-ethyl-2-methyl-c-propylsulfonyl, 2-ethyl-3-methyl-c-propylsulfonyl and the like may be mentioned.

A $C_{1-3}$ alkylsulfonyl group is an alkylsulfonyl group containing one to three carbon atoms and may be linear, branched or a $C_3$ cycloalkylsulfonyl group. As specific examples, methylsulfonyl, ethylsulfonyl, n-propylsulfonyl, i-propylsulfonyl, c-propylsulfonyl and the like may be mentioned.

Next, preferred structures of the respective substituents will be mentioned.

The substituent $R^1$ is preferably a hydrogen atom, a $C_{1-3}$ alkoxy group or a $C_{1-3}$ haloalkoxy group.

The substituent $R^1$ is more preferably a hydrogen atom or an ethoxy group, and further preferably a hydrogen atom.

The substituent $R^2$ is preferably a hydrogen atom, a halogen atom, a $C_{1-3}$ alkoxy group, a $C_{1-3}$ alkyl group, a $C_{1-3}$ alkylthio group or a $C_{1-3}$ alkylsulfonyl group (the $C_{1-3}$ alkoxy group, the $C_{1-3}$ alkyl group, the $C_{1-3}$ alkylthio group and the $C_{1-3}$ alkylsulfonyl group are unsubstituted or substituted with one or more halogen atoms).

The substituent $R^2$ is more preferably a halogen atom, a methyl group, a trifluoromethyl group, a difluoromethyl group, a fluoromethyl group, a trifluoromethoxy group or a difluoromethoxy group, further preferably a halogen atom.

The substituent Q is preferably any of the structures represented by the formula (X):

(X)

(wherein $R^3$ and $R^5$ mean hydrogen atoms, $R^4$ means a $C_{7-12}$ cycloalkyl group or a $C_{7-12}$ cycloalkenyl group, and T means an oxygen atom), the formula (VI):

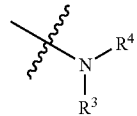

(VI)

(wherein $R^3$ means a hydrogen atom or a $C_{1-6}$ alkyl group (the $C_{1-6}$ alkyl group is unsubstituted or substituted with one or more halogen atoms), and $R^4$ means a $C_{1-20}$ alkyl group, a $C_{2-20}$ alkenyl group or a $C_{2-19}$ heterocyclyl group (the $C_{1-20}$ alkyl group, the $C_{2-20}$ alkenyl group and the $C_{2-19}$ heterocyclyl group are unsubstituted or substituted with one or more identical or different substituents selected from the substituent set $V^1$)), and the formula (VII):

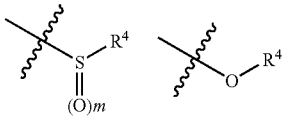

(VII)

(wherein m means 0, 1 or 2, and $R^4$ means a $C_{1-20}$ alkyl group, a $C_{2-20}$ alkenyl group or a $C_{2-19}$ heterocyclyl group (the $C_{1-20}$ alkyl group, the $C_{2-20}$ alkenyl group and the $C_{2-19}$ heterocyclyl group are unsubstituted or substituted with one or more identical or different substituents selected from the substituent set $V^1$)).

The substituent Q is more preferably any of the structures represented by the formula (VI):

(VI)

(wherein $R^3$ means a hydrogen atom, and $R^4$ means a $C_{3-12}$ cycloalkyl group, a $C_{3-12}$ cycloalkenyl group or a $C_{2-19}$ heterocyclyl group (the $C_{3-32}$ cycloalkyl group, the $C_{3-12}$ cycloalkenyl group and the $C_{2-19}$ heterocyclyl group are unsubstituted or substituted with one or more identical or different substituents selected from the substituent set $V^1$)), and the formula (VII):

(VII)

(wherein m means 0, 1 or 2, and $R^4$ means a $C_{3-12}$ cycloalkyl group, a $C_{3-12}$ cycloalkenyl group or a $C_{2-19}$ heterocyclyl group (the $C_{3-12}$ cycloalkyl group, the $C_{3-12}$ cycloalkenyl group and the $C_{2-19}$ heterocyclyl group are unsubstituted or substituted with one to three identical or different substituents selected from the substituent set $V^1$)).

The substituent Q is further preferably any of the structures represented by the formula (VI):

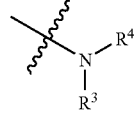

(VI)

(wherein $R^3$ means a hydrogen atom, and $R^4$ means a $C_{7-12}$ cycloalkyl group or a $C_{7-12}$ cycloalkenyl group (the $C_{7-12}$ cycloalkyl group and the $C_{7-12}$ cycloalkenyl group are unsubstituted or substituted with one or two identical or different substituents selected from the group consisting of halogen atoms, carboxy groups, carbamoyl groups, sulfamoyl groups, nitro groups, cyano groups, hydroxy groups, amino groups, mono-$C_{1-6}$ alkylamino groups, di-$C_{1-6}$ alkylamino groups, $C_{1-6}$ alkoxy groups, $C_{2-9}$ heterocyclyl groups, $C_{1-6}$ alkylthio groups, $C_{1-6}$ alkylsulfonyl groups, $C_{1-3}$ haloalkyl groups and $C_{1-3}$ haloalkoxy groups)), and the formula (VII):

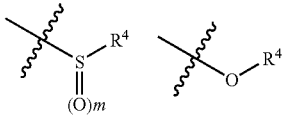

(VII)

(wherein m means 0, 1 or 2; and $R^4$ means a $C_{7-12}$ cycloalkyl group or a $C_{7-12}$ cycloalkenyl group (the $C_{7-12}$ cycloalkyl group and the $C_{7-12}$ cycloalkenyl group are unsubstituted or substituted with one to two identical or different substituents selected from the group consisting of carboxy groups, carbamoyl groups, sulfamoyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkoxy groups, $C_{2-9}$ heterocyclyl groups, $C_{1-6}$ alkylthio groups, $C_{1-6}$ alkylsulfonyl groups, $C_{1-3}$ haloalkyl groups and $C_{1-3}$ haloalkoxy groups)).

The substituent Q is particularly preferably represented by the formula (VI):

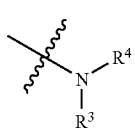

(VI)

(wherein $R^3$ means a hydrogen atom, and $R^4$ means a $C_{8-12}$ cycloalkyl group (the $C_{8-12}$ cycloalkyl group is unsubstituted or substituted with one or two identical or different substituents selected from the group consisting of carboxy groups, carbamoyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkoxy groups, $C_{2-9}$ heterocyclyl groups, $C_{1-6}$ alkylsulfonyl groups, $C_{1-3}$ haloalkyl groups and $C_{1-3}$ haloalkoxy groups)).

The substituent Q is more particularly preferably any of the structures represented by the formula (IV):

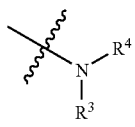

(VI)

(wherein $R^3$ means a hydrogen atom, and $R^4$ means any of the structures shown below):

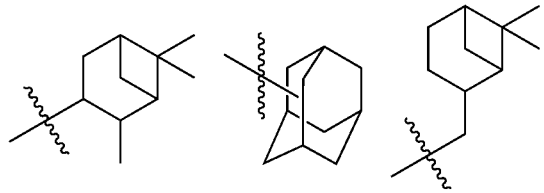

and the formula (VI):

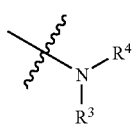

(VI)

(wherein $R^3$ means a hydrogen atom, and $R^4$ means any of the structures shown below).

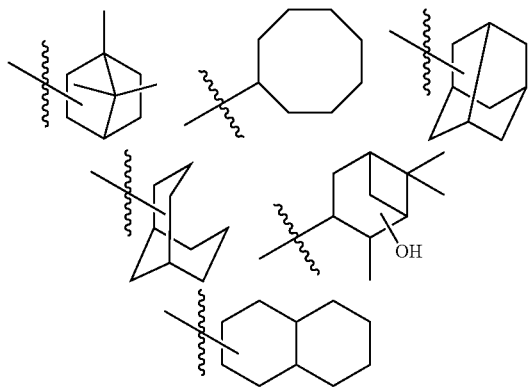

The substituent X is preferably a $C_{1-6}$ alkylene group (the $C_{1-6}$ alkylene group is unsubstituted or substituted with one or two identical or different substituents selected from the substituent set $V^1$).

The substituent X is more preferably a $C_{1-3}$ alkylene group, further preferably a methylene group, a 1,2-ethylene group or a 1,1-ethylene group, particularly preferably a methylene group.

The substituent Y is preferably a single bond or any of the structures represented by the formula (VIII):

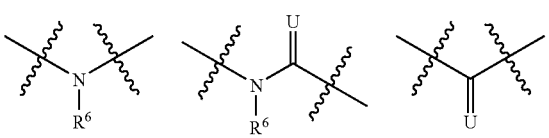

(VIII)

(wherein $R^6$ means a hydrogen atom or a $C_{1-3}$ alkyl group (the $C_{1-3}$ alkyl group is unsubstituted or substituted with one or more halogen atoms), and U means an oxygen atom or a sulfur atom).

The substituent Y is more preferably any of the structures represented by the formula (VIII):

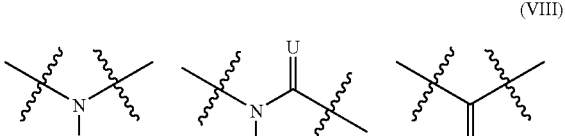

(VIII)

(wherein $R^6$ means a hydrogen atom, and U means an oxygen atom).

The substituent Z is preferably a $C_{1-6}$ alkyl group, a $C_{1-6}$ alkoxy group (the $C_{1-6}$ alkyl group and the $C_{1-6}$ alkoxy group are unsubstituted or substituted with one or two identical or different substituents selected from the substituent set $V^2$), a $C_{2-14}$ aryl group, a $C_{2-14}$ aryloxy group or a $C_{2-9}$ heterocyclyl group (the $C_{2-14}$ aryl group, the $C_{2-14}$ aryloxy group and the $C_{2-9}$ heterocyclyl group are unsubstituted or substituted with one or two identical or different substituents selected from the substituent set $V^2$).

The substituent Z is more preferably a $C_{1-6}$ alkyl group (the $C_{1-6}$ alkyl group is substituted with one $C_{2-9}$ heteroaryl group, one $C_{2-9}$ heterocyclyl group (the $C_{2-9}$ heteroaryl group and the $C_{2-9}$ heterocyclyl group are unsubstituted or substituted or one or two identical or different substituents selected from the substituent set $V^1$)).

The substituent Z is further preferably a $C_{1-6}$ alkyl group (the $C_{1-6}$ alkyl group is substituted with one $C_{2-9}$ heteroaryl group or one $C_{2-9}$ heterocyclyl group (the $C_{2-9}$ heteroaryl group and the $C_{2-9}$ heterocyclyl group are unsubstituted or substituted with one or two identical or different substituents selected from the group consisting of carboxy groups, carbamoyl groups, sulfamoyl groups, nitro groups, cyano groups, halogen atoms, hydroxy groups, amino groups, $C_{1-6}$ alkyl groups, mono-$C_{1-6}$ alkylamino groups, di-$C_{1-6}$ alkylamino groups, $C_{1-6}$ alkoxy groups, $C_{2-9}$ heterocyclyl groups, $C_{1-6}$ alkylthio groups, $C_{1-6}$ alkylsulfonyl groups, $C_{1-3}$ haloalkyl groups and $C_{1-3}$ haloalkoxy groups)).

The substituent Z is particularly preferably a $C_{1-3}$ alkyl group (the $C_{1-3}$ alkyl group is substituted with one substituent selected from the substituent set (XI):

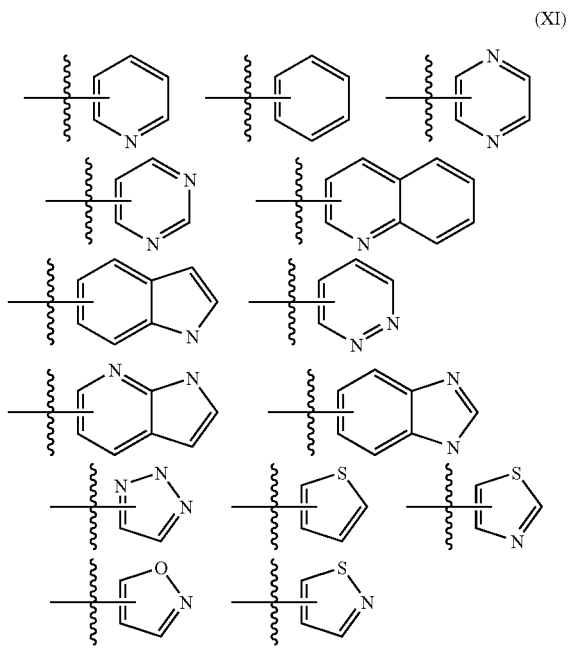

(XI)

(wherein each substituent is unsubstituted or substituted with one or two identical or different substituents selected from the group consisting of carboxy groups, carbamoyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkyl groups, $C_{1-6}$ alkoxy groups, $C_{2-9}$ heterocyclyl groups, $C_{1-6}$ alkylsulfonyl groups, $C_{1-3}$ haloalkyl groups and $C_{1-3}$ haloalkoxy groups)) or a $C_{1-3}$ alkyl group (the $C_{1-3}$ alkyl group is substituted with one substituent selected from the substituent set (XII):

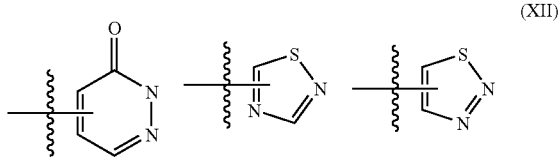

(XII)

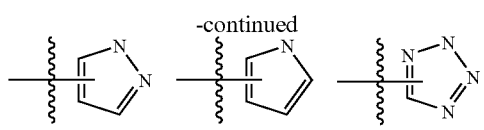

-continued (wherein each substituent is unsubstituted or substituted with one or two identical or different substituents selected from the group consisting of carboxy groups, carbamoyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkyl groups, $C_{1-6}$ alkoxy groups, $C_{2-9}$ heterocyclyl groups, $C_{1-6}$ alkylsulfonyl groups, $C_{1-3}$ haloalkyl groups and $C_{1-3}$ haloalkoxy groups)).

The substituent Z is more particularly preferably a (3-methylpyridyl)methyl group, a (3-methylpyridyl)ethyl group, a pyridylmethyl group, a pyridylethyl group, a (2-fluoropyridyl)ethyl group, a (3-chloropyridyl)ethyl group, a (3-dimethylaminopyridyl)methyl group, a pyridazinylethyl group, a pyridazinylpropyl group, a pyrimidinylethyl group, a pyrimidinylpropyl group, a (4-methylpyridazinyl)methyl group, a (3-dimethylaminopyridazinyl)methyl group, a (3-methylpyridazinyl)ethyl group, a (3-chloropyridazinyl)ethyl group, a (3-methoxypyridazinyl)ethyl group, a (3-chloro-6-methylpyridazinyl)ethyl group or a (3-methanesulfonylpyridyl)methyl group.

Favorable compounds as the P2X7 receptor inhibitor, the preventive, therapeutic or improving agent for diseases against which inhibition of the P2X7 receptor is effective and the therapeutic agent for rheumatoid arthritis of the present invention are as follows:

1) Compounds represented by the formula (I), wherein $R^1$ is a hydrogen atom, a $C_{1-3}$ alkoxy group or a $C_{1-3}$ haloalkoxy group,
$R^2$ is a hydrogen atom, a halogen atom, a $C_{1-3}$ alkoxy group, a $C_{1-3}$ alkyl group, a $C_{1-3}$ alkylthio group or a $C_{1-3}$ alkylsulfonyl group (the $C_{1-3}$ alkoxy group, the $C_{1-3}$ alkyl group, the $C_{1-3}$ alkylthio group and the $C_{1-3}$ alkylsulfonyl group are unsubstituted or substituted with one or more halogen atoms),
Q is any of the structures represented by the formula (X):

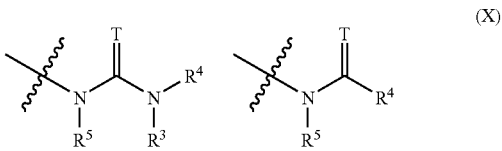

(X)

(wherein $R^3$ and $R^5$ mean hydrogen atoms, and $R^4$ means a $C_{7-12}$ cycloalkyl group or a $C_{7-12}$ cycloalkenyl group, and T means an oxygen atom of a sulfur atom), the formula (VI):

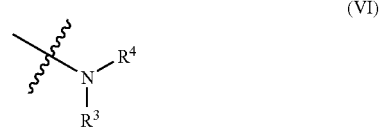

(VI)

(wherein $R^3$ means a hydrogen atom or a $C_{1-6}$ alkyl group (the $C_{1-6}$ alkyl group is unsubstituted or substituted with one or more halogen atoms), and $R^4$ means a $C_{1-20}$ alkyl group, a $C_{2-20}$ alkenyl group or a $C_{2-19}$ heterocyclyl group (the $C_{1-20}$ alkyl group, the $C_{2-20}$ alkenyl group and the $C_{2-19}$ heterocyclyl group are unsubstituted or substituted with one or more identical or different substituents selected from the substituent set $V^1$)), and the formula (VII):

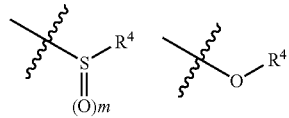

(VII)

(wherein m means 0, 1 or 2, and $R^4$ means a $C_{1-20}$ alkyl group, a $C_{2-20}$ alkenyl group or a $C_{2-19}$ heterocyclyl group (the $C_{1-20}$ alkyl group, the $C_{2-20}$ alkenyl group and the $C_{2-19}$ heterocyclyl group are unsubstituted or substituted with one or more identical or different substituents selected from the substituent set $V^1$)),
X is a $C_{1-6}$ alkylene group (the $C_{1-6}$ alkylene group is unsubstituted or substituted with one or two identical or different substituents selected from the substituent set $V^1$),
Y is a bond or any of the structure represented by the formula (VIII):

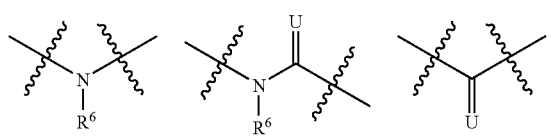

(VIII)

(wherein $R^6$ is a hydrogen atom or a $C_{1-6}$ alkyl group (the $C_{1-6}$ alkyl group is unsubstituted or substituted with one or more halogen atoms), and U means an oxygen atom), and Z is a $C_{1-6}$ alkyl group, a $C_{1-6}$ alkoxy group (the $C_{1-6}$ alkyl group and the $C_{1-6}$ alkoxy group are unsubstituted or substituted with one or two identical or different substituents selected from the substituent set $V^2$), a $C_{2-14}$ aryl group or a $C_{2-9}$ heterocyclyl group (the $C_{2-14}$ aryl group and the $C_{2-9}$ heterocyclyl group are unsubstituted or substituted with one substituent selected from the substituent set $V^2$), tautomers, prodrugs or pharmaceutically acceptable salts of the compounds or solvates thereof.

2) The compounds according to 1), wherein $R^1$ is a hydrogen atom or an ethoxy group, tautomers, prodrugs or pharmaceutically acceptable salts of the compounds or solvates thereof.

3) The compound according to 1) or 2), wherein $R^2$ is a halogen atom, a methyl group, a trifluoromethyl group, a difluoromethyl group, a fluoromethyl group, a trifluoromethoxy group or a difluoromethoxy group, tautomers, prodrugs or pharmaceutically acceptable salts of the compounds or solvates thereof.

4) The compounds according to any of 1) to 3), wherein Q is any of the structures represented by the formula (VI):

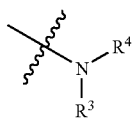

(VI)

(wherein $R^3$ means a hydrogen atom, and $R^4$ means a $C_{3-12}$ cycloalkyl group, a $C_{3-12}$ cycloalkenyl group or a $C_{2-19}$ heterocyclyl group (the $C_{3-12}$ cycloalkyl group, the $C_{3-12}$ cycloalkenyl group and the $C_{2-19}$ heterocyclyl group are unsubstituted or substituted with one to three identical or different substituents selected from the substituent set $V^1$)) and the formula (VII):

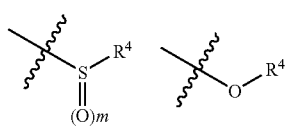

(VII)

(wherein m means 0, 1 or 2, $R^4$ means a $C_{3-12}$ cycloalkyl group, a $C_{3-12}$ cycloalkenyl group or a $C_{2-19}$ heterocyclyl group (the $C_{3-12}$ cycloalkyl group, the $C_{3-12}$ cycloalkenyl group and the $C_{2-19}$ heterocyclyl group are unsubstituted or substituted with one to three identical or different substituents selected from the substituent set $V^1$)), tautomers, prodrugs or pharmaceutically acceptable salts of the compounds or solvates thereof.

5) The compounds according to any of 1) to 4), wherein X is a $C_{1-3}$ alkylene group, tautomers, prodrugs or pharmaceutically acceptable salts of the compounds or solvates thereof.

6) The compounds according to any of 1) to 5), wherein the substituent Y is any of the structures represented by represented by the formula (VIII):

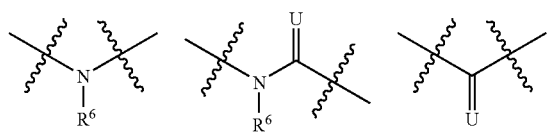

(VIII)

(wherein $R^6$ means a hydrogen atom, and U means an oxygen atom), tautomers, prodrugs or pharmaceutically acceptable salts of the compounds or solvates thereof.

7) The compounds according to any of 1) to 6), wherein the substituent Z is a $C_{1-6}$ alkyl group (the $C_{1-6}$ alkyl group is substituted with one $C_{2-9}$ heteroaryl group (the $C_{2-9}$ heteroaryl group is unsubstituted or substituted with one or two identical or different substituents selected from the substituent set $V^1$)), tautomers, prodrugs or pharmaceutically acceptable salts of the compounds or solvates thereof.

8) The compound according to any of 1) to 7), wherein $R^1$ is a hydrogen atom, tautomers, prodrugs or pharmaceutically acceptable salts of the compounds or solvates thereof.

9) The compounds according to any of 1) to 8), wherein $R^2$ is a halogen atom, tautomers, prodrugs or pharmaceutically acceptable salts of the compounds or solvates thereof.

10) The compound according to any of 1) to 9), wherein Q is any of the structures represented by the formula (VI):

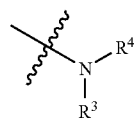

(VI)

(wherein $R^3$ means a hydrogen atom, and $R^4$ means a $C_{7-12}$ cycloalkyl group or a $C_{7-12}$ cycloalkenyl group (the $C_{7-12}$ cycloalkyl group and the $C_{7-12}$ cycloalkenyl group are unsubstituted or substituted with one or two identical or different substituents selected from the group consisting of carboxy groups, carbamoyl groups, sulfamoyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkoxy groups, $C_{2-9}$ heterocyclyl groups, $C_{1-6}$ alkylthio groups, $C_{1-6}$ alkylsulfonyl groups, $C_{1-3}$ haloalkyl groups and $C_{1-3}$ haloalkoxy groups)), and the formula (VII):

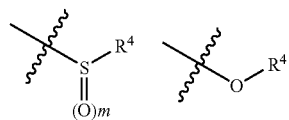

(VII)

(wherein m means 0, 1 or 2, and $R^4$ means a $C_{7-12}$ cycloalkyl group or a $C_{7-12}$ cycloalkenyl group (the $C_{7-12}$ cycloalkyl group and the $C_{7-12}$ cycloalkenyl group are unsubstituted or substituted with one or two identical or different substituents selected from the group consisting of carboxy groups, carbamoyl groups, sulfamoyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkoxy groups, $C_{2-9}$ heterocyclyl groups, $C_{1-6}$ alkylthio groups, $C_{1-6}$ alkylsulfonyl groups, $C_{1-3}$ haloalkyl groups and $C_{1-3}$ haloalkoxy groups)), tautomers, prodrugs or pharmaceutically acceptable salts of the compounds or solvates thereof.

11) The compounds according to any of 1) to 10), wherein X is a methylene group, a 1,2-ethylene group or a 1,1-ethylene group, tautomers, prodrugs or pharmaceutically acceptable salts of the compounds or solvates thereof.

12) The compounds according to any of 1) to 11), wherein the substituent Z is a $C_{1-6}$ alkyl group (the $C_{1-6}$ alkyl group is substituted with one $C_{2-9}$ heteroaryl group or one $C_{2-9}$ heterocyclyl group (the $C_{2-9}$ heteroaryl group and the $C_{2-9}$ heterocyclyl group are unsubstituted or substituted with one or two identical or different substituents selected from the group consisting of carboxy groups, carbamoyl groups, sulfamoyl groups, nitro groups, cyano groups, halogen atoms, hydroxy groups, amino groups, $C_{1-6}$ alkyl groups, mono-$C_{1-6}$ alkylamino groups, di-$C_{1-6}$ alkylamino groups, $C_{1-6}$ alkoxy groups, $C_{2-9}$ heterocyclyl groups, $C_{1-6}$ alkylthio groups, $C_{1-6}$ alkylsulfonyl groups, $C_{1-3}$ haloalkyl groups and $C_{1-3}$ haloalkoxy groups)), tautomers, prodrugs or pharmaceutically acceptable salts of the compounds or solvates thereof.

13) The compounds according to any of 1) to 12), wherein the substituent Q is represented by the formula (VI):

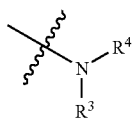

(VI)

(wherein $R^3$ means a hydrogen atom, and $R^4$ means a $C_{8-12}$ cycloalkyl group (the $C_{8-12}$ cycloalkyl group is unsubstituted or substituted with one or two identical or different substituents selected from the group consisting of carboxy groups, carbamoyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkoxy groups, $C_{2-9}$ heterocyclyl groups, $C_{1-6}$ alkylsulfonyl groups, $C_{1-3}$ haloalkyl groups and $C_{1-3}$ haloalkoxy groups)), tautomers, prodrugs or pharmaceutically acceptable salts of the compounds or solvates thereof.

14) The compounds according to any of 1) to 13), wherein the substituent Z is a $C_{1-3}$ alkyl group (the $C_{1-3}$ alkyl group is substituted with one substituent selected from the substituent set (XI):

(XI)

(wherein each substituent is unsubstituted or substituted with one or two identical or different substituents selected from the group consisting of carboxy groups, carbamoyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkyl groups, $C_{1-6}$ alkoxy groups, $C_{2-9}$ heterocyclyl groups, $C_{1-6}$ alkylsulfonyl groups, $C_{1-3}$ haloalkyl groups and $C_{1-3}$ haloalkoxy groups)) or a $C_{1-3}$ alkyl group (the $C_{1-3}$ alkyl group is substituted with one substituent selected from the substituent set (XII):

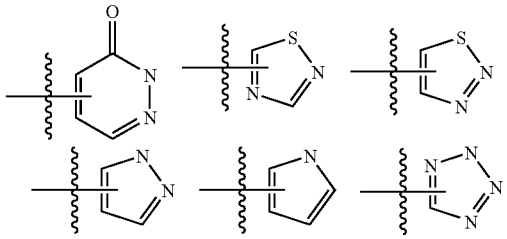

(XII)

(wherein each substituent is unsubstituted or substituted with one or two identical or different substituents selected from the group consisting of carboxy groups, carbamoyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkyl groups, $C_{1-6}$ alkoxy groups, $C_{2-9}$ heterocyclyl groups, $C_{1-6}$ alkylsulfonyl groups, $C_{1-3}$ haloalkyl groups and $C_{1-3}$ haloalkoxy groups)), tautomers, prodrugs or pharmaceutically acceptable salts of the compounds or solvates thereof.

15) The compounds according to any of 1) to 14), wherein Q is represented by the formula (VI):

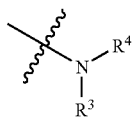
(VI)

(wherein R³ means a hydrogen atom, and R⁴ is any of the structures shown below):

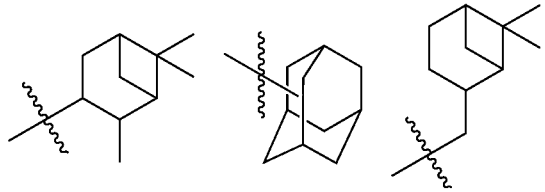

or the formula (VI):

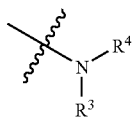
(VI)

(wherein R³ means a hydrogen atom, and R⁴ is any of the structures shown below),

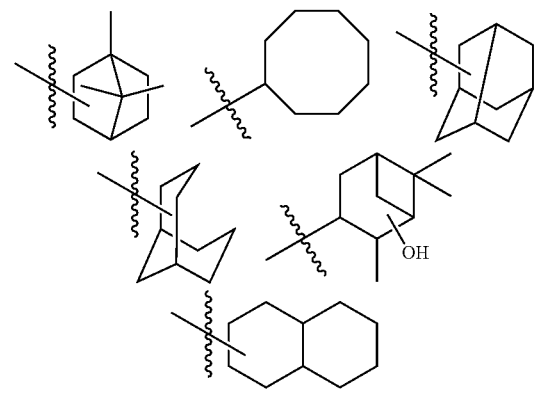

tautomers, prodrugs or pharmaceutically acceptable salts of the compounds or solvates thereof.

16) The compounds according to any of 1) to 15), wherein Z is a (3-methylpyridyl)methyl group, a pyridylmethyl group, a (3-methylpyridyl)ethyl group, a pyridylethyl group, a (2-fluoropyridyl)ethyl group, a (3-chloropyridyl)ethyl group, a (3-dimethylaminopyridyl)methyl group, a pyridazinylethyl group, a pyridazinylpropyl group, a pyrimidinylethyl group, a pyrimidinylpropyl group, a (4-methylpyridazinyl)methyl group, a (3-dimethylaminopyridazinyl)methyl group, a (3-methylpyridazinyl)ethyl group, a (3-chloropyridazinyl) ethyl group, a (3-methoxypyridazinyl)ethyl group, a (3-chloro-6-methylpyridazinyl)ethyl group or a (3-methanesulfonylpyridyl)methyl group, tautomers, prodrugs or pharmaceutically acceptable salts of the compounds or solvates thereof.

17) The compounds wherein $R^1$ is a hydrogen atom, $R^2$ is bromine, X is a methylene group, Y is —CONH—, and Q and Z are any of the following combinations in Table 1, tautomers, prodrugs or pharmaceutically acceptable salts of the compounds or solvates thereof. The symbols in Table 1 denote the flowing substituents.

TABLE 1

| Q | Z |
|---|---|
| Q1 | Z1 |
| Q2 | Z1 |
| Q3 | Z1 |
| Q4 | Z1 |
| Q5 | Z1 |
| Q6 | Z1 |
| Q7 | Z1 |
| Q8 | Z1 |
| Q9 | Z1 |
| Q10 | Z1 |
| Q1 | Z2 |
| Q2 | Z2 |
| Q3 | Z2 |
| Q4 | Z2 |
| Q5 | Z2 |
| Q6 | Z2 |
| Q7 | Z2 |
| Q8 | Z2 |
| Q9 | Z2 |
| Q10 | Z2 |
| Q1 | Z3 |
| Q2 | Z3 |
| Q3 | Z3 |
| Q4 | Z3 |
| Q5 | Z3 |
| Q6 | Z3 |
| Q7 | Z3 |
| Q8 | Z3 |
| Q9 | Z3 |
| Q10 | Z3 |
| Q1 | Z4 |
| Q2 | Z4 |
| Q3 | Z4 |
| Q4 | Z4 |
| Q5 | Z4 |
| Q6 | Z4 |
| Q7 | Z4 |
| Q8 | Z4 |
| Q9 | Z4 |
| Q10 | Z4 |
| Q1 | Z5 |
| Q2 | Z5 |
| Q3 | Z5 |
| Q4 | Z5 |
| Q5 | Z5 |
| Q6 | Z5 |
| Q7 | Z5 |
| Q8 | Z5 |
| Q9 | Z5 |
| Q10 | Z5 |
| Q1 | Z6 |
| Q2 | Z6 |
| Q3 | Z6 |
| Q4 | Z6 |
| Q5 | Z6 |
| Q6 | Z6 |
| Q7 | Z6 |
| Q8 | Z6 |
| Q9 | Z6 |
| Q10 | Z6 |
| Q1 | Z7 |
| Q2 | Z7 |
| Q3 | Z7 |
| Q4 | Z7 |
| Q5 | Z7 |

TABLE 1-continued

| Q | Z |
|---|---|
| Q6 | Z7 |
| Q7 | Z7 |
| Q8 | Z7 |
| Q9 | Z7 |
| Q10 | Z7 |
| Q1 | Z8 |
| Q2 | Z8 |
| Q3 | Z8 |
| Q4 | Z8 |
| Q5 | Z8 |
| Q6 | Z8 |
| Q7 | Z8 |
| Q8 | Z8 |
| Q9 | Z8 |
| Q10 | Z8 |
| Q1 | Z9 |
| Q2 | Z9 |
| Q3 | Z9 |
| Q4 | Z9 |
| Q5 | Z9 |
| Q6 | Z9 |
| Q7 | Z9 |
| Q8 | Z9 |
| Q9 | Z9 |
| Q10 | Z9 |
| Q1 | Z10 |
| Q2 | Z10 |
| Q3 | Z10 |
| Q4 | Z10 |
| Q5 | Z10 |
| Q6 | Z10 |
| Q7 | Z10 |
| Q8 | Z10 |
| Q9 | Z10 |
| Q10 | Z10 |
| Q1 | Z11 |
| Q2 | Z11 |
| Q3 | Z11 |
| Q4 | Z11 |
| Q5 | Z11 |
| Q6 | Z11 |
| Q7 | Z11 |
| Q8 | Z11 |
| Q9 | Z11 |
| Q10 | Z11 |
| Q1 | Z12 |
| Q2 | Z12 |
| Q3 | Z12 |
| Q4 | Z12 |
| Q5 | Z12 |
| Q6 | Z12 |
| Q7 | Z12 |
| Q8 | Z12 |
| Q9 | Z12 |
| Q10 | Z12 |
| Q1 | Z13 |
| Q2 | Z13 |
| Q3 | Z13 |
| Q4 | Z13 |
| Q5 | Z13 |
| Q6 | Z13 |
| Q7 | Z13 |
| Q8 | Z13 |
| Q9 | Z13 |
| Q10 | Z13 |
| Q1 | Z14 |
| Q2 | Z14 |
| Q3 | Z14 |
| Q4 | Z14 |
| Q5 | Z14 |
| Q6 | Z14 |
| Q7 | Z14 |
| Q8 | Z14 |
| Q9 | Z14 |
| Q10 | Z14 |
| Q1 | Z15 |
| Q2 | Z15 |
| Q3 | Z15 |
| Q4 | Z15 |
| Q5 | Z15 |
| Q6 | Z15 |
| Q7 | Z15 |
| Q8 | Z15 |
| Q9 | Z15 |
| Q10 | Z15 |
| Q1 | Z16 |
| Q2 | Z16 |
| Q3 | Z16 |
| Q4 | Z16 |
| Q5 | Z16 |
| Q6 | Z16 |
| Q7 | Z16 |
| Q8 | Z16 |
| Q9 | Z16 |
| Q10 | Z16 |
| Q1 | Z17 |
| Q2 | Z17 |
| Q3 | Z17 |
| Q4 | Z17 |
| Q5 | Z17 |
| Q6 | Z17 |
| Q7 | Z17 |
| Q8 | Z17 |
| Q9 | Z17 |
| Q10 | Z17 |
| Q1 | Z18 |
| Q2 | Z18 |
| Q3 | Z18 |
| Q4 | Z18 |
| Q5 | Z18 |
| Q6 | Z18 |
| Q7 | Z18 |
| Q8 | Z18 |
| Q9 | Z18 |
| Q10 | Z18 |
| Q1 | Z19 |
| Q2 | Z19 |
| Q3 | Z19 |
| Q4 | Z19 |
| Q5 | Z19 |
| Q6 | Z19 |
| Q7 | Z19 |
| Q8 | Z19 |
| Q9 | Z19 |
| Q10 | Z19 |
| Q1 | Z20 |
| Q2 | Z20 |
| Q3 | Z20 |
| Q4 | Z20 |
| Q5 | Z20 |
| Q6 | Z20 |
| Q7 | Z20 |
| Q8 | Z20 |
| Q9 | Z20 |
| Q10 | Z20 |
| Q1 | Z21 |
| Q2 | Z21 |
| Q3 | Z21 |
| Q4 | Z21 |
| Q5 | Z21 |
| Q6 | Z21 |
| Q7 | Z21 |
| Q8 | Z21 |
| Q9 | Z21 |
| Q10 | Z21 |
| Q1 | Z22 |
| Q2 | Z22 |
| Q3 | Z22 |
| Q4 | Z22 |
| Q5 | Z22 |
| Q6 | Z22 |
| Q7 | Z22 |
| Q8 | Z22 |
| Q9 | Z22 |
| Q10 | Z22 |
| Q1 | Z23 |

TABLE 1-continued

| Q | Z |
|---|---|
| Q2 | Z23 |
| Q3 | Z23 |
| Q4 | Z23 |
| Q5 | Z23 |
| Q6 | Z23 |
| Q7 | Z23 |
| Q8 | Z23 |
| Q9 | Z23 |
| Q10 | Z23 |
| Q1 | Z24 |
| Q2 | Z24 |
| Q3 | Z24 |
| Q4 | Z24 |
| Q5 | Z24 |
| Q6 | Z24 |
| Q7 | Z24 |
| Q8 | Z24 |
| Q9 | Z24 |
| Q10 | Z24 |
| Q1 | Z25 |
| Q2 | Z25 |
| Q3 | Z25 |
| Q4 | Z25 |
| Q5 | Z25 |
| Q6 | Z25 |
| Q7 | Z25 |
| Q8 | Z25 |
| Q9 | Z25 |
| Q10 | Z25 |
| Q1 | Z26 |
| Q2 | Z26 |
| Q3 | Z26 |
| Q4 | Z26 |
| Q5 | Z26 |
| Q6 | Z26 |
| Q7 | Z26 |
| Q8 | Z26 |
| Q9 | Z26 |
| Q10 | Z26 |
| Q1 | Z27 |
| Q2 | Z27 |
| Q3 | Z27 |
| Q4 | Z27 |
| Q5 | Z27 |
| Q6 | Z27 |
| Q7 | Z27 |
| Q8 | Z27 |
| Q9 | Z27 |
| Q10 | Z27 |
| Q1 | Z28 |
| Q2 | Z28 |
| Q3 | Z28 |
| Q4 | Z28 |
| Q5 | Z28 |
| Q6 | Z28 |
| Q7 | Z28 |
| Q8 | Z28 |
| Q9 | Z28 |
| Q10 | Z28 |
| Q1 | Z29 |
| Q2 | Z29 |
| Q3 | Z29 |
| Q4 | Z29 |
| Q5 | Z29 |
| Q6 | Z29 |
| Q7 | Z29 |
| Q8 | Z29 |
| Q9 | Z29 |
| Q10 | Z29 |
| Q1 | Z30 |
| Q2 | Z30 |
| Q3 | Z30 |
| Q4 | Z30 |
| Q5 | Z30 |
| Q6 | Z30 |
| Q7 | Z30 |
| Q8 | Z30 |
| Q9 | Z30 |
| Q10 | Z30 |

Q1 =

Q2 =

Q3 =

Q4 =

Q5 =

Q6 =

Q7 =

Q8 =

Q9 =

Q10 =

TABLE 1-continued

| Q | Z |
|---|---|

Z1 = [pyrimidine fused cyclopentane structure]

Z2 = [pyridazine-CH2-]

Z3 = [pyridin-4-yl-CH2-]

Z4 = [pyridin-4-yl-CH2CH2-]

Z5 = [pyridin-3-yl-CH2-]

Z6 = [pyridin-2-yl-CH2CH2-]

Z7 = [pyridin-4-yl-CH2CH2-]

Z8 = [pyrazin-2-yl-CH2-]

Z9 = [pyrimidin-4-yl-CH2-]

Z10 = [5-methylpyrazin-2-yl-CH2-]

Z11 = [pyridin-4-yl-CH(iPr)-]

Z12 = [pyridin-4-yl-CH(Me)-]

Z13 = [1-(pyridin-4-yl)cyclopropyl-]

Z14 = [2-hydroxypyrimidin-4-yl-CH2-]

Z15 = [3-methylpyridin-4-yl-CH2-]

Z16 = [2-hydroxypyridin-4-yl-CH2-]

Z17 = [2-methoxypyridin-4-yl-CH2-]

Z18 = [2-chloropyridin-4-yl-CH2-]

Z19 = [2-isopropylpyridin-4-yl-CH2-]

Z20 = [pyridin-4-yl N-oxide-CH2-]

Z21 = [pyridin-4-yl-C(Me)2-]

Z22 = [2,3-dihydro-1H-pyrrolo[3,4-c]pyridin-2-yl-]

Z23 = [5-cyanopyrimidin-4-yl-CH2-]

TABLE 1-continued
| Q | Z |
|---|---|
| | |
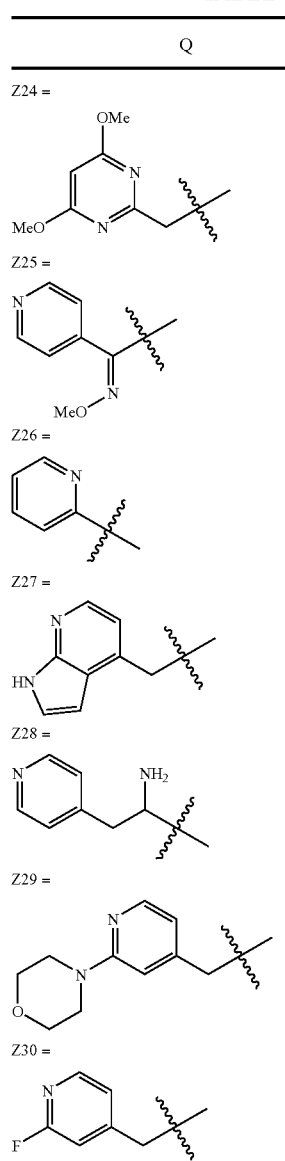
18) The compounds wherein R¹ is a hydrogen atom, R² is bromine, X is a methylene group, Y is —CONH—, and Q and Z are any of the above combinations in Table 1, tautomers, prodrugs or pharmaceutically acceptable salts of the compounds or solvates thereof (provided that in the case of 18), Q1 to Q10 and Z1 to Z30 in Table 1 denote the following substituents).
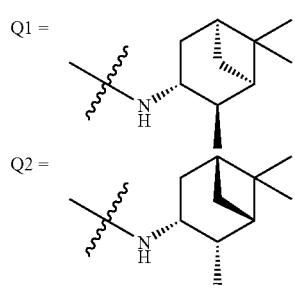
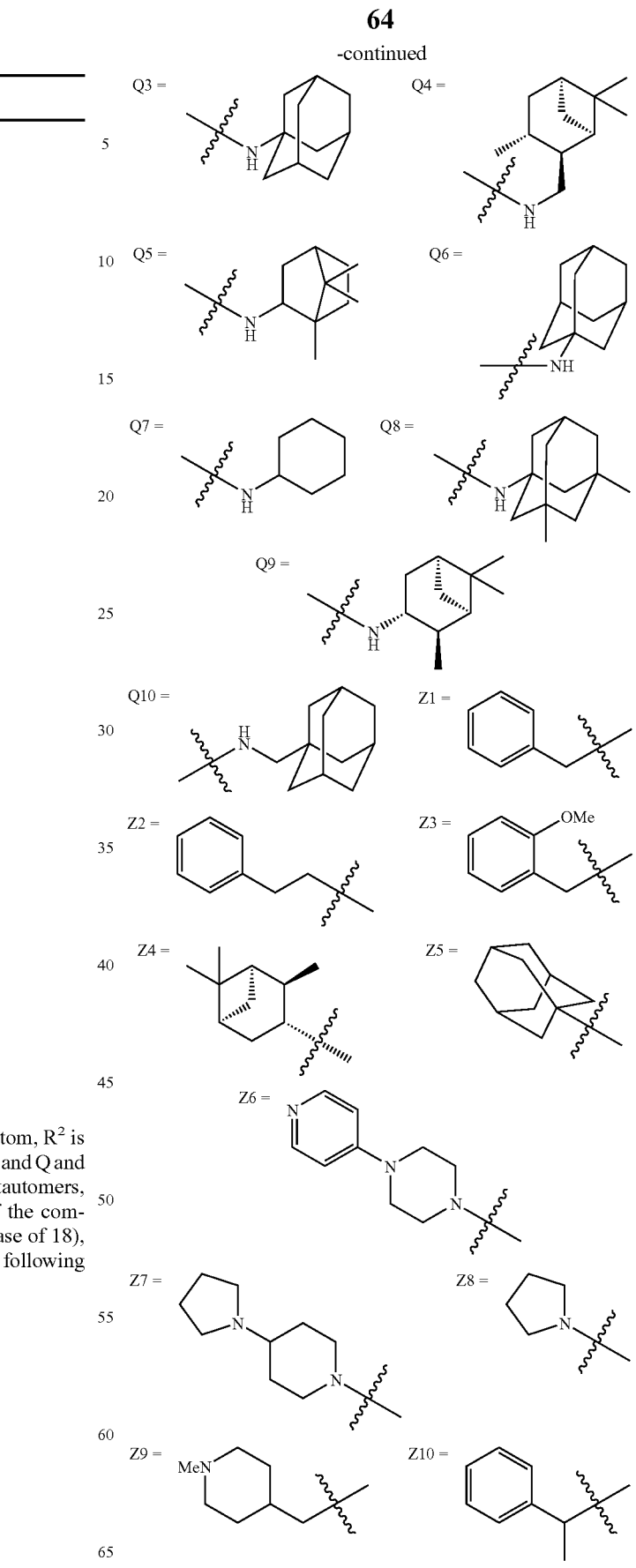

-continued

Z11 = 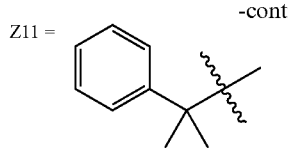
Z12 = 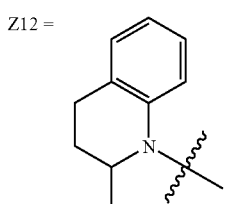
Z13 = 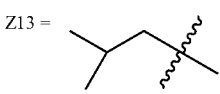
Z14 = 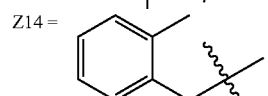
Z15 = 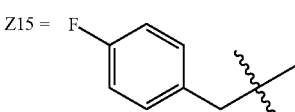
Z16 = 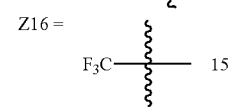
Z17 = 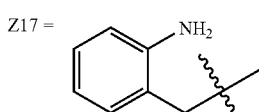
Z18 = 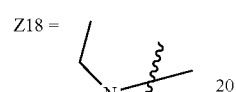
Z19 = 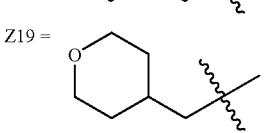
Z20 = 
Z21 = 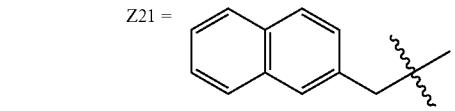
Z22 = 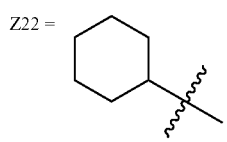
Z23 = 
Z24 = 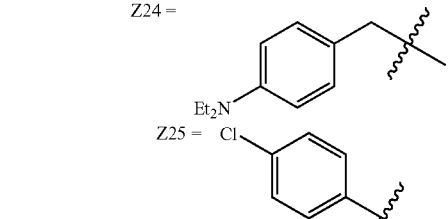
Z25 = 
Z26 = 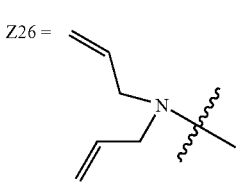
Z27 = 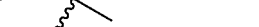
Z28 = 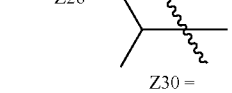
Z29 = 
Z30 = 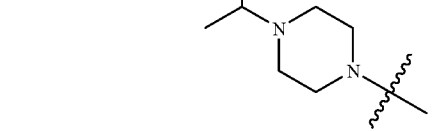

prodrugs or pharmaceutically acceptable salts of the compounds or solvates thereof (provided that in the case of 19), Q1 to Q10 and Z1 to Z30 in Table 1 denote the following substituents).

Q1 = 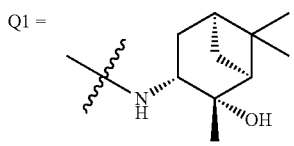
Q2 = 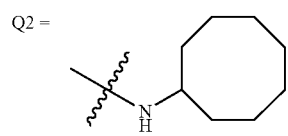
Q3 = 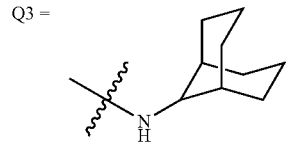
Q4 = 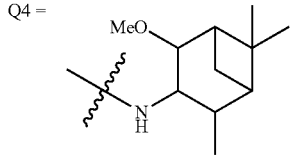
Q5 = 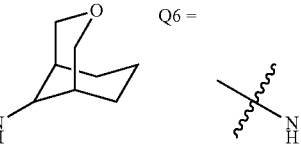
Q6 = 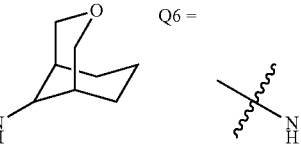
Q7 = 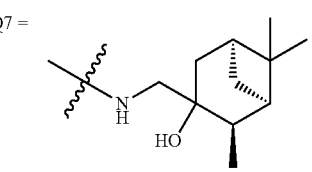
Q8 = 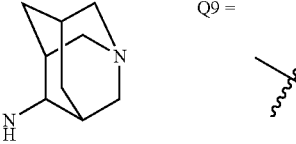
Q9 = 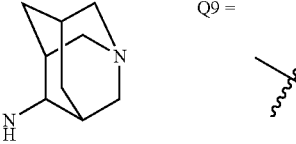
Q10 = 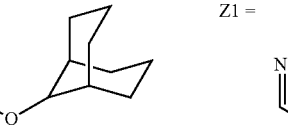
Z1 = 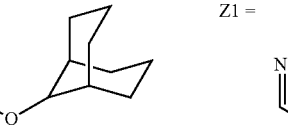
Z2 = 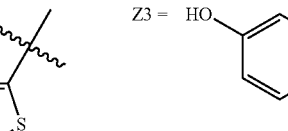
Z3 = 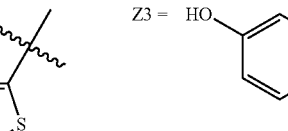
Z4 = 
Z5 = 

19) The compounds wherein $R^1$ is a hydrogen atom, $R^2$ is bromine, X is a methylene group, Y is —CONH—, and Q and Z are any of the above combinations in Table 1, tautomers, -continued Z6 = 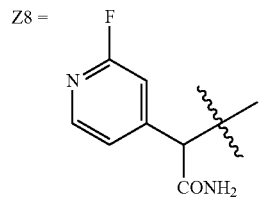
Z7 = 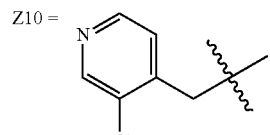
Z8 = 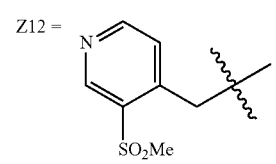
Z9 = 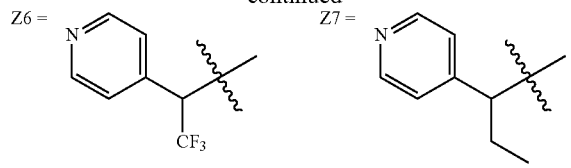
Z10 = 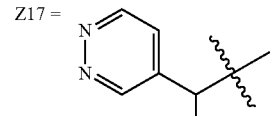
Z11 = 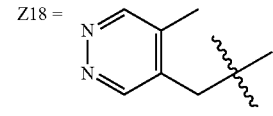
Z12 = 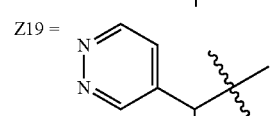
Z13 = 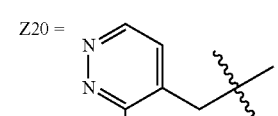
Z14 = 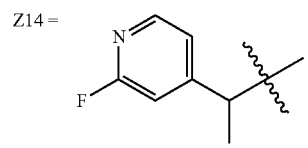
Z15 = 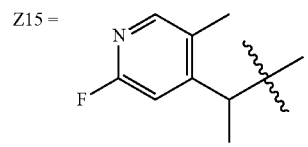
Z16 = 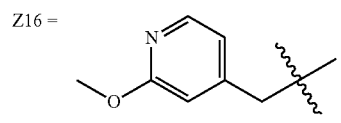
Z17 = 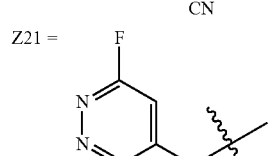
Z18 = 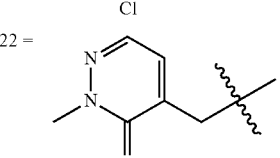
Z19 = 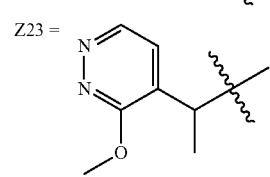
Z20 = 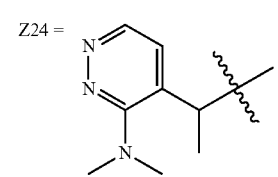
Z21 = 
Z22 = 
Z23 = 
Z24 =

-continued

Z25 = 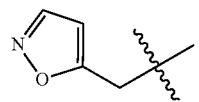
Z26 = 
Z27 = 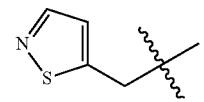
Z28 = 
Z29 = 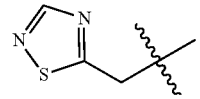
Z30 =

20) The compounds wherein $R^1$ is a hydrogen atom, $R^2$ is bromine, X is a methylene group, Y is —CONH—, and Q and Z are any of the above combinations in Table 1, tautomers, prodrugs or pharmaceutically acceptable salts of the compounds or solvates thereof (provided that in the case of 20), Q1 to Q10 and Z1 to Z30 in Table 1 denote the following substituents).

Q1 = 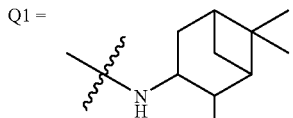
Q2 = 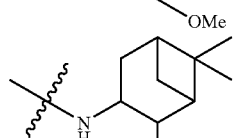
Q3 = 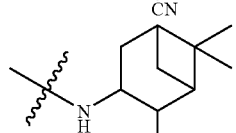
Q4 = 
Q5 = 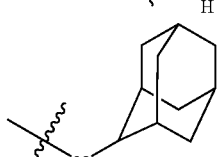
Q6 = 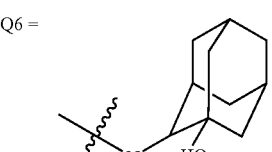
Q7 = 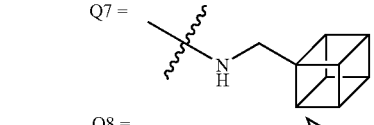
Q8 = 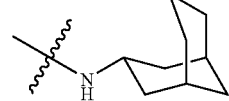

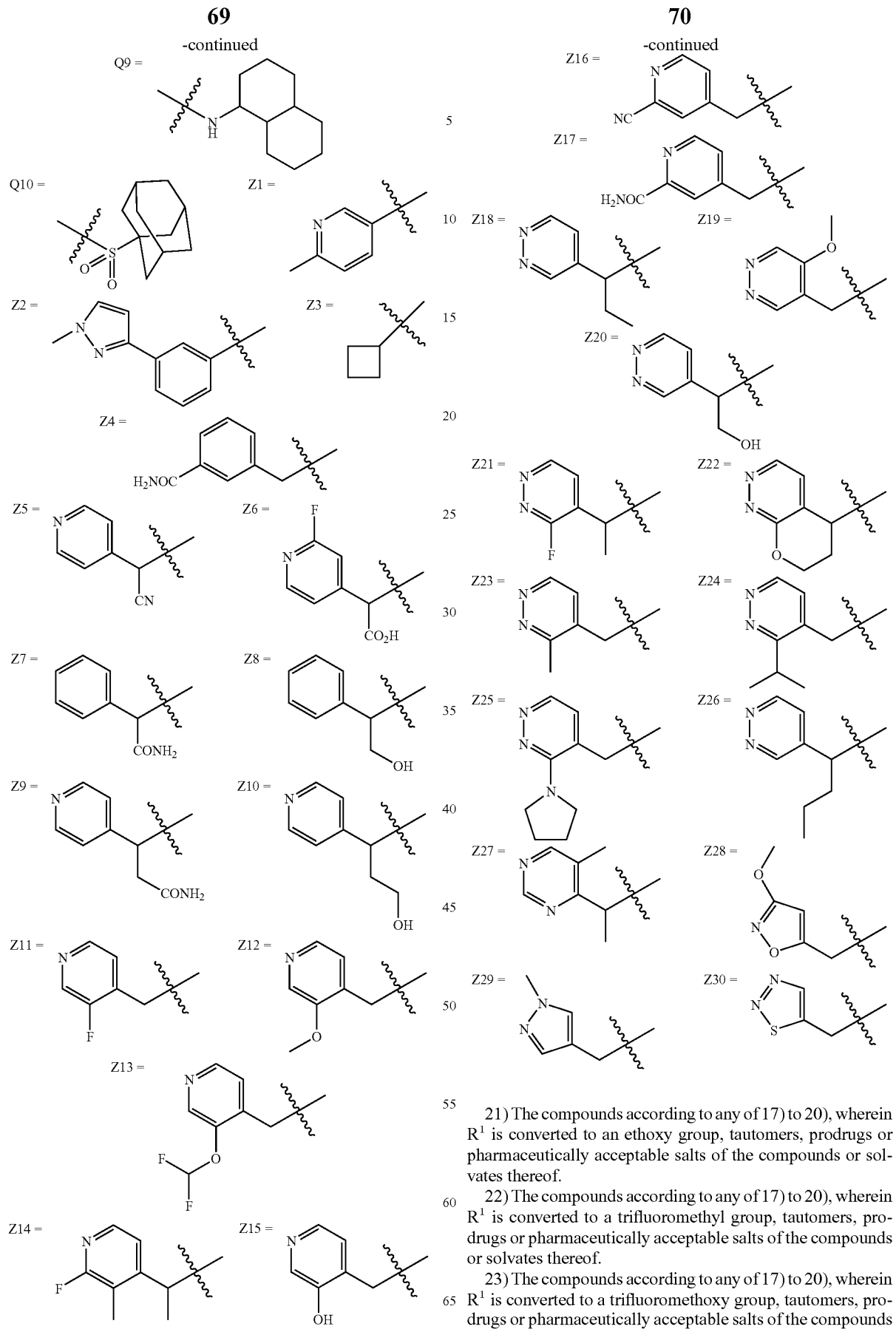

21) The compounds according to any of 17) to 20), wherein $R^1$ is converted to an ethoxy group, tautomers, prodrugs or pharmaceutically acceptable salts of the compounds or solvates thereof.

22) The compounds according to any of 17) to 20), wherein $R^1$ is converted to a trifluoromethyl group, tautomers, prodrugs or pharmaceutically acceptable salts of the compounds or solvates thereof.

23) The compounds according to any of 17) to 20), wherein $R^1$ is converted to a trifluoromethoxy group, tautomers, prodrugs or pharmaceutically acceptable salts of the compounds or solvates thereof.

24) The compounds according to any of 17) to 23), wherein R² is converted to chlorine, tautomers, prodrugs or pharmaceutically acceptable salts of the compounds or solvates thereof.

25) The compounds according to any of 17) to 23), wherein R² is converted to iodine, tautomers, prodrugs or pharmaceutically acceptable salts of the compounds or solvates thereof.

26) The compounds according to any of 17) to 23), wherein R² is converted to fluorine, tautomers, prodrugs or pharmaceutically acceptable salts of the compounds or solvates thereof.

27) The compounds according to any of 17) to 23), wherein R² is converted to a trifluoromethyl group, tautomers, prodrugs or pharmaceutically acceptable salts of the compounds or solvates thereof.

28) The compounds according to any of 17) to 23), wherein R² is converted to a methyl group, tautomers, prodrugs or pharmaceutically acceptable salts of the compounds or solvates thereof.

29) The compounds according to any of 17) to 23), wherein R² is converted to a methylthio group, tautomers, prodrugs or pharmaceutically acceptable salts of the compounds or solvates thereof.

30) The compounds according to any of 17) to 23), wherein R² is converted to a methylsulfonyl group, tautomers, prodrugs or pharmaceutically acceptable salts of the compounds or solvates thereof.

31) The compounds according to any of 17) to 23), wherein R² is converted to an ethylthio group, tautomers, prodrugs or pharmaceutically acceptable salts of the compounds or solvates thereof.

32) The compounds according to any of 17) to 23), wherein R² is converted to an ethylsulfonyl group, tautomers, prodrugs or pharmaceutically acceptable salts of the compounds or solvates thereof.

33) The compounds according to any of 17) to 23), wherein R² is converted to a cyclopropyl group, tautomers, prodrugs or pharmaceutically acceptable salts of the compounds or solvates thereof.

34) The compounds according to any of 17) to 23), wherein R² is converted to a cyclohexyl group, tautomers, prodrugs or pharmaceutically acceptable salts of the compounds or solvates thereof.

35) The compounds according to any of 17) to 23), wherein R² is converted to a trifluoromethoxy group, tautomers, prodrugs or pharmaceutically acceptable salts of the compounds or solvates thereof.

36) The compounds according to any of 17) to 23), wherein R² is converted to a difluoromethoxy group, tautomers, prodrugs or pharmaceutically acceptable salts of the compounds or solvates thereof.

37) The compounds according to any of 17) to 36), wherein X is converted to an ethylene group, tautomers, prodrugs or pharmaceutically acceptable salts of the compounds or solvates thereof.

38) The compounds according to any of 17) to 36), wherein X is converted to the following structure, tautomers, prodrugs or pharmaceutically acceptable salts of the compounds or solvates thereof.

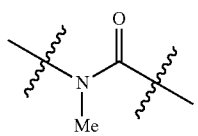

39) The compounds according to any of 17) to 36), wherein X is converted to the following structure, tautomers, prodrugs or pharmaceutically acceptable salts of the compounds or solvates thereof.

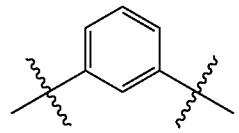 [SMILES: *c1cccc(*)c1]

40) The compounds according to any of 17) to 36), wherein X is converted to the following structure, tautomers, prodrugs or pharmaceutically acceptable salts of the compounds or solvates thereof.

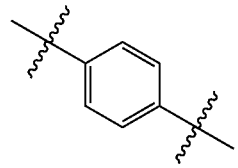 [SMILES: *c1ccc(*)cc1]

41) The compounds according to any of 17) to 36), wherein X is converted to a single bond, tautomers, prodrugs or pharmaceutically acceptable salts of the compounds or solvates thereof.

42) The compounds according to any of 17) to 41), wherein Y is converted to —CSNH—, tautomers, prodrugs or pharmaceutically acceptable salts of the compounds or solvates thereof.

43) The compounds according to any of 17) to 41), wherein Y is converted to —CO—, tautomers, prodrugs or pharmaceutically acceptable salts of the compounds or solvates thereof.

44) The compounds according to any of 17) to 41), wherein Y is converted to —CS—, tautomers, prodrugs or pharmaceutically acceptable salts of the compounds or solvates thereof.

45) The compounds according to any of 17) to 41), wherein Y is converted to a methylene group, tautomers, prodrugs or pharmaceutically acceptable salts of the compounds or solvates thereof.

46) The compounds according to any of 17) to 41), wherein Y is converted to —NH—, tautomers, prodrugs or pharmaceutically acceptable salts of the compounds or solvates thereof.

47) The compounds according to any of 17) to 41), wherein Y is converted to the following structure, tautomers, prodrugs or pharmaceutically acceptable salts of the compounds or solvates thereof.

48) The compounds according to any of 17) to 41), wherein Y is converted to the following structure, tautomers, prodrugs or pharmaceutically acceptable salts of the compounds or solvates thereof.

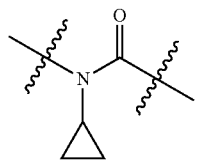 [SMILES: *C(=O)N(*)C1CC1]

49) The compounds according to any of 17) to 41), wherein Y is converted to the following structure, tautomers, prodrugs or pharmaceutically acceptable salts of the compounds or solvates thereof.

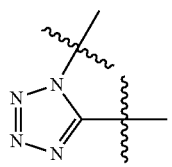 [SMILES: *c1nnnn1*]

50) The compounds according to any of 17) to 41), wherein Y is converted to —NHCO—, tautomers, prodrugs or pharmaceutically acceptable salts of the compounds or solvates thereof.

51) The compounds according to any of 17) to 41), wherein Y is converted to —O—, tautomers, prodrugs or pharmaceutically acceptable salts of the compounds or solvates thereof.

52) The compounds according to any of 17) to 41), wherein Y is converted to —S—, tautomers, prodrugs or pharmaceutically acceptable salts of the compounds or solvates thereof.

53) The compounds according to any of 17) to 41), wherein Y is converted to a single bond, tautomers, prodrugs or pharmaceutically acceptable salts of the compounds or solvates thereof.

54) The compounds according to any of 17) to 20), wherein $R^1$ is converted to an ethoxy group, and $R^2$ is converted to a phenyl group, tautomers, prodrugs or pharmaceutically acceptable salts of the compounds or solvates thereof.

55) The compounds according to any of 17) to 20), wherein $R^1$ is converted to a trifluoromethyl group, and $R^2$ is converted to a phenyl group, tautomers, prodrugs or pharmaceutically acceptable salts of the compounds or solvates thereof.

56) The compounds according to any of 17) to 20), wherein $R^2$ is converted to a phenyl group, tautomers, prodrugs or pharmaceutically acceptable salts of the compounds or solvates thereof.

57) The compounds according to any of 54) to 56), wherein $R^2$ is converted to a 4-pyridyl group, tautomers, prodrugs or pharmaceutically acceptable salts of the compounds or solvates thereof.

58) The compounds according to any of 54) to 56), wherein $R^2$ is converted to a 5-pyrimidyl group, tautomers, prodrugs or pharmaceutically acceptable salts of the compounds or solvates thereof.

59) P2X7 receptor inhibitors containing the compounds according to any of 1) to 58), tautomers, prodrugs or pharmaceutically acceptable salts of the compounds or solvates thereof, as an active ingredient.

60) Preventive, therapeutic and improving agents for diseases against which inhibition of the P2X7 receptor is effective, which contain the P2X7 receptor inhibitors according to 59) as an active ingredient.

61) Therapeutic agent for rheumatoid arthritis containing the P2X7 receptor inhibitors according to 59) as an active ingredient.

62) Medicament containing the compound according to any of 1) to 58), tautomers, prodrugs or pharmaceutically acceptable salts of the compounds or solvates thereof, as an active ingredient.

In the present invention, the compounds of the present invention represented by the formula (I) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios. Further, when the compounds of the present invention have two or more asymmetric centers, the compounds of the present invention can be in the form of diastereomers dues to optical isomerism about them. The compounds of the present invention may be in the form of a mixture of all these isomers in certain ratios. For example, diastereomer can be separated by techniques known well to those skilled in the art such as fractional crystallization, and optical isomers can be obtained by techniques well known in the field of organic chemistry for this purpose.

The compounds of the present invention represented by the formula (I) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds of the present invention represented by the formula (I) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, tartaric acid, benzenesulfonic acid, methanesulfonic acid and p-toluenesulfonic acid).

The compounds which serve as prodrugs are derivatives of the present invention having chemically or metabolically degradable groups which give pharmacologically active compounds of the present invention upon solvolysis or under physiological conditions in vivo. Methods for selecting or producing appropriate prodrugs are disclosed, for example, in Design of Prodrugs (Elsevier, Amsterdam 1985).

In the present invention, when the compound has a hydroxy group, acyloxy derivatives obtained by reacting the compound with appropriate acyl halides or appropriate acid anhydrides may, for example, be mentioned as prodrugs. Acyloxys particularly preferred as prodrugs include —OCOC$_2$H$_5$, —OCO(t-Bu), —OCOC$_{15}$H$_{31}$, —OCO(m-CO$_2$Na-Ph), —OCOCH$_2$CH$_2$CO$_2$Na, —OCOCH(NH$_2$)CH$_3$, —OCOCH$_2$N(CH$_3$)$_2$ and the like. When the compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —NHCO(CH$_2$)$_{20}$OCH$_3$, —NHCOCH(NH$_2$)CH$_3$ and the like.

The preventive, therapeutic and improving agents for diseases against which inhibition of the P2X7 receptor is effective which contain the P2X7 receptor inhibitors of the present invention, as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of medical compositions. These pharmaceutical preparations can be obtained by adding pharmacologically and pharmaceutically acceptable additives by conventional methods. Namely, for oral medicines, ordinary additives such as excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1000 mg/human/day in the case of oral drugs or rectal administration and about from 0.05 mg to 500 mg/human/day in the case of injections, though it depends on the age and conditions of the patient. The above-mentioned ranges are mere examples, and the dose should be determined from the conditions of the patient.

The present invention is used when the use of compounds which inhibit the P2X7 receptor are expected to improve pathological conditions. Such cases include, for example, prevention and therapy of swelling, exacerbation of pain and bone metabolism in rheumatoid arthritis, prevention and therapy of inflammatory bowel diseases, chronic obstructive pulmonary disease (COPD) and osteoarthritis, prevention and therapy of inflammatory pain and cancer pain and IL-1β-associated diseases such as Crohn's disease, emphysema, acute respiratory distress syndrome, adult respiratory distress syndrome, asthma, bronchitis, chronic pulmonary inflammatory diseases, silicosis, pulmonary sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, loosening of artificial joint implants, atherosclerosis, aortic aneurysm, congestive heart failure, myocardial infarction, stroke, cerebral ischemia, head trauma, neurotrauma, spinal cord injury, neurodegenerative disorder, Alzheimer's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, corneal scarring, scleritis, abnormal wound healing, burns, autoimmune diseases, Huntington's disease, diabetes, AIDS, cachexia, sepsis, septic shock, endotoxin shock, conjunctivitis shock, gram-negative sepsis, toxic shock syndrome, cerebral malaria, cardiac and renal reperfusion injury, thrombosis, glomerulonephritis, graft-versus-host reaction, homograft rejection, organ transplant toxicity, ulcerative colitis or muscle degeneration, but there is no restriction.

The compounds of the present invention can be prepared generally, but not restrictively, by the processes described below.

The compounds of the present invention can usually be purified by column chromatography, thin layer chromatography, high performance liquid chromatography (HPLC) or high performance liquid chromatography-mass spectrometry (LC-MS) and, if necessary, they may be obtained with high purity by recrystallization or washing with solvents.

As the base mentioned in the general processes for producing the compounds of the present invention, an alkali metal salt such as sodium carbonate, potassium carbonate, cesium carbonate, sodium hydrogen carbonate, potassium hydrogen carbonate, potassium hydroxide, sodium hydroxide, sodium hydride, lithium hydride, sodium amide, potassium t-butoxide, sodium t-butoxide, n-butyllithium or lithium diisopropylamide, an amine such as pyridine, triethylamine, diisopropylethylamine, pyrrolidine or N-methylpiperidine, a silane reagent represented by hexamethyldisilazane, sodium acetate or potassium acetate may be mentioned.

In the general processes for producing the compounds of the present invention, any solvent that is stable under the reaction conditions and inert enough not to hinder the reaction may be used without any particular restrictions, and for example, a sulfoxide solvent represented by dimethyl sulfoxide, an amide solvent represented by N,N-dimethylformamide or N,N-dimethylacetamide, an ether solvent represented by diethyl ether, dimethoxyethane, tetrahydrofuran, 1,4-dioxane or cyclopentyl methyl ether, a halogenated solvent represented by dichloromethane, chloroform or dichloroethane, a nitrile solvent represented by acetonitrile or propionitrile, an aromatic hydrocarbon solvent represented by benzene or toluene, a hydrocarbon solvent represented by hexane or heptane, an ester solvent represented by ethyl acetate, an alcohol solvent represented by methanol, ethanol, 1-propanol, 2-propanol or ethylene glycol or water may be mentioned. The reactions may be carried out in an arbitrary mixture of the above-mentioned solvents or in the absence of a solvent.

In the general process for producing the compounds of the present invention, the reaction temperature is selected appropriately from the range between −78° C. and the boiling point of the solvent used in the reaction, and the processes can be carried out under ordinary pressure or with application of pressure or microwave irradiation.

In the following description of the processes for producing the compounds of the present invention, the general formulae for the intermediates obtained in the respective steps of the processes for producing the compounds of the present invention and the end products of the processes cover precursors thereof. Herein, precursors mean compounds which can be converted to the desired products, if necessary, by hydrolysis, deprotection, reduction, oxidation, alkylation or the like, and for example, cover compounds protected by protecting groups acceptable in the field of organic chemistry. Protection and deprotection can be carried out by generally known protection and deprotection reactions (Protective Groups in Organic Synthesis, Fourth edition, written by T. W. Green, John Wiley & Sons Inc. (2006)).

For generally known syntheses of pyridazinone compounds, the following may be referred to:

New Heterocyclic Compounds (Shinpen Heterokan-Kagoubutsu) Basics (Kodansha 2004) pp. 1-14, 69-132, 176-207

Journal of Heterocyclic Chemistry, 33(6), 1579-1582; 1996

Comprehensive Heterocyclic Chemistry, Vol. 3, Part 2B, Pergamon Press

Journal of Heterocyclic Chemistry, 42, 427-435: 2005

WO9501343 and the like.

The compounds represented by the formula (I) wherein Q is represented by the following structure are prepared, for example, by the process represented by the following scheme (1).

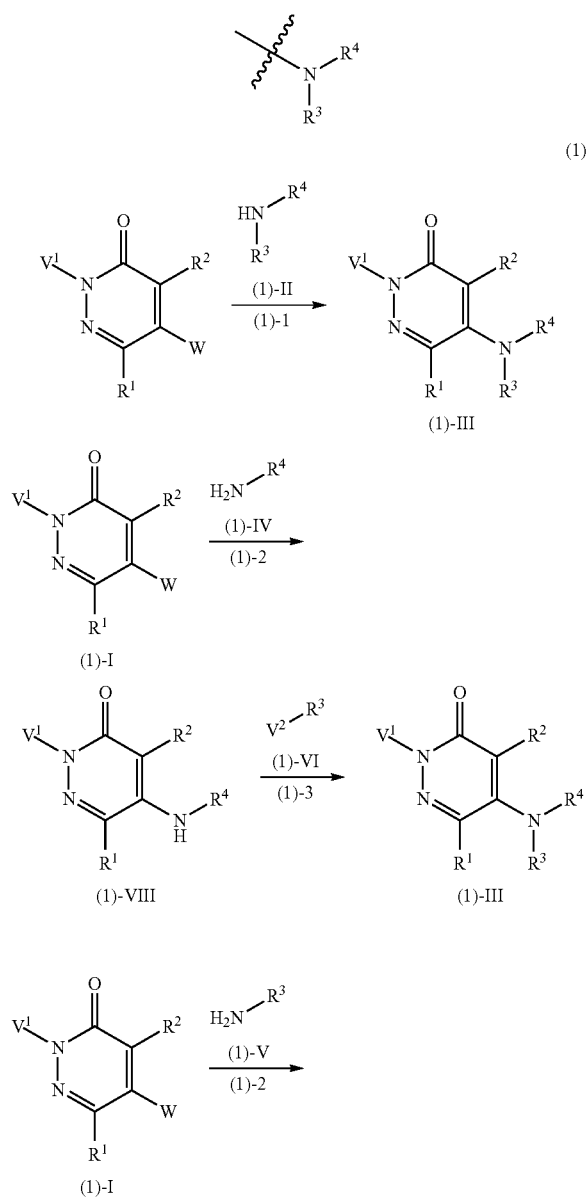

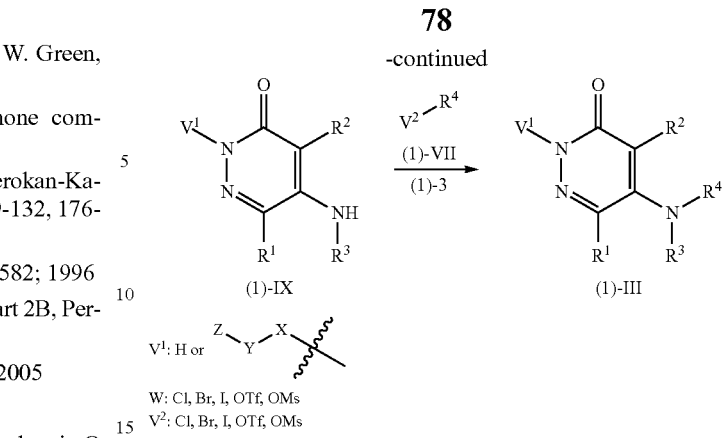

The reaction of (1)-I with an amine (1)-II, (1)-IV or (1)-V in a solvent with stirring, if necessary in the presence of a catalyst and/or a base such as potassium carbonate or triethylamine, if necessary under heating, gives (1)-III, (1)-VIII, (1)-IX or a precursor thereof (steps (1)-1 and (1)-2).

The subsequent reaction of (1)-VIII with (1)-VI or reaction of (1)-IX with (1)-VII in a solvent with stirring, if necessary in the presence of a catalyst and/or a base such as potassium carbonate or triethylamine, if necessary under heating, gives (1)-III or a precursor thereof (step (1)-3).

The compounds of the formula (I) wherein Q is either of the following structures are prepared, for example, by the process represented by the following scheme (2).

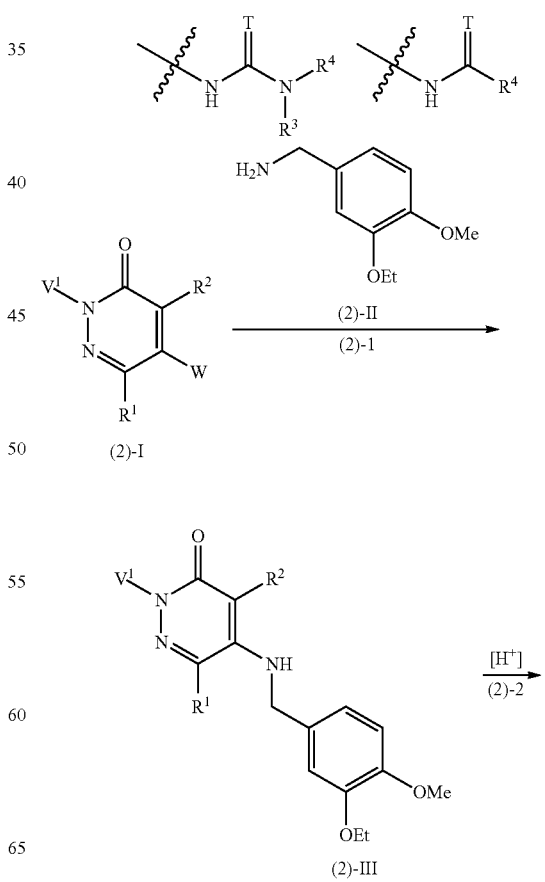

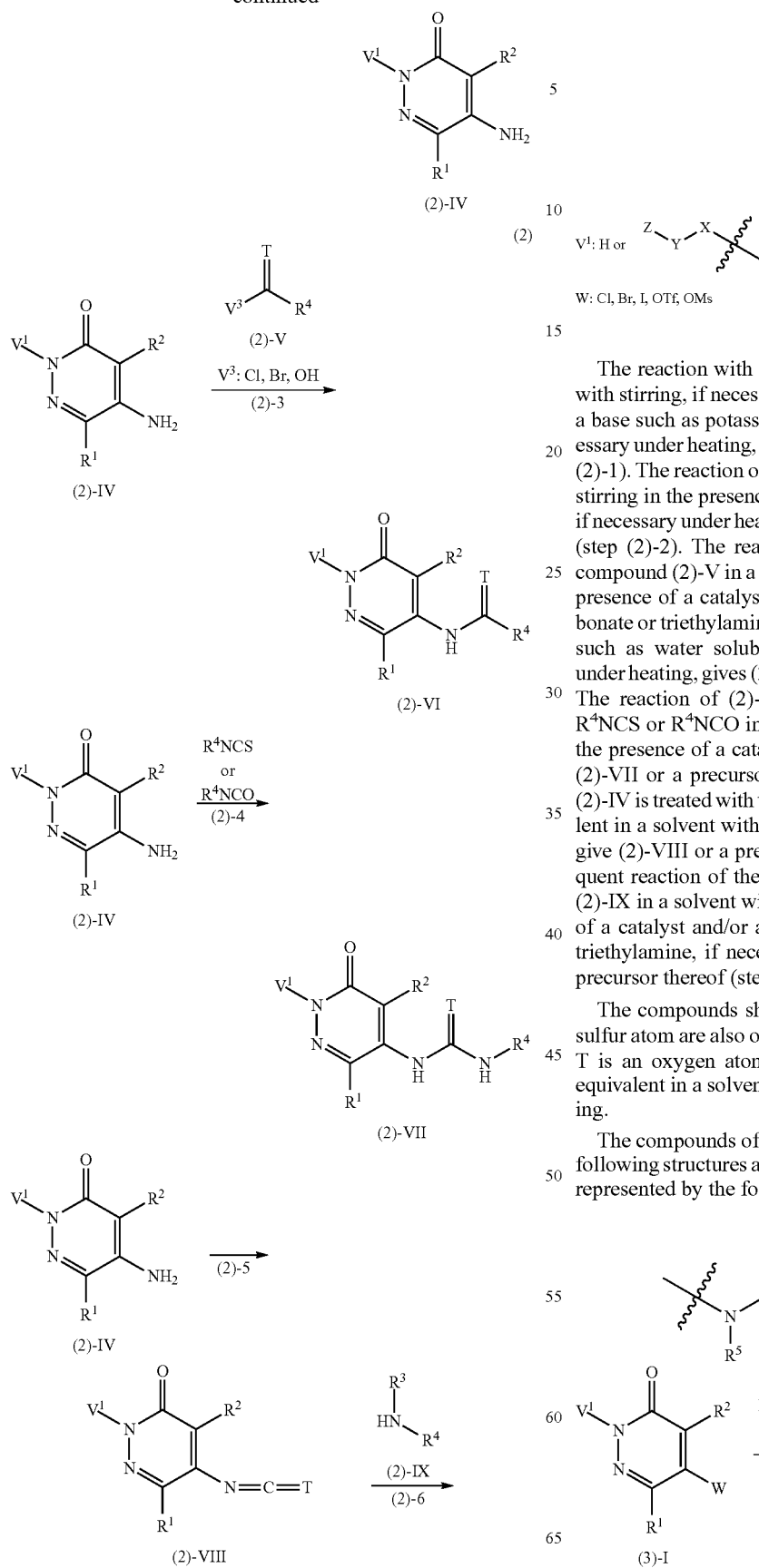

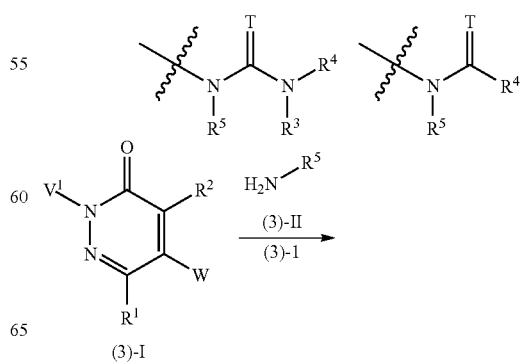

The reaction with compound (2)-I and (2)-II in a solvent with stirring, if necessary in the presence of a catalyst and/or a base such as potassium carbonate or triethylamine, if necessary under heating, gives (2)-III or a precursor thereof (step (2)-1). The reaction of the compound (2)-III in a solvent with stirring in the presence of an acid such as hydrochloric acid, if necessary under heating, gives (2)-IV or a precursor thereof (step (2)-2). The reaction of the compound (2)-IV with a compound (2)-V in a solvent with stirring, if necessary in the presence of a catalyst and/or a base such as potassium carbonate or triethylamine and/or by using a condensation agent such as water soluble carbodiimide (WSC), if necessary under heating, gives (2)-VI or a precursor thereof (step (2)-3). The reaction of (2)-IV with a compound represented by $R^4NCS$ or $R^4NCO$ in a solvent with stirring, if necessary in the presence of a catalyst, if necessary under heating, gives (2)-VII or a precursor thereof (step (2)-4). The compound (2)-IV is treated with thiophosgene, phosgene or their equivalent in a solvent with stirring, if necessary under heating, to give (2)-VIII or a precursor thereof (step (2)-5). The subsequent reaction of the compound (2)-VIII with a compound (2)-IX in a solvent with stirring, if necessary in the presence of a catalyst and/or a base such as potassium carbonate or triethylamine, if necessary under heating, gives (2)-X or a precursor thereof (step (2)-6).

The compounds shown in the scheme (2) wherein T is a sulfur atom are also obtainable from the compounds wherein T is an oxygen atom by using Lawesson's reagent or its equivalent in a solvent with stirring, if necessary under heating.

The compounds of the formula (I) wherein Q is any of the following structures are prepared, for example, by the process represented by the following scheme (3).

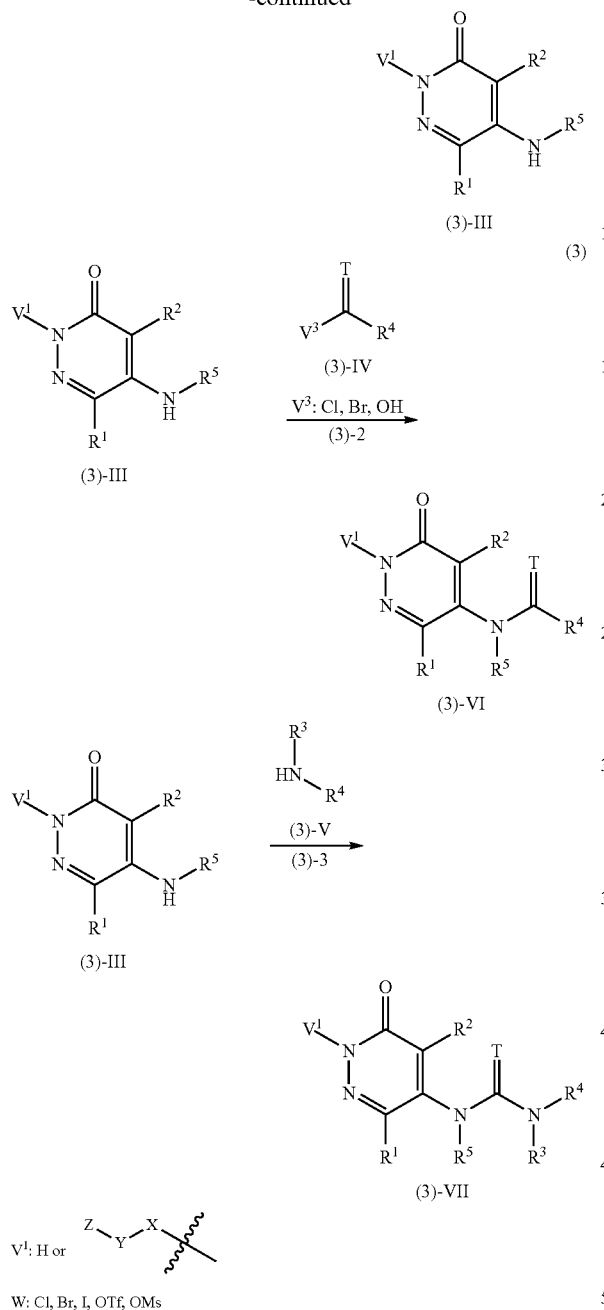

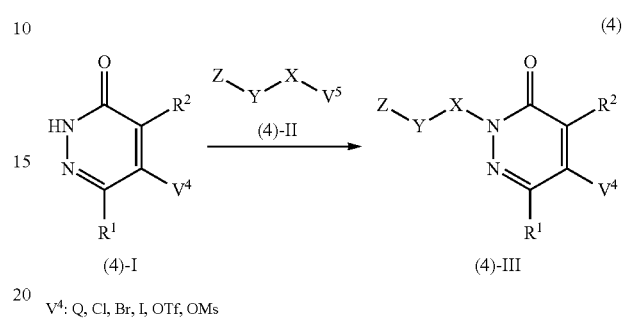

T is an oxygen atom by using Lawesson's reagent or its equivalent in a solvent with stirring, if necessary under heating.

The compounds of the formula (I) wherein X is a $C_{1-6}$ alkylene group are prepared, for example, by the process represented by the following scheme (4).

$V^4$: Q, Cl, Br, I, OTf, OMs

The reaction of compounds (4)-I and (4)-II in a solvent with stirring, if necessary in the presence of a catalyst and/or a base such as potassium carbonate or triethylamine, if necessary under heating, gives (4)-III or a precursor thereof.

The compounds of the formula (I) wherein X is a single bond or a $C_{1-6}$ alkylene group, and each of Y and Z is either of the following structures:

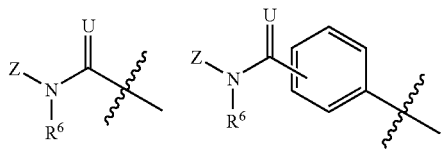

or X is a single bond or $C_{1-6}$ alkylene group, Y is either of the following structures:

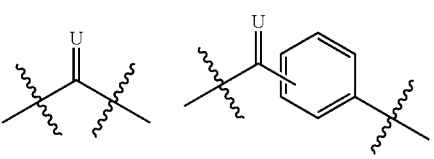

The reaction of compound (3)-I and (3)-II in a solvent with stirring, if necessary in the presence of a catalyst and/or a base such as potassium carbonate or triethylamine, if necessary under heating, gives (3)-III (step (3)-1). The reaction of the compound (3)-III with a compound (3)-IV in a solvent with stirring, if necessary in the presence of a catalyst and/or a base such as potassium carbonate or triethylamine and/or by using a condensation agent such as WSC, if necessary under heating, gives (3)-VI or a precursor thereof (step (3)-2). The compound (3)-III is treated with phosgene, thiophosgene or their equivalent in a solvent with stirring, if necessary under heating, and then reacted with (3)-V to give (3)-VII or a precursor thereof (step (3)-3).

The compounds shown in the scheme (3) wherein T is a sulfur atom are also obtainable from the compounds wherein and Z is a heterocyclyl group are prepared, for example, by the process represented by the following scheme (5).

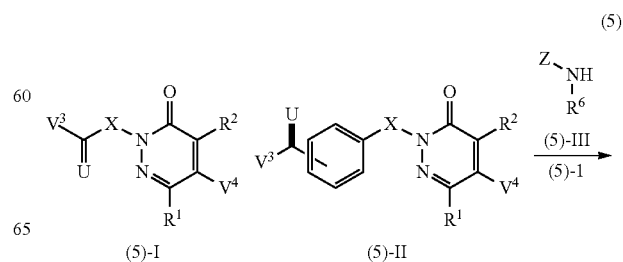

-continued

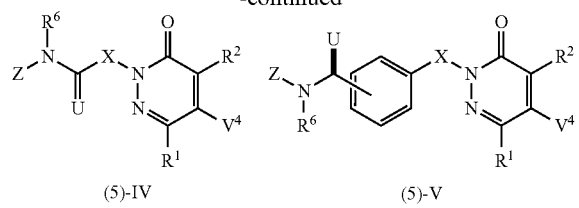

(5)-IV    (5)-V $V^3$: OH, Cl, Br
$V^4$: Q, Cl, Br, I, OTf, OMs

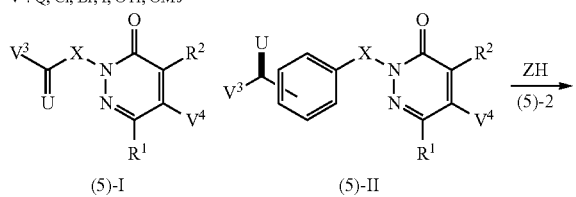

(5)-I    (5)-II

(5)-VI    (5)-VII $V^3$: OH, Cl, Br
$V^4$: Q, Cl, Br, I, OTf, OMs

The reaction of a compound (5)-I or (5)-II with a compound (5)-III in a solvent with stirring, if necessary in the presence of a catalyst and/or a base such as potassium carbonate or triethylamine, and/or by using a condensation agent such as WSC, if necessary under heating, gives (5)-IV or (5)-V or a precursor thereof (step (5)-1).

The reaction of a compound (5)-I or (5)-II with a compound ZH (wherein Z means a heterocyclyl group) in a solvent with stirring, if necessary in the presence of a catalyst and/or a base such as potassium carbonate or triethylamine and/or by using a condensation agent such as WSC, if necessary under heating, gives (5)-VI or (5)-VII or a precursor thereof (step (5)-2).

The compounds shown in the scheme (5) wherein U is a sulfur atom are also obtainable from the compounds wherein U is an oxygen atom by using Lawesson's reagent or its equivalent in a solvent with stirring, if necessary under heating.

The compounds shown in the scheme (5) wherein U is $NOR^{10}$ are also obtainable from the compounds wherein U is an oxygen atom in a solvent with stirring by using $H_2NOR^{10}$ or its equivalent, if necessary in the presence of an acid or a base if necessary under heating.

The compounds of the formula (I) wherein X is a $C_{1-6}$ alkylene, and each of Y and Z is any of the following structures:

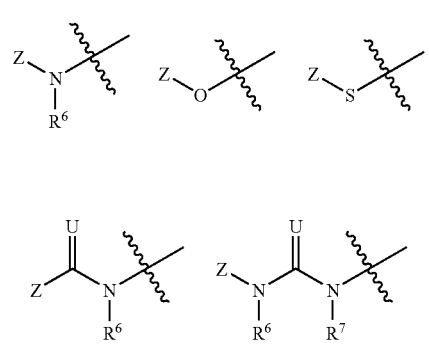

are prepared, for example, by the process represented by the following scheme (6).

(6)

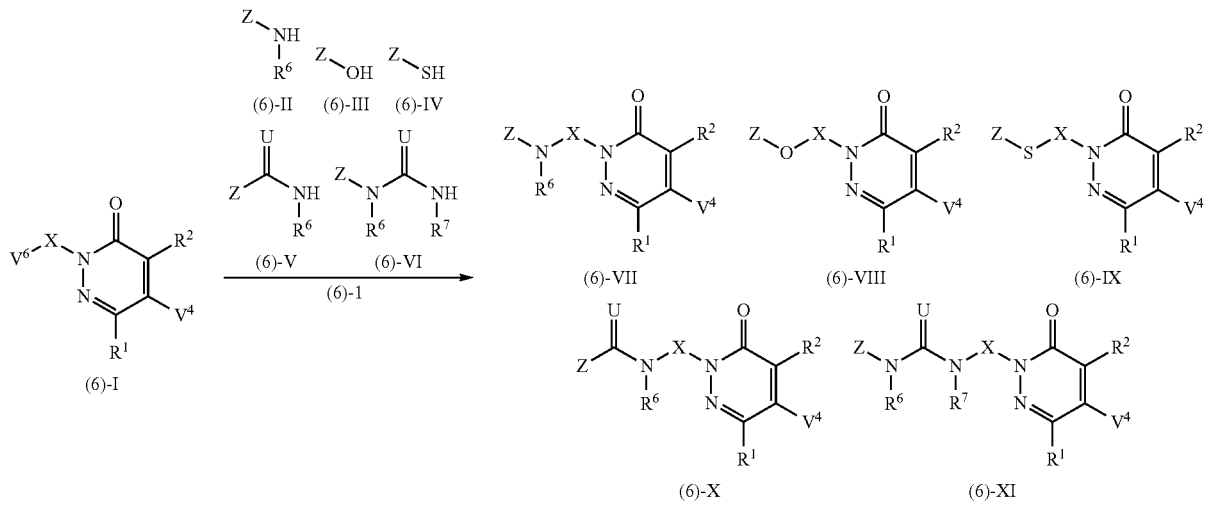

$V^6$: Cl, Br, I, OTf, OMs, OH
$V^4$: Q, Cl, Br, I, OTf, OMs

The reaction of a compound (6)-I with compounds (6)-II to (6)-VI in a solvent with stirring, if necessary in the presence of a catalyst and/or a base such as potassium carbonate or triethylamine and/or under Mitsunobu reaction conditions, if necessary under heating, gives (6)-VII to (6)-XI or precursors thereof (step (6)-1).

The compounds shown in the scheme (6) wherein U is a sulfur atom are also obtainable from the compounds wherein U is an oxygen atom by using Lawesson's reagent or its equivalent in a solvent with stirring, if necessary under heating.

In the compounds (6)-IX, —S— can be converted to —SO— or —$SO_2$— in a solvent with stirring by using an oxidizing agent such as m-chloroperbenzoic acid, if necessary under heating.

The compounds of the formula (I) wherein $R_2$ is a $C_{1-6}$ alkyl group, a $C_{2-6}$ alkenyl group, a $C_{1-6}$ alkoxy group or a $C_{2-14}$ aryl group are prepared, for example, by the process represented by the following scheme (7).

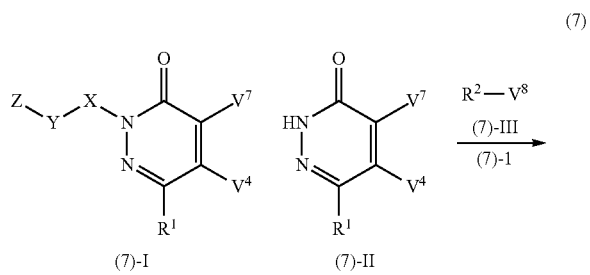

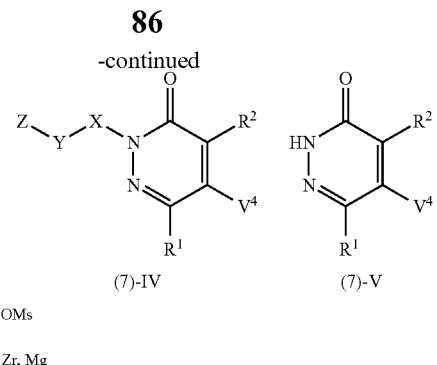

$V^4$: Q, Cl, Br, I, OTf, OMs
$V^7$: Cl, Br, OTf, OMs
$V^8$: B, Sn, Ti, Al, Zn, Zr, Mg

The reaction of (7)-I or (7)-II with an organic metal compounds (7)-III such as organic boronic acid, an organic boronate, an organic tin compound or an organic magnesium compound in a solvent with stirring, if necessary by using a transition metal catalyst such as tetrakistriphenylphosphinopalladium or (1,1'-bis(diphenylphosphino)ferrocene)dichloropalladium and/or a base such as potassium carbonate, triethylamine or sodium carbonate, if necessary under heating, gives (7)-IV or (7)-V or a precursor thereof (step (7)-1). (Organic Synthesis Guided by Transition Metals (Senikinzoku-ga Maneku Yuuki Gosei), written by Jiro Tsuji, 1997, Kagakudojin, and Cross-Coupling Reactions: A Practical Guide (Topics in Current Chemistry, vol. 219), edited by Norio Miyaura, Springer).

The compounds of the formula (I) wherein $R^2$ is a $C_{1-6}$ alkoxy group or a $C_{1-6}$ alkylthio group are prepared, for example, by the process represented by the following scheme (8).

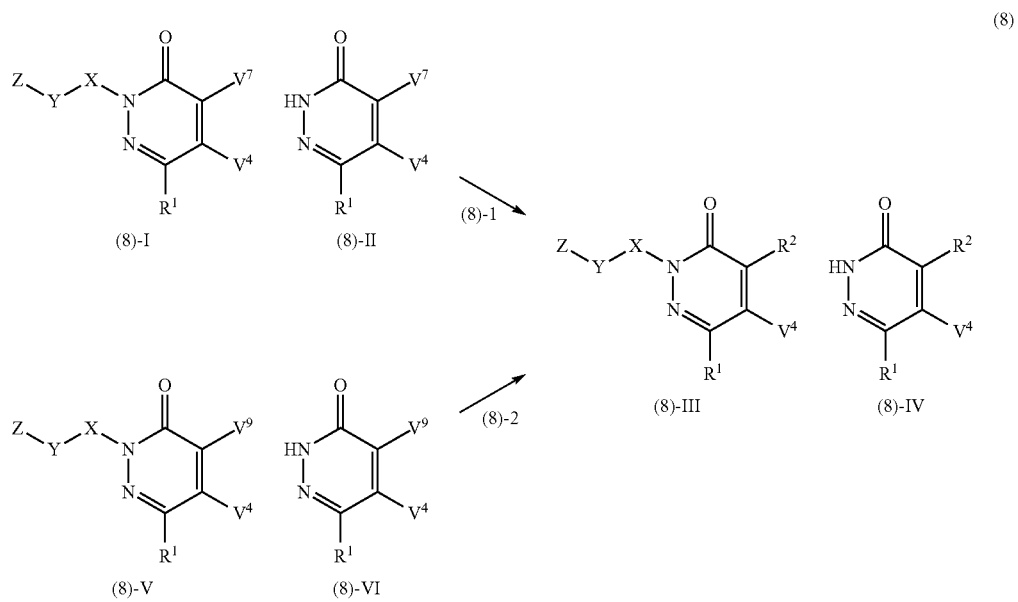

$V^4$: Q, Cl, Br, I, OTf, OMs
$V^7$: Cl, Br, I, OTf, OMs
$V^9$: SH, OH

The reaction of (8)-I or (8)-II with a corresponding alcohol or thiol in a solvent with stirring, if necessary in the presence of a catalyst and/or a base such as sodium hydride, triethylamine or sodium carbonate, if necessary under heating, gives (8)-III or (8)-IV or a precursor thereof (step (8)-1).

The reaction of (8)-V or (8)-VI with a corresponding alkyl halide, alkyl triflate or alcohol in a solvent with stirring, if necessary in the presence of a catalyst and/or a base such as potassium carbonate or triethylamine and/or under Mitsunobu reaction conditions, if necessary under heating, gives (8)-III or (8)-IV or a precursor thereof (step (8)-2).

The compounds of the formula (I) wherein $R^2$ is a $C_{1-6}$ alkylsulfonyl group are prepared, for example, from the compound (8)-III or (8)-IV wherein $R^2$ is a $C_{1-6}$ alkylthio group in a solvent with stirring by using an oxidizing agent such as m-chloroperbenzoic acid, if necessary under heating.

The amine compounds of the formula (1)-II, (1)-IV, (1)-V, 2-IX, 3-II, 3-V, 5-III and (6)-II are prepared from the corresponding nitrile compounds, acid amide compounds, oxime compounds, halides, ketone compounds, aldehyde compounds, alcohol compounds, boron compounds, epoxide compounds, acid imide compounds, carbamate compound and the like (Jikken Kagaku Koza 4th Edition, vol. 20, Organic Syntheses II, edited by the Chemical Society of Japan, Maruzen, Bioorganic & Medicinal Chemistry, 13, 4022, 2005, Kuramoti T. et al., Journal of Medicinal Chemistry, 50, 149, 2007, Journal of Organic Chemistry, 44, 2081, 1979, Acta Chemica Scandinavica, 19, 1741, 1965, Organic Letter, 5, 4497, 2003).

The compound of the formula (I) wherein Q is either of the following structures are prepared, for example, by the process represented by the following scheme (9).

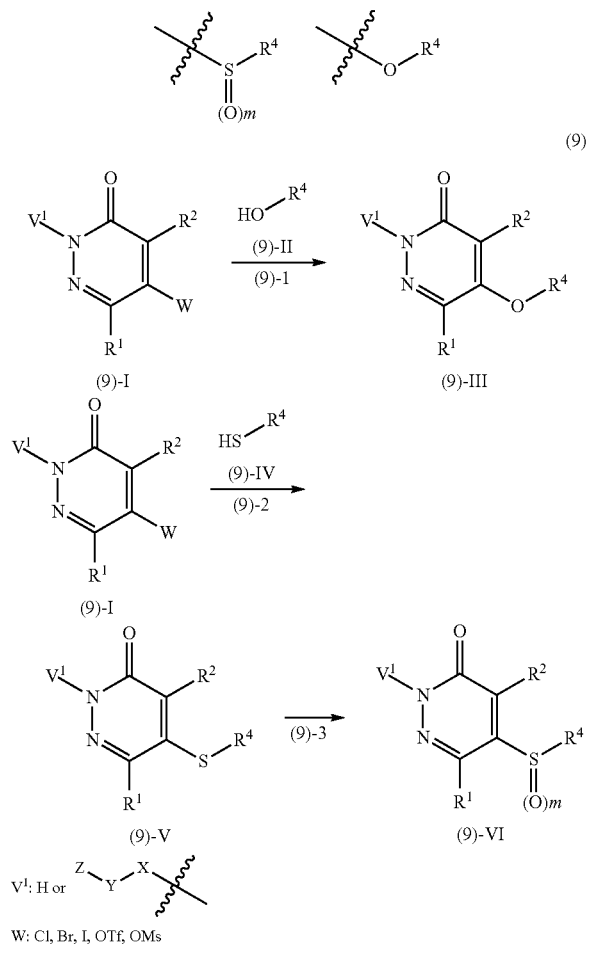

The reaction of (9)-I with an alcohol (9)-II or a thiol (9)-IV in a solvent with stirring, if necessary in the presence of a catalyst and/or a base such as potassium carbonate or triethylamine, if necessary under heating, gives (9)-III or (9)-V or a precursor thereof (steps (9)-1 and (9)-2).

The subsequent reaction of (9)-V in a solvent with stirring using an oxidizing agent such as m-chloroperbenzoic acid, if necessary under heating, can convert —S— to —SO— or —SO$_2$— (step (9)-3).

Now, the present invention will be described in further detail with reference to Reference Synthetic Examples, Synthetic Examples, Assay Examples and Formulation Examples. However, it should be understood that the present invention is by no means restricted by these specific Examples.

The $^1$H-NMR analysis was carried out at 300 MHz, and LC/MS was measured under the following conditions.

The compositions of the eluents used in silica gel column chromatography are represented on a volume basis.

LC/MS Condition 1

Column: Waters SunFire C18 (3.5 μm, 4.6×30 mm)

Eluent: acetonitrile/0.1 volume % aqueous formic acid (10/90→30/70)

LC/MS Condition 2

Column: Waters SunFire C18 (3.5 μm, 4.6×30 mm)

Eluent: acetonitrile/0.1 volume % aqueous formic acid (10/90→85/15)

LC/MS Conditions 3

Column: Waters Xterra MSC18 (3.5 μm, 2.1×20 mm)

Eluent: acetonitrile/0.2 volume % aqueous formic acid (20/80→90/10)

LC/MS Conditions 4

Column: Waters Xterra MSC18 (3.5 μm, 4.6×30 mm)

Eluent: acetonitrile/0.2 volume % aqueous formic acid (15/85→85/15)

LC/MS Condition 5

Column: Waters SunFire C18 (3.5 μm, 2.1×20 mm)

Eluent: acetonitrile/0.1 volume % aqueous formic acid (10/90→30/70)

LC/MS Condition 6

Column: Waters SunFire C18 (3.5 μm, 2.1×20 mm)

Eluent: acetonitrile/0.1 volume % aqueous formic acid (10/90→60/40)

LC/MS Condition 7

Column: Waters SunFire C18 (3.5 μm, 2.1×20 mm)

Eluent: acetonitrile/0.1 volume % aqueous formic acid (10/90→85/15)

LC/MS Condition 8

Column: Waters SunFire C18 (3.5 μm, 2.1×20 mm)

Eluent: acetonitrile/0.1 volume % aqueous formic acid (20/80→100/0)

LC/MS Condition 9

Column: Waters SunFire C18 (3.5 μm, 2.1×20 mm)

Eluent: acetonitrile/0.1 volume % aqueous formic acid (40/60→100/0)

REFERENCE SYNTHETIC EXAMPLE 1

N-(Pyridin-4-ylmethyl)cyclopropanamine

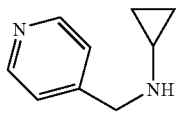 [SMILES: c1cc(CNC2CC2)ccn1]

Cyclopropylamine (69 µL, 0.99 mmol) in ethanol (1 mL) was mixed with 4-pyridinecarbaldehyde (86 µL, 0.99 mmol) at room temperature and refluxed at 90° C. for 2 hours. After completion of the reaction, the ethanol was evaporated azeotropically. The resulting reaction product in methanol (1 mL) was mixed with sodium borohydride (204 mg, 5.40 mmol) under cooling with ice and stirred at room temperature for 24 hours. After completion of the reaction, the reaction solution was mixed with ethyl acetate, and the organic layer was washed with saturated aqueous ammonium chloride, dried over anhydrous sodium sulfate and evaporated under reduced pressure to give the desired product (185 mg, quant.).

REFERENCE SYNTHETIC EXAMPLE 2

1-(Pyridin-4-yl)ethanamine

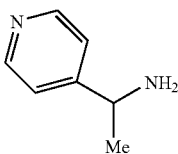

1-(Pyridin-4-yl)ethanol

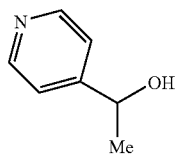

4-Pyridinecarbaldehyde (1.00 ml, 10.5 mmol) in tetrahydrofuran (10 mL) was mixed with methylmagnesium bromide (0.97 M in tetrahydrofuran, 19.5 mL, 18.9 mmol) under cooling with ice and stirred at room temperature for 5 hours. After quenching by adding water under cooling with ice, the reaction solution was mixed with ethyl acetate, and the organic layer was washed with saturated aqueous ammonium chloride, dried over anhydrous sodium sulfate and evaporated under reduced pressure to give the desired product (283 mg, 22% yield).

Morphology: pale yellow solid $^1$H-NMR (CDCl$_3$)

δ: 1.56 (s, 3H), 4.73 (s, 1H), 7.29-7.33 (m, 1H), 7.42 (dd, J=4.5, 1.5 Hz, 1H), 8.42-8.44 (m, 2H).

2-[1-(Pyridin-4-yl)ethyl]isoindoline-1,3-dione

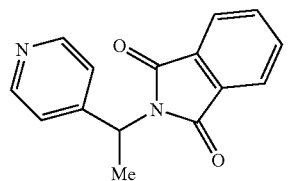 [SMILES: CC(c1ccncc1)N1C(=O)c2ccccc2C1=O]

A tetrahydrofuran solution (10 mL) of 1-(pyridin-4-yl)ethanol (283 mg, 2.32 mmol), phthalimide (375 mg, 2.55 mmol) and triphenylphosphine (686 mg, 2.55 mmol) was mixed with diisopropyl azodicarboxylate (40% in toluene, 1.34 mL, 2.55 mmol) and stirred at room temperature for 29 hours. After completion of the reaction, the reaction solution was mixed with ethyl acetate, and the organic layer was washed with saturated aqueous sodium chloride, dried over anhydrous sodium sulfate and evaporated under reduced pressure. The resulting residue was purified by silica gel column chromatography (chloroform/ethyl acetate=10/1) to give the desired product (283 mg, 48% yield).

LC/MS: Condition 2, retention time 1.24 min

LC/MS (ESI$^+$ (Electrospray Ionization)) m/z; 253 [M+1]$^+$ 1-(Pyridin-4-yl)ethanamine 2-[1-(Pyridin-4-yl)ethyl]isoindoline-1,3-dione (283 mg, 1.12 mmol) in methanol (3 mL) was mixed with hydrazine monohydrate (272 µL, 5.61 mmol) and stirred at room temperature for 16 hours. After completion of the reaction, the solid was filtered off with chloroform, and the filtrate was evaporated under reduced pressure repeatedly to give the desired product.

LC/MS: Condition 2, retention time 1.03 min

LC/MS (ESI$^+$) m/z; 123 [M+1]$^+$

REFERENCE SYNTHETIC EXAMPLE 3

(1R,2R,3R,5S)—N-Methylisopinocampheylamine

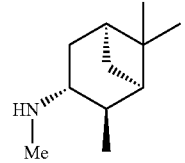

Methyl(1R,2R,3R,5S)-2,6,6-trimethylbicyclo[3.1.1]hept-3-ylcarbamate

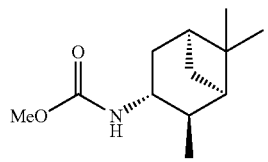

A tetrahydrofuran solution (10 mL) of (1R,2R,3R,5S)-isopinocampheylamine (1.0 mL, 5.89 mmol) and triethylamine (1.23 mL, 8.82 mmol) was mixed with methyl chloroformate (0.568 mL, 7.35 mmol) and stirred at room temperature for 15 minutes. After completion of the reaction, the reaction solution was mixed with ethyl acetate, and the organic layer was washed with saturated aqueous ammonium chloride and saturated aqueous sodium chloride, dried over anhydrous sodium sulfate and evaporated under reduced pressure to give the desired product (1.11 g, 89% yield).
Morphology: colorless oil (1R,2R,3R,5S)—N-Methylisopinocampheylamine Methyl (1R,2R,3R,5S)-2,6,6-trimethylbicyclo[3.1.1]hept-3-ylcarbamate (555 mg, 2.63 mmol) in tetrahydrofuran (10 mL) was mixed with lithium aluminum hydride (501 mg, 13.2 mmol) and refluxed at 90° C. for 3 hours. After cooling, the reaction solution was mixed with saturated aqueous sodium sulfate, and the organic layer was dried over anhydrous sodium sulfate and evaporated under reduced pressure. The resulting residue was purified by silica gel chromatography to give the desired product (180 mg, 41% yield).
Morphology: colorless oil

REFERENCE SYNTHETIC EXAMPLE 4

(1R,2R,3S,5S)-Isopinocampheylamine

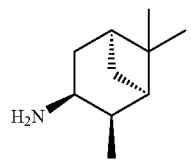

A tetrahydrofuran solution (10 mL) of (1R,2R,3R,5S)-2,6,6-trimethylbicyclo[3.1.1]hept-3-ol (500 mg, 3.24 mmol), phthalimide (525 mg, 3.57 mmol) and triphenylphosphine (936 mg, 3.57 mmol) was mixed with diisopropyl azodicarboxylate (1.9 M in toluene, 1.88 mL) and stirred at room temperature for 22 hours. After completion of the reaction, the solvent was removed by vacuum distillation, and the residue was mixed with water and extracted with ethyl acetate. From the resulting organic layer, the solvent was removed by vacuum distillation, and the residue was dissolved in methanol (10 mL) and stirred with hydrazine monohydrate (1.00 mL, 32.1 mmol) for 15 hours. After completion of the reaction, the solvent was removed by vacuum distillation, and the resulting residue was purified by silica gel chromatography (ethyl acetate) to give the desired product.
Morphology: light brown oil
LC/MS: condition 2, retention time 0.80 min
LC/MS (ESI$^+$) m/z; 154 [M+1]$^+$

REFERENCE SYNTHETIC EXAMPLE 5

(1S,2S,3R,5R)-Isopinocampheylamine

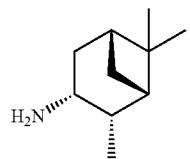

Synthesis was carried out in the same manner as in Reference Synthetic Example 4 by using (1S,2S,3R,5R)-2,6,6-trimethylbicyclo[3.1.1]heptan-3-ol.
Morphology: light brown oil
LC/MS: condition 2, retention time 0.81 min
LC/MS (ESI$^+$) m/z; 154 [M+1]$^+$

REFERENCE SYNTHETIC EXAMPLE 6

3,4,4-Trimethylcyclohex-2-enamine

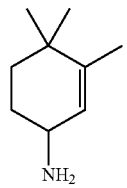

An ethanol-water solution (1:3, 4 mL) of 3,4,4-trimethylcyclohex-2-enone (500 mg, 3.62 mmol) and sodium acetate (356 mg, 4.35 mmol) was stirred with hydroxylamine sulfate (475 mg, 2.89 mmol) at 70° C. for 40 hours. After completion of the reaction, the reaction solution was extracted with ethyl acetate, and the resulting organic layer was evaporated under reduced pressure. The resulting residue was dissolved in tetrahydrofuran (5 mL), mixed with lithium aluminum hydride (412 mg, 10.9 mmol) at 0° C. and stirred at room temperature for 2 hours. After completion of the reaction, the reaction solution was mixed with saturated aqueous sodium sulfate, dried over anhydrous magnesium sulfate and filtered through celite, and the solvent was removed by vacuum distillation to give the desired product.
Morphology: colorless oil
LC/MS: condition 3, retention time 0.40 min
LC/MS (ESI$^+$) m/z; 140 [M+1]$^{30}$

REFERENCE SYNTHETIC EXAMPLE 7

1-(Pyridazin-4-yl)ethanamine Hydrochloride

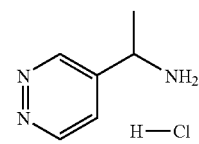

N-Methoxy-N-methylpyridazine-4-carboxamide

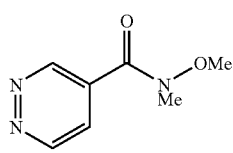 [SMILES: CON(C)C(=O)c1ccnnc1]

A N,N-dimethylformamide solution (16 mL) of 4-pydirazincarboxylic acid (1.61 g, 13.0 mmol), N-methyl-N-methoxyamine hydrochloride (2.54 g, 26.0 mmol), 1-(3-dimethylaminopropyl)-3-ethylcarbodiimide hydrochloride (6.23 g, 32.5 mmol), 1-hydroxybenzotriazole hydrate (catalytic amount) and triethylamine (9.06 mL, 65.0 mmol) was stirred at room temperature for 3 days. After completion of the reaction, the solvent was removed by vacuum distillation, and the residue was mixed with water and chloroform and filtered through celite. The filtrate was extracted with chloroform, and the extract was dried over anhydrous sodium sulfate and evaporated under reduced pressure. The resulting residue was purified by silica gel column chromatography (ethyl acetate) to give the desired product (94% yield).

Morphology: light brown oil
LC/MS: Condition 7, retention time 0.71 min
LC/MS (ESI$^+$) m/z; 168 [M+1]$^+$
$^1$H-NMR (CDCl$_3$)
δ: 3.42 (s, 3H), 3.58 (s, 3H), 7.76 (dd, J=5.4 and 2.0 Hz, 1H), 9.35 (d, J=5.4 Hz, 1H), 9.45 (d, J=2.0 Hz, 1H).

1-(Pyridazin-4-yl)ethanone

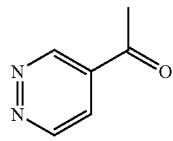

To N-methoxy-N-methylpyridazine-4-carboxamide (1.13 g, 6.76 mmol) in tetrahydrofuran (22 mL), methylmagnesium bromide (10.1 mL, 10.1 mmol, 1M in diethyl ether) was added dropwise at 0° C. in a nitrogen stream, and the resulting solution was stirred for 1 hour. After completion of the reaction, the reaction solution was mixed with saturated aqueous sodium chloride and extracted with chloroform, and the extract was dried over anhydrous sodium sulfate and evaporated under reduced pressure. The resulting residue was purified by silica gel column chromatography (hexane/ethyl acetate=1/2→0/1) to give the desired product (42% yield).

Morphology: pale yellow solid
LC/MS: Condition 7, retention time 0.75 min
LC/MS (ESI$^+$) m/z; 123 [M+1]$^+$
$^1$H-NMR (CDCl$_3$)
δ: 2.70 (s, 3H), 7.86 (dd, J=0.8 and 5.4 Hz, 1H), 9.48 (d, J=5.4 Hz, 1H), 9.61 (d, J=0.8 Hz, 1H).

N-Hydroxy-1-(pyridazin-4-yl)ethanimine Hydrochloride

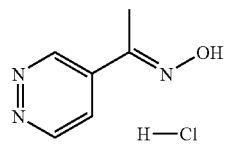

1-(Pyridazin-4-yl)ethanone (1.00 g, 8.19 mmol) and hydroxylamine hydrochloride (598 mg, 8.60 mmol) were stirred in ethanol (20 mL) at 90° C. for 10 minutes. After completion of the reaction, the reaction solution was evaporated under reduced pressure, and the resulting crude reaction product was used for the next step.

Morphology: brown solid
LC/MS: Condition 7, retention time 0.75 min
LC/MS (ESI$^+$) m/z; 138 [M+1]$^+$
$^1$H-NMR (CDCl$_3$)
δ: 2.69 (s, 3H), 7.86 (dd, J=0.8 and 5.3 Hz, 1H), 9.46 (d, J=5.3 Hz, 1H), 7.61 (d, J=0.8 Hz, 1H).

1-(Pyridazin-4-yl)ethanamine Hydrochloride

N-Hydroxy-1-(Pyridazin-4-yl)ethanimine hydrochloride (1.48 g, 8.53 mmol) and 10% palladium-carbon (0.15 g) were stirred in ethanol (30 mL) in a hydrogen stream at room temperature for 1 day. After completion of the reaction, the reaction solution was filtered through celite, and the filtrate was evaporated under reduced pressure. The resulting crude reaction product was used for the next step.

Morphology: brown amorphous
LC/MS: Condition 5, retention time 0.71 min
LC/MS (ESI$^+$) m/z; 124 [M+1]$^+$
$^1$H-NMR (CDCl$_3$)
δ: 1.56 (d, J=7.0 Hz, 3H), 4.52 (br d, J=7.0 Hz, 1H), 7.89 (dd, J=2.5 and 5.4 Hz, 1H), 8.8-9.1 (br s, 3H), 9.31 (d, J=5.4 Hz, 1H), 9.43 (d, J=2.5 Hz, 1H).

REFERENCE SYNTHETIC EXAMPLE 8 rac-2-[(Methoxymethoxy)methyl]-6,6-dimethylbicyclo[3.1.1]heptan-3-amine

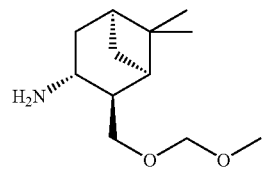

rac-2-[(Methoxymethoxy)methyl]-6,6-dimethylbicyclo[3.1.1]hept-2-ene

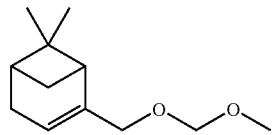

rac-(6,6-Dimethylbicyclo[3.1.1]hept-2-en-2-yl)methanol (10.0 g, 65.7 mmol), diisopropylethylamine (17.0 mL, 97.6 mmol) and chloromethyl methyl ether (6.5 mL, 85.6 mmol) were stirred in dichloromethane (100 mL) at room temperature for 1 day. After completion of the reaction, the reaction solution was mixed with saturated sodium hydrogen carbonate and extracted with chloroform. The organic layer was dried over anhydrous sodium sulfate and evaporated under reduced pressure. The resulting residue was purified by silica gel column chromatography (hexane-ethyl acetate=10/1) to give the desired product (100% yield).

Morphology: colorless oil
$^1$H-NMR (CDCl$_3$)
δ: 0.84 (s, 3H), 1.18 (d, J=8.7 Hz, 1H), 1.29 (s, 3H), 2.09-2.44 (m, 5H), 3.37 (s, 3H), 3.92 (s, 2H), 4.61 (s, 2H), 5.51 (s, 1H)

rac-2-[(Methoxymethoxy)methyl]-6,6-dimethylbicyclo[3.1.1]heptan-3-ol

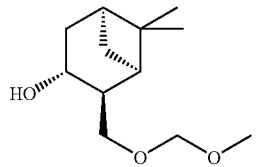

To rac-2-[(methoxymethoxy)methyl]-6,6-dimethylbicyclo[3.1.1]hept-2-ene (3.00 g, 15.3 mmol) in tetrahydrofuran (25 mL), a borane-tetrahydrofuran complex (0.99 M in tetrahydrofuran, 12 mL) was added gradually dropwise at 0° C., and then the resulting reaction solution was warmed to room temperature and stirred for 1 days. The reaction solution was cooled to 0° C., and 28 mass % aqueous ammonia (2 mL) and about 8 mass % aqueous sodium hypochlorite (28 g) were added gradually dropwise successively. The reaction solution was warmed to room temperature and stirred for 1 day. After completion of the reaction, the reaction solution was mixed with 1 M aqueous hydrochloric acid and extracted with ethyl acetate. The organic layer was dried over anhydrous sodium sulfate and evaporated under reduced pressure. The resulting residue was purified by silica gel column chromatography (hexane-ethyl acetate=10/1→4/1) to give rac-2-[(methoxymethoxy)methyl]-6,6-dimethylbicyclo[3.1.1]heptan-3-ol.

Separately, the aqueous layer was brought to pH=10 with 1 M aqueous sodium hydroxide and extracted with chloroform twice. The organic layer was dried over anhydrous sodium sulfate and evaporated under reduced pressure to give a crude reaction product containing rac-2-[(methoxymethoxy)methyl]-6,6-dimethylbicyclo[3.1.1]heptan-3-amine, which was used for the next step.

rac-2-[(Methoxymethoxy)methyl]-6,6-dimethylbicyclo[3.1.1]heptan-3-ol

Yield: 64%
Morphology: pale yellow oil
$^1$H-NMR (CDCl$_3$)
δ: 0.90 (s, 3H), 1.14 (d, J=9.6 Hz, 1H), 1.21 (s, 3H), 1.70-1.81 (m, 1H), 1.86-1.91 (m, 1H), 1.93-2.00 (m, 1H), 2.15-2.27 (m, 1H), 2.40-2.60 (m, 2H), 3.38 (s, 3H), 3.50-3.65 (m, 2H), 4.25-4.35 (m, 1H), 4.65 (s, 2H)

rac-2-[(Methoxymethoxy)methyl]-6,6-dimethylbicyclo[3.1.1]heptan-3-amine

Yield: 9%
Morphology: yellow oil

REFERENCE SYNTHETIC EXAMPLE 9

1-[3-(Morpholin-4-yl)pyridin-4-yl]methanamine

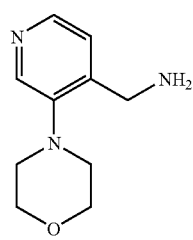

3-Chloro-5-(morpholin-4-yl)pyridin-4-ylcarbonitrile (103 mg, 0.462 mmol) in methanol (6 mL) was mixed with 10 mass % palladium-carbon (20 mg) in a nitrogen stream and stirred at room temperature in a hydrogen atmosphere for 6 hours. After completion of the reaction, the reaction solution was filtered through celite and evaporated under reduced pressure. The resulting crude reaction product was used for the next reaction without further purification (99% yield).
Morphology: ocher amorphous
$^1$H-NMR (CD$_3$OD)
δ: 3.02-3.06 (m, 4H), 3.84-3.89 (m, 4H), 4.31 (s, 2H), 7.49 (d, J=5.2 Hz, 1H), 8.41 (d, J=5.2 Hz, 1H), 8.51 (s, 1H)

REFERENCE SYNTHETIC EXAMPLE 10 rac-(6,6-Dimethylbicyclo[3.1.1]hept-2-en-2-yl)methyl Methyl Ether

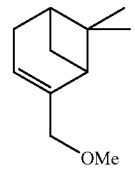

Synthesis was carried out in the same manner as in Reference Synthetic Example 8 by using methyl iodide (56% yield).
Morphology: pale yellow oil
$^1$H-NMR (CDCl$_3$)
δ: 0.84 (s, 3H), 1.18 (d, J=8.4 Hz, 1H), 1.29 (s, 3H), 2.09-2.44 (m, 5H), 3.29 (s, 3H), 3.77-3.79 (m, 2H), 5.48-5.50 (m, 1H)

REFERENCE SYNTHETIC EXAMPLE 11

4-(Methoxymethoxy)-2,6,6-trimethylbicyclo[3.1.1]hept-2-ene

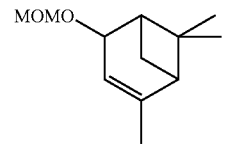

Synthesis was carried out in the same manner as in Reference Synthetic Example 8 by using 4,6,6-trimethylbicyclo[3.1.1]hept-3-en-2-ol (79% yield).
Morphology: colorless oil
$^1$H-NMR (CDCl$_3$)
δ: 0.84 (s, 3H), 1.18 (d, J=5.7 Hz, 1H), 1.34 (s, 3H), 1.73 (t, J=1.5 Hz, 3H), 1.94-1.98 (m, 1H), 2.33-2.48 (m, 2H), 3.38 (s, 3H), 4.35 (brs, 1H), 4.70 (dd, J=6.6, 8.7 Hz, 2H), 5.37 (brs, 1H)

REFERENCE SYNTHETIC EXAMPLE 12

5-Methoxytricyclo[3.3.1.1$^{3,7}$]decan-2-one

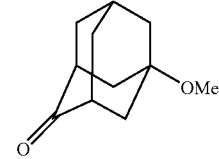 [SMILES: COC12CC3CC(C1)C(=O)C(C3)C2]

55% sodium hydride (40 mg, 0.917 mmol) in N,N-dimethylformamide (1 mL) was mixed with 5-hydroxy-2-adamantanone (100 mg, 0.602 mmol) and methyl iodide (750 μL, 12 mmol) at 0° C. and stirred at 50° C. for 8 hours. After completion of the reaction, the reaction solution was mixed with saturated aqueous sodium chloride and extracted with ethyl acetate. The organic layer was dried over anhydrous sodium sulfate and evaporated under reduced pressure. The resulting crude reaction product containing the desired product was used for the next step.

Morphology: colorless oil

REFERENCE SYNTHETIC EXAMPLE 13

5-(Methoxymethoxy)tricyclo[3.3.1.1$^{3,7}$]decan-2-one

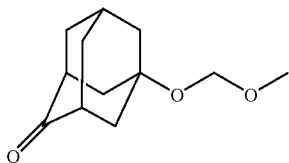

Synthesis was carried out in the same manner as in Reference Synthetic Example 12 by using chloromethyl methyl ether, and the resulting crude product containing the desired product was used for the next step.

Morphology: colorless oil

REFERENCE SYNTHETIC EXAMPLE 14

2-(1,3-Dioxolan-2-yl)-1-(pyridin-4-yl)ethanol

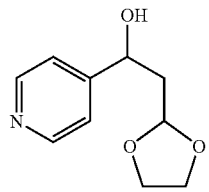 [SMILES: OC(CC1OCCO1)c1ccncc1]

4-Pyridinecarbaldehyde (0.5 ml, 5.25 mmol) in tetrahydrofuran (10 mL) was refluxed with (1,3-dioxolan-2-ylmethyl)magnesium bromide (0.5 M, 12.6 ml, 6.30 mmol) for 7 hours. After cooling, the reaction solution was quenched with saturated aqueous ammonium chloride and mixed with ethyl acetate, and the organic layer was washed with saturated aqueous ammonium chloride, dried over anhydrous sodium sulfate and evaporated under reduced pressure. The resulting crude reaction product was used for the next step without further purification (124 mg, 13%).

Morphology: pale yellow oil
$^1$H-NMR (CDCl$_3$)
δ: 2.00-2.10 (m, 2H), 3.70-4.06 (m, 4H), 4.15-4.25 (m, 1H), 4.90-5.06 (m, 1H), 7.32 (d, J=5.9 Hz, 2H), 8.52 (d, J=5.9 Hz, 2H).

REFERENCE SYNTHETIC EXAMPLES 15 TO 16

Compounds were synthesized in the same manner as in Reference Synthetic Example 1, and the yields and morphology of the resulting compounds, the LC/MS conditions used for their analysis and the observed peaks and retention times are shown in Table 2. "Crude" in the remarks column means that the crude reaction product was used for the next step without purification.

TABLE 2

| Reference Synthetic Example No. | Yield (%) | Morphology | LC/MS Condition | observed peak ESI$^+$ | observed peak ESI$^-$ | Retention time (min) | Remarks |
| --- | --- | --- | --- | --- | --- | --- | --- |
| 15 | | Colorless oil | | | | | Crude |
| 16 | | Colorless oil | | | | | Crude |

The structures of the compounds obtained are shown below.

15

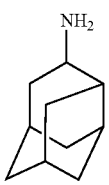

16

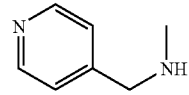

REFERENCE SYNTHETIC EXAMPLES 17 TO 24

Amines were synthesized in the same manner as in Reference Synthetic Example 2, and the yields and morphology of the resulting amines, the LC/MS conditions used for their analysis and the observed peaks and retention times are shown in Table 3. "Crude" in the remarks column means that the crude reaction product was used for the next step without purification.

TABLE 3

| Reference Synthetic Example No. | Yield (%) | Morphology | LC/MS Condition | observed peak ESI+ | observed peak ESI− | Retention time (min) | Remarks |
|---|---|---|---|---|---|---|---|
| 17 | | Orange oil | | | | | Crude |
| 18 | | Pale yellow oil | | | | | Crude |
| 19 | | Orange oil | | | | | Crude |
| 20 | | Yellow oil | | | | | Crude |
| 21 | | Orange oil | | | | | Crude |
| 22 | 49 | Pale yellow oil | 3 | 127 | — | 0.44 | Crude |
| 23 | | Pale yellow oil | | | | | Crude |
| 24 | | Pale yellow oil | | | | | Crude |

The structures of the compounds obtained are shown below.

17
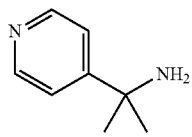

18
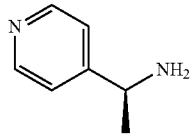

19
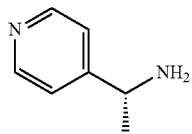

20
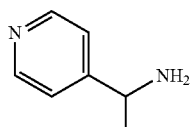

21
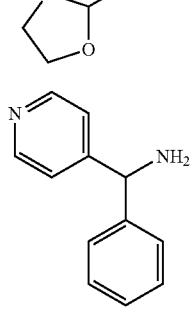

-continued

22
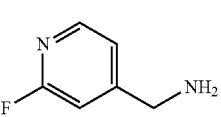

23
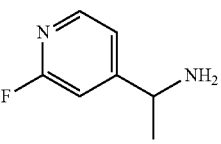

24
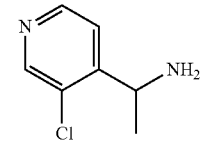

REFERENCE SYNTHETIC EXAMPLES 25 TO 28

Amines were synthesized in the same manner as in Reference Synthetic Example 4 by using ketones or aldehydes, and the yields and morphology of the resulting amines, the LC/MS conditions used for their analysis and the observed peaks and retention times are shown in Table 4. "Crude" in the remarks column means that the crude reaction product was used for the next step without purification.

TABLE 4

| Reference Synthetic Example No. | Yield (%) | Morphology | LC/MS Condition | observed peak ESI+ | observed peak ESI− | Retention time (min) | Remarks |
|---|---|---|---|---|---|---|---|
| 25 | | Colorless oil | | | | | Crude |
| 26 | | Pale yellow oil | | | | | Crude |
| 27 | | Orange oil | | | | | Crude |
| 28 | | Orange oil | | | | | Crude |

The structures of the compounds obtained are shown below.

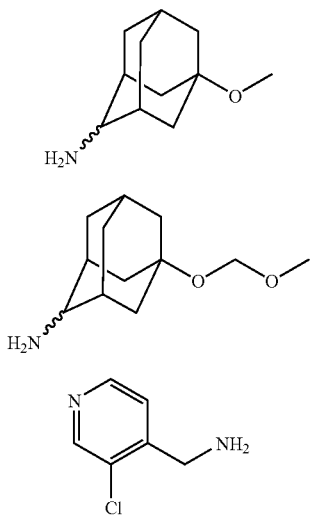

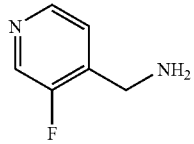

REFERENCE SYNTHETIC EXAMPLES 29 TO 30

Amines were synthesized in the same manner as in Reference Synthetic Example 7 by using ketones or aldehydes, and the yields and morphology of the resulting amines, the LC/MS conditions used for their analysis and the observed peaks and retention times are shown in Table 5. "Crude" in the remarks column means that the crude reaction product was used for the next step without purification.

TABLE 5

| Reference Synthetic Example No. | Yield (%) | Morphology | LC/MS Condition | observed peak ESI+ | observed peak ESI− | Retention time (min) | Remarks |
|---|---|---|---|---|---|---|---|
| 29 | | Pale pink oil | 3 | 159 | | 0.27 | Crude |
| 30 | | Orange oil | 7 | 177 | | 0.63 | Crude |

The structures of the compounds obtained are shown below.

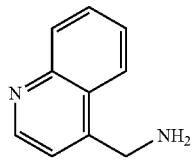

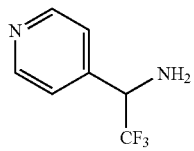

REFERENCE SYNTHETIC EXAMPLES 31 TO 33

Amines were synthesized in the same manner as in Reference Synthetic Example 8, and the yields and morphology of the resulting amines, the LC/MS conditions used for their analysis and the observed peaks and retention times are shown in Table 6. "Crude" in the remarks column means that the crude reaction product was used for the next step without purification.

TABLE 6

| Reference Synthetic Example No. | Yield (%) | Morphology | LC/MS Condition | observed peak ESI+ | observed peak ESI- | Retention time (min) | Remarks |
|---|---|---|---|---|---|---|---|
| 31 | | Red oil | | | | | Crude |
| 32 | | Colorless oil | | | | | Crude |
| 33 | 6 | Pale yellow oil | 7 | 184 | | 1.12 | |

The structures of the compounds obtained are shown below.

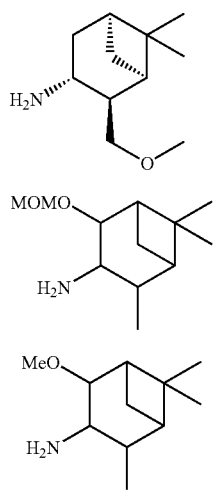

rac-31

32

33

REFERENCE SYNTHETIC EXAMPLES 34 TO 35

Amines were synthesized in the same manner as in Reference Synthetic Example 9, and the yields and morphology of the resulting amines, the LC/MS conditions used for their analysis and the observed peaks and retention times are shown in Table 7. "Crude" in the remarks column means that the crude reaction product was used for the next step without purification.

TABLE 7

| Reference Synthetic Example No. | Yield (%) | Morphology | LC/MS Condition | observed peak ESI+ | observed peak ESI- | Retention time (min) | Remarks |
|---|---|---|---|---|---|---|---|
| 34 | 99 | Pale yellow oil | | | | | Crude |
| 35 | 99 | Pale yellow oil | | | | | Crude |

The structures of the compounds obtained are shown below.

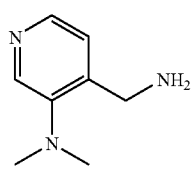

34

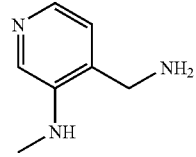

35

REFERENCE SYNTHETIC EXAMPLE 36

1-(Pyridin-4-yl)cyclopropanamine

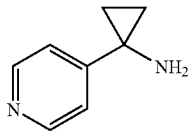

To 4-cyanopyridine (1.04 g, 10 mmol) in diethyl ether (50 mL), tetraisopropoxytitanium (3.27 mL, 11 mmol) and ethylmagnesium bromide (6.3 mL, 22 mmol, 3 M in diethyl ether) were added dropwise in a nitrogen stream at −78° C., and after 10 minutes, the reaction solution was warmed to room temperature and stirred for 1.5 hours and then stirred with a borane-tetrahydrofuran complex (21.5 mL, 20 mmol. 0.93 M in tetrahydrofuran) for 1 hour. After completion of the reaction, the reaction solution was diluted with diethyl ether (10 mL), and dilute hydrochloric acid (30 mL, 1 M) was added dropwise. After addition of aqueous sodium hydroxide (100 mL, 10% w/v), the reaction solution was extracted with ethyl acetate, and the extract was dried over anhydrous sodium sulfate and evaporated under reduced pressure. The resulting residue was purified by silica gel column chromatography (chloroform/methanol=9/1) to give the desired product (2.6% yield).

Morphology: ocher amorphous $^1$H-NMR (CDCl$_3$)

δ: 1.19-1.24 (m, 2H), 1.37-1.41 (m, 2H), 7.31 (d, J=6.9 Hz, 2H), 8.42 (d, J=6.9 Hz, 2H)

REFERENCE SYNTHETIC EXAMPLE 37

Ethyl 3-amino-3-(pyridin-4-yl)prop-2-enoate

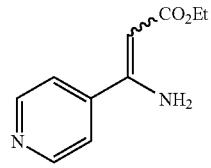 [SMILES: CCOC(=O)C=C(N)c1ccncc1]

Ethyl isonicotinoylacetate (1.00 g, 5.17 mmol) and ammonium formate (1.63 g, 25.8 mmol) were stirred in methanol (10 mL) at 70° C. for 18 hours. After completion of the reaction, the solvent was removed by vacuum distillation, and the residue was mixed with water and extracted with ethyl acetate. The organic layer was washed with saturated aqueous sodium chloride, dried over anhydrous sodium sulfate and evaporated under reduced pressure. The resulting crude reaction product was used for the next step without further purification.

Morphology: pale yellow solid
$^1$H-NMR (CDCl$_3$)
δ: 1.31 (t, J=7.2 Hz, 3H), 4.20 (q, J=7.2 Hz, 2H), 5.03 (s, 1H), 7.42 (d, J=6.2 Hz, 2H), 8.69 (d, J=6.2 Hz, 2H)

REFERENCE SYNTHETIC EXAMPLE 38

Ethyl 3-amino-3-(pyridin-4-yl)propanoate

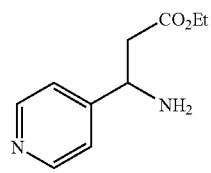 [SMILES: CCOC(=O)CC(N)c1ccncc1]

To ethyl 3-amino-3-(pyridin-4-yl)prop-2-enoate (0.98 g) in methanol (30 mL), 10% palladium-carbon (50 mg) was added in a nitrogen stream, and the reaction solution was stirred in a hydrogen atmosphere at room temperature for 3 days. After completion of the reaction, the reaction solution was filtered through celite, and the filtrate was evaporated. The resulting crude reaction product was used for the next step without further purification (42% yield, two steps).

Morphology: ocher amorphous
$^1$H-NMR (DMSO-d6)
δ: 1.09-1.12 (m, 3H), 2.58-2.65 (m, 2H), 3.93-4.08 (m, 2H), 4.13-4.17 (m, 1H), 7.32-7.38 (m, 2H), 8.45-8.48 (m, 2H)

REFERENCE SYNTHETIC EXAMPLE 39 rac-3-Amino-6,6-dimethylbicyclo[3.1.1]heptane-2-carbonitrile

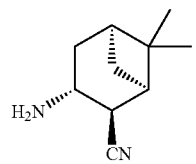

rac-2-[(Methoxymethoxy)methyl]-6,6-dimethylbicyclo[3.1.1]heptan-3-ol

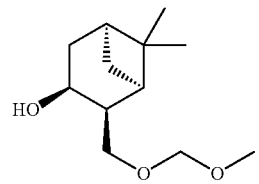

rac-2-[(Methoxymethoxy)methyl]-6,6-dimethylbicyclo[3.1.1]heptan-3-ol (2.00 g, 9.33 mmol) prepared in Reference Synthetic Example 8, silica gel (2 g) and pyridinium chlorochromate (4.00 g, 18.5 mmol) were stirred in dichloromethane (40 mL) at room temperature for 2 hours. After completion of the reaction, the reaction solution was filtered through celite, and the filtrate was evaporated. The resulting residue was purified by column chromatography (hexane/ethyl acetate=10/1→4/1) to give a crude reaction product. To lithium aluminum hydride (590 mg, 15.5 mmol) in tetrahydrofuran (50 mL), the crude product (1.64 g) in tetrahydrofuran (5 mL) was added dropwise at −10° C., and the resulting solution was stirred for 2 hours. After completion of the reaction, the reaction solution was mixed with ethyl acetate and a small amount of saturated aqueous ammonium chloride, dried over anhydrous sodium sulfate and filtered through celite, and the filtrate was evaporated under reduced pressure. The resulting residue was purified by silica gel column chromatography (hexane/ethyl acetate=10/1→5/1) to give the desired product (52% yield, two steps).

Morphology: colorless oil
$^1$H-NMR (CDCl$_3$)
δ: 1.01-1.04 (m, 4H), 1.16 (s, 3H), 1.83-1.89 (m, 1H), 1.89-1.92 (m, 2H), 2.24-2.30 (m, 1H), 2.44-2.52 (m, 1H), 2.60-2.70 (m, 1H), 2.90 (m, 1H), 3.38 (s, 3H), 3.40-3.47 (m, 1H), 4.12 (t, J=10.8 Hz, 1H), 4.47-4.58 (m, 1H), 4.65 (s, 2H)

rac-2-{2-[(Methoxymethoxy)methyl]-6,6-dimethylbicyclo[3.1.1]hept-3-yl}-1H-isoindole-1,3(2H)-dione

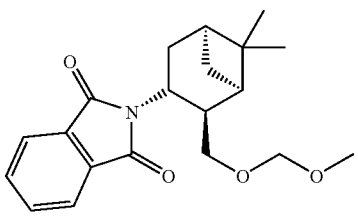

Synthesis was carried out in the same manner as in Reference Synthetic Example 2 by using rac-2-[(methoxymethoxy)methyl]-6,6-dimethylbicyclo[3.1.1]heptan-3-ol (59% yield).

Morphology: colorless oil
δ: 1.13 (s, 3H), 1.29 (s, 3H), 1.90-2.60 (m, 6H), 2.80-2.95 (m, 1H), 3.26 (s, 6H), 3.40-3.60 (m, 2H), 4.40-4.60 (m, 2H), 4.70-4.85 (m, 1H), 7.65-7.80 (m, 2H), 7.80-7.90 (m, 2H)

rac-2-[2-(Hydroxymethyl)-6,6-dimethylbicyclo[3.1.1]hept-3-yl]-1H-isoindole-1,3(2H)-dione

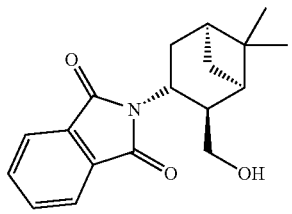

rac-2-{2-[(Methoxymethoxy)methyl]-6,6-dimethylbicyclo[3.1.1]hept-3-yl}-1H-isoindole-1,3(2H)-dione (0.97 g, 2.82 mmol) was stirred with hydrogen chloride-methanol (20 mL, 10% w/v) at room temperature for 1 day. After completion of the reaction, the reaction solution was evaporated under reduced pressure, and the residue was mixed with saturated aqueous sodium hydrogen carbonate and extracted with chloroform. The organic layer was dried over anhydrous sodium sulfate and evaporated under reduced pressure to give the desired product (100% yield).
Morphology: colorless oil
$^1$H-NMR (CDCl$_3$)
δ: 1.11 (s, 3H), 1.29 (s, 3H), 2.00-2.15 (m, 3H), 2.30-2.40 (m, 2H), 2.40-2.50 (m, 1H), 2.65-2.80 (m, 1H), 3.50-3.80 (m, 2H), 4.73 (q, J=9.0 Hz, 1H), 7.65-7.80 (m, 2H), 7.80-7.90 (m, 2H)

3-(1,3-Dioxo-1,3-dihydro-2H-isoindol-2-yl)-6,6-dimethylbicyclo[3.1.1]heptane-2-carbaldehyde

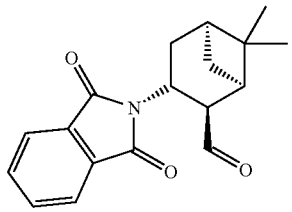

rac-2-[2-(Hydroxymethyl)-6,6-dimethylbicyclo[3.1.1]hept-3-yl]-1H-isoindole-1,3(2H)-dione (750 mg, 2.51 mmol), silica gel (0.75 g) and pyridinium chlorochromate (1.08 g, 5.01 mmol) were stirred in dichloromethane (20 mL) at room temperature for 2 hours. After completion of the reaction, the reaction solution was filtered through celite, and the filtrate was evaporated. The resulting residue was purified by column chromatography (hexane/ethyl acetate=5/1→3/1) to give the desired product (61% yield).
Morphology: colorless solid
δ: 0.94 (s, 3H), 1.31 (s, 3H), 2.05-2.21 (m, 3H), 2.45-2.60 (m, 2H), 2.60-2.70 (m, 1H), 3.48 (dd, J=7.5, 2.1 Hz, 1H), 5.40-5.55 (m, 1H), 7.65-7.80 (m, 2H), 7.80-7.90 (m, 2H), 9.71 (s, 1H)

rac-3-Amino-6,6-dimethylbicyclo[3.1.1]heptane-2-carbonitrile rac-3-(1,3-Dioxo-1,3-dihydro-2H-isoindol-2-yl)-6,6-dimethylbicyclo[3.1.1]heptane-2-carbaldehyde (100 mg, 0.336 mmol) and hydroxylamine hydrochloride (28 mg, 0.403 mmol) were stirred in formic acid (0.5 mL) at 110° C. for 3 hours. After completion of the reaction, the reaction solution was mixed with water and extracted with ethyl acetate. The organic layer was dried over anhydrous sodium sulfate to give a crude product. The crude product in methanol (3 mL) was stirred with hydrazine monohydrate (52 μL, 1.67 mmol) at room temperature for 1 day. The reaction solution was evaporated under reduced pressure, and the residue was mixed with ethanol (10 mL) and refluxed for 7 hours. After completion of the reaction, the reaction solution was evaporated under reduced pressure, and the resulting solid was filtered off with diisopropyl ether. The filtrate was evaporated under reduced pressure. The resulting crude reaction product containing the desired product was used for the next step.
Morphology: yellow oil

REFERENCE SYNTHETIC EXAMPLE 40 rac-2-(Difluoromethyl)-6,6-dimethylbicyclo[3.1.1]heptan-3-amine

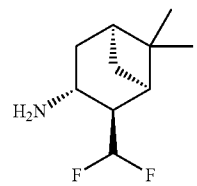

rac-3-(1,3-Dioxo-1,3-dihydro-2H-isoindol-2-yl)-6,6-dimethylbicyclo[3.1.1]heptane-2-carbaldehyde (122 mg, 0.41 mmol) prepared in Reference Synthetic Example 39 in dichloromethane (3 mL) was mixed with (diethylamino)sulfur trifluoride (180 μL, 1.36 mmol) at −78° C. and stirred at −78° C. for 1 hour and then at room temperature for 1 hour. After completion of the reaction, the reaction solution was mixed with saturated aqeuous sodium hydrogen carbonate and extracted with ethyl acetate. The organic layer was dried over anhydrous sodium sulfate and evaporated under reduced pressure to give a crude reaction product. The crude reaction product in ethanol (5 mL) was mixed with hydrazine monohydrate (100 μL, 1.87 mmol) and refluxed for 1 day. After completion of the reaction, the reaction solution was evaporated under reduced pressure, and the resulting solid was filtered off with chloroform. The filtrate was evaporated under reduced pressure. The resulting crude reaction product containing the desired product was used for the next step.
Morphology: orange oil

REFERENCE SYNTHETIC EXAMPLE 41

2-Aminotricyclo[3.3.1.1$^{3,7}$]decan-1-ol

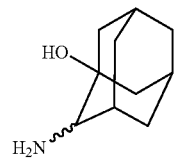

Tricyclo[3.3.1.1³,⁷]dec-1-yl carbamate

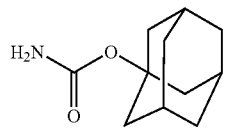

1-Adamantanol (1.52 g, 10.0 mmol) in dichloromethane (30 mL) was mixed with trichloroacetyl isocyanate (1.40 mL, 11.8 mmol) at 0° C., then warmed to room temperature and stirred for 2 hours. After completion of the reaction, the reaction solution was evaporated under reduced pressure, and the resulting crude reaction product was mixed with methanol (15 mL) and saturated aqueous potassium carbonate and stirred at 50° C. for 1 day. After completion of the reaction, the methanol was removed by vacuum distillation, and the residue was filtered. The resulting solid was washed with water and dried under reduced pressure to give the desired product (74% yield, 2 steps).

Morphology: colorless solid $^1$H-NMR (CDCl$_3$)

δ: 1.60 (s, 6H), 2.02 (s, 6H), 2.09 (s, 3H), 6.14 (bs, 2H)

2-Oxa-4-azatetracyclo[6.3.1.1⁶,¹⁰.0¹,⁵]tridecan-3-one

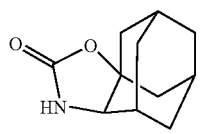 [SMILES: O=C1NC2C3CC4CC(C3)CC2(C4)O1]

Tricyclo[3.3.1.1³,⁷]dec-1-yl carbamate (100 mg, 0.512 mmol), iodobenzenediacetate (220 mg, 0.683 mmol), magnesium oxide (50 mg, 1.24 mmol) and rhodium (II) acetate dimer (22 mg, 0.050 mmol) were stirred in dichloromethane (3 mL) at 50° C. for 5 hours. After completion of the reaction, the reaction solution was filtered, and the solid was washed with chloroform and the filtrate was evaporated under reduced pressure. The resulting residue was purified by silica gel column chromatography (hexane/ethyl acetate=10/1→2/1) to give the desired product (77% yield).

Morphology: colorless solid

LC/MS: Condition 7, retention time 3.18 min

LC/MS (ESI⁺) m/z; 194 [M+1]⁺

2-Aminotricyclo[3.3.1.1³,⁷]decan-1-ol

2-Oxa-4-azatetracyclo[6.3.1.1⁶,¹⁰.0¹,⁵]tridecan-3-one (76 mg, 0.395 mmol) in 1,4-dioxane (1 mL) was stirred with 5 M aqueous potassium hydroxide at 70° C. for 1 day. After completion of the reaction, the reaction solution was extracted with chloroform, and the organic layer was dried over anhydrous sodium sulfate and evaporated under reduced pressure to give the desired product (70% yield).

Morphology: colorless solid

LC/MS: Condition 7, retention time 0.53 min

LC/MS (ESI⁺) m/z; 168 [M+1]⁺

REFERENCE SYNTHETIC EXAMPLE 42

2-(Aminomethyl)tricyclo[3.3.1.1³,⁷]decan-2-ol

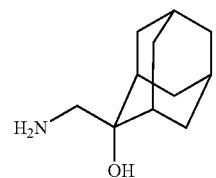 [SMILES: NCC1(O)C2CC3CC(C2)CC1C3]

2-Adamantanone (1.50 g, 10.0 mmol), zinc iodide (960 mg, 3.01 mmol) and trimethylsilyl cyanide (1.20 g, 12.1 mmol) were stirred in dichloromethane (30 mL) at room temperature for 1 day. After completion of the reaction, the reaction solution was mixed with saturated aqueous sodium hydrogen carbonate and extracted with chloroform. The organic layer was dried over anhydrous sodium sulfate and evaporated under reduced pressure to give a crude reaction product. To lithium aluminum hydride (750 mg, 19.8 mmol) in tetrahydrofuran (50 mL), the crude reaction product (2.31 g) in tetrahydrofuran (5 mL) was added dropwise at room temperature, and the resulting solution was stirred at 70° C. for 5 hours. After completion of the reaction, the reaction solution was mixed with chloroform and a small amount of saturated aqueous ammonium chloride, dried over anhydrous sodium sulfate and filtered through celite, and the filtrate was evaporated under reduced pressure. The resulting crude product containing the desired product was used for the next step.

Morphology: colorless solid $^1$H-NMR (CDCl$_3$)

δ: 1.50-1.60 (m, 2H), 1.60-1.90 (m, 10H), 2.20-2.30 (m, 2H), 2.87 (s, 2H)

REFERENCE SYNTHETIC EXAMPLE 43

2-(Aminomethyl)tricyclo[3.3.1.1³,⁷]decan-2-ol

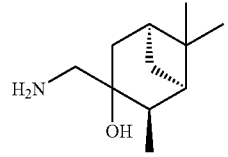

Synthesis was carried out in the same manner as in Reference Synthetic Example 42 by using (1R,2R,5S)-3-(aminomethyl)-2,6,6-trimethylbicyclo[3.1.1]heptan-3-ol.

Morphology: colorless oil

LC/MS: Condition 7, retention time 0.90 min

LC/MS (ESI⁺) m/z; 184 [M+1]⁺

REFERENCE SYNTHETIC EXAMPLE 44

2-Methyl-1-(pyridin-4-yl)propan-1-amine

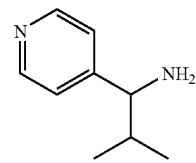

4-Pyridinecarbaldehyde (0.5 mL, 5.25 mmol) in tetrahydrofuran (10 mL) was mixed with lithium hexamethyldisilazide in tetrahydrofuran (1 M, 6.3 mL, 6.3 mmol) and stirred at 0° C. for 4 hours and then stirred with isopropylmagnesium bromide in tetrahydrofuran (0.98 M, 6.3 mL, 6.3 mmol) at room temperature for 16 hours. After completion of the reaction, 1 M aqueous hydrochloric acid was added, and the reaction solution was washed with ethyl acetate. After addition of 1 M aqueous sodium hydroxide, the combined aqueous layer was extracted with chloroform. The resulting organic layer was filtered through celite, and the filtrate was dried over anhydrous magnesium sulfate and evaporated under reduced pressure. The resulting crude reaction product containing the desired product was used for the next step.

Morphology: brown oil $^1$H-NMR (CDCl$_3$)

δ: 0.69 (d, J=6.9 Hz, 3H), 0.80 (d, J=6.6 Hz, 3H), 1.74 (ddd, J=6.9, 6.6, 6.3 Hz, 1H), 3.53 (d, J=6.3 Hz, 1H), 7.10 (d, J=4.8 Hz, 2H), 8.39 (d, J=4.8 Hz, 2H)

REFERENCE SYNTHETIC EXAMPLE 45

1-(Pyrimidin-4-yl)propan-1-amine

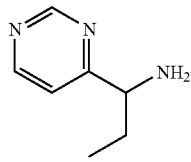

1-(5-Bromopyrimidin-4-yl)propan-1-ol

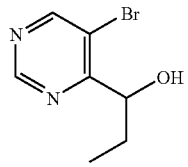

To 5-bromopyrimidine (2.39 g, 15.0 mmol) and propionaldehyde (1.05 g, 18.0 mmol) in diethyl ether (80 mL), lithium diisopropylamide (18 mmol) in diethyl ether (20 mL) was gradually added dropwise at 0° C. After the dropwise addition, the reaction mixture was warmed to room temperature and stirred at room temperature for 1 hour. After completion of the reaction, the reaction mixture was extracted by adding water and ethyl acetate, and the organic layer was dried over anhydrous magnesium sulfate and evaporated under reduced pressure. The resulting residue was purified by silica gel column chromatography (hexane/ethyl acetate=2.5/1) to give a mixture (colorless oil) containing the desired product, which was used for the next step (427 mg, 13% yield). 2-[1-(5-Bromopyrimidin-4-yl)propyl]isoindoline-1,3-dione

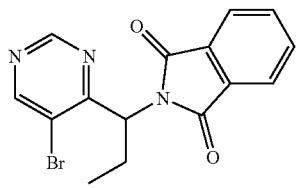 [SMILES: CCC(c1ncncc1Br)N1C(=O)c2ccccc2C1=O]

A tetrahydrofuran solution (10 mL) of 1-(5-bromopyrimidin-4-yl)propan-1-ol (427 mg, 1.97 mmol), phthalimide (353 mg, 2.40 mmol) and triphenylphosphine (629 mg, 2.40 mmol) was mixed with diisopropyl azodicarboxylate (40% in toluene, 1.04 mL, 2.40 mmol) under cooling with ice and stirred at room temperature for 16 hours. After completion of the reaction, the reaction solution was mixed with ethyl acetate, and the organic layer was washed with saturated aqueous sodium chloride, dried over anhydrous sodium sulfate and evaporated under reduced pressure. The resulting residue was purified by silica gel column chromatography (chloroform/ethyl acetate=10/1) to give the desired product (568 mg, 83% yield).

Morphology: colorless oil $^1$H-NMR (CDCl$_3$)

δ: 1.11 (t, J=7.5 Hz, 3H), 2.30-2.50 (m, 1H), 2.5-2.8 (m, 1H), 5.50 (dd, J=5.7 Hz, J=10.8 Hz, 1H), 7.71-7.78 (m, 2H), 7.84-7.89 (m, 2H), 8.75 (s, 1H), 9.07 (s, 1H)

2-[1-(Pyrimidin-4-yl)propyl]isoindoline-1,3-dione

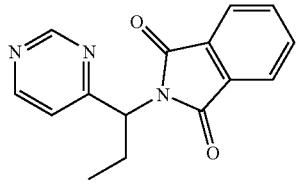 [SMILES: CCC(c1ccncn1)N1C(=O)c2ccccc2C1=O]

2-[1-(5-Bromopyrimidin-4-yl)propyl]isoindoline-1,3-dione (568 mg, 1.64 mmol), triethylamine (0.228 mL, 1.64 mmol) and 10% palladium-carbon (50 wt %, 100 mg) were stirred in methanol (10 mL) in a hydrogen atmosphere at room temperature for 1 day. The reaction solution was filtered through celite and evaporated under reduced pressure. The resulting residue was purified by silica gel column chromatography (hexane/ethyl acetate=1/1) give the desired product (292 mg, 66% yield).

Morphology: colorless oil $^1$H-NMR (CDCl$_3$)

δ: 1.05 (t, J=7.5 Hz, 3H), 2.30-2.70 (m, 2H), 5.34 (dd, J=5.7 Hz, J=10.8 Hz, 1H), 7.41 (d, J=5.4 Hz, 1H), 7.71-7.78 (m, 2H), 7.84-7.89 (m, 2H), 8.69 (d, J=5.4 Hz, 1H), 9.13 (s, 1H)

1-(Pyrimidin-4-yl)propan-1-amine

2-[1-(Pyrimidin-4-yl)propyl]isoindoline-1,3-dione (292 mg, 1.09 mmol) in methanol (2 mL) was stirred with hydrazine monohydrate (153 µL, 3.15 mmol) at room temperature for 16 hours. After completion of the reaction, the solid was filtered off with chloroform, and the filtrate was evaporated under reduced pressure repeatedly to give the desired product (84% yield).

Morphology: colorless oil $^1$H-NMR (CDCl$_3$)

δ: 0.93 (t, J=7.5 Hz, 3H), 1.60-1.90 (m, 2H), 3.86 (m, 1H), 7.34 (d, J=5.4 Hz, 1H), 8.67 (d, J=5.4 Hz, 1H), 9.16 (s, 1H)

REFERENCE SYNTHETIC EXAMPLE 46

1-(Pyrimidin-4-yl)ethanol

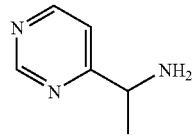

Synthesis was carried out in the same manner as in Reference Synthetic Example 45 by using acetaldehyde.
Morphology: colorless oil
¹H-NMR (CDCl₃)
δ: 1.44 (d, J=6.9 Hz, 3H), 4.12 (q, J=6.9 Hz, 1H), 7.38 (d, J=5.4 Hz, 1H), 8.68 (d, J=5.4 Hz, 1H), 9.16 (s, 1H)

REFERENCE SYNTHETIC EXAMPLE 47

(1-Methyl-1H-tetrazol-5-yl)methanamine

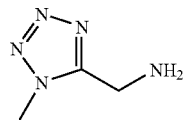

2-[(1-Methyl-1H-tetrazol-5-yl)methyl]isoindoline-1,3-dione

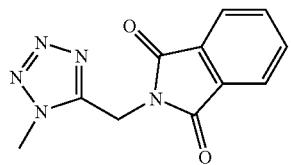 [SMILES: Cn1nnnc1CN1C(=O)c2ccccc2C1=O]

5-(Chloromethyl)-1-methyl-1H-tetrazole (a crude product 6.9 g prepared in accordance with Chemical & Pharmaceutical Bulletin, 37(2), 322-6:1989), was dissolved in 50 mL of dimethylformamide and stirred with potassium phthalimide (5.00 g, 27.0 mmol) and sodium iodide (391 mg, 2.60 mmol) at room temperature for 17 hours. After completion of the reaction, the reaction solution was mixed with water and extracted with ethyl acetate, and the extract was dried over anhydrous magnesium sulfate and evaporated under reduced pressure. The resulting residue was purified by silica gel column chromatography (hexane/ethyl acetate=1/1) to give the desired product (550 mg, 4% yield, two steps).
Morphology: colorless solid
LC/MS: Condition 7, retention time 1.98 min
LC/MS (ESI⁺) m/z; 244 [M+1]⁺
¹H-NMR (CDCl₃)
δ: 4.23 (s, 3H), 5.12 (s, 2H), 7.74-7.80 (m, 2H), 7.85-7.92 (m, 2H)

(1-Methyl-1H-tetrazol-5-yl)methanamine

2-[(1-Methyl-1H-tetrazol-5-yl)methyl]isoindoline-1,3-dione (122 mg, 0.50 mmol) in methanol (1 mL) was mixed with hydrazine monohydrate (122 μL, 2.50 mmol) and stirred at room temperature for 16 hours. After completion of the reaction, the solid was filtered off with chloroform. The filtrate was evaporated under reduced pressure repeatedly to give the desired product (98% yield).
Morphology: colorless oil
¹H-NMR (CDCl₃)
δ: 4.10 (s, 3H), 4.17 (s, 2H)

REFERENCE SYNTHETIC EXAMPLE 48

(5-Bromopyrimidin-4-yl)methanamine

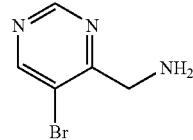

5-Bromo-4-methylpyrimidine

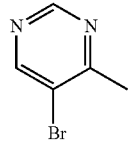

To 5-bromopyrimidine (17.3 g, 109 mmol) in diethyl ether (100 mL), methyllithium in diethyl ether (109 mmol, 1.09 M, 100 mL) was gradually added dropwise at room temperature, and the resulting reaction mixture was stirred at room temperature for 1 hour. After completion of the reaction, the reaction mixture was stirred with water (1.96 mL, 109 mmol) and 2,3-dichloro-5,6-dicyano-p-benzoquinone (24.7 g, 109 mmol) in tetrahydrofuran (150 mL) at room temperature for 16 hours. After completion of the reaction, water and ethyl acetate were added, and the organic layer was separated. The organic layer was washed with 1M aqueous sodium hydroxide, dried over anhydrous magnesium sulfate and evaporated under reduced pressure. The resulting residue was purified by silica gel column chromatography (hexane/ethyl acetate=1/1) to give the desired product (2.9 g, 15% yield).
Morphology: yellow oil
¹H-NMR (CDCl₃)
δ: 2.65 (s, 3H), 8.72 (s, 1H), 8.98 (s, 1H)

2-[(5-Bromopyrimidin-4-yl)methyl]isoindoline-1,3-dione

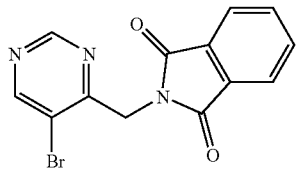 [SMILES: O=C1c2ccccc2C(=O)N1Cc1ncncc1Br]

5-Bromo-4-methylpyrimidine (2.90 g, 16.8 mmol) in acetic acid (40 mL) was stirred with bromine (3.18 g, 20.2 mmol) at 80° C. for 40 minutes. After completion of the reaction, the reaction solution was cooled, diluted with ethyl acetate and neutralized with water and 1 M aqueous sodium hydroxide, and the organic layer was separated, dried over anhydrous magnesium sulfate and evaporated under reduced pressure. The resulting residue was purified by silica gel column chromatography (hexane/ethyl acetate=7/1). The resulting product (3.69 g) was dissolved in 60 mL of dimethylformamide and heated with potassium phthalimide (2.84 g, 15.3 mmol) at 80° C. for 1 hour with stirring. After completion of the reaction, the reaction solution was mixed with water and extracted with chloroform, and the extract was dried over anhydrous magnesium sulfate and evaporated under reduced pressure. The resulting residue was purified by silica gel column chromatography (chloroform) to give the desired product (4.3 g, 80% yield).

Morphology: colorless solid
LC/MS: Condition 7, retention time 3.71 min
LC/MS (ESI$^+$) m/z; 317, 319 [M+1]$^+$
$^1$H-NMR (CDCl$_3$)
δ: 5.06 (s, 2H), 7.74-7.80 (m, 2H), 7.85-7.94 (m, 2H), 8.77 (s, 1H), 8.90 (s, 1H)

(5-Bromopyrimidin-4-yl)methanamine

Synthesis was carried out in the same manner as in Reference Synthetic Example 47 by using 2-[(5-bromopyrimidin-4-yl)methyl]isoindoline-1,3-dione (100% yield).

Morphology: colorless oil
$^1$H-NMR (CDCl$_3$)
δ: 4.06 (s, 2H), 8.72 (s, 1H), 9.09 (s, 1H)

REFERENCE SYNTHETIC EXAMPLE 49

(5-Methylpyirimidin-4-yl)methanamine

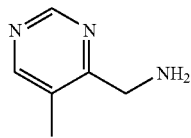

2-[(5-Methylpyirimidin-4-yl)methyl]isoindoline-1,3-dione

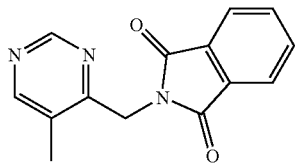 [SMILES: Cc1cncnc1CN1C(=O)c2ccccc2C1=O]

2-[(5-Bromopyrimidin-4-yl)methyl]isoindoline-1,3-dione (318 mg, 1.00 mmol), trimethylboroxine (126 mg, 1.32 mmol), [1,1'-bis(diphenylphosphono)ferrocene]dichloropalladium (II) dichloromethane complex (40.8 mg, 0.05 mmol) and potassium carbonate (276 mg, 2.00 mmol) were mixed with water (0.2 mL) and 1,4-dioxane (1.8 mL) and stirred at 110° C. for 1 hour. After completion of the reaction, the reaction solution was allowed to cool, and the solvent was removed by vacuum distillation. The resulting residue was mixed with 4 M hydrogen chloride/1,4-dioxane (10 mL) and stirred at room temperature for 16 hours. After completion of the reaction, the reaction solution was mixed with water and extracted with chloroform, and the extract was dried over anhydrous magnesium sulfate and evaporated under reduced pressure. The resulting residue was purified by silica gel column chromatography (hexane/ethyl acetate=1/2) to give the desired product (154 mg, 61% yield).

Morphology: dark brown solid
LC/MS: Condition 7, retention time 3.20 min
LC/MS (ESI$^+$) m/z; 254 [M+1]$^+$
$^1$H-NMR (CDCl$_3$)
δ: 2.41 (s, 3H), 4.94 (s, 2H), 7.74-7.80 (m, 2H), 7.85-7.94 (m, 2H), 8.46 (s, 1H), 8.85 (s, 1H)

(5-Methylpyrimidin-4-yl)methanamine

Synthesis was carried out in the same manner as in Reference Synthetic Example 45 by using 2-[(5-methylpyrimidin-4-yl)methyl]isoindoline-1,3-dione (100% yield).

Morphology: colorless oil
$^1$H-NMR (CDCl$_3$)
δ: 2.26 (s, 3H), 3.96 (s, 2H), 8.42 (s, 1H), 9.03 (s, 1H)

REFERENCE SYNTHETIC EXAMPLE 50

(S)-1-Amino-2-methylpropan-2-ol

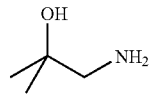

Isobutylene oxide (415 mg, 5.76 mmol) and 28 mass % aqueous ammonia were sealed in a reaction tube and heated at 120° C. for 30 minutes with stirring and microwave irradiation. The solvent was removed by vacuum distillation to give the desired product (44% yield).

Morphology: colorless oil
$^1$H-NMR (CDCl$_3$)
δ: 1.16 (s, 3H), 1.21 (s, 3H), 2.60 (s, 2H)

REFERENCE SYNTHETIC EXAMPLE 51

(S)-1-Amino-3-methoxypropan-2-ol

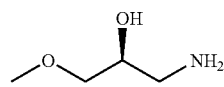

(R)-(−)-Glycidyl methyl ether (252 mg, 2.86 mmol) and 28 mass % aqueous ammonia were sealed in a reaction tube and heated at 120° C. for 30 minutes with stirring and microwave irradiation. The solvent was removed by vacuum distillation to give the desired product (75% yield).

Morphology: colorless oil
$^1$H-NMR (CDCl$_3$)
δ: 2.65-2.89 (m, 2H), 3.35-3.50 (m, 3H), 3.40 (s, 3H), 3.70-3.90 (m, 1H)

REFERENCE SYNTHETIC EXAMPLE 52

(S)-1-Methoxy-3-(methylamino)propan-2-ol

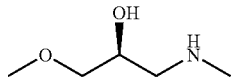

(R)-(−)-Glycidyl methyl ether (321 mg, 3.65 mmol) and 40 mass % methylamine-methanol (1 mL) were sealed in a reaction tube and heated at 120° C. for 30 minutes with stirring and microwave irradiation. The solvent was removed by vacuum distillation to give the desired product (88% yield).

Morphology: colorless oil $^1$H-NMR (CDCl$_3$)

δ: 2.44 (s, 3H), 2.55-2.70 (m, 2H), 3.35-3.50 (m, 3H), 3.40 (s, 3H), 3.82-3.92 (m, 1H)

REFERENCE SYNTHETIC EXAMPLE 53

(S)-1-Methoxy-3-(pyridin-4-ylmethylamino)propan-2-ol

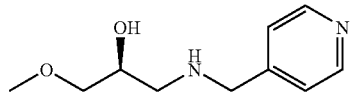

(R)-(−)-Glycidyl methyl ether (88 mg, 1 mmol) and 4-picolylamine (108 mg, 1 mmol) in methanol (1 mL) were sealed in a reaction tube and heated at 120° C. for 30 minutes with stirring and microwave irradiation. The solvent was removed by vacuum distillation. The resulting residue was purified by silica gel column chromatography (ethyl acetate) to give the desired product (17% yield).

Morphology: colorless oil $^1$H-NMR (CDCl$_3$)

δ: 2.60-2.80 (m, 2H), 3.35-3.50 (m, 2H), 3.40 (s, 3H), 3.87 (s, 2H), 3.87-3.92 (m, 1H), 7.26 (d, J=4.5 Hz, 2H), 8.55 (d, J=4.5 Hz, 2H)

REFERENCE SYNTHETIC EXAMPLE 54

1-(Pyridazin-4-yl)propan-1-amine

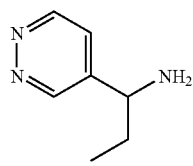

2-[1-(3,6-Dichloropyridazin-4-yl)propyl]isoindoline-1,3-dione

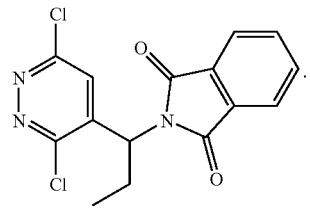 [SMILES: CCC(c1cc(Cl)nnc1Cl)N1C(=O)c2ccccc2C1=O]

3,6-Dichloropyridazine (596 mg, 4 mmol), 2-(1,3-dioxoisoindolin-2-yl)butanoic acid (1.59 g, 6.8 mmol), silver nitrate (67.9 mg, 0.4 mmol), trifluoroacetic acid (91.2 mg, 0.8 mmol) and water (10 mL) were heated at 70° C. with stirring, and to the resulting mixture, diammonium peroxodisulfate (1.64 g, 7.2 mmol) in water (2 mL) was added dropwise over 30 minutes. After the dropwise addition, the resulting reaction mixture was stirred at 70° C. for 30 minutes, then mixed with 10 mL of ethyl acetate and allowed to cool to room temperature. The reaction mixture was cooled with ice, then basified with 28% aqueous ammonia (to pH 9) and extracted with ethyl acetate. The resulting organic layer was washed with saturated aqueous sodium hydrogen carbonate and saturated aqueous sodium chloride, dried over anhydrous magnesium sulfate and evaporated under reduced pressure. The resulting residue was purified by silica gel column chromatography (chloroform/ethyl acetate=1/1) to give a crude product, which was used for the next reaction.

Morphology: colorless oil

LC/MS: Condition 7, retention time 4.30 min

LC/MS (ESI$^+$) m/z; 336, 338 [M+1]$^+$

2-[1-(Pyridazin-4-yl)propyl]isoindoline-1,3-dione

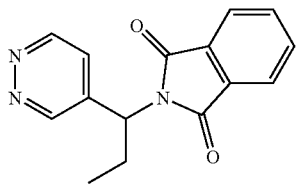 [SMILES: CCC(c1ccnnc1)N1C(=O)c2ccccc2C1=O]

2-[1-(3,6-Dichloropyridazin-4-yl)propyl]isoindoline-1,3-dione, triethylamine (1.11 mL, 8 mmol) and 10% palladium-carbon (50 wt %, 100 mg) were stirred in tetrahydrofuran in a hydrogen atmosphere (1 atm) at room temperature for 4 days. The reaction solution was filtered through celite and concentrated under reduced pressure, and the resulting residue was dissolved in chloroform, and the resulting organic layer was washed with water and saturated aqueous sodium hydrogen carbonate, dried over anhydrous magnesium sulfate and evaporated under reduced pressure. The residue was purified by silica gel column chromatography (hexane/ethyl acetate=1/3) to give the desired product (294 mg, 28% yield, two steps).

Morphology: colorless oil

LC/MS: Condition 7, retention time 4.30 min

LC/MS (ESI$^+$) m/z; 268 [M+1]$^+$ $^1$H-NMR (CDCl$_3$)

δ: 1.00 (t, J=7.5 Hz, 3H), 2.20-2.40 (m, 1H), 2.50-2.70 (m, 1H), 5.25 (dd, J=5.7 Hz, J=10.8 Hz, 1H), 7.76 (d, J=5.4 Hz, 1H), 7.71-7.78 (m, 2H), 7.84-7.89 (m, 2H), 9.18 (d, J=5.4 Hz, 1H), 9.29 (s, 1H)

1-(Pyridazin-4-yl)propan-1-amine

2-[1-(Pyridazin-4-yl)propyl]isoindoline-1,3-dione (91.8 mg, 0.34 mmol) in methanol (1 mL) was mixed with hydrazine monohydrate (83 μL, 1.7 mmol) at room temperature and stirred at 60° C. for 3 hours. After completion of the reaction, the solid was filtered off with chloroform, and the filtrate was evaporated under reduced pressure repeatedly to give the desired product (100% yield).
Morphology: colorless oil
$^1$H-NMR (CDCl$_3$)
δ: 0.92 (t, J=7.5 Hz, 3H), 1.60-2.05 (m, 2H), 3.91 (m, 1H), 7.47 (d, J=5.1 Hz, 1H), 9.11 (d, J=5.1 Hz, 1H), 9.18 (s, 1H)

REFERENCE SYNTHETIC EXAMPLE 55

(3-Methoxypyridazin-4-yl)methanamine

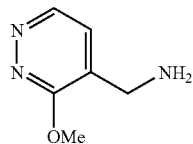

2-[(3-Methoxypyridazin-4-yl)methyl]isoindoline-1,3-dione

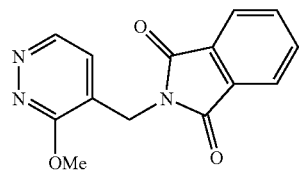 [SMILES: COc1nnccc1CN1C(=O)c2ccccc2C1=O]

Synthesis was carried out in the same manner as in Reference Synthetic Example 54 by using 3-chloro-6-methoxypyridazine and 2-(1,3-dioxoindolin-2-yl)acetic acid (33% yield, two steps).
Morphology: colorless solid
$^1$H-NMR (CDCl$_3$)
δ: 4.20 (s, 3H), 4.86 (s, 2H), 7.09 (d, J=4.8 Hz, 1H), 7.71-7.81 (m, 2H), 7.89-7.94 (m, 2H), 8.75 (d, J=4.8 Hz, 1H)

(3-Methoxypyridazin-4-yl)methanamine

Synthesis was carried out in the same manner as in Reference Synthetic Example 54 by using 2-[(3-methoxypyridazin-4-yl)methyl]isoindoline-1,3-dione (96% yield).
Morphology: colorless solid
$^1$H-NMR (CDCl$_3$)
δ: 3.84 (s, 2H), 4.17 (s, 3H), 7.39 (d, J=4.8 Hz, 1H), 8.79 (d, J=4.8 Hz, 1H)

REFERENCE SYNTHETIC EXAMPLE 56

4-(Aminomethyl)pyridazin-3[2H]-one

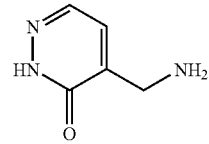

2-[(3-Oxo-2,3-dihydropyridazin-4-yl)methyl]isoindoline-1,3-dione

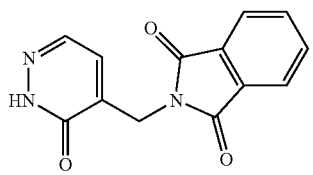

2-[(3-Methoxypyridazin-4-yl)methyl]isoindoline-1,3-dione (1.15 g, 4.27 mmol) in 1,4-dioxane (90 mL) was refluxed with 12 M hydrochloric acid (2 mL) for 1 hour. After completion of the reaction, the solvent was removed by vacuum distillation to give the desired product (1.1 g, 100% yield).
Morphology: colorless solid
$^1$H-NMR (DMSO-d6)
δ: 4.58 (s, 2H), 7.24 (d, J=3.6 Hz, 1H), 7.78 (d, J=3.6 Hz, 1H), 7.80-7.95 (m, 4H), 13.2 (s, 1H)

4-(Aminomethyl)pyridazin-3[2H]-one

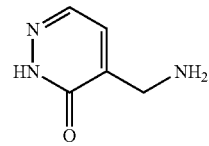

2-[(3-Oxo-2,3-dihydropyridazin-4-yl)methyl]isoindoline-1,3-dione (255 mg, 1.00 mmol) in methanol (2 mL) was mixed with hydrazine monohydrate (250 mg, 5.00 mmol) at room temperature and stirred at 60° C. for 3 hours. After completion of the reaction, the solid was filtered off with chloroform, and the filtrate was evaporated under reduced pressure repeatedly to give a crude reaction product containing the desired product, which was used for the next step.

REFERENCE SYNTHETIC EXAMPLE 57

4-(Aminomethyl)-2-methylpyridazin-3(2H)-one

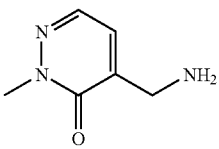

121

2-[(2-Methyl-3-oxo-2,3-dihydropyridazin-4-yl)methyl]isoindoline-1,3-dione

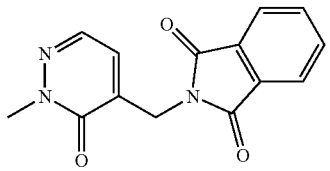 [SMILES: Cn1nccc(CN2C(=O)c3ccccc3C2=O)c1=O]

2-[(3-Oxo-2,3-dihydropyridazin-4-yl)methyl]isoindoline-1,3-dione (255 mg, 1.00 mmol) in dimethylformamide (3 mL) was heated with potassium carbonate (145 mg, 1.05 mmol) and methyl iodide (426 mg, 3.00 mmol) at 70° C. for 2 hours. After completion of the reaction, the solvent was removed by vacuum distillation, and the resulting residue was stirred with 4 M hydrogen chloride/1,4-dioxane (10 mL) at room temperature for 2 hours. After completion of the reaction, the reaction solution was mixed with water and extracted with ethyl acetate, and the extract was dried over anhydrous magnesium sulfate and evaporated under reduced pressure. The resulting residue was purified by silica gel column chromatography (ethyl acetate) to give the desired product (233 mg, 86% yield).

Morphology: yellow solid

LC/MS: Condition 7, retention time 3.05 min

LC/MS (ESI$^+$) m/z; 270 [M+1]$^+$ $^1$H-NMR (CDCl$_3$)

δ: 3.80 (s, 3H), 4.85 (s, 2H), 6.91 (d, J=3.9 Hz, 1H), 7.66 (d, J=3.9 Hz, 1H), 7.71-7.81 (m, 2H), 7.85-7.94 (m, 2H)

4-(Aminomethyl)-2-methylpyridazin-3(2H)-one

Synthesis was carried out in the same manner as in Reference Synthetic Example 56 by using 2-[(2-methyl-3-oxo-2,3-dihydropyridazin-4-yl)methyl]isoindoline-1,3-dione (100% yield).

Morphology: colorless amorphous $^1$H-NMR (CDCl$_3$)

δ: 3.80 (s, 3H), 3.82 (s, 2H), 7.22 (d, J=3.9 Hz, 1H), 7.74 (d, J=3.9 Hz, 1H)

REFERENCE SYNTHETIC EXAMPLE 58

[5-Bromo-4-(hexahydro-2,5-methanopentalen-3a(1H)-ylamino)-6-oxopyridazin-1(6H)-yl]acetic Acid

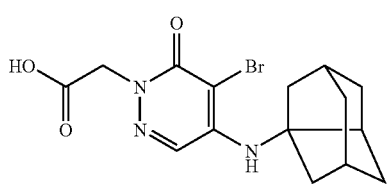 [SMILES: O=C(O)Cn1ncc(NC23CC4CC(CC2C4)C3)c(Br)c1=O]

122

Ethyl[5-bromo-4-(hexahydro-2,5-methanopentalen-3a(1H)-ylamino)-6-oxopyridazin-1(6H)-yl]acetate

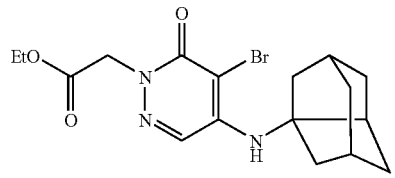 [SMILES: CCOC(=O)Cn1ncc(NC23CC4CC(CC2C4)C3)c(Br)c1=O]

Ethyl 2-(4,5-dibromo-6-oxopyridazin-1(6H)-yl)acetate (1.50 g, 4.41 mmol), 1-noradamantamine hydrochloride (1.15 g, 6.62 mmol) and triethylamine (1.83 mL, 13.2 mmol) were stirred in a 1,4-dioxane-water mixed solvent (1/1) at 90° C. for 1 day. After completion of the reaction, the reaction solution was mixed with ethyl acetate, and the organic layer was washed with saturated aqueous ammonium chloride and saturated aqueous sodium chloride, dried over anhydrous sodium sulfate and evaporated under reduced pressure. The resulting residue was purified by silica gel chromatography (hexane/ethyl acetate=1/1→0/1) to give the desired product (50% yield).

Morphology: colorless solid

LC/MS: Condition 7, retention time 4.76 min

LC/MS (ESI$^+$) m/z; 396, 398 [M+1]$^+$

LC/MS (ESI$^-$) m/z; 394, 396 [M-1]$^-$

[5-Bromo-4-(hexahydro-2,5-methanopentalen-3a(1H)-ylamino)-6-oxopyridazin-1(6H)-yl]acetic Acid Synthesis was carried out in the same manner as in Reference Synthetic Example 1 by using ethyl[5-bromo-4-(hexahydro-2,5-methanopentalen-3a(1H)-ylamino)-6-oxopyridazin-1(6H)-yl]acetate.

Yield: 100%

Morphology: colorless amorphous

REFERENCE SYNTHETIC EXAMPLE 59

[5-Chloro-4-(hexahydro-2,5-methanopentalen-3a(1H)-ylamino)-6-oxopyridazin-1(6H)-yl]acetic Acid

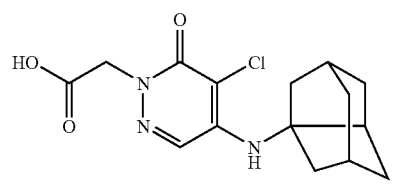 [SMILES: O=C(O)Cn1ncc(NC23CC4CC(CC2C4)C3)c(Cl)c1=O]

Synthesis was carried out in the same manner as in Reference Synthetic Example 58 by using ethyl 2-(4,5-dichloro-6-oxopyridazin-1(6H)-yl)acetate.

Yield: 61% (two steps)

Morphology: colorless solid

LC/MS: Condition 7, retention time 4.20 min

LC/MS (ESI$^+$) m/z; 324, 326 [M+1]$^+$

LC/MS (ESI$^-$) m/z; 322, 324 [M-1]$^-$

REFERENCE SYNTHETIC EXAMPLE 60

[5-Chloro-4-(1-adamantanamino)-6-oxopyridazin-1(6H)-yl]acetic Acid

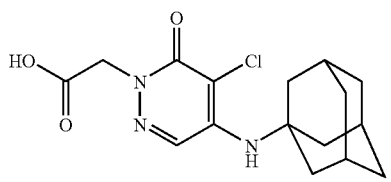 [SMILES: O=C(O)Cn1ncc(NC23CC4CC(CC(C4)C2)C3)c(Cl)c1=O]

Synthesis was carried out in the same manner as in Reference Synthetic Example 59 by using 1-adamantamine.
Yield: 23% (two steps)
Morphology: colorless solid

REFERENCE SYNTHETIC EXAMPLE 61

[5-Chloro-4-(2-adamantanamino)-6-oxopyridazin-1(6H)-yl]acetic Acid

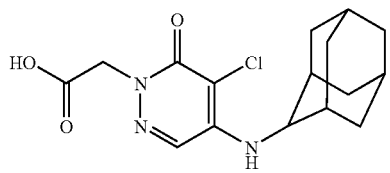 [SMILES: O=C(O)Cn1ncc(NC2C3CC4CC(C3)CC2C4)c(Cl)c1=O]

Synthesis was carried out in the same manner as in Reference Synthetic Example 59 by using 2-adamantamine.
Yield: 65% (two steps)
Morphology: colorless solid
LC/MS: Condition 7, retention time 4.20 min
LC/MS (ESI$^+$) m/z; 338, 340 [M+1]$^+$
LC/MS (ESI$^-$) m/z; 336, 338 [M−1]$^-$

REFERENCE SYNTHETIC EXAMPLE 62

[5-Chloro-4-{[(1S,2S,3R,5S)-2-hydroxy-2,6,6-trimethylbicyclo[3.1.1]hept-3-yl]amino}-6-oxopyridazin-1(6H)-yl]acetic Acid

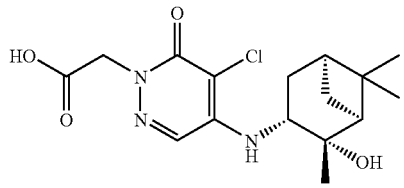 [SMILES: CC1(C)[C@@H]2C[C@@H](Nc3cnn(CC(=O)O)c(=O)c3Cl)[C@@](C)(O)[C@H]1C2]

Synthesis was carried out in the same manner as in Reference Synthetic Example 59 by using (1S,2S,3R,5S)-3-amino-2,6,6-trimethylbicyclo[3.1.1]heptan-2-ol.
Yield: 51% (two steps)
Morphology: colorless amorphous
LC/MS: Condition 7, retention time 3.85 min
LC/MS (ESI$^+$) m/z; 356, 358 [M+1]$^+$
LC/MS (ESI$^-$) m/z; 354, 356 [M−1]$^-$

REFERENCE SYNTHETIC EXAMPLE 63

[4-(Bicyclo[3.3.1]non-9-ylamino)-5-chloro-6-oxopyridazin-1(6H)-yl]acetic Acid

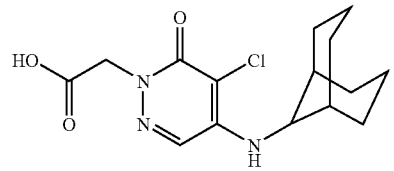 [SMILES: O=C(O)Cn1ncc(NC2C3CCCC2CCC3)c(Cl)c1=O]

Synthesis was carried out in the same manner as in Reference Synthetic Example 59 by using bicyclo[3.3.1]nonan-9-amine.
Yield: 49% (two steps)
Morphology: colorless solid
LC/MS: Condition 7, retention time 4.08 min
LC/MS (ESI$^+$) m/z; 326, 328 [M+1]$^+$
LC/MS (ESI$^-$) m/z; 324, 326 [M−1]$^-$

REFERENCE SYNTHETIC EXAMPLE 64

[4-(Bicyclo[3.3.1]non-9-ylamino)-5-bromo-6-oxopyridazin-1(6H)-yl]acetic Acid

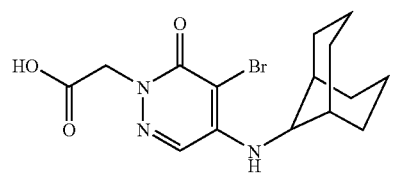 [SMILES: O=C(O)Cn1ncc(NC2C3CCCC2CCC3)c(Br)c1=O]

Synthesis was carried out in the same manner as in Reference Synthetic Example 58 by using bicyclo[3.3.1]nonan-9-amine.
Yield: 58% (two steps)
Morphology: colorless solid
LC/MS: Condition 7, retention time 4.08 min
LC/MS (ESI$^+$) m/z; 370, 372 [M+1]$^+$
LC/MS (ESI$^-$) m/z; 368, 370 [M−1]$^-$

REFERENCE SYNTHETIC EXAMPLE 65

2-(4,5-Dibromo-6-oxopyridazin-1(6H)-yl)-N-[1-(pyridin-4-yl)propyl]acetamide

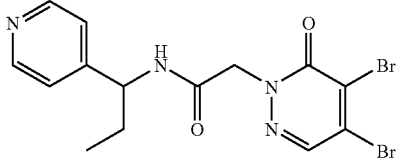 [SMILES: CCC(NC(=O)Cn1ncc(Br)c(Br)c1=O)c1ccncc1]

Synthesis was carried out in the same manner as in Synthetic Example 48 by using 2-(4,5-dibromo-6-oxopyridazin-1(6H)-yl)acetic acid.
Yield: 36%
Morphology: brown amorphous
LC/MS: Condition 7, retention time 0.90 min
LC/MS (ESI$^+$) m/z; 429, 431, 433 [M+1]$^+$
LC/MS (ESI$^-$) m/z; 427, 429, 431 [M−1]$^-$

REFERENCE SYNTHETIC EXAMPLE 66

2-(4,5-Dibromo-6-oxopyridazin-1(6H)-yl)-N-[1-(3-methylpyridin-4-yl)methyl]acetamide

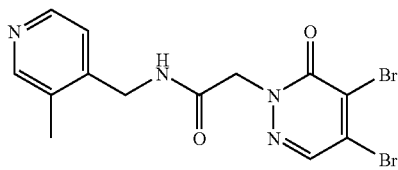 [SMILES: Cc1cnccc1CNC(=O)Cn1ncc(Br)c(Br)c1=O]

Synthesis was carried out in the same manner as in Synthetic Example 48 by using (3-methylpyridin-4-yl)methanamine.
Yield: 25%
Morphology: brown solid
LC/MS: Condition 7, retention time 0.90 min
LC/MS (ESI$^+$) m/z; 415, 417, 419 [M+1]$^+$
LC/MS (ESI$^-$) m/z; 413, 415, 417 [M−1]$^-$

REFERENCE SYNTHETIC EXAMPLE 67

2-(4,5-Dichloro-6-oxopyridazin-1(6H)-yl)-N-(pyridin-4-ylmethyl)acetamide

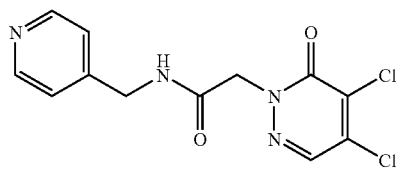 [SMILES: O=C(Cn1ncc(Cl)c(Cl)c1=O)NCc1ccncc1]

Synthesis was carried out in the same manner as in Synthetic Example 48 by using 2-(4,5-dichloro-6-oxopyridazin-1(6H)-yl)acetic acid.
Yield: 9%
Morphology: light brown solid
LC/MS: Condition 7, retention time 0.90 min
LC/MS (ESI$^+$) m/z; 313, 315 [M+1]$^+$
LC/MS (ESI$^-$) m/z; 311, 313 [M−1]$^-$

REFERENCE SYNTHETIC EXAMPLE 68

2-(4,5-Dichloro-6-oxopyridazin-1(6H)-yl)-N-[1-(pyridin-4-yl)propyl]acetamide

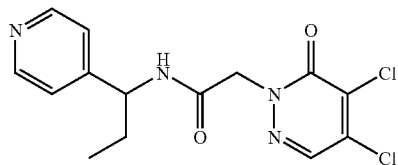 [SMILES: CCC(NC(=O)Cn1ncc(Cl)c(Cl)c1=O)c1ccncc1]

Synthesis was carried out in the same manner as in Reference Synthetic Example 67 by using 1-(pyridin-4-yl)propan-1-amine.
Yield: 45%
Morphology: brown amorphous
LC/MS: Condition 7, retention time 0.87 min
LC/MS (ESI$^+$) m/z; 341, 343 [M+1]$^+$
LC/MS (ESI$^-$) m/z; 339, 341 [M−1]$^-$

REFERENCE SYNTHETIC EXAMPLE 69

2-(4,5-Dichloro-6-oxopyridazin-1(6H)-yl)-N-[1-(3-methylpyridin-4-yl)methyl]acetamide

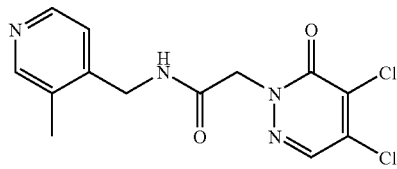

Synthesis was carried out in the same manner as in Reference Synthetic Example 66 by using 2-(4,5-dichloro-6-oxopyridazin-1(6H)-yl)acetic acid.
Yield: 39%
Morphology: brown solid
LC/MS: Condition 7, retention time 0.84 min
LC/MS (ESI$^+$) m/z; 327, 329 [M+1]$^+$
LC/MS (ESI$^-$) m/z; 325, 327 [M−1]$^-$

REFERENCE SYNTHETIC EXAMPLE 70

2-(4,5-Dichloro-6-oxopyridazin-1(6H)-yl)-N-[1-(pyridin-4-yl)ethyl]acetamide

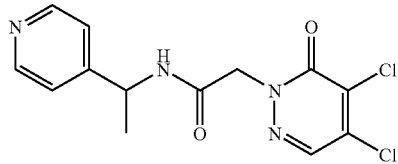

Synthesis was carried out in the same manner as in Reference Synthetic Example 67 by using 1-(pyridin-4-yl)ethanamine.
Yield: 59%
Morphology: colorless solid
LC/MS: Condition 7, retention time 0.64 min
LC/MS (ESI$^+$) m/z; 327, 329, 331 [M+1]$^+$
LC/MS (ESI$^-$) m/z; 325, 327, 329 [M−1]$^-$

REFERENCE SYNTHETIC EXAMPLE 71

2-[4,5-Dichloro-6-oxopyridazin-1(6H)-yl]-N-[(1R)-1-(pyridin-4-yl)ethyl]acetamide

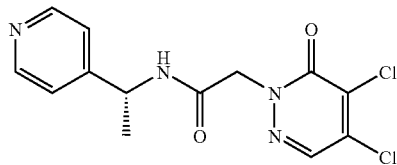 [SMILES: C[C@@H](NC(=O)Cn1ncc(Cl)c(Cl)c1=O)c1ccncc1]

Synthesis was carried out in the same manner as in Reference Synthetic Example 67 by using (1R)-1-(pyridin-4-yl)ethanamine.
Yield: 67%
Morphology: colorless amorphous
LC/MS: Condition 7, retention time 0.64 min
LC/MS (ESI⁺) m/z; 327, 329, 331 [M+1]⁺
LC/MS (ESI⁻) m/z; 325, 327, 329 [M−1]⁻

REFERENCE SYNTHETIC EXAMPLE 72

(5-Methylpyridazin-4-yl)methanamine

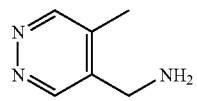

2-[(5-Methylpyridazin-4-yl)methyl]-1H-isoindole-1,3(2H)-dione

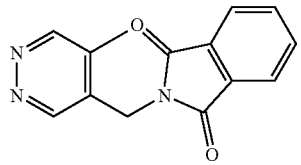 [SMILES: Cc1cnncc1CN1C(=O)c2ccccc2C1=O]

Synthesis was carried out in the same manner as in Reference Synthetic Example 54 by using 3,6-dichloro-4-methylpyridazine and 2-(1,3-dioxoisoindolin-2-yl)acetic acid. The obtained crude product was used for the next reaction.
Morphology: colorless solid
LC/MS: Condition 7, retention time 2.81 min
LC/MS (ESI⁺) m/z; 254 [M+1]⁺
¹H-NMR (CDCl₃)
δ: 2.52 (s, 3H), 4.88 (s, 2H), 7.76-7.80 (m, 2H), 7.87-7.91 (m, 2H), 8.98 (s, 1H), 9.05 (s, 1H)

(5-Methylpyridazin-4-yl)methanamine

Synthesis was carried out in the same manner as in Reference Synthetic Example 54 by using 2-[(5-methylpyridazin-4-yl)methyl]-1H-isoindole-1,3(2H)-dione (6% yield, three steps).
Morphology: colorless oil
¹H-NMR (CDCl₃)
δ: 2.34 (s, 3H), 3.95 (s, 2H), 8.93 (s, 1H), 9.17 (s, 1H)

REFERENCE SYNTHETIC EXAMPLE 73

(3-Chloropyridazin-4-yl)methanamine

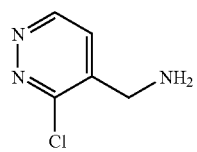

2-[(3-Chloropyridazin-4-yl)methyl]-1H-isoindole-1,3(2H)-dione

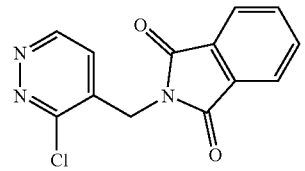 [SMILES: O=C1c2ccccc2C(=O)N1Cc1ccnnc1Cl]

2-[(3-Oxo-2,3-dihydropyridazin-4-yl)methyl]-1H-isoindole-1,3(2H)-dione (1.1 g, 4.27 mmol) was mixed with phosphoryl chloride (10 mL) and heated to reflux for 1 hour. After completion of the reaction, phosphoryl chloride was removed under reduced pressure. The resulting residue was diluted with chloroform and water. The organic layer was separated, dried over anhydrous magnesium sulfate, and the solvent was removed by vacuum distillation. The resulting residue was purified by silica gel column chromatography (hexane/ethyl acetate=9/1) to give the desired product (89% yield).
Morphology: colorless solid
LC/MS: Condition 7, retention time 3.33 min
LC/MS (ESI⁺) m/z; 274, 276 [M+1]⁺
¹H-NMR (CDCl₃)
δ: 4.97 (s, 2H), 7.26 (d, J=4.2 Hz, 1H), 7.82 (m, 2H), 7.93 (m, 2H), 9.05 (d, J=4.2 Hz, 1H)

(3-Chloropyridazin-4-yl)methanamine

Synthesis was carried out in the same manner as in Reference Synthetic Example 54 by using 2-[(3-chloropyridazin-4-yl)methyl]-1H-isoindole-1,3(2H)-dione (136.9 mg, 0.5 mmol) (90% yield).
Morphology: colorless solid
¹H-NMR (CDCl₃)
δ: 4.00 (s, 2H), 7.86 (d, J=4.2 Hz, 1H), 9.04 (d, J=4.2 Hz, 1H)

REFERENCE SYNTHETIC EXAMPLE 74

(3-Methylpyridazin-4-yl)methanamine

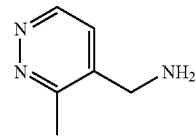

2-[(3-Methylpyridazin-4-yl)methyl]-1H-isoindole-1,3(2H)-dione

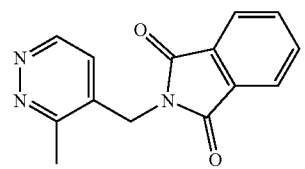 [SMILES: Cc1nnccc1CN1C(=O)c2ccccc2C1=O]

Synthesis was carried out in the same manner as in Reference Synthetic Example 49 by using 2-[(3-chloropyridazin-4-yl)methyl]-1H-isoindole-1,3(2H)-dione (136.5 mg, 0.5 mmol) (94.6 mg, 75% yield).
Morphology: colorless solid
LC/MS: Condition 7, retention time 2.55 min
LC/MS (ESI$^+$) m/z; 254 [M+1]$^+$
$^1$H-NMR (CDCl$_3$)
δ: 2.88 (s, 3H), 4.87 (s, 2H), 7.26 (d, J=4.8 Hz, 1H), 7.79 (m, 2H), 7.92 (m, 2H), 9.00 (d, J=4.8 Hz, 1H)

(3-Methylpyridazin-4-yl)methanamine

Synthesis was carried out in the same manner as in Reference Synthetic Example 54 by using 2-[(3-methylpyridazin-4-yl)methyl]-1H-isoindole-1,3(2H)-dione (108.8 mg, 0.43 mmol). The obtained crude product was used for the next reaction (100% yield).

REFERENCE SYNTHETIC EXAMPLE 75

4-(Aminomethyl)-N,N-dimethylpyridazin-3-amine

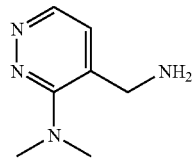

2-{[3-(Dimethylamino)pyridazin-4-yl]methyl}-1H-isoindole-1,3(2H)-dione

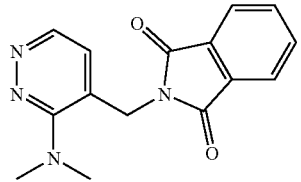 [SMILES: CN(C)c1nnccc1CN1C(=O)c2ccccc2C1=O]

2-[(3-Chloropyridazin-4-yl)methyl]-1H-isoindole-1,3 (2H)-dione (136.8 mg, 0.5 mmol) and 50% aqueous methylamine (1 mL) were sealed in a reaction tube and heated at 150° C. for 20 minutes with stirring and microwave irradiation. After completion of the reaction, the reaction mixture was cooled to room temperature, and the solvent was removed by vacuum distillation. The resulting residue was mixed with 4 M hydrogen chloride/1,4-dioxane (5 mL) and stirred at room temperature for 16 hours. After completion of the reaction, the mixture was concentrated under vacuum, treated with saturated aqueous sodium hydrogen carbonate and extracted with ethyl acetate and chloroform. The extract was dried over anhydrous magnesium sulfate and evaporated under reduced pressure. The resulting residue was purified by silica gel column chromatography (ethyl acetate) to give the desired product (79.6 mg, 56% yield).
Morphology: yellow solid
LC/MS: Condition 7, retention time 3.53 min
LC/MS (ESI$^+$) m/z; 283 [M+1]$^+$
$^1$H-NMR (CDCl$_3$)
δ: 3.07 (s, 6H), 4.87 (s, 2H), 6.95 (d, J=4.8 Hz, 1H), 7.77-7.81 (m, 2H), 7.90-7.94 (m, 2H), 8.69 (d, J=4.8 Hz, 1H)

4-(Aminomethyl)-N,N-dimethylpyridazin-3-amine

Synthesis was carried out in the same manner as in Reference Synthetic Example 54 by using 2-{[3-(dimethylamino)pyridazin-4-yl]methyl}-1H-isoindole-1,3(2H)-dione (79.6 mg, 0.28 mmol). The obtained crude product was used for the next reaction (100% yield).

REFERENCE SYNTHETIC EXAMPLE 76

1-(6-Chloro-3-methoxypyridazin-4-yl)ethanamine

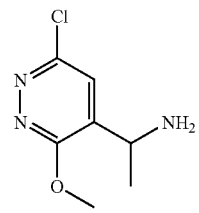

2-[1-(6-Chloro-3-methoxypyridazin-4-yl)ethyl]-1H-isoindole-1,3(2H)-dione

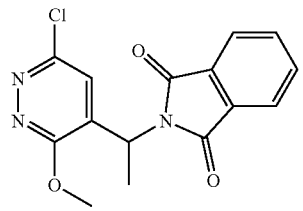 [SMILES: COc1nnc(Cl)cc1C(C)N1C(=O)c2ccccc2C1=O]

Synthesis was carried out in the same manner as in Reference Synthetic Example 54 by using 3-chloro-6-methoxypyridazine, 2-(1,3-dioxoisoindolin-2-yl)propanoic acid (91% yield).
Morphology: colorless solid
LC/MS: Condition 7, retention time 4.01 min
LC/MS (ESI$^+$) m/z; 318, 320 [M+1]$^+$
$^1$H-NMR (CDCl$_3$)
δ: 3.22 (d, J=7.2 Hz, 3H), 4.06 (s, 3H), 5.62 (q, J=7.2 Hz, 1H), 7.56 (s, 1 h), 7.72-7.77 (m, 2H), 7.81-7.85 (m, 2H)

1-(6-Chloro-3-methoxypyridazin-4-yl)ethanamine

Synthesis was carried out in the same manner as in Reference Synthetic Example 54 by using 2-[1-(6-chloro-3-methoxypyridazin-4-yl)ethyl]-1H-isoindole-1,3(2H)-dione (92% yield).
Morphology: colorless solid
$^1$H-NMR (CDCl$_3$)
δ: 1.37 (d, J=7.2 Hz, 3H), 4.15 (s, 3H), 4.35 (q, J=7.2 Hz, 1H), 7.50 (s, 1 h)

REFERENCE SYNTHETIC EXAMPLE 77

1-(3-Chloropyridazin-4-yl)ethanamine

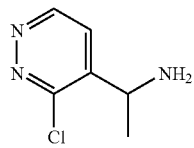

2-[1-(6-Chloro-3-oxo-2,3-dihydropyridazin-4-yl)ethyl]isoindoline-1,3-dione

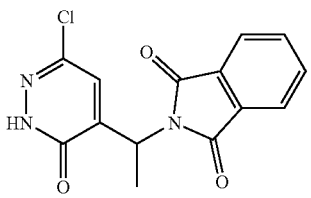 [SMILES: CC(c1cc(Cl)n[nH]c1=O)N1C(=O)c2ccccc2C1=O]

Synthesis was carried out in the same manner as in Reference Synthetic Example 56 by using 2-[1-(6-chloro-3-methoxypyridazin-4-yl)ethyl]-1H-isoindole-1,3(2H)-dione.
Morphology: colorless solid
¹H-NMR (CDCl₃)
δ: 1.78 (d, J=6.9 Hz, 3H), 5.62 (q, J=6.9 Hz, 1H), 7.38 (s, 1h), 7.72-7.77 (m, 2H), 7.81-7.85 (m, 2H), 11.02 (brs, 1H)

2-[1-(3-Chloropyridazin-4-yl)ethyl]-1H-isoindole-1,3(2H)-dione

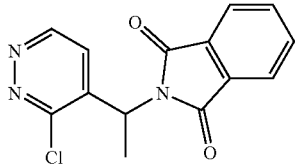 [SMILES: CC(c1ccnnc1Cl)N1C(=O)c2ccccc2C1=O]

2-[1-(6-Chloro-3-oxo-2,3-dihydropyridazin-4-yl)ethyl]isoindoline-1,3-dione (933 mg, 3.07 mmol), triethylamine (0.43 mL, 3.07 mmol), 10% palladium-carbon (50 wt %, 100 mg) were stirred in tetrahydrofuran (10 mL) under hydrogen atmosphere (1 atm) at room temperature for 16 hours. After filtering through celite, the filtrate was concentrated under vacuum. The residue was mixed with phosphoryl chloride (10 mL) and heated to reflux for 1 hour. After the reaction, phosphoryl chloride was removed by vacuum distillation. The resulting solid was dissolved with ethyl acetate, and the organic layer was washed with saturated aqueous sodium hydrogen carbonate. The organic layer was separated, dried over anhydrous magnesium sulfate, and the solvent wad removed by vacuum distillation. The resulting residue was purified by silica gel column chromatography (hexane/ethyl acetate 1:1) to give the desired product (543 mg, 62% yield, two steps).

Morphology: pale yellow solid
¹H-NMR (CDCl₃)
δ: 1.87 (d, J=7.2 Hz, 3H), 5.73 (q, J=7.2 Hz, 1H), 7.72-7.77 (m, 2H), 7.81-7.85 (m, 2H), 7.83 (d, J=4.8 Hz, 1H), 9.16 (d, J=4.8 Hz, 1H)

1-(3-Chloropyridazin-4-yl)ethanamine

Synthesis was carried out in the same manner as in Reference Synthetic Example 54 by using 2-[1-(3-chloropyridazin-4-yl)ethyl]-1H-isoindole-1,3(2H)-dione (50.3 mg, 0.175 mmol). The obtained crude product was used for the next reaction (100% yield).

REFERENCE SYNTHETIC EXAMPLE 78

(3-Isopropylpyridazin-4-yl)methanamine

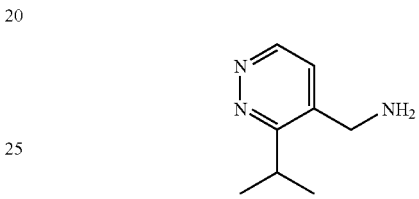

2-{[3-(Propan-2-yl)pyridazin-4-yl]methyl}-1H-isoindole-1,3(2H)-dione

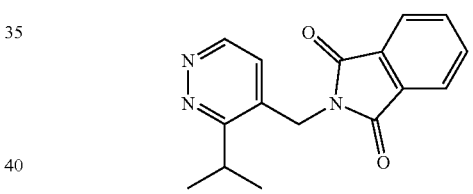

2-[(3-Chloropyridazin-4-yl)methyl]-1H-isoindole-1,3(2H)-dione (137 mg, 0.5 mmol), 4,4,5,5-tetramethyl-2-(prop-1-en-2-yl)-1,3,2-dioxaborolane (252 mg, 0.28 mL, 1.5 mmol), tetrakis(triphenylphosphine)palladium (57.8 mg, 0.05 mmol) and sodium carbonate (106 mg, 2.00 mmol) were mixed with water (0.2 mL) and 1,4-dioxane (0.9 mL) and stirred at 110° C. for 8 hours. After completion of the reaction, the reaction solution was cooled to room temperature, and the solvent was removed by vacuum distillation. The resulting residue was mixed with 4 M hydrogen chloride/1,4-dioxane (5 mL) and stirred at room temperature for 16 hours. After completion of the reaction, the reaction solution was mixed with water and extracted with chloroform, and the extract was dried over anhydrous magnesium sulfate and evaporated under reduced pressure. The resulting residue was purified by silica gel column chromatography (hexane/ethyl acetate=1/2). The obtained colorless solid (76 mg) and 10% palladium-carbon (50 wt %, 100 mg) were stirred in methanol (5 mL) under hydrogen atmosphere (1 atm) at room temperature for 16 hours. After filtering through celite, the filtrate was evaporated under reduce pressure. The resulting residue was purified by silica gel column chromatography (hexane/ethyl acetate=1/2) to give the desired product (76.3 mg, 54% yield).

Morphology: colorless solid
¹H-NMR (CDCl₃)

δ: 1.49 (d, J=6.6 Hz, 6H), 3.555 (sept, J=6.6 Hz, 1H), 4.94 (s, 2H), 7.23 (d, J=4.8 Hz, 1H), 7.79 (m, 2H), 7.92 (m, 2H), 8.98 (d, J=4.8 Hz, 1H)

(3-Isopropylpyridazin-4-yl)methanamine

Synthesis was carried out in the same manner as in Reference Synthetic Example 54 by using 2-{[3-(propan-2-yl)pyridazin-4-yl]methyl}-1H-isoindole-1,3(2H)-dione (50.3 mg, 0.175 mmol). The obtained crude product was used for the next reaction (100% yield).

REFERENCE SYNTHETIC EXAMPLE 79

1-(3-Methoxypyridazin-4-yl)ethanamine Hydrochloride

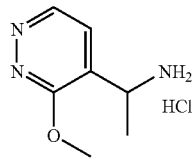

1-(6-Chloro-3-methoxypyridazin-4-yl)ethanamine (67.3 mg, 0.36 mmol) and 10% palladium-carbon (50 wt %, 20 mg) were stirred in methanol (5 mL) under hydrogen atmosphere (1 atm) at room temperature for 16 hours. After filtering through celite, the filtrate was evaporated under reduced pressure. The resulting crude reaction product was used for the next step.

REFERENCE SYNTHETIC EXAMPLE 80

1-[3-(Methylsulfonyl)pyridin-4-yl]methanamine Hydrochloride

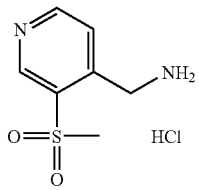

3-Chloro-5-(methylthio)isonicotinonitrile

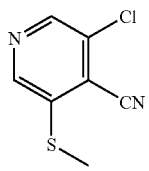

To a solution of 3,5-dichloroisonicotinonitrile (346 mg, 2 mmol) in N,N-dimethylformamide (2 mL) was added sodium thiomethoxide (141 mg, 2 mmol) at 0° C. The mixture was stirred at room temperature for 4 hours. After completion of the reaction, the solution was concentrated under reduced pressure. To the resulting residue was added saturated aqueous sodium hydrogen carbonate and the mixture was extracted with ethyl acetate. The combined organic layer was separated, dried over anhydrous magnesium sulfate and concentrated under reduced pressure. The resulting residue was purified by silica gel column chromatography (hexane/ethyl acetate=1/1) to give the desired product (92 mg, 25% yield).

Morphology: colorless solid $^1$H-NMR (CDCl$_3$)

δ: 2.67 (s, 3H), 8.47 (s, 1H), 8.50 (s, 1H)

3-Chloro-5-(methylsulfonyl)pyridine-4-carbonitrile

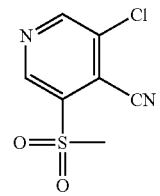

3-Chloro-5-(methylthio)isonicotinonitrile (92 mg, 0.5 mmol) was stirred with m-chloroperbenzoic acid (65 wt %, 265 mg, 1 mmol) in chloroform (5 mL) at 60° C. for 3 hours. After completion of the reaction, the reaction mixture was allowed to cool to room temperature and purified by silica gel column chromatography (ethyl acetate) to give the desired product (97 mg, 90%).

Morphology: colorless solid $^1$H-NMR (CDCl$_3$)

δ: 3.35 (s, 3H), 9.09 (s, 1H), 9.26 (s, 1H)

1-[3-(Methylsulfonyl)pyridin-4-yl]methanamine Hydrochloride

1-[5-(Methylsulfonyl)-1,2,3,4-tetrahydropyridin-4-yl]methanamine Hydrochloride

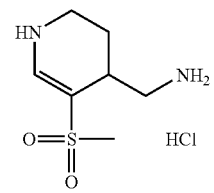

3-Chloro-5-(methylsulfonyl)pyridine-4-carbonitrile (97.2 mg, 0.449 mmol) and 10% palladium-carbon (50 wt %, 20 mg) were stirred in methanol (5 mL) under hydrogen (1 atm) at room temperature for 16 hours. After filtering through celite, the mixture was concentrated under vacuum to give a mixture of 1-[3-(methylsulfonyl)pyridin-4-yl]methanamine hydrochloride and 1-[5-(methylsulfonyl)-1,2,3,4-tetrahydropyridin-4-yl]methanamine hydrochloride. The mixture was used for the next reaction.

REFERENCE SYNTHETIC EXAMPLE 81

(3-Chloro-6-methylpyridazin-4-yl)methanamine

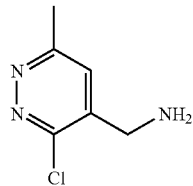

2-[1-(3,6-Dichloropyridazin-4-yl)ethyl]isoindoline-1,3-dione

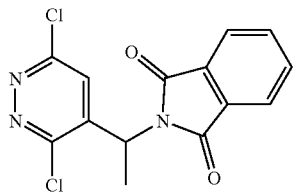 [SMILES: CC(c1cc(Cl)nnc1Cl)N1C(=O)c2ccccc2C1=O]

Synthesis was carried out in the same manner as in Reference Synthetic Example 54 by using 2-(1,3-dioxoisoindolin-2-yl)propanoic acid (16% yield).
Morphology: colorless solid
LC/MS: Condition 7, retention time 4.08 min
LC/MS (ESI$^+$) m/z; 322, 324, 326 [M+1]$^+$
$^1$H-NMR (CDCl$_3$)
δ: 1.86 (d, J=6.9 Hz, 3H), 5.68 (q, J=6.9 Hz, 1H), 7.72-7.77 (m, 2H), 7.81-7.85 (m, 2H)

2-[1-(3-Chloro-6-methylpyridazin-4-yl)ethyl]isoindoline-1,3-dione

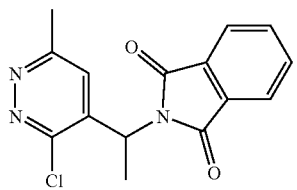 [SMILES: Cc1cc(C(C)N2C(=O)c3ccccc3C2=O)c(Cl)nn1]

2-[1-(3,6-Dichloropyridazin-4-yl)ethyl]isoindoline-1,3-dione (161 mg, 0.5 mmol), trimethylboroxine (0.209 mL, 1.5 mmol), [1,1'-bis(diphenylphosphino)ferrocene]dichloropalladium (II) dichloromethane complex (35.1 mg, 0.05 mmol) and potassium carbonate (82.9 mg, 0.6 mmol) were mixed with water (0.2 mL) and 1,4-dioxane (0.9 mL) and stirred at 110° C. for 8 hours. After completion of the reaction, the reaction solution was cooled to room temperature, and the solvent was removed by vacuum distillation. The resulting residue was mixed with 4 M hydrogen chloride/1,4-dioxane (10 mL) and stirred at room temperature for 16 hours. After completion of the reaction, the reaction solution was mixed with water and extracted with chloroform, and the extract was dried over anhydrous magnesium sulfate and evaporated under reduced pressure. The resulting residue was purified by preparative thin-layer chromatography (hexane/ethyl acetate=1/1) to give the desired product (29 mg, 19% yield).
Morphology: colorless solid
LC/MS: Condition 7, retention time 4.08 min
LC/MS (ESI$^+$) m/z; 302, 304 [M+1]$^+$
$^1$H-NMR (CDCl$_3$)
δ: 1.86 (d, J=7.2 Hz, 3H), 2.75 (s, 1H), 5.69 (q, J=7.2 Hz, 1H), 7.64 (s, 1H), 7.72-7.77 (m, 2H), 7.81-7.85 (m, 2H)

(3-Chloro-6-methylpyridazin-4-yl)methanamine

Synthesis was carried out in the same manner as in Reference Synthetic Example 54 by using 2-[1-(3-chloro-6-methylpyridazin-4-yl)ethyl]isoindoline-1,3-dione (91% yield).
Morphology: colorless oil
$^1$H-NMR (CDCl$_3$)
δ: 1.40 (d, J=6.6 Hz, 3H), 2.70 (s, 1H), 4.42 (q, J=6.6 Hz, 1H), 7.60 (s, 1H)

REFERENCE SYNTHETIC EXAMPLE 82

1-(Pyridazin-4-yl)butan-1-amine

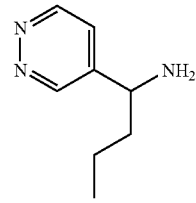

2-[1-(Pyridazin-4-yl)butyl]isoindoline-1,3-dione

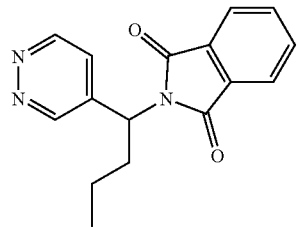 [SMILES: CCCC(c1ccnnc1)N1C(=O)c2ccccc2C1=O]

Synthesis was carried out in the same manner as in Reference Synthetic Example 54 by using 2-(1,3-dioxoisoindolin-2-yl)pentanoic acid (12% yield, two steps).
Morphology: colorless oil
$^1$H-NMR (CDCl$_3$)
δ: 0.99 (t, J=7.2 Hz, 3H), 1.36 (m, 2H), 2.10-2.25 (m, 1H), 2.50-2.70 (m, 1H), 5.36 (dd, J=6.0 Hz, J=7.2 Hz, 1H), 7.62 (m, 1H), 7.71-7.78 (m, 2H), 7.84-7.89 (m, 2H), 9.16 (d, J=5.1 Hz, 1H), 9.29 (s, 1H)

1-(Pyridazin-4-yl)butan-1-amine

Synthesis was carried out in the same manner as in Reference Synthetic Example 54 by using 2-[1-(pyridazin-4-yl)butyl]isoindoline-1,3-dione. The obtained crude product was used for the next reaction (100% yield).

REFERENCE SYNTHETIC EXAMPLE 83 TO 85

Amines were synthesized in the same manner as in Reference Synthetic Example 2, and the yields and morphology of the resulting amines, the LC/MS conditions used for their analysis and the observed peaks and retention times are shown in Table 8. "crude" in the remarks column means that the crude reaction product was used for the next step without purification.

TABLE 8

| Reference Synthetic Example No. | Yield (%) | Morphology | LC/MS Condition | observed peak ESI+ | observed peak ESI− | Retention time (min) | Remarks |
|---|---|---|---|---|---|---|---|
| 83 | | Orange oil | | | | | Crude |
| 84 | | Pale yellow oil | | | | | Crude |
| 85 | | Pale yellow oil | | | | | Crude |

The structures of the compounds obtained are shown below.

REFERENCE SYNTHETIC EXAMPLES 83 TO 85

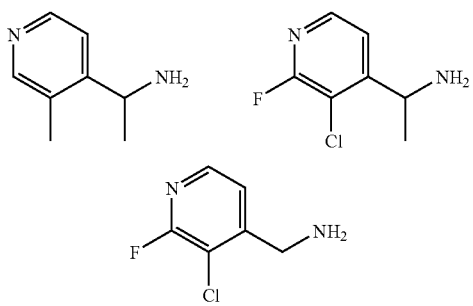

REFERENCE SYNTHETIC EXAMPLE 86

1-(3-Methylpyridin-4-yl)ethanol

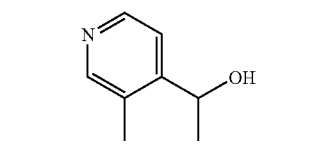

3-Methylpyridine-4-carbaldehyde

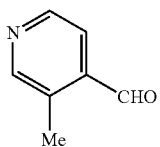

3-Chloropyridine-4-carbaldehyde (141.6 mg, 1.00 mmol), trimethylboroxine (278.4 μl 2.00 mmol), [1,1'-bis(diphenylphosphino)ferrocene]dichloropalladium (II) dichloromethane complex (81.6 mg, 0.10 mmol) and potassium carbonate (414.6 mg, 3.00 mmol) were mixed with water (0.2 mL) and 1,4-dioxane (1.8 mL) and stirred at 100° C. for 3 hours. After completion of the reaction, the reaction solution was allowed to cool, and the solvent was removed by vacuum distillation. The resulting crude reaction product containing the desired product was used for the next step (594.7 mg).

1-(3-Methylpyridin-4-yl)ethanol

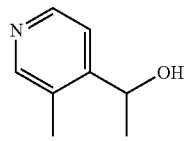

3-Methylpyridine-4-carbaldehyde (310.6 mg, 1.00 mmol) in tetrahydrofuran (6 mL) was mixed with methylmagnesium bromide (0.98 M in tetrahydrofuran, 4.74 mL, 4.65 mmol) under −78° C., and the mixture was warmed slowly to room temperature for 16 hours with stirring. After completion of the reaction, the reaction solution was mixed with saturated aqueous ammonium chloride and extracted with ethyl acetate, and the organic layer was dried over anhydrous sodium sulfate and evaporated under reduced pressure. The resulting crude reaction product containing the desired product was used for the next step (310.6 mg).

REFERENCE SYNTHETIC EXAMPLE 87

1-(3-Chloro-2-fluoropyridin-4-yl)ethanol

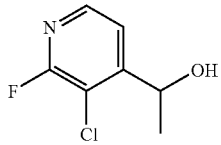

4-({[tert-Butyl(dimethyl)silyl]oxy}methyl)-2-fluoropyridine

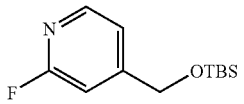

2-Fluoro-4-pyridinemethanol (508.5 mg, 4.00 mmol), t-butyldimethylsilylchloride (1.21 g, 8.00 mmol) and imidazole (1.09 g, 16.00 mmol) were stirred in dichloromethane (10 mL) at room temperature for an hour. After completion of the reaction, the reaction solution was mixed with ethyl acetate, and the resulting organic layer was washed with saturated aqueous ammonium chloride, dried over anhydrous sodium sulfate and evaporated under reduced pressure. The resulting residue was purified by silica gel column chromatography (hexane/ethyl acetate=10/1) to give the desired product (785.2 mg, 81% yield).

Morphology: colorless oil
$^1$H-NMR (CDCl$_3$)
δ: 0.01 (s, 6H), 0.83 (s, 9H), 4.60 (s, 2H), 6.80 (s, 1H), 6.97 (d, J=5.3 Hz, 1H), 8.02 (d, J=5.3 Hz, 1H).

4-({[tert-Butyl(dimethyl)silyl]oxy}methyl)-3-chloro-2-fluoropyridine

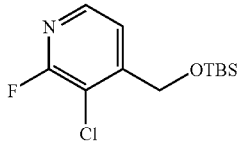

A tetrahydrofuran solution (10 mL) of 4-({[tert-butyl(dimethyl)silyl]oxy}methyl)-2-fluoropyridine (469.1 mg, 1.94 mmol) was mixed with lithium diisopropylamide (1.08 M in tetrahydrofuran, 2.16 mL, 2.33 mmol) under cooling with ice. The reaction mixture was stirred at 0° C. for an hour, then added to hexachloroethane (840.0 mg, 3.50 mmol) and warmed slowly to room temperature for 12 hours with stirring. After completion of the reaction, the reaction solution was mixed with ethyl acetate, and the organic layer was washed with saturated aqueous ammonium chloride, dried over anhydrous sodium sulfate and evaporated under reduced pressure. The resulting residue was purified by silica gel column chromatography (hexane/ethyl acetate=9/1 to 5/1) to give the desired product (157.7 mg, 30% yield).

Morphology: pale yellow oil
$^1$H-NMR (CDCl$_3$)
δ: 0.01 (s, 6H), 0.83 (s, 9H), 4.65 (s, 2H), 7.29 (d, J=5.1 Hz, 1H), 7.95 (d, J=5.1 Hz, 1H).

3-(Chloro-2-fluoropyridin-4-yl)methanol

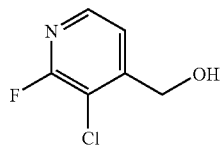

A tetrahydrofuran solution (10 mL) of 4-({[tert-butyl(dimethyl)silyl]oxy}methyl)-3-chloro-2-fluoropyridine (194.1 mg, 0.71 mmol) was mixed with tetra-n-butylammonium fluoride (1.0 M in tetrahydrofuran, 0.85 mL, 0.85 mmol) under cooling with ice, and the mixture was stirred at room temperature for 3 days. After completion of the reaction, the reaction solution was mixed with ethyl acetate, and the organic layer was washed with saturated aqueous sodium chloride, dried over anhydrous sodium sulfate and evaporated under reduced pressure. The resulting residue was purified by silica gel column chromatography (hexane/ethyl acetate=5:1 to 2:1, ethyl acetate/methanol=20/1 to 4/1) to give the desired product (99.1 mg, 86% yield).

Morphology: pale yellow oil
$^1$H-NMR (CDCl$_3$)
δ: 4.86 (s, 2H), 7.46 (d, J=4.6 Hz, 1H), 8.12 (d, J=4.6 Hz, 1H).

3-Chloro-2-fluoropyridine-4-carbaldehyde

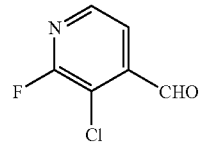

A chloroform solution (4 mL) of (3-chloro-2-fluoropyridin-4-yl)methanol (99.1 mg, 0.61 mmol) was mixed with manganese dioxide (308.6 mg, 3.55 mmol) and stirred at 80° C. for 1 day. After completion of the reaction, the reaction solution was allowed to cool and filtered through celite, and the filtrate was evaporated under reduced pressure. The resulting containing the desired product was used for the next step (56.1 mg).

Morphology: pale yellow oil
$^1$H-NMR (CDCl$_3$)
δ: 7.64 (d, J=5.0 Hz, 1H), 8.28 (d, J=5.0 Hz, 1H), 10.5 (s, 1H).

1-(3-Chloro-2-fluoropyridin-4-yl)ethanol

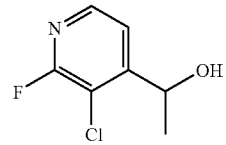

3-Chloro-2-fluoropyridine-4-carbaldehyde (56.1 mg, 0.35 mmol) in tetrahydrofuran (2 mL) was mixed with methylmagnesium bromide (0.98 M in tetrahydrofuran, 1.13 mL, 1.05 mmol) under −78° C., and the reaction mixture was warmed slowly to room temperature for 16 hours with stirring. After completion of the reaction, the reaction solution was mixed with saturated aqueous ammonium chloride and extracted with ethyl acetate, and the organic layer was dried over anhydrous sodium sulfate and evaporated under reduced pressure. The resulting crude reaction product containing the desired product was used for the next step (64.7 mg).

Morphology: pale yellow oil
$^1$H-NMR (CDCl$_3$)
δ: 1.49 (d, J=6.3 Hz, 1H), 5.27 (q, J=6.3 Hz, 1H), 7.49 (d, J=5.1 Hz, 1H), 8.08 (d, J=5.1 Hz, 1H), 10.5 (s, 1H).

REFERENCE SYNTHETIC EXAMPLE 88

Bicyclo[3.3.1]nonan-3-amine

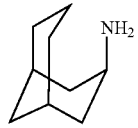

To bicyclo[3.3.1]non-6-en-3-amine (100 mg, 0.729 mmol) in ethanol (3 mL), 10% palladium-carbon (10 mg) was added in a nitrogen stream, and the reaction solution was stirred in a hydrogen stream at room temperature for 1 day. After completion of the reaction, the reaction solution was filtered through celite and the filtrate was evaporated under reduced pressure. The resulting crude reaction product was used for the next step without to further purification (98.5 mg).

Morphology: colorless solid

REFERENCE SYNTHETIC EXAMPLE 89

1-(1-{[2-(Trimethylsilyl)ethoxy]methyl}-1H-pyrazol-4-yl)ethanamine

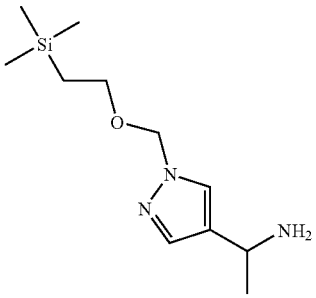 [SMILES: CC(N)c1cnn(COCC[Si](C)(C)C)c1]

N-Methoxy-N-methyl-1H-pyrazole-4-carboxamide

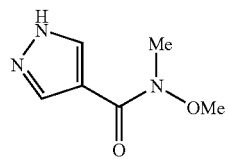 [SMILES: CON(C)C(=O)c1cn[nH]c1]

A N,N-dimethylformamide solution (3 mL) of 4-pyrazolecarboxylic acid (150 mg, 1.34 mmol), N,O-dimethylhydroxylamine hydrochloride (261.4 mg, 2.68 mmol), 1-ethyl-3-(3-dimethylaminopropyl)carbodiimide, hydrochloride (513.8 mg, 2.68 mmol), 1-hydroxybenzotriazoleimidazole anhydride (54.2 mg, 0.40 mmol), and triethylamine (0.38 mL, 2.68 mmol) was stirred for 1 day. After completion of the reaction, the reaction solution was mixed with ethyl acetate and washed with saturated aqueous sodium chloride. The organic layer was dried over anhydrous sodium sulfate and evaporated under reduced pressure. The resulting crude reaction product containing the desired product was used for the next step (142.7 mg).
Morphology: colorless oil
$^1$H-NMR (CDCl$_3$)
δ: 2.89 (s, 3H), 2.96 (s, 3H), 8.03 (s, 1H), 8.13 (s, 1H).

N-Methoxy-N-methyl-1-{[2-(trimethylsilyl)ethoxy]methyl}-1H-pyrazole-4-carboxamide

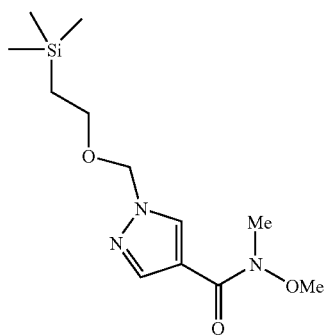 [SMILES: CON(C)C(=O)c1cnn(COCC[Si](C)(C)C)c1]

A dichloromethane solution (3 mL) of N-methoxy-N-methyl-1H-pyrazole-4-carboxamide (142.7 mg, 2.68 mmol) was mixed with 2-(trimethysilyl)ethoxymethyl chloride (0.47 mL, 2.68 mmol) and N,N-diisopropylethylamine (0.94 mL, 5.36 mmol) and stirred at room temperature for 16 hours. After completion of the reaction, the reaction solution was mixed with ethyl acetate washed with saturated aqueous sodium chloride and the organic layer was dried over anhydrous sodium sulfate and evaporated under reduced pressure. The resulting residue was purified by silica gel column chromatography (hexane/ethyl acetate=10/1) to give the desired product (325.8 mg, 85% yield).
Morphology: colorless oil
$^1$H-NMR (CDCl$_3$)
δ: 0.01 (s, 9H), 0.89-0.97 (m, 2H), 3.32 (s, 3H), 3.54-3.68 (m, 2H), 3.70 (s, 3H), 5.42 (s, 2H), 7.99 (s, 1H), 8.09 (s, 1H).

1-(1-{[2-(Trimethylsilyl)ethoxy]methyl}-1H-pyrazol-4-yl)ethanone

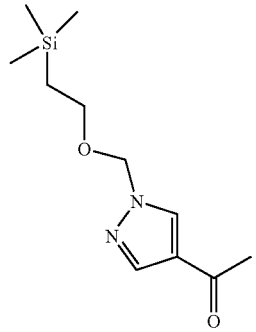 [SMILES: CC(=O)c1cnn(COCC[Si](C)(C)C)c1]

N-Methoxy-N-methyl-1-{[2-(trimethylsilyl)ethoxy]methyl}-1H-pyrazole-4-carboxamide (325.8 mg, 1.14 mmol) in tetrahydrofuran (2 mL) was mixed with methylmagnesium bromide (0.98 M in tetrahydrofuran, 4.32 mL, 4.23 mmol) under cooling with ice and the reaction mixture was warmed slowly to room temperature for 16 hours with stirring. After completion of the reaction, the reaction solution was mixed with saturated aqueous ammonium chloride, and extracted with ethyl acetate. The organic layer was dried over anhydrous sodium sulfate and evaporated under reduced pressure. The resulting residue was purified by silica gel column chromatography (hexane/ethyl acetate=2/1, to ethyl acetate/MeOH=20/1) to give the desired product (89.9 mg, 33% yield).
Morphology: colorless oil
$^1$H-NMR (CDCl$_3$)
δ: 0.01 (s, 9H), 0.94 (t, J=5.1 Hz, 2H), 2.46 (s, 3H), 3.61 (t, J=5.1 Hz, 2H), 5.46 (s, 2H), 7.95 (s, 1H), 8.09 (s, 1H).

1-(1-{[2-(Trimethylsilyl)ethoxy]methyl}-1H-pyrazol-4-yl)ethanol

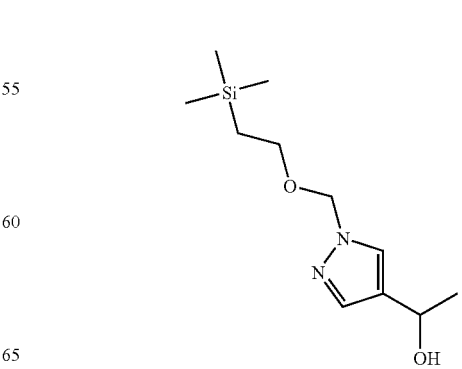

1-(1-{[2-(Trimethylsilyl)ethoxy]methyl}-1H-pyrazol-4-yl)ethanone (39.7 mg, 0.17 mmol) in methanol (2 mL) was mixed with sodium borohydride (12.5 mg, 0.34 mmol) and stirred at room temperature for 90 minutes. After completion of the reaction, the reaction solution was mixed with ethyl acetate and washed with saturated aqueous sodium chloride. The organic layer was dried over anhydrous sodium sulfate and evaporated under reduced pressure. The resulting crude reaction product containing the desired product was used for the next step (43.7 mg).

Morphology: colorless oil
$^1$H-NMR (CDCl$_3$)
δ: 0.01 (s, 9H), 0.92 (t, J=5.1 Hz, 2H), 1.54 (d, J=6.6 Hz 3H), 3.58 (t, J=5.1 Hz, 2H), 4.87-4.97 (m, 1H), 5.41 (s, 2H), 7.54-7.56 (m, 2H).

1-(1-{[2-(Trimethylsilyl)ethoxy]methyl}-1H-pyrazol-4-yl)ethanamine

Synthesis was carried out in the same manner as in Reference Synthetic Example 2 by using 1-(1-{[2-(trimethylsilyl)ethoxy]methyl}-1H-pyrazol-4-yl)ethanol. The obtained crude product was used for the next reaction.

Morphology: colorless oil

SYNTHETIC EXAMPLE 1

4-Bromo-2-(2-morpholino-2-oxoethyl)-5-[(1R,2R,3R,5S)-2,6,6-trimethylbicyclo[3.1.1]hept-3-ylamino]pyridazin-3(2H)one

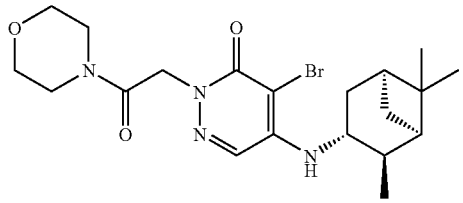 [SMILES: C[C@@H]1[C@H]2C[C@@H](C[C@H]1Nc1cnn(CC(=O)N3CCOCC3)c(=O)c1Br)C2(C)C]

4-Bromo-5-[(1R,2R,3R,5S)-2,6,6-trimethylbicyclo[3.1.1]hept-3-ylamino]pyridazin-3(2H)one

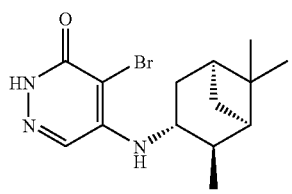

4,5-Dibromopyridazin-3(2H)-one (3.00 g, 11.8 mmol, prepared in accordance with Journal of Heterocyclic Chemistry, 33(6), 1579-1582; 1996) in dioxane-water (1:1, 30 mL) was stirred with triethylamine (4.94 mL, 35.5 mmol) and (1R,2R,3R,5S)-isopinocampheylamine (2.41 mL, 14.2 mmol) at 120° C. for 17 hours. After cooling, the reaction solution was mixed with 1 M aqueous hydrochloric acid and extracted with chloroform. The extract was dried over anhydrous magnesium sulfate and evaporated under reduced pressure. The resulting residue was purified by silica gel chromatography (chloroform/ethyl acetate=5/1) to give the desired product (1.26 g, 33% yield).

Morphology: yellow amorphous
LC/MS: Condition 3, retention time 4.07 min
LC/MS (ESI$^+$) m/z; 326, 328 [M+1]$^+$
$^1$H-NMR (CDCl$_3$)
δ: 0.95 (d, J=9.9 Hz, 1H), 1.18 (s, 3H), 1.19 (d, J=7.0 Hz, 3H), 1.28 (s, 3H), 1.70-1.75 (m, 1H), 1.90-2.10 (m, 2H), 2.40-2.50 (m, 1H), 2.60-2.70 (m, 1H), 3.80-3.90 (m, 1H), 4.82 (d, J=8.3 Hz, 1H), 7.56 (s, 1H), 11.21 (s, 1H).

Ethyl 2-{5-bromo-6-oxo-4-[(1R,2R,3R,5S)-2,6,6-trimethylbicyclo[3.1.1]hept-3-ylamino]pyridazin-1(6H)-yl}acetate

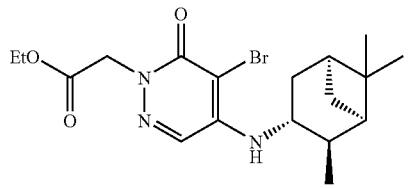 [SMILES: CCOC(=O)Cn1ncc(N[C@@H]2C[C@@H]3C[C@H]([C@H]2C)C3(C)C)c(Br)c1=O]

4-Bromo-5-[(1R,2R,3R,5S)-2,6,6-trimethylbicyclo[3.1.1]hept-3-ylamino]pyridazin-3(2H)-one (600 mg, 1.84 mmol) in N,N-dimethylformamide (6 mL) was mixed with ethyl bromoacetate (306 μL, 2.76 mmol) and potassium carbonate (381 mg, 2.76 mmol) at room temperature and stirred at 80° C. for 1.5 hours. After cooling, the reaction solution was mixed with saturated aqueous ammonium chloride and extracted with ethyl acetate. The resulting organic layer was washed with saturated aqueous ammonium chloride and saturated aqueous sodium chloride, dried over anhydrous magnesium sulfate and evaporated under reduced pressure. The resulting residue was purified by silica gel chromatography (chloroform/ethyl acetate=8/1) to give the desired product (670 mg, 88% yield).

Morphology: light brown oil
LC/MS: Condition 2, retention time 3.63 min
LC/MS (ESI$^+$) m/z; 412, 414 [M+1]$^+$
LC/MS (ESI$^-$) m/z; 410, 412 [M−1]$^-$
$^1$H-NMR (CDCl$_3$)
δ: 0.97 (d, J=10.2 Hz, 1H), 1.05 (s, 3H), 1.21 (d, J=7.4 Hz, 3H), 1.27 (s, 3H), 1.27 (t, J=7.0 Hz, 3H), 1.70-1.80 (m, 1H), 1.90-2.00 (m, 1H), 2.00-2.10 (m, 1H), 2.40-2.55 (m, 1H), 2.57-2.70 (m, 1H), 3.80-3.90 (m, 1H), 4.24 (q, J=7.0 Hz, 2H), 4.74 (d, J=8.2 Hz, 1H), 4.87 (s, 2H), 7.54 (s, 1H).

2-{5-Bromo-6-oxo-4-[(1R,2R,3R,5S)-2,6,6-trimethylbicyclo[3.1.1]hept-3-ylamino]pyridazin-1(6H)-yl}acetic Acid

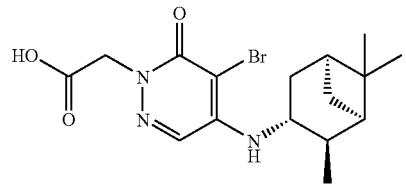 [SMILES: C[C@@H]1[C@H]2C[C@@H](C[C@H]1Nc1cnn(CC(=O)O)c(=O)c1Br)C2(C)C]

Ethyl 2-{5-bromo-6-oxo-4-[(1R,2R,3R,5S)-2,6,6-trimethylbicyclo[3.1.1]hept-3-ylamino]pyridazin-1(6H)-yl}acetate (646 mg, 1.57 mmol) in 1,4-dioxane (6.5 mL) was mixed with 1 M aqueous sodium hydroxide (4.71 mL, 4.71 mmol) and stirred at room temperature for 1 hour. After completion of the reaction, ethyl acetate was added, and the organic layer was washed with 1 M hydrochloric acid and saturated aqueous sodium chloride, dried over anhydrous magnesium sulfate and evaporated under reduced pressure to give the desired product (567 mg, 94% yield).

Morphology: pale yellow solid
LC/MS: Condition 3, retention time 4.12 min
LC/MS (ESI$^+$) m/z; 384, 386 [M+1]$^+$
LC/MS (ESI$^-$) m/z; 382, 384 [M−1]$^-$
$^1$H-NMR (CDCl$_3$)
δ: 0.97 (d, J=10.2 Hz, 1H), 1.05 (s, 3H), 1.18 (d, J=7.4 Hz, 3H), 1.27 (s, 3H), 1.70-1.80 (m, 1H), 1.90-2.00 (m, 1H), 2.00-2.10 (m, 1H), 2.40-2.50 (m, 1H), 2.60-2.70 (m, 1H), 3.80-3.90 (m, 1H), 4.82 (d, J=8.2 Hz, 1H), 4.92 (s, 2H), 6.23 (br s, 1H), 7.58 (s, 1H).

4-Bromo-2-(2-morpholino-2-oxoethyl)-5-[(1R,2R,3R,5S)-2,6,6-trimethylbicyclo[3.1.1]hept-3-ylamino]pyridazin-3(2H)-one 2-{5-Bromo-6-oxo-4-[(1R,2R,3R,5S)-2,6,6-trimethylbicyclo[3.1.1]hept-3-ylamino]pyridazin-1(6H)-yl}acetic acid (30 mg, 0.078 mmol), 1-(3-dimethylaminopropyl)-3-ethylcarbodiimide hydrochloride (22 mg, 0.117 mmol), 1-hydroxybenzotriazole anhydride (16 mg, 0.117 mmol) and triethylamine (16 μL, 0.117 mmol) in N,N-dimethylformamide (0.3 mL) was stirred with morpholine (10 μL, 0.117 mmol) at room temperature for 5 hours. After completion of the reaction, ethyl acetate was added, and the organic layer was washed with saturated aqueous ammonium sulfate and saturated aqueous sodium hydrogen carbonate and saturated aqueous sodium chloride, dried over anhydrous magnesium sulfate and evaporated under reduced pressure. The resulting residue was purified by silica gel chromatography (chloroform/ethyl acetate=1/1) to give the desired product (20 mg, 57% yield).

Morphology: colorless amorphous
LC/MS: Condition 3, retention time 4.18 min
LC/MS (ESI$^+$) m/z; 453, 455 [M+1]$^+$
LC/MS (ESI$^-$) m/z; 451, 453 [M−1]$^-$

SYNTHETIC EXAMPLES 2 TO 40

Compounds were synthesized in the same manner as in Synthetic Example 1, and the yields and morphology of the resulting compounds, the LC/MS conditions used for their analysis and the observed peaks and retention times are shown in Table 9.

TABLE 9

| Synthetic Example No. | Yield (%) | Morphology | LC/MS Condition | Observed peak ESI$^+$ | Observed peak ESI$^-$ | Retention time (min) |
|---|---|---|---|---|---|---|
| 2 | 39 | Colorless solid | | 499/501 | 497/499 | 4.35 |
| 3 | 97 | Pale yellow solid | 3 | 439/441 | 437/439 | 4.59 |
| 4 | 100 | Pale yellow solid | 3 | 459/461 | 457/459 | 4.70 |
| 5 | 73 | Pale yellow solid | 3 | 487/489 | 485/487 | 4.70 |
| 6 | 84 | Colorless solid | 3 | 552/554 | 550/552 | 4.72 |
| 7 | 77 | Colorless solid | 3 | 441/443 | 439/441 | 4.14 |
| 8 | 70 | Colorless solid | 3 | 474/476 | 472/474 | 3.52 |
| 9 | 19 | Pale yellow solid | 3 | 497/499 | 495/497 | 4.62 |
| 10 | 77 | Pale yellow solid | 3 | 479/481 | 477/479 | 4.84 |
| 11 | 86 | Pale yellow solid | 3 | 474/476 | 472/474 | 0.50 |
| 12 | 70 | Colorless solid | 3 | 474/476 | 472/474 | 3.79 |
| 13 | 86 | Colorless solid | 3 | 475/477 | 473/475 | 4.12 |
| 14 | 89 | Colorless solid | 3 | 488/490 | 486/488 | 3.54 |
| 15 | 84 | Colorless solid | 3 | 520/522 | 518/520 | 2.30 |
| 16 | 81 | Yellow solid | 2 | 529/531 | 527/529 | 2.47 |
| 17 | 40 | Colorless solid | 2 | 499/501 | 497/499 | 3.20 |
| 18 | 71 | Brown solid | 2 | 423/425 | 421/423 | 3.20 |
| 19 | 66 | Pale yellow oil | 2 | 496/498 | 494/496 | 2.30 |
| 20 | 16 | Pale yellow oil | 2 | 467/469 | 465/467 | 3.17 |
| 21 | 70 | Yellow solid | 2 | 494/496 | 492/494 | 2.30 |
| 22 | 34 | Pale yellow oil | 2 | 487/489 | 485/487 | 3.59 |
| 23 | 55 | Yellow solid | 2 | 451/453 | 449/451 | 3.48 |
| 24 | 48 | Colorless solid | 2 | 460/462 | 458/460 | 4.40 |
| 25 | 48 | Pale yellow oil | 3 | 460/462 | 458/460 | 3.77 |
| 26 | 50 | Dark green solid | 3 | 563/565 | 561/563 | 5.03 |
| 27 | 65 | Yellow oil | 3 | 501/503 | 499/501 | 3.69 |
| 28 | 100 | Yellow solid | 2 | 463/465 | 461/463 | 3.67 |
| 29 | 92 | Yellow oil | 3 | 515/517 | 513/515 | 5.14 |
| 30 | 12 | Yellow oil | 3 | 451/453 | — | 4.52 |
| 31 | 93 | Pale yellow solid | 3 | — | 517/519 | 5.09 |
| 32 | 100 | Pale yellow solid | 3 | 517/519 | 515/517 | 4.99 |
| 33 | 63 | Yellow oil | 3 | 503/505 | 501/503 | 4.65 |
| 34 | 13 | Yellow amorphous | 3 | 544/546 | 542/544 | 4.42 |
| 35 | 68 | Brown solid | 3 | 475/477 | 473/475 | 4.57 |
| 36 | 42 | Yellow solid | 3 | 529/531 | 527/529 | 3.70 |
| 37 | 63 | Yellow amorphous | 3 | 514/516 | 512/514 | 2.37 |
| 38 | 61 | Colorless amorphous | 2 | 488/490 | 486/488 | 3.54 |
| 39 | 18 | Pale yellow solid | 3 | 569/571 | 567/569 | 4.67 |
| 40 | 27 | Yellow amorphous | 3 | | | |

The structures of the compounds obtained in these Synthetic Examples are shown below.
SYNTHETIC EXAMPLES 2 TO 40
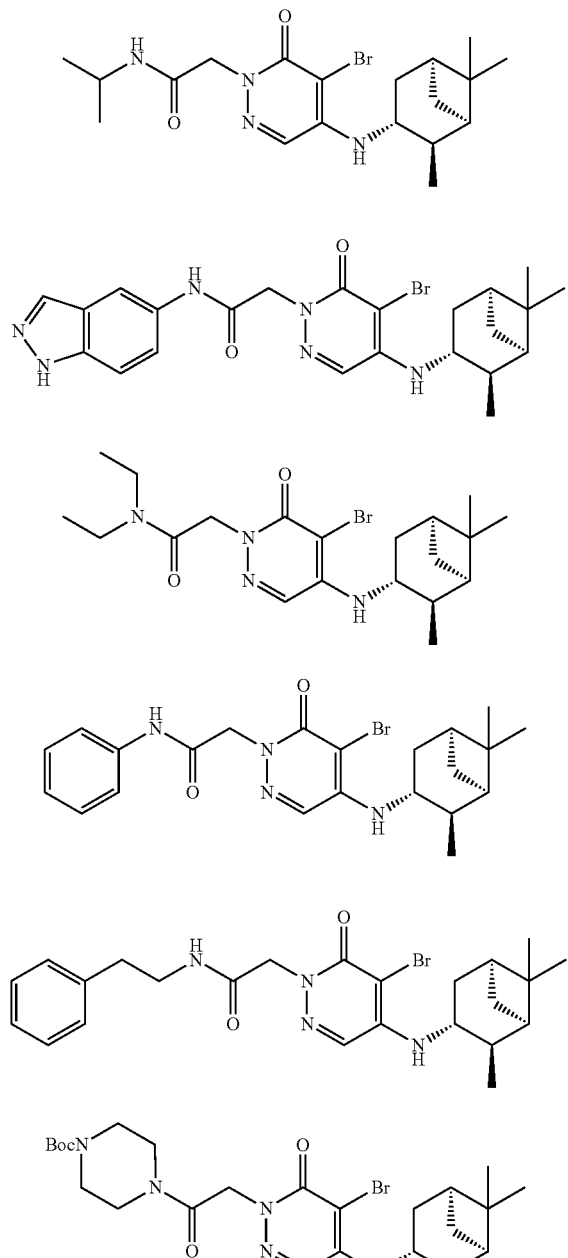
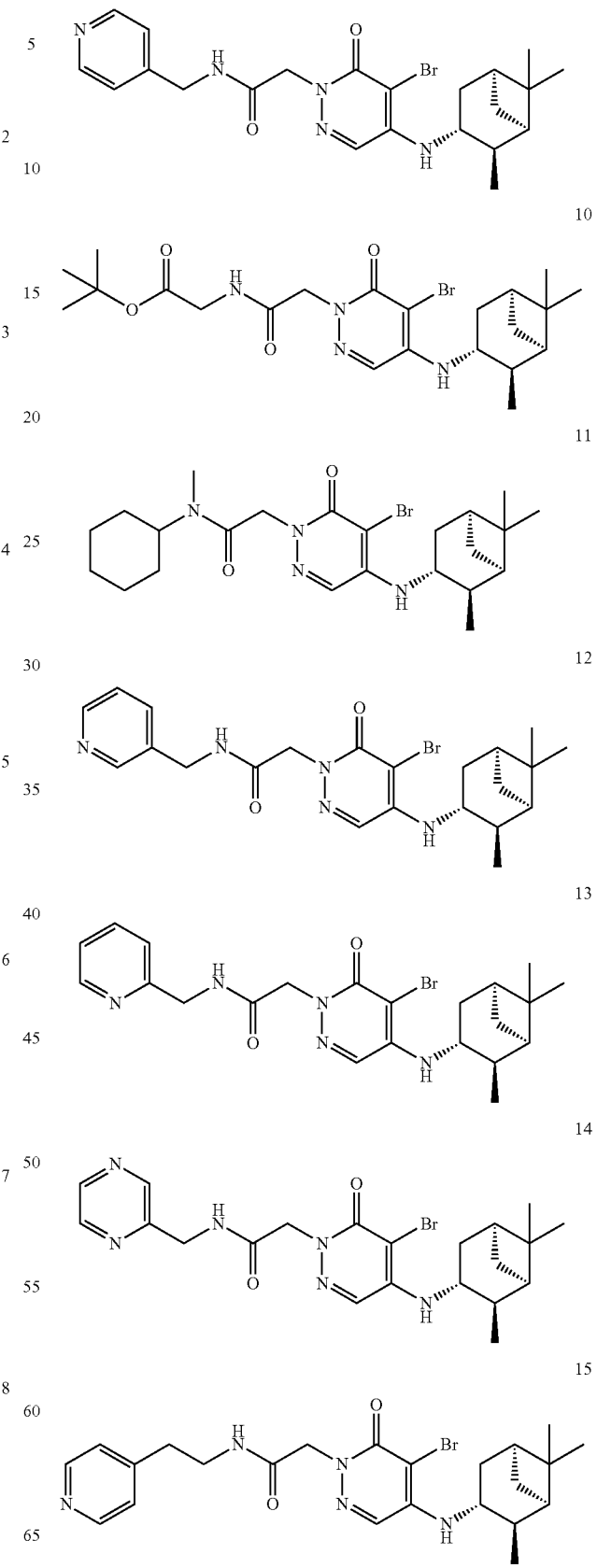

16
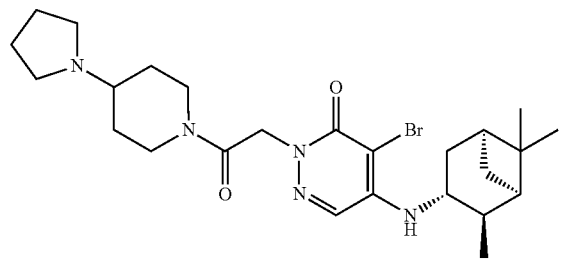
17
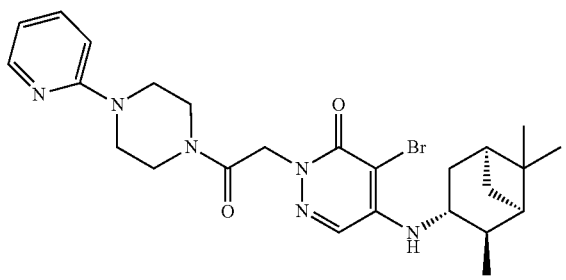
18
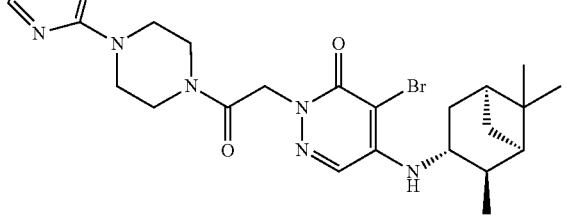
19
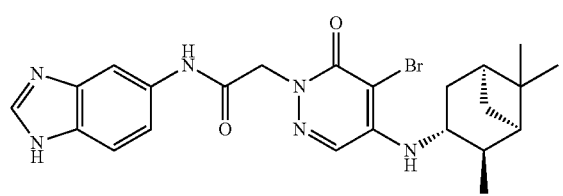
20
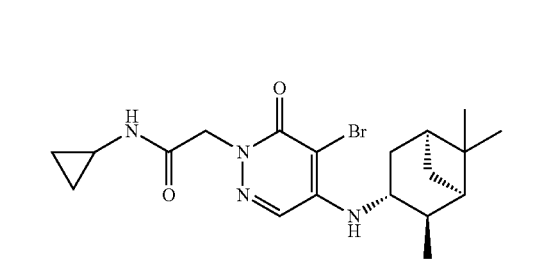
21
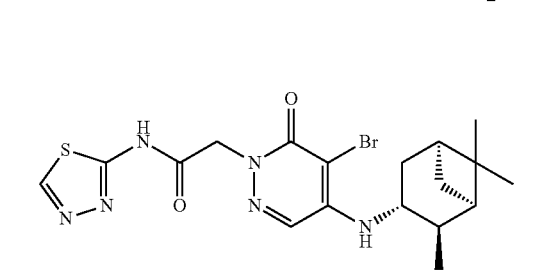
22
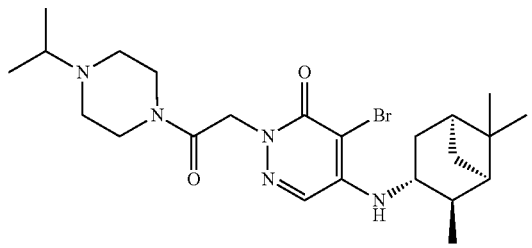
23
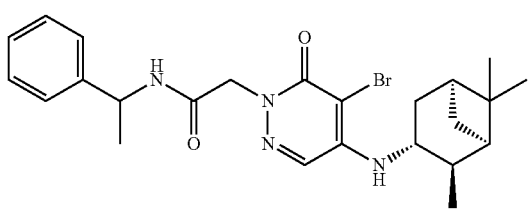
24
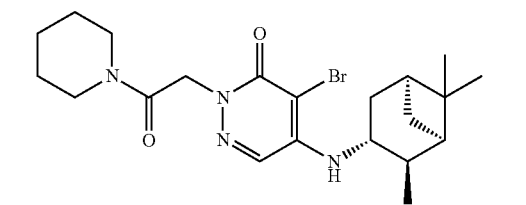
25
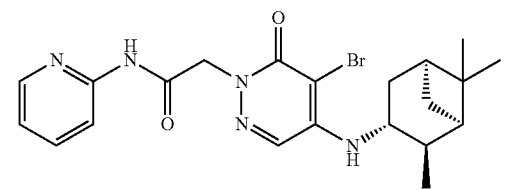
26
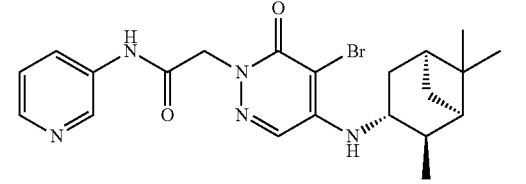
27
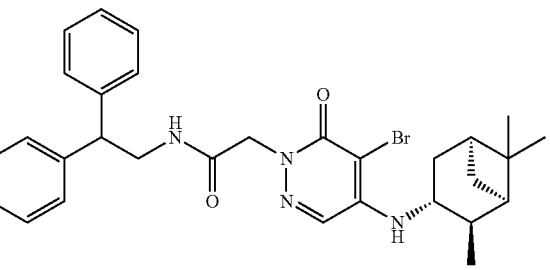

28
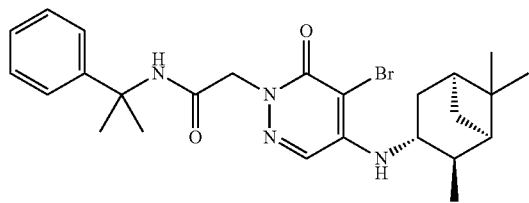
29
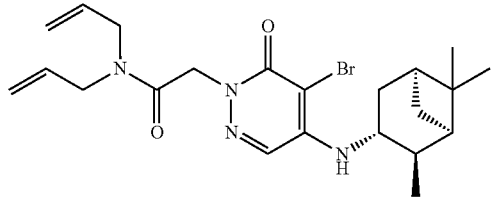
30
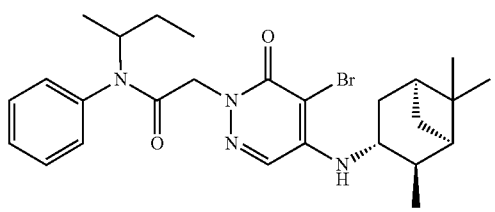
31
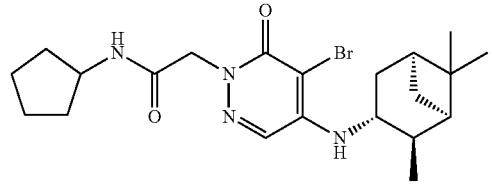
32
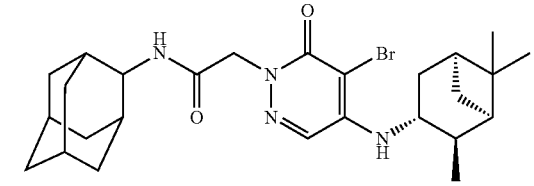
33
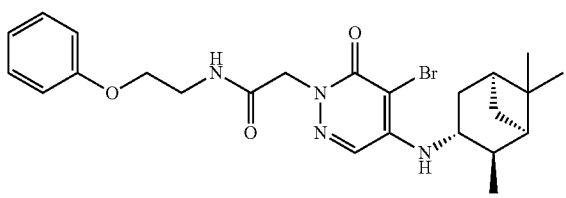
34
35
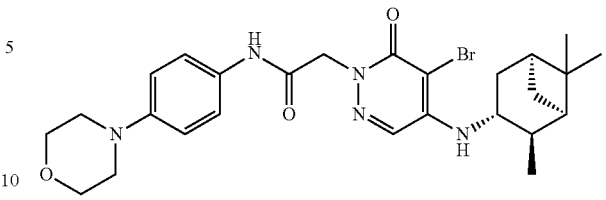
36
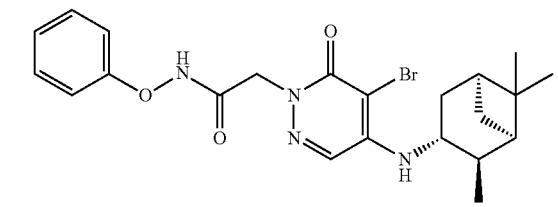
37
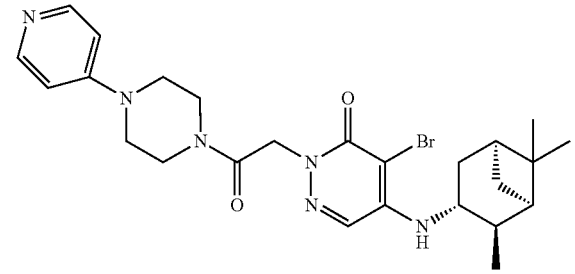
38
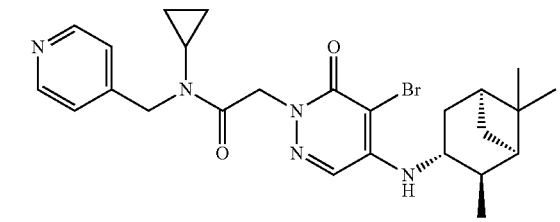
39
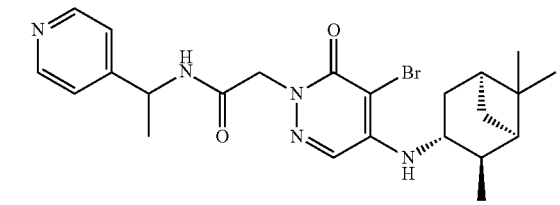
40
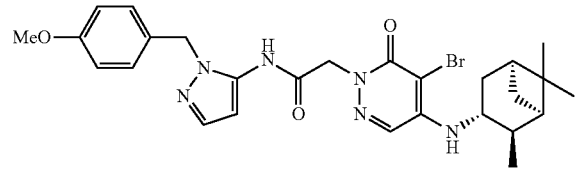

SYNTHETIC EXAMPLE 41

3-{5-Bromo-6-oxo-4-[(1R,2R,3R,5S)-2,6,6-trimethylbicyclo[3.1.1]hept-3-ylamino]pyridazin-1(6H)-yl}-N-(1-phenylethyl)propanamide

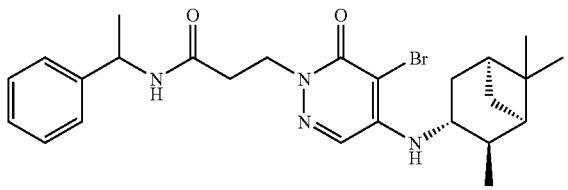 [SMILES: CC(NC(=O)CCn1ncc(N[C@@H]2C[C@@H]3C[C@H]([C@H]2C)C3(C)C)c(Br)c1=O)c1ccccc1]

Ethyl 3-{5-bromo-6-oxo-4-[(1R,2R,3R,5S)-2,6,6-trimethylbicyclo[3.1.1]hept-3-ylamino]pyridazin-1(6H)-yl}propanoate

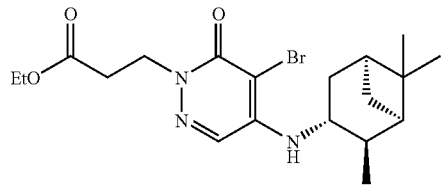 [SMILES: C[C@@H]1[C@H]2C[C@@H](C[C@H]1Nc1cnn(CCC(=O)O)c(=O)c1Br)C2(C)C]

4-Bromo-5-[(1R,2R,3R,5S)-2,6,6-trimethylbicyclo[3.1.1]hept-3-ylamino]pyridazin-3(2H)-one (320 mg, 0.637 mmol) in N,N-dimethylformamide (3.2 mL) was mixed with ethyl 3-bromopropionate (0.187 mL, 1.47 mmol) and potassium carbonate (244 mg, 1.76 mmol) at room temperature and stirred at 80° C. for 4 hours. After cooling, the reaction solution was mixed with saturated aqueous ammonium chloride and extracted with ethyl acetate. The resulting organic layer was washed with saturated aqueous ammonium chloride and saturated aqueous sodium chloride, dried over anhydrous magnesium sulfate and evaporated under reduced pressure to give the desired product (453 mg, quant.).
Morphology: light brown oil
LC/MS: Condition 1, retention time 4.75 min
LC/MS (ESI$^+$) m/z: 426, 428 [M+1]$^+$
LC/MS (ESI$^-$) m/z: 424, 426 [M−1]$^-$
$^1$H-NMR (CDCl$_3$)
δ: 0.97 (d, J=12.0 Hz, 1H), 1.05 (s, 3H), 1.18 (d, J=6.0 Hz, 3H), 1.25 (t, J=9.0 Hz, 3H), 1.27 (s, 3H), 1.68-1.75 (m, 1H), 1.90-2.00 (m, 1H), 2.00-2.10 (m, 1H), 2.40-2.55 (m, 1H), 2.55-2.70 (m, 1H), 2.81 (t, J=7.5 Hz, 2H), 3.81-3.90 (m, 1H), 4.15 (q, J=9.0 Hz, 2H), 4.44 (t, J=7.5 Hz, 2H), 4.68 (d, J=9.0 Hz, 1H), 7.50 (s, 1H).

3-{5-Bromo-6-oxo-4-[(1R,2R,3R,5S)-2,6,6-trimethylbicyclo[3.1.1]hept-3-ylamino]pyridazin-1(6H)-yl}propanoic Acid

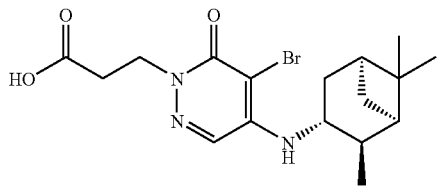

Ethyl 3-{5-bromo-6-oxo-4-[(1R,2R,3R,5S)-2,6,6-trimethylbicyclo[3.1.1]hept-3-ylamino]pyridazin-1(6H)-yl}propanoate (453 mg, 1.06 mmol) in 1,4-dioxane (4 mL) was stirred with 1 M aqueous sodium hydroxide (2.93 mL, 2.93 mmol) at room temperature for 1 hour. After completion of the reaction, ethyl acetate was added, and the organic layer was washed with 1 M hydrochloric acid and saturated aqueous sodium chloride, dried over anhydrous magnesium sulfate and evaporated under reduced pressure to give the desired product (314 mg, 80% yield).
Morphology: yellow solid
LC/MS: Condition 2, retention time 3.20 min
LC/MS (ESI$^+$) m/z: 398, 400 [M+1]$^+$
LC/MS (ESI$^-$) m/z: 396, 398 [M−1]$^-$
$^1$H-NMR (CDCl$_3$)
δ: 0.97 (d, J=10.2 Hz, 1H), 1.05 (s, 3H), 1.19 (d, J=6.9 Hz, 3H), 1.27 (s, 3H), 1.68-1.76 (m, 1H), 1.90-2.00 (m, 1H), 2.00-2.10 (m, 1H), 2.43-2.52 (m, 1H), 2.59-2.68 (m, 1H), 2.88 (t, J=6.9 Hz, 2H), 3.81-3.90 (m, 1H), 4.46 (t, J=6.9 Hz, 2H), 4.73 (d, J=8.4 Hz, 1H), 7.54 (s, 1H).

3-{5-Bromo-6-oxo-4-[(1R,2R,3R,5S)-2,6,6-trimethylbicyclo[3.1.1]hept-3-ylamino]pyridazin-1(6H)-yl}-N-(1-phenylethyl)propanamide

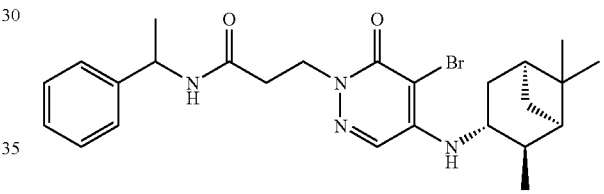

3-{5-Bromo-6-oxo-4-[(1R,2R,3R,5S)-2,6,6-trimethylbicyclo[3.1.1]hept-3-ylamino]pyridazin-1(6H)-yl}propanoic acid (32 mg, 0.080 mmol), 1-(3-dimethylaminopropyl)-3-ethylcarbodiimide hydrochloride (31 mg, 0.160 mmol), 1-hydroxybenzotriazole anhydride (11 mg, 0.080 mmol) and triethylamine (22 μL, 0.160 mmol) in N,N-dimethylformamide (1 mL) were stirred with 1-phenylethylamine (20 μL, 0.160 mmol) at room temperature for 24 hours. After completion of the reaction, ethyl acetate was added, and the organic layer was washed with saturated aqueous ammonium chloride and saturated aqueous sodium chloride, dried over anhydrous magnesium sulfate and evaporated under reduced pressure. The resulting residue was purified by silica gel chromatography (chloroform/methanol=15/1) to give the desired product (38 mg, 95% yield).
Morphology: yellow oil
LC/MS: Condition 3, retention time 4.67 min
LC/MS (ESI$^+$) m/z: 501, 503 [M+1]$^+$
LC/MS (ESI$^-$) m/z: 499, 501 [M−1]$^-$

SYNTHETIC EXAMPLES 42 TO 44

Compounds were synthesized in the same manner as in Synthetic Example 41, and the yields and morphology of the resulting compounds, the LC/MS conditions used for their analysis and the observed peaks and retention times are shown in Table 10.

TABLE 10

| Synthetic Example No. | Yield (%) | Morphology | LC/MS Condition | Observed peak ESI+ | Observed peak ESI− | Retention time (min) |
|---|---|---|---|---|---|---|
| 42 | 89 | Yellow oil | 7 | 437/439 | 435/437 | 3.15 |
| 43 | 82 | Yellow oil | 3 | 488/490 | 486/488 | 3.4 |
| 44 | 63 | Yellow oil | 3 | 474/476 | 472/474 | 3.73 |

The structures of the compounds obtained in these Synthetic Examples are shown below.

SYNTHETIC EXAMPLE 42 TO 44

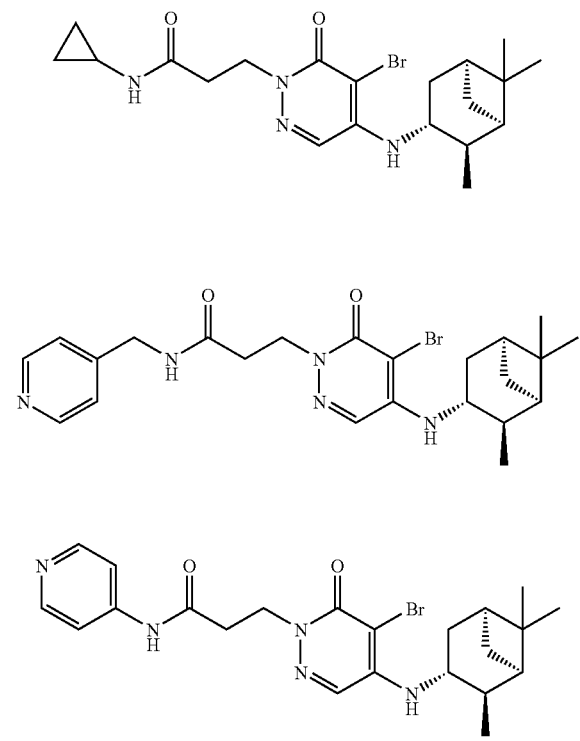

SYNTHETIC EXAMPLE 45

4-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)butanamide

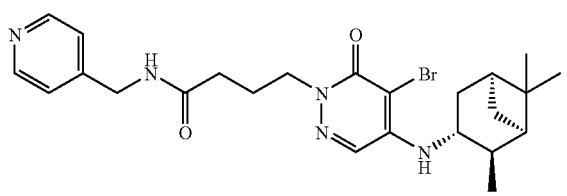 [SMILES: C[C@@H]1[C@H]2C[C@@H](C[C@H]1Nc1cnn(CCCC(=O)NCc3ccncc3)c(=O)c1Br)C2(C)C]

Ethyl 4-{5-bromo-6-oxo-4-[(1R,2R,3R,5S)-2,6,6-trimethylbicyclo[3.1.1]hept-3-ylamino]pyridazin-1(6H)-yl}butanoate 4-Bromo-5-[(1R,2R,3R,5S)-2,6,6-trimethylbicyclo[3.1.1]hept-3-ylamino]pyridazin-3(2H)-one (224 mg, 0.688 mmol) in N,N-dimethylformamide (2.2 mL) was mixed with ethyl 4-bromobutyrate (0.148 mL, 1.03 mmol) and potassium carbonate (142 mg, 1.03 mmol) at room temperature and stirred at 80° C. for 2 hours. After cooling, the reaction solution was mixed with saturated aqueous ammonium chloride and extracted with ethyl acetate. The resulting organic layer was washed with saturated aqueous ammonium chloride and saturated aqueous sodium chloride, dried over anhydrous magnesium sulfate and evaporated under reduced pressure to give the desired product (454 mg, quant.).

Morphology: yellow amorphous
LC/MS: Condition 2, retention time 3.74 min
LC/MS (ESI+) m/z: 440, 442 [M+1]+
LC/MS (ESI−) m/z: 438, 440 [M−1]−
$^1$H-NMR (CDCl$_3$)
δ: 0.98 (d, J=10.2 Hz, 1H), 1.06 (s, 3H), 1.19 (d, J=6.6 Hz, 3H), 1.27 (t, J=7.2 Hz, 3H), 1.27 (s, 3H), 1.67-1.77 (m, 1H), 1.90-1.98 (m, 1H), 2.00-2.08 (m, 1H), 2.18 (dd, J=6.9, 6.9 Hz, 2H), 2.37 (t, J=6.9 Hz, 2H), 2.45-2.55 (m, 1H), 2.58-2.70 (m, 1H), 3.80-3.90 (m, 1H), 4.14 (q, J=7.2 Hz, 2H), 4.36 (t, J=6.9 Hz, 2H), 4.68 (d, J=6.8 Hz, 1H), 7.52 (s, 1H).

4-{5-Bromo-6-oxo-4-[(1R,2R,3R,5S)-2,6,6-trimethylbicyclo[3.1.1]hept-3-ylamino]pyridazin-1(6H)-yl}butanoic Acid Ethyl 4-{5-bromo-6-oxo-4-[(1R,2R,3R,5S)-2,6,6-trimethylbicyclo[3.1.1]hept-3-ylamino]pyridazin-1(6H)-yl}butanoate (454 mg, 0.981 mmol) in 1,4-dioxane (4.5 mL) was stirred with 1 M aqueous sodium hydroxide (2.06 mL, 2.06 mmol) at room temperature for 6.5 hours. After completion of the reaction, ethyl acetate was added, and the organic layer was washed with 1 M hydrochloric acid and saturated aqueous sodium chloride, dried over anhydrous magnesium sulfate and evaporated under reduced pressure to give the desired product (182 mg, 64% yield).

Morphology: yellow amorphous
LC/MS: Condition 3, retention time 4.35 min
LC/MS (ESI$^+$) m/z: 412, 414 [M+1]$^+$
LC/MS (ESI$^-$) m/z: 410, 412 [M−1]$^-$
$^1$H-NMR (CDCl$_3$)
δ: 0.98 (d, J=10.2 Hz, 1H), 1.05 (s, 3H), 1.19 (d, J=7.2 Hz, 3H), 1.28 (s, 3H), 1.67-1.76 (m, 1H), 1.90-2.00 (m, 1H), 2.00-2.09 (m, 1H), 2.15 (dd, J=7.2, 6.6 Hz, 2H), 2.41 (t, J=7.2 Hz, 2H), 2.45-2.55 (m, 1H), 2.59-2.70 (m, 1H), 3.80-3.90 (m, 1H), 4.25 (t, J=6.6 Hz, 2H), 4.72 (d, J=8.1 Hz, 1H), 7.55 (s, 1H).

4-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)butanamide

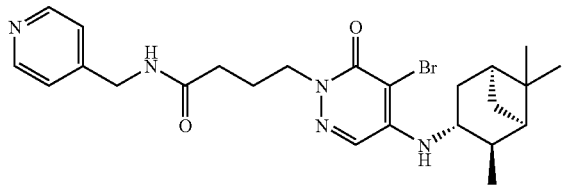 [SMILES: C[C@@H]1[C@H]2C[C@@H](C[C@H]1Nc1cnn(CCCC(=O)NCc3ccncc3)c(=O)c1Br)C2(C)C]

4-{5-Bromo-6-oxo-4-[(1R,2R,3R,5S)-2,6,6-trimethylbicyclo[3.1.1]hept-3-ylamino]pyridazin-1(6H)-yl}butanoic acid (38 mg, 0.091 mmol), 1-(3-dimethylaminopropyl)-3-ethylcarbodiimide hydrochloride (35 mg, 0.182 mmol), 1-hydroxybenzotriazole anhydride (12 mg, 0.091 mmol) and triethylamine (25 μL, 0.182 mmol) in N,N-dimethylformamide (1 mL) were stirred with 4-picolylamine (25 μL, 0.182 mmol) at room temperature for 24 hours. After completion of the reaction, ethyl acetate was added, and the organic layer was washed with saturated aqueous ammonium chloride and saturated aqueous sodium chloride, dried over anhydrous magnesium sulfate and evaporated under reduced pressure. The resulting residue was purified by silica gel chromatography (chloroform/methanol=15/1) to give the desired product (30 mg, 58% yield).

Morphology: pale yellow solid
LC/MS: Condition 3, retention time 3.67 min
LC/MS (ESI$^+$) m/z: 502, 504 [M+1]$^+$
LC/MS (ESI$^-$) m/z: 500, 502 [M−1]$^-$

SYNTHETIC EXAMPLE 46

2-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)propanamide

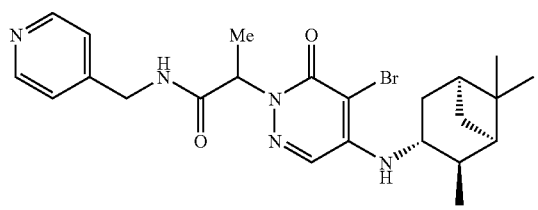 [SMILES: CC(C(=O)NCc1ccncc1)n1ncc(N[C@@H]2C[C@@H]3C[C@H]([C@H]2C)C3(C)C)c(Br)c1=O]

Ethyl 2-{5-bromo-6-oxo-4-[(1R,2R,3R,5S)-2,6,6-trimethylbicyclo[3.1.1]hept-3-ylamino]pyridazin-1(6H)-yl}propanoate

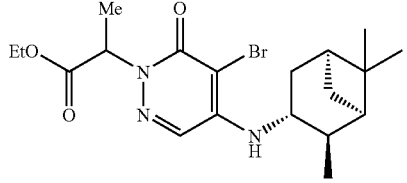 [SMILES: CCOC(=O)C(C)n1ncc(N[C@@H]2C[C@@H]3C[C@H]([C@H]2C)C3(C)C)c(Br)c1=O]

4-Bromo-5-[(1R,2R,3R,5S)-2,6,6-trimethylbicyclo[3.1.1]hept-3-ylamino]pyridazin-3(2H)-one (208 mg, 0.637 mmol) in N,N-dimethylformamide (2 mL) was mixed with ethyl 2-bromopropionate (124 μL, 0.955 mmol) and potassium carbonate (132 mg, 0.955 mmol) at room temperature and stirred at 80° C. for 2 hours. After cooling, the reaction solution was mixed with saturated aqueous ammonium chloride and extracted with ethyl acetate. The resulting organic layer was washed with saturated aqueous ammonium chloride and saturated aqueous sodium chloride, dried over anhydrous magnesium sulfate and evaporated under reduced pressure to give the desired product (149 mg, 55% yield).

Morphology: pale yellow oil
LC/MS: Condition 2, retention time 3.82 min
LC/MS (ESI$^+$) m/z: 426, 428 [M+1]$^+$
LC/MS (ESI$^-$) m/z: 424, 426 [M−1]$^-$
$^1$H-NMR (CDCl$_3$)
δ: 0.98 (d, J=9.9 Hz, 1H), 1.05 (s, 3H), 1.19 (d, J=7.2 Hz, 3H×½), 1.20 (d, J=7.2 Hz, 3H×½), 1.25 (t, J=7.2 Hz, 3H), 1.27 (s, 3H), 1.65 (d, J=7.2 Hz, 3H), 1.69-1.80 (m, 1H), 1.90-1.99 (m, 1H), 2.00-2.08 (m, 1H), 2.43-2.53 (m, 1H), 2.58-2.70 (m, 1H), 3.82-3.92 (m, 1H), 4.20 (q, J=7.2 Hz, 2H), 4.74 (d, J=8.1 Hz, 1H), 5.60 (q, J=7.2 Hz, 1H×½), 5.61 (q, J=7.2 Hz, 1H×½), 7.59 (s, 1H).

2-{5-Bromo-6-oxo-4-[(1R,2R,3R,5S)-2,6,6-trimethylbicyclo[3.1.1]hept-3-ylamino]pyridazin-1(6H)-yl}propanoic Acid

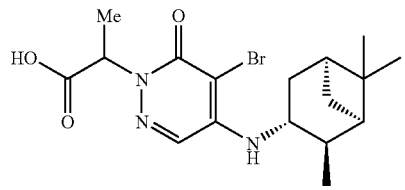 [SMILES: CC(C(=O)O)n1ncc(N[C@@H]2C[C@@H]3C[C@H]([C@H]2C)C3(C)C)c(Br)c1=O]

Ethyl 2-{5-bromo-6-oxo-4-[(1R,2R,3R,5S)-2,6,6-trimethylbicyclo[3.1.1]hept-3-ylamino]pyridazin-1(6H)-yl}propanoate (149 mg, 0.349 mmol) in 1,4-dioxane (1 mL) was stirred with 1 M aqueous sodium hydroxide (0.698 mL, 0.698 mmol) at room temperature for 5.5 hours. After completion of the reaction, ethyl acetate was added, and the organic layer was washed with 1 M hydrochloric acid and saturated aqueous sodium chloride, dried over anhydrous magnesium sulfate and evaporated under reduced pressure to give the desired product (220 mg, quant.).

Morphology: yellow solid
LC/MS: Condition 2, retention time 3.35 min
LC/MS (ESI⁺) m/z: 398, 400 [M+1]⁺
LC/MS (ESI⁻) m/z: 396, 398 [M−1]⁻
1H-NMR (CDCl₃)
δ: 0.97 (d, J=9.9 Hz, 1H), 1.05 (s, 3H), 1.18 (d, J=6.9 Hz, 3H), 1.27 (s, 3H), 1.66 (d, J=7.2 Hz, 3H), 1.70-1.78 (m, 1H), 1.90-1.98 (m, 1H), 2.00-2.08 (m, 1H), 2.42-2.51 (m, 1H), 2.60-2.70 (m, 1H), 3.80-3.92 (m, 1H), 4.79 (d, J=7.5 Hz, 2H), 5.41-5.58 (m, 1H), 7.54 (s, 1H).

2-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)propanamide

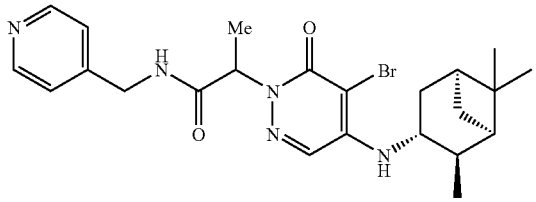 [SMILES: CC(C(=O)NCc1ccncc1)n1ncc(N[C@@H]2C[C@@H]3C[C@H]([C@H]2C)C3(C)C)c(Br)c1=O]

2-{5-Bromo-6-oxo-4-[(1R,2R,3R,5S)-2,6,6-trimethylbicyclo[3.1.1]hept-3-ylamino]pyridazin-1(6H)-yl}propanoic acid (40 mg, 0.099 mmol), 1-(3-dimethylaminopropyl)-3-ethylcarbodiimide hydrochloride (38 mg, 0.199 mmol), 1-hydroxybenzotriazole anhydride (4 mg, 0.03 mmol) and triethylamine (28 μL, 0.199 mmol) in N,N-dimethylformamide (1 mL) were stirred with 4-picolylamine (20 μL, 0.199 mmol) at room temperature for 17.5 hours. After completion of the reaction, ethyl acetate was added, and the organic layer was washed with saturated aqueous ammonium chloride and saturated aqueous sodium chloride, dried over anhydrous magnesium sulfate and evaporated under reduced pressure. The resulting residue was purified by silica gel chromatography (chloroform/methanol=20/1) to give the desired product (25 mg, 52% yield).
Morphology: yellow amorphous
LC/MS: Condition 2, retention time 2.25 min
LC/MS (ESI⁺) m/z: 488, 490 [M+1]⁺
LC/MS (ESI⁻) m/z: 486, 488 [M−1]⁻

SYNTHETIC EXAMPLE 47

4-Bromo-2-[2-(pyridin-4-ylmethylamino)ethyl]-5-[(1R,2R,3R,5S)-2,6,6-trimethylbicyclo[3.1.1]hept-3-ylamino]pyridazin-3(2H)-one

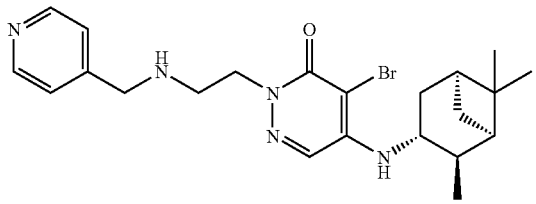 [SMILES: C[C@@H]1[C@H]2C[C@@H](C[C@H]1Nc1cnn(CCNCc3ccncc3)c(=O)c1Br)C2(C)C]

2-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide (35 mg, 0.073 mmol) in N,N-dimethylformamide (1 mL) was mixed with a borane tetrahydrofuran complex (1.13 M in tetrahydrofuran, 78 μL, 0.088 mmol) under cooling with ice and stirred at room temperature for 5.5 hours. After completion of the reaction, the reaction solution was mixed with saturated aqueous sodium chloride and extracted with ethyl acetate. The resulting organic layer was washed with saturated aqueous sodium chloride, dried over anhydrous magnesium sulfate and evaporated under reduced pressure to give the desired product (32 mg, 92% yield).
Morphology: colorless solid
LC/MS: Condition 2, retention time 3.34 min
LC/MS (ESI⁻) m/z: 458, 460 [M−1]⁻
¹H-NMR (CDCl₃)
δ: 0.98 (d, J=9.9 Hz, 1H), 1.05 (s, 3H), 1.19 (d, J=6.9 Hz, 3H), 1.19 (d, J=6.9 Hz, 3H), 1.28 (s, 3H), 1.70-1.78 (m, 1H), 1.92-1.97 (m, 1H), 1.99-2.05 (m, 1H), 2.46-2.52 (m, 2H), 2.60-2.69 (m, 2H), 3.83-3.93 (m, 1H), 4.51 (d, J=6.3 Hz, 1H), 4.84 (d, J=8.1 Hz, 1H), 4.89 (s, 2H), 7.38 (d, J=6.6 Hz, 2H), 7.60 (s, 1H), 8.46 (d, J=6.6 Hz, 2H).

SYNTHETIC EXAMPLE 48

2-[5-Bromo-4-(1,1,3,3-tetramethylbutylamino)-6-oxopyridazin-1(6H)-yl]-N-(pyridin-4-ylmethyl)acetamide

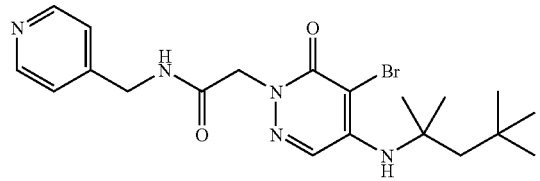 [SMILES: CC(C)(C)CC(C)(C)Nc1cnn(CC(=O)NCc2ccncc2)c(=O)c1Br]

Ethyl 2-(4,5-dibromo-6-oxopyridazin-1(6H)-yl)acetate

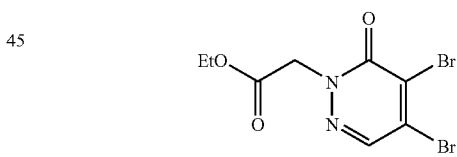

4,5-Dibromopyridazin-3(2H)-one (5.0 g, 19.7 mmol) in N,N-dimethylformamide (50 mL) was stirred with ethyl bromoacetate (3.28 g, 29.5 mmol) and potassium carbonate (4.08 g, 29.5 mmol) at 80° C. for 1 hour and 40 minutes. After completion of the reaction, ethyl acetate was added, and the organic layer was washed with saturated aqueous ammonium chloride three times and with saturated aqueous sodium chloride once, dried over anhydrous magnesium sulfate and evaporated under reduced pressure to give the desired product (7.42 g, 100% yield).
Morphology: brown solid
LC/MS: Condition 3, retention time 1.67 min
LC/MS (ESI⁺) m/z; 341, 343 [M+1]⁺
¹H-NMR (CDCl₃)
δ: 1.30 (t, J=7.0 Hz, 3H), 4.27 (q, J=7.0 Hz, 2H), 4.88 (s, 2H), 7.83 (s, 1H).

2-(4,5-Dibromo-6-oxopyridazin-1(6H)-yl)acetic Acid

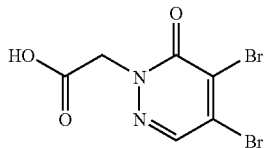 [SMILES: O=C(O)Cn1ncc(Br)c(Br)c1=O]

Ethyl 2-(4,5-dibromo-6-oxopyridazin-1(6H)-yl)acetate (6.01 g, 17.7 mmol) in 1,4-dioxane (60 mL) was stirred with 1 M aqueous sodium hydroxide (53.1 mL, 53.1 mmol) at room temperature for 1 hour. After completion of the reaction, the reaction solution was mixed with ethyl acetate and extracted with 1 M aqueous sodium hydroxide twice. The resulting aqueous layer was acidified to pH 1 with 1 M hydrochloric acid and extracted with ethyl acetate twice. The resulting organic layer was washed with saturated aqueous sodium chloride, dried over anhydrous magnesium sulfate and evaporated under reduced pressure to give the desired product (5.30 g, 88% yield).

Morphology: brown solid
$^1$H-NMR (DMSO-$d_6$)
δ: 4.82 (s, 2H), 8.21 (s, 1H).

2-(4,5-Dibromo-6-oxopyridazin-1(6H)-yl)-N-(pyridin-4-ylmethyl)acetamide

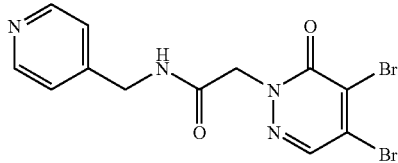 [SMILES: O=C(Cn1ncc(Br)c(Br)c1=O)NCc1ccncc1]

2-(4,5-Dibromo-6-oxopyridazin-1(6H)-yl)acetic acid (1.48 g, 4.38 mmol) in tetrahydrofuran (30 mL) was mixed with N,N-dimethylformamide (1 drop) and oxalyl chloride (570 μL, 6.53 mmol) at room temperature and stirred at room temperature for 30 minutes. The solvent was removed by distillation, and the residue was dissolved in tetrahydrofuran (10 mL) and added dropwise to 4-picolylamine (538 μL, 5.22 mmol) and triethylamine (1.22 mL, 8.70 mmol) in tetrahydrofuran (20 mL) and stirred at room temperature for 30 minutes. After completion of the reaction, the reaction solution was mixed with water and extracted with chloroform three times, and the extract was dried over anhydrous magnesium sulfate and evaporated under reduced pressure. The resulting solid was washed with 2-propanol-hexane to give the desired product (572 mg, 33% yield).

Morphology: pale gray solid
$^1$H-NMR (DMSO-$d_6$)
δ: 4.31 (d, J=6.2 Hz, 2H), 4.82 (s, 2H), 7.26 (d, J=6.2 Hz, 2H), 8.21 (s, 1), 8.50 (d, J=6.2 Hz, 2H), 8.80 (t, J=6.2 Hz, 1H).
LC/MS: Condition 3, retention time 0.45 min
LC/MS (ESI$^+$) m/z; 401, 403, 405 [M+1]$^+$
LC/MS (ESI$^-$) m/z; 399, 401, 403 [M-1]$^-$

2-[5-Bromo-4-(1,1,3,3-tetramethylbutylamino)-6-oxopyridazin-1(6H)-yl]-N-(pyridin-4-ylmethyl)acetamide 2-(4,5-Dibromo-6-oxopyridazin-1(6H)-yl)-N-(pyridin-4-ylmethyl)acetamide (50 mg, 124 μmol) in dioxane-water (1:1, 2 mL) was stirred with triethylamine (52 μL, 372 μmol) and 2,5,5-trimethylhexan-2-amine (16 mg, 112 μmol) at 90° C. for 26 hours. After completion of the reaction, the solvent was removed by vacuum distillation, and the residue was mixed with saturated aqueous sodium chloride and extracted with chloroform three times. The combined organic layer was dried over anhydrous magnesium sulfate, and the solvent was removed by vacuum distillation. The resulting residue was purified by silica gel chromatography (chloroform/methanol=10/1) to give the desired product (13 mg, 25% yield).

Morphology: colorless solid
LC/MS: Condition 4, retention time 1.85 min
LC/MS (ESI$^+$) m/z; 450, 452 [M+1]$^+$
LC/MS (ESI$^-$) m/z; 448, 450 [M-1]$^-$

SYNTHETIC EXAMPLES 49 TO 75

Compounds were synthesized in the same manner as in Synthetic Example 48, and the yields and morphology of the resulting compounds, the LC/MS conditions used for their analysis and the observed peaks and retention times are shown in Table 11.

TABLE 11

| Synthetic Example No. | Yield (%) | Morphology | LC/MS Condition | Observed peak ESI$^+$ | Observed peak ESI$^-$ | Retention time (min) |
|---|---|---|---|---|---|---|
| 49 | 40 | Colorless solid | 3 | 434/436 | | 2.55 |
| 50 | 10 | Colorless solid | 2 | 474/476 | 472/474 | 2.13 |
| 51 | 15 | Colorless solid | 3 | 472/474 | | 2.70 |
| 52 | 15 | Colorless solid | | | | |
| 53 | 23 | Pale yellow solid | 2 | 500/502 | | 2.34 |
| 54 | 31 | Colorless solid | 2 | 474/476 | 472/474 | 2.13 |
| 55 | 42 | Colorless solid | 3 | 408/410 | | 2.27 |
| 56 | 39 | Colorless solid | 3 | 474/476 | | 2.85 |
| 57 | 29 | Colorless solid | 3 | 420/422 | | 2.35 |
| 58 | 12 | Colorless solid | | | | |
| 59 | 38 | Colorless solid | 2 | 436/438 | 434/436 | 2.04 |
| 60 | 47 | Colorless solid | 3 | 486/488 | 484/486 | 3.63 |
| 61 | 28 | Colorless amorphous | 3 | 474/476 | 472/474 | 3.50 |
| 62 | 56 | Pale yellow solid | 4 | 476/478 | 474/476 | 2.04 |

TABLE 11-continued

| Synthetic Example No. | Yield (%) | Morphology | LC/MS Condition | Observed peak ESI+ | Observed peak ESI− | Retention time (min) |
|---|---|---|---|---|---|---|
| 63 | 43 | Colorless solid | 4 | 436/438 | 434/436 | 0.31 |
| 64 | 57 | Yellow solid | 4 | 422/424 | 420/422 | 0.35 |
| 65 | 40 | Pale yellow solid | 2 | 562/564 | 560/562 | 3.95 |
| 66 | 55 | Colorless solid | 3 | 506/508 | 504/506 | 4.49 |
| 67 | 32 | Pale yellow solid | 4 | 435/437 | 433/435 | 0.26 |
| 68 | 36 | Pale yellow solid | 4 | 488/490 | | 0.35 |
| 69 | 23 | Colorless solid | 2 | 474/476 | 472/474 | 2.16 |
| 70 | 59 | Brown solid | | | | |
| 71 | 62 | Yellow solid | | | | |
| 72 | 52 | Yellow solid | 4 | 410/412 | 408/410 | 0.34 |
| 73 | 54 | Colorless solid | 2 | 488/490 | 486/488 | 2.52 |
| 74 | 38 | Colorless solid | 4 | 472/474 | 470/472 | 1.89 |
| 75 | 43 | Colorless solid | 4 | 462/464 | 460/462 | 1.93 |

The structures of the compounds obtained in these Synthetic Examples are shown below.

SYNTHETIC EXAMPLES 49 TO 75

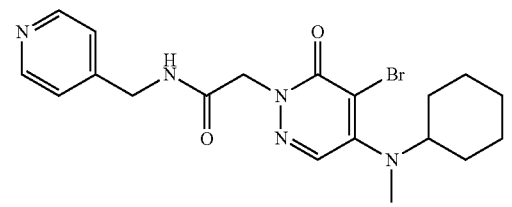

49

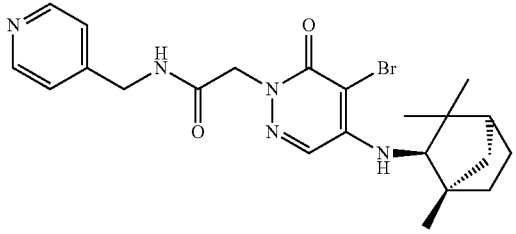

50

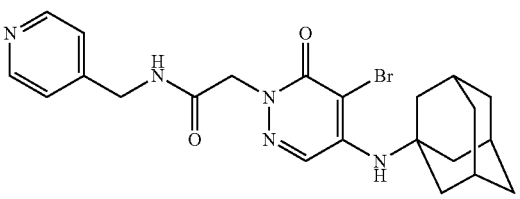

51

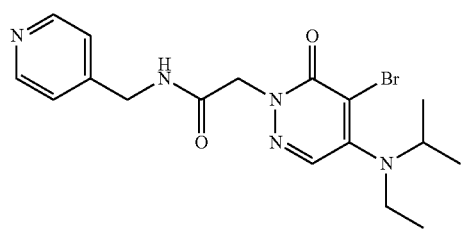

52

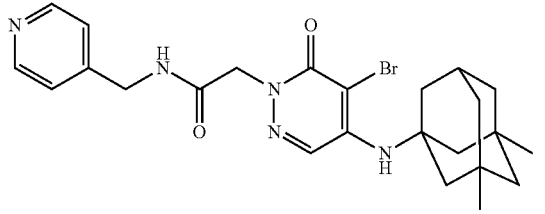

53

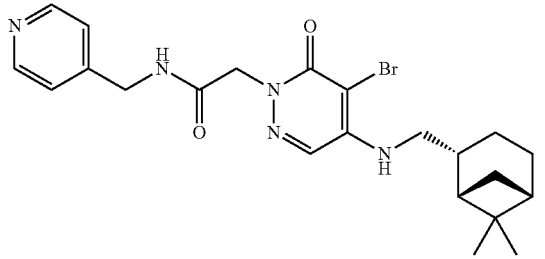

54

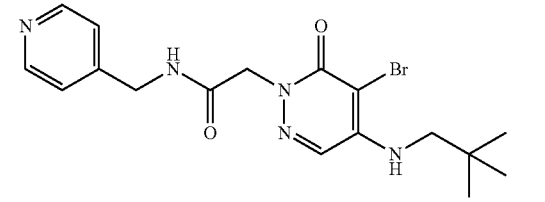

55

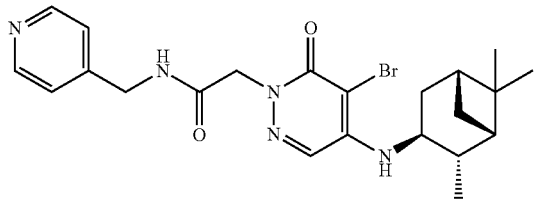

56

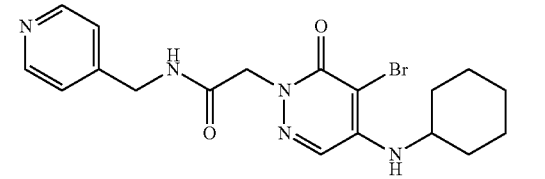

57

58
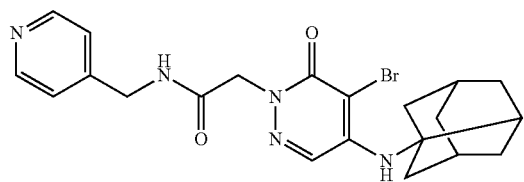
59
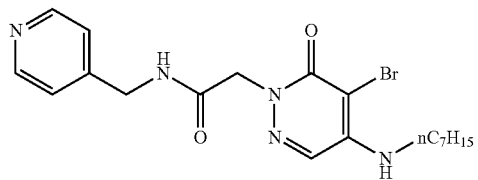
60
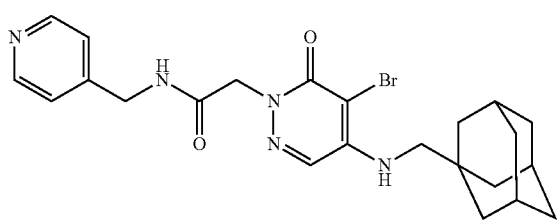
61
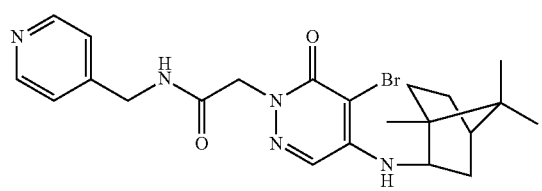
62
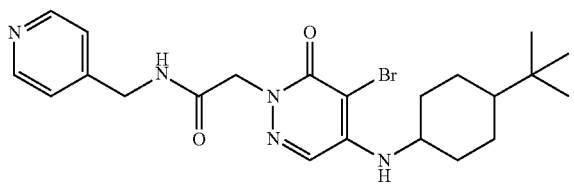
63
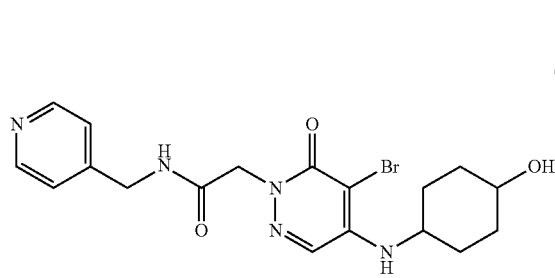
64
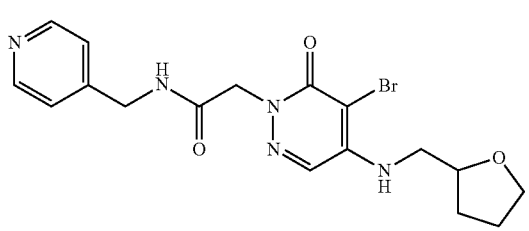
65
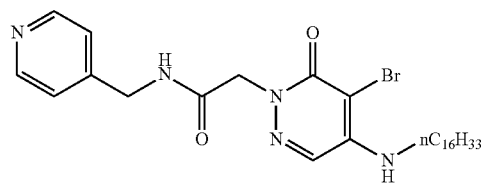
66
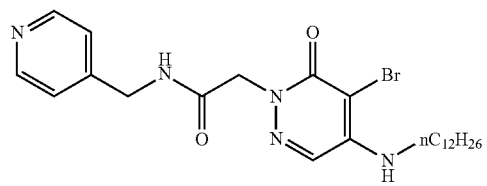
67
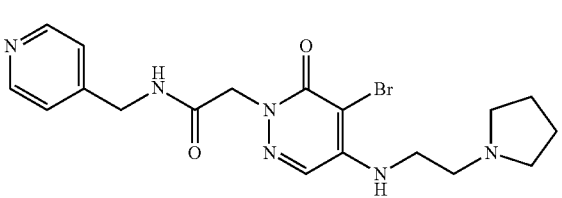
68
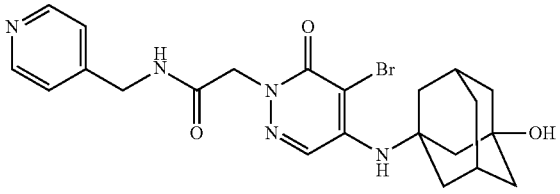
69
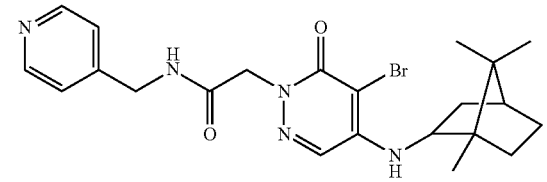
70
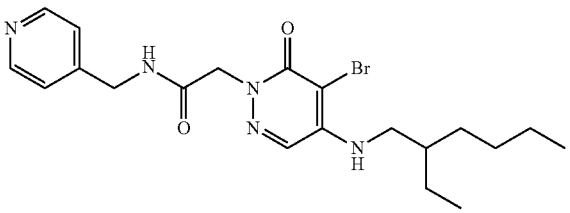
71
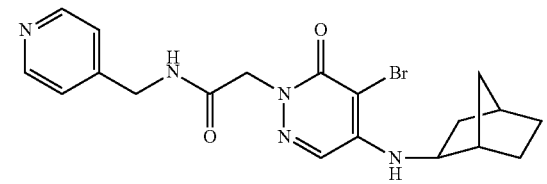

72

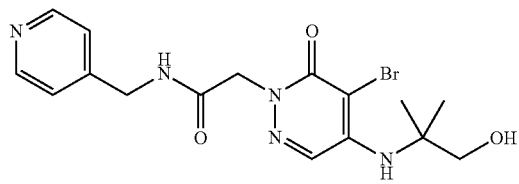

73

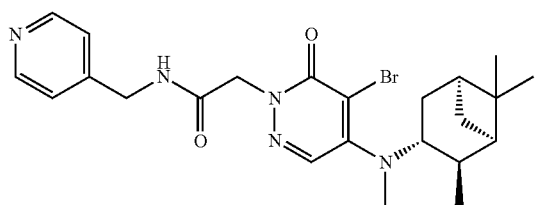

74

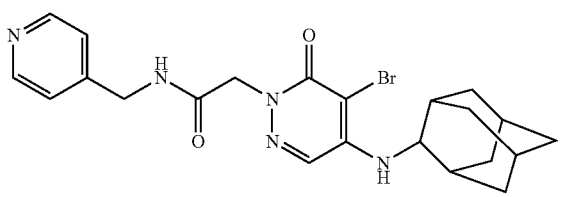

75

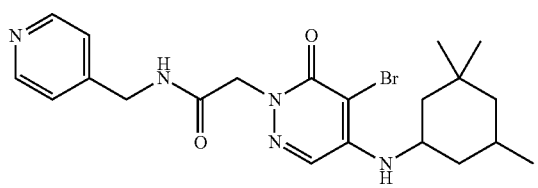

SYNTHETIC EXAMPLE 76

1-{5-Bromo-6-oxo-4-[(1R,2R,3R,5S)-2,6,6-trimethylbicyclo[3.1.1]hept-3-ylamino]pyridazin-1(6H)-yl}-N-isopropylmethanesulfonamide

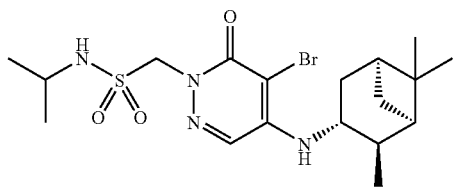 [SMILES: CC(C)NS(=O)(=O)Cn1ncc(N[C@@H]2C[C@@H]3C[C@H]([C@H]2C)C3(C)C)c(Br)c1=O]

Isopropylamine (0.262 mL, 3.07 mmol), chloromethylsulfonyl chloride (0.274 mL, 3.07 mmol) and triethylamine (0.856 mL, 6.14 mmol) were added to dichloromethane (2 mL) under cooling with ice, and the resulting mixture was stirred for 2 hours under cooling with ice. After completion of the reaction, the reaction mixture was mixed with ethyl acetate, and the organic layer was washed with saturated aqueous ammonium chloride and saturated aqueous sodium chloride, dried over anhydrous magnesium sulfate and evaporated under reduced pressure. The resulting reaction product was dissolved in N,N-dimethylformamide (3.2 mL) and mixed with potassium carbonate (267 mg, 1.93 mmol) and 4-bromo-5-[(1R,2R,3R,5S)-2,6,6-trimethylbicyclo[3.1.1]hept-3-ylamino]pyridazin-3(2H)-one (276 mg, 0.844 mmol) at room temperature and stirred at 80° C. for 4 hours. After cooling, the reaction solution was mixed with saturated aqueous ammonium chloride and extracted with ethyl acetate. The resulting organic layer was washed with saturated aqueous ammonium chloride and saturated aqueous sodium chloride, dried over anhydrous magnesium sulfate and evaporated under reduced pressure. The resulting residue was purified by silica gel chromatography (chloroform/methanol=80/1) to give the desired product (22 mg, 4% yield).

Morphology: colorless solid

LC/MS: Condition 2, retention time 3.50 min

LC/MS (ESI$^+$) m/z: 461, 463 [M+1]$^+$

LC/MS (ESI$^-$) m/z: 459, 461 [M−1]$^-$ $^1$H-NMR (CDCl$_3$)

δ: 0.97 (d, J=10.2 Hz, 1H), 1.05 (s, 3H), 1.19 (d, J=7.2 Hz, 3H), 1.27 (d, J=6.6 Hz, 3H×2), 1.28 (s, 3H), 1.61-1.78 (m, 1H), 1.92-1.98 (m, 1H), 2.02-2.08 (m, 1H), 2.46-2.52 (m, 1H), 2.59-2.68 (m, 1H), 3.70 (q, J=6.6 Hz, 1H), 3.81-3.92 (m, 1H), 4.49-4.52 (m, 1H), 4.85 (d, J=8.4 Hz, 1H), 5.42 (d, J=2.4 Hz, 2H), 7.63 (s, 1H).

SYNTHETIC EXAMPLE 77

4-Bromo-2-cyclopentyl-5-[(1R,2R,3R,5S)-2,6,6-trimethylbicyclo[3.1.1]hept-3-ylamino]pyridazin-3(2H)-one

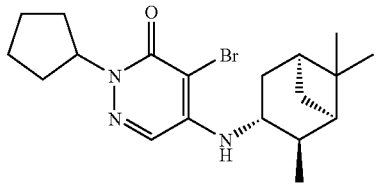 [SMILES: C[C@@H]1[C@H]2C[C@@H](C[C@H]1Nc1cnn(C3CCCC3)c(=O)c1Br)C2(C)C]

4-Bromo-5-[(1R,2R,3R,5S)-2,6,6-trimethylbicyclo[3.1.1]hept-3-ylamino]pyridazin-3(2H)-one (30 mg, 0.092 mmol) in N,N-dimethylformamide (0.9 mL) was mixed with bromocyclopentane (20 mg, 0.138 mmol) and potassium carbonate (19 mg, 0.138 mmol) at room temperature and stirred at 80° C. overnight. After cooling, the reaction solution was concentrated, mixed with water and extracted with ethyl acetate three times. The resulting organic layer was filtered through silica gel and evaporated under reduced pressure. The resulting residue was purified by silica gel chromatography (chloroform/ethyl acetate=1/1) to give the desired product (25 mg, 67% yield).

Morphology: colorless amorphous

LC/MS: Condition 3, retention time 5.22 min

LC/MS (ESI$^+$) m/z: 394, 396 [M+1]$^+$

LC/MS (ESI$^-$) m/z: 392, 394 [M−1]$^-$

SYNTHETIC EXAMPLES 78 TO 94

Compounds were synthesized in the same manner as in Synthetic Example 77, and the yields and morphology of the resulting compounds, the LC/MS conditions used for their analysis and the observed peaks and retention times are shown in Table 12.

TABLE 12

| Synthetic Example No. | Yield (%) | Morphology | LC/MS Condition | Observed peak ESI+ | Observed peak ESI- | Retention time (min) |
|---|---|---|---|---|---|---|
| 78 | 41 | Pale red solid | 3 | 456/458 | 454/456 | 4.90 |
| 79 | 49 | Pale yellow solid | 3 | 504/506 | 502/504 | 4.80 |
| 80 | 47 | Colorless oil | 3 | 412/414 | 410/412 | 4.84 |
| 81 | 47 | Colorless oil | 3 | 460/462 | 458/460 | 5.00 |
| 82 | 100 | Colorless amorphous | 3 | 469/471 | 467/469 | 5.03 |
| 83 | 49 | Light brown oil | 3 | 410/412 | 408/410 | 5.42 |
| 84 | 39 | Light brown amorphous | 3 | 515/517 | 513/515 | 5.18 |
| 85 | 60 | Colorless amorphous | 3 |  | 395/397 | 4.15 |
| 86 | 58 | Colorless amorphous | 3 | 513/515 | 511/513 | 4.90 |
| 87 | 36 | Colorless amorphous | 3 | 417 | 415/417 | 4.30 |
| 88 | 23 | Pale yellow solid | 3 | 542/544 | 540/542 | 4.64 |
| 89 | 55 | Colorless amorphous | 3 | 478/480 | 476/478 | 4.87 |
| 90 | 34 | Yellow oil | 3 | 469/471 | 467/469 | 4.84 |
| 91 | 60 | Pale yellow oil | 3 | 480/482 | 478/480 | 5.27 |
| 92 | 100 | Colorless amorphous | 2 | 528/530 | 526/528 | 3.69 |
| 93 | 48 | Colorless amorphous | 2 | 517/519 | 515/517 | 3.50 |
| 94 | 89 | Gray solid | 2 | 502/504 | 500/502 | 2.75 |

The structures of the compounds obtained in these Synthetic Examples are shown below.

SYNTHETIC EXAMPLES 78 TO 94

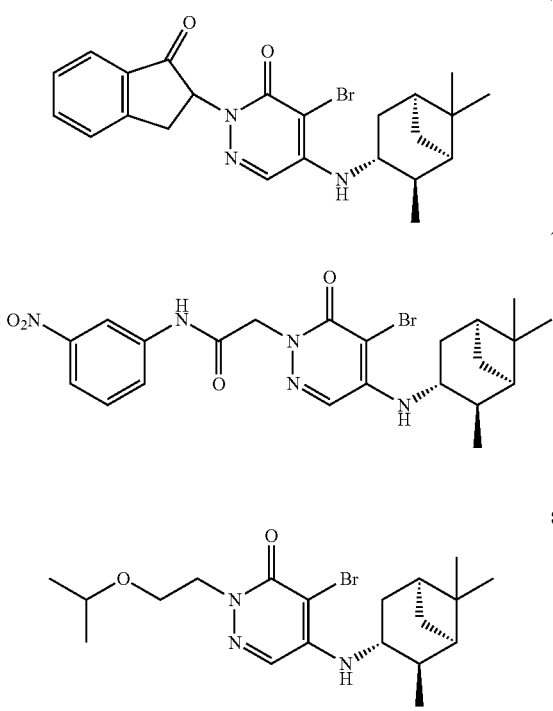

-continued

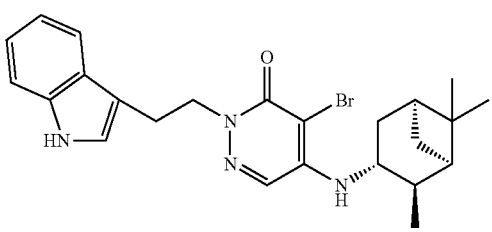

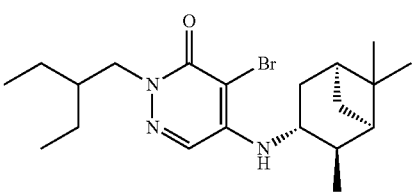

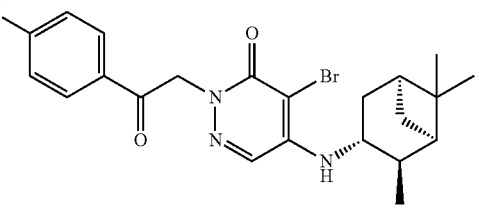

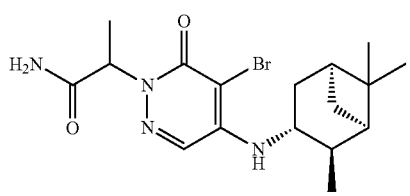

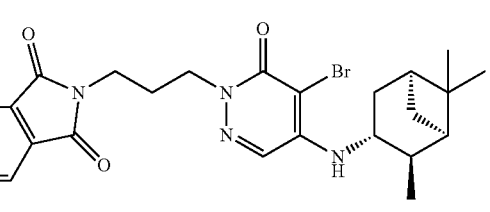

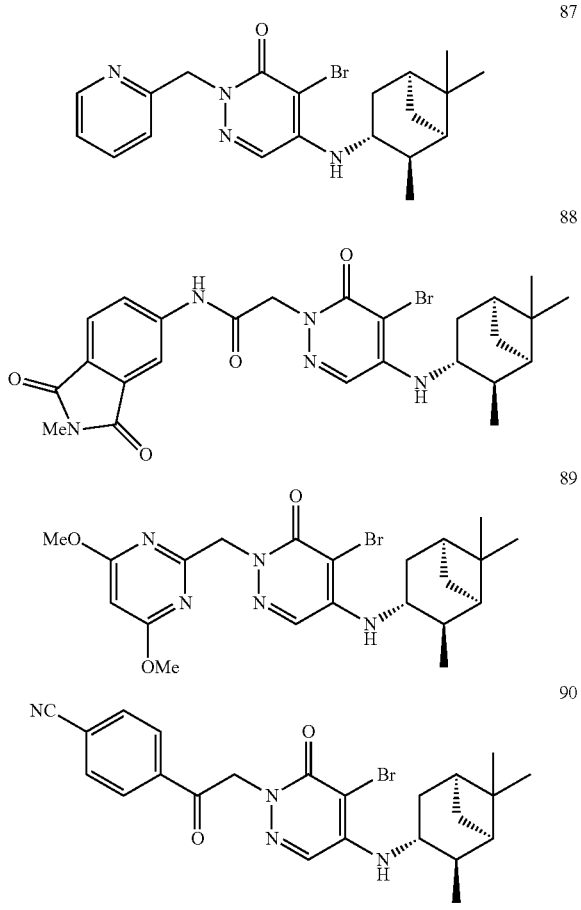

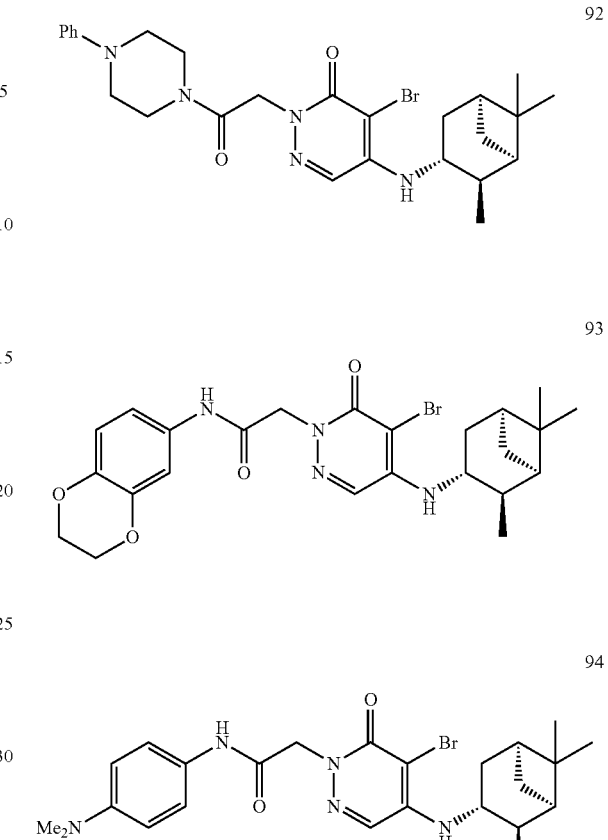

SYNTHETIC EXAMPLES 95 to 127

Compounds were synthesized in the same manner as in Synthetic Example 1, and the yields and morphology of the resulting compounds, the LC/MS conditions used for their analysis and the observed peaks and retention times are shown in Table 13.

TABLE 13

| Synthetic Example No. | Yield (%) | Morphology | LC/MS Condition | Observed peak ESI+ | Observed peak ESI− | Retention time (min) |
|---|---|---|---|---|---|---|
| 95 | 35 | Colorless amorphous | 2 | 486/488 | 484/486 | 2.38 |
| 96 | 100 | Yellow amorphous | 2 | 486/488 | 484/486 | 3.10 |
| 97 | 81 | Orange oil | 3 | 580/582 | 578/580 | 4.80 |
| 98 | 50 | Orange solid | 2 | 513/515 | 511/513 | 3.94 |
| 99 | 39 | Colorless solid | 2 | 508/510 | 506/508 | 3.35 |
| 100 | 36 | Pale yellow solid | 2 | 494/496 | 492/494 | 3.45 |
| 101 | 85 | Pale yellow solid | 2 | 498/500 | 496/498 | 3.29 |
| 102 | 92 | Colorless solid | 2 | 508/510 | 506/508 | 3.29 |
| 103 | 45 | Colorless solid | 2 | 475/477 | 473/475 | 2.94 |
| 104 | 41 | Colorless solid | 2 | 504/506 | 502/504 | 3.22 |
| 105 | 42 | Pale yellow solid | 2 | 559/561 | 557/559 | 2.25 |
| 106 | 19 | Colorless solid | 2 | 480/482 | 478/480 | 3.15 |
| 107 | 23 | Colorless solid | 2 | 514/516 | 512/514 | 3.44 |
| 108 | 24 | Colorless solid | 2 | 479/481 | 477/479 | 3.50 |
| 109 | 35 | Colorless solid | 2 | 493/495 | 491/493 | 3.60 |
| 110 | 38 | Colorless solid | 2 | 477/479 | 475/477 | 3.52 |
| 111 | 29 | Colorless solid | 2 | 489/491 | 487/489 | 3.07 |
| 112 | 87 | Pale yellow solid | 2 | 488/490 | 486/488 | 2.25 |

TABLE 13-continued

| Synthetic Example No. | Yield (%) | Morphology | LC/MS Condition | Observed peak ESI+ | Observed peak ESI− | Retention time (min) |
|---|---|---|---|---|---|---|
| 113 | 25 | Pale yellow oil | 2 | 503/505 | 501/503 | 3.34 |
| 114 | 67 | Pale yellow oil | 2 | 570/572 | 568/570 | 3.80 |
| 115 | 25 | Colorless solid | 2 | 517/519 | 515/517 | 3.47 |
| 116 | 53 | Colorless solid | 2 | 487/489 | 485/487 | 3.65 |
| 117 | 37 | Light brown solid | 2 | 488/490 | 486/488 | 3.13 |
| 118 | 51 | Pale yellow solid | 2 | 503/505 | 501/503 | 3.59 |
| 119 | 56 | Pale yellow oil | 2 | 499/501 | 497/499 | 3.69 |
| 120 | 50 | Colorless solid | 2 | 507/509 | 505/507 | 3.69 |
| 121 | 47 | Pale yellow solid | 2 | 541/543 | 539/541 | 3.74 |
| 122 | 62 | Pale yellow oil | 2 | 598/560 | 596/598 | 3.84 |
| 123 | 52 | Colorless solid | 2 | 513/515 | 511/513 | 2.38 |
| 124 | 46 | Colorless solid | 2 | 530/532 | 528/530 | 3.50 |
| 125 | 15 | Colorless solid | 2 | 558/560 | 556/558 | 2.38 |
| 126 | 23 | Colorless solid | 2 | 516/518 | 514/516 | 2.25 |
| 127 | 41 | Colorless solid | 2 | 464/466 | 462/464 | 3.19 |

The structures of the compounds obtained in these Synthetic Examples are shown below.

SYNTHETIC EXAMPLES 95 TO 127

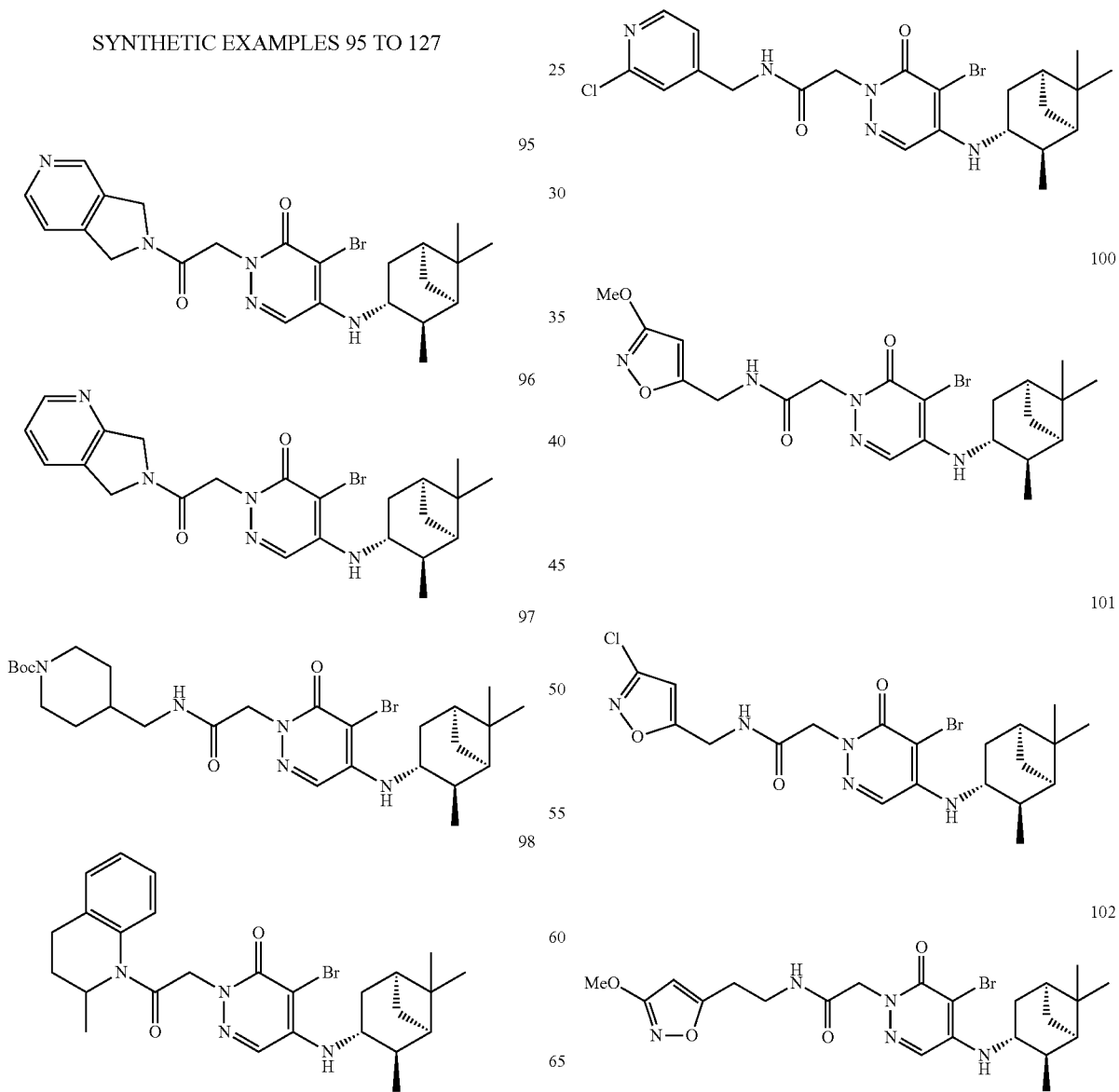

103 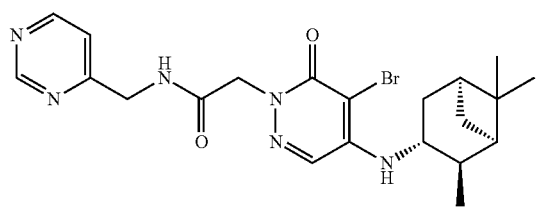
104 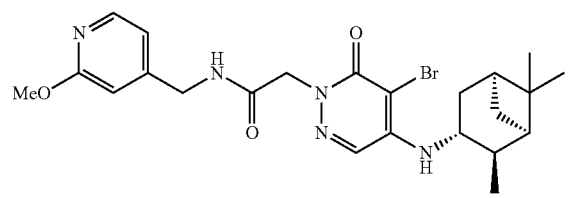
105 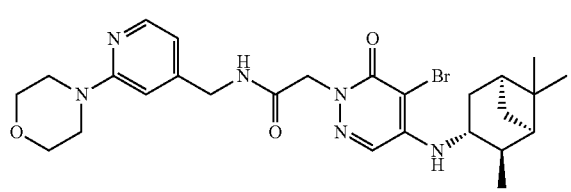
106 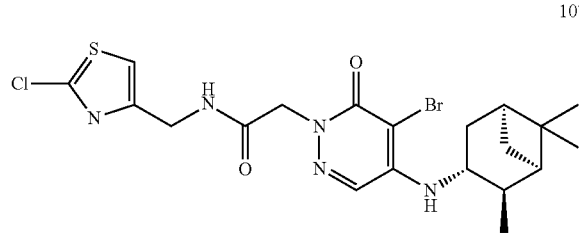
107 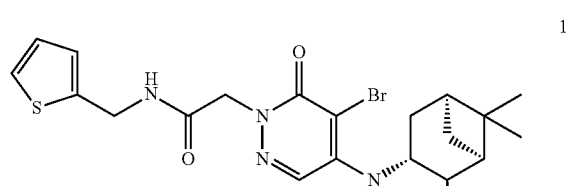
108 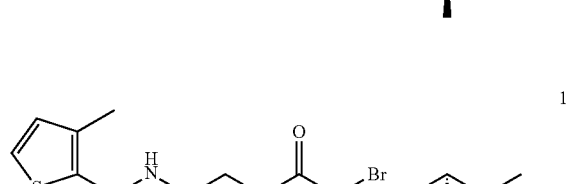
109 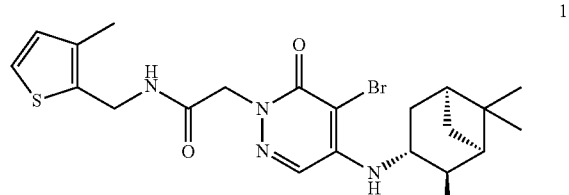
110 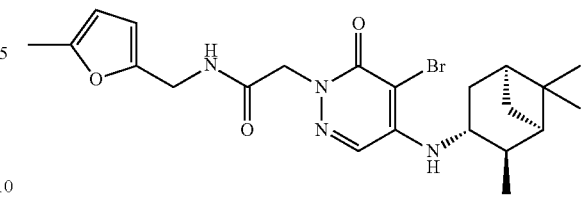
111 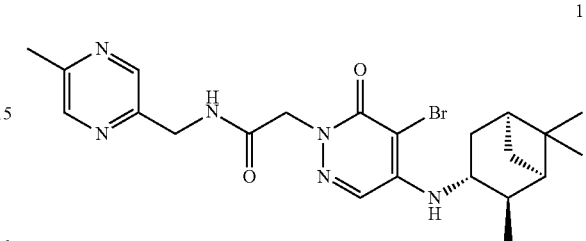
112 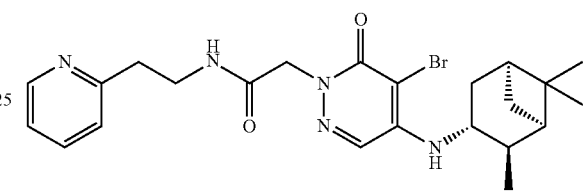
113 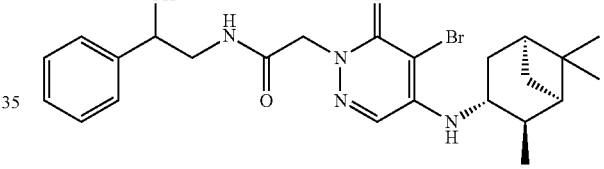
114 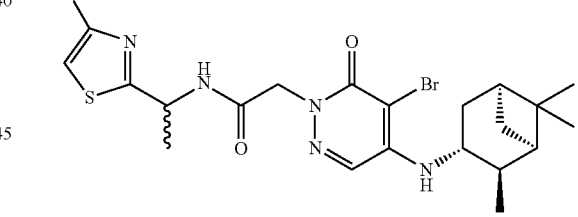
115 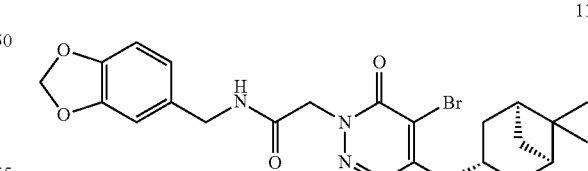
116 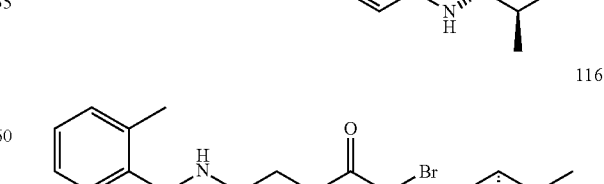

117
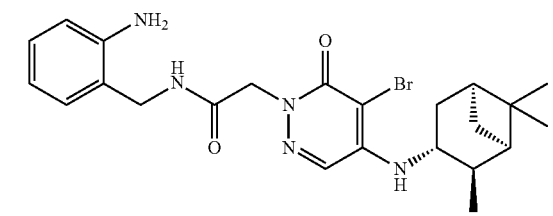
118
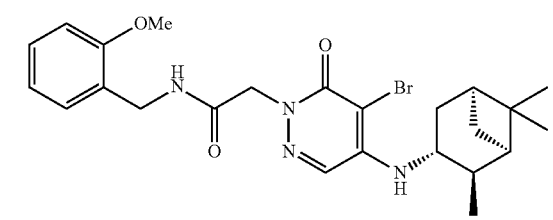
119
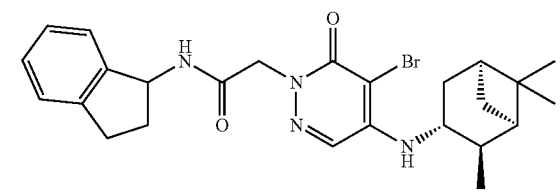
120
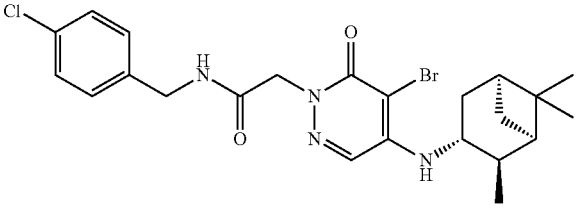
121
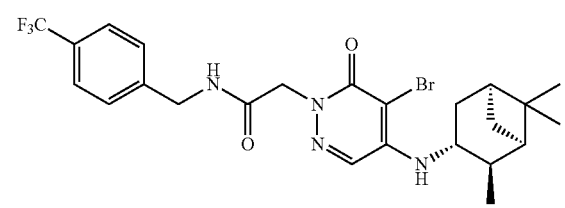
122
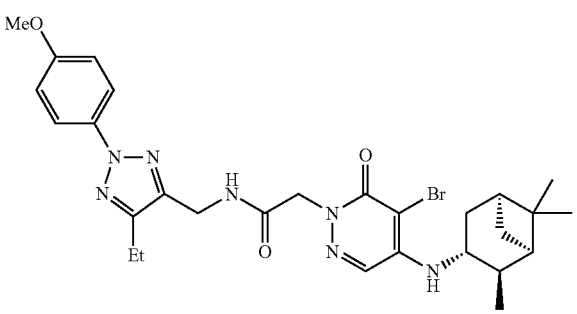
123
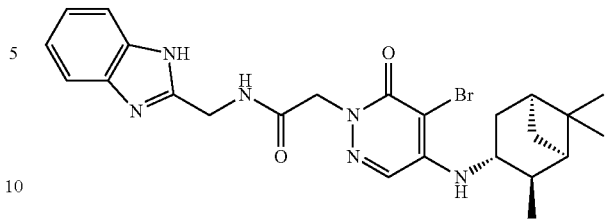
124
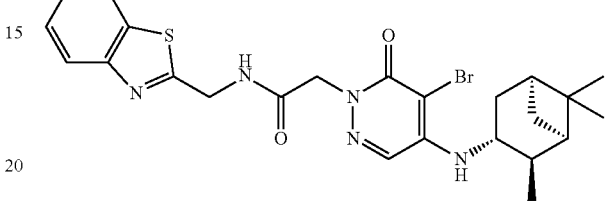
125
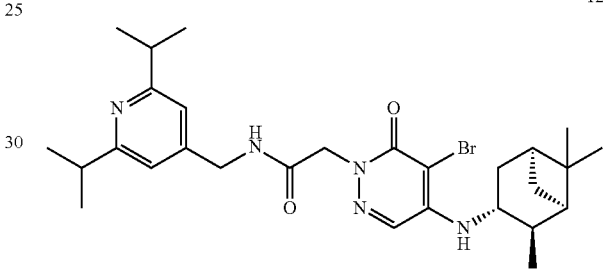
126
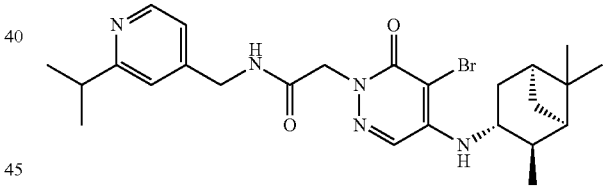
127
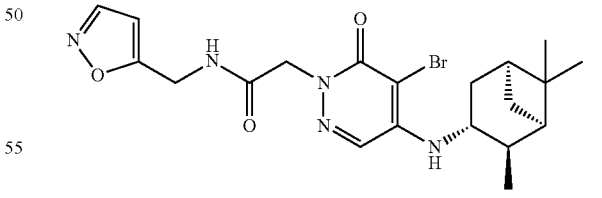
SYNTHETIC EXAMPLES 128 to 131
Compounds were synthesized in the same manner as in Synthetic Example 48, and the yields and morphology of the resulting compounds, the LC/MS conditions used for their analysis and the observed peaks and retention times are shown in Table 14.

TABLE 14

| Synthetic Example No. | Yield (%) | Morphology | LC/MS Condition | Observed peak ESI+ | Observed peak ESI− | Retention time (min) |
|---|---|---|---|---|---|---|
| 128 | 6 | Colorless solid | 2 | 474/476 | 472/474 | 2.17 |
| 129 | 4 | Colorless solid | 2 | 474/476 | 472/474 | 2.17 |
| 130 | 7 | Colorless solid | 2 | 474/476 | 472/474 | 2.15 |
| 131 | 5 | Colorless solid | 2 | 460/462 | 458/460 | 2.17 |

The structures of the compounds obtained in these Synthetic Examples are shown below.

SYNTHETIC EXAMPLES 128 TO 131

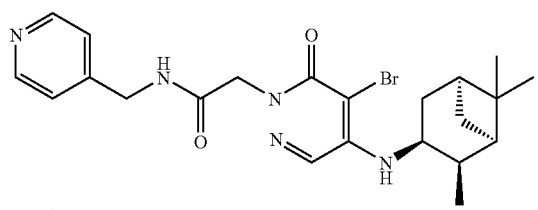

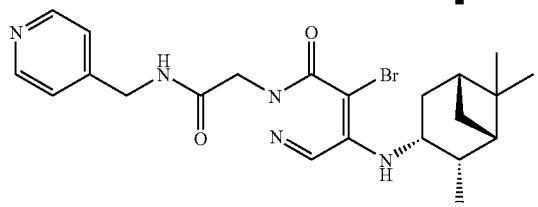

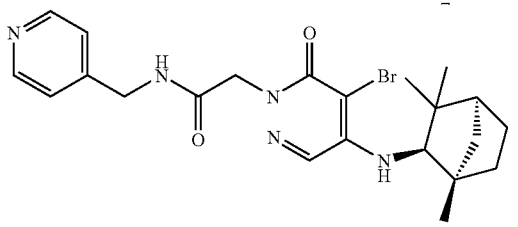

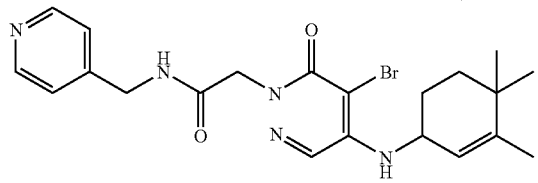

SYNTHETIC EXAMPLE 132

2-(2-{5-Bromo-6-oxo-4-[(1R,2R,3R,5S)-2,6,6-trimethylbicyclo[3.1.1]hept-3-ylamino]pyridazin-1(6H)-yl}acetamido)acetic Acid

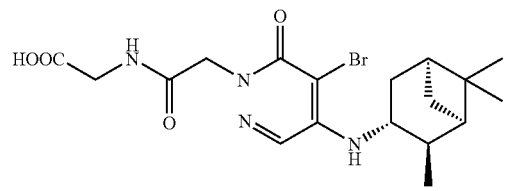 [SMILES: C[C@@H]1[C@H]2C[C@@H](C[C@H]1N/C(C=N)=C(\Br)C(=O)NCC(=O)NCC(=O)O)C2(C)C]

tert-Butyl 2-(2-{5-bromo-6-oxo-4-[(1R,2R,3R,5S)-2,6,6-trimethylbicyclo[3.1.1]hept-3-ylamino]pyridazin-1(6H)-yl}acetamido)acetate (18 mg, 0.036 mmol) prepared in Synthetic Example 10 in dichloromethane (1 mL) was stirred with trifluoroacetic acid (0.1 mL) at room temperature. After completion of the reaction, the reaction solution was concentrated to give the desired product (15 mg, 94% yield).

Morphology: pale green solid

LC/MS: Condition 3, retention time 3.97 min

LC/MS (ESI+) m/z: 441, 443 [M+1]+

LC/MS (ESI−) m/z: 439, 441 [M−1]−

SYNTHETIC EXAMPLE 133

Ethyl 2-{5-chloro-6-oxo-4-[(1R,2R,3R,5S)-2,6,6-trimethylbicyclo[3.1.1]hept-3-ylamino]pyridazin-1(6H)-yl}acetate

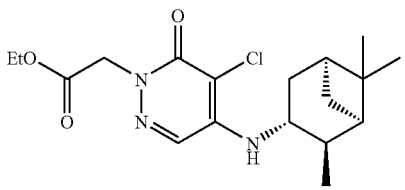 [SMILES: CCOC(=O)Cn1ncc(N[C@@H]2C[C@@H]3C[C@H]([C@H]2C)C3(C)C)c(Cl)c1=O]

4-Chloro-5-{(1R,2R,3R,5S)-2,6,6-trimethylbicyclo[3.1.1]hept-3-ylamino}pyridazin-3(2H)-one

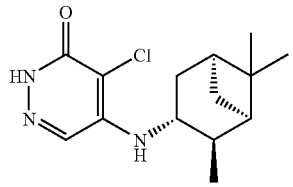

Synthesis was carried out in the same manner as in Synthetic Example 1 by using 4,5-dichloropyridazin-3(2H)-one (prepared in accordance with Journal of Heterocyclic Chemistry, 33(6), 1579-1582; 1996) (100% yield).

Morphology: pale yellow solid

LC/MS: Condition 3, retention time 4.09 min

LC/MS (ESI+) m/z: 282, 284 [M+1]+

LC/MS (ESI−) m/z: 280, 282 [M−1]−

Ethyl {5-chloro-6-oxo-4-[(1R,2R,3R,5S)-2,6,6-trim-ethylbicyclo[3.1.1]hept-3-ylamino]pyridazin-1(6H)-yl}acetate Synthesis was carried out in the same manner as in Synthetic Example 1 by using 4-chloro-5-[(1R,2R,3R,5S)-2,6,6-trimethylbicyclo[3.1.1]hept-3-ylamino]pyridazin-3(2H)-one (33% yield).
Morphology: colorless solid

SYNTHETIC EXAMPLES 134 TO 135

Synthesis of 2-{5-chloro-6-oxo-4-[(1R,2R,3R,5S)-2,6,6-trimethylbicyclo[3.1.1]hept-3-ylamino]pyridazin-1(6H)-yl}acetic Acid Synthesis was carried out in the same manner as in Synthetic Example 1 by using ethyl 2-{5-chloro-6-oxo-4-[(1R,2R,3R,5S)-2,6,6-trimethylbicyclo[3.1.1]hept-3-ylamino]pyridazin-1(6H)-yl}acetate (100% yield).
Morphology: colorless solid
Compounds were synthesized in the same manner as in Synthetic Example 1, and the yields and morphology of the resulting compounds, the LC/MS conditions used for their analysis and the observed peaks and retention times are shown in Table 15.

TABLE 15

| Synthetic Example No. | Yield (%) | Morphology | LC/MS Condition | Observed peak ESI+ | Observed peak ESI− | Retention time (min) |
|---|---|---|---|---|---|---|
| 134 | 78 | Colorless solid | 3 | 381/383 | 379/381 | 4.35 |
| 135 | 63 | Colorless solid | 3 | 430/432 | 428/430 | 3.34 |

The structures of the compounds obtained in these Synthetic Examples are shown below.

SYNTHETIC EXAMPLES 134 TO 135

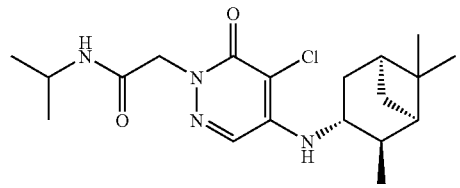

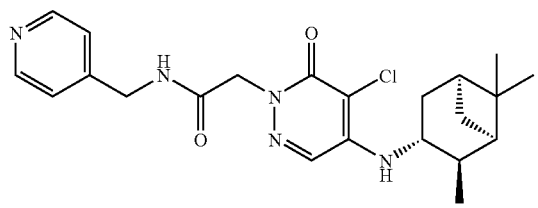

SYNTHETIC EXAMPLE 136

4-Chloro-2-{2-[4-(dimethylamino)phenyl]-2-oxoethyl}-5-[(1R,2R,3R,5S)-2,6,6-trimethylbicyclo[3.1.1]hept-3-ylamino]pyridazin-3(2H)-one

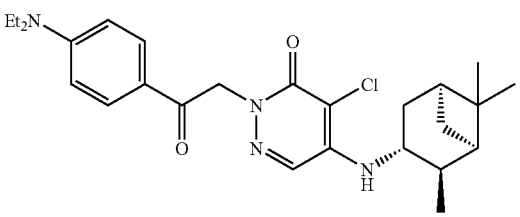

Synthesis was carried out in the same manner as in Synthetic Example 77 by using 4-chloro-5-[(1R,2R,3R,5S)-2,6,6-trimethylbicyclo[3.1.1]hept-3-ylamino]pyridazin-3(2H)-one (88% yield).
Morphology: orange solid
LC/MS: Condition 3, retention time 4.09 min
LC/MS (ESI+):471, 473 [M+1]+
LC/MS (ESI−):469, 471 [M−1]−

SYNTHETIC EXAMPLE 137

2-{2-[4-(Dimethylamino)phenyl]-2-oxoethyl}-5-[(1R,2R,3R,5S)-2,6,6-trimethylbicyclo[3.1.1]hept-3-ylamino]pyridazin-3(2H)-one

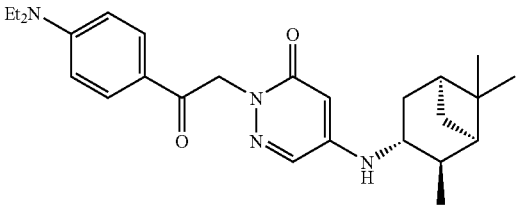

5-[(1R,2R,3R,5S)-2,6,6-Trimethylbicyclo[3.1.1]hept-3-ylamino]pyridazin-3(2H)-one

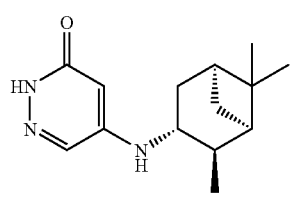 [SMILES: C[C@@H]1[C@H]2C[C@@H](C[C@H]1Nc1cn[nH]c(=O)c1)C2(C)C]

4-Bromo-5-[(1R,2R,3R,5S)-2,6,6-trimethylbicyclo[3.1.1]hept-3-ylamino]pyridazin-3(2H)-one (300 mg, 0.92 mmol) and 10% palladium-carbon (50 wt %, 30 mg) in methanol were stirred in a hydrogen stream at room temperature for 1 day. The reaction solution was filtered through celite, and the filtrate was concentrated to give the desired product (100% yield).

Morphology: pale yellow solid
LC/MS: Condition 3, retention time 3.70 min
LC/MS (ESI⁺):306 [M+1]⁺

Compounds were synthesized in the same manner as in Synthetic Example 1, and the yields and morphology of the resulting compounds, the LC/MS conditions used for their analysis and the observed peaks and retention times are shown in Table 16.

TABLE 16

| Synthetic Example No. | Yield (%) | Morphology | LC/MS Condition | Observed peak ESI⁺ | Observed peak ESI⁻ | Retention time (min) |
|---|---|---|---|---|---|---|
| 138 | 48 | Pale yellow solid | 3 | 347 | | 3.93 |
| 139 | 97 | Pale yellow solid | 3 | 396 | 394 | 2.22 |

2-{2-[4-(Dimethylamino)phenyl]-2-oxoethyl}-5-[(1R,2R,3R,5S)-2,6,6-trimethylbicyclo[3.1.1]hept-3-ylamino]pyridazin-3(2H)-one Synthesis was carried out in the same manner as in Synthetic Example 77 by using 5-[(1R,2R,3R,5S)-2,6,6-trimethylbicyclo[3.1.1]hept-3-ylamino]pyridazin-3(2H)-one.
Morphology: orange solid

SYNTHETIC EXAMPLES 138 TO 139

Ethyl 2-{6-oxo-4-[(1R,2R,3R,5S)-2,6,6-trimethylbicyclo[3.1.1]hept-3-ylamino]pyridazin-1(6H)-yl}acetate

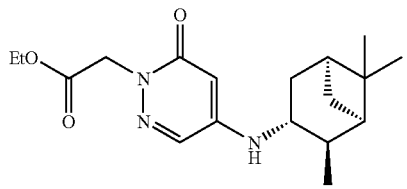 [SMILES: C[C@@H]1[C@H]2C[C@@H](C[C@H]1Nc1cnn(CC(=O)O)c(=O)c1)C2(C)C]

Synthesis was carried out in the same manner as in Synthetic Example 1 by using 5-[(1R,2R,3R,5S)-2,6,6-trimethylbicyclo[3.1.1]hept-3-ylamino]pyridazin-3(2H)-one (42% yield).
Morphology: pale yellow oil
LC/MS: Condition 3, retention time 4.17 min
LC/MS (ESI⁺):334 [M+1]⁺

2-{6-Oxo-4-[(1R,2R,3R,5S)-2,6,6-trimethylbicyclo[3.1.1]hept-3-ylamino]pyridazin-1(6H)-yl}acetic Acid

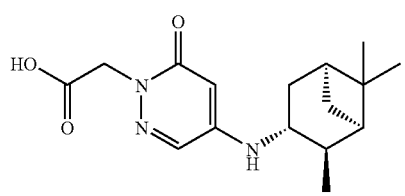

Synthesis was carried out in the same manner as in Synthetic Example 1 by using ethyl 2-{6-oxo-4-[(1R,2R,3R,5S)-2,6,6-trimethylbicyclo[3.1.1]hept-3-ylamino]pyridazin-1(6H)-yl}acetate.

The structures of the compounds obtained in these Synthetic Examples are shown below.

Syn. Ex. 138

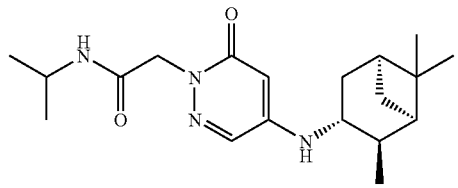

Syn. Ex. 139

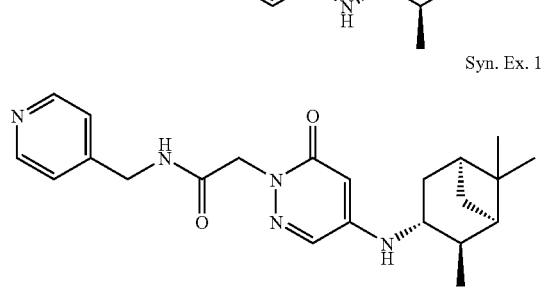

SYNTHETIC EXAMPLE 140

4-Chloro-6-ethoxy-2-{2-[4-(dimethylamino)phenyl]-2-oxoethyl}-5-[(1R,2R,3R,5S)-2,6,6-trimethylbicyclo[3.1.1]hept-3-ylamino]pyridazin-3(2H)-one

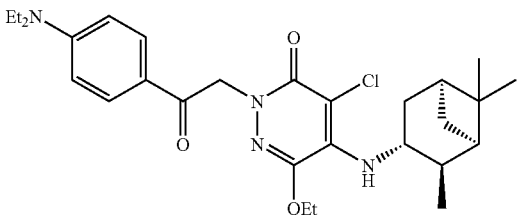

4-Chloro-6-ethoxy-5-[(1R,2R,3R,5S)-2,6,6-trimethylbicyclo[3.1.1]hept-3-ylamino]pyridazin-3(2H)-one

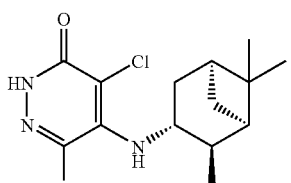

Synthesis was carried out in the same manner as in Synthetic Example 1 by using 4,5-dichloro-6-ethoxypyridazin-3(2H)-one (prepared in accordance with WO9501343) (77% yield).
Morphology: colorless solid
LC/MS: Condition 3, retention time 4.60 min
LC/MS (ESI$^+$):326, 328 [M+1]$^+$
LC/MS (ESI$^-$):324, 326 [M−1]$^-$ 4-Chloro-6-ethoxy-2-{2-[4-(dimethylamino)phenyl]-2-oxoethyl}-5-[(1R,2R,3R,5S)-2,6,6-trimethylbicyclo[3.1.1]hept-3-ylamino]pyridazin-3(2H)-one Synthesis was carried out in the same manner as in Synthetic Example 77 by using 4-chloro-6-ethoxy-5-[(1R,2R,3R,5S)-2,6,6-trimethylbicyclo[3.1.1]hept-3-ylamino]pyridazin-3(2H)-one (100% yield).
Morphology: pale yellow solid
LC/MS: Condition 3, retention time 5.52 min
LC/MS (ESI$^+$):515, 517 [M+1]$^+$
LC/MS (ESI$^-$):513, 515 [M−1]$^-$ Morphology: colorless solid
LC/MS: Condition 3, retention time 5.05 min
LC/MS (ESI$^+$):412, 414 [M+1]$^+$ 2-{5-Chloro-3-ethoxy-6-oxo-4-[(1R,2R,3R,5S)-2,6,6-trimethylbicyclo[3.1.1]hept-3-ylamino]pyridazin-1(6H)-yl}acetic Acid Synthesis was carried out in the same manner as in Synthetic Example 1 by using Ethyl 2-{5-chloro-3-ethoxy-6-oxo-4-[(1R,2R,3R,5S)-2,6,6-trimethylbicyclo[3.1.1]hept-3-ylamino]pyridazin-1(6H)-yl}acetate (89% yield).
Morphology: colorless solid
LC/MS: Condition 3, retention time 4.59 min
LC/MS (ESI$^+$):384, 386 [M+1]$^+$
LC/MS (ESI$^-$):382, 384 [M−1]$^-$ Compounds were synthesized in the same manner as in Synthetic Example 1, and the yields and morphology of the resulting compounds, the LC/MS conditions used for their analysis and the observed peaks and retention times are shown in Table 17.

TABLE 17

| Synthetic Example No. | Yield (%) | Morphology | LC/MS Condition | Observed peak ESI$^+$ | Observed peak ESI$^-$ | Retention time (min) |
|---|---|---|---|---|---|---|
| 141 | 77 | Colorless solid | 3 | 425/427 | 423/425 | 4.80 |
| 142 | 81 | Colorless solid | 3 | 474/476 | 472/474 | 4.02 |

SYNTHETIC EXAMPLES 141 TO 142

Synthesis of 2-{5-chloro-3-ethoxy-6-oxo-4-[(1R,2R,3R,5S)-2,6,6-trimethylbicyclo[3.1.1]hept-3-ylamino]pyridazin-1(6H)-yl}acetic Acid

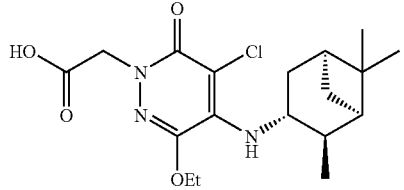

Ethyl 2-{5-chloro-3-ethoxy-6-oxo-4-[(1R,2R,3R,5S)-2,6,6-trimethylbicyclo[3.1.1]hept-3-ylamino]pyridazin-1(6H)-yl}acetate

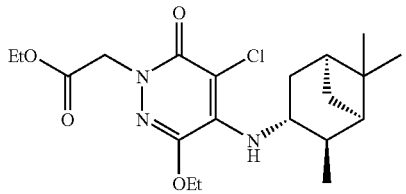 [SMILES: CCOc1nn(CC(=O)O)c(=O)c(Cl)c1N[C@@H]1C[C@@H]2C[C@H]([C@H]1C)C2(C)C]

Synthesis was carried out in the same manner as in Synthetic Example 1 by using 4-chloro-6-ethoxy-5-[(1R,2R,3R,5S)-2,6,6-trimethylbicyclo[3.1.1]hept-3-ylamino]pyridazin-3(2H)-one (96% yield).

The structures of the compounds obtained in these Synthetic Examples are shown below.

Syn. Ex. 141

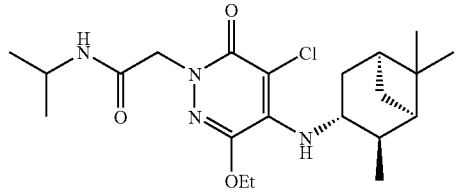

Syn. Ex. 142

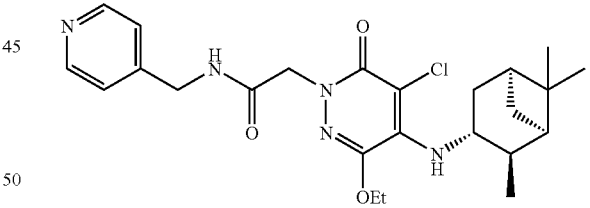

SYNTHETIC EXAMPLE 143

2-{3-Ethoxy-6-oxo-4-[(1R,2R,3R,5S)-2,6,6-trimethylbicyclo[3.1.1]hept-3-ylamino]pyridazin-1(6H)-yl}-N-isopropylacetamide

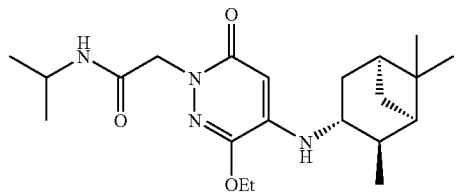 [SMILES: CCOc1nn(CC(=O)NC(C)C)c(=O)cc1N[C@@H]1C[C@@H]2C[C@H]([C@H]1C)C2(C)C]

6-Ethoxy-5-[(1R,2R,3R,5S)-2,6,6-trimethylbicyclo[3.1.1]hept-3-ylamino]pyridazin-3(2H)-one

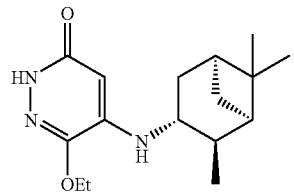 [SMILES: CCOc1n[nH]c(=O)cc1N[C@@H]1C[C@@H]2C[C@H]([C@H]1C)C2(C)C]

4-Chloro-6-ethoxy-5-[(1R,2R,3R,5S)-2,6,6-trimethylbicyclo[3.1.1]hept-3-ylamino]pyridazin-3(2H)-one (200 mg, 0.614 mmol) and 10% palladium-carbon (50 wt %, 40 mg) were stirred in methanol in a hydrogen stream at room temperature for 8 days. The reaction solution was filtered through celite and concentrated under reduced pressure to give the desired product (94% yield).
Morphology: pale yellow solid
LC/MS: Condition 2, retention time 3.15 min
LC/MS (ESI$^+$):292 [M+1]$^+$
LC/MS (ESI$^-$):290 [M−1]$^-$ Ethyl 2-{3-ethoxy-6-oxo-4-[(1R,2R,3R,5S)-2,6,6-trimethylbicyclo[3.1.1]hept-3-ylamino]pyridazin-1(6H)-yl}acetate

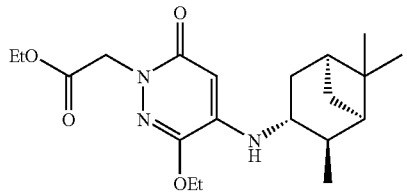 [SMILES: CCOc1nn(CC(=O)O)c(=O)cc1N[C@@H]1C[C@@H]2C[C@H]([C@H]1C)C2(C)C]

Synthesis was carried out in the same manner as in Synthetic Example 1 by using 6-ethoxy-5-[(1R,2R,3R,5S)-2,6,6-trimethylbicyclo[3.1.1]hept-3-ylamino]pyridazin-3(2H)-one (80% yield).
Morphology: colorless oil
LC/MS: Condition 3, retention time 4.72 min
LC/MS (ESI$^+$):378 [M+1]$^+$
LC/MS (ESI$^-$):376 [M−1]$^-$ 2-{3-Ethoxy-6-oxo-4-[(1R,2R,3R,5S)-2,6,6-trimethylbicyclo[3.1.1]hept-3-ylamino]pyridazin-1(6H)-yl}acetic Acid

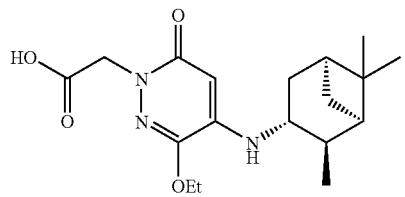

Synthesis was carried out in the same manner as in Synthetic Example 1 by using ethyl 2-{3-ethoxy-6-oxo-4-[(1R,2R,3R,5S)-2,6,6-trimethylbicyclo[3.1.1]hept-3-ylamino]pyridazin-1(6H)-yl}acetate (86% yield).
Morphology: colorless solid 2-{3-Ethoxy-6-oxo-4-[(1R,2R,3R,5S)-2,6,6-trimethylbicyclo[3.1.1]hept-3-ylamino]pyridazin-1(6H)-yl}-N-isopropylacetamide Synthesis was carried out in the same manner as in Synthetic Example 1 by using 2-{3-ethoxy-6-oxo-4-[(1R,2R,3R,5S)-2,6,6-trimethylbicyclo[3.1.1]hept-3-ylamino]pyridazin-1(6H)-yl}acetic acid (54% yield).
Morphology: colorless solid
LC/MS: Condition 3, retention time 4.43 min
LC/MS (ESI$^+$):391 [M+1]$^+$

SYNTHETIC EXAMPLE 144

2-{3-Ethoxy-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide

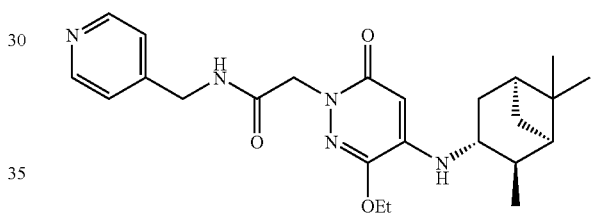

Synthesis was carried out in the same manner as in Synthetic Example 1 by using 2-{3-ethoxy-6-oxo-4-[(1R,2R,3R,5S)-2,6,6-trimethylbicyclo[3.1.1]hept-3-ylamino]pyridazin-1(6H)-yl}acetic acid (90% yield).
Morphology: colorless solid
LC/MS: Condition 3, retention time 3.70 min
LC/MS (ESI$^+$):440 [M+1]$^+$
LC/MS (ESI$^-$):438 [M−1]$^-$

SYNTHETIC EXAMPLE 145

Ethyl 2-{5-methylthio-6-oxo-4-[(1R,2R,3R,5S)-2,6,6-trimethylbicyclo[3.1.1]hept-3-ylamino]pyridazin-1(6H)-yl}acetate

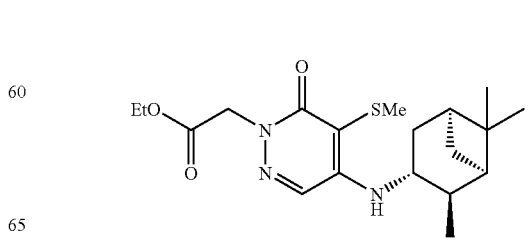

2-{5-Methylthio-6-oxo-4-[(1R,2R,3R,5S)-2,6,6-trimethylbicyclo[3.1.1]hept-3-ylamino]pyridazin-1(6H)-yl}acetic Acid

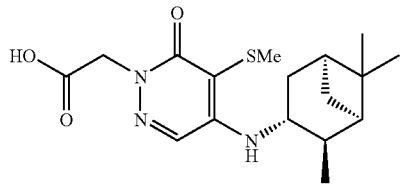 [SMILES: CSc1c(N[C@@H]2C[C@@H]3C[C@H]([C@H]2C)C3(C)C)cnn(CC(=O)O)c1=O]

Ethyl 2-{5-bromo-6-oxo-4-[(1R,2R,3R,5S)-2,6,6-trimethylbicyclo[3.1.1]hept-3-ylamino]pyridazin-1(6H)-yl}acetate (220 mg, 0.533 mmol) and sodium thiomethoxide (112 mg, 1.60 mmol) in toluene (22 mL) were stirred at 80° C. for 3 hours. After cooling, the reaction solution was stirred with 1,4-dioxane (6 mL) and 1 M aqueous sodium hydroxide (1.59 mL) at room temperature for 4 hours. After completion of the reaction, the reaction solution was mixed with toluene and extracted with 1 M aqueous sodium hydroxide twice. The resulting aqueous layer was acidified to pH 1 with 1 M hydrochloric acid and extracted with ethyl acetate twice, and the extract was dried over anhydrous sodium sulfate and evaporated under reduced pressure to give the desired product (169 mg, 90% yield).

Morphology: yellow amorphous

LC/MS: Condition 3, retention time 4.20 min

LC/MS (ESI$^+$):352 [M+1]$^+$

LC/MS (ESI$^-$):350 [M−1]$^-$ $^1$H-NMR (CDCl$_3$)

δ: 0.97 (d, J=9.9 Hz, 1H), 1.06 (s, 3H), 1.17 (d, J=7.5 Hz, 3H), 1.27 (s, 3H), 1.68-1.75 (m, 1H), 1.90-2.10 (m, 1H), 2.30 (s, 3H), 2.40-2.70 (m, 2H), 3.80-3.90 (m, 1H), 4.89 (s, 2H), 5.62 (d, J=8.3 Hz, 1H), 7.64 (s, 1H).

Ethyl 2-{5-methylthio-6-oxo-4-[(1R,2R,3R,5S)-2,6,6-trimethylbicyclo[3.1.1]hept-3-ylamino]pyridazin-1(6H)-yl}acetate 2-{5-Methylthio-6-oxo-4-[(1R,2R,3R,5S)-2,6,6-trimethylbicyclo[3.1.1]hept-3-ylamino]pyridazin-1(6H)-yl}acetic acid (105 mg, 0.299 mmol) in tetrahydrofuran (1 mL) was stirred with 1,1-carbonyldiimidazole (145 mg, 0.897 mmol) at room temperature for 1 hour and then with ethanol (0.2 mL) at room temperature for 1 hour. After completion of the reaction, ethyl acetate was added, and the resulting organic layer was washed with 1 M hydrochloric acid and saturated aqueous sodium chloride, dried over anhydrous magnesium sulfate. The resulting residue was purified by silica gel chromatography (hexane/ethyl acetate=1/1) to give the desired product (93 mg, 82% yield).

Morphology: yellow oil

LC/MS: Condition 3, retention time 4.65 min

LC/MS (ESI$^+$):380 [M+1]$^+$

LC/MS (ESI$^-$):378 [M−1]$^-$

SYNTHETIC EXAMPLE 146

2-{5-Methylthio-6-oxo-4-[(1R,2R,3R,5S)-2,6,6-trimethylbicyclo[3.1.1]hept-3-ylamino]pyridazin-1(6H)-yl}-N-pyridin-4-ylmethyl)acetamide

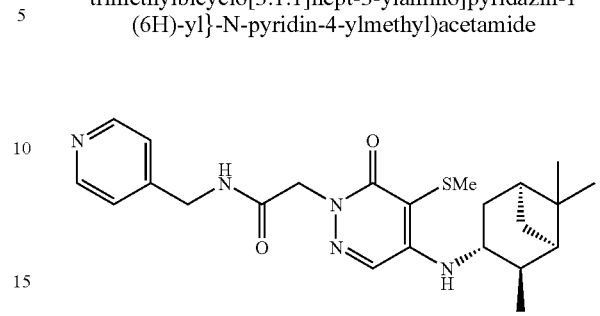

Synthesis was carried out in the same manner as in Synthetic Example 1 by using 2-{5-methylthio-6-oxo-4-[(1R,2R,3R,5S)-2,6,6-trimethylbicyclo[3.1.1]hept-3-ylamino]pyridazin-1(6H)-yl}acetic acid (85% yield).

Morphology: yellow amorphous

LC/MS: Condition 3, retention time 3.50 min

LC/MS (ESI$^+$):442 [M+1]$^+$

LC/MS (ESI$^-$):440 [M−1]$^-$

SYNTHETIC EXAMPLE 147

Ethyl 2-{5-methylsulfonyl-6-oxo-4-[(1R,2R,3R,5S)-2,6,6-trimethylbicyclo[3.1.1]hept-3-ylamino]pyridazin-1(6H)-yl}acetate

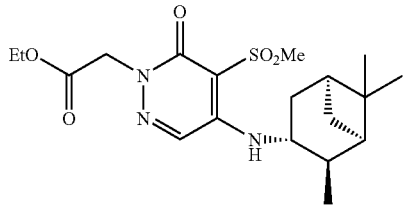 [SMILES: CCOC(=O)Cn1ncc(N[C@@H]2C[C@@H]3C[C@H]([C@H]2C)C3(C)C)c(S(C)(=O)=O)c1=O]

Ethyl 2-{5-methylthio-6-oxo-4-[(1R,2R,3R,5S)-2,6,6-trimethylbicyclo[3.1.1]hept-3-ylamino]pyridazin-1(6H)-yl}acetate (77 mg, 0.203 mmol) and m-chloroperbenzoic acid (60% purity, 150 mg, 0.609 mmol) in dichloromethane were stirred at 0° C. for 1 hour and 20 minutes. After completion of the reaction, the reaction solution was washed with saturated aqueous sodium thiosulfate, 1 M aqueous sodium hydroxide and saturated aqueous sodium chloride and dried over anhydrous magnesium sulfate. The resulting residue was purified by silica gel chromatography (hexane/ethyl acetate=4/1) to give the desired product (70 mg, 84% yield).

Morphology: colorless amorphous

LC/MS: Condition 3, retention time 4.49 min

LC/MS (ESI$^+$):412 [M+1]$^+$

LC/MS (ESI$^-$):410 [M−1]$^-$ $^1$H-NMR (CDCl$_3$)

δ: 0.97 (d, J=10.5 Hz, 1H), 1.03 (s, 3H), 1.17 (d, J=6.9 Hz, 3H), 1.27 (s, 3H), 1.75-1.85 (m, 1H), 1.90-2.05 (m, 2H), 2.40-2.50 (m, 1H), 2.55-2.65 (m, 1H), 3.38 (s, 3H), 3.85-3.95 (m, 1H), 4.78 (s, 2H), 7.67 (s, 1H), 8.36 (d, J=7.8 Hz, 1H).

SYNTHETIC EXAMPLE 148

2-{5-Methylsulfonyl-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide

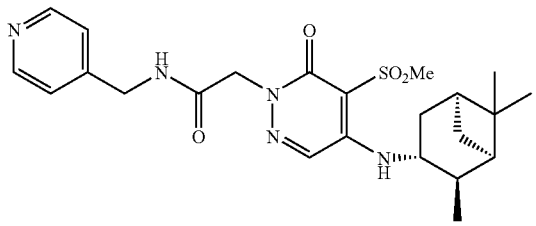 [SMILES: C[C@@H]1[C@H]2C[C@@H](C[C@H]1Nc1cnn(CC(=O)NCc3ccncc3)c(=O)c1S(C)(=O)=O)C2(C)C]

2-{5-Methylsulfonyl-6-oxo-4-[(1R,2R,3R,5S)-2,6,6-trimethylbicyclo[3.1.1]hept-3-ylamino]pyridazin-1(6H)-yl}acetic Acid

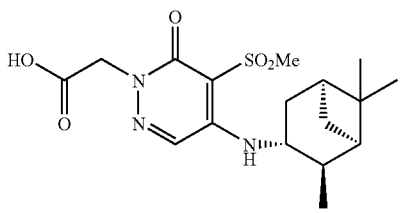 [SMILES: C[C@@H]1[C@H]2C[C@@H](C[C@H]1Nc1cnn(CC(=O)O)c(=O)c1S(C)(=O)=O)C2(C)C]

Synthesis was carried out in the same manner as in Synthetic Example 1 by using ethyl 2-[(5-Methylsulfonyl-6-oxo-4-[(1R,2R,3R,5S)-2,6,6-trimethylbicyclo[3.1.1]hept-3-ylamino]pyridazin-1(6H)-yl]acetate (92% yield).
Morphology: colorless solid
LC/MS: Condition 3, retention time 4.02 min
LC/MS (ESI$^+$):384 [M+1]$^+$
LC/MS (ESI$^-$):382 [M−1]$^-$ 2-{5-Methylsulfonyl-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide Synthesis was carried out in the same manner as in Synthetic Example 1 by using 2-{5-methylsulfonyl-6-oxo-4-[(1R,2R,3R,5S)-2,6,6-trimethylbicyclo[3.1.1]hept-3-ylamino]pyridazin-1(6H)-yl}acetic acid (52% yield).
Morphology: colorless solid
LC/MS: Condition 3, retention time 3.80 min
LC/MS (ESI$^+$):474 [M+1]$^+$
LC/MS (ESI$^-$):472 [M−1]$^-$

SYNTHETIC EXAMPLE 149

N-{5-Bromo-6-oxo-1-[2-oxo-2-(pyridin-4-ylmethylamino)ethyl]-1,6-dihydropyridazin-4-yl}adamantanecarboxamide

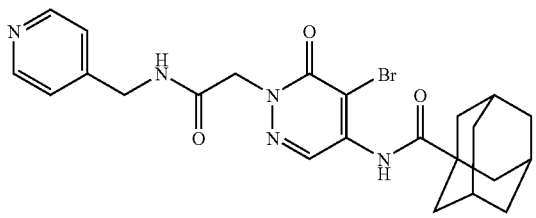 [SMILES: O=C(Cn1ncc(NC(=O)C23CC4CC(CC(C4)C2)C3)c(Br)c1=O)NCc1ccncc1]

Ethyl 2-[5-bromo-4-(4-ethoxy-3-methoxybenzylamino)-6-oxopyridazin-1(6H)-yl]acetate

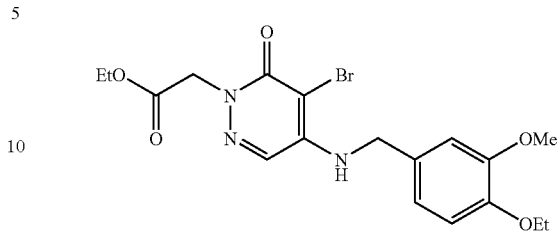

Ethyl 2-(4,5-dibromo-6-oxopyridazin-1(6H)-yl)acetate (500 mg, 1.47 mmol) and 3-ethoxy-4-methoxybenzylamine (960 mg, 4.41 mmol) in 1,4-dioxane-water (1:1, 5 mL) were stirred with triethylamine (0.615 mL) at 100° C. for 2.5 hours. After cooling, ethyl acetate was added, and the organic layer was washed with saturated aqueous ammonium chloride and saturated aqueous sodium chloride and dried over anhydrous magnesium sulfate, and the solvent was removed by distillation. The resulting residue was purified by silica gel chromatography (chloroform/2-propanol=20/1) to give the desired product (640 mg, 98% yield).
Morphology: pale yellow solid
LC/MS: Condition 3, retention time 3.70 min
LC/MS (ESI$^+$):440, 442 [M+1]$^+$
LC/MS (ESI$^-$):438, 440 [M−1]$^-$ Ethyl 2-(5-bromo-4-amino-6-oxopyridazin-1(6H)-yl)acetate

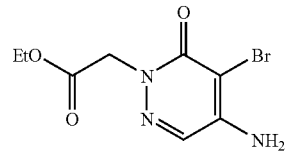 [SMILES: CCOC(=O)Cn1ncc(N)c(Br)c1=O]

Ethyl 2-[5-bromo-4-(4-ethoxy-3-methoxybenzylamino)-6-oxopyridazin-1(6H)-yl]acetate (570 mg, 1.29 mmol) in ethanol (11 mL) was stirred with concentrated hydrochloric acid (3.4 mL) at 90° C. for 4 hours. After cooling, the solvent was removed by distillation, and the residue was stirred with ethanol (10 mL) and 4 M hydrogen chloride-1,4-dioxane (1 mL) at 90° C. for 1 hour. After cooling, the solvent was removed by distillation. Toluene was added, and the resulting crystals were collected by filtration as the desired product (184 mg, 52% yield).
Morphology: light brown solid
LC/MS: Condition 3, retention time 3.70 min
LC/MS (ESI$^+$):276, 278 [M+1]$^+$
LC/MS (ESI$^-$):274, 276 [M−1]$^-$ 2-(5-Bromo-4-adamantanecarboxamido-6-oxopyridazin-1(6H)-yl)acetic Acid

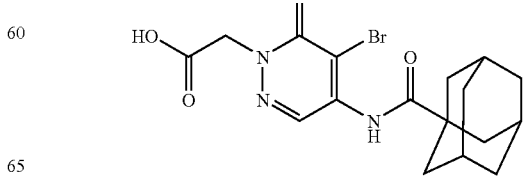

Ethyl 2-(5-bromo-4-amino-6-oxopyridazin-1(6H)-yl)acetate (100 mg, 0.362 mmol) in tetrahydrofuran (2 mL) was mixed with sodium hydride (58 mg, 1.46 mmol) and adamantanecarbonyl chloride (144 mg, 0.724 mmol) at room temperature and stirred at room temperature for 30 minutes. After completion of the reaction, the reaction solution was mixed with water and ethyl acetate and extracted with 1 M aqueous sodium hydroxide. The aqueous layer was acidified to pH 1 with 1 M hydrochloric acid and extracted with ethyl acetate. The extract was washed with saturated aqueous sodium chloride, dried over anhydrous sodium sulfate, and the solvent was removed by distillation to give the desired product.

Morphology: colorless solid
LC/MS: Condition 2, retention time 3.13 min
LC/MS (ESI$^+$):410, 412 [M+1]$^+$
LC/MS (ESI$^-$):408, 410 [M−1]$^-$ N-{5-Bromo-6-oxo-1-[2-oxo-2-(pyridin-4-ylmethylamino)ethyl]-1,6-dihydropyridazin-4-yl}adamantanecarboxamide Synthesis was carried out in the same manner as in Synthetic Example 1 by using 2-(5-bromo-4-adamantanecarboxamido-6-oxopyridazin-1(6H)-yl)acetic acid.

Morphology: colorless amorphous
LC/MS: Condition 2, retention time 2.20 min
LC/MS (ESI$^+$):500, 502 [M+1]$^+$
LC/MS (ESI$^-$):498, 500 [M−1]$^-$
$^1$H-NMR (CDCl$_3$)
δ: 1.50-2.00 (m, 10H), 2.00-2.20 (m, 5H), 4.47 (d, J=6.2 Hz, 2H), 4.93 (s, 2H), 6.69 (br t, J=6.2 Hz, 2H), 7.18 (d, J=4.5 Hz, 2H), 8.00 (s, 1H), 8.55 (d, J=4.5 Hz, 2H), 9.13 (s, 1H).

SYNTHETIC EXAMPLE 150

2-[5-Bromo-6-oxo-4-({[(1R,2R,3R,5S)-2,6,6-trimethylbicyclo[3.1.1]hept-3-yl]carbamoyl}amino)pyridazin-1(6H)-yl]-N-(pyridin-4-ylmethyl)acetamide

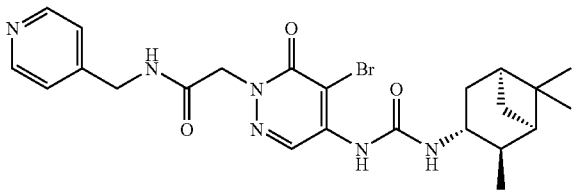 [SMILES: C[C@@H]1[C@H]2C[C@@H](C[C@H]1NC(=O)Nc1cnn(CC(=O)NCc3ccncc3)c(=O)c1Br)C2(C)C]

[5-Bromo-6-oxo-4-({[(1R,2R,3R,5S)-2,6,6-trimethylbicyclo[3.1.1]hept-3-yl]carbamoyl}amino)pyridazin-1(6H)-yl]acetic Acid

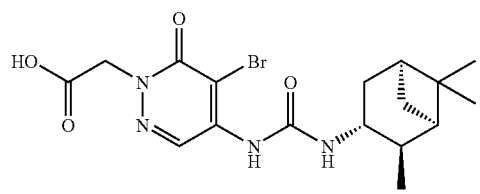 [SMILES: C[C@@H]1[C@H]2C[C@@H](C[C@H]1NC(=O)Nc1cnn(CC(=O)O)c(=O)c1Br)C2(C)C]

1,1-Carbonyldiimidazole (176 mg, 1.09 mmol) suspended in tetrahydrofuran (1 mL) was stirred with (1R,2R,3R,5S)-isopinocampheylamine (0.19 mL, 1.09 mmol) at room temperature for 1 hour. The reaction solution was added dropwise to ethyl 2-(5-bromo-4-amino-6-oxopyridazin-1(6H)-yl)acetate (100 mg, 0.362 mmol) and sodium hydride (58 mg, 1.45 mmol) in tetrahydrofuran, and the resulting reaction solution was stirred at room temperature for 2 hours. The reaction solution was mixed with 1 M aqueous sodium hydroxide and stirred at room temperature for 1 hour. The reaction solution was washed with diethyl ether, and the aqueous layer was acidified to pH 1 with 1 M hydrochloric acid and extracted with ethyl acetate. The extract was washed with saturated aqueous sodium chloride and dried over anhydrous magnesium sulfate, and the solvent was removed by distillation to give the desired product.

Morphology: colorless solid
LC/MS: Condition 2, retention time 3.13 min
LC/MS (ESI$^+$):427, 429 [M+1]$^+$
LC/MS (ESI$^-$):425, 427 [M−1]$^-$ 2-[5-bromo-6-oxo-4-({[(1R,2R,3R,5S)-2,6,6-trimethylbicyclo[3.1.1]hept-3-yl]carbamoyl}amino)pyridazin-1(6H)-yl]-N-(pyridin-4-ylmethyl)acetamide Synthesis was carried out in the same manner as in Synthetic Example 1 by using [5-bromo-6-oxo-4-({[(1R,2R,3R,5S)-2,6,6-trimethylbicyclo[3.1.1]hept-3-yl]carbamoyl}amino)pyridazin-1(6H)-yl]acetic acid.

Morphology: colorless amorphous
LC/MS: Condition 2, retention time 2.38 min
LC/MS (ESI$^+$):517, 519 [M+1]$^+$
LC/MS (ESI$^-$):515, 517 [M−1]$^-$
$^1$H-NMR (CDCl$_3$)
δ: 0.84 (d, J=9.9 Hz, 1H), 1.06 (s, 3H), 1.18 (d, J=4.8 Hz, 3H), 1.25 (s, 3H), 1.80-1.90 (m, 2H), 2.0 (br s, 1H), 2.40-2.50 (m, 1H), 2.70-2.80 (m, 1H), 4.10-4.20 (m, 1H), 4.45 (s, 2H), 4.95 (d, J=5.7 Hz, 2H), 6.80-6.90 (m, 1H), 7.26 (d, J=6.0 Hz, 2H), 8.36 (d, J=6.0 Hz, 2H), 9.00 (s, 1H).

SYNTHETIC EXAMPLE 151

2-{5-Ethylthio-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide

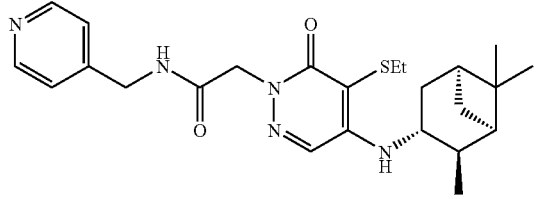 [SMILES: C[C@@H]1[C@H]2C[C@@H](C[C@H]1Nc1cnn(CC(=O)NCc3ccncc3)c(=O)c1-c1ccccc1)C2(C)C]

2-{5-Ethylthio-6-oxo-4-[(1R,2R,3R,5S)-2,6,6-trimethylbicyclo[3.1.1]hept-3-ylamino]pyridazin-1(6H)-yl}acetic Acid

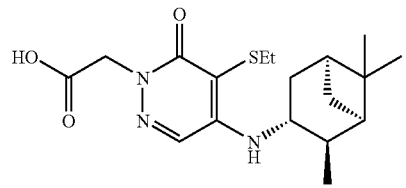

Synthesis was carried out in the same manner as in Synthetic Example 145 by using sodium thioethoxide (85% yield).

Morphology: brown amorphous
LC/MS: Condition 2, retention time 3.31 min
LC/MS (ESI$^+$):366 [M+1]$^+$
LC/MS (ESI$^-$):364 [M−1]$^-$ 2-{5-Ethylthio-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide

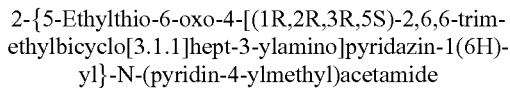

Synthesis was carried out in the same manner as in Synthetic Example 1 by using 2-{5-ethylthio-6-oxo-4-[(1R,2R,3R,5S)-2,6,6-trimethylbicyclo[3.1.1]hept-3-ylamino]pyridazin-1(6H)-yl}acetic acid. (78% yield)

Morphology: pale yellow amorphous
LC/MS: Condition 2, retention time 2.32 min
LC/MS (ESI$^+$):456 [M+1]$^+$
LC/MS (ESI$^-$):454 [M−1]$^-$

SYNTHETIC EXAMPLE 152

2-{5-Phenyl-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide

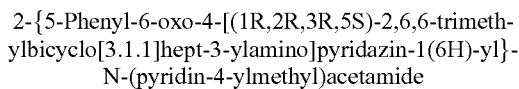

2-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide (50 mg, 0.105 mmol), phenylboronic acid (26 mg, 0.21 mmol) and tetrakistriphenylphosphinepalladium (13 mg, 0.011 mmol) in 2 M aqueous sodium carbonate-1-propanol (1:5, 2.4 mL) were stirred in a nitrogen stream at 100° C. overnight. After cooling, the reaction solution was concentrated, and the resulting residue was purified by silica gel chromatography (chloroform/methanol=20/1) to give the desired product (60 mg, 100% yield).

Morphology: pale yellow solid
LC/MS: Condition 2, retention time 2.37 min
LC/MS (ESI$^+$):472 [M+1]$^+$
LC/MS (ESI$^-$):470 [M−1]$^-$
$^1$H-NMR (CDCl$_3$)
δ: 0.74 (d, J=9.9 Hz, 1H), 1.02 (s, 3H), 1.13 (d, J=7.5 Hz, 3H), 1.21 (s, 3H), 1.60-1.70 (m, 1H), 1.80-1.85 (m, 1H), 1.95-2.05 (m, 1H), 2.30-2.40 (m, 1H), 2.50-2.60 (m, 1H), 3.75-3.90 (m, 1H), 4.34 (d, J=8.4 Hz, 1H), 4.44 (d, J=6.3 Hz, 2H), 4.87 (s, 2H), 7.13 (d, J=6.3 Hz, 2H), 7.30-7.60 (m, 5H), 7.77 (s, 1H), 8.51 (d, J=6.3 Hz, 2H).

SYNTHETIC EXAMPLE 153

2-{5-Cyclopropyl-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide

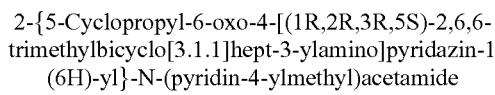

2-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide (62 mg, 0.131 mmol), cyclopropylboronic acid (45 mg, 0.524 mmol), [1,1′-bis(diphenylphosphino)ferrocene]dichloropalladium (II) (13 mg, 0.013 mmol) and potassium carbonate (72 mg, 0.524 mmol) in 1,4-dioxane-water (9/1, 0.7 mL) were stirred in a nitrogen stream at 100° C. for 6 hours. After cooling the reaction solution was concentrated, and the resulting residue was purified by silica gel chromatography (chloroform/methanol=8/1) to give the desired product (42 mg, 74% yield).

Morphology: light brown solid
LC/MS: Condition 2, retention time 2.20 min
LC/MS (ESI$^+$):436 [M+1]$^+$
LC/MS (ESI$^-$):434 [M−1]$^-$

SYNTHETIC EXAMPLE 154

2-{5-Methyl-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide

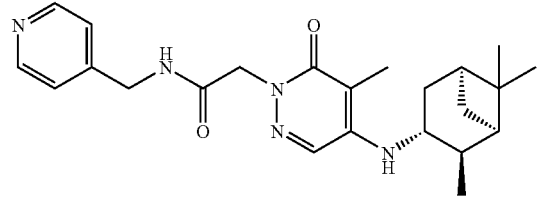 [SMILES: Cc1c(N[C@@H]2C[C@@H]3C[C@H]([C@H]2C)C3(C)C)cnn(CC(=O)NCc2ccncc2)c1=O]

Synthesis was carried out in the same manner as in Synthetic Example 153 by using trimethylboroxine (95% yield).

Morphology: pale gray amorphous
LC/MS: Condition 2, retention time 2.10 min
LC/MS (ESI$^+$):410 [M+1]$^+$
LC/MS (ESI$^-$):408 [M−1]$^-$

SYNTHETIC EXAMPLE 155

4-Bromo-2-[4-(pyridin-4-yl)butyl]-5-[(1R,2R,3R,5S)-2,6,6-trimethylbicyclo[3.1.1]hept-3-ylamino]pyridazin-3(2H)-one

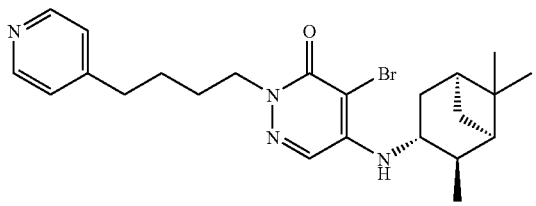 [SMILES: C[C@@H]1[C@H]2C[C@@H](C[C@H]1Nc1cnn(CCCCc3ccncc3)c(=O)c1Br)C2(C)C]

4-Bromo-5-[(1R,2R,3R,5S)-2,6,6-trimethylbicyclo[3.1.1]hept-3-ylamino]pyridazin-3(2H)-one (221 mg, 0.677 mmol) in N,N-dimethylformamide (4 mL) was mixed with 4-(4-chlorobutyl)pyridine hydrochloride (278 mg, 1.35 mmol) and potassium carbonate (375 mg, 2.71 mmol) at room temperature and stirred at 80° C. for 6.5 hours. After cooling, ethyl acetate was added, and the organic layer was washed with saturated aqueous ammonium chloride, dried over anhydrous magnesium sulfate and evaporated under reduced pressure. The resulting residue was purified by silica gel chromatography (chloroform/methanol=50/1) to give the desired product (38 mg, 12% yield).

Morphology: pale yellow oil
LC/MS: Condition 2, retention time 2.37 min
LC/MS (ESI+):459, 461 [M+1]+
LC/MS (ESI−):457, 459 [M−1]−
$^1$H-NMR (CDCl$_3$)
δ: 0.98 (d, J=10.2 Hz, 1H), 1.05 (s, 3H), 1.19 (d, J=6.9 Hz, 3H), 1.26 (s, 3H), 1.66-1.76 (m, 3H), 1.79-1.88 (m, 2H), 1.90-1.97 (m, 2H), 2.46-2.50 (m, 1H), 2.58-2.68 (m, 1H), 2.66 (t, J=7.2 Hz, 2H), 3.80-3.89 (m, 1H), 4.11 (t, J=6.9 Hz, 2H), 4.67 (d, J=8.4 Hz, 1H), 7.11 (d, J=6.0 Hz, 2H), 7.50 (s, 1H), 8.47 (d, J=6.0 Hz, 2H).

SYNTHETIC EXAMPLE 156

2-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)ethanethioamide

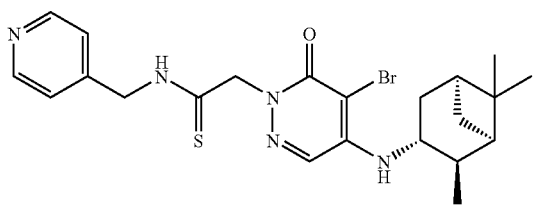 [SMILES: C[C@@H]1[C@H]2C[C@@H](C[C@H]1Nc1cnn(CC(=S)NCc3ccncc3)c(=O)c1Br)C2(C)C]

2-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide (99 mg, 0.208 mmol) in toluene (1 mL) was mixed with Lawesson's reagent (168 mg, 0.416 mmol) and refluxed at 120° C. for 1 hour. After cooling, the reaction solution was evaporated under reduced pressure. The resulting residue was purified by silica gel chromatography (chloroform/methanol=50/1) to give the desired product (28 mg, 27% yield).

Morphology: orange solid
LC/MS: Condition 2, retention time 2.40 min
LC/MS (ESI+):490, 492 [M+1]+
LC/MS (ESI−):488, 490 [M−1]−
$^1$H-NMR (CDCl$_3$)
δ: 0.97 (d, J=10.2 Hz, 1H), 1.05 (s, 3H), 1.19 (d, J=6.9 Hz, 3H), 1.29 (s, 3H), 1.69-1.77 (m, 1H), 1.92-1.98 (m, 1H), 2.00-2.07 (m, 1H), 2.47-2.53 (m, 1H), 2.60-2.69 (m, 1H), 3.82-3.95 (m, 1H), 4.85 (d, J=5.7 Hz, 1H+2H), 5.29 (s, 2H), 7.17 (d, J=6.0 Hz, 2H), 7.64 (s, 1H), 8.53 (d, J=6.0 Hz, 2H), 9.87 (s, 1H).

SYNTHETIC EXAMPLE 157

4-Bromo-2-{[1-(pyridin-4-ylmethyl)-1H-tetrazol-5-yl]methyl}-5-[(1R,2R,3R,5S)-2,6,6-trimethylbicyclo[3.1.1]hept-3-ylamino]pyridazin-3(2H)-one

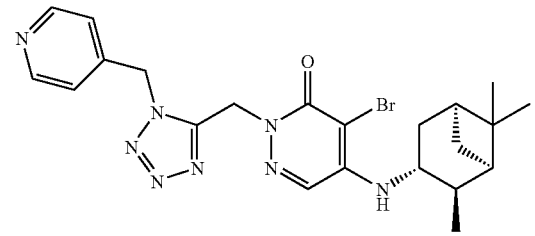 [SMILES: C[C@@H]1[C@H]2C[C@@H](C[C@H]1Nc1cnn(Cc3nnnn3Cc3ccncc3)c(=O)c1Br)C2(C)C]

2-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)ethanethioamide (38 mg, 0.077 mmol) in dichloromethane (1 mL) was mixed with azidotrimethylsilane (41 µL, 0.308 mmol) and iron trichloride (30 mg, 0.185 mmol) at room temperature and stirred at room temperature for 17 hours. After completion of the reaction, ethyl acetate was added, and the organic layer was washed with saturated aqueous sodium hydrogen carbonate, dried over anhydrous magnesium sulfate and evaporated under reduced pressure. The resulting residue was purified by silica gel chromatography (chloroform/methanol=50/1) to give the desired product (9 mg, 24% yield).

Morphology: orange solid
LC/MS: Condition 3, retention time 4.02 min
LC/MS (ESI+):499, 501 [M+1]+
LC/MS (ESI−):497, 499 [M−1]−
$^1$H-NMR (CDCl$_3$)
δ: 0.95 (d, J=10.2 Hz, 1H), 1.03 (s, 3H), 1.17 (d, J=7.2 Hz, 3H), 1.27 (s, 3H), 1.64-1.71 (m, 1H), 1.86-1.94 (m, 1H), 2.00-2.07 (m, 1H), 2.45-2.53 (m, 1H), 2.53-2.62 (m, 1H), 3.74-3.80 (m, 1H), 4.73 (d, J=7.5 Hz, 1H), 5.55 (s, 2H), 5.88 (s, 2H), 6.99 (d, J=6.0 Hz, 2H), 7.45 (s, 1H), 8.53 (d, J=6.0 Hz, 2H).

SYNTHETIC EXAMPLE 158

4-[(2-{5-Bromo-6-oxo-4-[(1R,2R,3R,5S)-2,6,6-trimethylbicyclo[3.1.1]hept-3-ylamino]pyridazin-1(6H)-yl}acetamido)methyl]pyridine 1-oxide

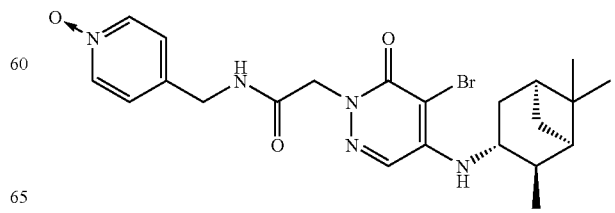

2-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)acetamide (50 mg, 0.105 mmol) and m-chloroperbenzoic acid (35 mg, 0.112 mmol) suspended in tetrahydrofuran (1.5 mL) were stirred at room temperature for 5 minutes and at 80° C. for 30 minutes. After cooling, the reaction solution was concentrated, and the resulting residue was purified by silica gel chromatography (chloroform/methanol=5/1) to give the desired product (49 mg, 95% yield).
Morphology: pale yellow solid
LC/MS: Condition 2, retention time 2.70 min
LC/MS (ESI$^+$):490, 492 [M+1]$^+$
LC/MS (ESI$^-$):488, 490 [M−1]$^-$

SYNTHETIC EXAMPLE 159

4-Bromo-2-{2-[4-(diethylamino)phenyl]-2-(methoxyimino)ethyl}-5-[(1R,2R,3R,5S)-2,6,6-trimethylbicyclo[3.1.1]hept-3-ylamino]pyridazin-3(2H)-one

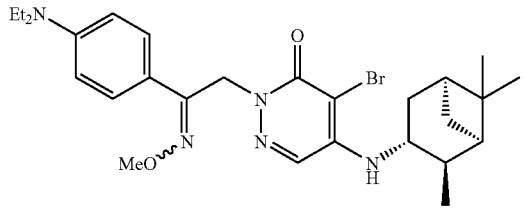

4-Bromo-2-{2-[4-(diethylamino)phenyl]-2-oxoethyl}-5-[(1R,2R,3R,5S)-2,6,6-trimethylbicyclo[3.1.1]hept-3-ylamino]pyridazin-3(2H)-one (50 mg, 0.097 mmol) and methoxamine hydrochloride (41 mg, 0.485 mmol) in ethanol (0.5 mL) were stirred at 80° C. for 1 hour. After cooling, ethyl acetate was added, and the organic layer was washed with saturated aqueous ammonium chloride and saturated aqueous sodium chloride and dried over anhydrous sodium sulfate. The solvent was removed by distillation. The resulting residue was purified by silica gel chromatography (hexane/ethyl acetate=3/1) to give the desired product (56 mg, 100% yield).
Morphology: pale yellow amorphous
LC/MS: Condition 2, retention time 3.99 min
LC/MS (ESI$^+$):544, 546 [M+1]$^+$
LC/MS (ESI$^-$):542, 544 [M−1]$^-$

SYNTHETIC EXAMPLE 160

4-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)benzamide

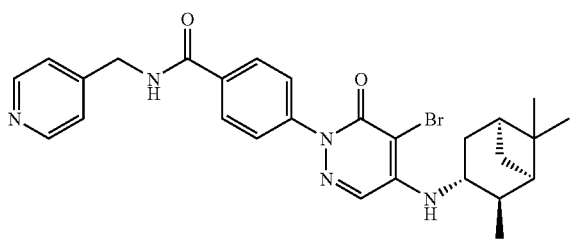 [SMILES: C[C@@H]1[C@H]2C[C@@H](C[C@H]1Nc1cnn(-c3ccc(C(=O)NCc4ccncc4)cc3)c(=O)c1Br)C2(C)C]

4-(4,5-Dibromo-6-oxopyridazin-1(6H)-yl)benzoic Acid

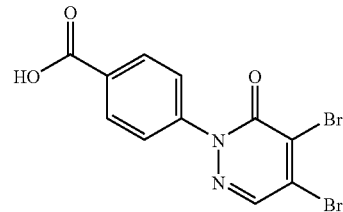

4-Hydrazinobenzoic acid (2.00 g, 13.1 mmol) in ethanol-water (1:1, 20 mL) was stirred with mucobromic acid (2.26 g, 8.76 mmol) and concentrated hydrochloric acid (10 mL) at 70° C. for 2 days. After cooling, the resulting crystals were collected by filtration, washed with ethanol and water and dried under reduced pressure to give the desired product (3.05 g, 62% yield).
Morphology: pale yellow solid
LC/MS: Condition 2, retention time 2.60 min
LC/MS (ESI$^+$):373, 375, 377 [M+1]$^+$
LC/MS (ESI$^-$):371, 373, 375 [M−1]$^-$ 4-{5-Bromo-6-oxo-4-[(1R,2R,3R,5S)-2,6,6-trimethylbicyclo[3.1.1]hept-3-ylamino]pyridazin-1(6H)-yl}benzoic Acid

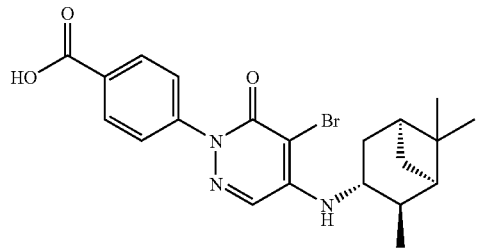 [SMILES: C[C@@H]1[C@H]2C[C@@H](C[C@H]1Nc1cnn(-c3ccc(C(=O)O)cc3)c(=O)c1Br)C2(C)C]

Synthesis was carried out in the same manner as in Synthetic Example 1 by using 4-(4,5-dibromo-6-oxopyridazin-1(6H)-yl)benzoic acid (35% yield).
Morphology: pale yellow amorphous
LC/MS: Condition 2, retention time 3.55 min
LC/MS (ESI$^+$):446, 448 [M+1]$^+$
LC/MS (ESI$^-$):444, 446 [M−1]$^-$ 4-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)benzamide Synthesis was carried out in the same manner as in Synthetic. Example 1 by using 4-{5-bromo-6-oxo-4-[(1R,2R,3R,5S)-2,6,6-trimethylbicyclo[3.1.1]hept-3-ylamino]pyridazin-1(6H)-yl}benzoic acid (54% yield).
Morphology: colorless solid
LC/MS: Condition 2, retention time 2.42 min
LC/MS (ESI$^+$):536, 538 [M+1]$^+$
LC/MS (ESI$^-$):534, 536 [M−1]$^-$
$^1$H-NMR (CDCl$_3$)
δ: 1.00 (d, J=10.0 Hz, 1H), 1.08 (s, 3H), 1.22 (d, J=7.0 Hz, 3H), 1.29 (s, 3H), 1.75-1.82 (m, 1H), 1.90-2.02 (m, 2H), 2.03-2.10 (m, 1H), 2.45-2.55 (m, 1H), 2.60-2.75 (m, 1H), 3.85-4.00 (m, 1H), 4.67 (d, J=6.0 Hz, 2H), 4.85 (d, J=9.0 Hz, 1H), 6.74-6.84 (br d, J=4.0 Hz, 1H), 7.24 (s, 1H), 7.70 (s, 1H), 7.73 (d, J=8.0 Hz, 2H), 7.90 (d, J=8.0 Hz, 2H), 8.56 (d, J=6.0 Hz, 2H).

SYNTHETIC EXAMPLE 161

4-Bromo-2-[(4-(pyrrolidine-1-carbonyl)phenyl]-5-[(1R,2R,3R,5S)-2,6,6-trimethylbicyclo[3.1.1]hept-3-ylamino]pyridazin-3(2H)-one

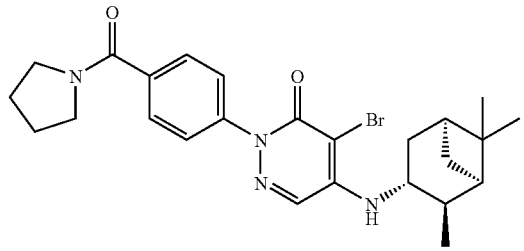 [SMILES: C[C@@H]1[C@H]2C[C@@H](C[C@H]1Nc1cnn(-c3ccc(C(=O)N4CCCC4)cc3)c(=O)c1Br)C2(C)C]

4-{5-Bromo-6-oxo-4-[(1R,2R,3R,5S)-2,6,6-trimethylbicyclo[3.1.1]hept-3-ylamino]pyridazin-1(6H)-yl}benzoic acid (30 mg, 0.067 mmol), pyrrolidine (8.3 µL, 0.10 mmol), 1-hydroxybenzotriazole anhydride (0.9 mg, 0.007 mmol) in dichloromethane (0.6 mL) was stirred with 1-(3-dimethylaminopropyl)-3-ethylcarbodiimide hydrochloride (16 mg, 0.080 mmol) at room temperature for 22 hours. After completion of the reaction, the solvent was removed by vacuum distillation, and the resulting residue was purified by silica gel chromatography (ethyl acetate) to give the desired product (35 mg, quant.).

Morphology: colorless solid
LC/MS: Condition 2, retention time 3.57 min
LC/MS (ESI$^+$):499, 501 [M+1]$^+$
LC/MS (ESI$^-$):497, 499 [M−1]$^-$
$^1$H-NMR (CDCl$_3$)
δ: 1.00 (d, J=11.0 Hz, 1H), 1.08 (s, 3H), 1.22 (d, J=7.0 Hz, 3H), 1.29 (s, 3H), 1.75-1.82 (m, 1H), 1.85-2.02 (m, 6H), 2.03-2.09 (m, 1H), 2.45-2.55 (m, 1H), 2.63-2.73 (m, 1H), 3.47 (t, J=7.0 Hz, 2H), 3.66 (t, J=7.0 Hz, 2H), 3.87-3.98 (m, 1H), 4.83 (d, J=8.0 Hz, 1H), 7.57-7.78 (m, 5H).

SYNTHETIC EXAMPLE 162

3-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)benzamide

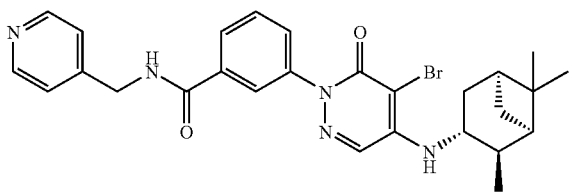 [SMILES: C[C@@H]1[C@H]2C[C@@H](C[C@H]1Nc1cnn(-c3cccc(C(=O)NCc4ccncc4)c3)c(=O)c1Br)C2(C)C]

3-(4,5-Dibromo-6-oxopyridazin-1(6H)-yl)benzoic Acid

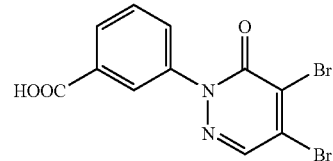 [SMILES: O=C(O)c1cccc(-n2ncc(Br)c(Br)c2=O)c1]

Synthesis was carried out in the same manner as in Synthetic Example 160 by using 3-hydrazinobenzoic acid.

Morphology: pale yellow amorphous
LC/MS: Condition 2, retention time 2.59 min
LC/MS (ESI$^+$):373, 375, 377 [M+1]$^+$
LC/MS (ESI$^-$):371, 373, 375 [M−1]$^-$ 3-{5-Bromo-6-oxo-4-[(1R,2R,3R,5S)-2,6,6-trimethylbicyclo[3.1.1]hept-3-ylamino]pyridazin-1(6H)-yl}benzoic Acid

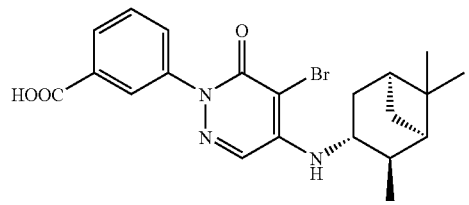 [SMILES: C[C@@H]1[C@H]2C[C@@H](C[C@H]1Nc1cnn(-c3cccc(C(=O)O)c3)c(=O)c1Br)C2(C)C]

Synthesis was carried out in the same manner as in Synthetic Example 160 by using 3-(4,5-dibromo-6-oxopyridazin-1(6H)-yl)benzoic acid (35% yield).

Morphology: colorless amorphous
LC/MS: Condition 2, retention time 3.54 min
LC/MS (ESI$^+$):446, 448 [M+1]$^+$
LC/MS (ESI$^-$):444, 446 [M−1]$^-$ 3-{5-Bromo-6-oxo-4-[(1R,2R,3R,5S)-2,6,6-trimethylbicyclo[3.1.1]hept-3-ylamino]pyridazin-1(6H)-yl}-N-(pyridin-4-ylmethyl)benzamide Synthesis was carried out in the same manner as in Synthetic Example 1 by using 3-{5-Bromo-6-oxo-4-[(1R,2R,3R,5S)-2,6,6-trimethylbicyclo[3.1.1]hept-3-ylamino]pyridazin-1(6H)-yl}benzoic acid (84% yield).

Morphology: colorless amorphous
LC/MS: Condition 2, retention time 2.43 min
LC/MS (ESI$^+$):536, 538 [M+1]$^+$
LC/MS (ESI$^-$):534, 536 [M−1]$^-$
$^1$H-NMR (CDCl$_3$)
δ: 1.00 (d, J=10.5 Hz, 1H), 1.08 (s, 3H), 1.22 (d, J=7.0 Hz, 3H), 1.29 (s, 3H), 1.73-1.82 (m, 1H), 1.89-2.02 (m, 2H), 2.04-2.08 (m, 1H), 2.47-2.55 (m, 1H), 2.63-2.72 (m, 1H), 3.89-3.99 (m, 1H), 4.63 (d, J=6.0 Hz, 2H), 4.86 (d, J=8.0 Hz, 1H), 7.19-7.25 (m, 2H), 7.48-7.55 (m, 1H), 7.68-7.74 (m, 2H), 7.84-7.88 (m, 1H), 8.06 (d, J=1.0 Hz, 1H), 8.51-8.55 (m, 2H).

SYNTHETIC EXAMPLE 163

4-Bromo-2-[3-(pyrrolidine-1-carbonyl)phenyl]-5-[(1R,2R,3R,5S)-2,6,6-trimethylbicyclo[3.1.1]hept-3-ylamino]pyridazin-3(2H)-one

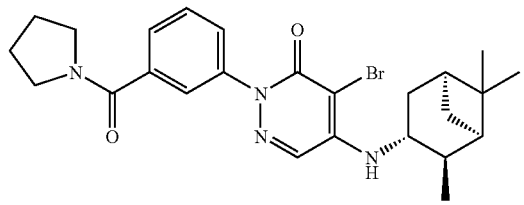 [SMILES: C[C@@H]1[C@H]2C[C@@H](C[C@H]1Nc1cnn(-c3cccc(C(=O)N4CCCC4)c3)c(=O)c1Br)C2(C)C]

Synthesis was carried out in the same manner as in Synthetic Example 161 by using 3-{5-bromo-6-oxo-4-[(1R,2R,3R,5S)-2,6,6-trimethylbicyclo[3.1.1]hept-3-ylamino]pyridazin-1(6H)-yl}benzoic acid (87% yield).
Morphology: colorless solid
LC/MS: Condition 2, retention time 3.59 min
LC/MS (ESI$^+$):499, 501 [M+1]$^+$
LC/MS (ESI$^-$):497, 499 [M−1]$^-$
$^1$H-NMR (CDCl$_3$)
δ: 1.00 (d, J=10.5 Hz, 1H), 1.07 (s, 3H), 1.22 (d, J=7.0 Hz, 3H), 1.29 (s, 3H), 1.75-1.82 (m, 1H), 1.86-2.01 (m, 6H), 2.02-2.10 (m, 1H), 2.47-2.55 (m, 1H), 2.63-2.73 (m, 1H), 3.52 (t, J=6.0 Hz, 2H), 3.64 (t, J=6.0 Hz, 2H) 3.88-3.94 (m, 1H), 4.83 (d, J=8.0 Hz, 1H), 7.46-7.55 (m, 2H), 7.62-7.67 (m, 1H) 7.69 (s, 1H), 7.84 (s, 1H).

SYNTHETIC EXAMPLE 164

4-Bromo-2-[2-oxo-2-(piperazin-1-yl)ethyl]-5-[(1R,2R,3R,5S)-2,6,6-trimethylbicyclo[3.1.1]hept-3-ylamino]pyridazin-3(2H)-one 2,2,2-trifluoroacetate

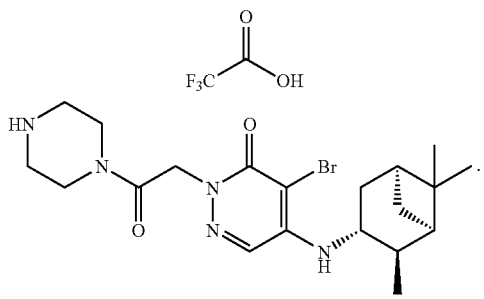

Synthesis was carried out in the same manner as in Synthetic Example 132 by using t-butyl 4-(2-{5-bromo-6-oxo-5-[(1R,2R,3R,5S)-2,6,6-trimethylbicyclo[3.1.1]hept-3-ylamino]pyridazin-1(6H)-yl}acetyl)piperazine-1-carboxylate (83% yield).
Morphology: pale yellow solid.
LC/MS: Condition 3, retention time 3.70 min
LC/MS (ESI$^+$):452, 454 [M+1]$^+$

SYNTHETIC EXAMPLE 165

4-Chloro-2-(2-{[1-(pyridin-4-yl)propyl]amino}ethyl)-5-[(1R,2R,3R,5S)-2,6,6-trimethylbicyclo[3.1.1]hept-3-ylamino]pyridazin-3(2H)-one

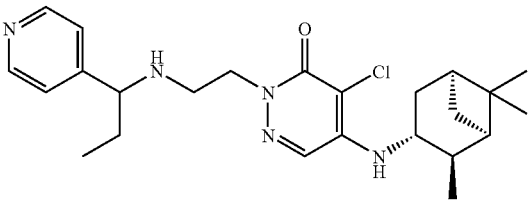 [SMILES: CCC(NCCn1ncc(N[C@@H]2C[C@@H]3C[C@H]([C@H]2C)C3(C)C)c(Cl)c1=O)c1ccncc1]

2-(5-Chloro-6-oxo-4-{[(1R,2R,3R,5S)-2,6,6-trimethylbicyclo[3.1.1]hept-3-yl]amino}pyridazin-1(6H)-yl)-N-(pyridin-4-ylmethyl)acetamide (40 mg, 0.0873 mmol) was added to lithium aluminum hydride (4.3 mg, 0.104 mmol) in tetrahydrofuran (1 mL) at 0° C., and the resulting reaction solution was stirred at room temperature for 1.5 hours. After completion of the reaction, the reaction solution was mixed with water, ethyl acetate and anhydrous magnesium sulfate and filtered, and the filtrate was evaporated under reduced pressure. The resulting residue was purified by preparative thin layer chromatography (chloroform/methanol=13/1) to give the desired product (9.5 mg, 25% yield).
Morphology: colorless amorphous
LC/MS: Condition 7, retention time 1.89 min
LC/MS (ESI$^+$):m/z; 444, 446 [M+1]$^+$
LC/MS (ESI$^-$):m/z; 442, 444 [M−1]$^-$
$^1$H-NMR (CDCl$_3$)
δ: 0.79 (t, J=7.4 Hz, 3H), 0.97 (d, J=9.9 Hz, 1H), 1.06 (s, 3H), 1.16-1.22 (m, 3H), 1.27 (s, 3H), 1.55-1.76 (m, 3H), 1.83-1.94 (m, 2H), 1.96-2.07 (m, 1H), 2.43-2.54 (m, 1H), 2.56-2.68 (m, 1H), 2.77-2.90 (m, 2H), 3.54 (t, J=6.6 Hz, 1H), 3.77-3.89 (m, 1H), 4.10-4.34 (m, 2H), 4.58 (d, J=8.1 Hz, 1H), 7.18 (d, J=5.7 Hz, 2H), 7.56 (s, 1H), 8.50 (d, J=5.7 Hz, 2H).

SYNTHETIC EXAMPLES 166 TO 222

Compounds were synthesized in the same manner as in Synthetic Example 1, and the yields and morphology of the resulting compounds, the LC/MS conditions used for their analysis and the observed peaks and retention times are shown in Table 18.

TABLE 18

| Synthetic Example No. | Yield (%) | Morphology | LC/MS Condition | Observed peak ESI$^+$ | Observed peak ESI$^-$ | Retention time (min) |
|---|---|---|---|---|---|---|
| 166 | 13 | Pale yellow amorphous | 2 | 488/490 | 486/488 | 2.27 |
| 167 | 58 | Pale yellow amorphous | 2 | 524/526 | 522/524 | 2.57 |
| 168 | 59 | Colorless solid | 2 | 491/493 | 489/491 | 3.09 |
| 169 | 16 | Yellow solid | 2 | 550/552 | 548/550 | 2.65 |

TABLE 18-continued

| Synthetic Example No. | Yield (%) | Morphology | LC/MS Condition | Observed peak ESI+ | Observed peak ESI− | Retention time (min) |
|---|---|---|---|---|---|---|
| 170 | 80 | Colorless solid | 7 | 488/490 | 486/488 | 3.19 |
| 171 | 100 | Colorless solid | 7 | 502/504 | 500/502 | 3.32 |
| 172 | 68 | Pale yellow solid | 7 | 503/505 | 501/503 | 3.92 |
| 173 | 21 | Pale yellow solid | 7 | 494/496 | 492/494 | 3.12 |
| 174 | 90 | Yellow solid | 7 | 508/510 | 506/508 | 4.17 |
| 175 | 31 | Colorless solid | 7 | 493/495 | 491/493 | 4.52 |
| 176 | 68 | Colorless solid | 7 | 555/557/559 | 553/555/557 | 4.22 |
| 177 | 38 | Colorless solid | 7 | 493/495 | 491/493 | 4.45 |
| 178 | 42 | Colorless solid | 7 | 505/507 | 503/505 | 4.54 |
| 179 | 97 | Yellow solid | 7 | 539/541 | 537/539 | 4.39 |
| 180 | 41 | Yellow solid | 7 | 477/479 | 475/477 | 4.12 |
| 181 | 23 | Colorless solid | 7 | 475/477 | 473/475 | 3.32 |
| 182 | 66 | Colorless solid | 7 | 559/561 | 557/559 | 4.67 |
| 183 | 63 | Pale yellow solid | 7 | 559/561 | 557/559 | 4.67 |
| 184 | 80 | Colorless solid | 7 | 500/502 | 498/500 | 4.34 |
| 185 | 16 | Yellow solid | 7 | 502/504 | 500/502 | 4.18 |
| 186 | 45 | Red solid | 7 | 492/494 | 490/492 | 4.54 |
| 187 | 95 | Colorless solid | 7 | 516/518 | 514/516 | 4.28 |
| 188 | 46 | Colorless solid | 7 | 465/467 | 463/465 | 4.68 |
| 189 | 29 | Colorless amorphous | 7 | 510/512 | 508/510 | 3.91 |
| 190 | 17 | Colorless solid | 7 | 498/500 | 496/498 | 4.88 |
| 191 | 7 | Colorless solid | 7 | 531/533 | 529/531 | 4.88 |
| 192 | 20 | Colorless solid | 7 | 507/509 | 505/507 | 4.94 |
| 193 | 4 | Colorless solid | 7 | 531/533 | 529/531 | 4.78 |
| 194 | 30 | Colorless solid | 7 | 503/505 | 501/503 | 4.78 |
| 195 | 25 | Colorless solid | 7 | 519/521 | 517/519 | 4.53 |
| 196 | 3 | Colorless solid | 7 | 518/520 | 516/518 | 4.81 |
| 197 | 45 | Colorless amorphous | 7 | 521/523 | 519/521 | 5.05 |
| 198 | 34 | Colorless solid | 7 | 566/568 | 564/566 | 4.86 |
| 199 | 20 | Colorless solid | 7 | 566/568 | 564/566 | 4.86 |
| 200 | 16 | Colorless solid | 7 | 580/582 | 578/580 | 5.03 |
| 201 | 8 | Colorless amorphous | 7 | 566/568 | 564/566 | 5.01 |
| 202 | 12 | Colorless solid | 7 | 413/415 | 411/413 | 4.38 |
| 203 | 39 | Colorless solid | 7 | 498/500 | 496/498 | 4.71 |
| 204 | 7 | Colorless solid | 7 | 473/475 | 471/473 | 4.81 |
| 205 | 14 | Colorless solid | 7 | 489/491 | 487/489 | 4.49 |
| 206 | 37 | Colorless solid | 7 | 439/441 | 437/439 | 4.45 |
| 207 | 16 | Colorless solid | 7 | 465/467 | 463/465 | 4.88 |
| 208 | 22 | Colorless solid | 7 | 479/481 | 477/479 | 5.05 |
| 209 | 31 | Colorless solid | 7 | 439/441 | 437/439 | 4.74 |
| 210 | 26 | Colorless solid | 7 | 437/439 | 435/437 | 4.65 |
| 211 | 100 | Colorless amorphous | 7 | 488/490 | 486/488 | 3.68 |
| 212 | 46 | Colorless amorphous | 7 | 492/494 | 490/492 | 4.66 |
| 213 | 100 | Pale yellow solid | 7 | 538/540 | 536/538 | 4.71 |
| 214 | 46 | Light brown amorphous | 7 | 475/477 | 473/475 | 4.28 |
| 215 | 6 | Colorless amorphous | 7 | 488/490 | 486/488 | 3.68 |
| 216 | 100 | Colorless solid | 3 | 504/506 | 502/504 | 3.63 |
| 217 | 91 | Colorless amorphous | 7 | 560/562 | 558/560 | 3.91 |
| 218 | 9 | Pale yellow oil | 7 | 560/562 | 558/560 | 3.60 |
| 219 | 43 | Pale yellow solid | 7 | 499/501 | 497/499 | 4.41 |
| 220 | 26 | Caramel amorphous | 7 | 489/491 | 487/489 | 4.10 |
| 221 | 72 | Colorless solid | 7 | 489/491 | 487/489 | 3.39 |
| 222 | 100 | Pale yellow solid | 7 | 492/494 | 490/492 | 4.58 |

The structures of the compounds obtained in these Synthetic Examples are shown below.
SYNTHETIC EXAMPLES 166 TO 192
166
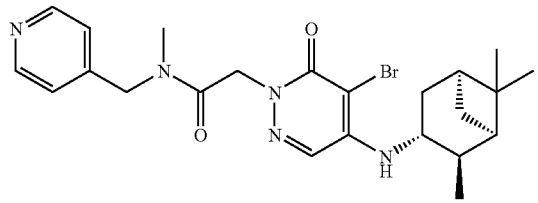
167
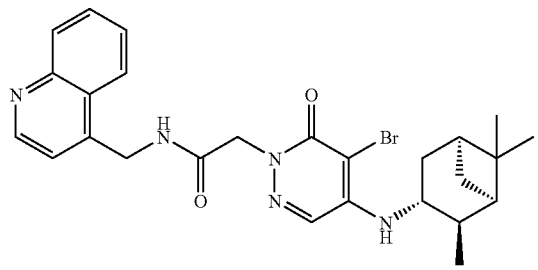
168
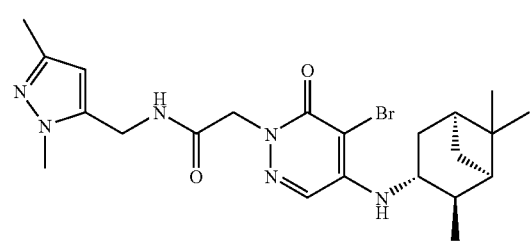
169
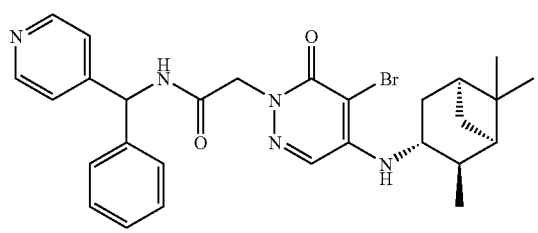
170
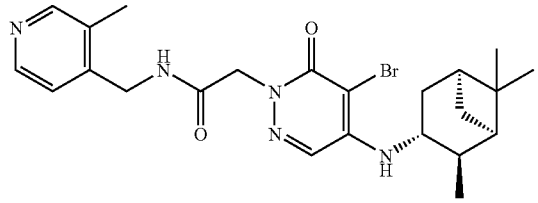
171
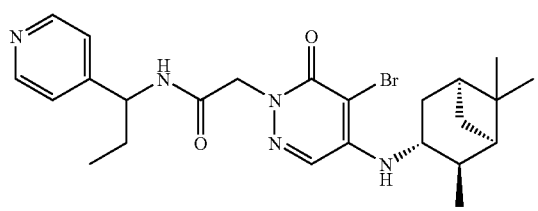
172
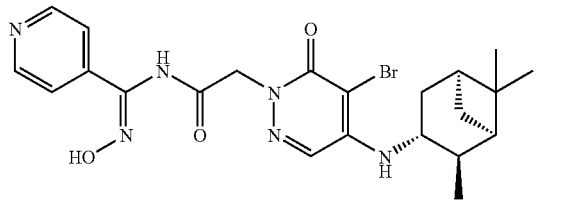
173
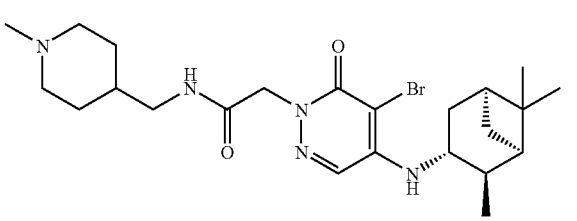
174
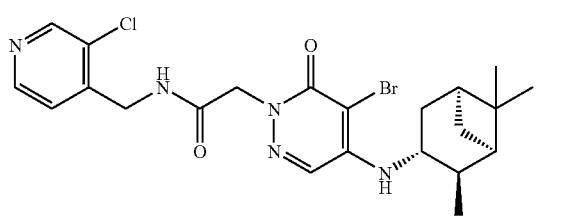
175
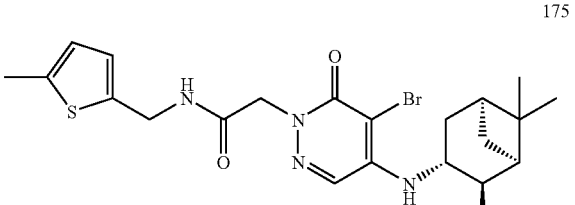
176
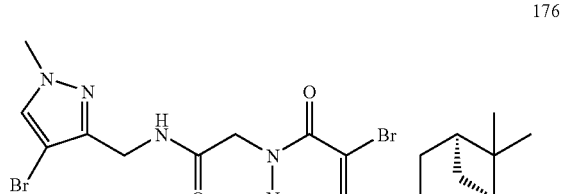
177
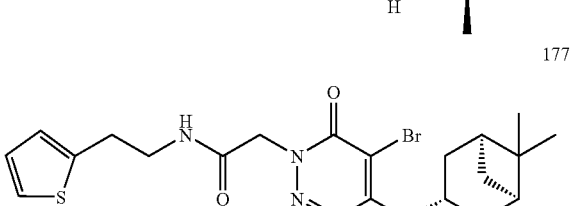
178
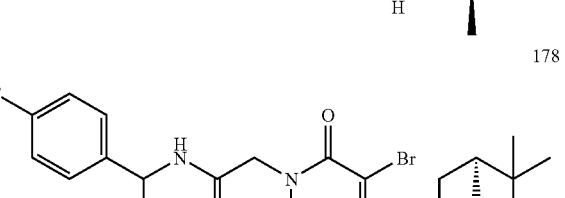

179
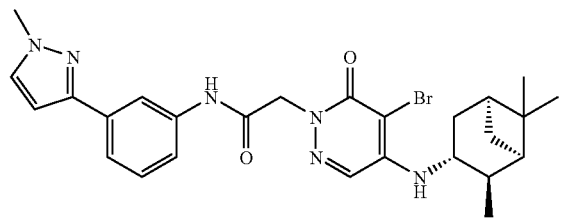
180
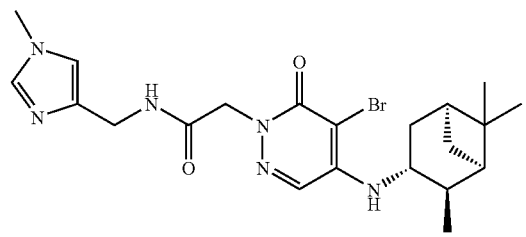
181
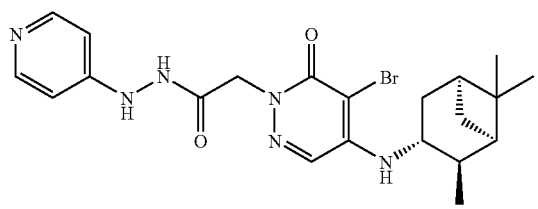
182
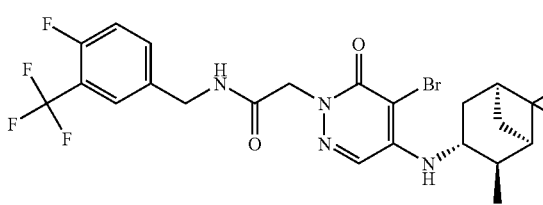
183
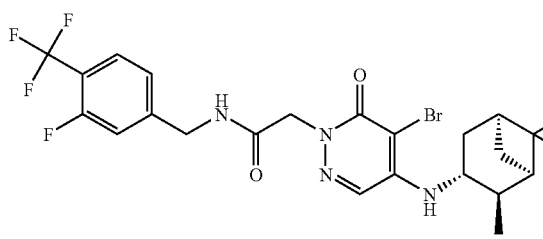
184
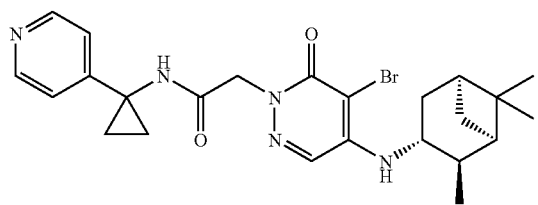
185
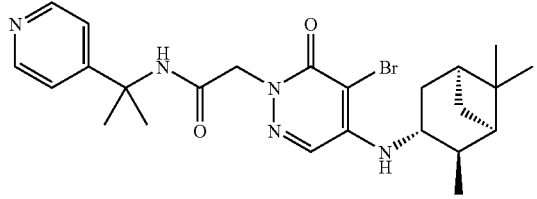
186
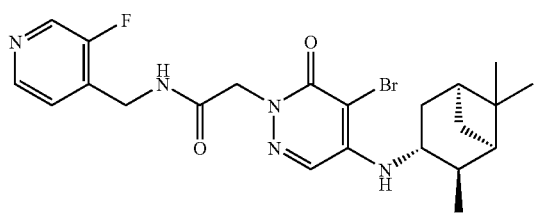
187
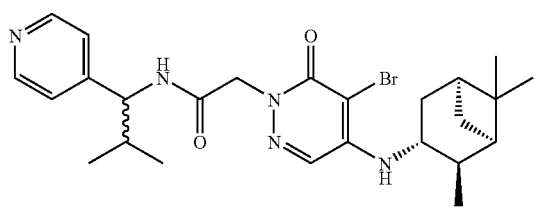
188
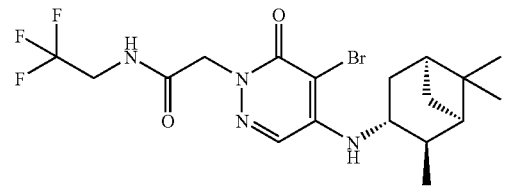
189
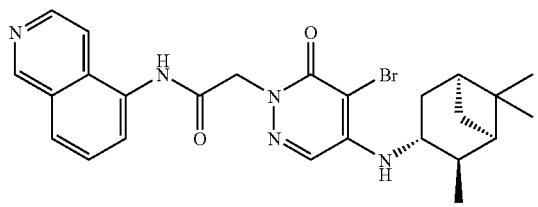
190
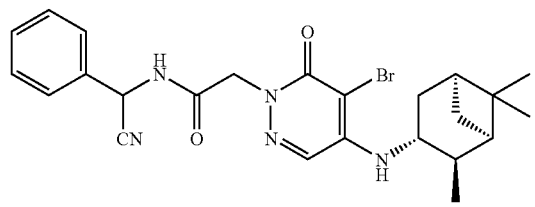
191
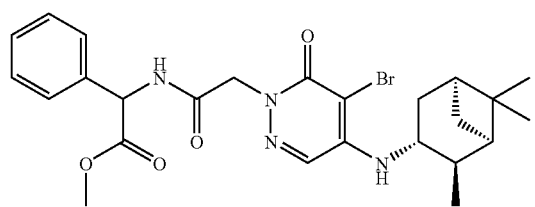

192
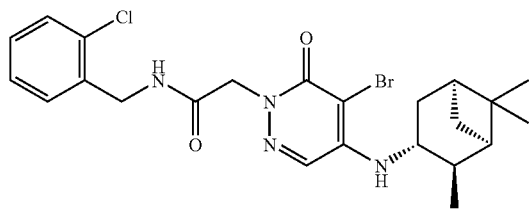
SYNTHETIC EXAMPLES 193 TO 222
193
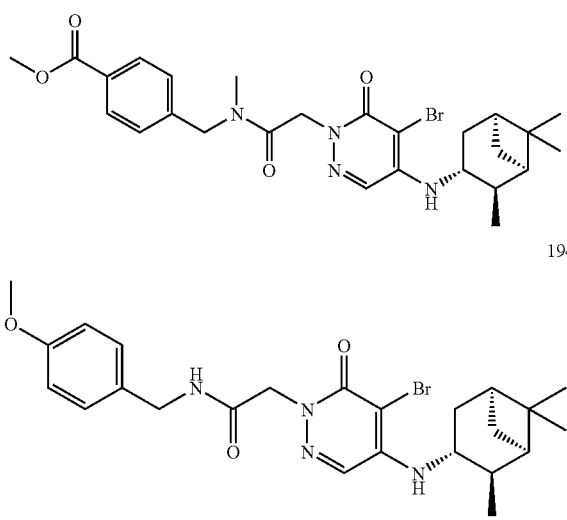
194
195
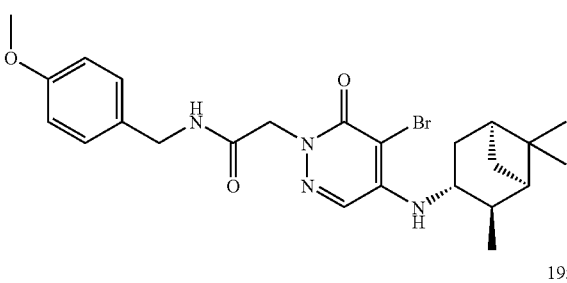
196
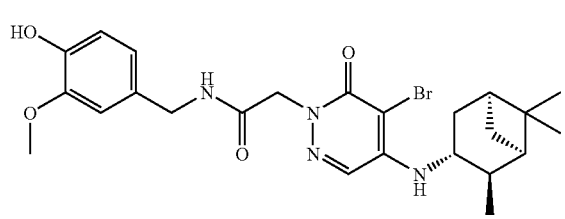
197
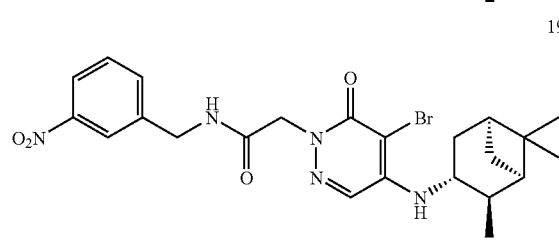
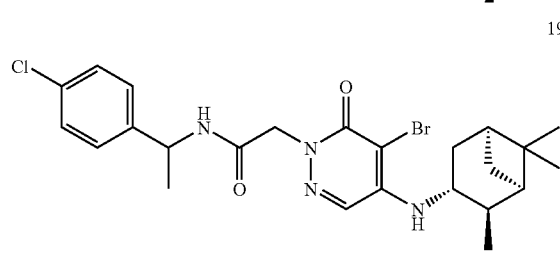
198
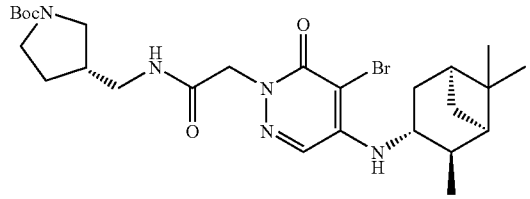
199
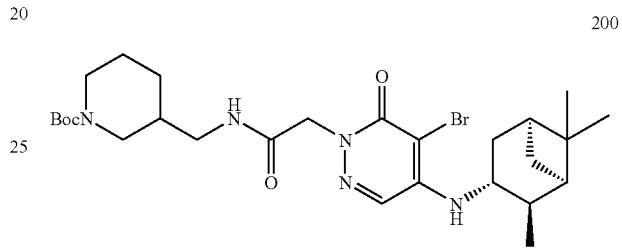
200
201
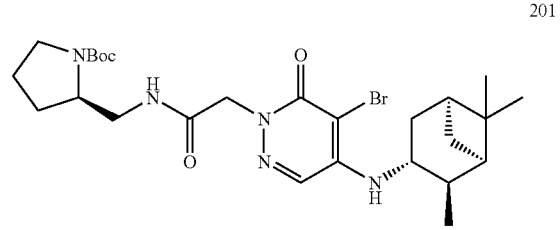
202
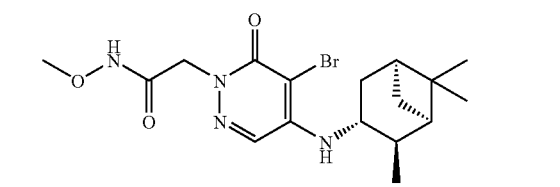
203
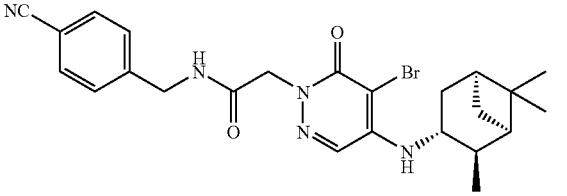
204
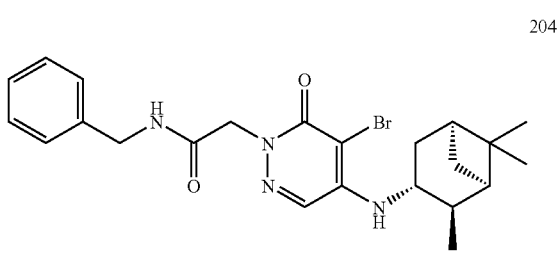

205
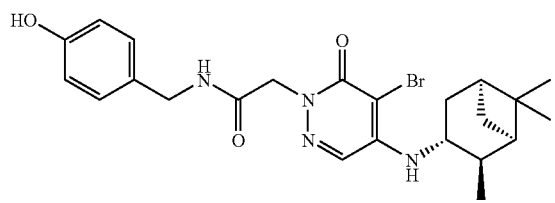
206
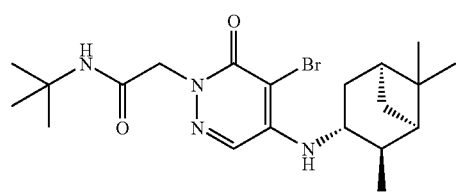
207
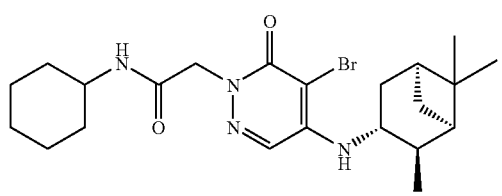
208
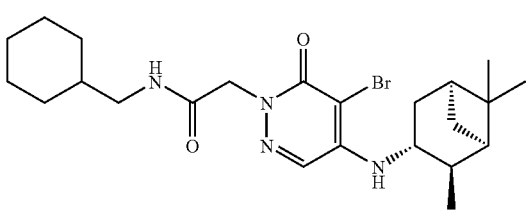
209
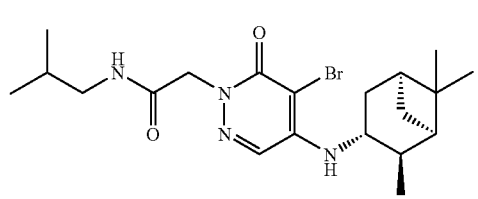
210
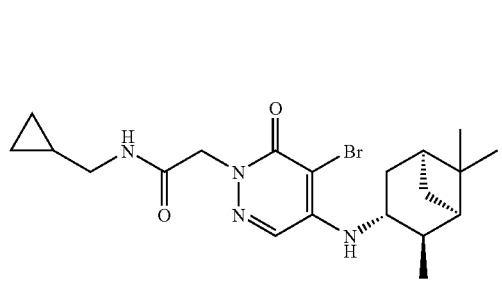
211
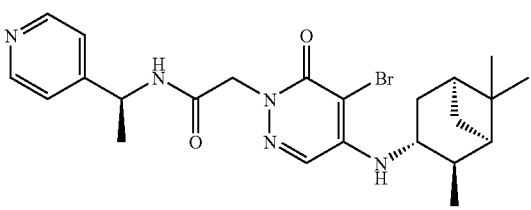
212
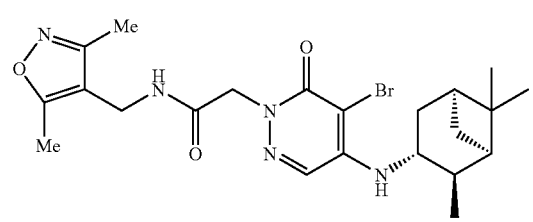
213
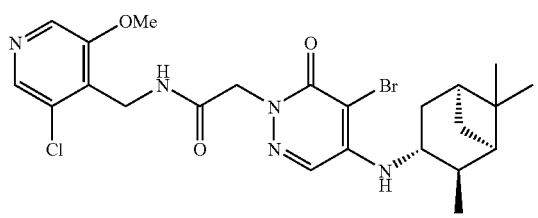
214
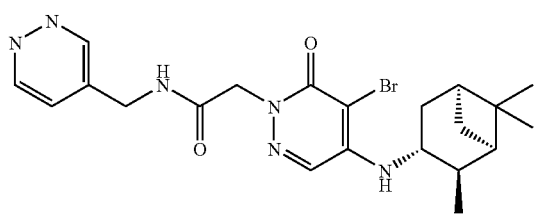
215
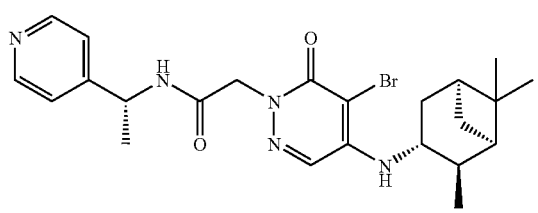
216
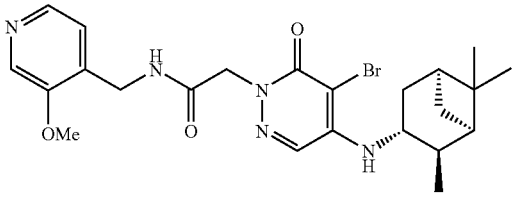
217
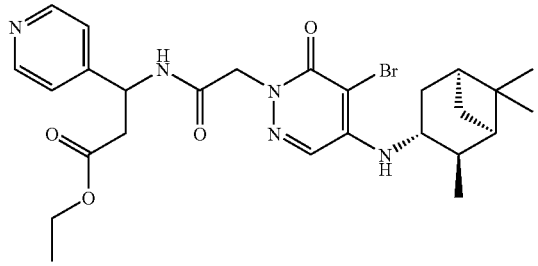

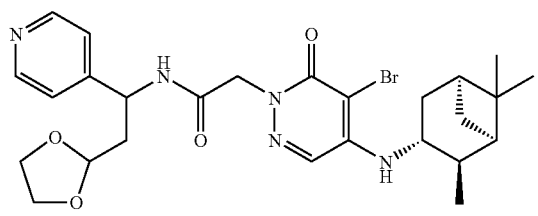

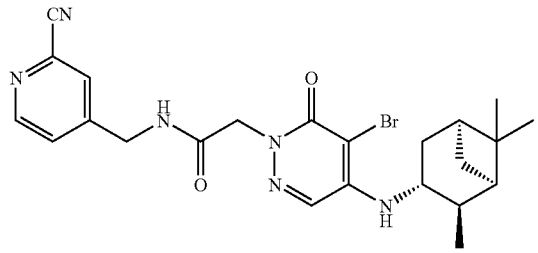

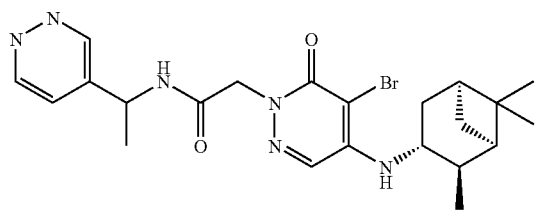

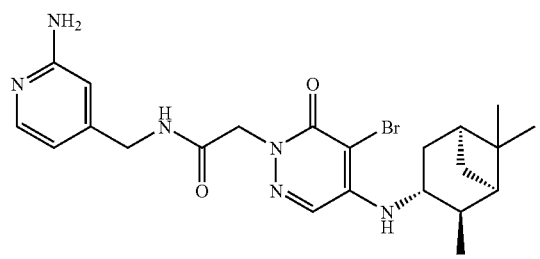

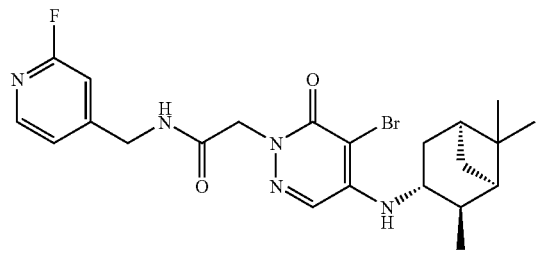

SYNTHETIC EXAMPLES 223 TO 294

Compounds were synthesized in the same manner as in Synthetic Example 1, and the yields and morphology of the resulting compounds, the LC/MS conditions used for their analysis and the observed peaks and retention times are shown in Table 19.

TABLE 19

| Synthetic Example No. | Yield (%) | Morphology | LC/MS Condition | Observed peak ESI+ | Observed peak ESI− | Retention time (min) |
| --- | --- | --- | --- | --- | --- | --- |
| 223 | 73 | Colorless solid | 7 | 458/460 | 456/458 | 3.27 |
| 224 | 51 | Colorless solid | 7 | 444/446 | 442/444 | 3.13 |
| 225 | 31 | Colorless oil | 7 | 416/418 | 414/416 | 3.58 |
| 226 | 82 | Colorless solid | 7 | 499/501 | 497/499 | 3.86 |
| 227 | 32 | Colorless amorphous | 7 | 416/418 | 414/416 | 4.01 |
| 228 | 66 | Colorless solid | 3 | 448/450 | 446/448 | 4.56 |
| 229 | 34 | Colorless amorphous | 7 | — | 418/420 | 4.61 |
| 230 | 64 | Colorless solid | 3 | 444/446 | 442/444 | 3.52 |
| 231 | 25 | Colorless solid | 7 | 393/395 | 391/393 | 4.46 |
| 232 | 21 | Colorless solid | 7 | 437/439 | 435/437 | 4.24 |
| 233 | 51 | Colorless solid | 7 | 516/518 | 514/516 | 3.53 |
| 234 | 27 | Colorless solid | 7 | — | 498/500 | 4.81 |
| 235 | 25 | Colorless solid | 7 | — | 498/500 | 4.58 |
| 236 | 21 | Colorless solid | 7 | — | 456/458 | 4.31 |
| 237 | 15 | Colorless solid | 7 | 430/432 | 428/430 | 3.56 |
| 238 | 4 | Colorless solid | 7 | — | 439/441 | 4.51 |
| 239 | 29 | Red solid | 7 | 446/448 | 444/446 | 4.48 |
| 240 | 22 | Colorless solid | 7 | 450/452 | 448/450 | 4.58 |
| 241 | 10 | Colorless oil | 7 | — | 482/484 | 4.58 |
| 242 | 25 | Colorless solid | 7 | 507/509 | 505/507 | 4.33 |
| 243 | 51 | Colorless amorphous | 7 | 487/489 | 485/487 | 4.65 |
| 244 | 54 | Colorless solid | 7 | 487/489 | 485/487 | 4.60 |
| 245 | 24 | Colorless amorphous | 7 | 514/516 | 512/514 | 4.58 |
| 246 | 17 | Colorless solid | 7 | 514/516 | 512/514 | 4.49 |
| 247 | 25 | Colorless amorphous | 7 | 472/474 | 470/472 | 3.78 |
| 248 | 21 | Colorless solid | 7 | 472/474 | 470/472 | 4.00 |
| 249 | 20 | Colorless solid | 7 | 472/474 | 470/472 | 3.91 |
| 250 | 17 | Colorless solid | 7 | 444/446 | 442/444 | 3.81 |
| 251 | 17 | Colorless amorphous | 7 | | | |
| 252 | 15 | Colorless solid | 7 | 544/546 | 520/522 | 4.33 |

TABLE 19-continued

| Synthetic Example No. | Yield (%) | Morphology | LC/MS Condition | Observed peak ESI+ | Observed peak ESI− | Retention time (min) |
|---|---|---|---|---|---|---|
| 253 | 45 | Colorless amorphous | 7 | 474/476 | 472/474 | 3.35 |
| 254 | 63 | Colorless solid | 7 | 455/457 | 453/455 | 4.33 |
| 255 | 71 | Colorless solid | 7 | 465/467 | 463/465 | 3.81 |
| 256 | 99 | Colorless oil | 7 | 439/441 | 437/439 | 4.48 |
| 257 | 7 | Colorless solid | 7 | 459/461 | 457/459 | 4.63 |
| 258 | 8 | Colorless solid | 7 | 460/462 | 458/460 | 4.74 |
| 259 | 25 | Colorless amorphous | 7 | 515/517 | 513/515 | 3.71 |
| 260 | 15 | Colorless solid | 7 | 446/448 | 444/446 | 4.63 |
| 261 | 2 | Colorless amorphous | 7 | 450/452 | 448/450 | 4.35 |
| 262 | 34 | Red amorphous | 7 | 501/503 | 499/501 | 3.93 |
| 263 | 99 | Colorless amorphous | 7 | 459/461 | 457/459 | 4.26 |
| 264 | 68 | Colorless amorphous | 7 | 478/480 | 476/478 | 4.55 |
| 265 | 37 | Colorless solid | 7 | 462/464 | 460/462 | 4.43 |
| 266 | 29 | Pale red amorphous | 7 | 430/432 | 428/430 | 3.60 |
| 267 | 19 | Pale purple solid | 7 | 464/466 | 462/464 | 4.61 |
| 268 | 15 | Colorless solid | 7 | 450/452 | 448/450 | 4.55 |
| 269 | 29 | Purple oil | 7 | 501/503 | 499/501 | 4.43 |
| 270 | 48 | Colorless solid | 7 | 459/461 | 457/459 | 4.38 |
| 271 | 42 | Pale purple solid | 7 | 459/461 | 457/459 | 4.38 |
| 272 | 10 | Colorless solid | 7 | 406/408 | 404/406 | 4.01 |
| 273 | 65 | Colorless solid | 7 | 446/448 | 444/446 | 3.45 |
| 274 | 58 | Colorless amorphous | 7 | 435/437 | 433/435 | 4.13 |
| 275 | 28 | Yellow amorphous | 7 | 445/447 | 443/445 | 4.05 |
| 276 | 27 | Colorless amorphous | 7 | 445/447 | 443/445 | 4.16 |
| 277 | 42 | Pale yellow amorphous | 7 | 473/475 | 471/473 | 3.43 |
| 278 | 25 | Pale yellow amorphous | 7 | 459/461 | 457/459 | 3.33 |
| 279 | 42 | Pale yellow amorphous | 7 | 515/517 | 513/515 | 3.45 |
| 280 | 60 | Colorless solid | 7 | 509/511 | 507/509 | 4.26 |
| 281 | 61 | Pale yellow amorphous | 7 | 445/447 | 443/445 | 4.10 |
| 282 | 71 | Colorless solid | 7 | 427/429 | 425/427 | 4.05 |
| 283 | 69 | Colorless amorphous | 7 | 441/443 | 439/441 | 4.14 |
| 284 | 28 | Colorless solid | 7 | 411/413 | 409/411 | 4.13 |
| 285 | 55 | Colorless amorphous | 7 | 518/520 | 516/518 | 3.48 |
| 286 | 94 | Colorless solid | 7 | 445/447 | 443/445 | 3.38 |
| 287 | 15 | Colorless solid | 7 | 498/500 | 496/498 | 4.31 |
| 288 | 80 | Colorless amorphous | 7 | 459/461 | 457/459 | 4.13 |
| 289 | 84 | Colorless amorphous | 7 | 461/463 | 459/461 | 4.05 |
| 290 | 82 | Colorless amorphous | 7 | 461/463 | 459/461 | 4.11 |
| 291 | 84 | Colorless solid | 7 | 447/449 | 445/447 | 4.05 |
| 292 | 35 | Colorless amorphous | 7 | 436/438 | 434/436 | 4.69 |
| 293 | 49 | Light brown amorphous | 7 | 431/433 | 429/431 | 4.23 |
| 294 | 49 | Pale yellow solid | 7 | 460/462 | 458/460 | 3.73 |

The structures of the compounds obtained in these Synthetic Examples are shown below.
Synthetic Examples 223 to 255
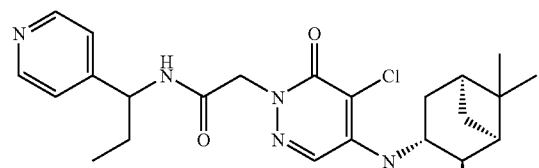
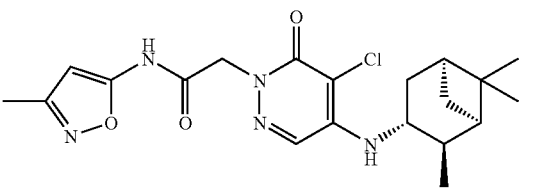

221
-continued
236
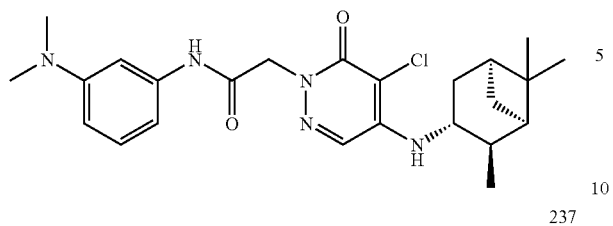
237
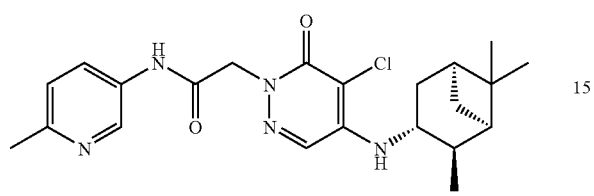
238
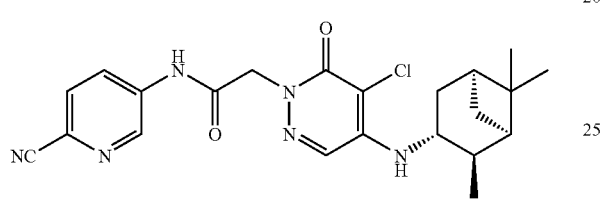
239
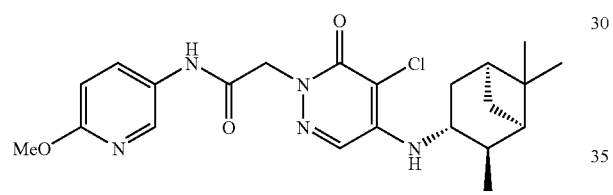
240
241
242
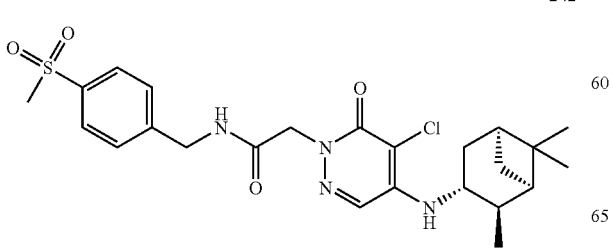
222
-continued
243
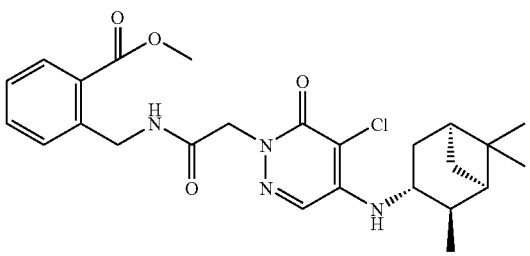
244
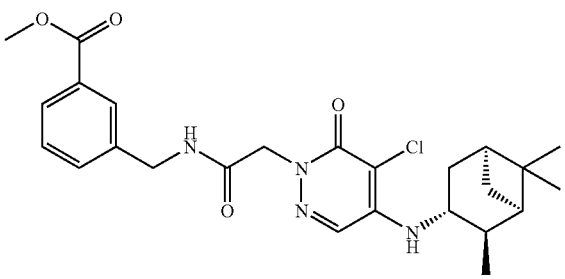
245
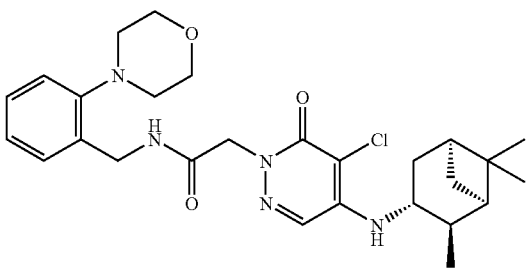
246
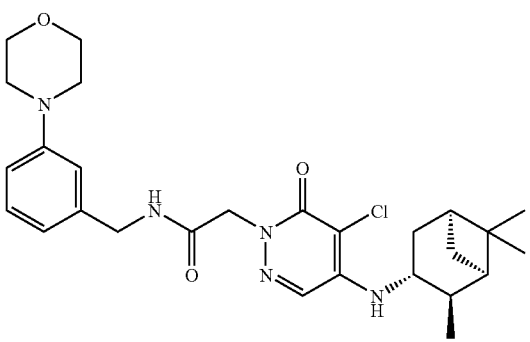
247
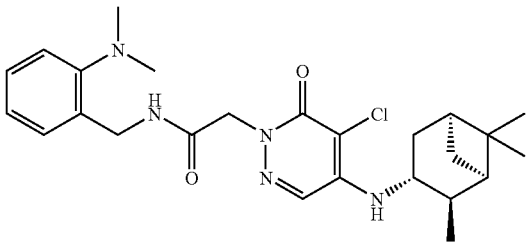

-continued
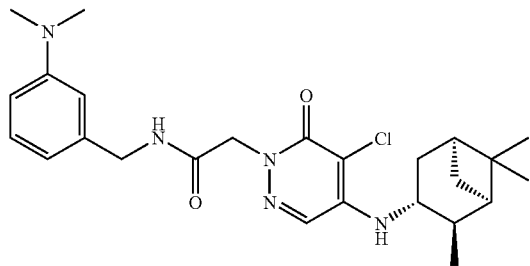
248
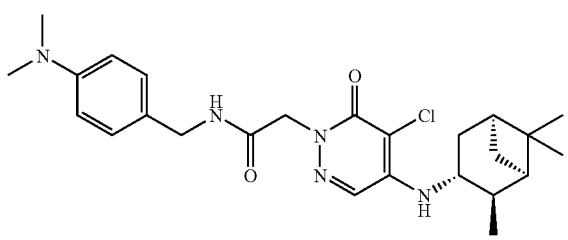
249
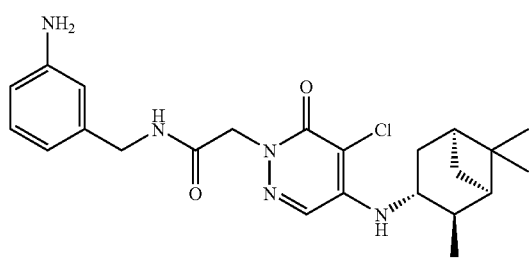
250
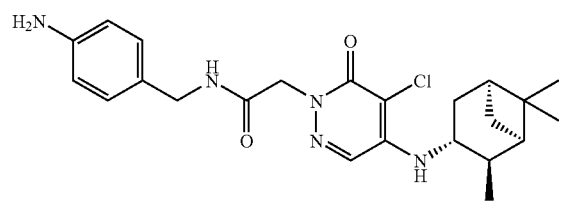
251
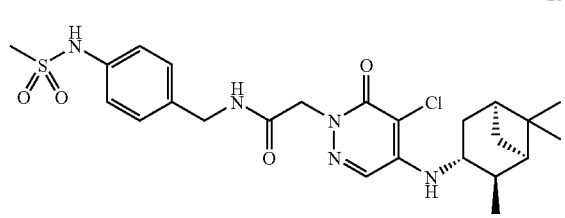
252
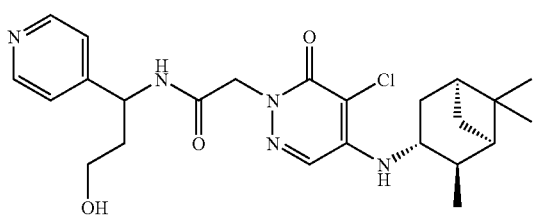
253
-continued
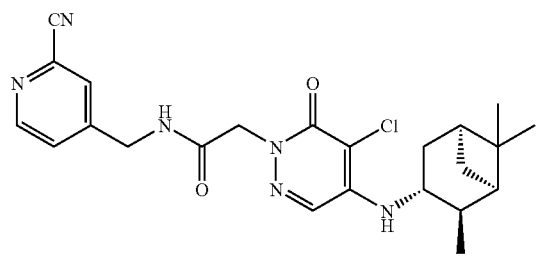
254
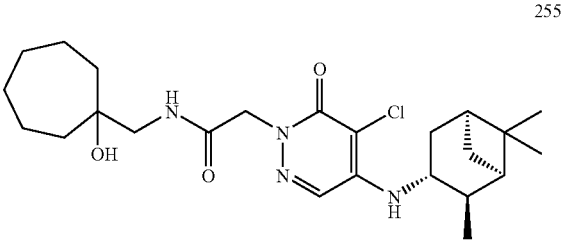
255
SYNTHETIC EXAMPLES 256 TO 294
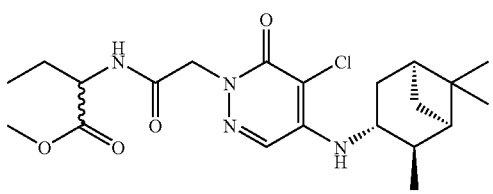
256
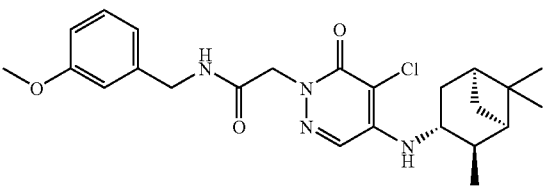
257
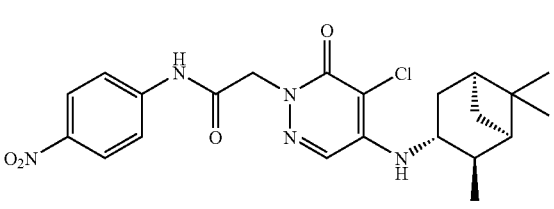
258
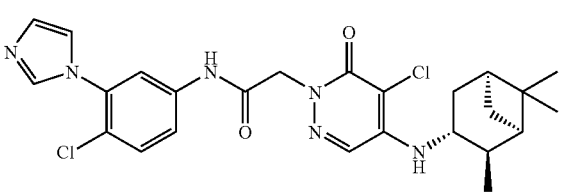
259

260
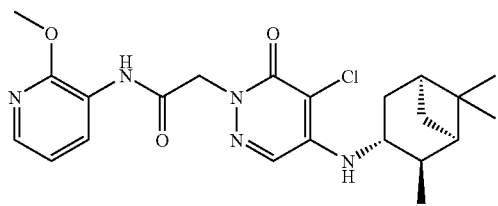
261
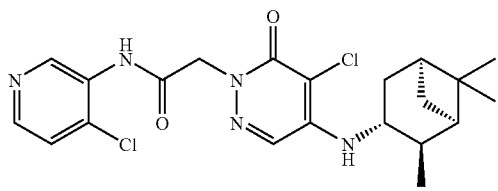
262
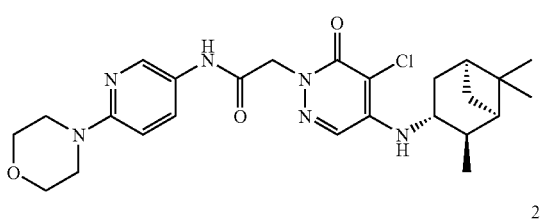
263
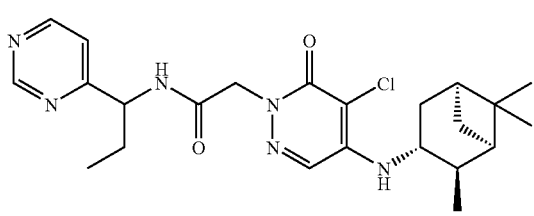
264
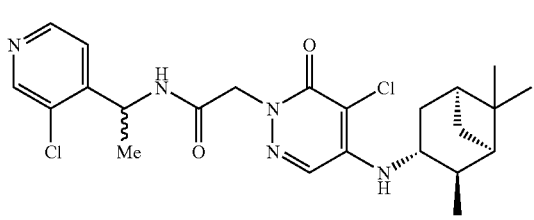
265
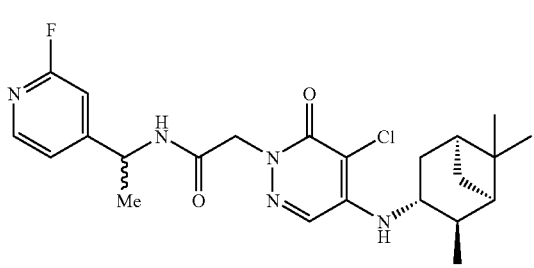
266
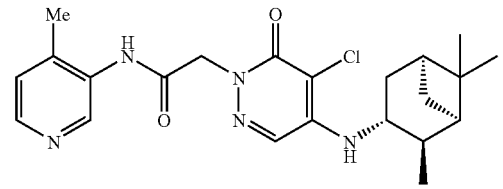
267
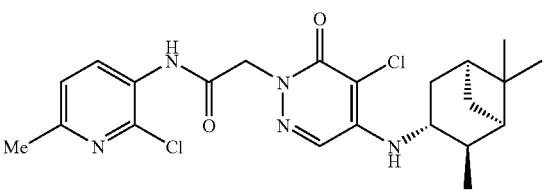
268
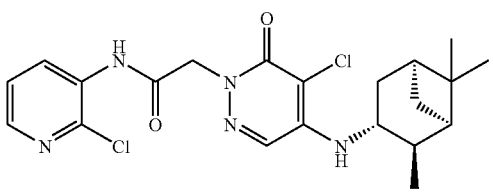
269
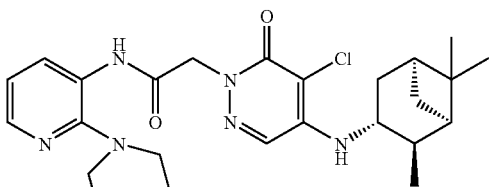
270
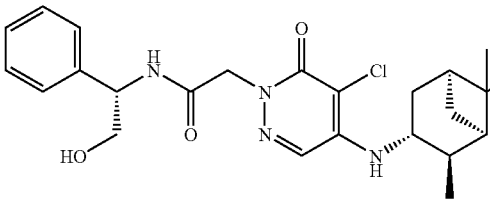
271
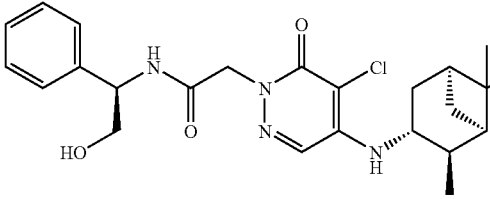
272
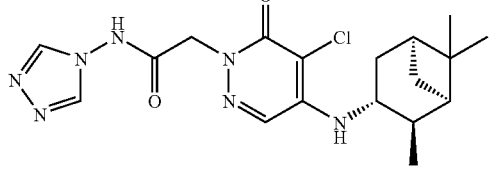
273
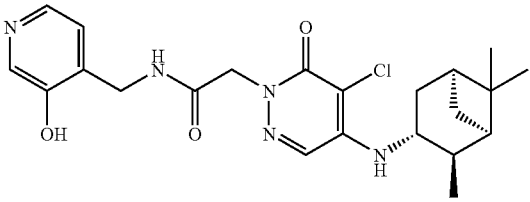

274
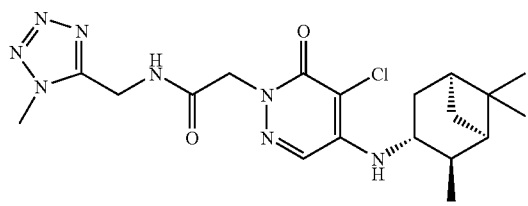
275
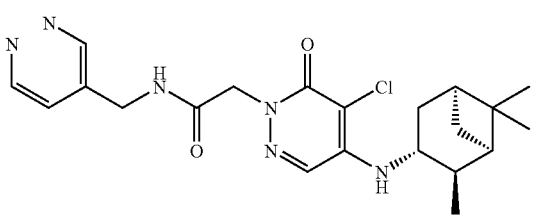
276
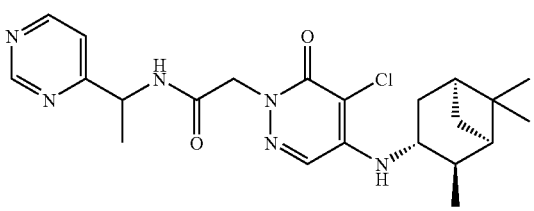
277
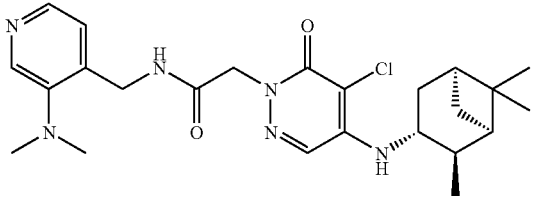
278
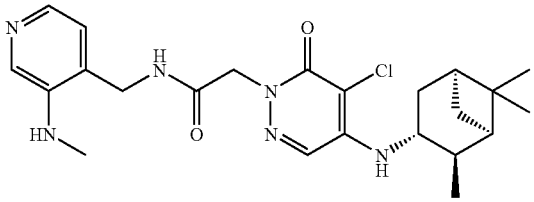
279
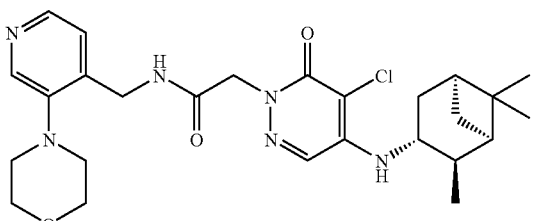
280
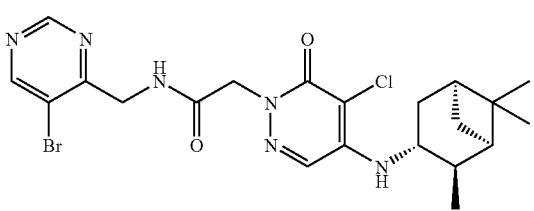
281
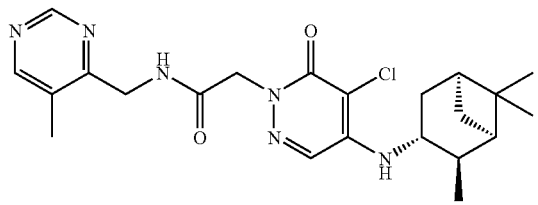
282
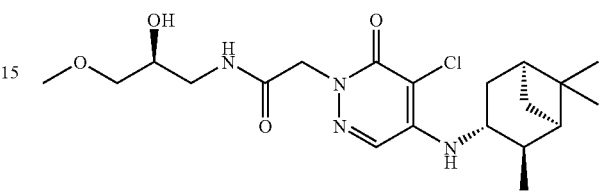
283
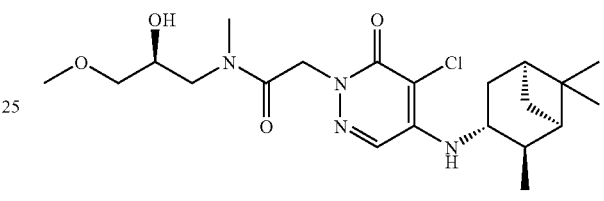
284
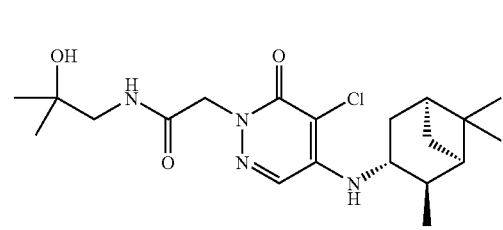
285
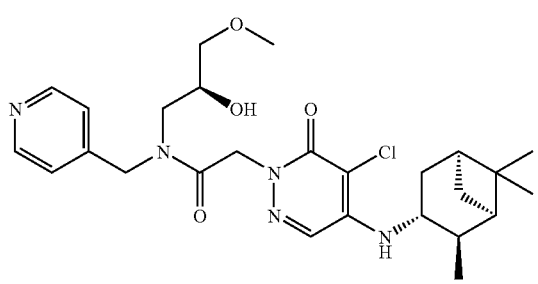
286
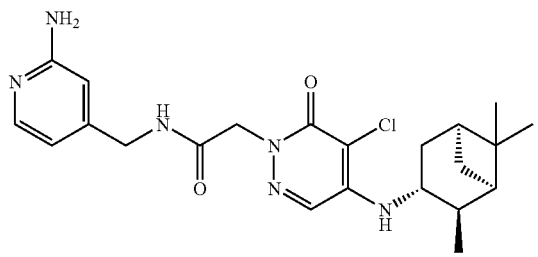

287

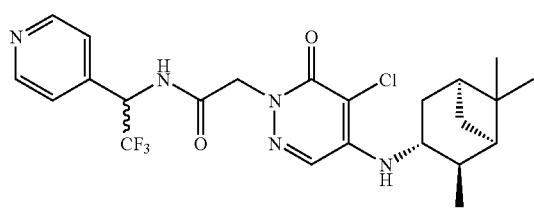

288

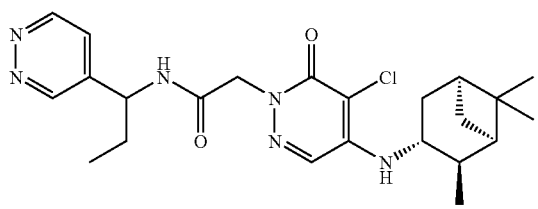

289

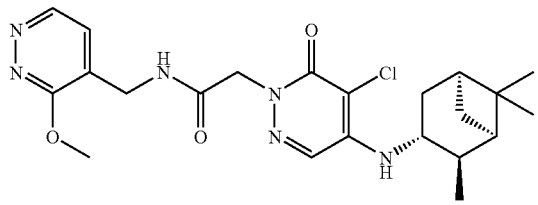

290

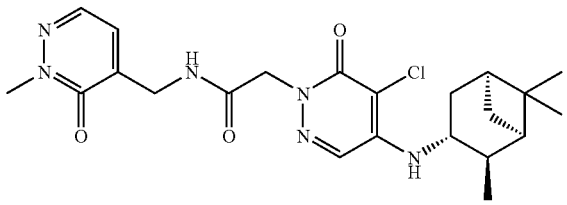

291

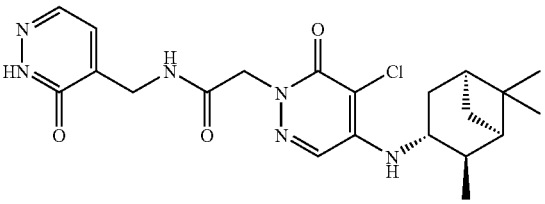

292

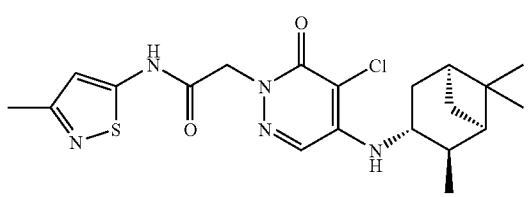

293

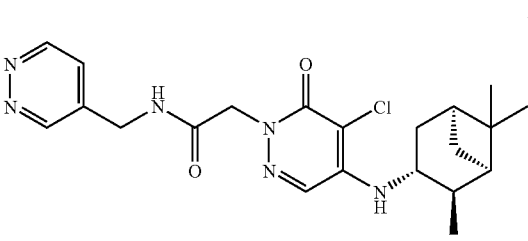

294

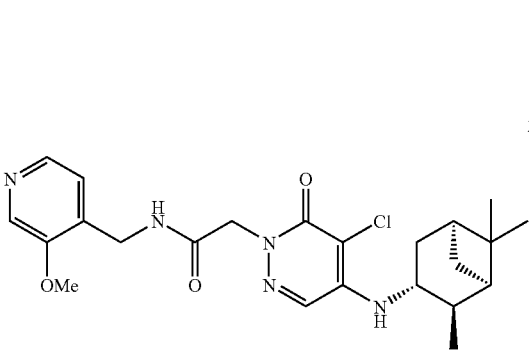

SYNTHETIC EXAMPLES 295 to 296

Compounds were synthesized from 2-{6-oxo-4-[(1R,2R, 3R,5S)-2,6,6-trimethylbicyclo[3.1.1]hept-3-ylamino]pyridazin-1(6H)-yl}acetic acid in the same manner as in Synthetic Example 1, and the yields and morphology of the resulting compounds, the LC/MS conditions used for their analysis and the observed peaks and retention times are shown in Table 20.

TABLE 20

| Synthetic Example No. | Yield (%) | Morphology | LC/MS Condition | Observed peak ESI+ | Observed peak ESI− | Retention time (min) |
|---|---|---|---|---|---|---|
| 295 | 68 | Colorless solid | 7 | 424 | 422 | 3.00 |
| 296 | 34 | Pale yellow solid | 7 | 410 | 408 | 2.90 |

The structures of the compounds obtained in these Synthetic Examples are shown below.

SYNTHETIC EXAMPLES 295 TO 296

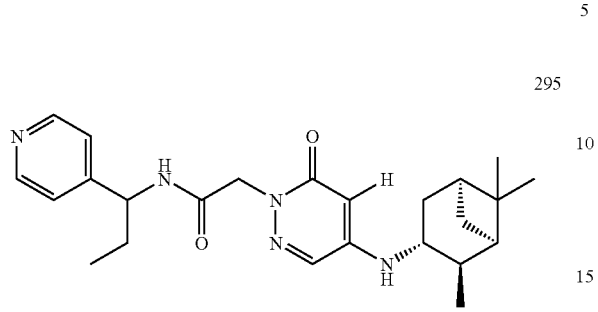

295

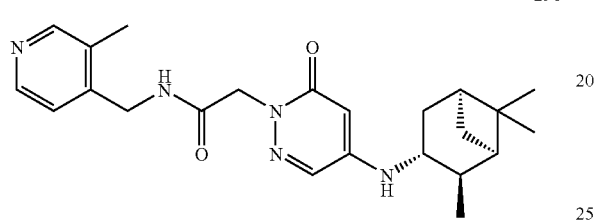

296

SYNTHETIC EXAMPLES 297 TO 311

Compounds were synthesized in the same manner as in Synthetic Example 77, and the yields and morphology of the resulting compounds, the LC/MS conditions used for their analysis and the observed peaks and retention times are shown in Table 21.

The structures of the compounds obtained in these Synthetic Examples are shown below.

SYNTHETIC EXAMPLES 297 TO 311

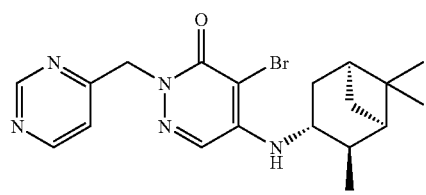

297

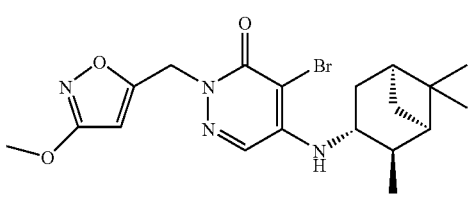

298

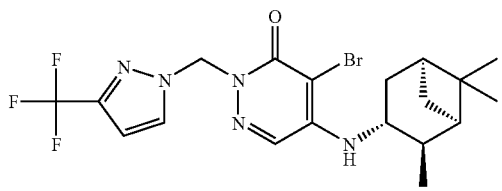

299

TABLE 21

| Synthetic Example No. | Yield (%) | Morphology | LC/MS Condition | Observed peak ESI+ | Observed peak ESI− | Retention time (min) |
| --- | --- | --- | --- | --- | --- | --- |
| 297 | 16 | Colorless amorphous | 7 | 418/420 | 416/418 | 4.15 |
| 298 | 28 | Colorless solid | 7 | 437/439 | 435/437 | 4.54 |
| 299 | 21 | Colorless amorphous | 7 | 474/476 | 472/474 | 4.82 |
| 300 | 23 | Colorless amorphous | 7 | 467/469 | 465/467 | 4.67 |
| 301 | 36 | Colorless amorphous | 7 | 441/443 | 439/441 | 4.72 |
| 302 | 40 | Colorless oil | 7 | 397/399 | 395/397 | 3.88 |
| 303 | 30 | Colorless amorphous | 7 | 446/448 | 444/446 | 4.39 |
| 304 | 38 | Colorless amorphous | 7 | 379/381 | 377/379 | 4.32 |
| 305 | 30 | Colorless amorphous | 7 | 572/574 | 570/572 | 5.43 |
| 306 | 86 | Colorless amorphous | 7 | 530/532 | 528/530 | 4.92 |
| 307 | 74 | Pale yellow amorphous | 7 | 530/532 | 528/530 | 4.95 |
| 308 | 30 | Colorless amorphous | 7 | 450/452 | 448/450 | 4.91 |
| 309 | 11 | Colorless solid | 7 | 478/480 | 476/478 | 4.60 |
| 310 | 79 | Pale yellow solid | 7 | 513/515 | 511/513 | 4.93 |
| 311 | 89 | Colorless amorphous | 7 |  | 443 | 4.18 |

300
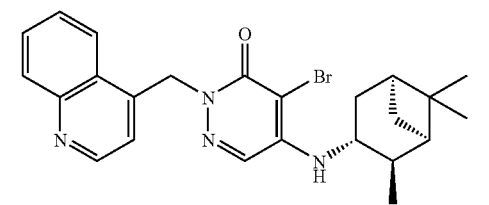
301
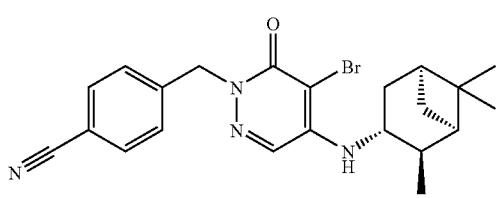
302
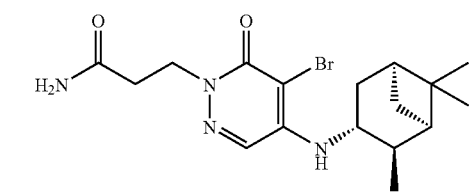
303
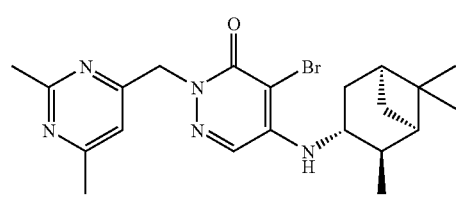
304
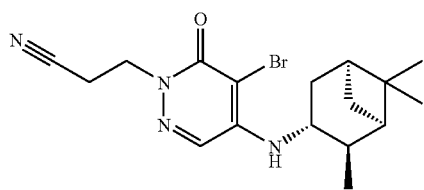
305
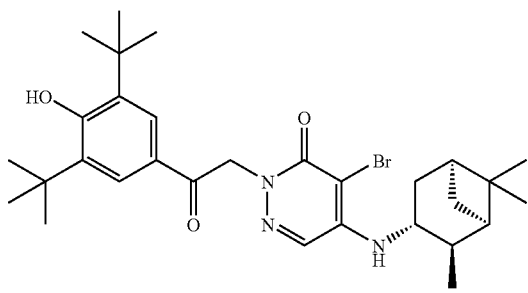
306
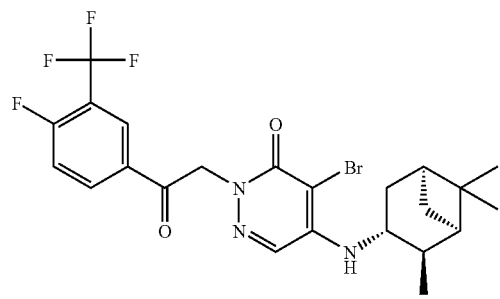
307
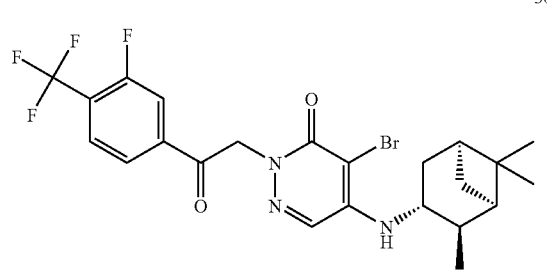
308
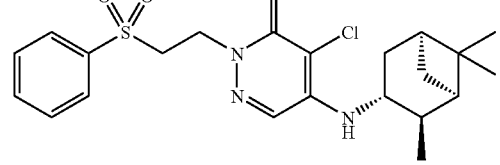
309
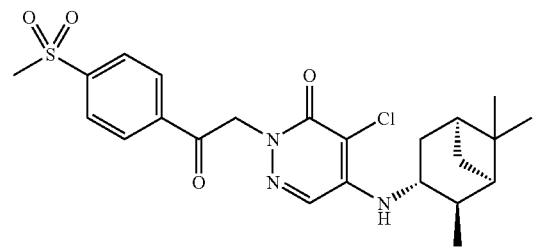
310
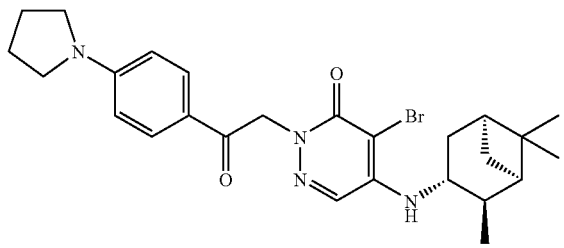
311
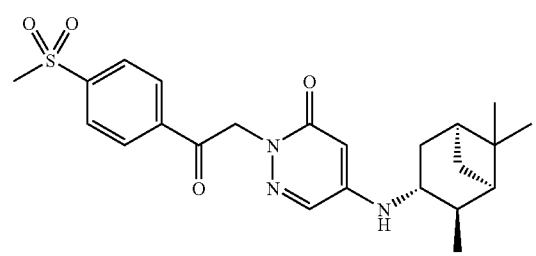

SYNTHETIC EXAMPLES 312 TO 334

Compounds were synthesized in the same manner as in Synthetic Example 48, and the yields and morphology of the resulting compounds, the LC/MS conditions used for their analysis and the observed peaks and retention times are shown in Table 22.

TABLE 22

| Synthetic Example No. | Yield (%) | Morphology | LC/MS Condition | Observed peak ESI+ | Observed peak ESI− | Retention time (min) |
|---|---|---|---|---|---|---|
| 312 | 35 | Light brown solid | 7 | 500/502 | 498/500 | 3.56 |
| 313 | 23 | Yellow solid | 7 | 458/460 | 456/458 | 3.09 |
| 314 | 9 | Colorless solid | 7 | 490/492 | 488/490 | 3.08 |
| 315 | 20 | Pale yellow amorphous | 7 | 504/506 | 502/504 | 3.41 |
| 316 | 1 | Pale yellow solid | 7 | 534/536 | 532/534 | 3.46 |
| 317 | 2 | Brown solid | 7 | 490/492 | 488/490 | 3.43 |
| 318 | 5 | Pale yellow solid | 7 | 504/506 | 502/504 | 3.56 |
| 319 | 19 | Colorless amorphous | 7 | 534/536 | 532/534 | 3.46 |
| 320 | 4 | Yellow solid | 7 | 490/492 | 488/490 | 3.03 |
| 321 | 19 | Pale yellow solid | 7 | 448/450 | 446/448 | 3.14 |
| 322 | 24 | Dark brown oil | 7 | 485/487 | 483/485 | 2.83 |
| 323 | 66 | Brown solid | 7 | 434/436 | 432/434 | 2.89 |
| 324 | 43 | Brown solid | 7 | 464/466 | 462/464 | 1.33 |
| 325 | 76 | Brown solid | 7 | 460/462 | 458/460 | 3.26 |
| 326 | 61 | Brown solid | 7 | 476/478 | 474/476 | 3.43 |
| 327 | 58 | Brown solid | 7 | 474/476 | 472/474 | 3.50 |
| 328 | 12 | Pale yellow oil | 7 | 510/512 | 508/510 | 3.28 |
| 329 | 49 | Colorless oil | 7 | 502/504 | 500/502 | 2.50 |
| 330 | 34 | Colorless oil | 7 | 532/534 | 530/532 | 2.80 |
| 331 | 20 | Colorless oil | 7 | 472/474 | 470/472 | 3.35 |
| 332 | 32 | Colorless amorphous | 7 | 488/490 | 486/488 | 2.36 |
| 333 | 50 | Pale yellow solid | 7 | 504/506 | 502/504 | 3.26 |
| 334 | 57 | Colorless solid | 7 | 502/504 | 500/502 | 2.95 |

The structures of the compounds obtained in these Synthetic Examples are shown below.

SYNTHETIC EXAMPLES 312 TO 334

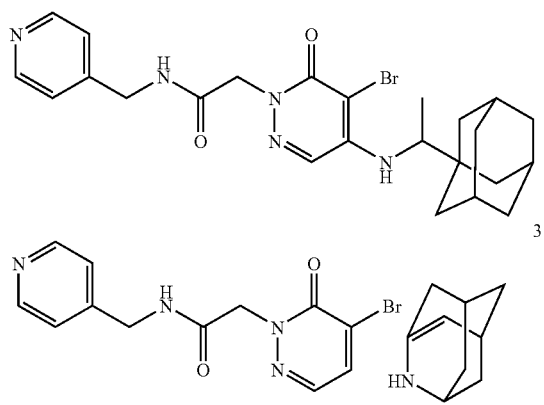

-continued

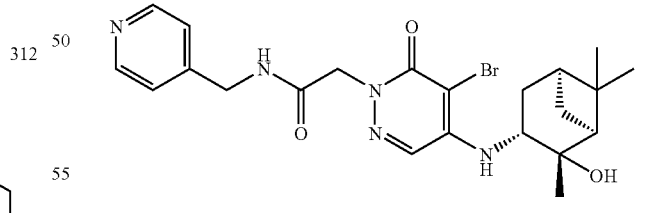

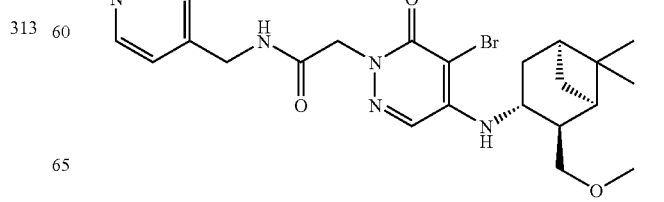

316
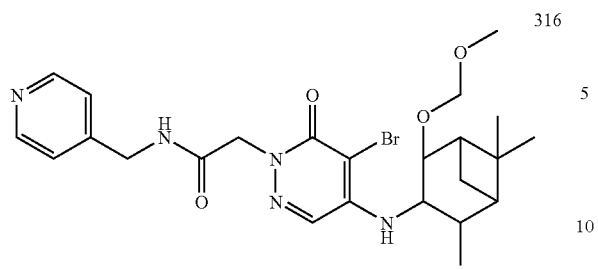
317
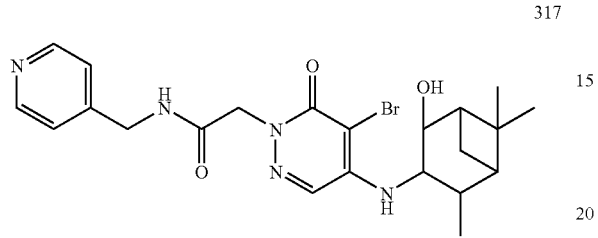
318
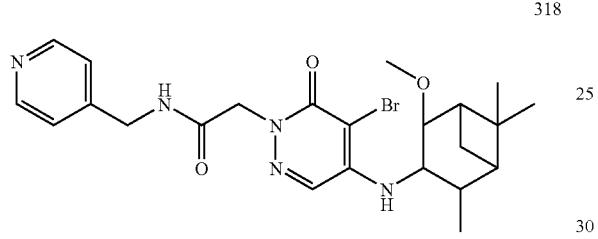
rac-319
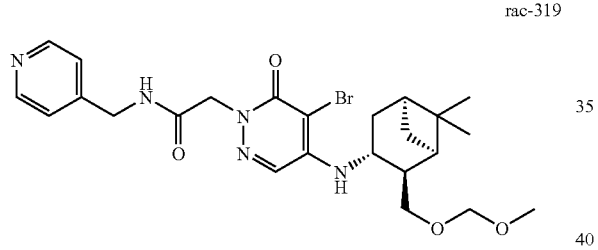
320
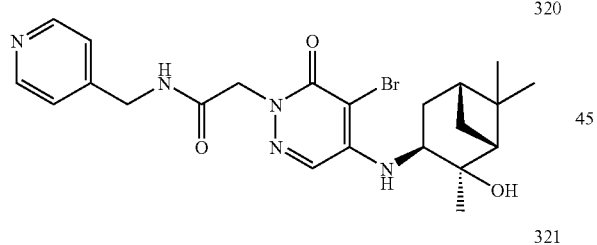
321
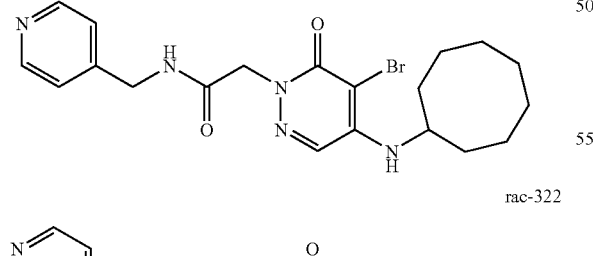
rac-322
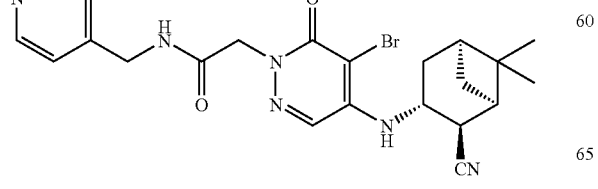
323
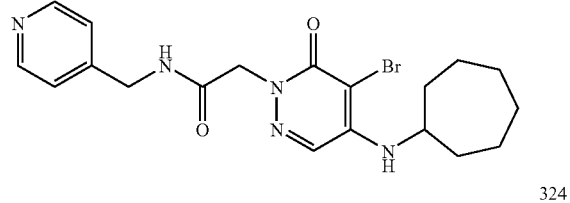
324
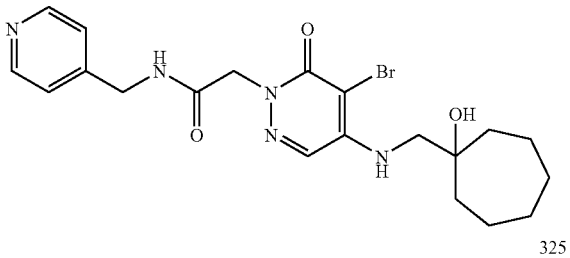
325
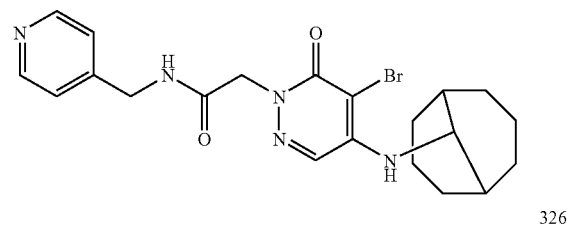
326
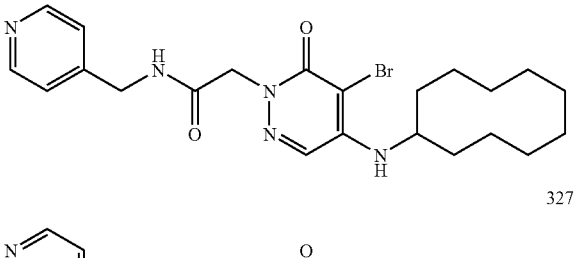
327
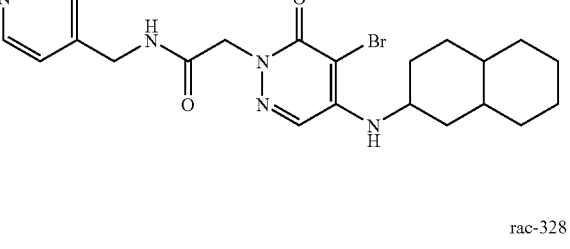
rac-328
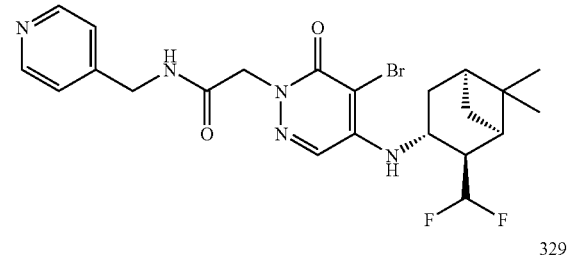
329
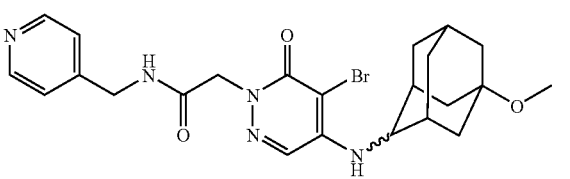

330

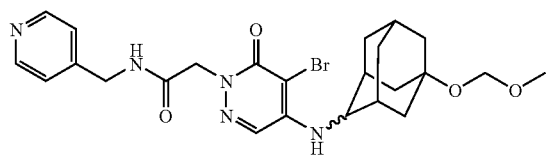

331

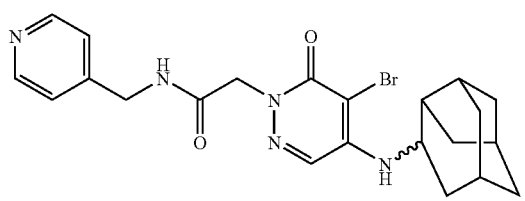

332

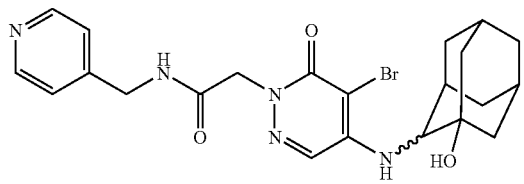

333

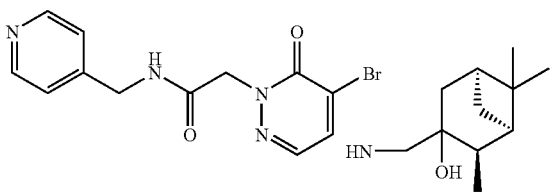

334

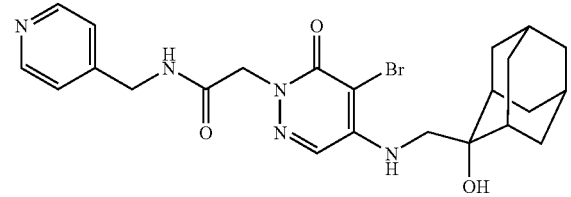

SYNTHETIC EXAMPLES 335 to 339

Compounds were synthesized from 2-(4,5-dibromo-6-oxopyridazin-1(6H)-yl)-N-[1-(pyridin-4-yl)propyl]acetamide, 2-(4,5-dibromo-6-oxopyridazin-1(6H)-yl)-N-[1-(3-methylpyridin-4-yl)methyl]acetamide, 2-(4,5-dichloro-6-oxopyridazin-1(6H)-yl)-N-(pyridin-4-ylmethyl)acetamide, 2-(4,5-dichloro-6-oxopyridazin-1(6H)-yl)-N-[1-(pyridin-4-yl)propyl]acetamide or 2-(4,5-dichloro-6-oxopyridazin-1(6H)-yl)-N-[1-(3-methylpyridin-4-yl)methyl]acetamide in the same manner as in Synthetic Example 48, and the yields and morphology of the resulting compounds, the LC/MS conditions used for their analysis and the observed peaks and retention times are shown in Table 23.

TABLE 23

| Synthetic Example No. | Yield (%) | Morphology | LC/MS Condition | Observed peak ESI+ | Observed peak ESI− | Retention time (min) |
|---|---|---|---|---|---|---|
| 335 | 15 | Pale yellow solid | 7 | 486/488 | 484/486 | 3.35 |
| 336 | 12 | Pale yellow solid | 7 | 472/474 | 470/472 | 3.18 |
| 337 | 28 | Pale yellow solid | 7 | 442/444 | 440/442 | 3.26 |
| 338 | 22 | Pale yellow solid | 7 | 428/430 | 426/428 | 3.08 |
| 339 | 13 | Pale yellow solid | 7 | 414/416 | 412/414 | 3.03 |

The structures of the compounds obtained in these Synthetic Examples are shown below.

SYNTHETIC EXAMPLES 335 TO 339

335

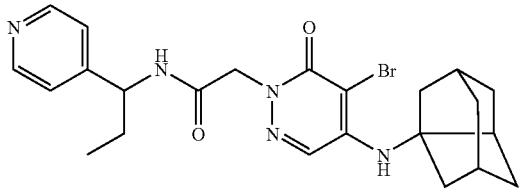

336

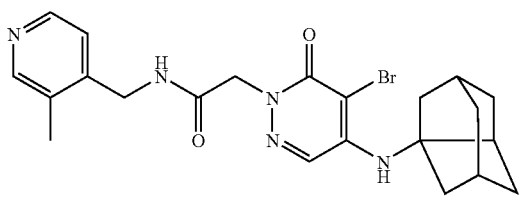

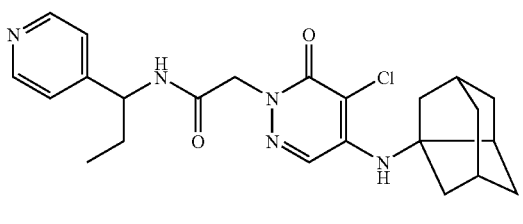

337

338

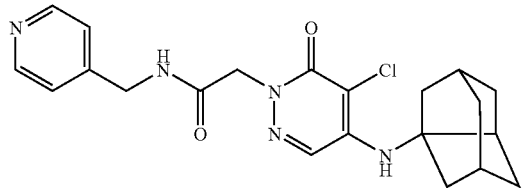

339

SYNTHETIC EXAMPLES 340 TO 354

Compounds were synthesized from [5-chloro-4-(hexahydro-2,5-methanopentalen-3a(1H)-ylamino)-6-oxopyridazin-1(6H)-yl]acetic acid or [5-bromo-4-(hexahydro-2,5-methanopentalen-3a(1H)-ylamino)-6-oxopyridazin-1(6H)-yl]acetic acid in the same manner as in Synthetic Example 1, and the yields and morphology of the resulting compounds, the LC/MS conditions used for their analysis and the observed peaks and retention times are shown in Table 24.

TABLE 24

| Synthetic Example No. | Yield (%) | Morphology | LC/MS Condition | Observed peak ESI+ | Observed peak ESI− | Retention time (min) |
|---|---|---|---|---|---|---|
| 340 | 100 | Pale yellow amorphous | 7 | 488/490 | 486/488 | 3.41 |
| 341 | 100 | Pale yellow amorphous | 7 | 444/446 | 442/444 | 3.33 |
| 342 | 100 | Colorless amorphous | 7 | 476/478 | 474/476 | 4.35 |
| 343 | 100 | Colorless amorphous | 7 | 432/434 | 430/432 | 4.26 |
| 344 | 67 | Colorless amorphous | 7 | 415/417 | 413/415 | 3.86 |
| 345 | 59 | Colorless amorphous | 7 | 459/461 | 457/459 | 3.93 |
| 346 | 73 | Pale yellow oil | 3 | 472/474 | 470/472 | 3.23 |
| 347 | 64 | Pale yellow amorphous | 3 | 428/430 | 426/428 | 3.18 |
| 348 | 63 | Pale yellow amorphous | 7 | 473/475 | 471/473 | 3.80 |
| 349 | 25 | Colorless amorphous | 7 | 457/459 | 455/457 | 3.18 |
| 350 | 40 | Colorless amorphous | 7 | 429/431 | 427/429 | 3.81 |
| 351 | 48 | Dark brown amorphous | 7 | 443/445 | 441/443 | 3.93 |
| 352 | 61 | Colorless amorphous | 7 | 429/431 | 427/429 | 3.70 |
| 353 | 59 | Colorless amorphous | 7 | 446/448 | 444/446 | 4.14 |
| 354 | 51 | Colorless amorphous | 7 | 462/464 | 460/462 | 4.11 |

The structures of the compounds obtained in these Synthetic Examples are shown below.

SYNTHETIC EXAMPLES 340 TO 354

SYNTHETIC EXAMPLES 355 TO 357

Compounds were synthesized from 2-(4,5-dibromo-6-oxopyridazin-1(6H)-yl)-N-[1-(pyridin-4-yl)propyl]acetamide, 2-(4,5-dibromo-6-oxopyridazin-1(6H)-yl)-N-[1-(3-methylpyridin-4-yl)methyl]acetamide or 2-(4,5-dichloro-6-oxopyridazin-1(6H)-yl)-N-[1-(3-methylpyridin-4-yl)methyl] acetamide in the same manner as in Synthetic Example 48, and the yields and morphology of the resulting compounds, the LC/MS conditions used for their analysis and the observed peaks and retention times are shown in Table 25.

TABLE 25

| Synthetic Example No. | Yield (%) | Morphology | LC/MS Condition | Observed peak ESI+ | Observed peak ESI− | Retention time (min) |
|---|---|---|---|---|---|---|
| 355 | 20 | Brown solid | 7 | 476/478 | 474/476 | 3.35 |
| 356 | 47 | Colorless solid | 7 | 462/464 | 460/462 | 3.20 |
| 357 | 54 | Colorless solid | 7 | 418/420 | 416/418 | 3.13 |

The structures of the compounds obtained in these Synthetic Examples are shown below.

SYNTHETIC EXAMPLES 355 TO 357

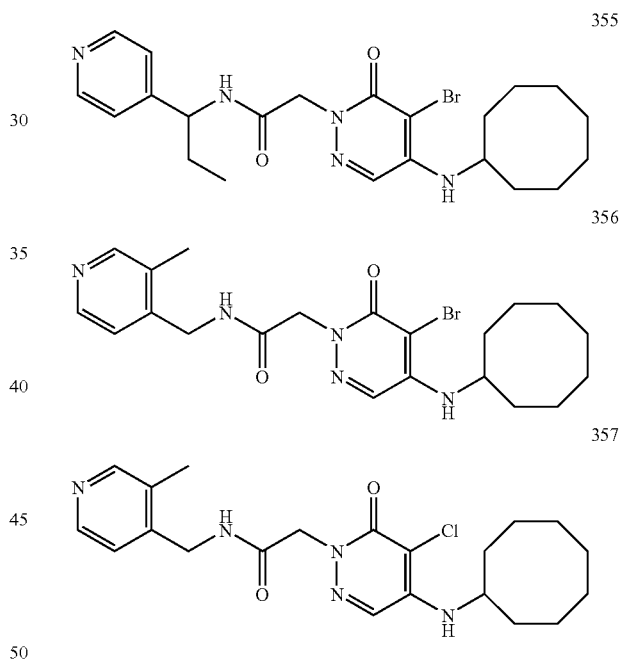

SYNTHETIC EXAMPLES 358 TO 361

Compounds were synthesized from 2-(4,5-dibromo-6-oxopyridazin-1(6H)-yl)-N-[1-(pyridin-4-yl)propyl]acetamide, 2-(4,5-dibromo-6-oxopyridazin-1(6H)-yl)-N-[1-(3-methylpyridin-4-yl)methyl]acetamide, 2-(4,5-dichloro-6-oxopyridazin-1(6H)-yl)-N-[1-(pyridin-4-yl)propyl]acetamide or 2-(4,5-dichloro-6-oxopyridazin-1(6H)-yl)-N-[1-(3-methylpyridin-4-yl)methyl]acetamide (1S,2S,3R,5S)-3-amino-2,6,6-trimethylbicyclo[3.1.1]heptan-2-ol in the same manner as in Synthetic Example 48, and the yields and morphology of the resulting compounds, the LC/MS conditions used for their analysis and the observed peaks and retention times are shown in Table 26.

TABLE 26

| Synthetic Example No. | Yield (%) | Morphology | LC/MS Condition | Observed peak ESI+ | Observed peak ESI− | Retention time (min) |
|---|---|---|---|---|---|---|
| 358 | 10 | Pale yellow solid | 7 | 518/520 | 516/518 | 3.36 |
| 359 | 9 | Pale yellow solid | 7 | 504/506 | 502/504 | 3.20 |
| 360 | 17 | Pale yellow solid | 7 | 474/476 | 472/474 | 3.33 |
| 361 | 13 | Pale yellow solid | 7 | 460/462 | 458/460 | 3.14 |

The structures of the compounds obtained in these Synthetic Examples are shown below.

SYNTHETIC EXAMPLES 358 TO 361

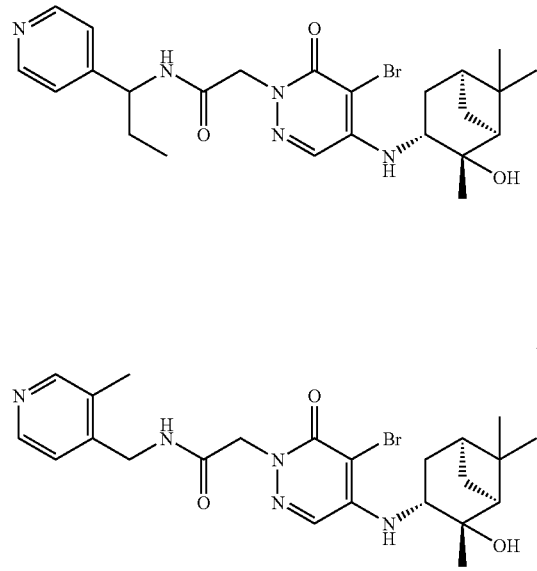

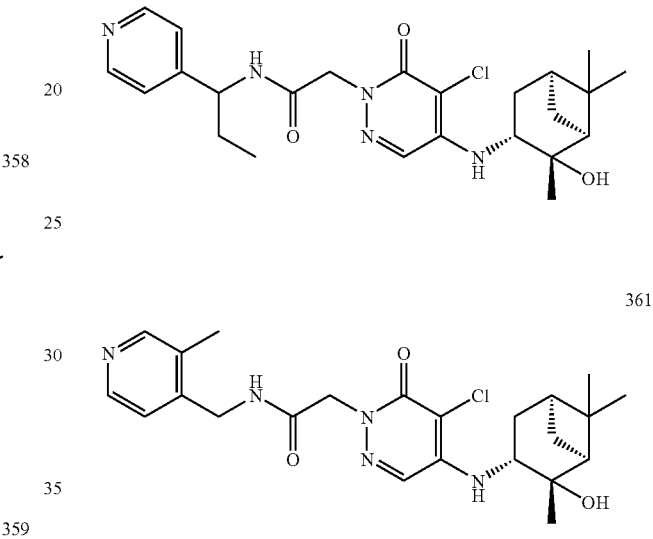

SYNTHETIC EXAMPLES 362 TO 365

Compounds were synthesized from (5-chloro-4-{[(1S,2S,3R,5S)-2-hydroxy-2,6,6-trimethylbicyclo[3.1.1]hept-2-yl]amino}-6-oxopyridazin-1(6H)-yl)acetic acid in the same manner as in Synthetic Example 1, and the yields and morphology of the resulting compounds, the LC/MS conditions used for their analysis and the observed peaks and retention times are shown in Table 27.

TABLE 27

| Synthetic Example No. | Yield (%) | Morphology | LC/MS Condition | Observed peak ESI+ | Observed peak ESI− | Retention time (min) |
|---|---|---|---|---|---|---|
| 362 | 25 | Colorless amorphous | 7 | 489/491 | 487/489 | 3.20 |
| 363 | 69 | Colorless amorphous | 7 | 494/496 | 492/494 | 4.03 |
| 364 | 32 | Colorless oil | 7 | 461/463 | 459/461 | 3.68 |
| 365 | 48 | Colorless oil | 7 | 478/480 | 476/478 | 4.03 |

The structures of the compounds obtained in these Synthetic Examples are shown below.

SYNTHETIC EXAMPLES 362 TO 365

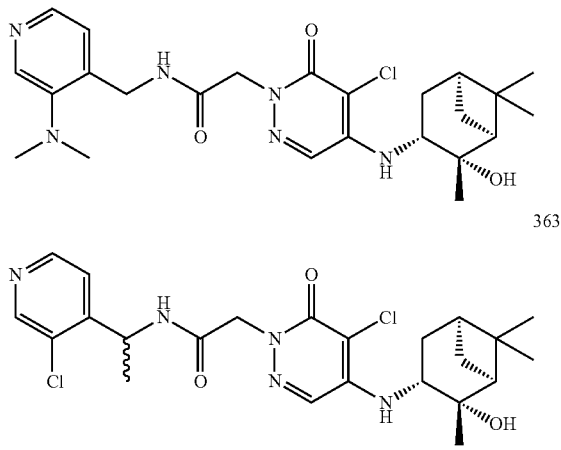

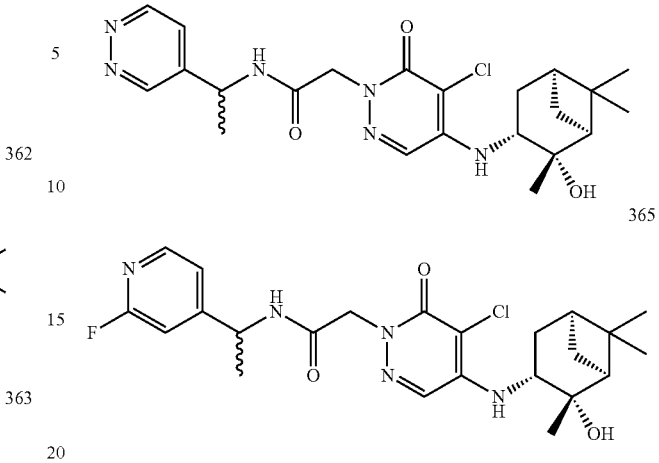

SYNTHETIC EXAMPLES 366 TO 367

Compounds were synthesized from [5-chloro-4-(2-adamantanamino)-6-oxopyridazin-1(6H)-yl]acetic acid in the same manner as in Synthetic Example 1, and the yields and morphology of the resulting compounds, the LC/MS conditions used for their analysis and the observed peaks and retention times are shown in Table 28.

TABLE 28

| Synthetic Example No. | Yield (%) | Morphology | LC/MS Condition | Observed peak ESI+ | Observed peak ESI− | Retention time (min) |
|---|---|---|---|---|---|---|
| 366 | 23 | Colorless amorphous | 7 | 471/473 | 469/471 | 3.33 |
| 367 | 60 | Pale yellow amorphous | 7 | 443/445 | 441/443 | 3.95 |

The structures of the compounds obtained in these Synthetic Examples are shown below.

SYNTHETIC EXAMPLES 366 TO 367

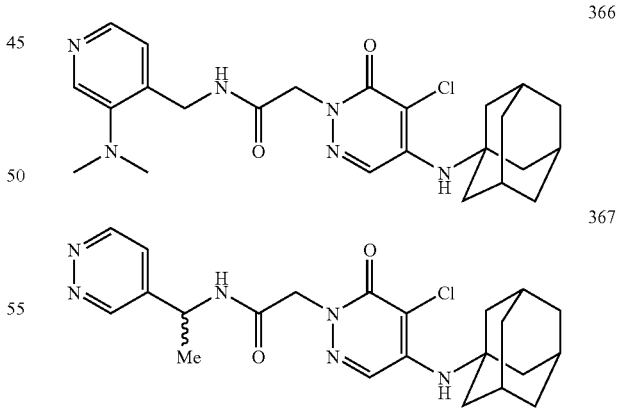

SYNTHETIC EXAMPLES 368 TO 369

Compounds were synthesized from 2-[4,5-dichloro-6-oxopyridazin-1(6H)-yl]-N-[(1R)-1-(pyridin-4-yl)ethyl]acetamide2-adamantamine or bicyclo[3.3.1]nonan-9-amine in the same manner as in Synthetic Example 48, and the yields and morphology of the resulting compounds, the LC/MS conditions used for their analysis and the observed peaks and retention times are shown in Table 29.

TABLE 29

| Synthetic Example No. | Yield (%) | Morphology | LC/MS Condition | Observed peak ESI+ | Observed peak ESI− | Retention time (min) |
|---|---|---|---|---|---|---|
| 368 | 49 | Light brown solid | 7 | 442/444 | 440/442 | 3.31 |
| 369 | 59 | Yellow solid | 7 | 430/432 | 428/430 | 3.26 |

The structures of the compounds obtained in these Synthetic Examples are shown below.

SYNTHETIC EXAMPLES 368 TO 369

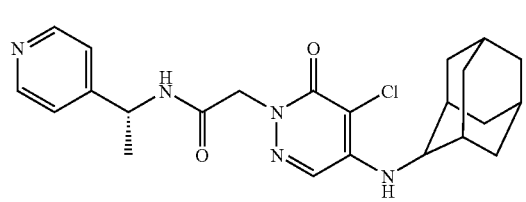

368

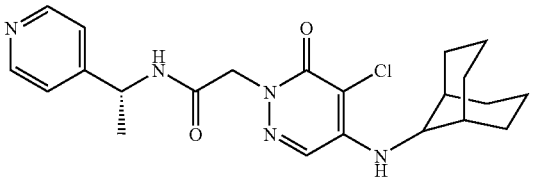

369

SYNTHETIC EXAMPLES 370 TO 371

Compounds were synthesized from [5-chloro-4-(2-adamantanamino)-6-oxopyridazin-1(6H)-yl]acetic acid in the same manner as in Synthetic Example 1, and the yields and morphology of the resulting compounds, the LC/MS conditions used for their analysis and the observed peaks and retention times are shown in Table 30.

TABLE 30

| Synthetic Example No. | Yield (%) | Morphology | LC/MS Condition | Observed peak ESI+ | Observed peak ESI− | Retention time (min) |
|---|---|---|---|---|---|---|
| 370 | 53 | Yellow amorphous | 7 | 443/445 | 441/443 | 3.93 |
| 371 | 24 | Colorless amorphous | 7 | 471/473 | 469/471 | 3.36 |

The structures of the compounds obtained in these Synthetic Examples are shown below.

SYNTHETIC EXAMPLES 370 TO 371

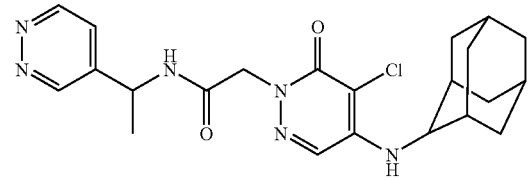

370

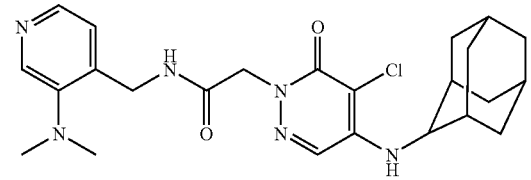

371

SYNTHETIC EXAMPLES 372 TO 378

Compounds were synthesized from [4-(bicyclo[3.1.1]non-9-ylamino)-5-bromo-6-oxopyridazin-1(6H)-yl]acetic acid or [4-(bicyclo[3.1.1]non-9-ylamino)-5-chloro-6-oxopyridazin-1(6H)-yl]acetic acid in the same manner as in Synthetic Example 1, and the yields and morphology of the resulting compounds, the LC/MS conditions used for their analysis and the observed peaks and retention times are shown in Table 31.

TABLE 31

| Synthetic Example No. | Yield (%) | Morphology | LC/MS Condition | Observed peak ESI+ | Observed peak ESI− | Retention time (min) |
| --- | --- | --- | --- | --- | --- | --- |
| 372 | 62 | Pale yellow amorphous | 7 | 475/477 | 473/475 | 3.95 |
| 373 | 28 | Colorless amorphous | 7 | 459/461 | 457/459 | 3.31 |
| 374 | 41 | Light brown solid | 7 | 431/433 | 429/431 | 3.98 |
| 375 | 48 | Colorless amorphous | 7 | 445/447 | 443/445 | 4.11 |
| 376 | 59 | Colorless amorphous | 7 | 431/433 | 429/431 | 4.88 |
| 377 | 48 | Colorless amorphous | 7 | 448/450 | 446/448 | 4.30 |
| 378 | 55 | Colorless solid | 7 | 464/466 | 462/464 | 4.26 |

The structures of the compounds obtained in these Synthetic Examples are shown below.

SYNTHETIC EXAMPLES 372 TO 378

372

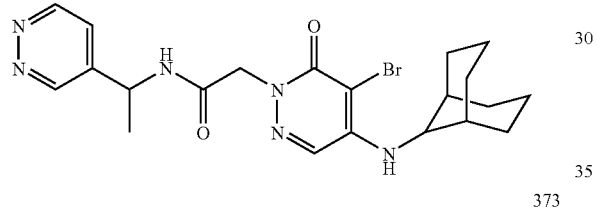

373

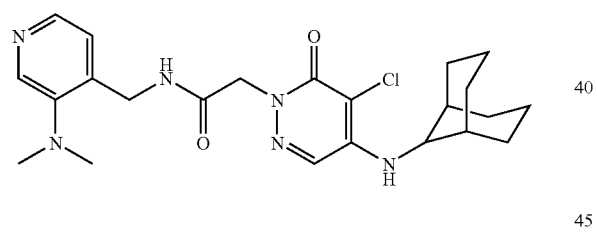

374

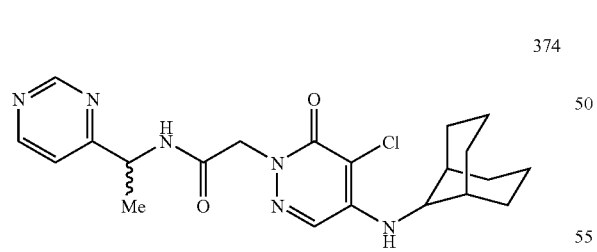

375

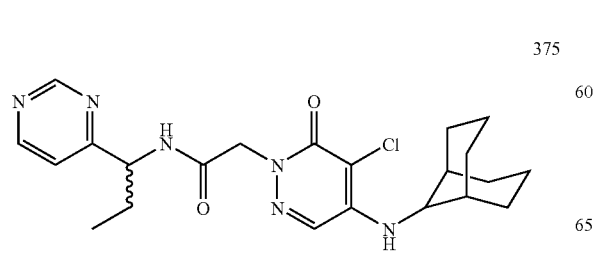

-continued

376

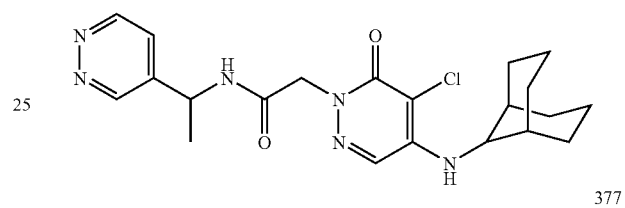

377

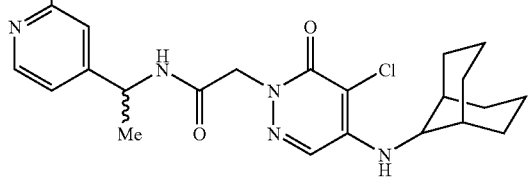

378

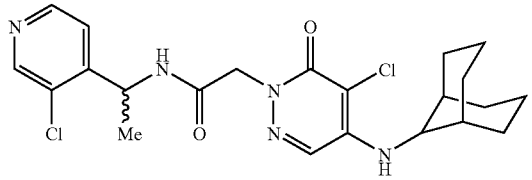

SYNTHETIC EXAMPLE 379

2-[6-Oxo-5-(pyridin-4-yl)-4-{[(1R,2R,3R,5S)-2,6,6-trimethylbicyclo[3.1.1]hept-3-yl]amino}pyridazin-1(6H)-yl]-N-(pyridin-4-ylmethyl)acetamide

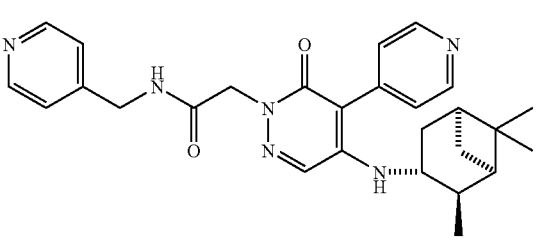

Synthesis was carried out in the same manner as in Synthetic Example 152 by using 4-pyridylboronic acid.

Yield: 91%

Morphology: colorless solid

LC/MS: Condition 2, retention time 1.70 min

LC/MS (ESI$^+$) m/z; 473 [M+1]$^+$

LC/MS (ESI$^-$) m/z; 471 [M−1]$^-$

SYNTHETIC EXAMPLE 380

2-[6-Oxo-5-(pyrimidin-5-yl)-4-{[(1R,2R,3R,5S)-2,6,6-trimethylbicyclo[3.1.1]hept-3-yl]amino}pyridazin-1(6H)-yl]-N-(pyridin-4-ylmethyl)acetamide

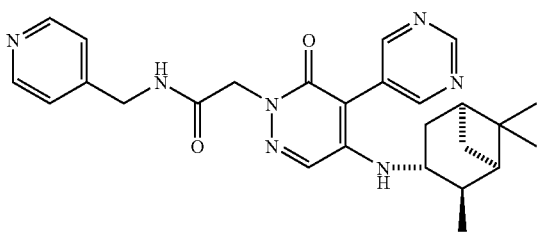

Synthesis was carried out in the same manner as in Synthetic Example 152 by using 4-pyrimidinylboronic acid.

Yield: 100%

Morphology: colorless solid

LC/MS: Condition 2, retention time 2.00 min

LC/MS (ESI$^+$) m/z; 474 [M+1]$^+$

LC/MS (ESI$^-$) m/z; 472 [M−1]$^-$

SYNTHETIC EXAMPLES 381 TO 383

4-Bromo-2-(tetrahydro-2H-pyran-2-yl)-5-{[(1R,2R,3R,5S)-2,6,6-trimethylbicyclo[3.1.1]hept-3-yl]amino}pyridazin-3(2H)-one

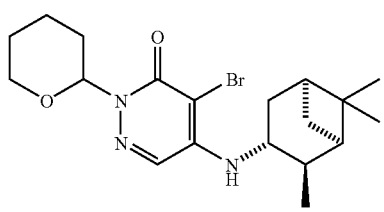

Synthesis was carried out in the same manner as in Synthetic Example 1 by using 4,5-dibromo-2-(tetrahydro-2H-pyran-2-yl)pyridazin-3(2H)-one.

Yield: 74%

Morphology: pale yellow amorphous

LC/MS: Condition 7, retention time 4.62 min

LC/MS (ESI$^-$) m/z; 408, 410 [M−1]$^-$

4-Hydroxy-2-(tetrahydro-2H-pyran-2-yl)-5-{[(1R,2R,3R,5S)-2,6,6-trimethylbicyclo[3.1.1]hept-3-yl]amino}pyridazin-3(2H)-one

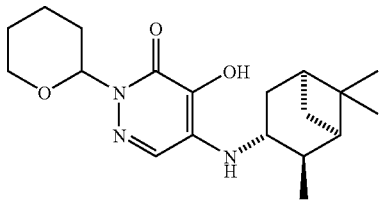

4-Bromo-2-(tetrahydro-2H-pyran-2-yl)-5-{[(1R,2R,3R,5S)-2,6,6-trimethylbicyclo[3.1.1]hept-3-yl]amino}pyridazin-3(2H)-one (200 mg, 0.49 mmol), tris(dibenzylideneacetone)dipalladium (9 mg, 0.01 mmol), potassium hydroxide (82 mg, 1.46 mmol) and 2-di-t-butylphosphino-2',4',6'-triisopropylbiphenyl (17 mg, 0.04 mmol) in 1,4-dioxane-water (1/1) were stirred in an argon stream at 100° C. for 1 hour. After completion of the reaction, the reaction solution was mixed with saturated aqueous ammonium chloride and extracted with chloroform three times, and the organic layer was dried over anhydrous sodium sulfate and evaporated under reduced pressure. The resulting residue was purified by silica gel column chromatography (hexane/ethyl acetate=3/1 to 1/1) to give the desired product (170 mg, 100% yield).

Morphology: pale yellow amorphous

LC/MS: Condition 7, retention time 4.39 min

LC/MS (ESI$^+$) m/z; 348 [M+1]$^+$

LC/MS (ESI$^-$) m/z; 346 [M−1]$^-$

4-Difluoromethoxy-2-(tetrahydro-2H-pyran-2-yl)-5-{[(1R,2R,3R,5S)-2,6,6-trimethylbicyclo[3.1.1]hept-3-yl]amino}pyridazin-3(2H)-one

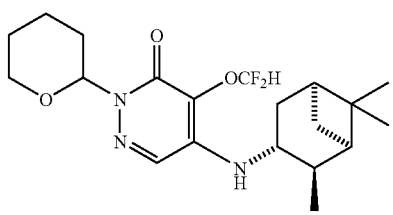

4-Hydroxy-2-(tetrahydro-2H-pyran-2-yl)-5-{[(1R,2R,3R,5S)-2,6,6-trimethylbicyclo[3.1.1]hept-2-yl]amino}pyridazin-3(2H)-one (170 mg, 0.49 mmol) in N,N-dimethylformamide (1.7 mL) was mixed with ethyl bromodifluoroacetate (94 μL, 0.73 mmol) and potassium carbonate (101 mg, 0.73 mmol) at room temperature and stirred at 65° C. for 1 hour. After completion of the reaction, ethyl acetate was added, and the organic layer was washed with saturated aqueous ammonium chloride and saturated aqueous sodium chloride, dried over anhydrous sodium sulfate and evaporated under reduced pressure. The resulting residue was purified by silica gel column chromatography (hexane/ethyl acetate=8/1 to 1/1) to give the desired product (104 mg, 54% yield).

Morphology: pale yellow oil

LC/MS: Condition 7, retention time 4.74 min

LC/MS (ESI$^-$) m/z; 396 [M−1]$^-$

257

4-Difluoromethoxy-5-{[(1R,2R,3R,5S)-2,6,6-trimethylbicyclo[3.1.1]hept-3-yl]amino}pyridazin-3(2H)-one

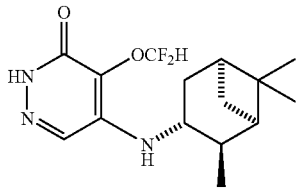

4-Difluoromethoxy-2-(tetrahydro-2H-pyran-2-yl)-5-{[(1R,2R,3R,5S)-2,6,6-trimethylbicyclo[3.1.1]hept-3-yl]amino}pyridazin-3(2H)-one (80 mg, 0.20 mmol) in acetic acid-tetrahydrofuran-water (5/1/1) was stirred at 90° C. for 3 hours and then stirred with two drops of concentrated hydrochloric acid for another 3 hours. After completion of the reaction, the reaction solution was evaporated under reduced pressure. The resulting residue was purified by silica gel column chromatography (hexane/ethyl acetate=4/1 to 1/1) to give the desired product (48 mg, 79% yield).

Morphology: colorless amorphous
LC/MS: Condition 7, retention time 4.15 min
LC/MS (ESI$^+$) m/z; 314 [M+1]$^+$
LC/MS (ESI$^-$) m/z; 312 [M−1]$^-$

258

[5-Difluoromethoxy-6-oxo-4-{[(1R,2R,3R,5S)-2,6,6-trimethylbicyclo[3.1.1]hept-3-yl]amino}pyridazin-1(6H)-yl]acetic Acid

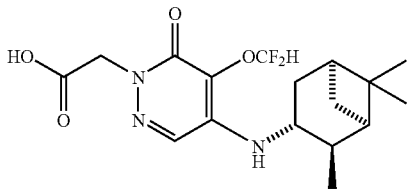

Synthesis was carried out in the same manner as in Synthetic Example 1 by using 4-difluoromethoxy-5-{[(1R,2R,3R,5S)-2,6,6-trimethylbicyclo[3.1.1]hept-3-yl]amino}pyridazin-3(2H)-one.

Yield: 79% (two steps)
Morphology: light brown amorphous
LC/MS: Condition 7, retention time 4.49 min
LC/MS (ESI$^+$) m/z; 372 [M+1]$^+$
LC/MS (ESI$^-$) m/z; 370 [M−1]$^-$ Compounds were synthesized in the same manner as in Synthetic Example 1, and the yields and morphology of the resulting compounds, the LC/MS conditions used for their analysis and the observed peaks and retention times are shown in Table 32.

TABLE 32

| Synthetic Example No. | Yield (%) | Morphology | LC/MS Condition | Observed peak ESI$^+$ | Observed peak ESI$^-$ | Retention time (min) |
|---|---|---|---|---|---|---|
| 381 | 32 | Light brown amorphous | 7 | 462 | 460 | 3.54 |
| 382 | 55 | Light brown amorphous | 7 | 490 | 488 | 3.69 |
| 383 | 49 | Light brown amorphous | 7 | 476 | 474 | 3.52 |

Synthetic Examples 381 to 383

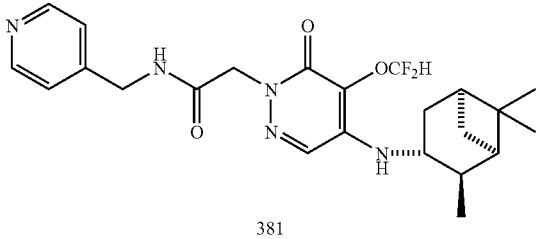

381

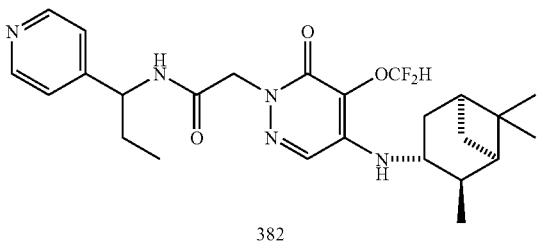

382

TABLE 32-continued

| Synthetic Example No. | Yield (%) | Morphology | LC/MS Condition | Observed peak ESI+ | Observed peak ESI− | Retention time (min) |
|---|---|---|---|---|---|---|

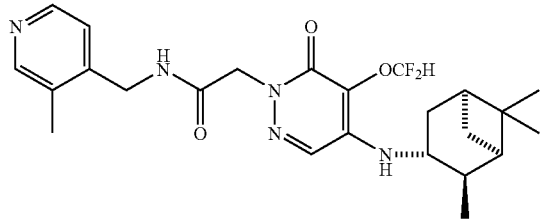

383

SYNTHETIC EXAMPLES 384 TO 386

4-Methoxy-2-(tetrahydro-2H-pyran-2-yl)-5-{[(1R,2R,3R,5S)-2,6,6-trimethylbicyclo[3.1.1]hept-3-yl]amino}pyridazin-3(2H)-one

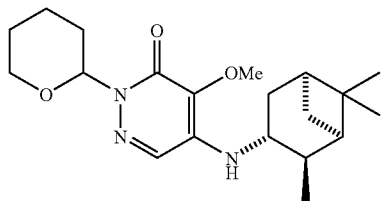

4-Hydroxy-2-(tetrahydro-2H-pyran-2-yl)-5-{[(1R,2R,3R,5S)-2,6,6-trimethylbicyclo[3.1.1]hept-3-yl]amino}pyridazin-3(2H)-one (250 mg, 0.72 mmol) in N,N-dimethylformamide (2.5 mL) was mixed with methyl iodide (70 μL, 0.76 mmol) and potassium carbonate (104 mg, 0.76 mmol) at room temperature and stirred at 65° C. for 1 hour. After completion of the reaction, ethyl acetate was added, and the organic layer was washed with saturated aqueous ammonium chloride and saturated aqueous sodium chloride, dried over anhydrous sodium sulfate and evaporated under reduced pressure. The resulting residue was purified by silica gel column chromatography (hexane/ethyl acetate=3/1 to 1/1) to give the desired product (154 mg, 59% yield).

Morphology: light brown oil

4-Methoxy-5-{[(1R,2R,3R,5S)-2,6,6-trimethylbicyclo[3.1.1]hept-3-yl]amino}pyridazin-3(2H)-one

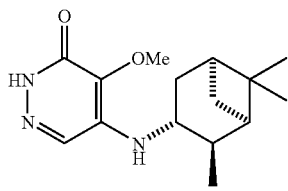

Synthesis was carried out in the same manner as in Synthetic Example 381 by using 4-methoxy-2-(tetrahydro-2H-pyran-2-yl)-5-{[(1R,2R,3R,5S)-2,6,6-trimethylbicyclo[3.1.1]hept-3-yl]amino}pyridazin-3(2H)-one.

Yield: 44%

Morphology: colorless solid

LC/MS: Condition 7, retention time 4.11 min

LC/MS (ESI+) m/z; 278 [M+1]+

[5-Methoxy-6-oxo-4-{[(1R,2R,3R,5S)-2,6,6-trimethylbicyclo[3.1.1]hept-3-yl]amino}pyridazin-1(6H)-yl] acetic Acid Synthesis was carried out in the same manner as in Synthetic Example 1 by using 4-methoxy-5-{[(1R,2R,3R,5S)-2,6,6-trimethylbicyclo[3.1.1]hept-3-yl]amino}pyridazin-3(2H)-one.

Yield: 55% (two steps)

Morphology: light brown amorphous

LC/MS: Condition 7, retention time 4.20 min

LC/MS (ESI+) m/z; 336 [M+1]+

LC/MS (ESI−) m/z; 334 [M−1]−

Compounds were synthesized in the same manner as in Synthetic Example 1, and the yields and morphology of the resulting compounds, the LC/MS conditions used for their analysis and the observed peaks and retention times are shown in Table 33.

TABLE 33

| Synthetic Example No. | Yield (%) | Morphology | LC/MS Condition | Observed peak ESI⁺ | Observed peak ESI⁻ | Retention time (min) |
|---|---|---|---|---|---|---|
| 384 | — | Pale yellow solid | 7 | 426 | 424 | 3.37 |
| 385 | — | Pale yellow amorphous | 7 | 454 | 452 | 3.51 |
| 386 | — | Pale yellow solid | 7 | 440 | 438 | 3.37 |

Synthetic Examples 384 to 386

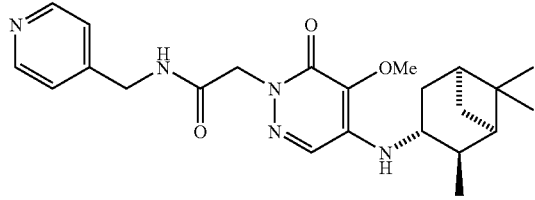

384

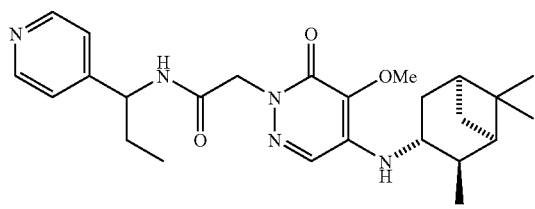

385

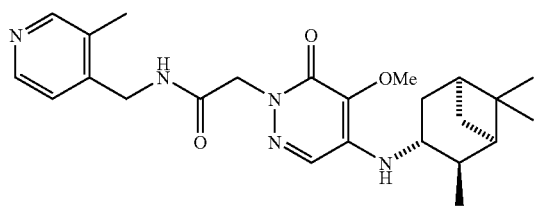

386

SYNTHETIC EXAMPLE 387

2-[5-Cyano-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide

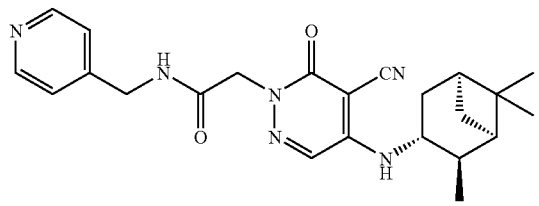

2-[5-Bromo-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide (100 mg, 0.21 mmol) in N-methylpyrrolidone (2.5 mL) was mixed with copper cyanide (100 mg, 1.05 mmol) at room temperature and stirred at 110° C. for 24 hours. After completion of the reaction, the reaction solution was mixed with water and extracted with ethyl acetate and chloroform. The extract was dried over anhydrous magnesium sulfate and evaporated under reduced pressure. The resulting residue was purified by silica gel column chromatography (chloroform/methanol=10/1) to give the desired product (4.3 mg, 5% yield).

Morphology: colorless solid

LC/MS: Condition 7, retention time 2.95 min

LC/MS (ESI⁺) m/z; 421 [M+1]⁺

LC/MS (ESI⁻) m/z; 419 [M−1]⁻

¹H-NMR (CDCl₃)

δ: 0.92-0.99 (m, 1H), 1.05 (s, 3H), 1.17 (d, J=7.2 Hz, 3H), 1.27 (s, 3H), 1.83-2.11 (m, 3H), 2.46-2.52 (m, 1H), 2.58-2.72

(m, 1H), 2.92-3.02 (m, 1H), 3.92-4.05 (m, 1H), 4.54 (d, J=6.0 Hz, 2H), 4.80 (s, 2H), 7.19 (d J=5.7 Hz, 2H), 6.68-6.78 (m, 1H), 8.51 (d, J=5.1 Hz, 2H)

SYNTHETIC EXAMPLE 388

4-[({5-Bromo-6-oxo-4-{[(1R,2R,3R,5S)-2,6,6-trimethylbicyclo[3.1.1]hept-3-yl]amino}pyridazin-1(6H)-yl]acetyl}amino)methyl]pyridine-2-carboxamide

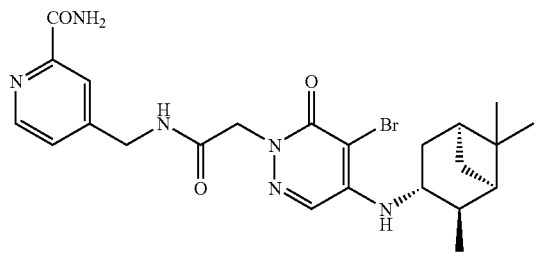 [SMILES: C[C@@H]1[C@H]2C[C@@H](C[C@H]1Nc1cnn(CC(=O)NCc3ccnc(C(N)=O)c3)c(=O)c1Br)C2(C)C]

2-[5-Bromo-6-oxo-4-{[(1R,2R,3R,5S)-2,6,6-trimethylbicyclo[3.1.1]hept-3-yl]amino}pyridazin-1(6H)-yl]-N-[(2-cyanopyridin-4-yl)methyl]acetamide (34.0 mg, 0.07 mmol) was dissolved in ethanol/30% aqueous potassium hydroxide (4 mL, 1:1) and stirred at 80° C. for 2 hours. After cooling, ethyl acetate was added, and the organic layer was washed with saturated aqueous ammonium chloride, dried over anhydrous sodium sulfate and evaporated under reduced pressure. The resulting residue was purified by silica gel column chromatography (ethyl acetate/methanol=8/1) to give the desired product.

Yield: 6%
Morphology: colorless solid
LC/MS: Condition 7, retention time 4.13 min
LC/MS (ESI$^+$) m/z; 517, 519 [M+1]$^+$
LC/MS (ESI$^-$) m/z; 515, 517 [M-1]$^-$

SYNTHETIC EXAMPLE 389

2-[5-Chloro-6-oxo-4-{[(1R,2R,3R,5S)-2,6,6-trimethylbicyclo[3.1.1]hept-3-yl]amino}-3-{[2-(trimethylsilyl)ethoxy]methoxy}pyridazin-1(6H)-yl]-N-(pyridin-4-ylmethyl)acetamide

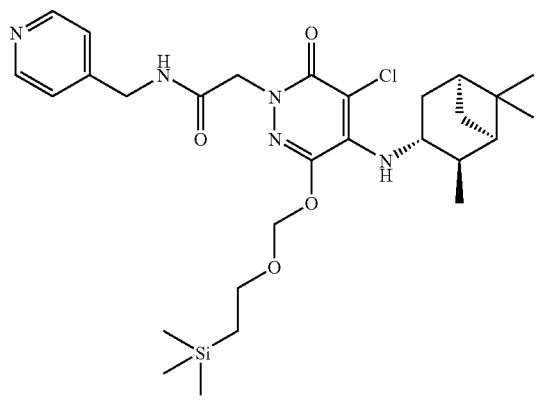 [SMILES: C[C@@H]1[C@H]2C[C@@H](C[C@H]1Nc1c(OCOCC[Si](C)(C)C)nn(CC(=O)NCc3ccncc3)c(=O)c1Cl)C2(C)C]

4-Chloro-5-{[(1R,2R,3R,5S)-2,6,6-trimethylbicyclo[3.1.1]hept-3-yl]amino}-6-{[2-(trimethylsilyl)ethoxy]methoxy}pyridazin-3(2H)-one

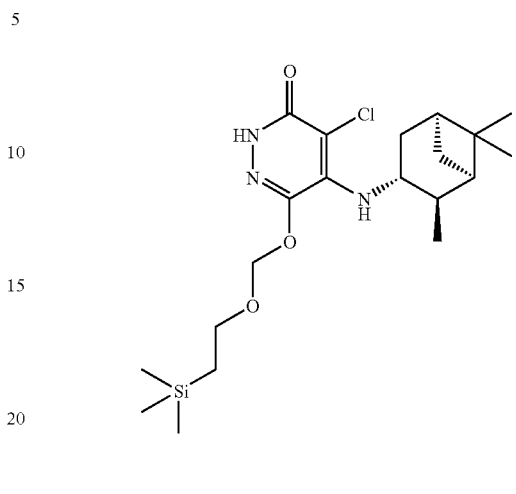

Synthesis was carried out in the same manner as in Synthetic Example 1 by using 4,5-dichloro-6-{[2-(trimethylsilyl)ethoxy]methoxy}pyridazin-3(2H)-one, and the resulting crude reaction product was used for the next step.

Ethyl[5-chloro-6-oxo-4-{[(1R,2R,3R,5S)-2,6,6-trimethylbicyclo[3.1.1]hept-3-yl]amino}-3-{[2-(trimethylsilyl)ethoxy]methoxy}pyridazin-1(6H)-yl]acetate

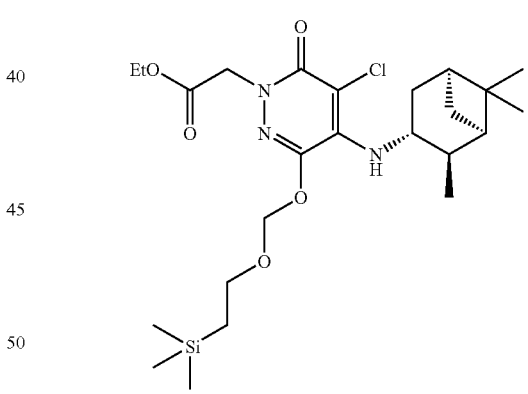

Synthesis was carried out in the same manner as in Synthetic Example 1 by using 4-Chloro-5-{[(1R,2R,3R,5S)-2,6,6-trimethylbicyclo[3.1.1]hept-3-yl]amino}-6-{[2-(trimethylsilyl)ethoxy]methoxy}pyridazin-3(2H)-one (27% yield, two steps).

Morphology: colorless amorphous
LC/MS: Condition 7, retention time 5.77 min
LC/MS (ESI$^+$) m/z; 514, 516 [M+1]$^+$
LC/MS (ESI$^-$) m/z; 512, 514 [M-1]$^-$

[5-Chloro-6-oxo-4-{[(1R,2R,3R,5S)-2,6,6-trimethylbicyclo[3.1.1]hept-3-yl]amino}-3-{[2-(trimethylsilyl)ethoxy]methoxy}pyridazin-1(6H)-yl]acetic Acid

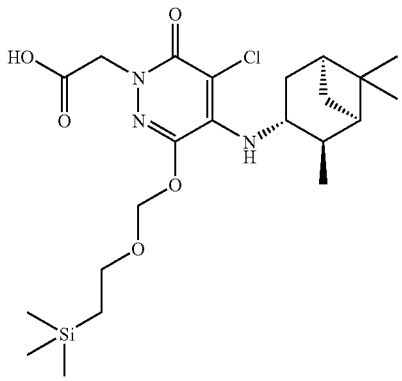 [SMILES: C[C@@H]1[C@H]2C[C@@H](C[C@H]1Nc1c(OCOCC[Si](C)(C)C)nn(CC(=O)O)c(=O)c1Cl)C2(C)C]

Synthesis was carried out in the same manner as in Synthetic Example 1 by using ethyl[5-chloro-6-oxo-4-{[(1R,2R,3R,5S)-2,6,6-trimethylbicyclo[3.1.1]hept-3-yl]amino}-3-{[2-(trimethylsilyl)ethoxy]methoxy}pyridazin-1(6H)-yl]acetate (99% yield).
Morphology: colorless oil 2-[5-Chloro-6-oxo-4-{[(1R,2R,3R,5S)-2,6,6-trimethylbicyclo[3.1.1]hept-3-yl]amino}-3-{[2-(trimethylsilyl)ethoxy]methoxy}pyridazin-1(6H)-yl]-N-(pyridin-4-ylmethyl)acetamide Synthesis was carried out in the same manner as in Synthetic Example 1 by using [5-chloro-6-oxo-4-{[(1R,2R,3R,5S)-2,6,6-trimethylbicyclo[3.1.1]hept-3-yl]amino}-3-{[2-(trimethylsilyl)ethoxy]methoxy}pyridazin-1(6H)-yl]acetic acid (29% yield).
Morphology: colorless amorphous
LC/MS: Condition 7, retention time 4.44 min
LC/MS (ESI$^+$) m/z; 576, 578 [M+1]$^+$
LC/MS (ESI$^-$) m/z; 574, 576 [M−1]$^-$
$^1$H-NMR (CDCl$_3$)
δ: 0.01 (s, 9H), 0.85-0.98 (m, 3H), 0.99 (s, 3H), 1.12 (dd, J=6.9, 0.9 Hz, 3H), 1.24 (s, 3H), 1.67 (dd, J=13.9, 6.1 Hz, 1H), 1.78-1.91 (m, 2H), 1.93-2.02 (m, 1H), 2.42-2.48 (m, 1H), 2.56 (t, J=11.6 Hz, 1H), 3.66-3.77 (m, 2H), 4.54 (m, 2H), 4.66-4.73 (m, 1H), 4.80-4.92 (m, 3H), 5.27 (s, 2H), 7.18-7.22 (m, 2H), 7.98 (s, 1H), 8.50-8.54 (m, 2H)

SYNTHETIC EXAMPLE 390

2-[5-Chloro-3-hydroxy-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide Hydrochloride

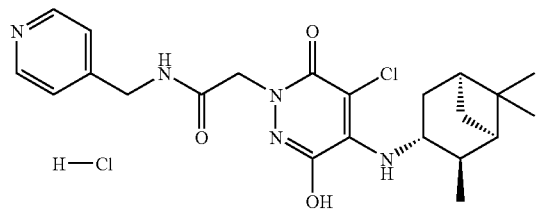 [SMILES: C[C@@H]1[C@H]2C[C@@H](C[C@H]1Nc1c(O)nn(CC(=O)NCc3ccncc3)c(=O)c1Cl)C2(C)C ; Cl]

2-[5-Chloro-6-oxo-4-{[(1R,2R,3R,5S)-2,6,6-trimethylbicyclo[3.1.1]hept-3-yl]amino}-3-{[2-(trimethylsilyl)ethoxy]methoxy}pyridazin-1(6H)-yl]-N-(pyridin-4-ylmethyl)acetamide (12 mg, 0.0208 mmol) in methanol (1 mL) was stirred with 10 mass % hydrogen chloride-methanol (5 mL) at 60° C. for 5 hours. After completion of the reaction, the reaction solution was concentrated under reduced pressure and purified by preparative HPLC to give the desired product.
Morphology: colorless amorphous
LC/MS: Condition 7, retention time 4.18/4.32 min
LC/MS (ESI$^+$) m/z; 446, 448 [m+1]$^+$
LC/MS (ESI$^-$) m/z; 444, 446 [M−1]$^-$

SYNTHETIC EXAMPLE 391

2-[5-Bromo-3-nitro-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide

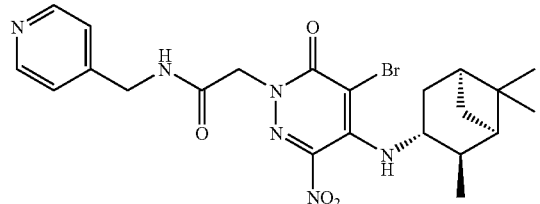

4,5-Dibromo-6-nitropyridazin-3(2H)-one

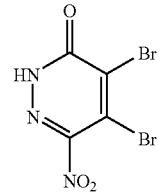

To 4,5-dibromopyridazin-3(2H)-one (2 g, 7.87 mmol) in concentrated sulfuric acid (12 mL), fuming nitric acid (978 μL, 23.8 mmol) was gradually added at 100° C. with stirring, and the resulting reaction solution was stirred at 100° C. for 3 hours. After completion of the reaction, the reaction solution was cooled to room temperature and poured onto ice-cold water. The precipitated crystals were collected by filtration and dried under reduced pressure to give the desired product (2.2 g, 93%).
Morphology: colorless solid
LC/MS: Condition 7, retention time 3.23 min
LC/MS (ESI$^+$) m/z; 298, 300, 302 [M+1]$^+$
LC/MS (ESI$^-$) m/z; 296, 298, 300 [M−1]$^-$ 4-Bromo-6-nitro-5-{[(1R,2R,3R,5S)-2,6,6-trimethylbicyclo[3.1.1]hept-3-yl]amino}pyridazin-3(2H)-one

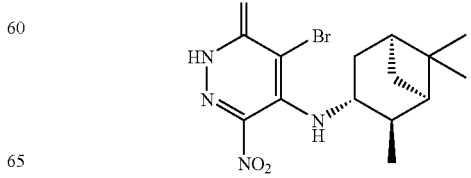

Synthesis was carried out in the same manner as in Synthetic Example 1 by using 4,5-dibromo-6-nitropyridazin-3(2H)-one (48% yield).
Morphology: yellow solid
LC/MS: Condition 7, retention time 4.73 min
LC/MS (ESI⁺) m/z; 371, 373 [M+1]⁺
LC/MS (ESI⁻) m/z; 369, 371 [M−1]⁻

Ethyl[5-bromo-3-nitro-6-oxo-4-{[(1R,2R,3R,5S)-2,6,6-trimethylbicyclo[3.1.1]hept-3-yl]amino}pyridazin-1(6H)-yl]acetate

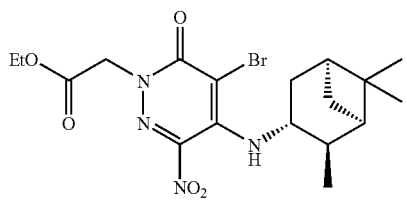 [SMILES: C[C@@H]1[C@H]2C[C@@H](C[C@H]1Nc1c([N+](=O)[O-])nn(CC(=O)O)c(=O)c1Br)C2(C)C]

Synthesis was carried out in the same manner as in Synthetic Example 1 by using 4-bromo-6-nitro-5-{[(1R,2R,3R,5S)-2,6,6-trimethylbicyclo[3.1.1]hept-3-yl]amino}pyridazin-3(2H)-one (90% yield).
Morphology: yellow oil
LC/MS: Condition 7, retention time 5.18 min
LC/MS (ESI⁺) m/z; 457, 459 [M+1]⁺
LC/MS (ESI⁻) m/z; 455, 457 [M−1]⁻

[5-Bromo-3-nitro-6-oxo-4-{[(1R,2R,3R,5S)-2,6,6-trimethylbicyclo[3.1.1]hept-3-yl]amino}pyridazin-1(6H)-yl]acetic Acid

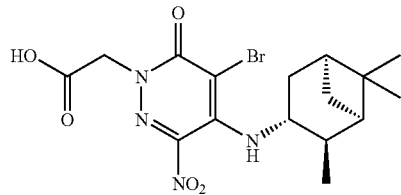

Synthesis was carried out in the same manner as in Synthetic Example 1 by using ethyl[5-bromo-3-nitro-6-oxo-4-{[(1R,2R,3R,5S)-2,6,6-trimethylbicyclo[3.1.1]hept-3-yl]amino}pyridazin-1(6H)-yl]acetate (83% yield).
Morphology: yellow oil
LC/MS: Condition 7, retention time 4.88 min
LC/MS (ESI⁺) m/z; 429, 431 [M+1]⁺
LC/MS (ESI⁻) m/z; 427, 429 [M−1]⁻

2-[5-Bromo-3-nitro-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide Synthesis was carried out in the same manner as in Synthetic Example 1 by using [5-bromo-3-nitro-6-oxo-4-{[(1R,2R,3R,5S)-2,6,6-trimethylbicyclo[3.1.1]hept-3-yl]amino}pyridazin-1(6H)-yl]acetic acid (56% yield).
Morphology: yellow oil
LC/MS: Condition 7, retention time 3.80 min
LC/MS (ESI⁺) m/z; 519, 521 [M+1]⁺

LC/MS (ESI⁻) m/z; 517, 519 [M−1]⁻
¹H-NMR (CDCl₃)
δ: 0.90 (d, J=10.2 Hz, 1H), 1.00 (s, 3H), 1.13 (d, J=7.2 Hz, 3H), 1.25 (s, 3H), 1.67-1.73 (m, 1H), 1.86-1.95 (m, 2H), 1.96-2.04 (m, 1H), 2.43-2.64 (m, 2H), 4.48 (d, J=6.3 Hz, 2H), 4.49-4.61 (m, 1H), 4.88 (s, 2H), 6.45 (d, J=9.3 Hz, 1H), 6.86-6.94 (m, 1H), 7.19 (d, J=6.3 Hz, 2H), 8.54 (d, J=6.3 Hz, 2H)

SYNTHETIC EXAMPLE 392

2-[3-Amino-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide

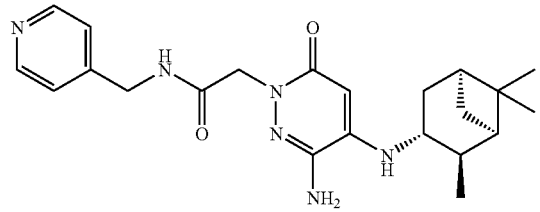 [SMILES: C[C@@H]1[C@H]2C[C@@H](C[C@H]1Nc1cc(=O)n(CC(=O)NCc3ccncc3)nc1N)C2(C)C]

2-[5-Bromo-3-nitro-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide (11 mg, 0.0211 mmol) in methanol (1 mL) was stirred with 10 mass % palladium-carbon (about 5 mg) in a hydrogen atmosphere at room temperature for 2.5 hours. The reaction solution was filtered through celite and evaporated under reduced pressure. The resulting residue was purified by silica gel column chromatography (chloroform/methanol=10/1) to give the desired product (1.5 mg, 17% yield).
Morphology: colorless amorphous
LC/MS: Condition 7, retention time 3.03 min
LC/MS (ESI⁺) m/z; 411 [M+1]⁺
LC/MS (ESI⁻) m/z; 409 [M−1]⁻

SYNTHETIC EXAMPLE 393

2-[3-Amino-5-bromo-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide

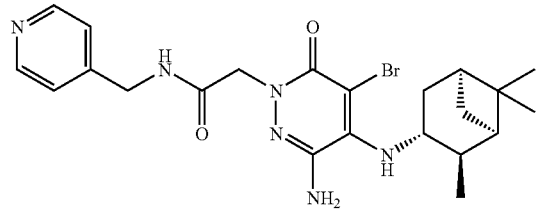

2-[5-Bromo-3-nitro-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide (32 mg, 0.0616 mmol) in ethyl acetate (3 mL) was stirred with tin (II) chloride dihydrate (72 mg, 0.319 mmol) at room temperature for 2 hours. After completion of the reaction, the reaction solution was basified to pH 9-10 with aqueous sodium hydroxide and filtered through celite. The filtrate was extracted with ethyl acetate, and the extract was dried over anhydrous magnesium sulfate and evaporated under reduced pressure. The resulting residue was purified by silica gel column chromatography (chloroform/methanol=6/1) to give the desired product (13 mg, 43% yield).

Morphology: colorless solid
LC/MS: Condition 7, retention time 3.43 min
LC/MS (ESI$^+$) m/z; 489, 491 [M+1]$^+$
LC/MS (ESI$^-$) m/z; 487, 489 [M−1]$^-$
$^1$H-NMR (DMSO-d6)
δ: 0.97-1.03 (m, 6H), 1.14 (d, J=9.6 Hz, 1H), 1.21 (s, 3H), 1.67 (dd, J=12.9, 6.7 Hz, 1H), 1.79 (t, J=6.1 Hz, 1H), 1.90-1.97 (m, 1H), 2.07-2.14 (m, 1H), 2.26-2.44 (m, 2H), 4.30 (d, J=6.3 Hz, 2H), 4.51 (s, 2H), 4.73-4.79 (m, 1H), 5.30 (d, J=9.9 Hz, 1H), 5.70 (s, 2H), 7.25 (d, J=6.0 Hz, 2H), 8.45-8.55 (m, 3H)

SYNTHETIC EXAMPLE 394

4-Bromo-2-(pyridin-4-ylmethyl)-5-{[(1R,2R,3R,5S)-2,6,6-trimethylbicyclo[3.1.1]hept-3-yl]amino}pyridazin-3(2H)-one

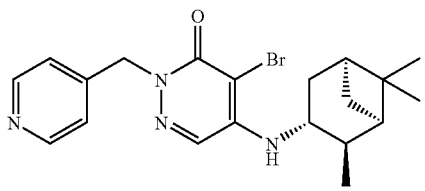 [SMILES: C[C@@H]1[C@H]2C[C@@H](C[C@H]1Nc1cnn(Cc3ccncc3)c(=O)c1Br)C2(C)C]

4,5-Dibromo-2-(pyridin-4-ylmethyl)pyridazin-3(2H)-one

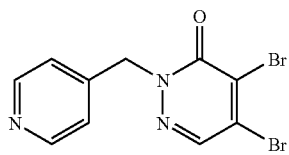 [SMILES: O=c1c(Br)c(Br)cnn1Cc1ccncc1]

4-Picolylhydrazine hydrochloride (500 mg, 3.13 mmol), mucobromic acid (807 mg, 3.13 mmol) and concentrated hydrochloric acid (500 μL) in ethanol (5 mL) were stirred at 90° C. for 1 day. After completion of the reaction, the resulting crystals were collected by filtration, washed with methanol and dried to give the desired product (59% yield).
Morphology: colorless solid
LC/MS: Condition 7, retention time 3.70 min
LC/MS (ESI$^+$) m/z; 344, 346, 348 [M+1]$^+$
$^1$H-NMR (CDCl$_3$)
δ: 2.50 (m, 2H), 5.57 (s, 1H), 7.83 (d, J=6.6 Hz, 2H), 8.82 (d, J=6.6 Hz, 2H).

4-Bromo-2-(pyridin-4-ylmethyl)-5-{[(1R,2R,3R,5S)-2,6,6-trimethylbicyclo[3.1.1]hept-3-yl]amino}pyridazin-3(2H)-one Synthesis was carried out in the same manner as in Synthetic Example 48 by using 4,5-dibromo-2-(pyridin-4-ylmethyl)pyridazin-3(2H)-one.
Yield: 86%
Morphology: pale pink oil

SYNTHETIC EXAMPLE 395

2-[5-Bromo-6-oxo-4-{[(1R,2R,3R,5S)-2,6,6-trimethylbicyclo[3.1.1]hept-3-yl]amino}pyridazin-1(6H)-yl]-N-[(3S)-pyrrolidin-3-ylmethyl]acetamide

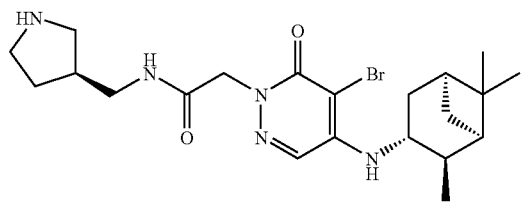 [SMILES: C[C@@H]1[C@H]2C[C@@H](C[C@H]1Nc1cnn(CC(=O)NC[C@H]3CCNC3)c(=O)c1Br)C2(C)C]

t-Butyl (3S)-3-[({[5-bromo-6-oxo-4-{[(1R,2R,3R,5S)-2,6,6-trimethylbicyclo[3.1.1]hept-3-yl]amino}pyridazin-1(6H)-yl]acetyl}amino)methyl]pyrrolidine-1-carboxylate (72.5 mg, 0.13 mmol) in dichloromethane (2 mL) was mixed with trifluoroacetic acid (19.7 μL, 0.26 mmol) at room temperature and stirred at room temperature for 12 hours. After completion of the reaction, ethyl acetate was added, and the organic layer was washed with saturated aqueous sodium hydrogen carbonate, dried over anhydrous sodium sulfate and evaporated under reduced pressure. The resulting residue was purified by silica gel column chromatography (ethyl acetate/methanol=20/1) to give the desired product.
Yield: 29.6 mg (49%)
Morphology: pale yellow amorphous
LC/MS: Condition 7, retention time 3.50 min
LC/MS (ESI$^+$) m/z; 466, 468 [M+1]$^+$
LC/MS (ESI$^-$) m/z; 464, 466 [M−1]$^-$

SYNTHETIC EXAMPLE 396

2-[5-Bromo-6-oxo-4-{[(1R,2R,3R,5S)-2,6,6-trimethylbicyclo[3.1.1]hept-3-yl]amino}pyridazin-1(6H)-yl]-N-[(2R)-pyrrolidin-2-ylmethyl]acetamide

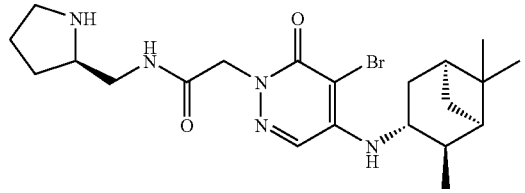 [SMILES: C[C@@H]1[C@H]2C[C@@H](C[C@H]1Nc1cnn(CC(=O)NC[C@H]3CCCN3)c(=O)c1Br)C2(C)C]

Synthesis was carried out in the same manner as in Synthetic Example 395 by using tert-butyl (2R)-2-[({[5-bromo-6-oxo-4-{[(1R,2R,3R,5S)-2,6,6-trimethylbicyclo[3.1.1]hept-3-yl]amino}pyridazin-1(6H)-yl]acetyl}amino)methyl]pyrrolidine-1-carboxylate.
Yield: 38.5 mg (52%)
Morphology: pale yellow amorphous
LC/MS: Condition 7, retention time 3.51 min
LC/MS (ESI$^+$) m/z; 466, 468 [M+1]$^+$
LC/MS (ESI$^-$) m/z; 464, 466 [M−1]$^-$

SYNTHETIC EXAMPLE 397

2-[5-Bromo-6-oxo-4-{[(1R,2R,3R,5S)-2,6,6-trimethylbicyclo[3.1.1]hept-3-yl]amino}pyridazin-1(6H)-yl]-N-(piperidin-4-ylmethyl)acetamide

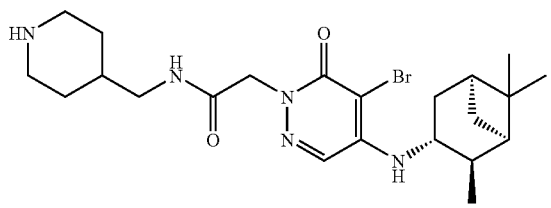 [SMILES: C[C@@H]1[C@H]2C[C@@H](C[C@H]1Nc1cnn(CC(=O)NCC3CCNCC3)c(=O)c1Br)C2(C)C]

t-Butyl 4-[({[5-bromo-6-oxo-4-{[(1R,2R,3R,5S)-2,6,6-trimethylbicyclo[3.1.1]hept-3-yl]amino}pyridazin-1(6H)-yl]acetyl}amino)methyl]piperidine-1-carboxylate (34.4 mg, 0.06 mmol) was dissolved in 4 M hydrogen chloride/1,4-dioxane (1 mL) and stirred at room temperature for 2 hours. After completion of the reaction, ethyl acetate was added, and the organic layer was washed with saturated aqueous ammonium chloride and saturated aqueous sodium chloride, dried over anhydrous magnesium sulfate and evaporated under reduced pressure. The resulting residue was purified by silica gel column chromatography (chloroform/methanol=50/1) to give the desired product.
Yield: 19.1 mg (67%)
Morphology: yellow amorphous
LC/MS: Condition 7, retention time 3.10 min
LC/MS (ESI⁺) m/z; 480, 482 [M+1]⁺
LC/MS (ESI⁻) m/z; 478, 480 [M−1]⁻

SYNTHETIC EXAMPLE 398

2-[5-Bromo-6-oxo-4-{[(1R,2R,3R,5S)-2,6,6-trimethylbicyclo[3.1.1]hept-3-yl]amino}pyridazin-1(6H)-yl]-3-(pyridin-4-yl)propanoic Acid

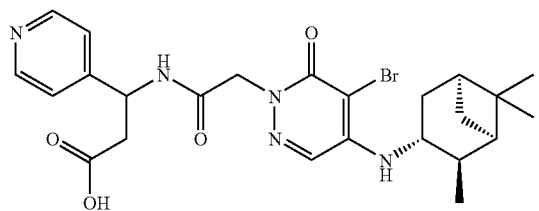 [SMILES: C[C@@H]1[C@H]2C[C@@H](C[C@H]1Nc1cnn(CC(=O)NC(CC(=O)O)c3ccncc3)c(=O)c1Br)C2(C)C]

Ethyl 2-[5-bromo-6-oxo-4-{[(1R,2R,3R,5S)-2,6,6-trimethylbicyclo[3.1.1]hept-3-yl]amino}pyridazin-1(6H)-yl]-3-(pyridin-4-yl)propanoate (165 mg, 0.294 mmol) in 1,4-dioxane (4 mL) was stirred with 1 M aqueous sodium hydroxide (1 mL) at room temperature for 4 hours. After completion of the reaction, the reaction solution was neutralized with 1 M hydrochloric acid and extracted with ethyl acetate. The extract was dried over anhydrous magnesium sulfate and evaporated under reduced pressure to give the desired product (156 mg, quant).
Morphology: colorless solid
LC/MS: Condition 7, retention time 3.68 min
LC/MS (ESI⁺) m/z; 532, 534 [M+1]⁺
LC/MS (ESI⁻) m/z; 530, 532 [M−1]⁻

SYNTHETIC EXAMPLE 399

N-{2-[5-Bromo-6-oxo-4-{[(1R,2R,3R,5S)-2,6,6-trimethylbicyclo[3.1.1]hept-3-yl]amino}pyridazin-1(6H)-yl]ethyl}pyridine-4-carboxamide

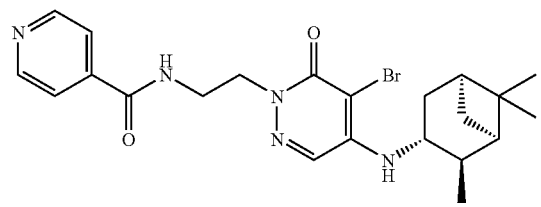 [SMILES: C[C@@H]1[C@H]2C[C@@H](C[C@H]1Nc1cnn(CCNC(=O)c3ccncc3)c(=O)c1Br)C2(C)C]

2-{2-[5-Bromo-6-oxo-4-{[(1R,2R,3R,5S)-2,6,6-trimethylbicyclo[3.1.1]hept-3-yl]amino}pyridazin-1(6H)-yl]ethyl}-1H-isoindole-1,3(2H)-dione

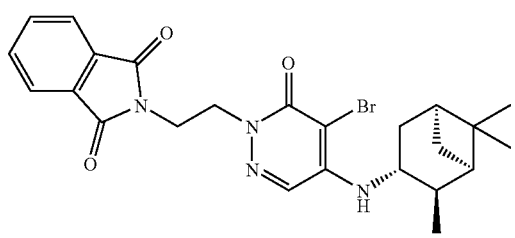 [SMILES: C[C@@H]1[C@H]2C[C@@H](C[C@H]1Nc1cnn(CCN3C(=O)c4ccccc4C3=O)c(=O)c1Br)C2(C)C]

4-Bromo-5-{[(1R,2R,3R,5S)-2,6,6-trimethylbicyclo[3.1.1]hept-3-yl]amino}pyridazin-3(2H)-one (100 mg, 0.306 mmol) and potassium carbonate (51 mg, 0.0369 mmol) in N,N-dimethylformamide (3 mL) were stirred with 2-(2-bromoethyl)-1H-isoindole-1,3(2H)-dione (93 mg, 0.366 mmol) at 80° C. for 7 hours. After completion of the reaction, the reaction solution was mixed with aqueous ammonium chloride and extracted with ethyl acetate. The extract was dried over anhydrous magnesium sulfate and evaporated under reduced pressure. The resulting residue was used for the next reaction without purification.
LC/MS: Condition 7, retention time 4.14 min
LC/MS (ESI⁺) m/z; 499, 501 [M+1]⁺

2-(2-Aminoethyl)-4-bromo-5-{[(1R,2R,3R,5S)-2,6,6-trimethylbicyclo[3.1.1]hept-3-yl]amino}pyridazin-3(2H)-one

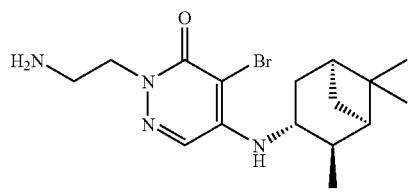 [SMILES: C[C@@H]1[C@H]2C[C@@H](C[C@H]1Nc1cnn(CCN)c(=O)c1Br)C2(C)C]

2-{2-[5-Bromo-6-oxo-4-{[(1R,2R,3R,5S)-2,6,6-trimethylbicyclo[3.1.1]hept-3-yl]amino}pyridazin-1(6H)-yl]ethyl}-1H-isoindole-1,3(2H)-dione prepared above in methanol (6 mL) was stirred with hydrazine monohydrate (50 μL, 1.6 mmol) at 80° C. for 6 hours. After completion of the reaction, the solvent was removed by vacuum distillation, and the resulting residue was purified by silica gel column chromatography (ethyl acetate/methanol=4/1) to give the desired product (32 mg, 28% yield).

Morphology: colorless amorphous
LC/MS: Condition 7, retention time 3.38 min
LC/MS (ESI$^+$) m/z; 369, 371 [M+1]$^+$
LC/MS (ESI$^-$) m/z; 367, 369 [M−1]$^-$
$^1$H-NMR (CDCl$_3$)
δ: 0.97 (d, J=9.9 Hz, 1H), 1.05 (8, 3H), 1.19 (d, J=6.9 Hz, 3H), 1.27 (s, 3H), 1.69-1.77 (m, 1H), 1.88-2.08 (m, 3H), 2.43-2.51 (m, 1H), 2.56-2.69 (m, 1H), 3.11 (t, J=6.0 Hz, 2H), 3.78-3.91 (m, 1H), 4.22 (t, J=6.0 Hz, 2H), 4.67 (d, J=8.4 Hz, 1H), 7.52 (s, 1H)

N-{2-[5-Bromo-6-oxo-4-{[(1R,2R,3R,5S)-2,6,6-trimethylbicyclo[3.1.1]hept-3-yl]amino}pyridazin-1(6H)-yl]ethyl}pyridine-4-carboxamide 2-(2-Aminoethyl)-4-bromo-5-{[(1R,2R,3R,5S)-2,6,6-trimethylbicyclo[3.1.1]hept-3-yl]amino}pyridazin-3(2H)-one (28 mg, 0.0758 mmol) and triethylamine (21 μL, 0.152 mmol) in dichloromethane (1 mL) were stirred with pyridine-4-carbonyl chloride (20 mg, 0.112 mmol) at room temperature for 5 hours. After completion of the reaction, the reaction solution was mixed with water and extracted with ethyl acetate, and the extract was dried over anhydrous magnesium sulfate and evaporated under reduced pressure. The resulting residue was purified by silica gel column chromatography (ethyl acetate/methanol=9/1) to give the desired product (19 mg, 52% yield).

Morphology: colorless amorphous
LC/MS: Condition 7, retention time 4.35 min
LC/MS (ESI$^+$) m/z; 474, 476 [M+1]$^+$
LC/MS (ESI$^-$) m/z; 472, 474 [M−1]$^-$
$^1$H-NMR (CDCl$_3$)
δ: 0.96 (d, J=10.5 Hz, 1H), 1.06 (s, 3H), 1.19 (d, J=6.9 Hz, 3H), 1.27 (s, 3H), 1.72 (ddd, J=14.1, 5.7, 2.4 Hz, 1H), 1.89-2.05 (m, 3H), 2.43-2.51 (m, 1H), 2.58-2.70 (m, 1H), 3.79-3.91 (m, 3H), 4.48-4.54 (m, 2H), 4.80 (d, J=8.7 Hz, 1H), 7.57 (s, 1H), 7.68-7.78 (m, 2H), 8.17 (m, 1H), 8.72-8.75 (m, 2H)

SYNTHETIC EXAMPLE 400

N-{2-[5-Bromo-6-oxo-4-{[(1R,2R,3R,5S)-2,6,6-trimethylbicyclo[3.1.1]hept-3-yl]amino}pyridazin-1(6H)-yl]ethyl}pyridine-3-carboxamide

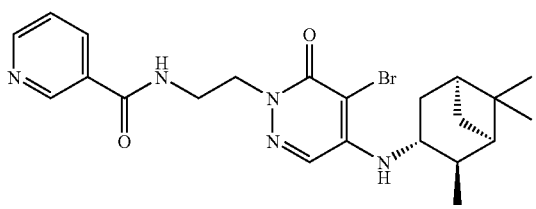 [SMILES: C[C@@H]1[C@H]2C[C@@H](C[C@H]1Nc1cnn(CCNC(=O)c3cccnc3)c(=O)c1Br)C2(C)C]

Synthesis was carried out in the same manner as in Synthetic Example 399 by using pyridine-3-carbonyl chloride (20% yield).

Morphology: colorless amorphous
LC/MS: Condition 7, retention time 4.40 min
LC/MS (ESI$^+$) m/z; 474, 476 [M+1]$^+$
LC/MS (ESI$^-$) m/z; 472, 474 [M−1]$^-$

SYNTHETIC EXAMPLE 401

2-({[5-Chloro-6-oxo-4-{[(1R,2R,3R,5S)-2,6,6-trimethylbicyclo[3.1.1]hept-3-yl]amino}pyridazin-1(6H)-yl]acetyl}amino)butyric Acid

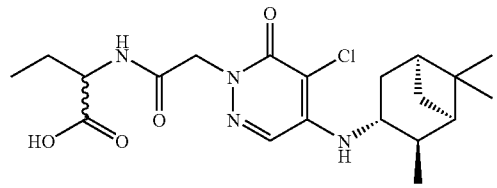 [SMILES: CCC(NC(=O)Cn1ncc(N[C@@H]2C[C@@H]3C[C@H]([C@H]2C)C3(C)C)c(Cl)c1=O)C(=O)O]

Ethyl 2-({[5-chloro-6-oxo-4-{[(1R,2R,3R,5S)-2,6,6-trimethylbicyclo[3.1.1]hept-3-yl]amino}pyridazin-1(6H)-yl]acetyl}amino)butyrate (64 mg, 0.145 mmol) in 1,4-dioxane (2 mL) was stirred with 1 M aqueous sodium hydroxide (435 μL, 0.435 mmol) at room temperature for 2 hours. After completion of the reaction, the reaction solution was neutralized with 1 M hydrochloric acid and extracted with ethyl acetate. The extract was dried over anhydrous magnesium sulfate and evaporated under reduced pressure to give the desired product.

Morphology: colorless solid
LC/MS: Condition 7, retention time 4.24 min
LC/MS (ESI$^+$) m/z; 425, 427 [M+1]$^+$
LC/MS (ESI$^-$) m/z; 423, 425 [M−1]$^-$

SYNTHETIC EXAMPLE 402

2-({[5-Chloro-6-oxo-4-{[(1R,2R,3R,5S)-2,6,6-trimethylbicyclo[3.1.1]hept-3-yl]amino}pyridazin-1(6H)-yl]acetyl}amino)butanamide

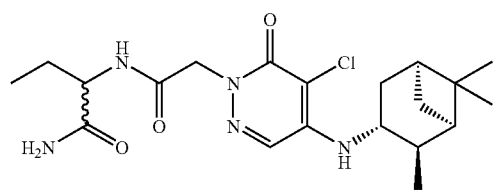 [SMILES: CCC(NC(=O)Cn1ncc(N[C@@H]2C[C@@H]3C[C@H]([C@H]2C)C3(C)C)c(Cl)c1=O)C(N)=O]

2-({[5-Chloro-6-oxo-4-{[(1R,2R,3R,5S)-2,6,6-trimethylbicyclo[3.1.1]hept-3-yl]amino}pyridazin-1(6H)-yl]acetyl}amino)butyric acid (48 mg, 0.113 mmol) in N,N-dimethylformamide (2 mL) was stirred with di-1H-imidazolylmethanone (55 mg, 0.340 mmol) at room temperature for 2 days and then with 30% aqueous ammonia (0.2 mL) at room temperature for 5 hours. After completion of the reaction, the reaction solution was mixed with water and extracted with ethyl acetate. The extract was dried over anhydrous magnesium sulfate and evaporated under reduced pressure. The residue was purified by silica gel column chromatography (ethyl acetate) to give the desired product (14 mg, 29% yield).

Morphology: colorless amorphous
LC/MS: Condition 7, retention time 4.08 min
LC/MS (ESI$^+$) m/z; 424, 426 [M+1]$^+$
LC/MS (ESI$^-$) m/z; 422, 424 [M−1]$^-$

SYNTHETIC EXAMPLE 403

({[5-Bromo-6-oxo-4-{[(1R,2R,3R,5S)-2,6,6-trimethylbicyclo[3.1.1]hept-3-yl]amino}pyridazin-1(6H)-yl]acetyl}amino)(phenyl)acetic Acid

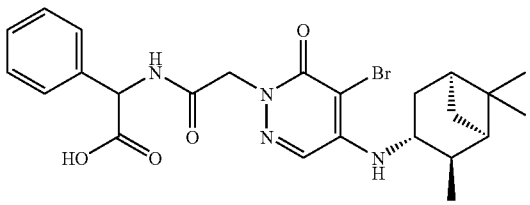 [SMILES: C[C@@H]1[C@H]2C[C@@H](C[C@H]1Nc1cnn(CC(=O)NC(C(=O)O)c3ccccc3)c(=O)c1Br)C2(C)C]

Synthesis was carried out in the same manner as in Synthetic Example 401 by using methyl({[5-bromo-6-oxo-4-{[(1R,2R,3R,5S)-2,6,6-trimethylbicyclo[3.1.1]hept-3-yl]amino}pyridazin-1(6H)-yl]acetyl}amino)(phenyl)acetate (99% yield).
Morphology: colorless amorphous
LC/MS: Condition 7, retention time 4.91 min
LC/MS (ESI⁻) m/z; 515, 517 [M−1]⁻

SYNTHETIC EXAMPLE 404

N-(2-Amino-2-oxo-1-phenylethyl)-2-[5-bromo-6-oxo-4-{[(1R,2R,3R,5S)-2,6,6-trimethylbicyclo[3.1.1]hept-3-yl]amino}pyridazin-1(6H)-yl]acetamide

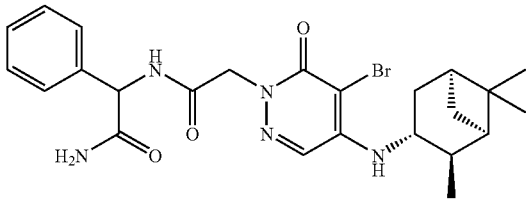 [SMILES: C[C@@H]1[C@H]2C[C@@H](C[C@H]1Nc1cnn(CC(=O)NC(C(N)=O)c3ccccc3)c(=O)c1Br)C2(C)C]

Synthesis was carried out in the same manner as in Synthetic Example 402 by using ({[5-bromo-6-oxo-4-{[(1R,2R,3R,5S)-2,6,6-trimethylbicyclo[3.1.1]hept-3-yl]amino}pyridazin-1(6H)-yl]acetyl}amino)(phenyl)acetic acid (21% yield).
Morphology: colorless solid
LC/MS: Condition 7, retention time 4.60 min
LC/MS (ESI⁺) m/z; 516, 518 [M+1]⁺
LC/MS (ESI⁻) m/z; 514, 516 [M−1]⁻

SYNTHETIC EXAMPLE 405

[5-Bromo-6-oxo-4-{[(1R,2R,3R,5S)-2,6,6-trimethylbicyclo[3.1.1]hept-3-yl]amino}pyridazin-1(6H)-yl]-2-fluoro-N-(pyridin-4-ylmethyl)acetamide

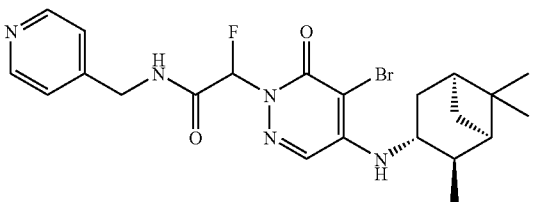 [SMILES: C[C@@H]1[C@H]2C[C@@H](C[C@H]1Nc1cnn(C(F)C(=O)NCc3ccncc3)c(=O)c1Br)C2(C)C]

Ethyl[5-bromo-6-oxo-4-{[(1R,2R,3R,5S)-2,6,6-trimethylbicyclo[3.1.1]hept-3-yl]amino}pyridazin-1(6H)-yl]fluoroacetate

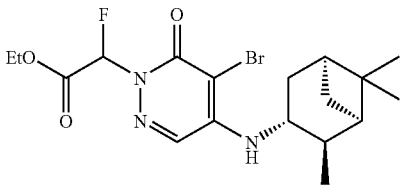 [SMILES: CCOC(=O)C(F)n1ncc(N[C@@H]2C[C@@H]3C[C@H]([C@H]2C)C3(C)C)c(Br)c1=O]

Synthesis was carried out in the same manner as in Synthetic Example 1 by using ethyl bromofluoroacetate (49% yield).
Morphology: pale yellow amorphous
LC/MS: Condition 7, retention time 5.01 min
LC/MS (ESI⁺) m/z; 430, 432 [M+1]⁺
LC/MS (ESI⁻) m/z; 428, 430 [M−1]⁻

[5-Bromo-6-oxo-4-{[(1R,2R,3R,5S)-2,6,6-trimethylbicyclo[3.1.1]hept-3-yl]amino}pyridazin-1(6H)-yl]fluoroacetic Acid

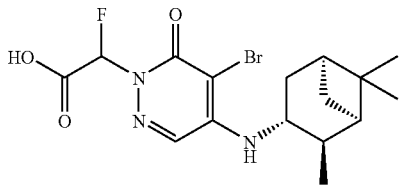 [SMILES: C[C@@H]1[C@H]2C[C@@H](C[C@H]1Nc1cnn(C(F)C(=O)O)c(=O)c1Br)C2(C)C]

Synthesis was carried out in the same manner as in Synthetic Example 1 by using ethyl[5-bromo-6-oxo-4-{[(1R,2R,3R,5S)-2,6,6-trimethylbicyclo[3.1.1]hept-3-yl]amino}pyridazin-1(6H)-yl]fluoroacetate, and the crude product was used for the next reaction.
LC/MS: Condition 7, retention time 5.15, 5.43 min
LC/MS (ESI⁺) m/z; 402, 404 [M+1]⁺

[5-Bromo-6-oxo-4-{[(1R,2R,3R,5S)-2,6,6-trimethylbicyclo[3.1.1]hept-3-yl]amino}pyridazin-1(6H)-yl]-2-fluoro-N-(pyridin-4-ylmethyl)acetamide Synthesis was carried out in the same manner as in Synthetic Example 1 by using [5-bromo-6-oxo-4-{[(1R,2R,3R,5S)-2,6,6-trimethylbicyclo[3.1.1]hept-3-yl]amino}pyridazin-1(6H)-yl]fluoroacetic acid (5% yield, two steps).
Morphology: colorless oil
LC/MS: Condition 7, retention time 3.75 min
LC/MS (ESI⁺) m/z; 492, 494 [M+1]⁺
LC/MS (ESI⁻) m/z; 490, 492 [M−1]⁻

SYNTHETIC EXAMPLE 406

3-Oxo-2-{2-oxo-2-[(pyridin-4-ylmethyl)amino]ethyl}-5-{[(1R,2R,3R,5S)-2,6,6-trimethylbicyclo[3.1.1]hept-3-yl]amino}-2,3-dihydropyridazine-4-carboxylic Acid

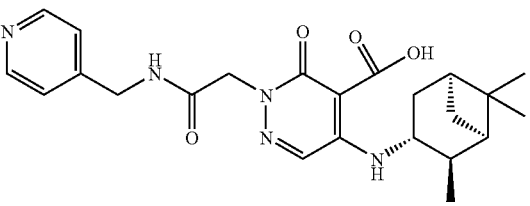 [SMILES: C[C@@H]1[C@H]2C[C@@H](C[C@H]1Nc1cnn(CC(=O)NCc3ccncc3)c(=O)c1C(=O)O)C2(C)C]

Synthesis was carried out in the same manner as in Synthetic Example 388 by using 2-[5-cyano-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide (3% yield).

Morphology: colorless oil
LC/MS: Condition 7, retention time 3.49 min
LC/MS (ESI+) m/z; 440 [M+1]+
LC/MS (ESI−) m/z; 438 [M−1]−

SYNTHETIC EXAMPLE 407

4-[({[5-Chloro-6-oxo-4-{[(1R,2R,3R,5S)-2,6,6-trimethylbicyclo[3.1.1]hept-3-yl]amino}pyridazin-1(6H)-yl]acetyl}amino)methyl]pyridine-2-carboxamide

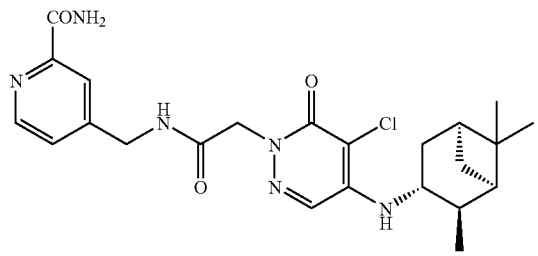 [SMILES: C[C@@H]1[C@H]2C[C@@H](C[C@H]1Nc1cnn(CC(=O)NCc3ccnc(C(N)=O)c3)c(=O)c1Cl)C2(C)C]

Synthesis was carried out in the same manner as in Synthetic Example 388 by using 2-[5-chloro-6-oxo-4-{[(1R,2R,3R,5S)-2,6,6-trimethylbicyclo[3.1.1]hept-3-yl]amino}pyridazin-1(6H)-yl]-N-[(2-cyanopyridin-4-yl)methyl]acetamide.

Yield: 79%
Morphology: colorless solid
LC/MS: Condition 7, retention time 4.06 min
LC/MS (ESI+) m/z; 473, 475 [M+1]+
LC/MS (ESI−) m/z; 471, 473 [M−1]−

SYNTHETIC EXAMPLE 408

4-Chloro-2-{2-[4-(diethylamino)phenyl]-2-oxoethyl}-5-(hexahydro-2,5-methanopentalen-3a(1H)-ylamino)pyridazin-3(2H)-one

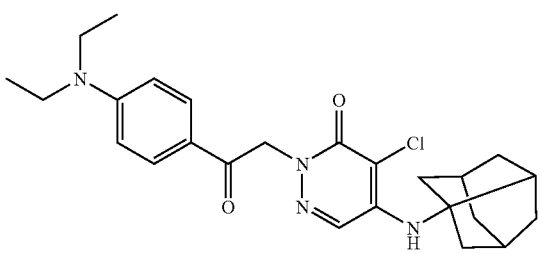 [SMILES: CCN(CC)c1ccc(C(=O)Cn2ncc(NC34CC5CC(CC3C5)C4)c(Cl)c2=O)cc1]

4,5-Dichloro-2-{2-[4-(diethylamino)phenyl]-2-oxoethyl}pyridazin-3(2H)-one

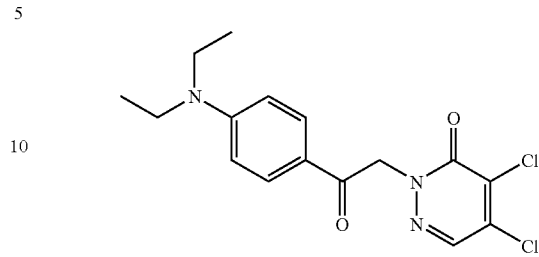

Synthesis was carried out in the same manner as in Synthetic Example 48 by using 2-bromo-1-[4-(diethylamino)phenyl]ethanone (yield 61%).

Morphology: yellow solid
$^1$H-NMR (CDCl$_3$)
δ: 1.22 (t, J=7.1 Hz, 6H), 3.19 (q, J=7.9 Hz, 4H), 5.53 (s, 2H), 6.65 (d, J=9.0 Hz, 2H), 7.83 (s, 1H), 7.85 (d, J=9.0 Hz, 2H)

4-Chloro-2-{2-[4-(diethylamino)phenyl]-2-oxoethyl}-5-(hexahydro-2,5-methanopentalen-3a(1H)-ylamino)pyridazin-3(2H)-one 4,5-Dichloro-2-{2-[4-(diethylamino)phenyl]-2-oxoethyl}pyridazin-3(2H)-one (30 mg, 0.0846 mmol), hexahydro-2,5-methanopentalen-3a(1H)-amine (22 mg, 0.126 mmol) and triethylamine (59 μL, 0.423 mmol) were stirred in N,N-dimethylacetamide (1 mL) at 90° C. for 3 days. After completion of the reaction, the reaction solution was mixed with aqueous ammonium chloride and extracted with ethyl acetate. The extract was dried over anhydrous magnesium sulfate and evaporated under reduced pressure. The resulting residue was purified by silica gel column chromatography (ethyl acetate/hexane=1/1) to give the desired product (7 mg, 17% yield).

Morphology: colorless oil
LC/MS: Condition 7, retention time 4.93 min
LC/MS (ESI+) m/z; 455, 457 [M+1]+

SYNTHETIC EXAMPLE 409

3-[5-Bromo-6-oxo-4-{[(1R,2R,3R,5S)-2,6,6-trimethylbicyclo[3.1.1]hept-3-yl]amino}pyridazin-1(6H)-yl]-N-[(1-hydroxycycloheptyl)methyl]benzamide

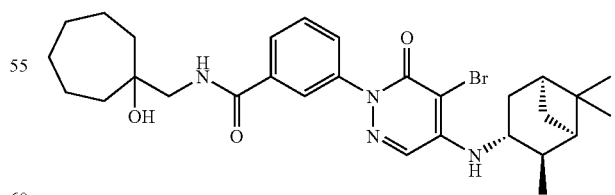

Synthesis was carried out in the same manner as in Synthetic Example 162 by using 1-(aminomethyl)cycloheptanol (47% yield).

Morphology: pale yellow amorphous
LC/MS: Condition 7, retention time 4.88 min
LC/MS (ESI+) m/z; 571, 573 [M+1]+

LC/MS (ESI⁻) m/z; 569, 571 [M−1]⁻
¹H-NMR (CDCl₃)
δ: 1.00 (d, J=10.2 Hz, 1H), 1.08 (s, 3H), 1.23 (d, J=6.9 Hz, 3H), 1.29 (s, 3H), 1.39-1.85 (m, 12H), 1.92-2.13 (m, 3H), 2.48-2.78 (m, 3H), 3.45 (d, J=5.7 Hz, 2H), 3.89-4.00 (m, 2H), 4.85 (d, J=7.8 Hz, 1H), 6.84-6.91 (m, 1H), 7.50 (t, J=7.8 Hz, 1H), 7.69-7.75 (m, 2H), 7.82 (d, J=7.8 Hz, 1H), 8.00 (s, 1H)

SYNTHETIC EXAMPLE 410

4-[5-Bromo-6-oxo-4-{[(1R,2R,3R,5S)-2,6,6-trimethylbicyclo[3.1.1]hept-3-yl]amino}pyridazin-1(6H)-yl]-N-[(1-hydroxycyloheptyl)methyl]benzamide

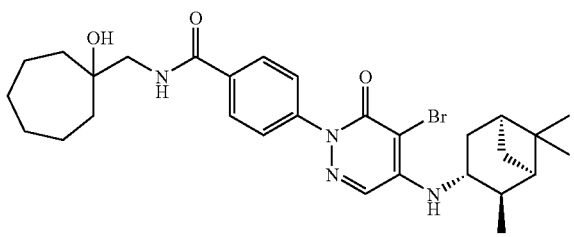 [SMILES: C[C@@H]1[C@H]2C[C@@H](C[C@H]1Nc1cnn(-c3ccc(C(=O)NCC4(O)CCCCCC4)cc3)c(=O)c1Br)C2(C)C]

Synthesis was carried out in the same manner as in Synthetic Example 160 by using 1-(aminomethyl)cycloheptanol (43% yield).
Morphology: pale yellow amorphous
LC/MS: Condition 7, retention time 4.83 min
LC/MS (ESI⁺) m/z; 571, 573 [M+1]⁺
LC/MS (ESI⁻) m/z; 569, 571 [M−1]⁻
¹H-NMR (CDCl₃)
δ: 1.00 (d, J=9.9 Hz, 1H), 1.08 (s, 3H), 1.22 (d, J=7.2 Hz, 3H), 1.29 (s, 3H), 1.39-1.83 (m, 13H), 1.93-2.11 (m, 3H), 2.45-2.56 (m, 1H), 2.62-2.74 (m, 1H), 3.46 (d, J=5.7 Hz, 2H), 3.88-3.99 (m, 1H), 4.84 (d, J=8.1 Hz, 1H), 6.67 (br.s, 1H), 7.70 (s, 1H), 7.72 (d, J=8.7 Hz, 2H), 7.85 (d, J=8.7 Hz, 2H)

SYNTHETIC EXAMPLE 411

4-Chloro-2-{2-[4-(diethylamino)phenyl]-2-hydroxyethyl}-5-{[(1R,2R,3R,5S)-2,6,6-trimethylbicyclo[3.1.1]hept-3-yl]amino}pyridazin-3(2H)-one

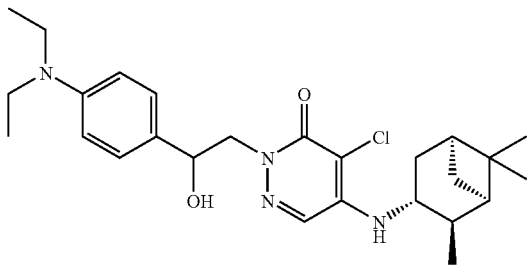 [SMILES: CCN(CC)c1ccc(C(O)Cn2ncc(N[C@@H]3C[C@@H]4C[C@H]([C@H]3C)C4(C)C)c(Cl)c2=O)cc1]

4-Chloro-2-{2-[4-(diethylamino)phenyl]-2-oxoethyl-}-5-{[(1R,2R,3R,5S)-2,6,6-trimethylbicyclo[3.1.1]hept-3-yl]amino}pyridazin-3(2H)-one (42 mg, 0.0891 mmol) in tetrahydrofuran (2 mL) was added dropwise to lithium aluminum hydride (11 mg, 0.315 mmol) in tetrahydrofuran (2 mL) at 0° C. and stirred at room temperature for 10 minutes. After completion of the reaction, the reaction solution was mixed with aqueous sodium hydroxide, anhydrous, sodium sulfate, then filtered and evaporated under reduced pressure. The residue was purified by preparative thin layer chromatography (hexane/ethyl acetate=1/1) to give the desired product (14 mg, 33% yield).
Morphology: pale yellow amorphous
LC/MS: Condition 7, retention time 3.68 min
LC/MS (ESI⁺) m/z; 455, 457 [M−18]⁺
LC/MS (ESI⁻) m/z; 471, 473 [M−1]⁻
¹H-NMR (CDCl₃)
δ: 0.97 (d, J=10.2 Hz, 1H), 1.06 (s, 3H), 1.13-1.23 (m, 9H), 1.27 (s, 3H), 1.65-1.77 (m, 1H), 1.81-2.08 (m, 3H), 2.44-2.53 (m, 1H), 2.58-2.67 (m, 1H), 3.35 (q, J=7.0 Hz, 4H), 3.73-3.92 (m, 2H), 4.26-4.53 (m, 2H), 4.65 (d, J=9.3 Hz, 1H), 6.67 (d, J=8.4 Hz, 2H), 7.29 (d, J=8.4 Hz, 2H), 7.62 (s, 1H)

SYNTHETIC EXAMPLE 412

3-[5-Chloro-6-oxo-4-{[(1R,2R,3R,5S)-2,6,6-trimethylbicyclo[3.1.1]hept-3-yl]amino}pyridazin-1(6H)-yl]-N-[(2S)-2-hydroxy-3-methoxypropyl]propanamide

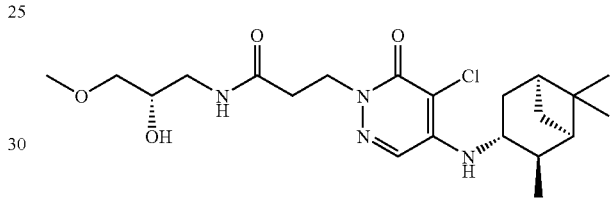

Synthesis was carried out in the same manner as in Synthetic Example 41 by using (S)-1-amino-3-methoxypropan-2-ol.
Yield: 67%
Morphology: colorless amorphous
LC/MS: Condition 7, retention time 4.03 min
LC/MS (ESI⁺) m/z; 441, 443 [M+1]⁺
LC/MS (ESI⁻) m/z; 439, 441 [M−1]⁻

SYNTHETIC EXAMPLE 413

3-[5-Chloro-6-oxo-4-{[(1R,2R,3R,5S)-2,6,6-trimethylbicyclo[3.1.1]hept-3-yl]amino}pyridazin-1(6H)-yl]-N-[(2S)-2-hydroxy-3-methoxypropyl]-N-methylpropanamide

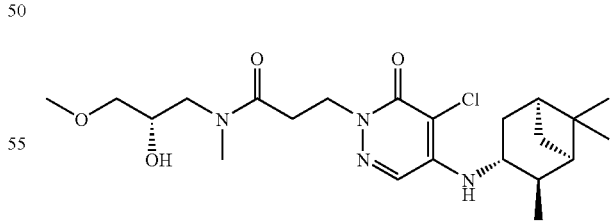

Synthesis was carried out in the same manner as in Synthetic Example 41 by using (S)-1-methoxy-3-(methylamino)propan-2-ol.
Yield: 60%
Morphology: colorless amorphous
LC/MS: Condition 7, retention time 4.16 min
LC/MS (ESI⁺) m/z; 455, 457 [M+1]⁺
LC/MS (ESI⁻) m/z; 453, 455 [M−1]⁻

SYNTHETIC EXAMPLE 414

Ethyl({4-[({[5-chloro-oxo-4-{[(1R,2R,3R,5S)-2,6,6-trimethylbicyclo[3.1.1]hept-3-yl]amino}pyridazin-1(6H)-yl]acetyl}amino)methyl]pyridin-3-yl}oxy)acetate

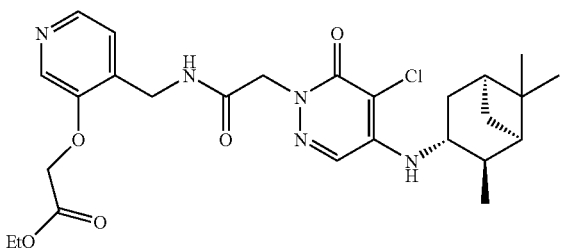 [SMILES: CCOC(=O)COc1cnccc1CNC(=O)Cn1ncc(N[C@@H]2C[C@@H]3C[C@H]([C@H]2C)C3(C)C)c(Cl)c1=O]

2-[5-Chloro-6-oxo-4-{[(1R,2R,3R,5S)-2,6,6-trimethylbicyclo[3.1.1]hept-3-yl]amino}pyridazin-1(6H)-yl]-N-[(3-hydroxypyridin-4-yl)methyl]acetamide (12.7 mg, 0.03 mmol) in acetone (2 mL) was mixed with ethyl bromoacetate (4.4 μL, 0.04 mmol) and potassium carbonate (5.9 mg, 0.04 mmol) at room temperature and stirred at 50° C. for 1 hour. After cooling, the reaction solution was mixed with saturated aqueous ammonium chloride and extracted with ethyl acetate. The resulting organic layer was dried over anhydrous sodium sulfate and evaporated under reduced pressure. The resulting residue was purified by silica gel column chromatography (ethyl acetate/methanol=20/1) to give the desired product (4.8 mg, 30%).

Morphology: pale yellow oil
LC/MS: Condition 7, retention time 3.89 min
LC/MS (ESI$^+$) m/z; 532, 534 [M+1]$^+$
LC/MS (ESI$^-$) m/z; 530, 532 [M−1]$^-$

SYNTHETIC EXAMPLES 415 TO 416

Compounds were synthesized in the same manner as in Synthetic Example 414, and the yields and morphology of the resulting compounds, the LC/MS conditions used for their analysis and the observed peaks and retention times are shown in Table 34.

TABLE 34

| Synthetic Example No. | Yield (%) | Morphology | LC/MS Condition | Observed peak ESI$^+$ | Observed peak ESI$^-$ | Retention time (min) |
|---|---|---|---|---|---|---|
| 415 | 59 | Yellow solid | 7 | 485/487 | 483/485 | 3.98 |
| 416 | 81 | Colorless amorphous | 7 | 594/596 | 592/594 | 3.51 |

Synthetic Examples 415 to 416

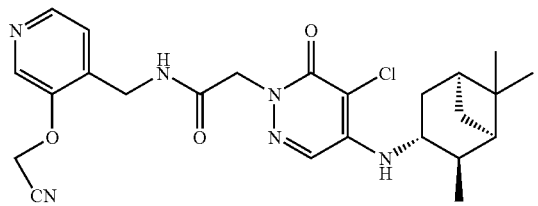

415

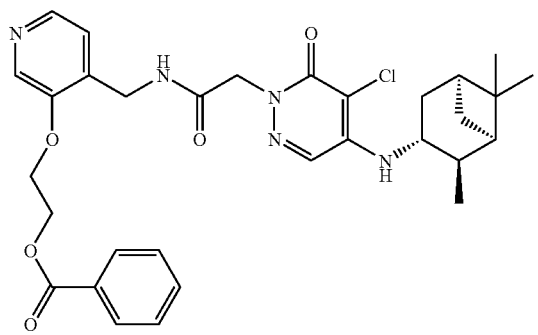

416

SYNTHETIC EXAMPLE 417

2-[5-Chloro-6-oxo-4-{[(1R,2R,3R,5S)-2,6,6-trimethylbicyclo[3.1.1]hept-3-yl]amino}pyridazin-1(6H)-yl]-N-{[3-(2-hydroxyethoxy)pyridin-4-yl]methyl}acetamide

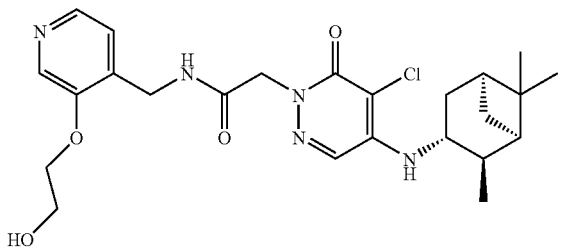 [SMILES: C[C@@H]1[C@H]2C[C@@H](C[C@H]1Nc1cnn(CC(=O)NCc3ccncc3OCCO)c(=O)c1Cl)C2(C)C]

2-({4-[({[5-Chloro-6-oxo-4-{[(1R,2R,3R,5S)-2,6,6-trimethylbicyclo[3.1.1]hept-3-yl]amino}pyridazin-1(6H)-yl]acetyl}amino)methyl]pyridin-3-yl}oxy)ethyl benzoate (23.8 mg, 0.04 mmol) in methanol (2 mL) was mixed with 1 M aqueous sodium hydroxide (0.12 mL, 0.12 mmol) at room temperature and stirred at room temperature for 1 hour. After completion of the reaction, the reaction solution was evaporated azeotropically with ethanol, and the resulting residue was purified by silica gel chromatography (ethyl acetate/methanol=10/1 to 8/1) to give the desired product (19.7 mg, 100% yield).
Morphology: colorless solid
LC/MS: Condition 7, retention time 3.45 min
LC/MS (ESI+) m/z; 490, 492 [M+1]+
LC/MS (ESI−) m/z; 488, 490 [M−1]−

SYNTHETIC EXAMPLE 418

2-[5-Chloro-6-oxo-4-{[(1R,2R,3R,5S)-2,6,6-trimethylbicyclo[3.1.1]hept-3-yl]amino}pyridazin-1(6H)-yl]-N-[(3-isopropyloxypyridin-4-yl)methyl]acetamide

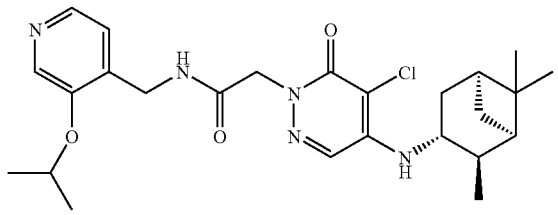 [SMILES: CC(C)Oc1cnccc1CNC(=O)Cn1ncc(N[C@@H]2C[C@@H]3C[C@H]([C@H]2C)C3(C)C)c(Cl)c1=O]

2-[5-Chloro-6-oxo-4-{[(1R,2R,3R,5S)-2,6,6-trimethylbicyclo[3.1.1]hept-3-yl]amino}pyridazin-1(6H)-yl]-N-[(3-hydroxypyridin-4-yl)methyl]acetamide (26.6 mg, 0.06 mmol) in tetrahydrofuran (1 mL) was mixed with 2-propanol (10.9 mg, 0.18 mmol), triphenylphosphine (23.6 mg, 0.09 mmol) and diethyl azodicarboxylate in toluene (2.2 M, 0.04 mL, 0.09 mmol) at 0° C. and stirred at room temperature for 4 hours. After completion of the reaction, the reaction solution was evaporated under reduced pressure, and the resulting residue was purified by silica gel chromatography (ethyl acetate/methanol 20/1) to give the desired product (4.48 mg, 15%).
Morphology: colorless amorphous
LC/MS: Condition 7, retention time 3.71 min
LC/MS (ESI+) m/z; 488, 490 [M+1]+
LC/MS (ESI−) m/z; 486, 488 [M−1]−

SYNTHETIC EXAMPLE 419

4-Chloro-2-{(2S)-2-hydroxy-3-[(pyridin-4-ylmethyl)amino]propyl}-5-{[(1R,2R,3R,5S)-2,6,6-trimethylbicyclo[3.1.1]hept-3-yl]amino}pyridazin-3(2H)-one

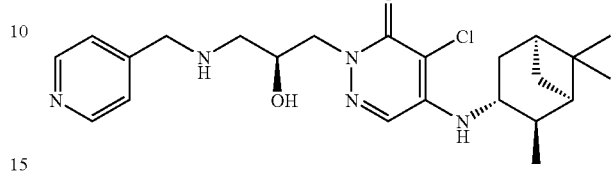

4-Chloro-2-[(2R)-oxiran-2-ylmethyl]-5-{[(1R,2R,3R,5S)-2,6,6-trimethylbicyclo[3.1.1]hept-3-yl]amino}pyridazin-3(2H)-one

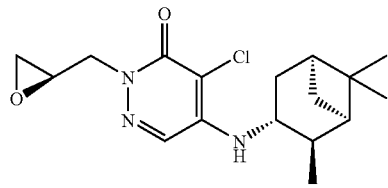 [SMILES: C[C@@H]1[C@H]2C[C@@H](C[C@H]1Nc1cnn(C[C@@H]3CO3)c(=O)c1Cl)C2(C)C]

4-Chloro-5-{[(1R,2R,3R,5S)-2,6,6-trimethylbicyclo[3.1.1]hept-3-yl]amino}pyridazin-3(2H)-one (120 mg, 0.425 mmol) in N,N-dimethylformamide (2 mL) was mixed with (2S)-oxiran-2-ylmethyl 4-methylbenzenesulfonate (117 mg, 0.513 mmol) and potassium carbonate (71 mg, 0.0514 mmol) at room temperature and stirred at 80° C. for 3 hours. After cooling, the reaction solution was mixed with water and extracted with ethyl acetate, and the extract was evaporated under reduced pressure. The resulting crude product was used for the next reaction without purification.
LC/MS: Condition 7, retention time 4.44 min
LC/MS (ESI+) m/z; 338, 340 [M+1]+
LC/MS (ESI−) m/z; 336, 338 [M−1]−

4-Chloro-2-{(2S)-2-hydroxy-3-[(pyridin-4-ylmethyl)amino]propyl}-5-{[(1R,2R,3R,5S)-2,6,6-trimethylbicyclo[3.1.1]hept-3-yl]amino}pyridazin-3(2H)-one 4-Chloro-2-[(2R)-oxiran-2-ylmethyl]-5-{[(1R,2R,3R,5S)-2,6,6-trimethylbicyclo[3.1.1]hept-3-yl]amino}pyridazin-3(2H)-one (0.141 mmol) in ethanol (2 mL) was stirred with 1-(pyridin-4-yl)methanamine (17 μL, 0.17 mmol) at 80° C. for 8 hours. After cooling, the reaction solution was concentrated, mixed with water and extracted with ethyl acetate, and the extract was evaporated under reduced pressure. The residue was purified by preparative thin layer chromatography (chloroform/methanol=9/1) to give the desired product (19 mg, 29% yield).
Morphology: colorless amorphous
LC/MS: Condition 7, retention time 3.13 min
LC/MS (ESI+) m/z; 446, 448 [M+1]+
LC/MS (ESI−) m/z; 444, 446 [M−1]−
$^1$H-NMR (CDCl$_3$)
δ: 0.97 (d, J=10.2 Hz, 1H), 1.06 (s, 3H), 1.19 (d, J=6.9 Hz, 3H), 1.28 (s, 3H), 1.65-1.77 (m, 1H), 1.92-2.08 (m, 3H), 2.45-2.54 (m, 1H), 2.57-2.76 (m, 3H), 3.82-3.93 (m, 3H), 4.08-4.13 (m, 1H), 4.24-4.39 (m, 2H), 4.67 (d, J=8.4 Hz, 1H), 7.25-7.29 (m, 2H), 7.62 (s, 1H), 8.52-8.55 (m, 2H)

SYNTHETIC EXAMPLE 420

1-[5-Bromo-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)cyclobutanecarboxamide

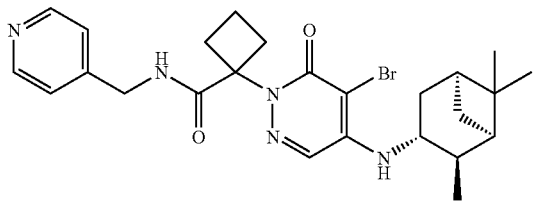 [SMILES: C[C@@H]1[C@H]2C[C@@H](C[C@H]1Nc1cnn(C3(C(=O)NCc4ccncc4)CCC3)c(=O)c1Br)C2(C)C]

Ethyl 1-[5-bromo-6-oxo-4-{[(1R,2R,3R,5S)-2,6,6-trimethylbicyclo[3.1.1]hept-3-yl]amino}pyridazin-1(6H)-yl]cyclobutanecarboxylate

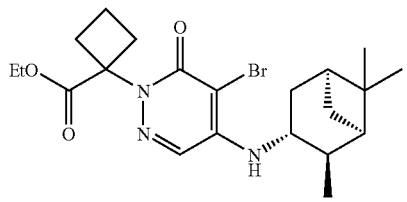 [SMILES: C[C@@H]1[C@H]2C[C@@H](C[C@H]1Nc1cnn(C3(C(=O)O)CCC3)c(=O)c1Br)C2(C)C]

4-Bromo-5-{[(1R,2R,3R,5S)-2,6,6-trimethylbicyclo[3.1.1]hept-3-yl]amino}pyridazin-3(2H)-one (112.8 mg, 0.35 mmol) in N,N-dimethylformamide (2 mL) was mixed with ethyl 1-bromocyclobutanecarboxylate (85.8 µL, 0.53 mmol) and potassium carbonate (73.0 mg, 0.53 mmol) at room temperature and stirred at 150° C. for 2 hours in a microwave reactor. After cooling, the reaction solution was mixed with saturated aqueous ammonium chloride and extracted with ethyl acetate. The resulting organic layer was dried over anhydrous sodium sulfate and evaporated under reduced pressure. The resulting crude product containing the desired product was used for the next reaction (222.1 mg).
Morphology: orange oil
LC/MS: Condition 7, retention time 5.11 min
LC/MS (ESI$^+$) m/z; 452, 454 [M+1]$^+$
LC/MS (ESI$^-$) m/z; 450, 452 [M−1]$^-$ 2-(5-Bromo-6-oxo-4-{[(1R,2R,3R,5S)-2,6,6-trimethylbicyclo[3.1.1]hept-3-yl]amino}pyridazin-1(6H)-yl)cyclobutaneacetic Acid

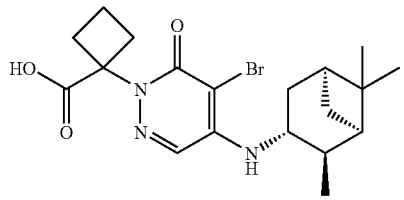

Ethyl 1-(5-bromo-6-oxo-4-{[(1R,2R,3R,5S)-2,6,6-trimethylbicyclo[3.1.1]hept-3-yl]amino}pyridazin-1(6H)-yl)-N-(pyridin-4-ylmethyl)cyclobutanecarboxylate (222.1 mg, 0.35 mmol) in 1,4-dioxane (2 mL) was stirred with 1 M aqueous sodium hydroxide (1.06 mL, 1.06 mmol) at room temperature for 4.5 hours. After completion of the reaction, the reaction solution was mixed with ethyl acetate, and the organic layer was washed with 1 M hydrochloric acid and saturated aqueous sodium chloride, dried over anhydrous sodium sulfate and evaporated under reduced pressure. The resulting crude product containing the desired product was used for the next step (120.3 mg, 81% yield).
Morphology: orange oil
LC/MS: Condition 7, retention time 4.60 min
LC/MS (ESI$^+$) m/z; 424, 426 [M+1]$^+$
LC/MS (ESI$^-$) m/z; 422, 424 [M−1]$^-$ 1-(5-Bromo-6-oxo-4-{[(1R,2R,3R,5S)-2,6,6-trimethylbicyclo[3.1.1]hept-3-yl]amino}pyridazin-1(6H)-yl)-N-(pyridin-4-ylmethyl)cyclobutanecarboxamide 2-(5-Bromo-6-oxo-4-{[(1R,2R,3R,5S)-2,6,6-trimethylbicyclo[3.1.1]hept-3-yl]amino}pyridazin-1(6H)-yl)cyclobutaneacetic acid (108.7 mg, 0.256 mmol), 1-(3-dimethylaminopropyl)-3-ethylcarbodiimide hydrochloride (98.2 mg, 0.512 mmol), 1-hydroxybenzotriazole anhydride (10.8 mg, 0.08 mmol) and triethylamine (71.4 µL, 0.512 mmol) in N,N-dimethylformamide (1 mL) were stirred with 4-picolylamine (51.3 µL, 0.512 mmol) at room temperature for 22 hours. After completion of the reaction, ethyl acetate was added, and the organic layer was washed with saturated aqueous ammonium chloride and saturated aqueous sodium chloride, dried over anhydrous sodium sulfate and evaporated under reduced pressure. The resulting residue was purified by silica gel column chromatography (ethyl acetate/methanol=20/1) to give the desired product (53.8 mg, 41% yield).
Morphology: pale yellow amorphous
LC/MS: Condition 7, retention time 3.68 min
LC/MS (ESI$^+$) m/z; 514, 516 [M+1]$^+$
LC/MS (ESI$^-$) m/z; 512, 514 [M−1]$^-$
$^1$H-NMR (CDCl$_3$)
δ: 0.98 (d, J=10.5 Hz, 1H), 1.06 (s, 3H), 1.18-1.21 (m, 2H), 1.27 (d, J=7.5 Hz, 3H), 1.28 (s, 3H), 1.65-1.75 (m, 1H), 1.90-2.00 (m, 2H), 2.04-2.17 (m, 2H), 2.28-2.37 (m, 1H), 2.45-2.55 (m, 1H), 2.62-2.70 (m, 1H), 2.84-2.96 (m, 1H), 3.16-3.25 (m, 1H), 3.80-4.00 (m, 1H), 4.47 (d, J=6.0 Hz, 2H), 4.82 (d, J=8.4 Hz, 1H), 7.25-7.27 (m, 2H), 7.67 (s, 1H), 8.52 (d, J=6.3 Hz, 2H)

SYNTHETIC EXAMPLE 421

2-(5-Chloro-6-oxo-4-{[(1R,2R,3R,5S)-2,6,6-trimethylbicyclo[3.1.1]hept-3-yl]amino}pyridazin-1(6H)-yl)acetamide

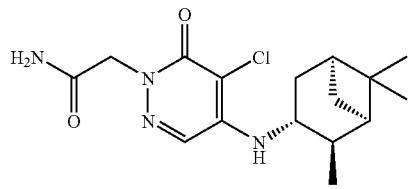 [SMILES: C[C@@H]1[C@H]2C[C@@H](C[C@H]1Nc1cnn(CC(N)=O)c(=O)c1Cl)C2(C)C]

Synthesis was carried out in the same manner as in Synthetic Example 402 by using [5-chloro-6-oxo-4-{[(1R,2R, 3R,5S)-2,6,6-trimethylbicyclo[3.1.1]hept-3-yl]amino}pyridazin-1(6H)-yl]acetic acid.

Morphology: colorless solid
LC/MS: Condition 7, retention time 4.01 min
LC/MS (ESI$^+$) m/z; 339, 341 [M+1]$^+$
LC/MS (ESI$^-$) m/z; 337, 339 [M−1]$^-$

SYNTHETIC EXAMPLE 422

2-[5-Chloro-6-oxo-4-{[(1R,2R,3R,5S)-2,6,6-trimethylbicyclo[3.1.1]hept-3-yl]amino}pyridazin-1(6H)-yl]-N—[(Z)-(methoxyimino)methyl]acetamide

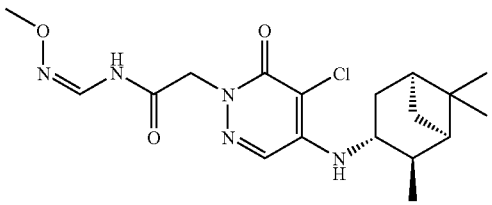

2-[5-Chloro-6-oxo-4-{[(1R,2R,3R,5S)-2,6,6-trimethylbicyclo[3.1.1]hept-3-yl]amino}pyridazin-1(6H)-yl]acetamide (32 mg, 0.0944 mmol) in tetrahydrofuran/N,N-dimethylformamide (1/0.1 mL) was stirred with 1,1-dimethoxy-N,N-dimethylmethanamine (25 µL, 0.188 mmol) at room temperature for 3 hours. The reaction solution was concentrated and stirred with tetrahydrofuran/water (1/2 mL) and methoxyamine hydrochloride (12 mg, 0.143 mmol) at room temperature for 2 hours. After completion of the reaction, the reaction solution was mixed with water and extracted with ethyl acetate, and the extract was dried over anhydrous magnesium sulfate and evaporated under reduced pressure to give the desired product (29 mg, 78% yield).

Morphology: colorless solid
LC/MS: Condition 7, retention time 4.43 min
LC/MS (ESI$^-$) m/z; 394, 396 [M−1]$^-$

SYNTHETIC EXAMPLE 423

3-[5-Chloro-6-oxo-4-{[(1R,2R,3R,5S)-2,6,6-trimethylbicyclo[3.1.1]hept-3-yl]amino}pyridazin-1(6H)-yl]-N—[(Z)-(methoxyimino)methyl]propanamide

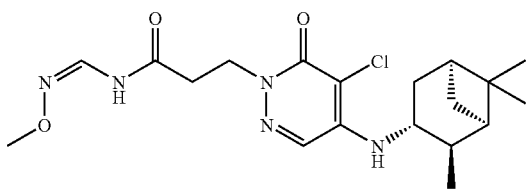

Synthesis was carried out in the same manner as in Synthetic Example 422 by using 3-[5-chloro-6-oxo-4-{[(1R,2R,3R,5S)-2,6,6-trimethylbicyclo[3.1.1]hept-3-yl]amino}pyridazin-1(6H)-yl]propanamide.

Morphology: colorless amorphous
LC/MS: Condition 7, retention time 4.38 min
LC/MS (ESI$^+$) m/z; 410, 412 [M+1]$^+$
LC/MS (ESI$^-$) m/z; 408, 410 [M−1]$^-$

SYNTHETIC EXAMPLE 424 rac-2-[5-Bromo-4-{[2-(hydroxymethyl)-6,6-dimethylbicyclo[3.1.1]hept-3-yl]amino}-6-oxopyridazin-1(6H)-yl]-N-(pyridin-4-ylmethyl)acetamide

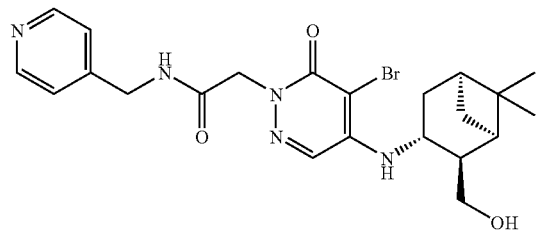 [SMILES: CC1(C)[C@H]2C[C@@H]1[C@@H](CO)[C@H](Nc1cnn(CC(=O)NCc3ccncc3)c(=O)c1Br)C2]

rac-2-[5-Bromo-4-({2-[(methoxymethoxy)methyl]-6,6-dimethylbicyclo[3.1.1]hept-3-yl}amino)-6-oxopyridazin-1(6H)-yl]-N-(pyridin-4-ylmethyl)acetamide (35 mg, 0.0655 mmol) in 10 mass % hydrogen chloride-methanol (3 mL) was stirred at 60° C. for 1 hour. After completion of the reaction, the reaction solution was evaporated under reduced pressure, and the resulting solid was collected by filtration, then mixed with saturated aqueous sodium hydrogen sulfate and extracted with chloroform. The organic layer was dried over anhydrous sodium sulfate and evaporated under reduced pressure to give the desired product (37% yield).

Morphology: colorless oil
LC/MS: Condition 7, retention time 2.88 min
LC/MS (ESI$^+$) m/z; 490, 492 [M+1]$^+$
LC/MS (ESI$^-$) m/z; 488, 490 [M−1]$^-$

SYNTHETIC EXAMPLE 425 rac-2-[5-Bromo-4-({2-[(dimethylamino)methyl]-6,6-dimethylbicyclo[3.1.1]hept-3-yl}amino)-6-oxopyridazin-1(6H)-yl]-N-(pyridin-4-ylmethyl)acetamide

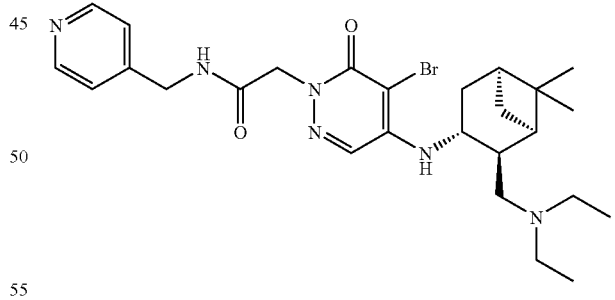

rac-2-[5-Bromo-4-{[2-(hydroxymethyl)-6,6-dimethylbicyclo[3.1.1]hept-3-yl]amino}-6-oxopyridazin-1(6H)-yl]-N-(pyridin-4-ylmethyl)acetamide (43 mg, 0.0877 mmol) in dichloromethane (3 mL) was mixed with (diethylamino)sulfur trifluoride (17 µL, 0.128 mmol) at −78° C. and stirred at −78° C. for 10 minutes and then stirred at room temperature for 1 hour. After completion of the reaction, the reaction solution was mixed with saturated aqueous sodium hydrogen carbonate and extracted with ethyl acetate. The organic layer was dried over anhydrous sodium sulfate and evaporated under reduced pressure. The resulting residue was purified by thin layer silica gel chromatography (chloroform/methanol=10/1) to give the desired product (16% yield).
Morphology: colorless oil
¹H-NMR (CDCl₃)
δ: 1.00-1.10 (m, 9H), 1.27 (s, 3H), 1.77-1.86 (m, 1H), 2.05-2.10 (m, 2H), 2.16-2.32 (m, 1H), 2.50-2.60 (m, 1H), 2.60-2.75 (m, 1H), 2.95-3.20 (m, 4H), 3.65-4.10 (m, 3H), 4.44 (d, J=6.0 Hz, 2H), 4.80-5.05 (m, 3H), 7.17 (d, J=5.7 Hz, 2H), 7.61 (s, 1H), 8.52 (d, J=6.0 Hz, 2H)

SYNTHETIC EXAMPLE 426

2-{5-Bromo-4-[(5-hydroxytricyclo[3.3.1.1³,⁷]dec-2-yl)amino]-6-oxopyridazin-1(6H)-yl}-N-(pyridin-4-ylmethyl)acetamide Hydrochloride

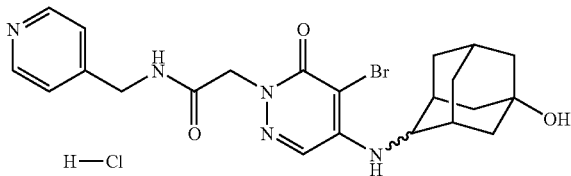 [SMILES: O=C(Cn1ncc(NC2C3CC4CC2CC(O)(C4)C3)c(Br)c1=O)NCc1ccncc1 ; Cl]

2-[5-Bromo-4-{[5-(methoxymethoxy)tricyclo[3.3.1.1³,⁷]dec-2-yl]amino}-6-oxopyridazin-1(6H)-yl]-N-(pyridin-4-ylmethyl)acetamide (30 mg, 0.0563 mmol) in 10 mass % hydrogen chloride-methanol (3 mL) was stirred at room temperature for 1 hour. After completion of the reaction, the reaction solution was evaporated under reduced pressure, and the resulting solid was collected by filtration and dried to give the desired product (51% yield).
Morphology: colorless solid
LC/MS: Condition 7, retention time 0.93 min
LC/MS (ESI⁺) m/z; 488, 490 [M+1]⁺
LC/MS (ESI⁻) m/z; 486, 488 [M−1]⁻

SYNTHETIC EXAMPLE 427

3-[({[5-Chloro-6-oxo-4-{[(1R,2R,3R,5S)-2,6,6-trimethylbicyclo[3.1.1]hept-3-yl]amino}pyridazin-1(6H)-yl]acetyl}amino)methyl]benzamide

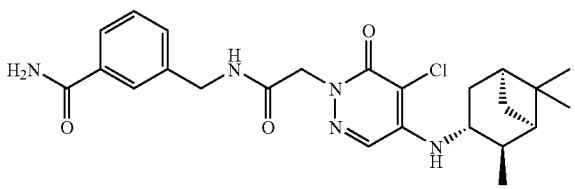 [SMILES: C[C@@H]1[C@H]2C[C@@H](C[C@H]1Nc1cnn(CC(=O)NCc3cccc(C(N)=O)c3)c(=O)c1Cl)C2(C)C]

3-[({[5-Chloro-6-oxo-4-{[(1R,2R,3R,5S)-2,6,6-trimethylbicyclo[3.1.1]hept-3-yl]amino}pyridazin-1(6H)-yl]acetyl}amino)methyl]benzoic acid (23 mg, 0.0472 mmol) in 1,4-dioxane (1 mL) was stirred with 1 M aqueous sodium hydroxide (100 µL, 0.100 mmol) at room temperature for 24 hours. The reaction solution was diluted with ethyl acetate and neutralized with water and 1 M hydrochloric acid, and the organic layer was separated, dried over anhydrous sodium sulfate and evaporated under reduced pressure.
The residue was dissolved in N,N-dimethylformamide (2 mL) and stirred with di-1H-imidazolylmethanone (38 mg, 0.234 mmol) at room temperature for 6 hours and then with 30% aqueous ammonia (0.15 mL) at room temperature for 15 hours. After completion of the reaction, the reaction solution was mixed with water and extracted with ethyl acetate. The extract was washed with 1 M aqueous sodium hydroxide, dried over anhydrous magnesium sulfate and evaporated under reduced pressure to give the desired product (16 mg, 71% yield).
Morphology: caramel amorphous
LC/MS: Condition 7, retention time 4.16 min
LC/MS (ESI⁺) m/z; 472, 474 [M+1]⁺
LC/MS (ESI⁻) m/z; 470, 472 [M−1]⁻

SYNTHETIC EXAMPLE 428

3-({[5-Bromo-6-oxo-4-{[(1R,2R,3R,5S)-2,6,6-trimethylbicyclo[3.1.1]hept-3-yl]amino}pyridazin-1(6H)-yl]acetyl}amino)-3-(pyridin-4-yl)propanamide

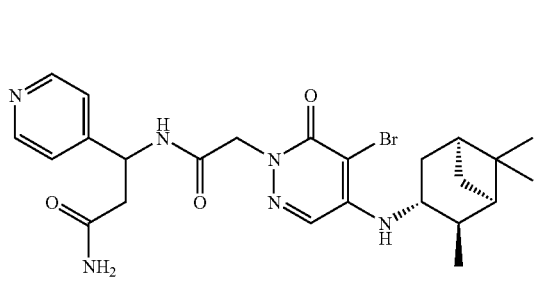 [SMILES: C[C@@H]1[C@H]2C[C@@H](C[C@H]1Nc1cnn(CC(=O)NC(CC(N)=O)c3ccncc3)c(=O)c1Br)C2(C)C]

Synthesis was carried out in the same manner as in Synthetic Example 402 by using 3-({[5-bromo-6-oxo-4-{[(1R,2R,3R,5S)-2,6,6-trimethylbicyclo[3.1.1]hept-3-yl]amino}pyridazin-1(6H)-yl]acetyl}amino)-3-(pyridin-4-yl)propanoic acid (50% yield).
Morphology: colorless amorphous
LC/MS: Condition 7, retention time 3.60 min
LC/MS (ESI⁺) m/z; 531, 533 [M+1]⁺
LC/MS (ESI⁻) m/z; 529, 531 [M−1]⁻

SYNTHETIC EXAMPLE 429

2-[5-Hydroxy-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide

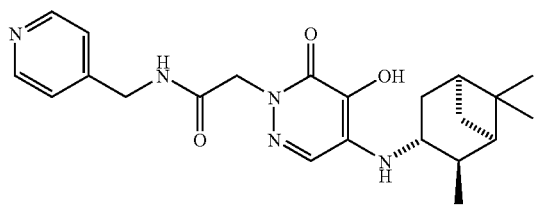

Synthesis was carried out in the same manner as in Synthetic Example 381 by using 2-[5-bromo-6-oxo-4-{[(1R,2R,3R,5S)-2,6,6-trimethylbicyclo[3.1.1]hept-3-yl]amino}pyridazin-1(6H)-yl]-N-(pyridin-4-ylmethyl)acetamide.
Morphology: colorless solid
¹H-NMR (CDCl₃)
δ: 0.94 (d, J=10.3 Hz, 1H), 1.04 (s, 3H), 1.16 (d, J=7.0 Hz, 3H), 1.25 (s, 3H), 1.6-1.7 (m, 1H), 1.8-1.9 (m, 2H), 2.0 (s, 1H), 2.4-2.5 (m, 1H), 2.5-2.7 (m, 1H), 3.77 (m, 1H), 4.45 (s, 2H), 4.90 (s, 2H), 7.24 (s, 2H), 7.37 (s, 1H), 7.72 (s, 1H), 8.48 (s, 2H).

SYNTHETIC EXAMPLE 430

2-[5-Bromo-6-oxo-4-(tricyclo[3.3.1.1$^{3,7}$]dec-1-ylsulfanyl)pyridazin-1-(6H)-yl]-N-(pyridin-4-ylmethyl)acetamide

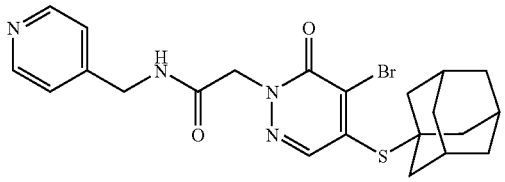 [SMILES: O=C(Cn1ncc(SC23CC4CC(CC(C4)C2)C3)c(Br)c1=O)NCc1ccncc1]

Synthesis was carried out in the same manner as in Synthetic Example 48 by using 1-adamantanethiol (15% yield).

Morphology: colorless oil
LC/MS: Condition 7, retention time 3.51 min
LC/MS (ESI$^+$) m/z; 489, 491 [M+1]$^+$
LC/MS (ESI$^-$) m/z; 487, 489 [M−1]$^-$

SYNTHETIC EXAMPLE 431

2-{5-Bromo-6-oxo-4-[2-(tricyclo[3.3.1.1$^{3,7}$]dec-1-yl)ethoxy]pyridazin-1(6H)-yl}-N-(pyridin-4-ylmethyl)acetamide

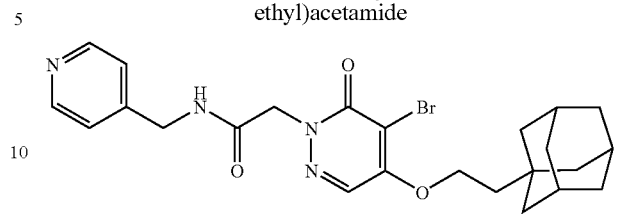

2-{4,5-Dibromo-6-oxopyridazin-1(6H)-yl}-N-(pyridin-4-ylmethyl)acetamide (48 mg, 0.119 mmol) and 1-adamantanethanol (92 mg, 0.510 mmol) in 1,4-dioxane (2 mL) were stirred with 6 M aqueous sodium hydroxide (50 µL, 0.300 mmol) at 100° C. for 6 hours. After completion of the reaction, the reaction solution was mixed with saturated aqueous sodium chloride and extracted with ethyl acetate. The organic layer was dried over anhydrous sodium sulfate and evaporated under reduced pressure. The resulting residue was purified by silica gel column chromatography (hexane/ethyl acetate=3/1 to 0/1) to give the desired product (9% yield).

Morphology: colorless oil
LC/MS: Condition 7, retention time 3.86 min
LC/MS (ESI$^+$) m/z; 501, 503 [M+1]$^+$
LC/MS (ESI$^-$) m/z; 499, 501 [M−1]$^-$
Pharmacological Analysis

SYNTHETIC EXAMPLES 432 TO 449

Compounds were synthesized in the same manner as in Synthetic Example 1, and the yields and morphology of the resulting compounds, the LC/MS conditions used for their analysis and the observed peaks and retention times are shown in Table 35.

TABLE 35

| Synthetic Example No. | Yield (%) | Morphology | LC/MS Condition | Observed peak ESI$^+$ | Observed peak ESI$^-$ | Retention time (min) |
| --- | --- | --- | --- | --- | --- | --- |
| 432 | 74 | Colorless amorphous | 7 | 445/447 | 443/445 | 4.01 |
| 433 | 68 | Colorless amorphous | 7 | 465/467 | 463/465 | 4.24 |
| 434 | 67 | Colorless amorphous | 7 | 445/447 | 443/445 | 3.98 |
| 435 | 45 | Yellow amorphous | 7 | 474/476 | 472/474 | 3.71 |
| 436 | 73 | Pale yellow amorphous | 7 | 458/460 | 456/458 | 3.46 |
| 437 | 6 | Pale yellow solid | 7 | 460/462 | 458/460 | 4.35 |
| 438 | 79 | colorless amorphous | 7 | 509/511 | 507/509 | 4.58 |
| 439 | 61 | colorless amorphous | 7 | 479/481 | 477/479 | 4.40 |
| 440 | 57 | Light brown amorphous | 7 | 473/475 | 471/473 | 4.24 |
| 441 | 25 | Colorless amorphous | 7 | 475/477 | 473/475 | 4.28 |
| 442 | 23 | Colorless amorphous | 7 | 508/510 | 506/508 | 4.21 |
| 443 | 73 | Colorless amorphous | 7 | 493/495 | 491/493 | 4.33 |

TABLE 35-continued

| Synthetic Example No. | Yield (%) | Morphology | LC/MS Condition | Observed peak ESI+ | Observed peak ESI− | Retention time (min) |
|---|---|---|---|---|---|---|
| 444 | 100 | Pale brown solid | 7 | 489/491 | 487/489 | 4.93 |
| 445 | 53 | Pale yellow amorphous | 7 | 471/473 | 469/471 | 4.68 |
| 446 | 68 | Colorless amorphous | 7 | 473/475 | 471/473 | 4.28 |
| 447 | 12 | Light brown solid | 7 | 512/514 | 510/512 | 4.13 |
| 448 | 28 | Colorless oil | 7 | 482/484 | 480/482 | 4.50 |
| 449 | 25 | Colorless amorphous | 7 | 496/498 | 494/496 | 4.68 |

The structures of the compounds obtained in Synthetic Examples are shown below.

SYNTHETIC EXAMPLES 432 TO 449

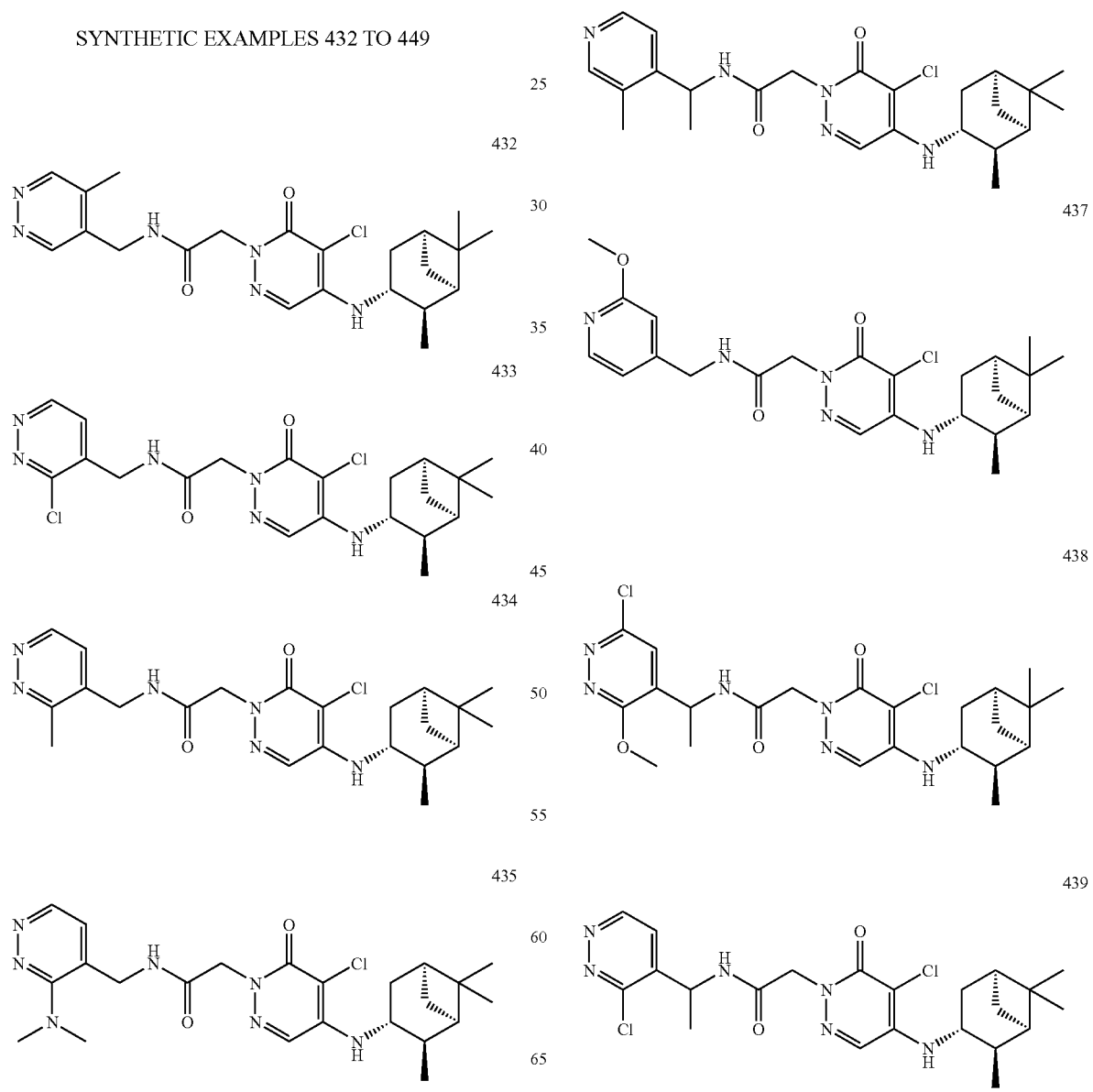

440

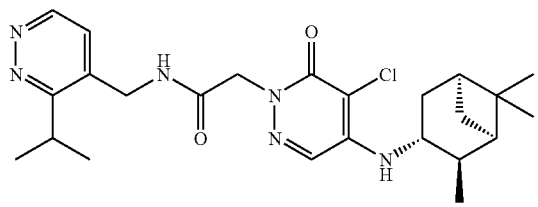

441

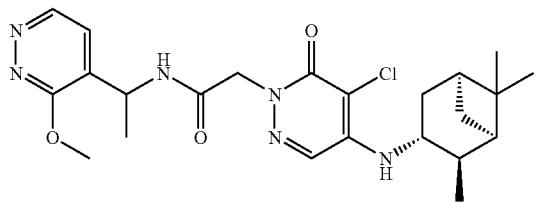

442

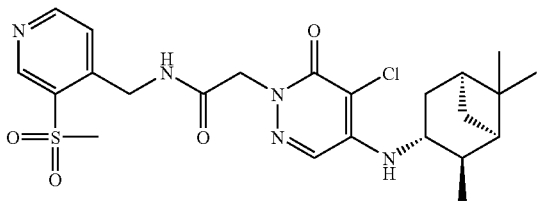

443

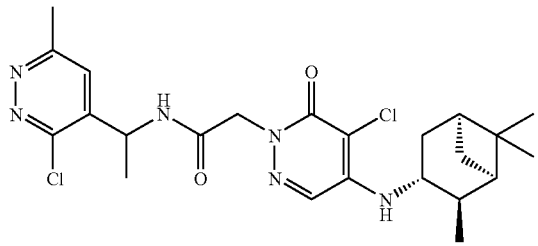

444

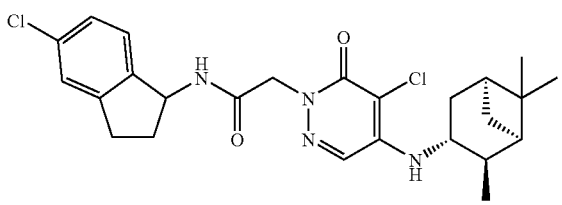

445

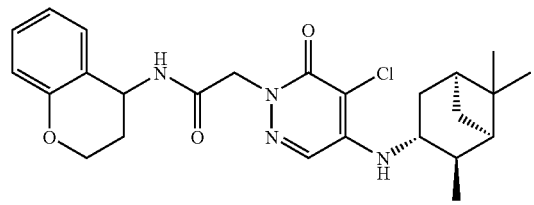

446

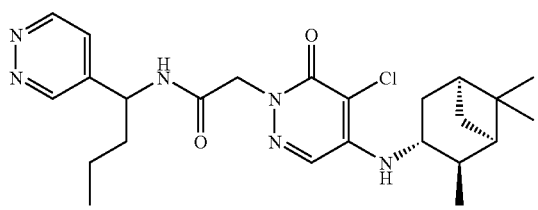

447

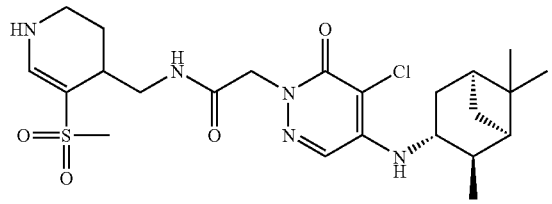

448

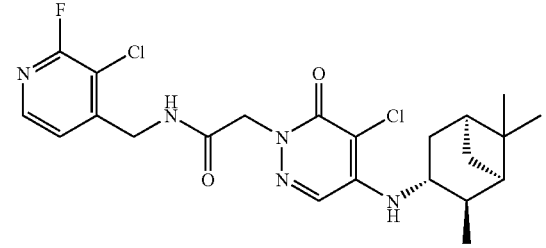

449

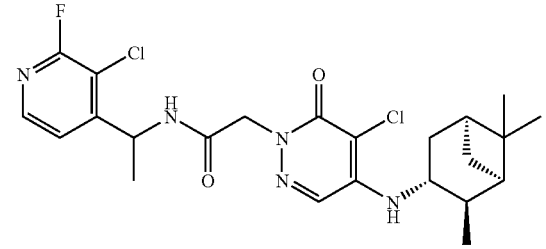

SYNTHETIC EXAMPLES 450

2-[5-Chloro-6-oxo-4-{[(1R,2R,3R,5S)-2,6,6-trimethylbicyclo[3.1.1]hept-3-yl]amino}pyridazin-1(6H)-yl]-N-[(2-hydroxypyridin-4-yl)methyl]acetamide 2-[5-Bromo-6-oxo-4-{[(1R,2R,3R,5S)-2,6,6-trimethylbicyclo[3.1.1]hept-3-yl]amino}pyridazin-1(6H)-yl]-N-[(2-methoxypyridin-4-yl)methyl]acetamide (55.3 mg, 0.11 mmol) in 1,4-dioxane (1 mL) was mixed with 12 M hydrochloric acid (1 drop) at 100° C. for 11 hours. After completion of the reaction, the reaction solution was neutralized with saturated aqueous sodium hydrogen carbonate and extracted with chloroform. The organic layer was dried over anhydrous sodium sulfate and evaporated under reduced pressure. The resulting residue was purified by silica gel column chromatography (ethyl acetate/methanol=50/1) to give the desired product. (2.8 mg, 6% yield)

Morphology: pale yellow oil

LC/MS: Condition 7, retention time 4.00 min

LC/MS (ESI$^+$) m/z; 446, 448 [M+1]$^+$

LC/MS (ESI$^-$) m/z; 444, 446 [M−1]$^+$

SYNTHETIC EXAMPLE 451

4-Chloro-2-{[3-(pyridin-4-yl)-1,2,4-oxadiazol-5-yl]methyl}-5-{[(1R,2R,3R,5S)-2,6,6-trimethylbicyclo[3.1.1]hept-3-yl]amino}pyridazin-3(2H)-one

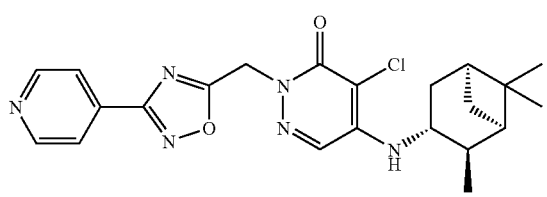 [SMILES: C[C@@H]1[C@H]2C[C@@H](C[C@H]1Nc1cnn(Cc3nc(-c4ccncc4)no3)c(=O)c1Cl)C2(C)C]

To [5-chloro-6-oxo-4-{[(1R,2R,3R,5S)-2,6,6-trimethylbicyclo[3.1.1]hept-3-yl]amino}pyridazin-1(6H)-yl]acetic acid (80 mg, 0.235 mmol) in dichloromethane (3 mL), N'-hydroxypyridine-4-carboximidamide (38.6 mg, 0.281 mmol) and N,N'-dicyclohexylcarbodiimide (58.2 mg, 0.282 mmol) were added and stirred at room temperature for 18 hours. After completion of the reaction, the solid was filtered off with chloroform, and the filtrate was evaporated under reduced pressure. The resulting oil in toluene (2 mL) was stirred at 110° C. for 5 hours and the solvent was evaporated under reduced pressure. The resulting residue was purified by silica gel column chromatography (hexane/ethyl acetate=1/4) to give the desired product (78 mg, 75% yield).

Morphology: pale yellow amorphous
LC/MS: Condition 7, retention time 4.55 min
LC/MS (ESI$^+$) m/z; 441, 443 [M+1]$^+$
LC/MS (ESI$^-$) m/z; 439, 441 [M−1]$^+$
$^1$H-NMR (CDCl$_3$)
δ: 0.98 (d, J=10.2 Hz, 1H), 1.06 (s, 3H), 1.21 (d, J=7.2 Hz, 3H), 1.28 (s, 3H), 1.76 (ddd, J=13.8, 5.7, 2.1 Hz, 1H), 1.91-2.09 (m, 3H), 2.44-2.72 (m, 2H), 3.83-3.95 (m, 1H), 4.74 (d, J=7.5 Hz, 1H), 5.62 (s, 2H), 7.68 (s, 1H), 7.92 (d, 6.3 Hz, 2H), 8.75 (d, J=6.3 Hz, 2H).

SYNTHETIC EXAMPLES 452 TO 456

Compounds were synthesized from 2-(4,5-dichloro-6-oxopyridazin-1(6H)-yl)-N-[1-(pyridin-4-yl)ethyl]acetamide in the same manner as in Synthetic Example 48, and the yields and morphology of the resulting compounds, the LC/MS conditions used for their analysis and the observed peaks and retention times are shown in Table 36.

The structures of the compounds obtained in these Synthetic Examples are shown below.

Synthetic Examples 452 to 455

452

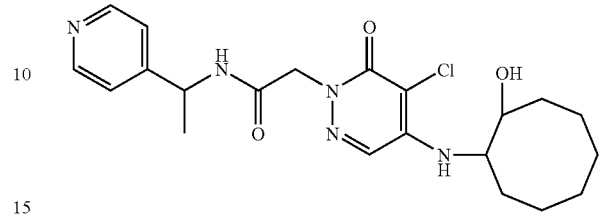

453

454

455

TABLE 36

| Synthetic Example No. | Yield (%) | Morphology | LC/MS Condition | Observed peak ESI$^+$ | Observed peak ESI$^-$ | Retention time (min) |
|---|---|---|---|---|---|---|
| 452 | 12 | Colorless amorphous | 7 | 434/436 | 432/434 | 1.81 |
| 453 | 13 | Colorless amorphous | 7 | 444/446 | 442/444 | 3.43 |
| 454 | 40 | Colorless amorphous | 7 | 474/476 | 472/474 | 3.31 |
| 455 | 38 | Colorless amorphous | 7 | 430/432 | 428/430 | 3.25 |

SYNTHETIC EXAMPLE 456

2-[5-Bromo-6-oxo-4-{[(1R,2R,3R,5S)-2,6,6-trimethylbicyclo[3.1.1]hept-3-yl]oxy}pyridazin-1(6H)-yl]-N-(pyridin-4-ylmethyl)acetamide

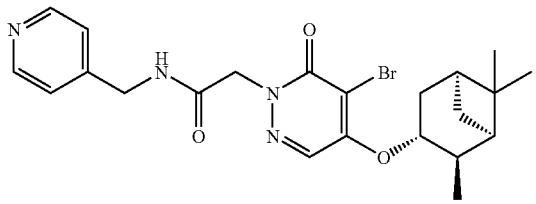 [SMILES: C[C@@H]1[C@H]2C[C@@H](C[C@H]1Oc1cnn(CC(=O)NCc3ccncc3)c(=O)c1Br)C2(C)C]

To 2-(4,5-dibromo-6-oxopyridazin-1(6H)-yl)-N-(pyridin-4-ylmethyl)acetamide (50 mg, 0.124 mmol) and (1R,2R,3R,5S)-(−)-isopinocampheol (50 mg, 0.324 mmol) in 1,4-dioxane (2 mL), sodium hydride (15 mg, 0.313 mmol) was added at 0° C., and stirred at 100° C. for 5 days. After completion of the reaction, the reaction mixture was mixed with water and extracted with chloroform and ethyl acetate. The combined organic layer was evaporated under reduced pressure. The resulting residue was purified by silica gel column chromatography (ethyl acetate) to give the desired product (1.7 mg, 3% yield).
Morphology: colorless amorphous
LC/MS: Condition 7, retention time 3.68 min
LC/MS (ESI$^+$) m/z; 475, 477 [M+1]$^+$
LC/MS (ESI$^-$) m/z; 473, 475 [M−1]$^-$

SYNTHETIC EXAMPLE 457

2-(5-Chloro-6-oxo-4-{[(1R,2R,3R,5S)-2,6,6-trimethylbicyclo[3.1.1]hept-3-yl]amino}pyridazin-1(6H)-yl)-N-[1-(1H-pyrazol-4-yl)ethyl]acetamide

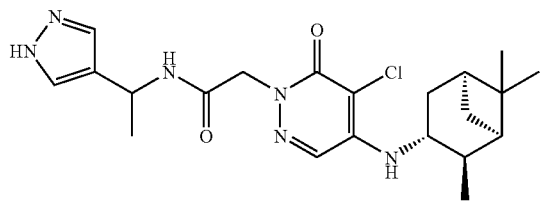 [SMILES: CC(NC(=O)Cn1ncc(N[C@@H]2C[C@@H]3C[C@H]([C@H]2C)C3(C)C)c(Cl)c1=O)c1cn[nH]c1]

2-(5-Chloro-6-oxo-4-{[(1R,2R,3R,5S)-2,6,6-trimethylbicyclo[3.1.1]hept-3-yl]amino}pyridazin-1(6H)-yl)-N-[1-(1-{[2-(trimethylsilyl)ethoxy]methyl}-1H-pyrazol-4-yl)ethyl]acetamide

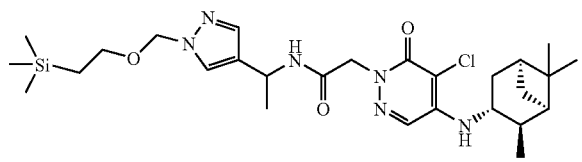

Synthesis was carried out in the same manner as in Synthetic Example 1 by using 1-(1-{[2-(trimethylsilyl)ethoxy] methyl}-1H-pyrazol-4-yl)ethanamine. The obtained crude product was used for the next reaction.
LC/MS: Condition 7, retention time 4.94 min
LC/MS (ESI$^+$) m/z; 563, 565 [M+1]$^+$
LC/MS (ESI$^-$) m/z; 561, 563 [M−1]$^-$ 2-(5-Chloro-6-oxo-4-{[(1R,2R,3R,5S)-2,6,6-trimethylbicyclo[3.1.1]hept-3-yl]amino}pyridazin-1(6H)-yl)-N-[1-(1H-pyrazol-4-yl)ethyl]acetamide 2-(5-Chloro-6-oxo-4-{[(1R,2R,3R,5S)-2,6,6-trimethylbicyclo[3.1.1]hept-3-yl]amino}pyridazin-1(6H)-yl)-N-[1-(1-{[2-(trimethylsilyl)ethoxy]methyl}-1H-pyrazol-4-yl)ethyl]acetamide (56.2 mg, 0.10 mmol) was mixed with 4 M hydrogen chloride/1,4-dioxane (2 mL) and stirred at 100° C. for 5 hours. After completion of the reaction, the reaction solution was evaporated under reduced pressure. The resulting residue was purified by silica gel column chromatography (ethyl acetate/MeOH=20/1) to give the desired product (5.2 mg, 12% yield).
Morphology: pale yellow solid
LC/MS: Condition 7, retention time 4.13 min
LC/MS (ESI$^+$) m/z; 433, 435 [M+1]$^+$
LC/MS (ESI$^-$) m/z; 431, 433 [M−1]$^-$

TEST EXAMPLE 1

Dye Assay

Human P2X7 (hP2×7) was cloned from a normal human brain total RNA library by reverse transcription (using SuperScript II (Invitrogen)) and PCR (using KOD-plus-(TOYOBO)). PCR primers were designed according to hP2X7 sequence registered in GENBANK with a putative amino acid sequence consisting of 595 amino acid residues. The PCR fragments were inserted into pcDNA3.1/myc-HisA vector (Invitrogen) and sequenced for confirmation.

HEK293 cells were transfected with hP2×7/pcDNA3.1/myc-HisA by lipofection, and 1 day later, the cells were treated with 1 mg/mL G418, and resistant cells were selected by appropriately dilution. The resistant cells were cloned by reseeding at a low density. Each clone was analyzed by a die assay (described in the next paragraph) to select one clone highly responsive to 2'(3')-O-(4-benzoylbenzoyl)adenosine 5'-triphosphate (BzATP), a highly selective ligand for the P2X7 receptor, which was used for screening of P2X7 receptor antagonists.

P2X7 receptor antagonists were screened by a dye uptake assay using HEK293 cells stably expressing hP2×7. Cells were plated on a type I collagen-coated black/clear bottom 96-well plate at 20000 cells/well and a day later, treated with varying concentrations of various test compounds for 30 minutes, then treated with a dye (Yo-Pro-1) (final concentration 2 µM) and BzATP (final concentration 0.1 mM) and incubated for 90 minutes. Then, the fluorescence (indicating the BzATP-induced Yo-Pro-1 uptake mediated by the P2X7 receptor) was measured with a microplate reader (excitation wavelength: 485 nm, emission wavelength: 535 nm). The % inhibition rates were calculated and plotted against the logarithms of the concentrations to determine IC$_{50}$. The results are shown in Tables 37 to 39.

TABLE 37

| Synthetic Example No. | IC$_{50}$ (µM) |
|---|---|
| 2 | 0.051 |
| 6 | 0.086 |

TABLE 37-continued

| Synthetic Example No. | IC$_{50}$ (μM) |
|---|---|
| 9 | 0.0035 |
| 12 | 0.020 |
| 14 | 0.021 |
| 19 | 0.038 |
| 23 | 0.034 |
| 32 | 0.063 |
| 39 | 0.0063 |
| 46 | 0.014 |
| 47 | 0.021 |
| 51 | 0.016 |
| 54 | 0.026 |
| 60 | 0.071 |
| 61 | 0.041 |
| 65 | 0.32 |
| 74 | 0.022 |
| 79 | 0.046 |
| 84 | 0.0041 |
| 87 | 0.062 |
| 88 | 0.044 |
| 89 | 0.035 |
| 94 | 0.064 |
| 99 | 0.039 |
| 100 | 0.054 |
| 103 | 0.014 |
| 104 | 0.057 |
| 106 | 0.044 |
| 127 | 0.019 |
| 134 | 0.020 |
| 135 | 0.0042 |
| 137 | 0.023 |
| 140 | 0.015 |
| 146 | 0.070 |
| 154 | 0.022 |
| 156 | 0.024 |
| 158 | 0.045 |
| 159 | 0.077 |
| 162 | 0.051 |

TABLE 38

| Synthetic Example No. | IC$_{50}$ (μM) |
|---|---|
| 167 | 0.022 |
| 169 | 0.30 |
| 170 | 0.0031 |
| 171 | 0.0043 |
| 172 | 0.31 |
| 178 | 0.030 |
| 183 | 0.23 |
| 190 | 0.054 |
| 197 | 0.032 |
| 198 | 0.098 |
| 201 | 0.090 |
| 202 | 0.14 |
| 205 | 0.058 |
| 208 | 0.084 |
| 209 | 0.042 |
| 212 | 0.030 |
| 214 | 0.0039 |
| 216 | 0.012 |
| 219 | 0.031 |
| 220 | 0.0042 |
| 222 | 0.0043 |
| 226 | 0.084 |
| 227 | 0.038 |
| 230 | 0.0028 |
| 232 | 0.037 |
| 240 | 0.19 |
| 247 | 0.032 |
| 252 | 0.13 |
| 253 | 0.036 |
| 254 | 0.027 |
| 259 | 0.027 |
| 262 | 0.055 |
| 264 | 0.0014 |

TABLE 38-continued

| Synthetic Example No. | IC$_{50}$ (μM) |
|---|---|
| 265 | 0.0039 |
| 270 | 0.030 |
| 271 | 0.014 |
| 275 | 0.0035 |
| 277 | 0.0037 |
| 281 | 0.19 |
| 288 | 0.0030 |
| 292 | 0.068 |
| 293 | 0.0035 |
| 294 | 0.0054 |
| 295 | 0.23 |
| 308 | 0.23 |
| 314 | 0.034 |
| 321 | 0.038 |
| 325 | 0.0089 |
| 326 | 0.16 |
| 331 | 0.019 |
| 335 | 0.013 |
| 337 | 0.0082 |
| 338 | 0.0053 |
| 343 | 0.025 |
| 345 | 0.034 |
| 347 | 0.0050 |
| 348 | 0.026 |
| 351 | 0.045 |
| 354 | 0.0026 |
| 355 | 0.027 |
| 358 | 0.010 |
| 360 | 0.014 |
| 361 | 0.018 |
| 362 | 0.0031 |
| 363 | 0.0028 |
| 364 | 0.0034 |
| 365 | 0.0027 |
| 366 | 0.0026 |
| 367 | 0.0030 |
| 368 | 0.0026 |
| 369 | 0.0021 |
| 372 | 0.0032 |
| 373 | 0.0028 |
| 374 | 0.0060 |
| 376 | 0.0027 |
| 377 | 0.0023 |
| 378 | 0.0015 |
| 379 | 0.24 |
| 382 | 0.025 |
| 385 | 0.039 |
| 387 | 0.037 |
| 390 | 0.27 |
| 394 | 0.22 |
| 402 | 0.12 |
| 403 | 0.074 |
| 404 | 0.047 |
| 405 | 0.021 |
| 406 | 0.040 |
| 409 | 0.071 |
| 415 | 0.039 |
| 420 | 0.12 |
| 428 | 0.027 |
| 430 | 0.058 |

TABLE 39

| Synthetic Example No. | IC$_{50}$ (μM) |
|---|---|
| 432 | 0.0021 |
| 433 | 0.0062 |
| 435 | 0.0032 |
| 438 | 0.0017 |
| 439 | 0.0020 |
| 441 | 0.0019 |
| 442 | 0.0017 |
| 443 | 0.0056 |

TABLE 39-continued

| Synthetic Example No. | IC$_{50}$ (μM) |
|---|---|
| 447 | 0.042 |
| 448 | 0.014 |
| 453 | 0.016 |

TEST EXAMPLE 2

IL-1β Assay

Human whole blood from healthy volunteers was diluted with equal volume of saline and peripheral blood mononuclear cells were collected by using a Limphoprep tube (Daiichi Pure Chemicals), washed with physiological saline and seeded onto a 96-well plate with a medium containing 1-10 ng/mL LPS (SIGMA). 30 minutes later, the cells were treated with varying concentrations of various compounds and incubated for 30 minutes. Then, the cells were treated with BzATP (final concentration 1 mM) or ATP (final concentration 5 mM) and incubated for 120 minutes. The cells were centrifugated to collect supernatants, and the concentration of IL-1β in supernatants were determined by IL-1β HTRF kit (CIS biointernational). The % inhibition rates were calculated and plotted against the logarithms of the concentrations to determine IC$_{50}$. The results are shown in Tables 40 to 42.

TABLE 40

| Synthetic Example No. | IC$_{50}$ (μM) |
|---|---|
| 9 | 0.047 |
| 39 | 0.019 |
| 47 | 0.061 |
| 84 | 0.082 |

TABLE 41

| Synthetic Example No. | IC$_{50}$ (μM) |
|---|---|
| 171 | 0.033 |
| 214 | 0.039 |
| 216 | 0.038 |
| 230 | 0.0031 |
| 264 | 0.0033 |
| 277 | 0.0043 |
| 325 | 0.040 |
| 358 | 0.038 |
| 378 | 0.0015 |

TABLE 42

| Synthetic Example No. | IC$_{50}$ (μM) |
|---|---|
| 432 | 0.017 |
| 433 | 0.051 |
| 435 | 0.036 |
| 442 | 0.027 |

FORMULATION EXAMPLE 1

A granule preparation containing the following ingredients is prepared.

| Ingredients | |
|---|---|
| Compound represented by the formula (I) | 10 mg |
| Lactose | 700 mg |
| Corn Starch | 274 mg |
| HPC-L | 16 mg |
| | 1000 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

FORMULATION EXAMPLE 2

A powder preparation for capsulation containing the following ingredients is prepared.

| Ingredients | |
|---|---|
| Compound represented by the formula (I) | 10 mg |
| Lactose | 79 mg |
| Corn Starch | 10 mg |
| Magnesium Stearate | 1 mg |
| | 100 mg |

A compound represented by the formula (I) and lactose are sifted through a 60-mesh sieve. Corn starch is sifted though a 120-mesh sieve. They are mixed with magnesium stearate in a V-type blender. The 10% powder is put in hard gelatin capsules No. 5, 100 mg each.

FORMULATION EXAMPLE 3

A granule preparation for capsulation containing the following ingredients is prepared.

| Ingredients | |
|---|---|
| Compound represented by the formula (I) | 15 mg |
| Lactose | 90 mg |
| Corn Starch | 42 mg |
| HPC-L | 3 mg |
| | 150 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

FORMULATION EXAMPLE 4

A tablet preparation containing the following ingredients is prepared.

| Ingredients | |
| --- | --- |
| Compound represented by the formula (I) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (I), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

FORMULATION EXAMPLE 5

An intravenous preparation is prepared as follows.

| | |
| --- | --- |
| Compound represented by the formula (I) | 100 mg |
| Saturated Fatty Acid Glyceride | 1000 mL |

Solutions having the above-mentioned composition are usually administered to a patient intravenously at a rate of 1 ml per 1 minute.

INDUSTRIAL APPLICABILITY

The compounds of the present invention which inhibit activation of the P2X7 receptor are useful as preventive, therapeutic and improving agents for diseases against which activation of the P2X7 receptor is effective, especially as anti-rheumatoid arthritis agents with anti-inflammatory action, anti-pain action and bone metabolism improving action, drugs for inflammatory bowel diseases or anti-pain agents for inflammatory pain or cancer pain, and are useful as medicines.

The entire disclosures of Japanese Patent Application No. 2007-284189 filed on Oct. 31, 2007 and Japanese Patent Application No. 2008-229921 filed on Sep. 8, 2008 including specifications, claims and summaries are incorporated herein by reference in their entireties.

The invention claimed is:

1. A compound represented by the formula (I):

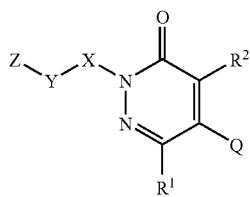

(I)

wherein $R^1$ means a hydrogen atom, a hydroxy group, a nitro group, a cyano group, a carboxy group, a carbamoyl group, an amino group, a halogen atom, a $C_{1-6}$ alkyl group, a $C_{2-6}$ alkenyl group, a $C_{2-6}$ alkynyl group or a $C_{1-6}$ alkoxy group, wherein the $C_{1-6}$ alkyl group, the $C_{2-6}$ alkenyl group, the $C_{2-6}$ alkynyl group and the $C_{1-6}$ alkoxy group are unsubstituted or substituted with one or more halogen atoms, $R^2$ means a hydrogen atom, a hydroxy group, a nitro group, a cyano group, a carboxy group, a carbamoyl group, an amino group, a halogen atom, a $C_{1-6}$ alkyl group, a $C_{2-6}$ alkenyl group, a $C_{1-6}$ alkoxyl group, a mono-$C_{1-6}$ alkylamino group, a di-$C_{1-6}$ alkylamino group, a $C_{1-6}$ alkylthio group or a $C_{1-6}$ alkylsulfonyl group, wherein the $C_{1-6}$ alkyl group, the $C_{2-6}$ alkenyl group, the $C_{1-6}$ alkoxy group, the mono-$C_{1-6}$ alkylamino, the di-$C_{1-6}$ alkylthio group and the $C_{1-6}$ alkylsulfonyl group are unsubstituted or substituted with one or more halogen atoms, Q means a structure represented by the formula (VI):

(VI)

wherein $R^3$ means a hydrogen atom, and $R^4$ means a $C_{7-12}$ cycloalkyl group or a $C_{7-12}$ cycloalkenyl group, wherein the $C_{7-12}$ cycloalkyl group and the $C_{7-12}$ cycloalkenyl group are unsubstituted or substituted with one or two identical or different substituents selected from the group consisting of halogen atoms, carboxy group, carbamoyl groups, sulfamoyl groups, nitro groups, cyano groups, hydroxy groups, amino groups, mono-$C_{1-6}$ alkylamino groups, di-$C_{1-6}$ alkylamino groups, $C_{1-6}$ alkoxy groups, $C_{2-9}$ heterocyclyl groups, $C_{1-6}$ alkylthio groups, $C_{1-6}$ alkylsulfonyl groups, $C_{1-3}$ haloalkyl groups and $C_{1-3}$ haloalkoxy groups, X means a $C_{1-6}$ alkylene group which is unsubstituted or substituted with one or two identical or different substituents selected from the substituent set $V^1$, Y means a $C_{6-14}$ arylene group, a $C_{2-9}$ heterocyclylene group, wherein the $C_{6-14}$ arylene group and the $C_{2-9}$ heterocyclylene group are unsubstituted or substituted with one or more identical or different substituents selected from a substituent set $V^2$, or any one of the structures represented by the formula (III):

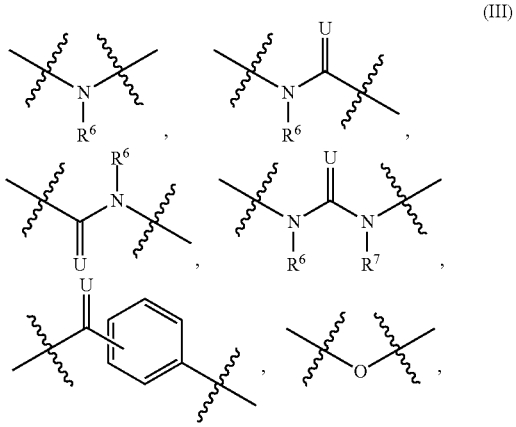

(III)

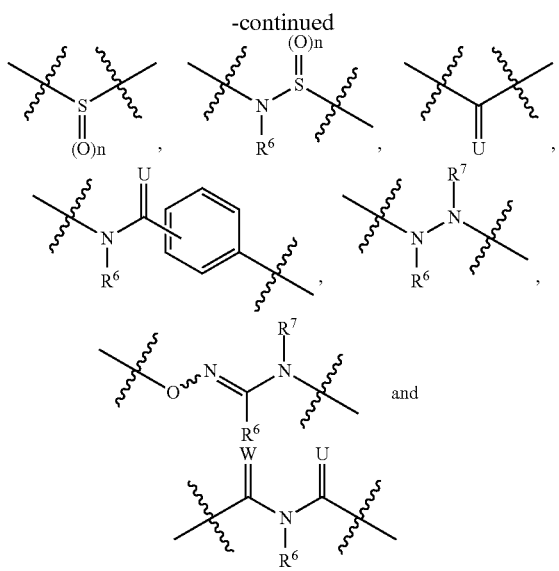

wherein each of $R^6$ and $R^7$ independently means a hydrogen atom, a $C_{1-6}$ alkyl group, a $C_{2-6}$ alkenyl group, wherein the $C_{1-6}$ alkyl group and the $C_{2-6}$ alkenyl group are unsubstituted or substituted with one or more identical or different substituents selected from the substituent set $V^1$, or a $C_{1-3}$ haloalkyl group, each of U and W independently means an oxygen atom, a sulfur atom or $NOR^{10}$, wherein $R^{10}$ means a hydrogen atom, a $C_{1-3}$ alkyl group or a $C_{1-3}$ haloalkyl group, and n means 0, 1 or 2), Z means a hydrogen atom, a $C_{1-6}$ alkyl group, a $C_{2-6}$ alkenyl group, a $C_{1-6}$ alkoxy group, a $C_{3-12}$ cycloalkyl group, a $C_{3-12}$ cycloalkenyl group, wherein the $C_{1-6}$ alkyl group, the $C_{2-6}$ alkenyl group, the $C_{1-6}$ alkoxy group, the $C_{3-12}$ cycloalkyl group and the $C_{3-12}$ cycloalkenyl group are unsubstituted or substituted with one or more identical or different substituents selected from the substituent set $V^2$, a $C_{6-14}$ aryl group, a $C_{2-9}$ aromatic heterocyclic group, a fused $C_{6-14}$ aryl group, a fused $C_{2-9}$ aromatic heterocyclic group, a $C_{6-14}$ aryloxy group, $C_{2-9}$ aromatic heterocyclyloxy group, or a $C_{2-9}$ heterocyclyl group, wherein the $C_{6-14}$ aryl group, the $C_{2-9}$ aromatic heterocyclic group, the fused $C_{6-14}$ aryl group, the fused $C_{2-9}$ aromatic heterocyclic group, the $C_{6-14}$ aryloxy group, the $C_{2-9}$ aromatic heterocyclyloxy group, and the $C_{2-9}$ heterocyclyl group are unsubstituted or substituted with one or more identical or different substituents selected from the substituent set $V^2$, the substituent set $V^1$ consists of carboxy groups, carbamoyl groups, sulfamoyl groups, phosphono groups, sulfo groups, tetrazolyl groups, formyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkyl groups, $C_{2-6}$ alkenyl groups, $C_{1-6}$ alkoxy groups, $C_{2-9}$ heterocyclyl groups, $C_{1-6}$ alkylthio groups and $C_{1-6}$ alkylsulfonyl groups, wherein the mono-$C_{1-6}$ alkylamino groups, the di-$C_{1-6}$ alkylamino groups, the $C_{1-6}$ alkyl groups, the $C_{2-6}$ alkenyl groups, the $C_{1-6}$ alkoxy groups, the $C_{2-9}$ heterocyclyl groups, the $C_{1-6}$ alkylthio groups and the $C_{1-6}$ alkylsulfonyl groups are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more hydroxy groups, one or more amino groups, one or more mono-$C_{1-6}$ alkylamino groups, one or more di-$C_{1-6}$ alkylamino groups, one or more $C_{1-6}$ alkylthio groups or one or more $C_{1-6}$ alkylsulfonyl groups, and the substituent set $V^2$ consists of the substituent set $V^1$, $C_{6-14}$ aryl groups, $C_{2-9}$ aromatic heterocyclic groups, fused $C_{6-14}$ aryl groups, and $C_{2-9}$ aromatic heterocyclic groups, wherein the $C_{6-14}$ aryl groups, the $C_{2-9}$ aromatic heterocyclic group, the fused $C_{6-14}$ aryl groups, and $C_{2-9}$ aromatic heterocyclic group are unsubstituted or substituted with one or more identical or different substituents selected from the substituent set $V^1$, a tautomer or pharmaceutically acceptable salt of the compound.

2. A compound represented by the formula (I):

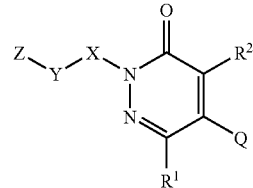

wherein $R^1$ means a hydrogen atom, a hydroxy group, a cyano group, a carboxy group, a carbamoyl group, an amino group, a halogen atom, a $C_{1-6}$ alkyl group, a $C_{2-6}$ alkenyl group, a $C_{2-6}$ alkynyl group or a $C_{1-6}$ alkoxy group, wherein the $C_{1-6}$ alkyl group, the $C_{2-6}$ alkenyl group, the $C_{2-6}$ alkynyl group and the $C_{1-6}$ alkoxy group are unsubstituted or substituted with one or more halogen atoms, $R^2$ means a hydrogen atom, a hydroxy group, a cyano group, a carboxy group, a carbamoyl group, an amino group, a halogen atom, a $C_{1-6}$ alkyl group, a $C_{2-6}$ alkenyl group, a $C_{1-6}$ alkoxy group, a $C_{1-6}$ alkylthio group or a $C_{1-6}$ alkylsulfonyl group, wherein the $C_{1-6}$ alkyl group, the $C_{2-6}$ alkenyl group, the $C_{1-6}$ alkoxy group, the $C_{1-6}$ alkylthio group and the $C_{1-6}$ alkylsulfonyl group are unsubstituted or substituted with one or more halogen atoms, Q is as defined in claim 1, X means a $C_{1-6}$ alkylene group, wherein the $C_{1-6}$ alkylene group is unsubstituted or substituted with one or more identical or different substituents selected from the substituent set $V^1$, Y means a $C_{6-14}$ arylene group a $C_{2-9}$ heterocyclylene group, wherein the $C_{6-14}$ arylene group and the $C_{2-9}$ heterocyclylene group are unsubstituted or substituted with one or more identical or different substituents selected from a substituent set $V^2$, or any one of the structures represented by the formula (V):

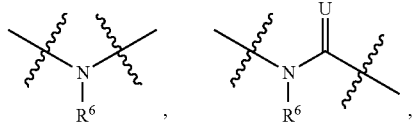

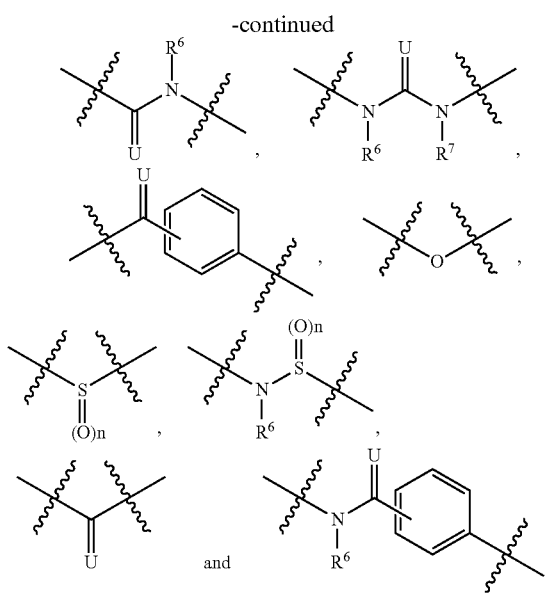

wherein each of $R^6$ and $R^7$ independently means a hydrogen atom, a $C_{1-6}$ alkyl group, a $C_{2-6}$ alkenyl group or a $C_{1-3}$ haloalkyl group, U means an oxygen atom, a sulfur atom or $NOR^{10}$, wherein $R^{10}$ means a hydrogen atom, a $C_{1-3}$ alkyl group or a $C_{1-3}$ haloalkyl group, and n means 0, 1 or 2, Z means a $C_{1-6}$ alkyl group, a $C_{2-6}$ alkenyl group, a $C_{1-6}$ alkoxy group, a $C_{3-12}$ cycloalkyl group, a $C_{3-12}$ cycloalkenyl group, wherein the $C_{1-6}$ alkyl group, the $C_{2-6}$ alkenyl group, the $C_{1-6}$ alkoxy group, the $C_{3-12}$ cycloalkyl group and the $C_{3-12}$ cycloalkenyl group are unsubstituted or substituted with one or more identical or different substituents selected from the substituent set $V^2$, a $C_{6-14}$ aryl group, a $C_{2-9}$ aromatic heterocyclic group, a fused $C_{6-14}$ aryl group, a fused $C_{2-9}$ aromatic heterocyclic group, a $C_{6-14}$ aryloxy group, a $C_{2-9}$ aromatic heterocyclic group, or a $C_{2-9}$ heterocyclyl group, wherein the $C_{6-14}$ aryl group, the $C_{2-9}$ aromatic heterocyclic group, the fused $C_{6-14}$ aryl group, the fused $C_{2-9}$ aromatic heterocyclic group, the $C_{6-14}$ aryloxy group, the $C_{2-9}$ aromatic heterocyclyloxy group, and the $C_{2-9}$ heterocyclyl group are unsubstituted or substituted with one or more identical or different substituents selected from the substituent set $V^2$, the substituent set $V^1$ consists of carboxy groups, carbamoyl groups, sulfamoyl groups, phosphono groups, sulfo groups, tetrazolyl groups, formyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkyl groups, $C_{2-6}$ alkenyl groups, $C_{1-6}$ alkoxy groups, $C_{2-9}$ heterocyclyl groups, $C_{1-6}$ alkylthio groups and $C_{1-6}$ alkylsulfonyl groups, wherein the mono-$C_{1-6}$ alkylamino groups, the di-$C_{1-6}$ alkylamino groups, the $C_{1-6}$ alkyl groups, the $C_{2-6}$ alkenyl groups, the $C_{1-6}$ alkoxy groups, the $C_{2-9}$ heterocyclyl groups, the $C_{1-6}$ alkylthio groups and the $C_{1-6}$ alkylsulfonyl groups are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more hydroxy groups, one or more amino groups, one or more mono-$C_{1-6}$ alkylamino groups, one or more di-$C_{1-6}$ alkylamino groups, one or more $C_{1-6}$ alkylthio groups or one or more $C_{1-6}$ alkylsulfonyl groups, and the substituent set $V^2$ consists of the substituent set $V^1$, $C_{6-14}$ aryl groups, $C_{2-9}$ aromatic heterocyclic groups, fused $C_{6-14}$ aryl groups, fused $C_{2-9}$ aromatic heterocyclic groups, wherein the $C_{6-14}$ aryl groups, the $C_{2-9}$ aromatic heterocyclic group, the fused $C_{6-14}$ aryl groups, and the fused $C_{2-9}$ aromatic heterocyclic groups are unsubstituted or substituted with one or more identical or different substituents selected from the substituent set $V^1$, a tautomer or pharmaceutically acceptable salt of the compound.

3. The compound according to claim 1, wherein $R^1$ is a hydrogen atom, a $C_{1-3}$ alkoxy group or a $C_{1-3}$ haloalkoxy group, a tautomer or pharmaceutically acceptable salt of the compound.

4. The compound according to claim 3, wherein $R^1$ is a hydrogen atom or an ethoxy group, a tautomer or pharmaceutically acceptable salt of the compound.

5. The compound according to claim 1, wherein $R^2$ is a hydrogen atom, a halogen atom, a $C_{1-3}$ alkoxy group, a $C_{1-3}$ alkyl group, a $C_{1-3}$ alkylthio group or a $C_{1-3}$ alkylsulfonyl group, wherein the $C_{1-3}$ alkoxy group, the $C_{1-3}$ alkyl group, the $C_{1-3}$ alkylthio group and the $C_{1-3}$ alkylsulfonyl group are unsubstituted or substituted with one or more halogen atoms, a tautomer or pharmaceutically acceptable salt of the compound.

6. The compound according to claim 5, wherein $R^2$ is a halogen atom, a tautomer or pharmaceutically acceptable salt of the compound.

7. The compound according to claim 1, wherein X means a $C_{1-6}$ alkylene group which is unsubstituted or substituted with one or two identical or different substituents selected from the substituent set $V^1$, Y means any one of the structures represented by the formula (VIII):

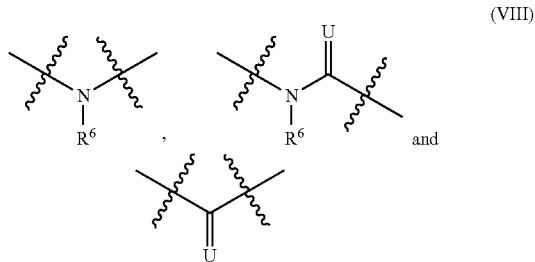

(VIII)

wherein $R^6$ means a hydrogen atom or a $C_{1-6}$ alkyl group which is unsubstituted or substituted with one or more halogen atoms, and U means an oxygen atom or a sulfur atom, and Z means a $C_{1-6}$ alkyl group, a $C_{1-6}$ alkoxy group, wherein the $C_{1-6}$ alkyl group and the $C_{1-6}$ alkoxy group are unsubstituted or substituted with one or two identical or different substituents selected from the substituent set $V^2$, a $C_{6-14}$ aryl group, a $C_{2-9}$ aromatic heterocyclic group, a $C_{6-14}$ aryloxy group, a $C_{2-9}$ aromatic heterocyclyloxy group, or a $C_{2-9}$ heterocyclyl group, wherein the $C_{6-14}$ aryl group, the $C_{2-9}$ aromatic heterocyclic group, the $C_{6-14}$ aryloxy group, the $C_{2-9}$ aromatic heterocyclyloxy group, and the $C_{2-9}$ heterocyclyl group are unsubstituted or substituted with one substituent selected from the substituent set $V^2$, a tautomer or pharmaceutically acceptable salt of the compound.

8. The compound according to claim 7, wherein Z means a $C_{1-6}$ alkyl group which is substituted with a $C_{2-9}$ heteroaryl group which is unsubstituted or substituted with one or two identical or different substituents selected from the substituent set $V^1$, a tautomer or pharmaceutically acceptable salt of the compound.

9. The compound according to claim 2, wherein $R^1$ is a hydrogen atom, a $C_{1-3}$ alkoxy group or a $C_{1-3}$ haloalkoxy group, a tautomer or pharmaceutically acceptable salt of the compound.

10. The compound according to claim 9, wherein $R^1$ is a hydrogen atom or an ethoxy group, a tautomer or pharmaceutically acceptable salt of the compound.

11. The compound according to claim 2, wherein $R^2$ is a hydrogen atom, a halogen atom, a $C_{1-3}$ alkoxy group, a $C_{1-3}$ alkyl group, a $C_{1-3}$ alkylthio group or a $C_{1-3}$ alkylsulfonyl group, wherein the $C_{1-3}$ alkoxy group, the $C_{1-3}$ alkyl group, the $C_{1-3}$ alkylthio group and the $C_{1-3}$ alkylsulfonyl group are unsubstituted or substituted with one or more halogen atoms, a tautomer or pharmaceutically acceptable salt of the compound.

12. The compound according to claim 11, wherein $R^2$ is a halogen atom, a tautomer or pharmaceutically acceptable salt of the compound.

13. The compound according to claim 2, wherein X means a $C_{1-6}$ alkylene group which is unsubstituted or substituted with one or two identical or different substituents selected from the substituent set $V^1$, Y means any one of the structures represented by the formula (VIII):

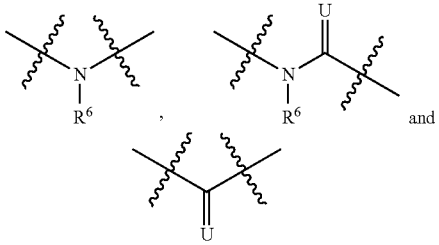

(VIII)

wherein $R^6$ means a hydrogen atom or a $C_{1-6}$ alkyl group, and U means an oxygen atom or a sulfur atom, and Z means a $C_{1-6}$ alkyl group, a $C_{1-6}$ alkoxy group, wherein the $C_{1-6}$ alkyl group and the $C_{1-6}$ alkoxy group are unsubstituted or substituted with one or two identical or different substituents selected from the substituent set $V^2$, a $C_{6-14}$ aryl group, a $C_{2-9}$ aromatic heterocyclic group, a $C_{6-14}$ aryloxy group, a $C_{2-9}$ aromatic heterocyclyloxy group, or a $C_{2-9}$ heterocyclyl group, wherein the $C_{6-14}$ aryl group, the $C_{2-9}$ aromatic heterocyclic group, the $C_{6-14}$ aryloxy group, the $C_{2-9}$ aromatic heterocyclyloxy group, and the $C_{2-9}$ heterocyclyl group are unsubstituted or substituted with one substituent selected from the substituent set $V^2$, a tautomer or pharmaceutically acceptable salt of the compound.

14. The compound according to claim 13, wherein Z means a $C_{1-6}$ alkyl group which is substituted with a $C_{2-9}$ heteroaryl group which is unsubstituted or substituted with one or two identical or different substituents selected from the substituent set $V^1$, a tautomer or pharmaceutically acceptable salt of the compound.

15. A compound represented by the formula (I):

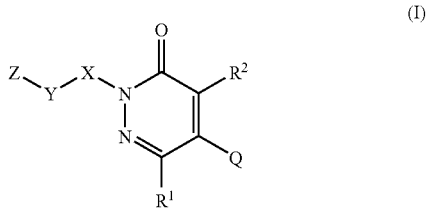

(I)

wherein $R^1$ means a hydrogen atom, a hydroxy group, a cyano group, a carboxy group, a carbamoyl group, an amino group, a halogen atom, a $C_{1-6}$ alkyl group, a $C_{2-6}$ alkenyl group, a $C_{2-6}$ alkynyl group or a $C_{1-6}$ alkoxy group, wherein the $C_{1-6}$ alkyl group, the $C_{2-6}$ alkenyl group, the $C_{2-6}$ alkynyl group and the $C_{1-6}$ alkoxy group are unsubstituted or substituted with one or more halogen atoms, $R^2$ means a $C_{6-14}$ aryl group or $C_{2-9}$ aromatic heterocyclic group which is unsubstituted or substituted with one or more identical or different substituents selected from a substituent set $V^2$, Q means a structure represented by the formula (VI):

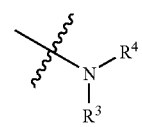

(VI)

wherein $R^3$ means a hydrogen atom, and $R^4$ means a $C_{7-12}$ cycloalkyl group or a $C_{7-12}$ cycloalkenyl group, wherein the $C_{7-12}$ cycloalkyl group and the $C_{7-12}$ cycloalkenyl group are unsubstituted or substituted with one or two identical or different substituents selected from the group consisting of halogen atoms, carboxy groups, carbamoyl groups, sulfamoyl groups, nitro groups, cyano groups, hydroxy groups, amino groups, mono-$C_{1-6}$ alkylamino groups, di-$C_{1-6}$ alkylamino groups, $C_{1-6}$ alkoxy groups, $C_{2-9}$ heterocyclyl groups, $C_{1-6}$ alkylthio groups, $C_{1-6}$ alkylsulfonyl groups, $C_{1-3}$ haloalkyl groups and $C_{1-3}$ haloalkoxy groups, and X means a $C_{1-6}$ alkylene group which is unsubstituted or substituted with one or more identical or different substituents selected from the substituent set $V^1$, Y means a structure represented by the formula (IX):

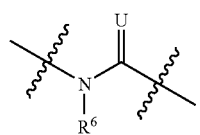

(IX)

wherein $R^6$ means a hydrogen atom, a $C_{1-6}$ alkyl group, a $C_{2-6}$ alkenyl group or a $C_{1-3}$ haloalkyl group, and U means an oxygen atom, a sulfur atom or $NOR^{10}$, wherein $R^{10}$ means a hydrogen atom, a $C_{1-3}$ alkyl group or a $C_{1-3}$ haloalkyl group, Z means a hydrogen atom, a $C_{1-6}$ alkyl group, a $C_{2-6}$ alkenyl group, a $C_{1-6}$ alkoxy group, a $C_{3-12}$ cycloalkyl group, a $C_{3-12}$ cycloalkenyl group, wherein the $C_{1-6}$ alkyl group, the $C_{2-6}$ alkenyl group, the $C_{1-6}$ alkoxy group, the $C_{3-12}$ cycloalkyl group and the $C_{3-12}$ cycloalkenyl group are unsubstituted or substituted with one or more identical or different substituents selected from the substituent set $V^2$, a $C_{6-14}$ aryl group, a $C_{2-9}$ aromatic heterocyclic group, a fused $C_{6-14}$ aryl group, a fused $C_{2-9}$ aromatic heterocyclic group or a $C_{2-9}$ heterocyclyl group, wherein the $C_{6-14}$ aryl group, the $C_{2-9}$ aromatic heterocyclic group, the fused $C_{6-14}$ aryl group, the fused $C_{2-9}$ aromatic heterocyclic group and the $C_{2-9}$ heterocyclyl group are unsubstituted or substituted with one or more identical or different substituents selected from the substituent set $V^2$, the substituent set $V^1$ consists of carboxy groups, carbamoyl groups, sulfamoyl groups, phosphono groups, sulfo groups, tetrazolyl groups, formyl groups, nitro groups, cyano groups, halogen atoms, hydroxy groups, amino groups, mono-$C_{1-6}$ alkylamino groups, di-$C_{1-6}$ alkylamino groups, $C_{1-6}$ alkyl groups, $C_{2-6}$ alkenyl groups, $C_{1-6}$ alkoxy groups, $C_{2-9}$ heterocyclyl groups, $C_{1-6}$ alkylthio groups and $C_{1-6}$ alkylsulfonyl groups, wherein the mono-$C_{1-6}$ alkylamino groups, the di-$C_{1-6}$ alkylamino groups, the $C_{1-6}$ alkyl groups, the $C_{2-6}$ alkenyl groups, the $C_{1-6}$ alkoxy groups, the $C_{2-9}$ heterocyclyl groups, the $C_{1-6}$ alkylthio groups and the $C_{1-6}$ alkylsulfonyl groups are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more hydroxy groups, one or more amino groups, one or more mono-$C_{1-6}$ alkylamino groups, one or more di-$C_{1-6}$ alkylamino groups, one or more $C_{1-6}$ alkylthio groups or one or more $C_{1-6}$ alkylsulfonyl groups, and the substituent set $V^2$ consists of the substituent set $V^1$, $C_{6-14}$ aryl groups, $C_{2-9}$ aromatic heterocyclic groups, fused $C_{6-14}$ aryl groups, fused $C_{2-9}$ aromatic heterocyclic groups, wherein the $C_{6-14}$ aryl groups, the $C_{2-9}$ aromatic heterocyclic groups, the fused $C_{6-14}$ aryl groups, and the fused $C_{2-9}$ aromatic heterocyclic groups are unsubstituted or substituted with one or more identical or different substituents selected from the substituent set $V^1$, a tautomer or pharmaceutically acceptable salt of the compound.

16. The compound according to claim 15, wherein $R^1$ is a hydrogen atom, a $C_{1-3}$ alkoxy group or a $C_{1-3}$ haloalkoxy group, $R^2$ is a $C_{6-14}$ aryl group or $C_{2-9}$ aromatic heterocyclic group, Q is as defined in claim 15, and Z means a $C_{1-6}$ alkyl group which is substituted with a $C_{2-9}$ heteroaryl group which is unsubstituted or substituted with one or two identical or different substituents selected from the substituent set $V^1$, a tautomer or pharmaceutically acceptable salt of the compound.

17. A medicinal composition comprising the compound according to claim 1, a tautomer or pharmaceutically acceptable salt of the compound, and a pharmaceutically acceptable additive.

18. A medicinal composition comprising the compound according to claim 2, a tautomer or pharmaceutically acceptable salt of the compound, and a pharmaceutically acceptable additive.

19. A medicinal composition comprising the compound according to claim 15, a tautomer or pharmaceutically acceptable salt of the compound, and a pharmaceutically acceptable additive.

* * * * *